US009181559B2

(12) United States Patent
Patterson et al.

(10) Patent No.: US 9,181,559 B2
(45) Date of Patent: Nov. 10, 2015

(54) GENERATION OF HIGH POLYHYDROXYBUTYRATE PRODUCING OILSEEDS

(75) Inventors: Nii Patterson, Chelmsford, MA (US); Jihong Tang, Brighton, MA (US); Jixiang Han, Maryland Heights, MO (US); Venkata Tavva, Chikkadpally (IN); Andrew Hertig, Cambridge, MA (US); Zhigang Zhang, Watertown, MA (US); Thomas Martin Ramseier, Newtown, MA (US); Karen Bohmert-Tatarev, Brookline, MA (US); Oliver P. Peoples, Arlington, MA (US); Kristi D. Snell, Belmont, MA (US)

(73) Assignee: Metabolix, Inc., Cambridge, MA (US)

( * ) Notice: Subject to any disclaimer, the term of this patent is extended or adjusted under 35 U.S.C. 154(b) by 465 days.

(21) Appl. No.: 13/395,702

(22) PCT Filed: Sep. 15, 2010

(86) PCT No.: PCT/US2010/048963

§ 371 (c)(1),
(2), (4) Date: Mar. 13, 2012

(87) PCT Pub. No.: WO2011/034946

PCT Pub. Date: Mar. 24, 2011

(65) Prior Publication Data

US 2012/0180162 A1 Jul. 12, 2012

Related U.S. Application Data

(60) Provisional application No. 61/242,522, filed on Sep. 15, 2009.

(51) Int. Cl.

| | |
|---|---|
| ***C12N 15/82*** | (2006.01) |
| ***C12N 15/63*** | (2006.01) |
| ***A01H 5/00*** | (2006.01) |
| ***A01H 5/10*** | (2006.01) |

(52) U.S. Cl.

CPC ........ *C12N 15/8214* (2013.01); *C12N 15/8257* (2013.01)

(58) Field of Classification Search

None

See application file for complete search history.

(56) References Cited

U.S. PATENT DOCUMENTS

| | | | |
|---|---|---|---|
| 4,535,060 | A | 8/1985 | Comai |
| 5,034,322 | A | 7/1991 | Rogers |
| 5,073,675 | A | 12/1991 | Jones |
| 5,268,463 | A | 12/1993 | Jefferson |
| 5,276,268 | A | 1/1994 | Strauch |
| 5,463,175 | A | 10/1995 | Barry |
| 5,519,164 | A | 5/1996 | Mullner |
| 5,527,695 | A | 6/1996 | Hodges |
| 5,530,196 | A | 6/1996 | Fraley |
| 5,668,298 | A | 9/1997 | Waldron |
| 5,767,378 | A | 6/1998 | Bojsen |
| 5,811,272 | A | 9/1998 | Snell |
| 6,072,050 | A | 6/2000 | Bowen |
| 6,316,262 | B1 | 11/2001 | Huisman |
| 6,437,220 | B1 | 8/2002 | Broun |
| 6,444,878 | B1 | 9/2002 | Donaldson |
| 6,586,658 | B1 | 7/2003 | Peoples |
| 7,045,684 | B1 | 5/2006 | Held |
| 2002/0182690 | A1 | 12/2002 | Cannon |
| 2008/0275208 | A1 | 11/2008 | Skraly |

FOREIGN PATENT DOCUMENTS

| | | |
|---|---|---|
| WO | 2006101983 | 9/2006 |
| WO | 2010102293 | 9/2010 |

OTHER PUBLICATIONS

Bohmert et al, 2002, Plant Physiology, 128:1282-1290.*

Akasofu, at al., "Nucleotide sequence of the gene for the *Vigna mungo* sulfhydryl-endopeptidase (SH-EP).", Nucleic Acids Res., 18:1892 (1990)

Barfield and Pua, "Gene transfer in plants of *Brassica juncea* using *Agrobacterium tumefaciens*-mediated transformation" , Plant Cell Reports, 10:308-14 (1991).

Bohmert, et al., "Metabolic Engineering: Plastids as Bioreactors" , Mol Biol Biotech Plant Organ, 3:559-585 (2004).

Bohmert, et al., "Constitutive expression of the beta-ketothiolase gene in transgenic plants. A major obstacle for obtaining polyhydroxybutyrate-producing plants" , Plant Physiol., 128:1282-90 (2002).

Bohmert, et al., "Transgenic *Arabidopsis* plants can accumulate polyhydroxybutyrate to up to 4% of their fresh weight" , Planta, 211:841-5 (2000).

Cubitt, et al., "Understanding, improving and using green fluorescent proteins" , Trends Biochem. Sci. 20:448-455 (1995).

(Continued)

*Primary Examiner* — David H Kruse
*Assistant Examiner* — Jason Deveau Rosen
(74) *Attorney, Agent, or Firm* — Pabst Patent Group LLP

(57) ABSTRACT

Transgenic plants, plant material, plant cells, and genetic constructs for synthesis of biopolymers, for example polyhydroxyalkanoates ("PHA") are provided. In one embodiment, the transgenic plants synthesize polyhydroxybutyrate ("PHB"). In one embodiment the transgenic plant encodes siRNA for one or more of the genes encoding enzymes for producing PHA. In a more preferred embodiment, the siRNA expression is under the control of an inducible regulatory element. In another embodiment, the transgenic plant contains transgenes that encode expression enzymes that will degrade the polymer. In a preferred embodiment, the expression of these enzymes is under the control of a germination specific, inducible, or minimal promoter. In another embodiment, the transgenic plant contains transgenes encoding enzymes that increase carbon flow for polymer synthesis. In a preferred embodiment, these transgenes encode enzymes that increase carbon flow in the Calvin Cycle.

17 Claims, 6 Drawing Sheets

(56) References Cited

OTHER PUBLICATIONS

Czarnecka, et al., "Regulatory domains of the Gmhsp17.5-E heat shock promoter of soybean" , Mel. Cell Biol. 9:3457-63 (1989).
Dale and Ow, "Gene transfer with subsequent removal of the selection gene from the host genome" , PNAS, 88: 10558-10562 (1991).
Eisen, et al., "Cluster analysis and display of genome-wide expression patterns" , PNAS, 95:14863-8 (1998).
Ellerstrom, et al "Functional dissection of a napin gene promoter: identification of promoter elements required for embryo and endosperm-specific transcription" , Plant Molecular Biology, 32:1019-27 (1996).
Erikson, at al., "A conditional marker gene allowing both positive and negative selection in plants" , Nat Biotechnol., 22:455-8 (2004).
Esser,et el., "Extrannuclear Inheritance: Mitochondrial genetic and biogenesis" , Prog. Botany, 66:91-111 (2005).
Fry, et al., "Transformation of *Brassica napus* with *Agrobacterium tumefaciens* Based Vectors" , Plant Cell Reports, 6:321-5 (1987).
Hirai and Kodama, "RNAi vectors for manipulation of gene expression in higher plants" , Open Plant Sci.J., 2:21-30 (2008).
Hood, et. al., "The hypervirulence of *Agrobacterium tumefaciens* A281 is encoded in a region of pTiBo542 outside of T-DNA" , J. Bacteriol. 168:1291-1301 (1986).
Houmiel, et al., "Poly(beta-hydroxybutyrate) production in oilseed leukoplasts of *Brassica napus*" , Planta, 209:547-50 (1999).
Iida, et al., "Positive and negative cis-regulatory regions in the soybean glycinin promoter identified by quantitative transient gene expression" , Plant Cell Reports, 14:539-44 (1995).
Ito, et al., "D-3-hydroxybutyrate dehydrogenase from *Pseudomonas tragi*: molecular cloning of the enzyme gene and crystal structure of the enzyme" , J Mol Biol., 355:722-33 (2006).
Jefferson, et al., "GUS fusions: beta-glucuronidase as a sensitive and versatile gene fusion marker in higher plants" , EMBO J. 6: 3901-7 (1987).
Jendrossek and Handrick, "Microbial degradation of polyhydroxyalkanoates" , Annu Rev Microbiol 56: 403-432 (2002).
Jendrossek, "Polyhydroxyalkanoate granules are complex subcellular organelles (carbonosomes)." , J. Bacteriol. 191(10): 3195-3202 (2009).
Kourtz, et al., "Chemically inducible expression of the PHB biosynthetic pathway in *Arabidopsis*" , Transgenic Res, 16:759-69 (2007).
Lazo, et al. , "A DNA transformation-competent *Arabidopsis* genomic library in *Agrobacterium*" , Biotechnology, 9: 963-987 (1991).
Le, et al., "Global analysis of gene activity during *Arabidopsis* seed development and identification of seed-specific transcription factors" , PNAS, 107, 8063-70 (2010).
Lefebvre, et al,, "increased sedoheptulose-1,7-bisphosphatase activity in transgenic tobacco plants stimulates photosynthesis and growth from an early stage in development" , Plant Physiol., 138, 451-60 (2005).
Lössl, et al., "Inducible trans-activation of plastid transgenes: expression of the *R. eutropha* phb operon in transplastomic tobacco" , Plant Cell Physiol, 46:1462-71(2005).
Madison and Huisman, "Metabolic engineering of poly(3-hydroxyalkanoates): from DNA to plastic" , Microbiol Mol Biol Rev., 63:21-53 (1999).
McCormick, et al., "Leaf disc transformation of cultivated tomato (*L. esculentum*) using *Agrobacterium tumefaciens*" , Plant Cell Reports, 5:81-4 (1986).
Medberry, et al., "Intra-chromosomal rearrangements generated by Cre-lox site-specific recombination" , Nucleic Acids Res. 23: 485-90 (1995).
Miyagawa, et al, "Overexpression of a cyanobacterial fructose-1,6-1 sedoheptulose-1,7-bisphosphatase in tobacco enhances photosynthesis and growth" , Nat. Biotechnol., 19:965-9 (2001).
Nawrath, et al., "Targeting of the polyhydroxybutyrate biosynthetic pathway to the plastids of *Arabidopsis thaliana* results in high levels of polymer accumulation" , PNAS, 91:12760-4 (1994).
Pang, et al, "An improved green fluorescent protein gene as a vital marker in plants" , Plant Physiol. 112:893-900 (1996).
Peoples and Sinskey, "Poly-beta-hydroxybutyrate (PHB) biosynthesis in Alcaligenes eutrophus H16. Identification and characterization of the PHB polymerase gene (phbC)" , J. Biol. Chem. 264:15298-303 (1989).
Raines, "The Calvin cycle revisited" , Photosynthesis Research, 75:1-10 (2003).
Rowley, et al., "The upstream domain of soybean oleosin genes contains regulatory elements similar to those of legume storage proteins" , Biochim Biophys Acta, 1345:1-4 (1997).
Ruiz and Daniell, "Engineering cytoplasmic male sterility via the chloroplast genome by expression of [beta]-ketothiolase" , Plant Physio, 138:1232-46 (2005).
Saegusa, et al., "Cloning of an intracellular Poly[D(-)-3-Hydroxybutyrate]depolymerase gene from *Ralstonia eutropha* H16 and characterization of the gene product" , J. Bacteria 183, 94-100 (2001).
Slater, et al., "Metabolic engineering of *Arabidopsis* and *Brassica* for poly(3-hydroxybutyrate-co-3-hydroxyvalerate) copolymer production" , Nat. Biotechnol., 17:1011-6 (1999).
Snell and Peoples, "Polyhydroxyalkanoate polymers and their production in transgenic plants" , Metab. Eng. 4:29-40 (2002).
Staub and Maliga , "Accumulation of D1 polypeptide in tobacco plastids is regulated via the untranslated region of the psbA mRNA" , EMBO J., 12:601-6 (1993).
Sullivan, et al., "Isolation and characterization of a maize chlorophyll a/b binding protein gene that produces high levels of mRNA in the dark" , Mol. Gen. Genet., 215:431-40 (1989).
Suriyamongkol, et al., "Biotechnological approaches for the production of polyhydroxyalkanoates in microorganisms and plants—a review" , Biotechnol Adv,25:148-75 (2007).
Svab and Maliga, "High-frequency plastid transformation in tobacco by selection for a chimeric aadA gene" , PNAS, 90:913-7 (1993).
Svab, et al., "Stable transformation of plastids in higher plants" , PNAS, 87:8526-30 (1990).
Tamoi, et al., "Molecular characterization and resistance to hydrogen peroxide of two fructose-1,6-bisphosphatases from *Synechococcus* PCC 7942" , Archives of Biochemistry and Biophysics, 334, 27-36 (1996).
Tokiwa and Calabia, "Degradation of microbial polyesters" , Biotech. Lett , 26:1181-9 (2004).
Valentin,et al., "PHA production, from bacteria to plants" , Int. J. Biol. Macromol., 25 :303-6 (1999).
Van Beilen, et al., "Production of renewable polymers from crop plants" , Plant J, 54:684-701 (2008).
Verma, et al., "A simplified floral dip method for transformation of *Brassica napus* and *B. carinata*" , J Plant Biochem Biotech., 17:197-200 (2008).

* cited by examiner

FIG. 6

Alignment of FBPases in plasmids pMBXS407 and pMBXS408

```
FBPase from pMBXS407
          10        20        30        40        50        60        70
80
VEKTIGLEIIEVVEQAAIASARLMGKGEKNEADRVAVEAMRVRMNQVEMLGRIVIGEGERDEAPMLYIGEEVGIYRD
ADK
::::::::::::::::::::::::::::::::::::::::::::::::::::::::::::::::::::::::::::::
:::
VEKTIGLEIIEVVEQAAIASARLMGKGEKNEADRVAVEAMRVRMNQVEMLGRIVIGEGERDEAPMLYIGEEVGIYRD
ADK
          10        20        30        40        50        60        70
80
FBPase from pMBXS408

FBPase from pMBXS407
          90       100       110       120       130       140       150
160
RAGVPAGKLVEIDIAVDPCEGTNLCAYGQPGSMAVLAISEKGGLFAAPDFYMKKLAAPPAAKGKVDINKSATENLKI
LSE
::::::::::::::::::::::::::::::::::::::::::::::::::::::::::::::::::::::::::::::
:::::::
RAGVPAGKLVEIDIAVDPCEGTNLCAYGQPGSMAVLAISEKGGLFAAPDFYMKKLAAPPAAKGKETSIKSATENLKI
LSE
          90       100       110       120       130       140       150
160
FBPase from pMBXS408
```

FIG. 6 continued pg. 2

```
FBPase from pMBXS407
         170        180        190        200        210        220        230
240
CLDRAIDELVVVVMDRPRHKELIQEIRQAGARVRLISDGDVSAAISCGFAGTNTHALMGIGAAPEGVISAAAMRCLG
GHF
:::::::::::::::::::::::::::::::::::::::::::::::::::::::::::::::::::::::::::::
:::
CLDRAIDELVVVVMDRPRHKELIQEIRQAGARVRLISDGDVSAAISCGFAGTNTHALMGIGAAPEGVISAAAMRCLG
GHF
         170        180        190        200        210        220        230
240
FBPase from pMBXS408

FBPase from pMBXS407
         250        260        270        280        290        300        310
320
QGQLIYDPEVVKTGLIGESRESNIARLQEMGITDPDRVYDANELASGQEVLFAACGITPGLLMEGVRFFKGGARTQS
LVI
:::::::::::::::::::::::::::::::::::::::::::::::::::::::::::::::::::::::::::::
:::
QGQLIYDPEVVKTGLIGESRESNIARLQEMGITDPDRVYDANELASGQEVLFAACGITPGLLMEGVRFFKGGARTQS
LVI
         250        260        270        280        290        300        310
320
FBPase from pMBXS408
```

*FIG. 6 continued pg. 3*

```
FBPase from pMBXS407
          330       340       350
SSQSRTARFVDTVHMFDDVKTVSLR*  (SEQ ID NO: 10)
:::::::::::::::::::::::::
SSQSRTARFVDTVHMFDDVKTVSLPLIPDPKWRPER*  (SEQ ID NO: 11)
          330       340       350
FBPase from pMBXS408
```

GENERATION OF HIGH POLYHYDROXYBUTYRATE PRODUCING OILSEEDS

CROSS REFERENCE TO RELATED APPLICATIONS

This application is a filing under 35 U.S.C. §371 of PCT/US2010/048963 filed with the Patent Cooperation Treaty on Sep. 15, 2010, which claims priority to and benefit of U.S. Provisional Application No. 61/242,522, filed Sep. 15, 2009, all of which are herein incorporated in their entirety by reference.

REFERENCE TO SEQUENCE LISTING

The Sequence Listing submitted Mar. 13, 2012, as a text file named "MBX_078_ST25.txt," created on Sep. 15, 2010, and having a size of 244 Kilo bytes is hereby incorporated by reference.

FIELD OF THE INVENTION

The invention is generally related to the field of polymer production in transgenic plants. Methods for generating industrial oilseeds producing high levels of polyhydroxybutyrate (PHB) and industrial oilseeds producing high levels of PHB are described.

BACKGROUND OF THE INVENTION

Production of polyhydroxyalkanoates (PHAs), a family of naturally occurring renewable and biodegradable plastics, in crops has the potential of providing a renewable source of polymers, chemical intermediates and bio-energy from one crop if plant residues remaining after polymer isolation are converted to liquid fuels and/or energy. PHAs can provide an additional revenue stream that would make bioenergy crops more economically viable.

PHAs are a natural component of numerous organisms in multiple ecosystems and accumulate in a wide range of bacteria as a granular storage material when the microbes are faced with an unfavorable growth environment, such as a limitation in an essential nutrient (Madison et al., *Microbiol. Mol. Biol. Rev.,* 1999, 63, 21-53; Suriyamongkol et al., *Biotechnol Adv,* 2007, 25, 148-175). The monomer unit composition of these polymers is largely dictated by available carbon source as well as the native biochemical pathways present in the organism. Today PHAs are produced industrially from renewable resources in bacterial fermentations providing an alternative to plastics derived from fossil fuels. PHAs possess properties enabling their use in a variety of applications currently served by petroleum-based plastics and are capable of matching or exceeding the perfounance characteristics of fossil fuel derived plastics with a broad spectrum of properties that can be obtained by varying the monomer composition of homo- and co-polymers, or by manipulating properties such as molecular weight (Sudesh et al., *Prog. Polym. Sci.,* 2000, 25, 1503-1555; Sudesh et al., *CLEAN—Soil, Air, Water,* 2008, 36, 433-442).

Industrial production of PHAs in crop plants would provide a low cost, renewable source of plastics. Production of PHAs in plants has been an as yet unsolved goal for plant scientists and has previously been demonstrated in a number of crops unsuitable for industrial production or in industrially useful crops at levels to low to be commercially attractive [for review, see (Suriyamongkol et al., *Biotechnol Adv,* 2007, 25, 148-175); (van Beilen et al., *The Plant Journal,* 2008, 54, 684-701) and references within] including maize (Poirier et al., 2002, Polyhydroxyalkanoate production in transgenic plants, in Biopolymers, Vol 3a, Steinbuchel, A. (ed), Wiley-VHC Verlag GmbH, pgs 401-435), sugarcane (Purnell et al., *Plant Biotechnol. J.,* 2007, 5, 173-184), switchgrass (Somleva et al., *Plant Biotechnol J,* 2008, 6, 663-678), flax (Wrobel et al., *J. Biotechnol.,* 2004, 107, 41-54; Wrobel-Kwiatkowsk et al., *Biotechnol Prog,* 2007, 23, 269-277), cotton (John et al., *Proceedings of the National Academy of Sciences of the United States of America,* 1996, 93, 12768-12773), alfalfa (Small et al., *Crop Set.,* 2002, 42, 919-927), tobacco (Arai et al., *Plant Biotechnol.,* 2001, 18, 289-293; Bohmert et al., *Plant Physiol.,* 2002, 128, 1282-1290; Lossl et al., *Plant Cell Reports,* 2003, 21, 891-899; Lössl et al., *Plant Cell Physiol,* 2005, 46, 1462-1471), potato (Bohmert et al., *Plant Physiol.,* 2002, 128, 1282-1290), and oilseed rape (Valentin et al., *Int. J. Biol. Macromol.,* 1999, 25, 303-306; Slater et al., *Nat. Biotechnol.,* 1999, 17, 1011-1016.). Most of the efforts to produce PHAs in plants have focused on production of the homopolymer P3HB or the copolymer poly-3-hydroxybutyrate-co-3-hydroxyvalerate (P3HBV). While there have been some efforts to produce medium chain length PHAs in plants, these studies have yielded barely detectable levels of polymer (Romano et al., *Planta,* 2005, 220, 455-464; Mittendorf et al., *Proceedings of the National Academy of Sciences of the United States of America,* 1998, 95, 13397-13402; Poirier et al., *Plant Physiol.,* 1999, 121, 1359-1366; Matsumoto, *Journal of Polymers and the Environment,* 2006, 14, 369-374; Wang et al., *Chinese Science Bulletin,* 2005, 50, 1113-1120).

To date, the highest levels of polymer have been obtained when the homopolymer poly-3-hydroxybutyrate (P3HB or PHB) is produced in plastids (Suriyamongkol et al., *Biotechnol Adv,* 2007, 25, 148-175; van Beilen et al., *The Plant Journal,* 2008, 54, 684-701; Bohmert et al., *Molecular Biology and Biotechnology of Plant Organelles,* 2004, 559-585). This is likely due to the high flux of acetyl-CoA, the precursor for PHB in these organelles during fatty acid biosynthesis (Bohmert et al., *Molecular Biology and Biotechnology of Plant Organelles,* 2004, 559-585). Expression of three genes encoding β-ketothiolase, acetoacetyl CoA reductase, and PHA synthase, allows the conversion of acetyl-CoA within the plastid to PHB. Previous work has reported producing levels of PHB in *Brassica napus* up to a maximum of 7.7% of seed weight, a level too low for commercial production Therefore, it is an object of the invention to provide methods and compositions for producing transgenic oilseeds having commercially viable levels of polyhydroxyalkanoates in the seed, for example greater than 7%, 10%, 15%, or 19% polyhydroxyalkanoate or more of the total dry seed weight and capable of germinating.

SUMMARY OF THE INVENTION

Transgenic oilseed plants, plant material, plant cells, and genetic constructs for synthesis of polyhydroxyalkanoates ("PHA") are provided. In the preferred embodiment, the transgenic oilseed plants synthesize polyhydroxybutyrate ("PHB") in the seed. Host plants, plant tissue, and plant material have been engineered to express genes encoding enzymes in the biosynthetic pathway for PHB production such that polymer precursors in the plastid are polymerized to polymer. Genes utilized include phaA, phaB, phaC, all of which are known in the art. The genes can be introduced in the plant, plant tissue, or plant cell using conventional plant molecular biology techniques.

It has been discovered, using a different screening method to identify transgenic lines than those used in all other reported studies, that very high levels of PHB can be produced in the oilseed but that oilseeds with high levels of PHB fail to germinate or germinate but produce impaired seedlings which do not survive to produce viable fertile plants. The failure to produce viable progeny explains why previous researchers failed to demonstrate that commercial levels of PHB can be produced in transgenic oilseeds.

In one embodiment the transgenes encoding PHA biosynthesis are expressed in a seed specific manner such that the PHA accumulates in the seed. In this embodiment it is preferred that the level of PHA accumulated is greater than %, 8%, 9%, 10%, 11%, 12%, 13%. 14%, 15%, 16%, 17%, 18% and 19% of the dry weight of the seed. In another embodiment these transgenic oilseeds encode one or more additional transgenes to improve the germination efficiency of high PHA producing oilseeds where the level of PHA in the oilseed is greater than 8% by weight and where the seeds germinate to at least 10%, 20%, 40%, 60%, 80%, 90%, 100% of the level of seeds from the unmodified parental line or seeds with low levels of PHA.

These additional transgenes can encode siRNA for one or more of the genes encoding enzymes for producing PHA. These additional transgenes can encode one or more genes involved in the PHA degradation pathway. These additional transgenes can encode one or more enzymes involved in photosynthesis pathways. In a more preferred embodiment, these additional transgenes can be expressed under the control of an inducible regulatory element or promoter. In another embodiment, these additional transgenes can be placed under the control of a minimal promoter such that very low levels of expression are obtained. In another embodiment, these additional transgenes can be placed under the control of a germination specific promoter, such as the promoter from *Vigna mungo* sulphydryl-endopeptidase gene (SH-EP promoter; Akasofu et al., 1990 Nucleic Acids Research. 18, 1892). In another embodiment the transgenic oilseed may encode combinations of these additional transgenes, for example transgenes encoding siRNA plus transgenes encoding one of more enzymes involved in photosynthesis pathways. Other combinations of the additional transgenes or other transgenes and approaches to solving this previously unknown problem will be obvious to those skilled in the art.

Transgenic plants useful for the invention include dicots or monocots. Preferred host plants are oilseed plants, but are not limited to members of the Brassica family including *B. napus, B. rapa, B. carinata* and *B. juncea*; industrial oilseeds such as *Camelina sativa*, Crambe, Jatropha, castor; *Arabidopsis thaliana; Calendula, Cuphea*; maize; soybean; cottonseed; sunflower; palm; coconut; safflower; peanut; mustards including *Sinapis alba*; and tobacco.

Other embodiments provide plant material and plant parts of the transgenic plants including seeds, flowers, stems, and leaves. The oilseeds can be used for the extraction of PHA biopolymer or as a source of PHA biopolymer based chemical intermediates. The residual parts of the seed can be used as meal for animal feed or steam and power generation and a source of vegetable oil for industrial oelochemicals or biofuel.

BRIEF DESCRIPTION OF THE DRAWINGS

FIG. 6 is a protein sequence alignment of FBPase/SBPase genes in transformation vectors pMBXS407 and pMBXS408. Vector pMBXS407 contains a gene encoding a FBPase/SBPase with 100% homology to the FBPase/SBPase protein from *Synechococcus elongatus* PCC 7942 listed in accession CP000100. Transformation vector pMBXS408 contains a gene encoding a FBPase/SBPase with 100% homology to the FBPase/SBPase protein from *Synechococcus elongatus* PCC 7942 listed in accession D83512.

DETAILED DESCRIPTION OF THE INVENTION

Definitions

Figure 1:
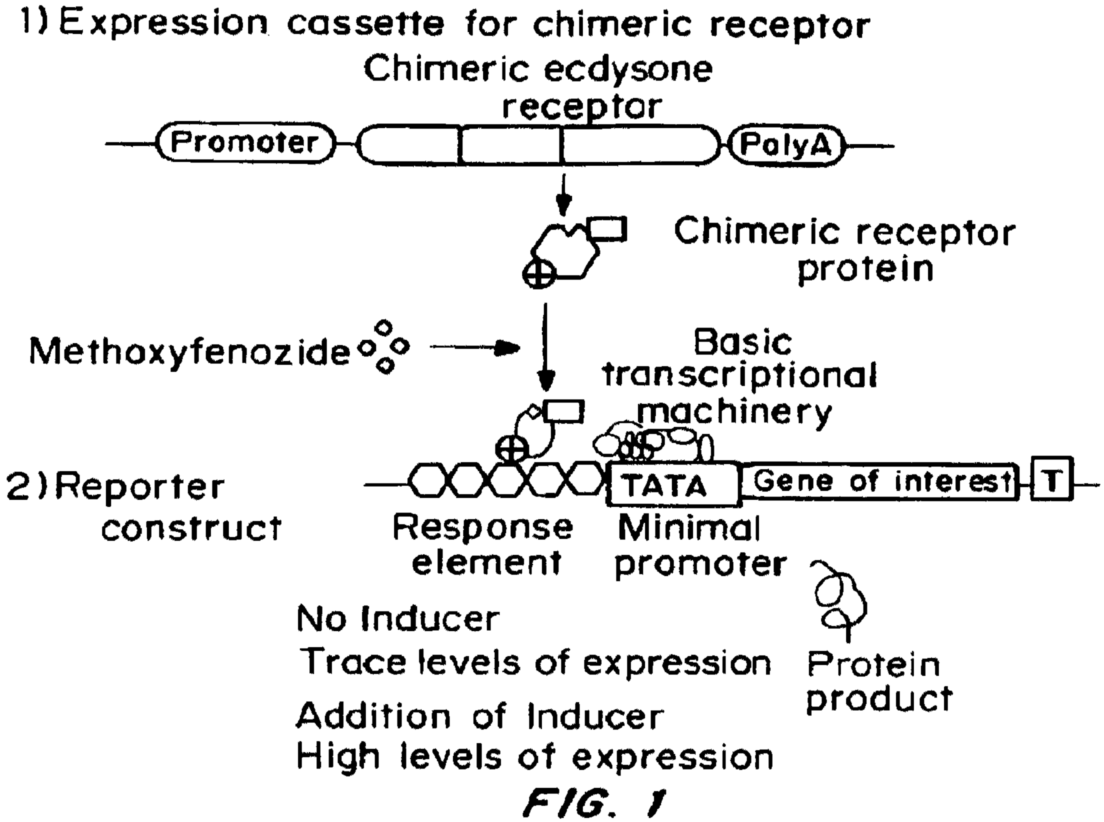
FIG. 1 is a schematic diagram describing an ecdysone inducible promoter system.

Unless otherwise indicated, the disclosure encompasses all conventional techniques of plant breeding, microbiology, cell biology and recombinant DNA, which are within the skill of the art. See, e.g., Sambrook and Russell, Molecular Cloning: A Laboratory Manual, 3rd edition (2001); Current Protocols In Molecular Biology [(F. M. Ausubel, et al. eds., (1987)]; Plant Breeding Principles and Prospects (Plant Breeding, Vol 1) M. D. Hayward, N. O. Bosemark, I. Romagosa; Chapman & Hall, (1993.); Coligan, Dunn, Ploegh, Speicher and Wingfeld, eds. (1995) Current Protocols in Protein Science (John Wiley & Sons, Inc.); the series Methods in Enzymology (Academic Press, Inc.): PCR 2: A Practical Approach (M. J. MacPherson, B. D. Hames and G. R. Taylor eds. (1995)].

Unless otherwise noted, technical terms are used according to conventional usage. Definitions of common terms in molecular biology may be found in Lewin, Genes VII, published by Oxford University Press, 2000; Kendrew et al. (eds.), The Encyclopedia of Molecular Biology, published by Wiley-Interscience, 1999; and Robert A. Meyers (ed.), Molecular Biology and Biotechnology, a Comprehensive Desk Reference, published by VCH Publishers, Inc., 1995; Ausubel et al. (1987) Current Protocols in Molecular Biology, Green Publishing; Sambrook and Russell. (2001) Molecular Cloning: A Laboratory Manual 3rd. edition.

A number of terms used herein are defined and clarified in the following section.

The term PHB refers to polyhydroxybutyrate and is used interchangeably with the term PHA which refers to polyhydroxyalkanoate.

The term PHB also encompasses copolymers of hydroxybutyrate with other hydroxyacid monomers.

The term “PHA copolymer” refers to a polymer composed of at least two different hydroxyalkanoic acid monomers.

The term “PHA homopolymer” refers to a polymer that is composed of a single hydroxyalkanoic acid monomer.

As used herein, a “vector” is a replicon, such as a plasmid, phage, or cosmid, into which another DNA segment may be inserted so as to bring about the replication of the inserted segment. The vectors can be expression vectors.

As used herein, an "expression vector" is a vector that includes one or more expression control sequences As used herein, an "expression control sequence" is a DNA sequence that controls and regulates the transcription and/or translation of another DNA sequence. Control sequences that are suitable for prokaryotes, for example, include a promoter, optionally an operator sequence, a ribosome binding site, and the like. Eukaryotic cells are known to utilize promoters, polyadenylation signals, and enhancers.

As used herein, "operably linked" means incorporated into a genetic construct so that expression control sequences effectively control expression of a coding sequence of interest.

As used herein, "transformed" and "transfected" encompass the introduction of a nucleic acid into a cell by a number of techniques known in the art.

"Plasmids" are designated by a lower case "p" preceded and/or followed by capital letters and/or numbers.

As used herein the term "heterologous" means from another host. The other host can be the same or different species.

The term "cell" refers to a membrane-bound biological unit capable of replication or division.

The term "construct" refers to a recombinant genetic molecule including one or more isolated polynucleotide sequences.

Genetic constructs used for transgene expression in a host organism comprise in the 5'-3' direction, a promoter sequence; a nucleic acid sequence encoding the desired transgene product; and a termination sequence. The open reading frame may be orientated in either a sense or anti-sense direction. The construct may also comprise selectable marker gene(s) and other regulatory elements for expression.

The term "plant" is used in it broadest sense. It includes, but is not limited to, any species of woody, ornamental or decorative, crop or cereal, fruit or vegetable plant, and photosynthetic green algae (e.g., *Chlamydomonas reinhardtii*). It also refers to a plurality of plant cells that are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture. The term "plant part" as used herein refers to a plant structure, a plant organ, or a plant tissue.

A non-naturally occurring plant refers to a plant that does not occur in nature without human intervention. Non-naturally occurring plants include transgenic plants and plants produced by non-transgenic means such as plant breeding.

The term "plant cell" refers to a structural and physiological unit of a plant, comprising a protoplast and a cell wall. The plant cell may be in form of an isolated single cell or a cultured cell, or as a part of higher organized unit such as, for example, a plant tissue, a plant organ, or a whole plant.

The term "plant cell culture" refers to cultures of plant units such as, for example, protoplasts, cell culture cells, cells in plant tissues, pollen, pollen tubes, ovules, embryo sacs, zygotes and embryos at various stages of development.

The term "plant material" refers to leaves, stems, roots, flowers or flower parts, fruits, pollen, egg cells, zygotes, seeds, cuttings, cell or tissue cultures, or any other part or product of a plant.

A "plant organ" refers to a distinct and visibly structured and differentiated part of a plant such as a root, stem, leaf, flower bud, or embryo.

"Plant tissue" refers to a group of plant cells organized into a structural and functional unit. Any tissue of a plant, whether in a plant or in culture, is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

"Seed germination" refers to growth of an embryonic plant contained within a seed resulting in the formation and emergence of a seedling.

"Cotyledon" refers to the embryonic first leaves of a seedling.

"Early plantlet development" refers to growth of the cotyledon containing seedling to form a plantlet.

II. Transgenic Plants

Transgenic plants have been developed that produce increased levels of biopolymers such as polyhydroxyalkanoates (PHAs) in seeds. Methods and constructs for engineering plants for seed specific production of PHA, in particular PHB, are described. One embodiment provides transgenic plants for the direct, large scale production of PHAs in crop plants or in energy crops where a plant by-product, such as oil, can be used for production of energy. Proof of concept studies for polyhydroxybutyrate (PHB) synthesis in canola (Valentin et al., *Int. J. Biol. Macromol.,* 1999, 25, 303-306; Houmiel et al., *Planta,* 1999, 209, 547-550; Slater et al., *Nat. Biotechnol.,* 1999, 17, 1011-1016.) has been reported. There have been instances where high level PHB production in plastids of plants has led to decreases in total plant growth (Bohmert et al., *Molecular Biology and Biotechnology of Plant Organelles,* 2004, 559-585; Bohmert et al., *Planta,* 2000, 211, 841-845) for unidentified reasons. There have been several studies that have attempted to alleviate this problem by inducible expression of enzymes (Bohmert et al., *Plant Physiol.,* 2002, 128, 1282-1290; Lössl et al., *Plant Cell Physiol,* 2005, 46, 1462-1471; Kourtz et al., *Transgenic Res,* 2007, 16, 759-769).

Transgenic oilseeds comprising at least about 8% dry weight PHA are provided. One embodiment provides transgenic oilseeds having at least 10% PHA dry weight and which are impaired in germination and plant survival. In other embodiments we provide transgenic oilseeds with high levels of PHA, greater than 8% of the weight of the seed and with improved seed germination and survival producing fertile plants. In this case at least about 5%, 10%, 15%, 20%, 50%, 75% or 100% of the transgenic oilseeds have the ability to germinate and survive.

A. Genetic Constructs for Transformation

Suitable genetic constructs include expression cassettes for enzymes for production of polyhydroxyalkanoates, in particular from the polyhydroxybutyrate biosynthetic pathway. In one embodiment, the construct contains operatively linked in the 5' to 3' direction, a seed specific promoter that directs transcription of a nucleic acid sequence in the nucleus; a nucleic acid sequence encoding one of the PHB biosynthetic enzymes; and a 3' polyadenylation signal that increases levels of expression of transgenes. In one embodiment, enzymes for formation of polymer precursors are targeted to the plastid using appropriate plastid-targeting signals. In another embodiment, a cassette containing DNA sequences homologous to a portion of one of the transgenes and designed to promote RNA interference (RNAi) is included. In an alternative embodiment, this cassette for RNAi contains an intron between an inverted repeat. In another embodiment, a cassette with homology to one of the PHB pathway genes is designed to produce antisense RNA thus attenuating the level of translation into protein. In still another embodiment, the PHA pathway is expressed directly from the plastid genome using appropriate plastidial promoters and regulatory sequences.

In one embodiment, the construct contains operatively linked in the 5' to 3' direction, a promoter that directs transcription of a nucleic acid sequence in the nucleus; a nucleic acid sequence encoding genes for PHA degradation to enable seed germination; and a 3' polyadenylation signal that increases levels of expression of transgenes. In one embodiment, enzymes for degradation of polymer are targeted to the plastid using appropriate plastid-targeting signals. In another embodiment, enzymes for polymer degradation include a depolymerase and/or dehydrogenase.

In one embodiment, the construct contains operatively linked in the 5' to 3' direction, a promoter that directs transcription of a nucleic acid sequence in the nucleus; a nucleic acid sequence encoding a gene to capable of increasing photosynthesis in a plant; and a 3' polyadenylation signal that increases levels of expression of transgenes. In one embodiment, genes to increase photosynthesis include enzymes capable of increasing carbon flow through the Calvin Cycle. In one embodiment, enzymes for increasing photosynthesis are targeted to the plastid using appropriate plastid-targeting signals.

DNA constructs useful in the methods described herein include transformation vectors capable of introducing transgenes into plants. As used herein, "transgenic" refers to an organism in which a nucleic acid fragment containing a heterologous nucleotide sequence has been introduced. The transgenes in the transgenic organism are preferably stable and inheritable. The heterologous nucleic acid fragment may or may not be integrated into the host genome.

Several plant transformation vector options are available, including those described in "Gene Transfer to Plants" (Potrykus, et al., eds.) Springer-Verlag Berlin Heidelberg New York (1995); "Transgenic Plants: A Production System for Industrial and Pharmaceutical Proteins" (Owen, et al., eds.) John Wiley & Sons Ltd. England (1996); and "Methods in Plant Molecular Biology: A Laboratory Course Manual" (Maliga, et al. eds.) Cold Spring Laboratory Press, New York (1995). Plant transformation vectors generally include one or more coding sequences of interest under the transcriptional control of 5' and 3' regulatory sequences, including a promoter, a transcription termination and/or polyadenylation signal, and a selectable or screenable marker gene. For the expression of two or more polypeptides from a single transcript, additional RNA processing signals and ribozyme sequences can be engineered into the construct (U.S. Pat. No. 5,519,164). This approach has the advantage of locating multiple transgenes in a single locus, which is advantageous in subsequent plant breeding efforts.

Engineered minichromosomes can also be used to express one or more genes in plant cells. Cloned telomeric repeats introduced into cells may truncate the distal portion of a chromosome by the formation of a new telomere at the integration site. Using this method, a vector for gene transfer can be prepared by trimming off the arms of a natural plant chromosome and adding an insertion site for large inserts (Yu et al., Proc Natl Acad Sci USA, 2006, 103, 17331-6; Yu et al., *Proc Natl Acad Sci USA,* 2007, 104, 8924-9). The utility of engineered minichromosome platforms has been shown using Cre/lox and FRT/FLP site-specific recombination systems on a maize minichromosome where the ability to undergo recombination was demonstrated (Yu et al., *Proc Natl Acad Sci USA,* 2006, 103, 17331-6; Yu et al., *Proc Natl Acad Sci USA,* 2007, 104, 8924-9). Such technologies could be applied to minichromosomes, for example, to add genes to an engineered plant. Site specific recombination systems have also been demonstrated to be valuable tools for marker gene removal (Kerbach, S. et al., *Theor Appl Genet,* 2005, 111, 1608-1616), gene targeting (Chawla, R. et al., *Plant Biotechnol J,* 2006, 4, 209-218; Choi, S. et al., *Nucleic Acids Res,* 2000, 28, E19; Srivastava, V, & Ow, D W, *Plant Mol Biol,* 2001, 46, 561-566; Lyznik, L A, et al., *Nucleic Acids Res,* 1993, 21, 969-975), and gene conversion (Djukanovic, V, et al., *Plant Biotechnol J,* 2006, 4, 345-357).

An alternative approach to chromosome engineering in plants involves in vivo assembly of autonomous plant minichromosomes (Carlson et al., *PLoS Genet,* 2007, 3, 1965-74). Plant cells can be transformed with centromeric sequences and screened for plants that have assembled autonomous chromosomes de novo. Useful constructs combine a selectable marker gene with genomic DNA fragments containing centromeric satellite and retroelement sequences and/or other repeats.

Another approach is Engineered Trait Loci ("ETL") technology (U.S. Pat. No. 6,077,697 to Hadlaczky et al.; US Patent Application 2006/0143732). This system targets DNA to a heterochromatic region of plant chromosomes, such as the pericentric heterochromatin, in the short arm of acrocentric chromosomes. Targeting sequences may include ribosomal DNA (rDNA) or lambda phage DNA. The perieentric rDNA region supports stable insertion, low recombination, and high levels of gene expression. This technology is also useful for stacking of multiple traits in a plant (US Patent Application 2006/0246586, 2010/0186117 and PCT WO 2010/037209).

Zinc-finger nucleases (ZFNs) are also useful in that they allow double strand DNA cleavage at specific sites in plant chromosomes such that targeted gene insertion or deletion can be performed (Shukla et al., *Nature*, 2009; Townsend et al., *Nature*, 2009).

For direct expression of transgenes from the plastid genome, a vector to transform the plant plastid chromosome by homologous recombination (as described in U.S. Pat. No. 5,545,818 to McBride et al.) is used in which case it is possible to take advantage of the prokaryotic nature of the plastid genome and insert a number of transgenes as an operon. WO 2010/061186 describes an alternative method for introducing genes into the plastid chromosome using an adapted endogenous cellular process for the transfer of RNAs from the cytoplasm to the plastid where they are incorporated by homologous recombination.

A transgene may be constructed to encode a multifunctional enzyme through gene fusion techniques in which the coding sequences of different genes are fused with or without linker sequences to obtain a single gene encoding a single protein with the activities of the individual genes. Transgenes encoding a bifunctional protein containing thiolase and reductase activities (Kourtz, L., K. et al. (2005), Plant Biotechnol. 3: 435-447) and a trifunctional protein having each of the three enzyme activities required for PHB expression in plants (Mullaney and Rehm (2010), Journal of Biotechnology 147: 31-36) have been described. Such synthetic fusion gene/enzyme combinations can be further optimized using molecular evolution technologies.

A transgene may be constructed to encode a series of enzyme activities separated by intein sequences such that on expression, two or more enzyme activities are expressed from a single promoter as described by Snell in U.S. Pat. No. 7,026,526 to Metabolix, Inc.

1. Genes involved in Polyhydroxyalkanoate Synthesis

In a preferred embodiment, the products of the transgenes are enzymes and other factors required for production of a biopolymer, such as a polyhydroxyalkanoate (PHA).

For PHA production, transgenes encode enzymes such as beta-ketothiolase, acetoacetyl-CoA reductase, PHB ("short chain") synthase, PHA ("long chain") synthase, threonine dehydratase, dehydratases such as 3-OH acyl ACP, isomerases such as A 3-cis, A 2-trans isomerase, propionyl-CoA synthetase, hydroxyacyl-CoA synthetase, hydroxyacyl-CoA transferase, R-3-hydroxyacyl-ACP:CoA transferase, thioesterase, fatty acid synthesis enzymes and fatty acid beta-oxidation enzymes. Useful genes are well known in the art, and are disclosed for example by Snell and Peoples *Metab. Eng.* 4: 29-40 (2002); Bohmert et. al in *Molecular Biology and Biotechnology of Plant Organelles*. H. Daniell, C. D. Chase Eds., Kluwer Academic Publishers, Netherlands, 2004, pp. 559-585; (Suriyamongkol et al., *Biotechnol Adv,* 2007, 25, 148-175; van Beilen et al., *The Plant Journal,* 2008, 54, 684-701).

PHA Svnthases

Examples of PHA synthases include a synthase with medium chain length substrate specificity, such as phaC1 from *Pseudomonas oleovorans* (WO 91/000917; Huisman, et al. *J. Biol. Chem.* 266, 2191-2198 (1991)) or *Pseudomonas aeruginosa* (Timm, A. & Steinbuchel, A. *Eur. J. Biochem.* 209: 15-30 (1992)), the synthase from *Alcaligenes eutrophus* with short chain length specificity (Peoples, O. P. & Sinskey, A. J. *J. Biol. Chem.* 264:15298-15303 (1989)), or a two subunit synthase such as the synthase from *Thiocapsa pfennigii* encoded by phaE and phaC (U.S. Pat. No. 6,011,144). Other useful PHA synthase genes have been isolated from, for example, *Alcaligenes* latus (Accession ALU47026), *Burkholderia* sp. (Accession AF153086), *Aeromonas caviae* (Fukui & Doi, *J. Bacteriol.* 179: 4821-30 (1997)), *Acinetobacter* sp.
strain RA3849 (Accession L37761), *Rhodospirillum rubrum* (U.S. Pat. No. 5,849,894), *Rhodococcus ruber* (Pieper & Steinbuechel, *FEMS Microbiol. Lett.* 96(1): 73-80 (1992)), *Nocardia corallina* (Hall et. al., *Can. J. Microbiol.* 44: 687-91 (1998)), *Arthrospira* sp. PCC 8005 (Accessions ZP_07166315 and ZP_07166316), *Cyanothece* sp. PCC 7425 (Accessions ACL46371 and ACL46370) and *Synechocystis* sp. PCC6803 (Accession BAA17430; Hein et al. (1998), Archives of Microbiology 170: 162-170).

PHA synthases with broad substrate specificity useful for producing copolymers of 3-hydroxybutyrate and longer chain length (from 6 to 14 carbon atoms) hydroxyacids have also been isolated from *Pseudomonas* sp. A33 (Appl. Microbiol. Biotechnol. 42: 901-909 (1995)) and *Pseudomonas* sp. 61-3 (Accession AB014757; Kato, et al. Appl. Microbiol. Biotechnol. 45: 363-370 (1996)).

A range of PHA synthase genes and genes encoding additional metabolic steps useful in PHA biosynthesis are described by Madison and Huisman. *Microbiology and Molecular biology Reviews* 63:21-53 (1999)) and Suriyamongkol et al. (Suriyamongkol et al., *Biotechnol Adv,* 2007, 25, 148-175).

Hydratase and Dehydrogenase

An alpha subunit of beta-oxidation multienzyme complex pertains to a multifunctional enzyme that minimally possesses hydratase and dehydrogenase activities. The subunit may also possess epimerase and Δ3-cis, Δ2-trans isomerase activities. Examples of alpha subunits of the beta-oxidation multienzyme complex are FadB from *E. coli* (DiRusso, C. C. J. Bacterial. 1990, 172, 6459-6468), FaoA from *Pseudomonas fragi* (Sato, S., Hayashi, et al. J. Biochem. 1992, 111, 8-15), and the *E. coli* open reading frame f714 that contains homology to multifunctional α subunits of the β-oxidation-complex (Genbank Accession #1788682). A β subunit of the β-oxidationcomplex refers to a polypeptide capable of forming a multifunctional enzyme complex with its partner α subunit. The β subunit possesses thiolase activity. Examples of β subunits are FadA from *E. coli* (DiRusso, C. C. *J. Bacterial.* 172: 6459-6468 (1990)), FaoB from *Pseudomonas fragi* (Sato, S., Hayashi, M., Imamura, S., Ozeki, Y., Kawaguchi, A. *J. Biochem.* 111: 8-15 (1992)), and the *E. coli* open reading frame f436 that contains homology to α subunits of the β-oxidation complex (Genbank Accession #AE000322; gene b2342).

Reductases

The transgene can encode a reductase. A reductase refers to an enzyme that can reduce β-ketoacyl CoAs to R-3-OH-acyl CoAs, such as the NADH dependent reductase from *Chromatium vinosum* (Liebergesell, M., & Steinbuchel, A. *Eur. J. Biochem.* 209: 135-150 (1992)), the NADPH dependent reductase from *Alcaligenes eutrophus* (Accession J04987, Peoples, O. P. & Sinskey, A. J. *J. Biol. Chem.* 264: 15293-15297 (1989))), the NADPH reductase from *Zoogloea ramigera* (Accession P23238; Peoples, O. P. & Sinskey, A. J. Molecular Microbiology 3: 349-357 (1989)) or the NADPH reductase from *Bacillus megaterium* (U.S. Pat. No. 6,835,820), *Alcaligenes latus* (Accession ALU47026), *Rhizobium meliloti* (Accession RMU17226), *Paracoccus denitrificans* (Accession D49362), *Burkholderia* sp. (Accession AF153086), *Pseudomonas* sp. strain 61-3 (Accession AB014757), *Acinetobacter* sp. strain RA3849 (Accession L37761), *P. denitrificans*, (Accession P50204), and *Synechocystis* sp. Strain PCC6803 (Taroncher-Oldenburg et al., (2000), Appl. Environ. Microbiol. 66: 4440-4448).

Thiolases

The transgene can encode a thiolase. A beta-ketothiolase refers to an enzyme that can catalyze the conversion of acetyl CoA and an acyl CoA to a β-ketoacyl CoA, a reaction that is reversible. An example of such thiolases are PhaA from *Alcaligenes eutropus* (Accession J04987, Peoples, O. P. & Sinskey, A. J. J. Biol. Chem. 264: 15293-15297 (1989)), BktB from *Alcaligenes eutrophus* (Slater et al. *J Bacteriol.* 180(8): 1979-87 (1998)), and thiolases from the following *Rhizobium meliloti* (Accession RMU17226), *Z. ramigera* (Accession P07097), *Paracoccus denitrificans* (Accession D49362), *Burkholderia* sp. (Accession AF153086), *Alcaligenes latus* (Accession ALU47026), *Allochromatium vinosum* (Accession P45369), *Thiocystis violacea* (Accession P45363); *Pseudomonas* sp. strain 61-3 (Accession AB014757), *Acinetobacter* sp. strain RA3849 (Accession L37761) and *Synechocystis* sp. Strain PCC6803 (Taroncher-Oldenburg et al., (2000), Appl. Environ. Microbiol. 66: 4440-4448).

Oxidases

An acyl CoA oxidase refers to an enzyme capable of converting saturated acyl CoAs to Δ2 unsaturated acyl CoAs. Examples of acyl CoA oxidases are PDX1 from *Saccharomyces cerevisiae* (Dmochowska, et al. Gene, 1990, 88, 247-252) and ACX1 from *Arabidopsis thaliana* (Genbank Accession #AF057044).

Catalases

The transgene can also encode a catalase. A catalase refers to an enzyme capable of converting hydrogen peroxide to hydrogen and oxygen. Examples of catalases are KatB from *Pseudomonas aeruginosa* (Brown, et al. *J. Bacterial.* 177:

6536-6544 (1995)) and KatG from *E. coli* (Triggs-Raine, B. L. & Loewen, P. C. *Gene* 52: 121-128 (1987)).

2. siRNA

The disclosed constructs and transgenic plants may also produce small inhibitory RNA molecules (siRNA) that can be single stranded or double stranded RNA molecules generally less than 200 nucleotides in length. Such molecules are generally less than 100 nucleotides and usually vary from 10 to 100 nucleotides in length. In a preferred format, siRNA molecules have 11, 12, 13, 14, 15, 16, 17, 18, 19, 20, 21, 22, 23, 24, 25, 26, 27, 28, 29 or 30 nucleotides and bind to and inhibit translation of mRNA encoding one or more of the genes involved in production of polyhydroxyalkanoates discussed above. The term "siRNA" means a small interfering RNA that is a short-length, preferably double-stranded RNA that is not toxic. Generally, there is no particular limitation in the length of siRNA as long as it does not show toxicity. "siRNAs" can be, for example, 15 to 49 bp, preferably 15 to 35 bp, and more preferably 21 to 30 bp long. Alternatively, the double-stranded RNA portion of a final transcription product of siRNA to be expressed can be, for example, 15 to 49 bp, preferably 15 to 35 bp, and more preferably 21 to 30 bp long. The double-stranded RNA portions of siRNAs in which two RNA strands pair up are not limited to the completely paired ones, and may contain nonpairing portions due to mismatch (the corresponding nucleotides are not complementary), bulge (lacking in the corresponding complementary nucleotide on one strand), and the like. Nonpairing portions can be contained to the extent that they do not interfere with siRNA formation. The "bulge" used herein preferably comprise 1 to 2 nonpairing nucleotides, and the double-stranded RNA region of siRNAs in which two RNA strands pair up contains preferably 1 to 7, more preferably 1 to 5 bulges. In addition, the "mismatch" used herein is contained in the double-stranded RNA region of siRNAs in which two RNA strands pair up, preferably 1 to 7, more preferably 1 to 5, in number. In a preferable mismatch, one of the nucleotides is guanine, and the other is uracil. Such a mismatch is due to a mutation from C to T, G to A, or mixtures thereof in DNA coding for sense RNA, but not particularly limited to them. Furthermore, the double-stranded RNA region of siRNAs in which two RNA strands pair up may contain both bulge and mismatched, which sum up to, preferably 1 to 7, more preferably 1 to 5 in number. The terminal structure of siRNA may be either blunt or cohesive (overhanging) as long as siRNA can silence, reduce, or inhibit the target gene expression due to its RNAi effect. The cohesive (overhanging) end structure is not limited only to the 3' overhang, and the 5' overhanging structure may be included as long as it is capable of inducing the RNAi effect. In addition, the number of overhanging nucleotide is not limited to the already reported 2 or 3, but can be any numbers as long as the overhang is capable of inducing the RNAi effect. For example, the overhang consists of 1 to 8, preferably 2 to 4 nucleotides. Herein, the total length of siRNA having cohesive end structure is expressed as the sum of the length of the paired double-stranded portion and that of a pair comprising overhanging single-strands at both ends. For example, in the case of 19 bp double-stranded RNA portion with 4 nucleotide overhangs at both ends, the total length is expressed as 23 bp. Furthermore, since this overhanging sequence has low specificity to a target gene, it is not necessarily complementary (antisense) or identical (sense) to the target gene sequence. Furthermore, as long as siRNA is able to maintain its gene silencing effect on the target gene, siRNA may contain a low molecular weight RNA (which may be a natural RNA molecule such as tRNA, rRNA or viral RNA, or an artificial RNA molecule), for example, in the overhanging portion at its one end.

In addition, the terminal structure of the "siRNA" is not necessarily the cut off structure at both ends as described above, and may have a stem-loop structure in which ends of one side of double-stranded RNA are connected by a linker RNA. The length of the double-stranded RNA region (stem-loop portion) can be, for example, 15 to 49 bp, preferably 15 to 35 bp, and more preferably 21 to 30 bp long. Alternatively, the length of the double-stranded RNA region that is a final transcription product of siRNAs to be expressed is, for example, 15 to 49 bp, preferably 15 to 35 bp, and more preferably 21 to 30 bp long. Furthermore, there is no particular limitation in the length of the linker as long as it has a length so as not to hinder the pairing of the stem portion. For example, for stable pairing of the stem portion and suppression of the recombination between DNAs coding for the portion, the linker portion may have a clover-leaf tRNA structure. Even though the linker has a length that hinders pairing of the stem portion, it is possible, for example, to construct the linker portion to include introns so that the introns are excised during processing of precursor RNA into mature RNA, thereby allowing pairing of the stem portion. In the case of a stem-loop siRNA, either end (head or tail) of RNA with no loop structure may have a low molecular weight RNA. As described above, this low molecular weight RNA may be a natural RNA molecule such as tRNA, rRNA or viral RNA, or an artificial RNA molecule.

The design of the siRNA molecules can be achieved using conventional software. Because the nucleotide sequences of all of the genes involved in PHA production are known, one of skill in the art could input this sequence data into the siRNA software to design specific siRNA molecules that can be expressed by the transgenic plant to inhibit expression of one or more transgenes involved in PHA production.

3. PHB Degradation Pathway enzymes

The disclosed constructs may contain a transgene expressing a PHA depolymerase. There are two kinds of depolymerases, one that is used by micro-organisms to degrade polymer intracellularly (intracellular depolymerases, and another that is secreted from the micro-organism to degrade extracellular polymer (extracellular depolymerases). There are also depolymerases with specificity for short chain length polymers such as PHS (EC 3.1.1.75) and depolymerases with specificity for medium chain length polymers (EC 3.1.1.76). Depolymerases suitable for this invention include but are not limited to the intracellular depolymerase PhaZ3 from *Cupriavidus necator* (formerly known as *Ralstonia eutropha*) (Accession AAP74581), the intracellular depolymerase PhaZ2 from *Cupriavidus necator* (Accession AAP74580), the intracellular depolymerase PhaZ1 from *Ralstonia eutropha* (Accession AB017612) (Saegusa, H., M. Shiraki, et al., 2001, J. Bacteriol. 183: 94-100; York, G. M. et al., 2003, J. Bacteriol. 185: 3788-3794), the extracellular depolymerase from *Rhodospirillum rubrum* (Accession AAL30107), and the extracellular depolymerase from *Ralstonia picketti* (Accession J04223). The degradation of PHAs as well as references for suitable depolymerases are reviewed in Tokiwa & Calabia (Tokiwa and Calabia, (2004), Biotechnology Letters 26: 1181-1189), Jeddrossek (Jendrossek, D. (2009), J. Bacteriol. 191(10): 3195-3202), and Jendrossek and Handrick (Jendrossek and Handrick (2002). Annu Rev Microbiol 56: 403-432) which are herein incorporated by reference in their entirety.

Figure 3:
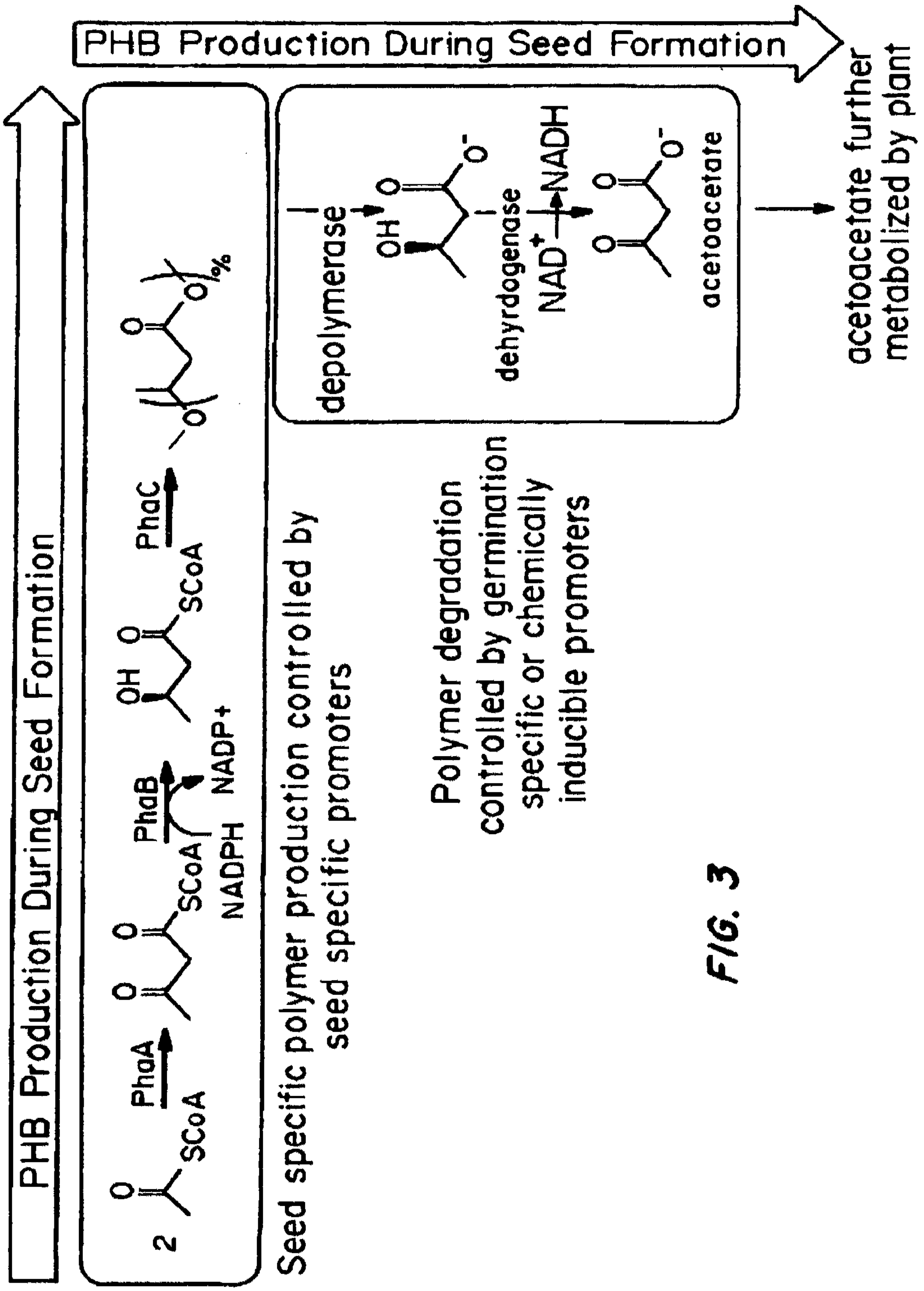
FIG. 3 is a schematic diagram describing a strategy for using a polymer degradation pathway to enable seed germination.

The disclosed constructs may also contain a transgene encoding a 3-hydroxybutyrate dehydrogenase (EC 1.1.1.30). This enzyme catalyzes the conversion of 3-hydroxybutrate to acetoacetate (FIG. 3). Suitable 3-hydroxybutrate dehydrogenases include but are not limited to the D(−)-3-hydroxybutyrate dehydrogenase (hbdh) from *Pseudomonas fragi* (Accession AB183516), *Bordetella pertussis* (Accession BX640418), *Ralstonia eutropha* (Accession AF145230), *Pseudomonas aeruginosa* (Accession AE004626), *Azospirillum brasilense* (Accession AF355575), *Caulobacter crescentus* (Accession AE005999), *Brucella melitensis* (Accession AE009469), and *Rhodobacter* (Accession AF037323).

4. Additional Enzymes to Enhance Photosynthesis and/or Carbon Flux

The disclosed constructs may also contain expression cassettes for one or more transgenes encoding enzymes capable of increasing photosynthesis, increasing carbon flow through the Calvin cycle in photosynthesis, or increasing regeneration of ribulose 1,5-bisphosphate, the acceptor molecule in the Calvin cycle that upon fixation of $CO_2$, is converted to two molecules of 3-phosphoglycerate.

Candidate enzymes include but are not limited to sedoheptulose 1,7-bisphosphatase (SBPase, EC 3.1.3.37), fructose 1,6-bisphosphatase (FBPase, EC 3.1.3.11), a bi-functional enzyme encoding both SBPase and FBPase activities, transketolase (EC 2.2.1.1), and aldolase (EC 4.1.2.13). SBPase, transketolase, and aldolase activities have been shown to have an impact on the control of carbon fixed by the Calvin cycle (Raines, 2003*, Photosynthesis Research,* 75, 1-10) which could be attributed to an increase in ribulose 1,5-bisphosphate regenerative capacity.

Bifunctional enzymes that contain both FBPase and SBPase activities have been reported from for example *Ralstonia eutropha* H16 (Accession number AAA69974), *Synechococcus elongatus* PCC 7942 (Accession numbers D83512 and CP000100), *Synechococcus* sp. WH 7805 (Accession number ZP_01124026), *Butyrivibrio crossotus* DSM 2876 (Accession number EFF67670), *Rothia mucilaginosa* DY-18 (Accession number YP_003363264), *Thiobacillus denitrificans* ATCC 25259 (Accession number AAZ98530), *Methylacidiphilum infernorum* V4 (Accession number ACD83413), *Nitrosomonas europaea* ATCC 19718 (Accession number CAD84432), *Vibrio vulnificus* CMCP6 (Accession number AA009802), and *Methanohalophilus mahii* DSM 5219 (Accession number YP_003542799).

The FBPase/SBPase gene from *Synechococcus elongatus* PCC 7942 has previously been expressed in tobacco and enhanced both photosynthesis and plant growth (Miyagawa, 2001*, Nat. Biotechnol.,* 19, 965-969). Expression of an *Arabidopsis* SBPase cDNA in tobacco also has resulted in greater biomass and increased photosynthetic capacity (Raines, 2003*, Photosynthesis Research,* 75, 1-10; Lefebvre et al., 2005*, Plant Physiol.* 138, 451-460).

Enzymes possessing SBPase activity that could be used to increase the flow of carbon within the Calvin cycle include for example the sedoheptulose-1,7-bisphosphatase from *Zea mays* (Accession NP_001148402), the sedoheptulose-1,7-bisphosphatase from *Arabidopsis thaliana* (Accession AAB33001), or the sedoheptulose-1,7-bisphosphatase from *Triticum aestivum* (Accession P46285).

Enzymes possessing FBPase that could be used to increase the flow of carbon within the Calvin cycle include for example the protein encoded by the fbpI gene from *Synechococcus elongatus* PCC 6301 (Accession number AP008231.1), a D-fructose 1,6-bisphosphatase from *Synechococcus elongatus* PCC 7942 (Accession number CP000100), the gene encoding fructose-1,6-bisphosphatase from *Zea mays* (Accession NP_001147459), the gene encoding fructose-1,6-bisphosphatase from Saccharum hybrid cultivar 1-165-7052 (Accession CAA61409) and the fructose-1,6-bisphosphatase from *Pisum sativum* (Accession AAD10213).

Enzymes possessing transketolase activity that could be used to increase the flow of carbon within the Calvin cycle include for example the transketolase from Cyanobacterium UCYN-A (Accession YP_003421778), the transketolase from *Spinacia* oleracea (Accession AAD 10219), the transketolase from Rhodbacter capsulatus SB 1003 (Accession AAC32307), and the transketolase from *Esherichia coli* K-12 MG1655 (Accession AAA69102).

Enzymes possessing adolase activity that could be used to increase the flow of carbon within the Calvin cycle include for example the aldolase from *Synechococcus* sp. CC9902 (ACCESSION YP_378043) the ketose-bisphosphate aldolase from *Crocosphaera watsonii* WH 8501 (ACCESSION EAM50168), the fructose-bisphosphate aldolase 1 from *Rhodobacter sphaeroides* (Accession number P27995), and the fructose-1,6-/sedoheptulose-1,7-bisphosphate aldolase from Nitrobacter vulgaris (Accession P37102).

Co-expression of RUBISCO with one or more of the above enzymes could further increase the rate of photosynthesis.

5. Promoters

Plant promoters can be selected to control the expression of the transgene in different plant tissues or organelles for all of which methods are known to those skilled in the art (Gasser & Fraley, *Science* 244:1293-99 (1989)). In one embodiment, promoters are selected from those of eukaryotic or synthetic origin that are known to yield high levels of expression in plant and algae cytosol. In another embodiment, promoters are selected from those of plant or prokaryotic origin that are known to yield high expression in plastids. In certain embodiments the promoters are inducible. Inducible plant promoters are known in the art.

Suitable constitutive promoters for nuclear-encoded expression include, for example, the core promoter of the Rsyn7 promoter and other constitutive promoters disclosed in U.S. Pat. No. 6,072,050; the core CAMV 35S promoter, (Odell et al. (1985) *Nature* 313:810-812); rice actin (McElroy et al. (1990) *Plant Cell* 2:163471); ubiquitin (Christensen et al. (1989) *Plant Mol. Biol.* 12:619-632 and Christensen et al. (1992) *Plant Mot Biol.* 18:675-689); pEMU (Last et al. (1991) *Theor. Appl. Genet.* 81:581-588); MAS (Velten et al. (1984) *EMBO J.* 3:2723-2730); and ALS promoter (U.S. Pat. No. 5,659,026). Other constitutive promoters include, for example, U.S. Pat. Nos. 5,608,149; 5,608,144; 5,604,121; 5,569,597; 5,466,785; 5,399,680; 5,268,463; 5,608,142.

"Tissue-preferred" promoters can be used to target a gene expression within a particular tissue such as seed, leaf or root tissue. Tissue-preferred promoters include Yamamoto et al. (1997) *Plant J.* 12(2)255-265; Kawamata et al. (1997) *Plant Cell Physiol.* 38(7):792-803; Hansen et al (1997) *Mol. Gen. Genet.* 254(3):337-343; Russell et al. (1997) *Transgenic Res.* 6(2):157-168; Rinehart et al. (1996) *Plant Physiol.* 112(3): 1331-1341; Van Camp et al (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108. Such seed-preferred promoters include, but are not limited to, Cim1 (cytokinin-induced message); cZ19B1 (maize 19 kDa zein); milps (myo-inositol-1-phosphate synthase); and ce1A (cellulose synthase). Gama-zein is a preferred endosperm-specific promoter. Glob-1 is a preferred embryo-specific promoter. For dicots, seed-specific promoters include, but are not limited to, bean β-phaseolin, napin β-conglycinin, soybean lectin, cruciferin, oleosin, the *Lesquerella* hydroxylase promoter, and the like. For monocots, seed-specific promoters include, but are not limited to, maize 15 kDa zein, 22 kDa zein, 27 kDa zein, g-zein, waxy, shrunken 1, shrunken 2, globulin 1, etc. Additional seed specific promoters useful for practicing this invention are described in the Examples disclosed herein.

Leaf-specific promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and may be selected from the many available from the literature or isolated de novo from various compatible species. See, for example, Hire et al. (1992) *Plant Mol. Biol.* 20(2): 207-218 (soybean root-specific glutamine synthetase gene); Keller and Baumgartner (1991) Plant Cell 3(10):1051-1061 (root-specific control element in the GRP 1.8 gene of French bean); Sanger et al. (1990) Plant Mol. Biol. 14(3):433-443 (root-specific promoter of the mannopine synthase (MAS) gene of *Agrobacterium tumefaciens*); and Miao et al. (1991) Plant Cell 3(1):1 1'-22 (full-length cDNA clone encoding cytosolic glutamine synthetase (GS), which is expressed in roots and root nodules of soybean). See also U.S. Pat. Nos. 5,837,876; 5,750,386; 5,633,363; 5,459,252; 5,401,836; 5,110,732; and 5,023,179.

Plastid specific promoters include the PrbcL promoter [Allison L. A. et al., EMBO 15: 2802-2809 (1996); Shiina T. et al., Plant Cell 10: 1713-1722 (1998)]; the PpsbA promoter [Agrawal O K, et al., Nucleic Acids Research 29: 1835-1843 (2001)]; the Prrn 16 promoter [Svab Z & Maliga P., Proc. Natl. Acad. Sci. USA 90: 913-917 (1993), Allison L A et al., EMBO 15: 2802-2809 (1996)]; the PaccD promoter (WO97/06250; Hajdukiewicz P T J et al., EMBO J. 16: 4041-4048 (1997)).

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize 1n2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. *Proc. Natl. Acad. Sci. USA* 88:10421-10425 (1991) and McNellis et al. *Plant J.* 14(2): 247-257 (1998)) and tetracycline-inducible and tetracycline-repressible promoters (see, for example, Gatz et al. *Mol. Gen. Genet.* 227:229-237 (1991), and U.S. Pat. Nos. 5,814,618 and 5,789,156), herein incorporated by reference in their entirety.

In one embodiment, coordinated expression of the three transgenes, phaA, phaB, and phaC, necessary for conversion of acetyl-CoA to PHB is controlled by a seed specific promoter, such as the soybean oleosin promoter (Rowley et al., *Biochim Biophys Acta,* 1997, 1345, 1-4) or the promoter from the lesquerlla hydroxylase gene (U.S. Pat. No. 6,437,220 B1). In another embodiment, coordinated expression of the three transgenes, phaA, phaB, and phaC, necessary for conversion of acetyl-CoA to PHB is controlled by a promoter active primarily in the biomass plant, such as the maize chlorophyll A/B binding protein promoter (Sullivan et al., *Mol. Gen. Genet.,* 1989, 215, 431-40). It has been previously shown that plants transformed with multi-gene constructs produced higher levels of polymer than plants obtained from crossing single transgene lines (Valentin et al., *Int. J. Biol. Macromol.,* 1999, 25, 303-306; Bohmert et al., *Planta,* 2000, 211, 841-845).

In one embodiment, the final molecular weight of the polymer produced is controlled by the choice of promoter for expression of the PHA synthase gene. As described in U.S. Pat. No. 5,811,272, high PHA synthase activity will lower polymer molecular weight and low PHA synthase activity will increase polymer molecular weight. In another embodiment, a strong promoter is used for expression of the genes encoding plastid-targeted monomer producing enzymes while a weaker promoter is used to control expression of synthase.

6. Transcription Termination Sequences

At the extreme 3' end of the transcript of the transgene, a polyadenylation signal can be engineered. A polyadenylation signal refers to any sequence that can result in polyadenylation of the mRNA in the nucleus prior to export of the mRNA to the cytosol, such as the 3' region of nopaline synthase (Bevan, M., Barnes, W. M., Chilton, M. D. Nucleic Acids Res. 1983, 11, 369-385).

7. Selectable Markers

Genetic constructs may encode a selectable marker to enable selection of plastid transformation events. There are many methods that have been described for the selection of transformed plants [for review see (Miki et al., *Journal of Biotechnology,* 2004, 107, 193-232) and references incorporated within]. Selectable marker genes that have been used extensively in plants include the neomycin phosphotransferase gene nptII (U.S. Pat. Nos. 5,034,322, U.S. Pat. No. 5,530,196), hygromycin resistance gene (U.S. Pat. No. 5,668,298), the bar gene encoding resistance to phosphinothricin (U.S. Pat. No. 5,276,268), the expression of aminoglycoside 3"-adenyltransferase (aadA) to confer spectinomycin resistance (U.S. Pat. No. 5,073,675), the use of inhibition resistant 5-enolpyruvyl-3-phosphoshikimate synthetase (U.S. Pat. No. 4,535,060) and methods for producing glyphosate tolerant plants (U.S. Pat. No. 5,463,175; U.S. Pat. No. 7,045,684). Methods of plant selection that do not use antibiotics or herbicides as a selective agent have been previously described and include expression of glucosamine-6-phosphate deaminase to inactive glucosamine in plant selection medium (U.S. Pat. No. 6,444,878) and a positive/negative system that utilizes D-amino acids (Erikson et al., *Nat Biotechnol,* 2004, 22, 455-8). European Patent Publication No. EP 0 530 129 A1 describes a positive selection system which enables the transformed plants to outgrow the non-transformed lines by expressing a transgene encoding an enzyme that activates an inactive compound added to the growth media. U.S. Pat. No. 5,767,378 describes the use of mannose or xylose for the positive selection of transgenic plants. Methods for positive selection using sorbitol dehydrogenase to convert sorbitol to fructose for plant growth have also been described (WO 2010/102293). Screenable marker genes include the beta-glucuronidase gene (Jefferson et al., 1987, *EMBO J.* 6: 3901-3907; U.S. Pat. No. 5,268,463) and native or modified green fluorescent protein gene (Cubitt et al., 1995, *Trends Biochem. Sci.* 20: 448-455; Pan et al., 1996, *Plant Physiol.* 112: 893-900).

Transformation events can also be selected through visualization of fluorescent proteins such as the fluorescent proteins from the nonbioluminescent *Anthozoa* species which include DsRed, a red fluorescent protein from the *Discosoma* genus of coral (Matz et al. (1999), *Nat Biotechnol* 17: 969-73). An improved version of the DsRed protein has been developed (Bevis and Glick (2002), Nat Biotech 20: 83-87) for reducing aggregation of the protein. Visual selection can also be performed with the yellow fluorescent proteins (YFP) including the variant with accelerated maturation of the signal (Nagai, T. et al. (2002), Nat Biotech 20: 87-90), the blue fluorescent protein, the cyan fluorescent protein, and the green fluorescent protein (Sheen et al. (1995), Plant J 8: 777-84; Davis and Vierstra (1998), Plant Molecular Biology 36: 521-528). A summary of fluorescent proteins can be found in Tzfira et al. (Tzfira et al. (2005), Plant Molecular Biology 57: 503-516) and Verkhusha and Lukyanov (Verkhusha, V. V. and K. A. Lukyanov (2004), Nat Biotech 22: 289-296) whose references are incorporated in entirety. Improved versions of many of the fluorescent proteins have been made for various applications. Use of the improved versions of these proteins or the use of combinations of these proteins for selection of transformants will be obvious to those skilled in the art. It is also practical to simply analyze progeny from transformation events for the presence of the PHB thereby avoiding the use of any selectable marker.

For plastid transformation constructs, a preferred selectable marker is the spectinomycin-resistant allele of the plastid 16S ribosomal RNA gene (Staub J M, Maliga P, *Plant Cell* 4: 39-45 (1992); Svab Z, Hajdukiewicz P, Maliga P, *Proc. Natl. Acad. Sci. USA* 87: 8526-8530 (1990)). Selectable markers that have since been successfully used in plastid transformation include the bacterial aadA gene that encodes aminoglycoside 3'-adenyltransferase (AadA) conferring spectinomycin and streptomycin resistance (Svab et al., *Proc. Natl. Acad. Sci. USA,* 1993, 90, 913-917), nptII that encodes aminoglycoside phosphotransferase for selection on kanamycin (Caner H, Hockenberry Tenn., Svab Z, Maliga P., *Mol. Gen. Genet.* 241: 49-56 (1993); Lutz K A, et al., *Plant J.* 37: 906-913 (2004); Lutz K A, et al., *Plant Physiol.* 145: 1201-1210 (2007)), aphA6, another aminoglycoside phosphotransferase (Huang F-C, et al, *Mol. Genet. Genomics* 268: 19-27 (2002)), and chloramphenicol acetyltransferase (Li, W., et al. (2010), Plant Mol Biol, DOI_10.1007/s11103-010-9678-4). Another selection scheme has been reported that uses a chimeric betaine aldehyde dehydrogenase gene (BADH) capable of converting toxic betaine aldehyde to nontoxic glycine betaine. (Daniell H, et al., *Curr. Genet.* 39: 109-116 (2001)).

8. Plastid Targeting Signals

Plastid targeting sequences are known in the art and include the chloroplast small subunit of ribulose-1,5-bisphosphate carboxylase (Rubisco) (de Castro Silva Filho et al, *Plant Mol. Biol.* 30:769-780 (1996); Schnell et al. *J. Biol. Chem.* 266(5):3335-3342 (1991)); 5-(enolpyruvyl)shikimate-3-phosphate synthase (EPSPS) (Archer et al. *J. Bioenerg. Biomemb.* 22(6):789-810 (1990)); tryptophan synthase (Zhao et al. *J. Biol. Chem.* 270(11):6081-6087 (1995)); plastocyanin (Lawrence et al. *J. Biol. Chem.* 272(33):20357-20363 (1997)); chorismate synthase (Schmidt et al. *J. Biol. Chem.* 268(36):27447-27457 (1993)); and the light harvesting chlorophyll a/b binding protein (LHBP) (Lamppa et al. *J. Biol. Chem.* 263:14996-14999 (1988)). See also Von Heijne et al. *Plant Mol. Biol. Rep.* 9:104-126 (1991); Clark et al. *J. Biol. Chem.* 264:17544-17550 (1989); Della-Cioppa et al. *Plant Physiol.* 84:965-968 (1987); Romer et al. *Biochem. Biophys. Res. Commun.* 196:1414-1421 (1993); and Shah et al. *Science* 233:478-481 (1986). Alternative plastid targeting signals have also been described in the following: US 2008/0263728; Miras, S. et al. (2002), J Biol Chem 277(49): 47770-8; Miras, S. et al. (2007), J Biol Chem 282: 29482-29492.

B. Exemplary Host Plants

Plants transformed in accordance with the present disclosure may be monocots or dicots. The transformation of suitable agronomic plant hosts using vectors for nuclear transformation or direct plastid transformation can be accomplished with a variety of methods and plant tissues. Representative plants useful in the methods disclosed herein include the Brassica family including *B. napus, B. rapa, B. carinata* and *B. juncea*; industrial oilseeds such as *Camelina sativa*, Crambe, Jatropha, castor; *Calendula, Cuphea, Arabidopsis thaliana*; maize; soybean; cottonseed; sunflower; palm; coconut; safflower; peanut; mustards including Sinapis alba; sugarcane flax and tobacco, also are useful with the methods disclosed herein. Representative tissues for transformation using these vectors include protoplasts, cells, callus tissue, leaf discs, pollen, and meristems.

C. Methods of Plant Transformation

Transformation protocols as well as protocols for introducing nucleotide sequences into plants may vary depending on the type of plant or plant cell targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606), *Agrobacterium*-mediated transformation (Townsend et al., U.S. Pat. No. 5,563,055; Zhao et al. WO US98/01268), direct gene transfer (Paszkowski et al. (1984) *EMBO J.* 3:2717-2722), and ballistic particle acceleration (see, for example, Sanford et al., U.S. Pat. No. 4,945,050; Tomes et al. (1995) *Plant Cell, Tissue, and Organ Culture: Fundamental Methods*, ed. Gamborg and Phillips (Springer-Verlag, Berlin); and McCabe et al. *Biotechnology* 6:923-926 (1988)). Also see Weissinger et al. *Ann. Rev. Genet.* 22:421-477 (1988); Sanford et al. Particulate Science and Technology 5:27-37 (1987) (onion); Christou et al. *Plant Physiol.* 87:671-674 (1988) (soybean); McCabe et al. (1988) BioTechnology 6:923-926 (soybean); Finer and McMullen *In Vitro Cell Dev. Biol.* 27P:175-182 (1991) (soybean); Singh et al. *Theor. Appl. Genet.* 96:319-324 (1998) (soybean); Dafta et al. (1990) *Biotechnology* 8:736-740 (rice); Klein et al. *Proc. Natl. Acad. Sci. USA* 85:4305-4309 (1988) (maize); Klein et al. *Biotechnology* 6:559-563 (1988) (maize); Tomes, U.S. Pat. No. 5,240,855; Buising et al., U.S. Pat. Nos. 5,322,783 and 5,324,646; Tomes et al. (1995) in Plant Cell, Tissue, and Organ Culture Fundamental Methods, ed. Gamborg (Springer-Verlag, Berlin) (maize); Klein et al. Plant Physiol. 91:440-444 (1988) (maize); Fromm et al. *Biotechnology* 8:833-839 (1990) (maize); Hooykaas-Van Slogteren et al. *Nature* 311:763-764 (1984); Bowen et al., U.S. Pat. No. 5,736,369 (cereals); Bytebier et al. *Proc. Natl. Acad. Sci. USA* 84:5345-5349 (1987) (Liliaceae); De Wet et al. in The Experimental Manipulation of Ovule Tissues, ed. Chapman et al. (Longman, N.Y.), pp. 197-209 (1985) (pollen); Kaeppler et al. *Plant Cell Reports* 9:415-418 (1990) and Kaeppler et al. *Theor. Appl. Genet.* 84:560-566 (1992) (whisker-mediated transformation); D'Halluin et al. *Plant Cell* 4:1495-1505 (1992) (electroporation); Li et al. *Plant Cell Reports* 12:250-255 (1993) and Christou and Ford Annals of Botany 75:407-413 (1995) (rice); Osjoda et al. *Nature Biotechnology* 14:745-750 (1996) (maize via *Agrobacterium*

*tumefaciens*); all of which are herein incorporated by reference in their entirety. Methods for transforming plant protoplasts are available including transformation using polyethylene glycol (PEG), electroporation, and calcium phosphate precipitation (see for example Potrykus et al., 1985, Mol. Gen. Genet., 199, 183-188; Potrykus et al., 1985, Plant Molecular Biology Reporter, 3, 117-128), Methods for plant regeneration from protoplasts have also been described [Evans et al., in Handbook of Plant Cell Culture, Vol 1, (Macmillan Publishing Co., New York, 1983); Vasil, IK in Cell Culture and Somatic Cell Genetics (Academic, Orlando, 1984)].

Methods for transformation of plastids such as chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation may be accomplished by transactivation of a silent plastid-borne transgene by tissue-preferred expression of a nuclear-encoded and plastid-directed RNA polymerase (McBride et al., *Proc. Natl. Acad. Sci. USA,* 1994, 91:7301-7305) or by use of an integrase, such as the phiC31 phage site-specific integrase, to target the gene insertion to a previously inserted phage attachment site (Lutz et al., *Plant J,* 2004, 37, 906-13). Plastid transformation vectors can be designed such that the transgenes are expressed from a promoter sequence that has been inserted with the transgene during the plastid transformation process or, alternatively, from an endogenous plastidial promoter such that an extension of an existing plastidial operon is achieved (Herz et al., *Transgenic Research,* 2005, 14, 969-982). Inducible gene expression from the plastid genome using a synthetic riboswitch has also been reported (Verhounig et al. (2010), Proc Natl Acad Sci USA 107: 6204-6209). Methods for designing plastid transformation vectors are described by Lutz et al. (Lutz et al., *Plant Physiol,* 2007, 145, 1201-10).

Recombinase technologies which are useful for producing the disclosed transgenic plants include the cre-lox, FLP/FRT and Gin systems. Methods by which these technologies can be used for the purpose described herein are described for example in (U.S. Pat. No. 5,527,695; Dale And Ow, 1991, *Proc. Natl. Acad. Sci. USA* 88: 10558-10562; Medberry et al., 1995*, Nucleic Acids Res.* 23: 485-490).

D. Methods for Reproducing Transgenic Plants

Following transformation by any one of the methods described above, the following procedures can be used to obtain a transformed plant expressing the transgenes: select the plant cells that have been transformed on a selective medium; regenerate the plant cells that have been transformed to produce differentiated plants; select transformed plants expressing the transgene producing the desired level of desired polypeptide(s) in the desired tissue and cellular location.

In plastid transformation procedures, further rounds of regeneration of plants from explants of a transformed plant or tissue can be performed to increase the number of transgenic plastids such that the transformed plant reaches a state of homoplasmy (all plastids contain uniform plastomes containing transgene insert).

The cells that have been transformed may be grown into plants in accordance with conventional techniques. See, for example, McCormick et al. *Plant Cell Reports* 5:81-84 (1986). These plants may then be grown, and either pollinated with the same transformed variety or different varieties, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

In some scenarios, it may be advantageous to insert a multi-gene pathway into the plant by crossing of lines containing portions of the pathway to produce hybrid plants in which the entire pathway has been reconstructed. This is especially the case when high levels of product in a seed compromises the ability of the seed to germinate or the resulting seedling to survive under normal soil growth conditions. Hybrid lines can be created by crossing a line containing one or more PHB genes with a line containing the other gene(s) needed to complete the PHB biosynthetic pathway. Use of lines that possess cytoplasmic male sterility (Esser, K. et al., 2006, Progress in Botany, Springer Berlin Heidelberg. 67, 31-52) with the appropriate maintainer and restorer lines allows these hybrid lines to be produced efficiently. Cytoplasmic male sterility systems are already available for some *Brassicaceae* species (Esser, K. et al., 2006, Progress in Botany, Springer Berlin Heidelberg. 67, 31-52). These *Brassicaceae* species can be used as gene sources to produce cytoplasmic male sterility systems for other oilseeds of interest such as *Camelina.*

E. Methods and Compositions for Increasing Germination

The serendipitous discovery that high PHB levels can be achieved in transgenic oilseeds expressing the PHA biosynthesis genes and that this results in significant impairment of subsequent germination and early plant development provides a clear demonstration that commercial levels of PHA can be produced in transgenic oilseeds and in addition presents additional opportunities to understand and control those factors effecting the germination process. In many cases we have observed that seed germination does take place but early plant development is significantly impaired resulting ultimately in dead plants. We have also demonstrated that seeds containing high levels of PHB can be propagated using tissue culture methods providing sucrose as a carbon source. Based on the observation of strong chlorosis and in many cases bleaching of the initial first cotyledons, it is possible that the presence of high levels of PHB in the oilseed plastids may negatively impact chloroplast formation in the cotyledons such that they become chlorotic. One possible solution to this would be to express PHB degradation enzymes during seed germination and the early stages of plant development. In some examples we demonstrate that expressing a PHB polymerase in high PHB producing lines has some benefits in terms of germination and survival. Another possibility is that expression of PHB genes necessary for high PHB requires strong seed specific promoters and the expression from these promoters may carry over into the early stages of seed germination and early plant development. The expression of the PHB genes during germination could divert stored carbon to PHB instead of plant development. Possible solutions to this include inhibiting expression of the PHB genes during germination and early plant development using additional transgene(s) encoding siRNA genes to inhibit expression of one or more of the PHB genes during germination and early development. An alternative solution is to use different seed specific promoters whose expression profile is high enough during seed development to achieve PHB levels of greater 8% but whose expression is low enough during germination and early seed development that the plant is not affected. These alternative promoters can be used to control the expression of one or more of the PHA biosynthetic genes. In some of our Examples described herein we have identified a series of promoters for this approach.

Another possible scenario is that both the presence of PHB and/or expression of PHB genes during germination impairs photosynthesis during the critical stages of germination and early plantlet development resulting in failure of the seedlings to survive. The first two cotyledons of high PUB producers do become chlorotic or bleached. A possible solution to this would be to express additional transgenes encoding enzymes involved in the photosynthetic pathway to enhance photosynthetic flux of carbon. One example of such an enzyme is the cyanobacterial FBPase/SBPase. Each of these possible solutions can be used alone or in combination to generate viable oilseed plants which can germinate and survive normally in the field at levels of at least 25%, 50%, 75% or 100% of the unmodified parental line and produce PHA at greater than 8% by weight of the seed.

III. Methods for Use

The disclosed genetic constructs can be used to produce industrial oilseed plants for high levels of PHA production. Specifically, PHA is produced in the seed.

The transgenic plants can be grown and harvested. The polyhydroxyalkanoate can be isolated from the oilseeds and the remaining plant material can be used as a feedstock for industrial use, preferably for the production of oleochemicals, energy or for use as feed for animals. The polyhydroxyalkanoate harvested from the plants can then be used to produce plastics, rubber material, coating material, and binders for paints, or as a feedstock for producing chemical derivatives such as hydroxyacids, esters, alkenoic acids or amines. PHA also has several medical applications.

The present invention will be further understood by reference to the following non-limiting examples.

EXAMPLES

Example 1

Design and Construction of Transformation Vectors for Production of PHB in Oilseeds Five different vectors for seed specific expression of the PHB pathway were constructed containing different seed specific promoters for production of PHB in oilseeds (Table 1). Vector pMBXS490, a pCAMBIA based plasmid (Centre for Application of Molecular Biology to International Agriculture, Canberra, Australia), contains the following gene expression cassettes: (1) an expression cassette for PHA synthase containing the promoter from the soybean oleosin isoform A gene, a DNA fragment encoding the signal peptide of the small subunit of rubisco from pea (*P. sativum*) and the first 24 amino acids of the mature protein (Cashmore, A. R. 1983, In Genetic Engineering of Plants, pp. 29-38), a DNA fragment encoding a hybrid PHA synthase (PhaC; U.S. Pat. No. 6,316,262) in which the first nine amino acids at the N-terminus of this synthase are derived from the *Pseudomonas oleovorans* phaC1 gene and the remainder of the synthase coding sequence is derived from *Zoogloea ramigera* phaC gene, and the 3' termination sequence from the soybean oleosin isoform A gene; (2) an expression cassette for reductase containing the promoter from the soybean oleosin isoform A gene, a DNA fragment encoding the signal peptide and the first 24 amino acids of the mature protein of the small subunit of rubisco from pea, a DNA fragment encoding a NADPH dependent reductase (PhaB) from *Ralstonia eutropha eutropha* (Peoples, O. & A. Sinskey, 1989, J. Biol. Chem., 264, 15293-15297), and the 3' termination sequence from the soybean oleosin isoform A gene; (3) an expression cassette for thiolase containing the promoter from the soybean glycinin (gy1) gene (Iida et al., 1995, Plant Cell Reports, 14, 539-544), a DNA fragment encoding the signal peptide and the first 24 amino acids of the mature protein of the small subunit of rubisco from pea, the phaA gene encoding a β-ketothiolase (PhaA) from *Ralstonia eutropha* (Peoples, O. & A. Sinskey, 1989, J. Biol. Chem., 264, 15293-15297), and a 3' termination sequence from the soybean glycinin gene; (4) an expression cassette for DsRed, a protein that can be visualized in seeds by placing them in light of the appropriate wavelength, containing the promoter from the cassaya mosaic virus (CMV), a DNA fragment encoding a modified red fluorescent protein from *Discosoma* sp. (DsRed) in which eleven amino acids have been added to the C-terminus to increase solubility and/or prevent aggregation of the protein, and a termination sequence from the *Agrobacterium tumefaciens* nopaline synthase gene.

TABLE 1

Summary of transformation vectors containing seed specific promoters

| Plasmid | Promoter controlling expression of pha genes | Selectable or visible marker |
|---|---|---|
| pMBXS490 | Oleosin | DsRed |
| pMBXS364 | LH | DsRed |
| pMBXS355 | LH | bar |
| pMBXS491 | Napin | DsRed |
| pMBXS492 | Glycinin | DsRed |

Promoters are as follows: LH, promoter from the *Lesquerella fendleri* bifunctional oleate 12-hydroxylase:saturate gene (U.S. Pat. No. 6,437,220 Bi); Oleosin, promoter from the soybean oleosin isoform A gene (Rowley and Herman, 1997, Biochim. Biophys. Acta 1345, 1-4); Napin, promoter from the *Brassica napus* napin gene (Ellenstrom, M. et al., 1996, Plant Molecular Biology, 32: 1019-1027); Glycinin, promoter from the soybean glycinin (gy1) gene (fida, A. et al., 1995, Plant Cell Reports, 14, 539-544).

Vectors pMBXS364, pMBXS355, pMBXS491, and pMBXS492 contain the same PHB pathway genes as pMBXS490 with the exception that the expression of these genes is under the control of different promoters as outlined in Table 1. Vector pMBXS355 contains an expression cassette for the bar gene, encoding phosphinothricin acetyltransferase whose expression is under the control of the 355 promoter. Expression of the bar gene allows selection of transformants based on their resistance to bialaphos. All other vectors in Table 1 contain expression cassettes for DsRed allowing the identification of transgenic seeds under the appropriate wavelength of light.

Example 2

Transformation of *Camelina*

In preparation for plant transformation experiments, seeds of *Camelina sativa* cultivar Suneson or Celine were sown directly into 4 inch pots filled with soil (Metro mix) in the greenhouse. Growth conditions were maintained at 24° C. during the day and 18° C. during the night. Plants were grown until flowering. Plants with a number of unopened flower buds were used in 'floral dip' transformations.

*Agrobacterium* strain GV3101 was transformed with the construct of interest using electroporation. A single colony of GV3101 containing the construct of interest was obtained from a freshly streaked plate and was inoculated into 5 mL LB medium. After overnight growth at 28° C., 2 mL of culture was transferred to a 500-mL flask containing 300 mL of LB and incubated overnight at 28° C. Cells were pelleted by centrifugation (6,000 rpm, 20 min), and diluted to an OD600 of ~0.8 with infiltration medium containing 5% sucrose and 0.05% (v/v) Silwet-L77 (Lehle Seeds, Round Rock, Tex., USA). *Camelina* plants were transformed by "floral dip" using transformation constructs as follows. Pots containing plants at the flowering stage were placed inside a 460 mm height vacuum desiccator (Bel-Art, Pequannock, N.J., USA). Inflorescences were immersed into the *Agrobacterium* inoculum contained in a 500-ml beaker. A vacuum (85 kPa) was applied and held for 5 min. Plants were removed from the desiccator and were covered with plastic bags in the dark for 24 h at room temperature. Plants were removed from the bags and returned to normal growth conditions within the greenhouse for seed formation.

To identify *Camelina* seeds expressing DsRed, fully mature seeds were harvested from transformed plants and placed in a desiccator with anhydrous calcium sulfate as desiccant for at least 2 days prior to screening. DsRed expressing seeds were visualized in a darkroom with a green LumaMax LED flashlight (Lab Safety Supply, Inc., Janesville, Wis.) and a pair of KD's Dark Red glasses (Pacific Coast Sunglasses Inc., Santa Maria, Calif.).

To identify bialaphos resistant seeds, seeds from floral dip transformations were sterilized in 70% ethanol and 10% bleach, and washed in water. Sterilized seeds were placed on germination and selection medium in square Petri dishes. The germination and selection medium contained 10 mg/L bialaphos (Gold BioTechnology, B0178-500) in ½×MS medium, which was made with Murashige & Skoog medium mixture (Caisson Labs, MSP09) at half concentration. The plates were sealed and placed in a growth chamber for germination under a 16-h photoperiod, 3,000 lux light intensity, and temperatures of 23/20° C. at day/night. Seedlings with greenish cotyledons were picked and transferred to soil about six days after initiation of germination.

Example 3

Production of PHB in Seeds of *Camelina*

In initial transformation experiments with pMBXS490, 24 DsRed positive seeds were isolated. Four of these seeds were sacrificed to determine their PHB content using a previously described gas chromatography/butanolysis technique performed essentially as previously described (Somleva et al., 2008*, Plant Biotechnol. J.,* 663-678). These four seeds contained 19.9, 12.0, 9.8, and 6.4% dwt PHB in the seed. When other seeds from this transformation were planted in soil, seedlings possessed whitish cotyledons and their growth was severely impaired. Only a few $T_1$ seeds with low levels of PHB were capable of germination and survival in soil in a greenhouse. These seedlings were still weak and possessed white or variegated cotyledons.

In transformations of pMBXS355 and pMBXS364, seeds from transformed plants were screened for resistance to bialophos and or visual screening for DsRed, respectively. Despite having the same promoter controlling the expression of the PHB biosynthetic pathway, the maximum PHB production in pMBXS355 (0.54% PHB) was significantly lower than the amount produced by pMBXS364 (3.4%) (Table 2). This is likely due to difficulty in distinguishing between weak pMBXS355 seedlings that produced higher levels of PHB and the non-transformed, bialophos sensitive seedlings.

TABLE 2

Comparison of PHB production in Lines isolated using bialaphos selection or visual screening

| Vector | Selectable or Screenable Marker | #of Lines Tested | #of Lines w/ PHB in T2 Seeds | Range of PHB Production (% seed weight) |
|---|---|---|---|---|
| pMBXS355 | Bar[1] | 204 | 5 | 0.05 to 0.54% |
| pMBXS364 | DsRed[2] | 170 | 85 | 0.5 to 3.4% |

[1]Selection of transformants performed by germination of seeds on tissue culture plates containing 10 mg/L bialaphos.
[2]Selection of transformants performed by visual screening for DsRed expression.

In transformations with pMBX491 and pMBX492 containing the PHB genes under the control of the napin and glycinin promoters, respectively, were healthier than transformants obtained from pMBX490 transformations. For pMBX491, T2 seeds were isolated containing 8% PHB in DsRed seeds picked from the segregating population. These seeds possessed a 75% germination rate and a 60% survival rate under greenhouse conditions in soil. The cotyledons after 11 days were chlorotic and the growth of this line was significantly delayed compared to wild-type. For pMBX492, T2 seeds were isolated containing 6.9% PHB in DsRed seeds picked from the segregating population. These seeds possessed a 75% germination rate and a 70% survival rate under greenhouse conditions in soil. After 11 days, the cotyledons and first true leaves of this transformant were green. The growth of this line was somewhat delayed compared to wild-type but faster than the pMBXS491 line.

The 19% dwt PHB produced in a single seed obtained from Camelina plants transformed with construct pMBXS490 was an unexpected result and is the highest level of PHB reported in oilseeds to date. Previous studies with *Brassica napus* produced up to 73% dwt PHB. These seeds were obtained from transformation of *Brassica napus* using stem segments as the explants and selection of the transformed explants (Fry, J. et al., 1987, 6, 321-325) using glyphosate resistance obtained from expression of a gene encoding 5-enolpyruvylshikimate-3-phosphate synthase. Researchers did not report any germination issues with seeds isolated from the transformed plants [Houmiel et al., 1999, Planta, 209, 547-550; Valentin et al., 1999, Int. J. Biol. Macromol. 25, 303-306].

The use of DsRed as a visual marker in *Camelina* enabled the identification of high PHB producing seeds that would not have germinated in a typical seed screening procedure where an antibiotic or herbicide selectable marker, such as glyphosate resistance, is employed to provide resistance to the selection agent during seed germination and seedling development in tissue culture medium.

Example 4

Transformation of *Brassica Napus, Brassica Carinata*, and *Brassica Juncea*

Transformation of *Brassica Carinata*

*Brassica carinata* can be transformed using a previously described floral dip method (Shiv et al., 2008, Journal of Plant Biochemistry and Biotechnology 17, 1-4). Briefly constructs of interest are transformed into *Agrobacterium* strain GV-3101 and cells are grown in liquid medium. Cells are harvested and resuspended in a transformation medium consisting of V2 MS salts, 5% sucrose, and 0.05% Silwet L-77. *Brassica carinata* plants are grown in a greenhouse until inflorescences develop and approximately 25% of their flowers are opened. Plants are submerged in the prepared *Agrobacterium* solution for approximately 1 minute, and covered for 24 hours. Plants are returned to the greenhouse and allowed to set seed. Transformed seeds are screened by picking DsRed seeds under the appropriate wavelength of light as described above.

Transformation of *Brassica Napus*

*Brassica* seeds are surface sterilized in 10% commercial bleach (Javex, Colgate-Palmolive) for 30 min with gentle shaking. The seeds are washed three times in sterile distilled water and placed in germination medium comprising Murashige-Skoog (MS) salts and vitamins, 3% (w/v) sucrose and 0.7% (w/v) phytagar, pH 5.8 at a density of 20 per plate and maintained at 24° C. an a 16 h light/8 h dark photoperiod at a light intensity of 60-80 $\mu Em^{-2} s^{-1}$ for 4-5 days.

Constructs of interest are introduced into *Agrobacterium tumefacians* strain EHA101 (Hood et. al., 1986, J. Bacterial. 168: 1291-1301) by electroporation. Prior to transformation of cotyledonary petioles, single colonies of strain EHA101 harboring each construct are grown in 5 ml of minimal medium supplemented with appropriate antibiotics for 48 hr at 28° C. One ml of bacterial suspension was pelleted by centrifugation for 1 min in a microfuge. The pellet was resuspended in 1 ml minimal medium.

For transformation, cotyledons are excised from 4 or in some cases 5 day old seedlings so that they included ~2 mm of petiole at the base. Individual cotyledons with the cut surface of their petioles are immersed in diluted bacterial suspension for 1 s and immediately embedded to a depth of ~2 mm in co-cultivation medium, MS medium with 3% (w/v) sucrose and 0.7% phytagar and enriched with 20 μM benzyladenine. The inoculated cotyledons are plated at a density of 10 per plate and incubated under the same growth conditions for 48 h. After co-cultivation, the cotyledons are transferred to regeneration medium comprising MS medium supplemented with 3% sucrose, 20 μM benzyladenine, 0.7% (w/v) phytagar, pH 5.8, 300 mg/L timentinin and 20 mg/L kanamycin sulfate.

After 2-3 weeks regenerant shoots obtained are cut and maintained on "shoot elongation" medium (MS medium containing, 3% sucrose, 300 mg/L timentin, 0.7% (w/v) phytagar, 300 mg/L timentinin and 20 mg/L kanamycin sulfate, pH 5.8) in Magenta jars. The elongated shoots are transferred to "rooting" medium comprising MS medium, 3% sucrose, 2 mg/L indole butyric acid, 0.7% phytagar and 500 mg/L carbenicillin. After roots emerge, plantlets are transferred to potting mix (Redi Earth, W. R. Grace and Co.). The plants are maintained in a misting chamber (75% relative humidity) under the same growth conditions. Plants are allowed to self pollinate to produce seeds. Seeds are screened by visualization of DsRed as described above.

*Brassica napus* can also be transformed using the floral dip procedure described by Shiv et al. (Shiv et al., 2008, Journal of Plant Biochemistry and Biotechnology 17, 1-4) as described above for *Brassica carinata.*

Transformation of *Brassica Juncea*

*Brassica juncea* can be transformed using hypocotyl explants according to the methods described by Barfield and Pua (Barfield and Pua, Plant Cell Reports, 10, 308-314) or Pandian et al. (Pandian, et al., 2006, Plant Molecular Biology Reporter 24: 103a-103i) as follows.

*B. juncea* seeds are sterilized 2 min in 70% (v/v) ethanol and washed for 20 min in 25% commercial bleach (10 g/L hypochlorite). Seeds are rinsed 3× in sterile water. Surface-sterilized seeds are plated on germination medium (1×MS salts, 1×MS vitamins, 30 g/L sucrose, 500 mg/L MES. pH 5.5) and kept in the cold room for 2 days. Seeds are incubated for 4-6 days at 24° C. under low light (20 $\mu m\ m^{-1}s^{-1}$). Hypocotyl segments are excised and rinsed in 50 mL of callus induction medium (1×MS salts, 1×B5 vitamins, 30 g/L sucrose, 500 mg/L MES, 1.0 mg/L 2,4-D, 1.0 mg/L kinetin pH 5.8) for 30 min without agitation. This procedure is repeated but with agitation on orbital shaker (~140 g) for 48 h at 24° C. in low light (10 $\mu m\ m^{-1}s^{-1}$).

*Agrobacterium* can be prepared as follows: Cells of *Agrobacterium* strain AGL1 (Lazo, G. et al. (1991) Biotechnology, 9: 963-967) containing the construct of interest are grown in 5 mL of LB medium with appropriate antibiotic at 28° C. for 2 days. The 5 mL culture is transferred to 250 mL flask with 45 mL of LB and cultured for 4 h at 28° C. Cells is pelleted and resuspended in BM medium (1×MS salts, 1×135 vitamins, 30 g/L sucrose, 500 mg/L MES, pH 5.8). The optical density at 600 nm is adjusted to 0.2 with BM medium and used for inoculation.

Explants are cocultivated with *Agrobacterium* for 20 min after which time the *Agrobacterium* suspension is removed. Hypocotyl explants are washed once in callus induction medium after which cocultivation proceeds for 48 h with gentle shaking on orbital shaker. After several washes in CIM, explants are transferred to selective shoot-inducing medium (500 mg/L AgNO2, 0.4 mg/L zeatin riboside, 2.0 mg/L benzylamino purine, 0.01 mg/L GA, 200 mg/L Timentin appropriate selection agent and 8 g/L agar added to basal medium) plates for regeneration at 24° C. Root formation is induced on root-inducing medium (0.5×MS salts, 0.5×B5 vitamins, 10 g/L sucrose, 500 g/L MES, 0.1 mg/L indole-3-butyric acid, 200 mg/L Timentin, appropriate selection agent and 8 g/L agar, pH 5.8).

Plantlets are transferred to or removed from agar, gently washed, and transferred to potting soil in pots. Plants are grown in a humid environment for a week and then transferred to the greenhouse.

Example 5

Managing Gene Expression During Germination, RNA Interference Constructs

To control PHB formation during seed germination, a series of RNA interference (RNAi) constructs were designed where the RNAi element was targeted to either synthase, thiolase, or reductase. The RNAi element was designed with an intron between an inverted repeat of the stretch of the gene targeted for RNAi interference. Expression of the RNAi element was controlled by a chemically inducible promoter. A summary of the RNAi constructs is shown in Table 3. All constructs for RNAi interference contain the PHB expression cassettes and DsRed expression cassette of pMBXS490.

TABLE 3

Summary of RNAi interference transformation vectors

| Vector | RNAi interference target | Promoter for expression of GRVH |
|---|---|---|
| phaA-RNAi/35S | phaA | 35S |
| phaC-RNAi/35S | phaC | 35S |
| phaA-RNAi/glyP | phaA | glycinin promoter |
| phaC-RNAi/glyP | phaC | glycinin promoter |

Plasmid phaA-RNAi/35S contains the following expression cassettes for inducible expression of the RNAi element with homology to a stretch of the phaA gene: (1) an expression cassette for a chimeric ecdysone receptor consisting of the double enhanced version of the 35S promoter from cauliflower mosaic virus, the grvH gene encoding a chimeric ecdysone receptor that contains a DNA-binding domain derived from the human glucocorticoid receptor, the transcriptional activation domain from the Herpes simplex viral protein VP16, and the ligand-binding domain from the ecdysone receptor of *Heliothis virescens*, and the 3' termination sequence of the nopaline synthase gene from *Agrobacterium tumefaciens*; (2) an expression cassette for the RNAi element consisting of a DNA fragment encoding six copies of glucocorticoid response element (GRE) derived from the promoter region of mouse mammary tumor virus (MTV), a minimal promoter (MP) derived from the 35S promoter from cauliflower mosaic virus, a 0.60 kb DNA fragment derived from the gene encoding a β-ketothiolase (PhaA) from *Ralstonia eutropha*, a 1.13 kb DNA sequence from the intron 1 of fatty acid desaturase 2 (FAD2) from *Arabidopsis thaliana*, the same 0.6 kb DNA fragment of phaA described previously arranged in an antisense orientation to make a hairpin structure for RNA interference (RNAi), and the 3' termination sequence of the gene for rib-1,5-bisphospate carboxylase (rbcs) small subunit from pea (*P. sativum*). The design of this construct contains the necessary genetic components such that upon the addition of inducing agent, the chimeric ecdysone receptor binds to the glucocorticoid response elements located upstream of a minimal 35S promoter and transactivates expression of the RNAi element (FIG. 1). In the absence of inducing agent, some leakiness of the expression from the minimal promoter is expected.

Three additional vectors were made that differed from phaA-RNAi/35S in either the target of their RNAi element or the promoter used for expression of the chimeric ecdysone receptor (GRVH) (Table 3).

Figure 2:
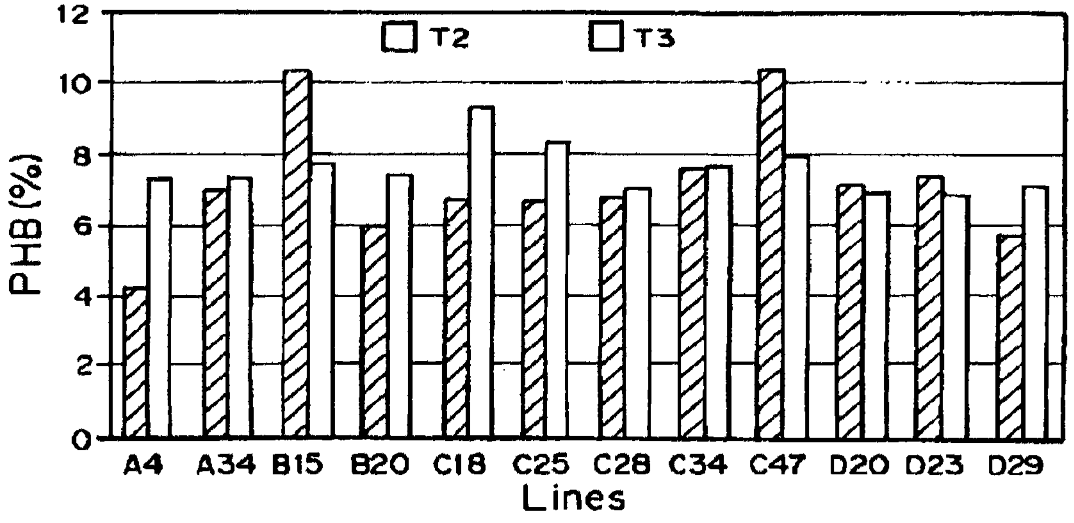
FIG. 2 is a bar graph showing percent PHB content in select T2 and T3 PHB producing seeds obtained from transformations of vectors containing the PHB pathway genes and a cassette for siRNA to either the thiolase or synthase gene. A lines were obtained from transformations with vector pPhaA-RNAi/35S. B lines were obtained from transformations with vector pPhaA-RNAi/glyP. C lines were obtained from transformations with vector pPhaC-RNAi/35S. D lines were obtained from transformations with vector pPhaC-RNAi/glyP.

Transgenic Camelina plants were produced as described previously and transformed seeds were isolated by visual screening of DsRed expression. Seeds were germinated and plants were grown in a greenhouse and treated with methoxyfenozide inducing agent during flowering and seed formation. A portion of the seed was used for analysis of PHB. Seeds containing 10% PHB were isolated (FIG. 2). T2 seeds were placed on a piece of filter paper and soaked in inducing agent prior to transfer to soil.

T2 seeds from the above transformations were germinated and grown in soil in a greenhouse producing T2 seedlings. Untreated T2 plants were allowed to set seed and T3 seeds from select lines were collected and the polymer content was measured using the previously described gas chromatography/butanolysis procedures. Several lines producing greater than 7% dwt PHB in both the T2 and T3 generations were obtained (FIG. 3). No difference between plants treated with inducing agent or treated with water was observed. This suggests that the inducible promoter element is not controllable under the conditions used for the experiments but that there is some basal level of expression from the minimal promoter in front of the RNAi element.

The germination and survival of select seeds were analyzed under high light conditions (up to 1250 microMoles $m^{-2}$ $s^{-1}$ light intensity) at a constant temperature of 14° C. and their survival rate was compared to seeds obtained from pMBXS364 transformations and wild-type seeds (Table 4). Seeds were tested in high light conditions since high PHB producing lines obtained from transformations with pMBXS490 and pMBXS364 in general possess whitish cotyledons that might be impaired in photosynthesis. The lighting program used in the HID chamber was as follows: 6 am to 7 am, 300 microMoles $m^{-2}$ $s^{-1}$; 7 am to 8 am, 750 microMoles $M^{-2}s^{-1}$; 8 am to 3 pm, 1250 microMoles $m^{-2}$ $s^{-1}$; 3 pm to 5 pm, ramp down from 1250 to microMoles $m^{-2}s^{-1}$; 5 pm to 6 am, no light. Under these conditions, 80% of the control wild-type line survived after 18 days under high light growth conditions. None of the pMBXS364 lines survived these growth conditions. The majority of the RNAi lines tested possessed greater than 50% survival, with some as high as 85-95%.

TABLE 4

Survival of RNAi Lines Compared to Wild-type and pMBXS364 Lines Grown Under High Light Conditions

| Transformation Construct | Line | % PHB | % survivability in high light growth chamber* |
|---|---|---|---|
| phaA-RNAi/35S | A18 | 7.15 | 95 |
| phaC-RNAi/35S | C5 | 7.92 | 85 |
| phaA-RNAi/glyP | B12 | 5.54 | 85 |
| phaA-RNAi/35S | A8 | 5.1 | 85 |
| wild-type | Celine | 0 | 85 |
| phaC-RNAi/35S | C39 | 6.43 | 80 |
| phaA-RNAi/glyP | B1 | 6.5 | 70 |
| phaA-RNAi/35S | A31 | 5.5 | 70 |
| phaA-RNAi/glyP | B15 | 7.77 | 60 |
| phaC-RNAi/35S | C28 | 7.09 | 60 |
| phaC-RNAi/35S | C47 | 8 | 50 |
| phaA-RNAi/35S | A34 | 7.74 | 30 |
| phaA-RNAi/35S | A4 | 7.45 | 25 |
| phaA-RNAi/glyP | B14 | 6.1 | 25 |
| phaC-RNAi/glyP | D29 | 7.14 | 0 |
| pMBXS364 | 284A | 4.4 | 0 |
| pMBXS364 | 328A | 8 | 0 |

*20 seeds of each line were planted to measure survivabilty

High PHB containing seeds can be screened for germination ability prior to planting in soil by plating the seeds on wet filter paper to determine if they germinate. If seeds are impaired in germination or possess chlorotic seedlings, this filter paper can be transferred to tissue culture medium containing ½×MS agar medium (prepared from Murashige & Skoog salts with vitamins, Caisson Labs, MSP09) supplemented with 2% sucrose,

Example 6

Managing Gene Expression During Germination, Controlled Polymer Degradation During Germination To prevent or limit PHB formation during seed germination, constructs were designed containing genes encoding a pathway for controlled polymer degradation during seed germination. PHB production would proceed during seed formation and polymer degradation would occur during seed germination (FIG. 3). Genes encoding PHA depolymerase and 3-hydroxybutyrate dehydrogenase were chosen for degradation of polymer. These genes are expected to convert PHB to 3-hydroxybutyrate and 3-hydroxybutryate to acetoacetate, compounds that could be further metabolized by the germinating seedling. Since construct pMBXS490 enabled high PHB production, albeit with poor germination/seedling survival, it was used as a starting plasmid to build future transformation constructs. Plant transformation construct pMBXVT1, is a pCAMBIA based vector containing seed specific expression of PHA genes and cassettes for expression of the depolymerase and 3-hydroxybutyrate dehydrogenase under the control of germination specific promoters. Expression cassettes for the PHB biosynthetic genes and DsRed are as described for pMBXS490. Additional expression cassettes in pMBXVT1 are as follows: 1) an expression cassette for depolymerase containing the promoter from *Vigna mungo* sulphydryl-endopeptidase gene (SH-EP promoter; Akasofu et al., 1990 Nucleic Acids Research. 18, 1892), a DNA fragment encoding the signal peptide and the first 24 amino acids of the mature protein of the small subunit of rubisco from pea, a DNA fragment encoding an intracellular polyhydroxybutyrate depolymerase (PhaZal) from *Ralstonia eutropha* (Saegusa et al., 2001, J. Bacteriol. 183, 94-100), and a termination sequence from the *Pisum sativum* rbcS-E9 gene; 2) an expression cassette for 3-hydroxybutyrate dehydrogenase containing the SH-EP promoter, a DNA fragment encoding the signal peptide and the first 24 amino acids of the mature protein of the small subunit of rubisco from pea, a DNA fragment encoding D(−)-3-hydroxybutyrate dehydrogenase (hbdh) from *Pseudomonas fragi* (Ito et al., 2006 J. Mol. Biol. 355, 722-733), and the termination sequence from the *Pisum sativum* rbcS-E9 gene.

Figure 4:
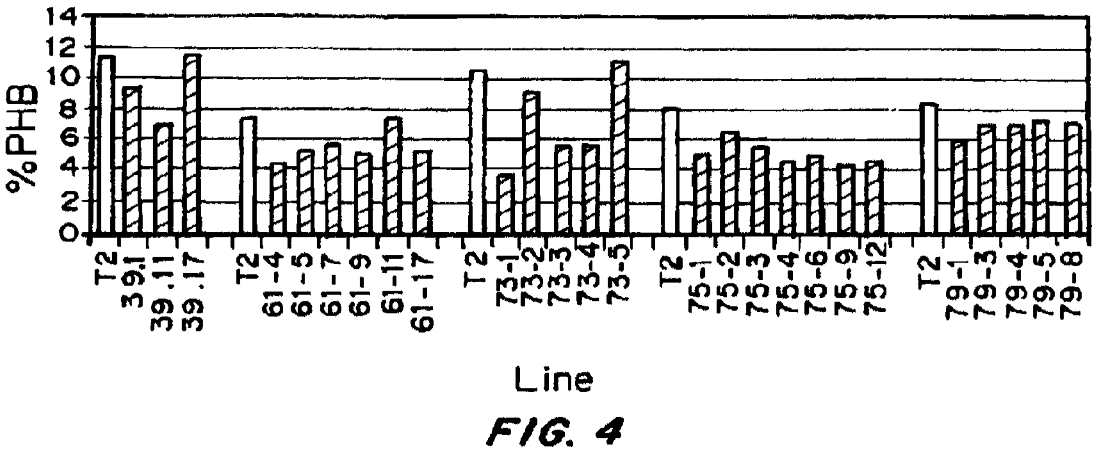
FIG. 4 is a bar graph showing percent PHB content in select T2 and T3 PHB producing seeds obtained from transformations of vector pMBXVT1 containing the PHB pathway genes expressed under the control of seed specific promoters and expression cassettes for a degradation pathway consisting of depolymerase and dehydrogenase expressed under the control of a germination specific promoter.

Construct pMBXVT1 was transformed into *Camelina* as previously described and $T_1$ seeds were selected by visualization of DsRed. $T_1$ seeds were either planted directly into soil or germinated on filter paper and transplanted into soil. The resulting $T_2$ seeds were tested for PHB using the previously described gas chromatography/butanolysis techniques. $T_2$ seeds containing up to 11.3% PHB were isolated (Table 5) however these seeds produced seedlings that did not survive in soil conditions. Germination of $T_2$ seeds on filter paper was measured and the percent survival was calculated. One line containing 5.75% PHB with 100% survival in soil was isolated. Lines that possessed severely impaired germination in soil or on filter paper (i.e. line containing 11.3% PHB) were rescued by germination on tissue culture medium as follows. Seeds were surface sterilized with 70% alcohol for 2 minutes and with 10% commercial bleach for 10 minutes. The seeds were washed thoroughly at least 3 times with sterile water before transferring them on to agar plates. Seeds were cold treated at 4° C. by plating them on agar media containing ½ strength Murashige and Skoog basal salts and Gamborg's vitamins (Sigma Chemical Company, St. Louis, Mo.) supplemented with 2% sucrose. Plates were incubated at 4° C. for 72 hours and then transferred to a tissue culture chamber set at 20° C. Seedlings were transferred to soil once they had obtained true leaves and were then transferred to the greenhouse. $T_3$ seeds were generated from the $T_2$ lines and evaluated for PHB content. A graph comparing T2 and T3 seeds from select lines is shown in FIG. 4.

TABLE 5

% PHB and % Survival in Select Lines Transformed with Vector pMBXVTI

| T1 Lines | % PHB in T2 Seeds | % Survival of T2 seedlings* | T2 seedling phenotype |
|---|---|---|---|
| 18 | 0 | 100% | Green |
| 65 | 2.67 | 100% | Green |
| 13 | 4.18 | 100% | Green |
| 41 | 5.75 | 100% | Chlorotic |
| 60 | 6.13 | 75% | Chlorotic |
| 24 | 6.38 | 0 | Albino |
| 61 | 7.41 | 0 | Albino |
| 39 | 11.34 | 0 | Albino |

*% survival after germination on filter paper, transfer to soil, and growth in a greenhouse Additional transformation vectors for inducible expression of the PHB depolymerase and 3-hydroxybutyrate dehydrogenase were also constructed. These constructs contain the expression cassettes of pMBXS490 for the PHB biosynthetic pathway and DsRed genes as well as inducible expression cassettes for PHB depolymerase and 3-hydroxybutyrate dehydrogenase. The inducible expression cassettes rely on the binding of a chimeric receptor (VP16:GAL4:CfEcR gene), whose expression is under the control of a constitutive promoter, to the inducing agent and response element (FIG. 1). The chimeric receptor contains a transcriptional activation domain from Herpes simplex viral protein (VP16 AD), a binding domain from yeast GAL4 transcription activator (GAL4 DBD), and a ligand binding domain from the *Choristoneura fumiferana* ecdysone receptor (CfEcR). This binding initiates transcription of the PHB depolymerase and 3-hydroxybutyrate dehydrogenase genes placed behind a DNA sequence containing a minimal 35S promoter with five copies of the 19 bp yeast GAL4 response elements upstream of the minimal promoter for chemical induction. Upon addition of a chemical inducing agent, the chimeric receptor protein transactivates expression of the target gene(s) cloned under the control of the GAL4 response elements and the minimal promoter. Four separate constructs were constructed that differ in the length of their minimal promoter sequence and/or the promoter that drives the expression of the chimeric receptor (Table 6).

TABLE 6

Inducible promoter constructs for expression of PIM depolymerase and 3-hydroxybutyrate dehydrogenase.

| Vector | Minimal promoter sequence | Promoter driving expression of chimeric receptor* |
|---|---|---|
| pMBXVT3 | −46 | MMV promoter |
| pMBXVT4 | −31 | MMV promoter |
| pMBXVT5 | −46 | SH-EP promoter |
| pMBXVT6 | −31 | SH-EP promoter |

*MMV promoter, constitutive promoter from mirabilis mosaic virus

*SH-EP promoter, germination specific promoter from *Vigna mungo* sulphydryl-endopeptidasegene With these constructs, the addition of inducing agent was expected to yield good expression of the PHB depolymerase and 3-hydroxybutyrate dehydrogenase at the growth stage in which the inducing agent was applied. In the absence of inducing agent, a basal level of expression due to the leakiness of the promoter was expected.

Constructs were transformed into *Camelina*, using the transformation methods described above, and the chemical inducing agent was applied from flowering to harvest of the $T_1$ seeds. The chemical inducing agent used for this purpose was methoxyfenozide applied to the plants in the form of the commercial pesticide Intrepid (Dow AgroSciences, Indianapolis, Ind.). Concentrations for application ranged from 66 to 100 μM. Intrepid was also applied during germination of $T_1$ seeds, and again from flowering to harvest of the $T_2$ seeds. The $T_2$ seeds were then split into two groups. The first received no inducing agent (allowing the accumulation of PHB in the seeds). The other was treated with the inducing agent to limit PHB accumulation in the seeds, possibly improving seed germination. No significant difference in the levels of PHB in seeds that had been treated with Intrepid during flowering and seed development were observed compared to controls.

The survival of $T_2$ seedlings was determined by germinating seeds on filter paper and then transferring seedlings to soil (Table 7). $T_2$ seeds with poor germination were rescued by germinating on ½ strength Murashige and Skoog basal salts with Gamborg's vitamins supplemented with 2% sucrose as described above. Lines were grown in the greenhouse to produce $T_3$ seeds.

TABLE 7

% PHB and % Survival in Select Lines Transformed with Vectors pMBXVT3, pMBXVT4, pMBXVT5, and pMBXVT6

| Construct | Ti Line | % PHB in T2 seeds | Survival of T2 seedlings* | T2 seedling phenotype |
|---|---|---|---|---|
| pMBXVT3 | 2 | 0 | 100% | Green |
| | 66 | 2.39 | 100% | Chlorotic |
| | 71 | 7.11 | 35% | Chlorotic |
| | 72 | 7.66 | 0 | Albino |
| | 70 | 8.17 | 75% | Chlorotic |
| | 74 | 9.51 | 0 | Albino |
| pMBXVT4 | 36 | 0 | 100% | Green |
| | 42 | 4.53 | 100% | Chlorotic |
| | 48 | 8.04 | 30% | Albino |
| | 49 | 8.34 | 0 | Albino |
| | 54 | 9.1 | 70% | Albino-chlorotic |
| | 56 | 9.14 | 30% | Chlorotic |
| | 22 | 9.6 | 0 | Albino |
| | 57 | 12.32 | 0 | Albino |
| pMBXVT5 | 4 | 0 | 100% | Green-chlorotic |
| | 15 | 2.74 | 100% | Chlorotic |
| | 10 | 9.24 | 0 | Albino |
| pMBXVT6 | 1 | 0 | 100% | Green |
| | 6 | 3.46 | 100% | Chlorotic |
| | 9 | 8.86 | 10% | Albino |
| | 8 | 10.19 | 0 | Albino |
| | 5 | 10.75 | 0 | Albino |

*% survival after germination on filter paper, transfer to soil, and growth in a greenhouse.

Since the $T_2$ seeds from these lines had in general better germination and seedling viability than seeds obtained from transfounations with plasmid pMBXS490, leaky expression from the inducible promoter controlling the expression of depolymerase and 3-hydroxybutyrate dehydrogenase may have occurred such that sufficient amounts of these enzymes are produced to increase germination and seedling viability of high PHB producing seeds without significantly compromising PHB yield.

$T_2$ seeds that were unable to germinate and survive on filter paper were rescued by germinating on ½ strength Murashige and Skoog basal salts with Gamborg's vitamins supplemented with 2% sucrose and 15 μM methoxyfenozide as described above. All lines were grown in the greenhouse to produce $T_3$ seeds.

High PHB containing seeds can be screened for germination ability by plating the seeds on wet filter paper to determine if they germinate. If seeds are impaired in germination or possess chlorotic seedlings, this filter paper can be transferred to tissue culture medium containing ½×MS agar medium (prepared from Murashige & Skoog salts with vitamins, Caisson Labs, MSP09) supplemented with 2% sucrose,

Example 7

Expression of Depolymerase and 3-Hydroxybutyrate Dehydrogenase using a Heat Shock Promoter Plasmid pMBXS430 was prepared to test the use of a heat shock inducible promoter to control expression of depolymerase and 3-hydroxybutyrate dehydrogenase genes. This plasmid is the same as pMBXVT1 with the exception that the germination specific promoter controlling the expression of depolymerase and 3-hydroxybutyrate dehydrogenase genes has been replaced by a heat shock inducible promoter from the soybean small heat shock (Gmhsp17.5E) gene (Czarnecka, E. et al., 1989, Mol. Cell. Biol. 9, 3457-3463). Plasmid pMBXS430 was transformed into Camelina according to the methods described above and seeds were screened for DsRed expression. Isolated $T_1$ seeds were germinated on ½×MS agar medium (Murashige & Skoog salts with vitamins, Caisson Labs, MSP09) supplemented with 2% sucrose, transferred to soil in the greenhouse, and allowed to set seed. $T_2$ seeds were analyzed for PHB levels (FIG. 26). Up to 11.63% PHB was obtained. A homozygous plant derived from this line produced up to 11.64% PHB in T3 seeds.

Example 8

Production of Hybrid Lines that are not Capable of Germinating

In previous experiments in *Arabidopsis*, lower levels of PHB were obtained when lines expressing individual PHB genes were crossed to produce a plant containing the entire PHB biosynthetic pathway (Nawrath, C., Y. Poirier, et al., 1994, Proc. Natl. Acad. Sci. USA 91, 12760-12764) than when multi-gene constructs containing the entire PHB biosynthetic pathway were constructed and transformed (Bohmert, K., I. et al., 2000, Planta 211, 841-845;U.S. Pat. No. 6,448,473). This observation led to the subsequent predominant use of multi-gene constructs for PHB production in plants. However, in some scenarios, it may be advantageous to insert a multi-gene pathway into the plant by crossing of lines containing portions of the pathway to produce hybrid plants in which the entire pathway has been reconstructed. This is especially the case when high levels of product in a seed compromises the ability of the seed to germinate or the resulting seedling to survive under normal soil growth conditions. Hybrid lines can be created by crossing a line containing one or more PHB genes with a line containing the other gene(s) needed to complete the PHB biosynthethic pathway. Use of lines that possess cytoplasmic male sterility (Esser, K. et al., 2006, Progress in Botany, Springer Berlin Heidelberg. 67, 31-52) with the appropriate maintainer and restorer lines allows these hybrid lines to be produced efficiently. Cytoplasmic male sterility systems are already available for some Brassicaceae species (Esser, K. et al., 2006, Progress in Botany, Springer Berlin Heidelberg. 67, 31-52). These Brassicaceae species can be used as gene sources to produce cytoplasmic male sterility systems for other oilseeds of interest such as Camelina. Cytoplasmic male sterility has also been reported upon expression of a β-ketothiolase from the chloroplast genome in tobacco (Ruiz, O. N. and H. Daniell, 2005, Plant Physiol. 138, 1232-1246). Male sterility has also been reported upon expression of the faoA gene encoding the α-subunit of the fatty acid β-oxidationcomplex from *Pseudomonas putida* (U.S. Pat. No. 6,586,658).

Figure 5:
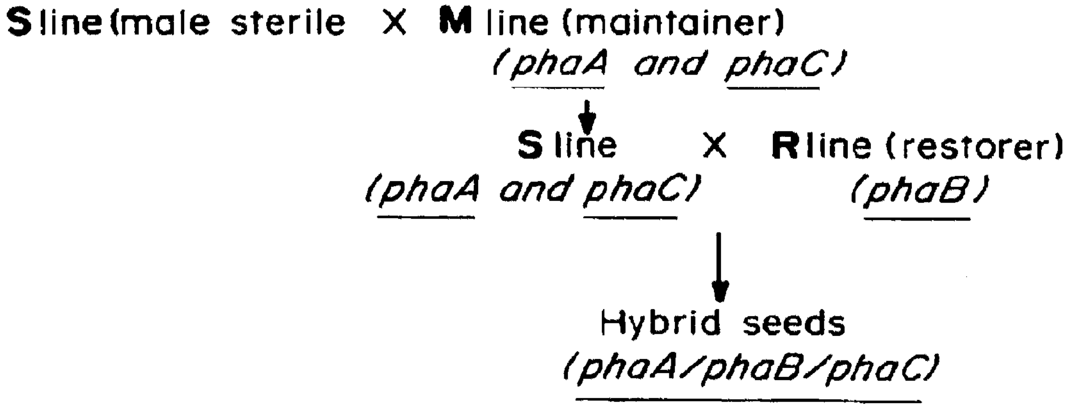
FIG. 5 is a schematic diagram describing a strategy for creating hybrid seeds using cytoplasmic male sterility.

High PHB producing lines that are not capable of germination can be produced using oilseed lines that possess cytoplasmic male sterility (CMS) controlled by an extranuclear genome (i.e. mitochondria or chloroplast). The male sterile line is typically maintained by crossing with a maintainer line that is genetically identical except that it possesses normal fertile cytoplasm and is therefore male fertile. Transformation of the maintainer line with one or more genes for the PHB biosynthetic pathway and crossing this modified maintainer line [FIG. 5, M line (phaA and phaC)] with the original male sterile line [FIG. 5, S line (CMS)] will produce a male sterile line possessing a portion of the PHB biosynthetic pathway. In this example, insertion of the phaA and phaC genes into the maintainer line and crossing with the original male cytoplasmic sterile line will form a male sterile line containing the phaA and phaC genes [FIG. 5, S line, (phaA and phaC)].

Fertility can be restored to this line using a "restorer line" that carries the appropriate nuclear restorer genes. Alternatively, the restorer line can be transformed with the remaining genes required to complete the PHB biosynthetic pathway [FIG. 5, R line (phaB)] and crossed with the previously created male sterile line containing phaA and phaC [FIG. 5, S line (phaA and phaC)] to produce a hybrid line containing the entire PHB biosynthetic pathway [FIG. 5, Hybrid seeds (phaA, phaB, and phaC)].

Crosses can be performed in the field by planting multiple rows of the male sterile line, the line that will produce the seed, next to a few rows of the male fertile line. Harvested seed can be used for subsequent plantings or as the PHB containing seed for crushing and extraction. When expression cassettes for the PHB genes in this example are controlled by strong promoters, such as the soybean oleosin promoter, high PHB producing seeds generated in this manner will possess weak seedlings upon germination and will not be able to survive field conditions under normal growth circumstances unless treated with a material that promotes seedling strength/vigor. This adds a level of gene containment.

Cytoplasmic male sterility systems are already available for some Brassicaceae species (Esser, K., 2006, Progress in Botany, Springer Berlin Heidelberg. 67, 31-52). These Brassicaceae species can be used as gene sources to produce cytoplasmic male sterility systems for other oilseeds of interest such as Camelina. Cytoplasmic male sterility has also been reported upon expression of a β-ketothiolase from the chloroplast genome in tobacco (Ruiz, O. N. and H. Daniell, 2005, Plant Physiol. 138, 1232-1246). Overexpression of β-ketothiolase in Camelina to generate a male sterile line and subsequent crossing with a line expressing phaB and phaC could also be used for hybrid seed production.

Male sterile lines have also been produced in Brassica napus by overexpression of the faoA gene from Pseudomonas putida under the control of the a phaseolin promoter sequence (U.S. Pat. No. 6,586,658).

Double haploid technology can be used to speed up the breeding process. In the double haploid technique, immature pollen grains (haploids) are exposed to treatments that result in doubling of the existing genetic material resulting in homozygous, true breeding material in a single generation.

Example 9

Improved Germination Efficiency of High PHB Producing Seeds Using Promoters that are not Active or Minimally Active During Seed Germination and Seedling Development Use of a promoter for expression of PHB genes that is active during seed development but inactive or minimally active during seed germination and seedling development would allow the production of high PHB producing seeds that can readily germinate under field conditions. To determine if candidate promoters in our PHB production constructs were active during germination, each promoter was put in an expression cassette with the reporter gene β-glucuronidase (GUS). Seedlings were germinated and seedlings were stained with X-Gluc (5-bromo-4-chloro-3-indolylbeta-D-glucuronide). GUS expression was observed with all seed specific promoters tested in germinating seedlings (Table 8). In addition, promoters from the lesquerella hydroxylase gene, the napin gene, and the glycinin gene yielded GUS staining in their first true leaves.

TABLE 8

GUS expression patterns of seed specific promoters during seed formation and germination.

| | GUS expression during seed formation, Days after flowering (DAF) | | | | | GUS expression during seed germination, Days after Germination (DAG) | | Staining in true leaf |
|---|---|---|---|---|---|---|---|---|
| Promoter | 4 DAF | 6 DAF | 8 DAF | 10 DAF | 12 DAF | 1 DAG | 10 DAG | (7 to 10 DAG) |
| 35S | ND* | ND | ND | ND | ND | 8 | 8 | 8 |
| LH | 0 | 1 | 3 | 8 | 9.5 | 8 | 8 | 8 |
| Oleosin | 0.5 | 1.2 | 1.5 | 7 | 10 | 8 | 8 | 0 |
| P3 | 0 | 2 | 3 | 6 | 10 | 8 | 8 | 0 |
| Napin | 3 | 4 | 9 | 10 | 10 | 8 | 8 | 8 |
| Glycinin | 3 | 4 | 9 | 10 | 10 | 8 | 8 | 8 |

*ND, not determined;
Numbers represent qualitative, visual measurement of staining intensity (0 = no staining, 10 = dark blue staining).
Promoters are as follows: 35S, promoter from the cauliflower mosaic virus 35S gene; LH, promoter from the Lesquerella fendleri bifunctional oleate 12-hydroxylase:saturate gene; Oleosin, promoter from the soybean oleosin isoform A gene; P3, promoter from a seed specific gene in Arabidopsis thaliana (U.S. Pat. No. 7,405,345); Napin, promoter from the Brassica napus napin gene; Glycinin, promoter from the soybean glycinin (gy1) gene.

A search for candidate promoters that were active during seed development but inactive or minimally active during seed germination was performed using a filtered DNA microarray dataset of 9,611 genes from Arabidopsis (Le et al., 2010, Proc. Natl. Acad. Sci. USA, 107, 8063-8070).

Unbiased hierarchical clustering (Eisen et al., 1998, Proc. Natl. Acad. Sci. USA 95:14863-14868) of the filtered microarray dataset was performed with five manually defined reference profiles (Table 9). Reference profile 1 was set to be highly expressed at the 24-h post-pollination seed. Reference profiles 2 and 3 were set to be highly expressed in both the globular-stage and cotyledon-stage seed, since these stages are developmentally close and were identified to exhibit similar expression patterns. Reference profiles 4 and 5 were also set to be highly expressed in both the mature-green-stage and postmature-green-stage seed. All non-seed stages, including the unfertilized ovule, seedling, leaf, root, stem, and floral buds were set to zero.

TABLE 9

Predefined search profiles to identify genes with similar expression patterns.

| Reference Profiles | OV | 24H | GLOB | COT | MG | PMG | SDLG | L | R | S | F |
|---|---|---|---|---|---|---|---|---|---|---|---|
| Ref1_24H | 0 | 10,000 | 1,000 | 500 | 200 | 20 | 0 | 0 | 0 | 0 | 0 |
| Ref2_GLOB | 0 | 1,000 | 10,000 | 5,000 | 200 | 20 | 0 | 0 | 0 | 0 | 0 |
| Ref3_COT | 0 | 200 | 5,000 | 10,000 | 200 | 20 | 0 | 0 | 0 | 0 | 0 |
| Ref4_MG | 0 | 50 | 200 | 200 | 10,000 | 5,000 | 0 | 0 | 0 | 0 | 0 |
| Ref5_PGM | 0 | 50 | 200 | 200 | 5,000 | 10,000 | 0 | 0 | 0 | 0 | 0 |

*Abbreviations are as follows: OV, unfertilized ovule; 24H, 24-h postpollination seed; GLOB, globular-stage seed; COT, cotyledon-stage seed; MG, mature-green-stage seed; PMG, postmature-green-stage seed; SDLG, seedling; L, leaf; R, root; S, stem; F, floral buds.

Hierarchical clustering analysis identified several genes which showed similar expression patterns as the five reference profiles. Genes with expression values in non-seed stages were removed from the set of identified genes. 81 genes whose promoter region may be suitable for PHB production in seeds with little to no PHB gene expression in seedlings were identified (Table 10).

TABLE 10

Genes in *Arabidopsis thaliana* with the pre-defined seed specific expression profiles identified by genome-wide similarity analysis.

| AGI ID | 24H | GLOB | COT | MG | PMG | Functional Category | Descriptions |
|---|---|---|---|---|---|---|---|
| 24H genes (ref1_24H) | | | | | | | |
| AT4G13090 | 303 | | | | | Cell Structure | xyloglucan:xyloglucosyl transferase, |
| GLOB genes (ref2_GLOB) | | | | | | | |
| AT3G28490 | | 155 | | | | Secondary Metabolism | oxidoreductase, 2OG-Fe(II) oxygenase family protein |
| AT3G03260 | | 505 | 165 | | | Transcription | homeobox-leucine zipper family protein/ lipid-binding START domain-containing protein |
| AT5G09490 | | 1019 | 438 | | | Protein Synthesis | 40S ribosomal protein S15 (RPS15B) |
| AT2G17750 | | 1045 | 449 | | | Unclassified-Proteins With cDNA Support | similar to unknown protein [*Arabidopsis thaliana*] |
| AT2G43660 | | 1477 | 614 | | | Cell Structure | glycosyl hydrolase family protein 17 |
| AT5G46040 | 423 | 2556 | 1110 | | | Transporter | proton-dependent oligopeptide transport (POT) family protein |
| AT5G46820; AT5G46810 | | 3108 | 1072 | | | Protein Destination & Storage | similar to unknown protein [*Arabidopsis thaliana*] |
| AT1G49800 | | 4482 | 1552 | | | Unclassified-Proteins With cDNA Support | unknown protein |
| COT genes (ref3_COT) | | | | | | | |
| AT2G26320 | | 108 | 191 | | | Transcription | MADS-box protein (AGL33) |
| AT5G63740 | | 121 | 196 | | | Unclassified-Proteins With Unknown Function | zinc finger protein-related |
| AT5G23650 | | 158 | 301 | | | Transcription | myb family transcription factor |
| AT4G22400 | | 324 | 305 | | | Unclassified-Proteins With cDNA Support | similar to unknown protein [*Arabidopsis thaliana*] (TAIR:AT4G18320.1) |
| AT1G20730 | | 196 | 308 | | | Unclassified-Proteins With Unknown Function | similar to metal ion binding [*Arabidopsis thaliana*] |

TABLE 10-continued

Genes in *Arabidopsis thaliana* with the pre-defined seed specific expression profiles identified by genome-wide similarity analysis.

| AGI ID | 24H | GLOB | COT | MG | PMG | Functional Category | Descriptions |
|---|---|---|---|---|---|---|---|
| AT4G29620 | | 315 | 322 | | | Metabolism | cytidine deaminase, putative/cytidine aminohydrolase, putative |
| AT1G61330; AT1G61320 | | 304 | 327 | | | Unclassified-Proteins With Unknown Function | [AT1G61330, F-box family protein] |
| AT1G16980 | | 349 | 441 | | | Metabolism | ATTPS2 (*Arabidopsis thaliana* trehalose-phosphatase/synthase 2); |
| AT1G61090 | | 242 | 471 | | | Unclassified-Proteins With cDNA Support | similar to unknown protein [*Arabidopsis thaliana*] (TAIR:AT1G61095.1) |
| AT3G03410 | | 464 | 755 | | | Signal Transduction | calmodulin-related protein, putative |
| AT2G03190 | | 688 | 873 | | | Protein Destination & Storage | ASK16 (*ARABIDOPSIS* SKP1-LIKE 16); ubiquitin-protein ligase |
| AT1G62340 | | 561 | 965 | | | Protein Destination & Storage | ALE1 (ABNORMAL LEAF SHAPE 1); subtilase |
| AT5G39440 | | 634 | 1356 | | | Signal Transduction | SnRK1.3 (SNF1-RELATED PROTEIN KINASE 1.3); kinase |
| AT2G20160 | 235 | 1118 | 1390 | | | Protein Destination & Storage | MEO (MEIDOS); ubiquitin-protein ligase |
| AT5G07260 | | 908 | 1564 | 472 | | Transcription | homeobox protein-related |
| AT5G10220 | | 1539 | 1834 | | | Intracellular Traffic | ANN6 (ANN6, ANNEXIN *ARABIDOPSIS* 6); |
| AT2G32370 | | 1208 | 2373 | | | Transcription | homeobox-leucine zipper family protein |
| MG genes (ref4_MG) | | | | | | | |
| AT3G29190 | | | | 374 | | Secondary Metabolism | terpene synthase/cyclase family protein |
| AT5G20420 | | | | 411 | | Transcription | CHR42 (chromatin remodeling 42); ATP binding/DNA binding/ helicase |
| AT1G65670 | | | | 548 | | Metabolism | CYP702A1 (CYTOCHROME P450, FAMILY 702, SUBFAMILY A, POLYPEPTIDE 1); oxygen binding |
| AT1G25270 | | | 74 | 669 | 291 | Unclassified-Proteins With Unknown Function | similar to nodulin MtN21 family protein [*Arabidopsis thaliana*] |
| AT3G04370 | | | | 675 | 354 | Protein Destination & Storage | similar to 33 kDa secretory protein-related [*Arabidopsis thaliana*] |
| AT5G20860 | | | | 918 | 468 | Cell Structure | pectinesterase family protein |
| AT1G19200 | | | | 923 | 480 | Metabolism | senescence-associated protein-related |
| AT3G02940 | | | | 1058 | 504 | Transcription | MYB107 (myb domain protein 107); DNA binding/transcription factor |
| AT3G04190; AT3G04180 | | | | 1503 | 613 | Protein Destination & Storage | [AT3G04190, germin-like protein, putative];[AT3G04180, germin-like protein, putative] |

TABLE 10-continued

Genes in *Arabidopsis thaliana* with the pre-defined seed specific expression profiles identified by genome-wide similarity analysis.

| AGI ID | 24H | GLOB | COT | MG | PMG | Functional Category | Descriptions |
|---|---|---|---|---|---|---|---|
| AT4G26200 | | 110 | 532 | 1899 | 1372 | Secondary Metabolism | ACS7 (1-Amino-cyclopropane-1-carboxylate synthase 7) |
| AT4G25980 | | | | 1922 | 673 | Disease & Defense | cationic peroxidase, putative |
| AT3G44460 | | | 131 | 2459 | 1602 | Transcription | DPBF2 (BASIC LEUCINE ZIPPER TRANSCRIPTION FACTOR 67) |
| AT5G07500 | | | 283 | 2533 | 1287 | Transcription | PEI1; nucleic acid binding/transcription factor |
| AT1G09500 | | 167 | 238 | 3736 | 1929 | Cell Structure | cinnamyl-alcohol dehydrogenase family/ CAD family |
| AT3G26790 | | 110 | 1666 | 4347 | 3489 | Transcription | FUS3 (FUSCA 3); DNA binding/transcription factor |
| AT3G04170 | | | | 5495 | 2836 | Disease & Defense | germin-like protein, putative |
| AT5G09640 | | | 294 | 6073 | 5155 | Protein Destination & Storage | SNG2 (SINAPOYLGLUCOSE ACCUMULATOR 2); serine carboxypeptidase |
| AT2G41400; AT2G41390 | | | | 6470 | 3905 | Unclassified-Proteins With cDNA Support | [AT2G41400, similar to unknown protein [*Arabidopsis thaliana*] |
| AT5G62800 | | 165 | 647 | 8770 | 6241 | Protein Destination & Storage | seven in absentia (SINA) family protein |
| AT1G68380 | | 391 | 644 | 10065 | 5196 | Unclassified-Proteins With cDNA Support | similar to unknown protein [*Arabidopsis thaliana*] (TAIR:AT1G68390.1) |
| AT4G34520 | | | 872 | 13764 | 7891 | Metabolism | FAE1 (FATTY ACID ELONGATION1); acyltransferase |
| PMG genes (ref5_PMG) | | | | | | | |
| AT2G13230 | | | | | 243 | | Transposon |
| AT5G65070 | | | | 170 | 290 | Transcription | AGL69, AT5G65070.1, F15O5.3, F15O5_3, FCL4, MADS AFFECTING FLOWERING 4, MAF4 |
| AT1G28640 | | | 116 | 611 | 872 | Metabolism | GDSL-motif lipase, putative |
| AT3G44830 | | | 167 | 746 | 1463 | Metabolism | lecithin:cholesterol acyltransferase family protein/LACT family protein |
| AT5G27160 | | | | 955 | 2127 | Unclassified-Proteins With NO cDNA Support | similar to unknown protein [*Arabidopsis thaliana*] (TAIR:AT4G07520.1) |
| AT2G47120 | | | | 2135 | 2508 | Metabolism | short-chain dehydrogenase/reductase (SDR) family protein |
| AT5G04380 | | | | 1613 | 3626 | Secondary Metabolism | S-adenosyl-L-methionine:carboxyl methyltransferase family protein |
| AT2G05580 | | | | 1854 | 4694 | | Pseudogene |
| AT2G19320 | | | | 2711 | 6063 | Unclassified-Proteins With cDNA Support | unknown protein |
| AT1G80090 | | | | 4279 | 9624 | Intracellular Traffic | CBS domain-containing protein |

TABLE 10-continued

Genes in *Arabidopsis thaliana* with the pre-defined seed specific expression profiles identified by genome-wide similarity analysis.

| AGI ID | 24H | GLOB | COT | MG | PMG | Functional Category | Descriptions |
|---|---|---|---|---|---|---|---|
| AT1G29680 | | | | 7245 | 14695 | Unclassified-Proteins With cDNA Support | similar to unknown protein [*Arabidopsis thaliana*] (TAIR:AT5G45690.1) |
| AT5G55240 | | | | 7153 | 17877 | Metabolism | caleosin-related family protein/embryo-specific protein, putative |
| AT3G60730 | | | | 11623 | 17970 | Cell Structure | pectinesterase family protein |
| AT4G10020 | | | | 8315 | 18624 | Metabolism | short-chain dehydrogenase/reductase (SDR) family protein |
| AT1G65090 | | | 1463 | 16059 | 21943 | Unclassified-Proteins With cDNA Support | similar to unknown protein [*Arabidopsis thaliana*] (TAIR:AT5G36100.1) |
| AT4G31830 | | | | 17553 | 22567 | Unclassified-Proteins With cDNA Support | similar to conserved hypothetical protein [*Medicago truncatula*] (GB:ABE93904.1) |
| AT1G47540 | | | 2019 | 22709 | 23291 | Disease & Defense | trypsin inhibitor, putative |
| AT2G33520 | | | | 8853 | 24230 | Unclassified-Proteins With Unknown Function | similar to proline-rich family protein [*Arabidopsis thaliana*] (TAIR:AT1G12810.1) |
| AT1G17810 | | | | 22927 | 36488 | Transporter | BETA-TIP (BETA-TONOPLAST INTRINSIC PROTEIN); water channel |
| AT3G54940 | | | 932 | 23046 | 39824 | Protein Destination & Storage | cysteine proteinase, putative |
| AT2G15010 | | | | 23354 | 41533 | Disease & Defense | thionin, putative |
| AT4G26740 | | | | 25242 | 42155 | Unclassified-Proteins With Unknown Function | ATS1 (*ARABIDOPSIS THALIANA* SEED GENE 1); calcium ion binding |
| AT3G01570 | | | 863 | 45006 | 56213 | Metabolism | glycine-rich protein/oleosin |
| AT1G48130 | | | | 33289 | 57281 | Disease & Defense | ATPER1 (*Arabidopsis thaliana* 1-cysteine peroxiredoxin 1); antioxidant |
| AT3G27660 | | | 814 | 50089 | 60589 | Protein Destination & Storage | OLEO4 (OLEOSIN4) |
| AT5G40420 | | | 1165 | 43377 | 61168 | Protein Destination & Storage | OLEO2 (OLEOSIN 2) |
| AT1G73190 | | | | 30814 | 61180 | Intracellular Traffic | ALPHA-TIP/TIP3;1 (ALPHA-TONOPLAST INTRINSIC PROTEIN); water channel |
| AT1G03890 | | | | 46026 | 63059 | Protein Destination & Storage | cupin family protein |
| AT1G04560 | | | | 44729 | 65571 | Disease & Defense | AWPM-19-like membrane family protein |
| AT1G05510 | | | | 28938 | 67087 | Unclassified-Proteins With cDNA Support | similar to unknown protein [*Arabidopsis thaliana*] (TAIR:AT2G31985.1) |
| AT2G27380 | | | 1542 | 33222 | 67621 | Cell Structure | ATEPR1 (*Arabidopsis thaliana* extensin proline-rich 1) |
| AT4G25140 | | | 440 | 58084 | 78774 | Protein Destination & Storage | OLEO1 (OLEOSIN1) |

TABLE 10-continued

Genes in *Arabidopsis thaliana* with the pre-defined seed specific expression profiles identified by genome-wide similarity analysis.

| AGI ID | 24H | GLOB | COT | MG | PMG | Functional Category | Descriptions |
|---|---|---|---|---|---|---|---|
| AT4G27160 | | | | 64367 | 78804 | Protein Destination & Storage | 2S seed storage protein 3/ 2S albumin storage protein/NWMU2-2S albumin 3 |
| AT1G03880 | | | | 96008 | 119281 | Protein Destination & Storage | CRU2 (CRUCIFERIN 2); nutrient reservoir |

* Blank cells indicate no gene expression in that seed stage [consensus detection call of "AA", as defined in Le et al. (2010)].
Pre-defined gene expression profiles used to generate data are listed in Table 9.
Abbreviations are as follows: 24H, 24-h post-pollination seed; GLOB, globular-stage seed; COT, cotyledon-stage seed; MG, mature-green-stage seed; PMG, postmature-green-stage seed;

To further narrow down the list of suitable promoters, the following criteria were used: (1) genes were selected that exhibited different temporal profiles, i.e. were highest expressed in a particular seed development stage; (2) genes with medium and high expression levels were chosen and genes with low expression levels were omitted; and (3) preference was given to genes whose function was established. These criteria resulted in the selection of 17 genes, three of which appear to encode isoenzymes due to their high sequence homology (Table 11). Use of the promoters from these genes may lead to seeds with high PHB content and high germination/survival. One skilled in the art will recognize that other suitable promoters may be identified by modifying the predefined search profiles described in Table 9.

TABLE 11

Genes with candidate promoters for high PHB production in seeds that have high germination and survival

| AGI ID | GLOB | COT | MG | PMG | Descriptions |
|---|---|---|---|---|---|
| AT5G46820; AT5G46810 | **3,108** | 1,072 | | | [AT5G46820, similar to unknown protein [*Arabidopsis thaliana*] (TAIR:AT5G46810.1); similar to hypothetical protein 25.t00048 [*Brassica oleracea*] (GB:ABD64955.1); contains InterPro domain Protein of unknown function DUF239, plant; (InterPro: IPR004314)];[AT5 |
| AT5G09490 | **1,019** | 438 | | | 40S ribosomal protein S15 (RPS15B) |
| AT2G32370 | 1,208 | **2,373** | | | homeobox-leucine zipper family protein/ lipid-binding START domain-containing protein |
| AT5G07260 | 908 | **1,564** | 472 | | homeobox protein-related |
| AT1G16980 | 349 | 441 | | | ATTPS2 (*Arabidopsis thaliana* trehalose-phosphatase/ synthase 2); transferase, transferring glycosyl groups |

TABLE 11-continued

Genes with candidate promoters for high PHB production in seeds that have high germination and survival

| AGI ID | GLOB | COT | MG | PMG | Descriptions |
|---|---|---|---|---|---|
| AT4G34520 | | 872 | **13,764** | 7,891 | FAE1 (FATTY ACID ELONGATION1); acyltransferase |
| AT2G41400; AT2G41390 | | | **6,470** | 3,905 | [AT2G41400, similar to unknown protein [*Arabidopsis thaliana*] (TAIR:AT2G41390.1)]; [AT2G41390, similar to unknown protein [*Arabidopsis thaliana*] (TAIR:AT2G41400.1)] |
| AT3G04190; AT3G04180 | | | **1,503** | 613 | [AT3G04190, germin-like protein, putative];[AT3G04180, germin-like protein, putative] |
| AT1G03880 | | | 96,008 | **119,281** | CRUZ (CRUCIFERIN 2); nutrient reservoir |
| AT4G27160 | | | 64,367 | 78,804 | 2S seed storage protein 3/2S albumin storage protein/NWMU2-2S albumin 3 |
| AT4G25140 | | 440 | 58,084 | 78,774 | OLEO1 (OLEOSIN 1) |
| AT5G40420 | | 1,165 | 43,377 | **61,168** | OLEO2 (OLEOSIN 2) |
| AT3G27660 | | 814 | 50,089 | **60,589** | OLEO4 (OLEOSIN 4) |
| AT5G04380 | | | 1,613 | **3,626** | S-adenosyl-L-methionine:carboxyl methyltransferase family protein |

*Numbers in bold indicate the peak expression values of a particular gene in the specified seed development stage. Two AGI ID numbers indicate highly homologous proteins.

Example 10

Increasing Flux through the Calvin Cycle: Design and Construction of Transformation Vectors Expressing a Gene Encoding FBPase/SBPase with Genes Encoding the PHB Biosynthetic Enzymes in Oilseeds Since expression of a gene encoding the FBPase/SBPase gene from *Synechococcus elongatus* PCC 7942 (Miyagawa, Y., 2001, Nat Biotechnol, 19, 965-9) and a SBPase cDNA from *Arabidopsis* (Raines, 2003, *Photosynthesis Research,* 75, 1-10; Lefebvre et al., 2005, *Plant Physiol.* 138, 451-460) have previously been shown to enhance photosynthesis and plant growth when expressed in tobacco, insertion of an expression cassette for this gene into plasmid pMBXS490 was performed to see if the health and survival rate of high PHB producing seedlings could be improved. Transformation vectors pMBXS407 and pMBXS408 were prepared that contain the expression cassettes for plastid targeted PHB enzymes from plasmid pMBXS490 and an additional cassette for expression of a FBPase/SBPase gene under the control of the 355 promoter from the cauliflower mosaic virus. Two different sequences for FBPase/SBPase gene from *Synechococcus elongatus* PCC 7942 are listed in the NCBI database, accession numbers D83512 and CP000100. These two sequences differ at amino acids145 to 148 and at their C-terminus (FIG. 6). Transformation vectors pMBXS407 and pMBXS408 were constructed in which the FBPase/SBPase genes were fused at the 5' end to a DNA sequence encoding a signal peptide of the small subunit of pea and the first 24 amino acids of the mature protein [Cashmore, A. R. (1983). Nuclear Genes Encoding the Small Subunit of Ribulose-1,5-Bisphosphate Carboxylase. Genetic Engineering of Plants. T. Kosuge, Meredith, C. P. & Hollaender, A. New York, Plenum: 29-38] allowing transport of the proteins into the plastids. Transformation vector pMBXS407 contains a gene encoding a FBPase/SBPase with 100% homology to the FBPase/SBPase protein from *Synechococcus elongatus* PCC 7942 listed in accession CP000100. Transformation vector pMBXS408 contains a gene encoding a FBPase/SBPase with 100% homology to the FBPase/SBPase protein from *Synechococcus elongatus* PCC 7942 listed in accession D83512. Even though this gene is listed in accession D83512 as a fructose-1,6-bisphosphatase-I gene, the presence of both FBPase and SBPase activities in the encoded protein has been verified enzymatically (Tamoi, M., et al., 1996, Archives of Biochemistry and Biophysics, 334, 27-36). Transformation vectors pMBXS407 and pMBXS408 were transformed into Camelina and T1 seeds were isolated based on DsRed expression. T1 lines were further propagated and second generation (T2) transgenic seeds were produced. The highest PHB producing lines (i.e. greater than 10% PHB) were generated by germination of seeds in tissue culture medium containing 2% sucrose. The base tissue culture medium was ½×MS agar medium made with Murashige and Skoog medium mixture [Caisson Labs]. Further propagation yielded T3 transgenic seeds that produced PHB at levels up to 13% of the seed weight. Select lines were used in germination trials under controlled greenhouse conditions (Table 12). In general, seedlings generated from the pMBXS407 transformations possessed healthier seedlings and with greater survival rates than seedlings generated from pMBXS408 or pMBXS490 transformations. During the initial stages of growth, transgenic seedlings from the pMBXS407 transformation showed significant increases in growth and biomass production when compared to transgenic seedlings transformed with pMBXS408 and pMBXS490 transformed plants. This increased growth and biomass production persisted through growth of the plants to maturity. The change in shoot biomass in the transgenic plants that may be due to overexpression of the FBPase/SBPase gene in pMBXS407 was correlated to both an increase in stem diameter and leaf surface area.

TABLE 12

PHB content and % survival of T3 linestransformed with construct pMBXS497

| Line | PHB Content (% PHB in Seeds) | % survival 10 to 11 days after planting in soil* |
|---|---|---|
| 407A-9.9-30 | 10.45 | 0 |
| 8-32 | 9 | 55 |
| 8-39 | 8.5 | 65 |
| 8-23 | 8 | 70 |
| 8-25 | 7 | 95 |
| 8-36 | 7 | 45 |
| 78-37 | 6 | 80 |

*Percent survival test performed by germinating seeds directly in soil in a greenhouse To test the effects of plastid targeted, seed specific expression of FBPase/SBPase on PHB production, transformation vector pMBXS511 was prepared. This vector contains the PHB gene and DsRed expression cassettes in pMBXS490 and an additional cassette for expression of the *Synechococcus elongatus* PCC 7942 FBPase/SBPase gene listed in accession gb|CP000100.1 under the control of the seed specific oleosin promoter. In pMBXS511, the plastid targeting sequence from pea including the first 24 amino acids of the mature protein is attached to the 5' end of the FBPase/SBPase to direct the import of the protein into the plastids.

```
Vector: pMBXS490
                                             (SEQ ID NO: 1)
  1  GGGGATCCGT ACGTAAGTAC GTACTCAAAA TGCCAACAAA
     TAAAAAAAAA

 51  GTTGCTTTAA TAATGCCAAA ACAAATTAAT AAAACACTTA
     CAACACCGGA

101  TTTTTTTTAA TTAAAATGTG CCATTTAGGA TAAATAGTTA
     ATATTTTTAA

151  TAATTATTTA AAAAGCCGTA TCTACTAAAA TGATTTTTAT
     TTGGTTGAAA

201  ATATTAATAT GTTTAAATCA ACACAATCTA TCAAAATTAA
     ACTAAAAAAA

251  AAATAAGTGT ACGTGGTTAA CATTAGTACA GTAATATAAG
     AGGAAAATGA

301  GAAATTAAGA AATTGAAAGC GAGTCTAATT TTTAAATTAT
     GAACCTGCAT

351  ATATAAAAGG AAAGAAAGAA TCCAGGAAGA AAAGAAATGA
     AACCATGCAT

401  GGTCCCCTCG TCATCACGAG TTTCTGCCAT TTGCAATAGA
     AACACTGAAA

451  CACCTTTCTC TTTGTCACTT AATTGAGATG CCGAAGCCAC
     CTCACACCAT

501  GAACTTCATG AGGTGTAGCA CCCAAGGCTT CCATAGCCAT
     GCATACTGAA

551  GAATGTCTCA AGCTCAGCAC CCTACTTCTG TGACGTGTCC
     CTCATTCACC

601  TTCCTCTCTT CCCTATAAAT AACCACGCCT CAGGTTCTCC
     GCTTCACAAC

651  TCAAACATTC TCTCCATTGG TCCTTAAACA CTCATCAGTC
     ATCACCGCGG

701  CCGCGGAATT CATGGCTTCT ATGATATCCT CTTCCGCTGT
     GACAACAGTC

751  AGCCGTGCCT CTAGGGGGCA ATCCGCCGCA GTGGCTCCAT
     TCGGCGGCCT
```

-continued

```
 801 CAAATCCATG ACTGGATTCC CAGTGAAGAA GGTCAACACT
     GACATTACTT

 851 CCATTACAAG CAATGGTGGA AGAGTAAAGT GCATGCAGGT
     GTGGCCTCCA

 901 ATTGGAAAGA AGAAGTTTGA GACTCTTTCC TATTTGCCAC
     CATTGACGAG

 951 AGATTCTAGA GTGACTGACG TTGTCATCGT ATCCGCCGCC
     CGCACCGCGG

1001 TCGGCAAGTT TGGCGGCTCG CTGGCCAAGA TCCCGGCACC
     GGAACTGGGT

1051 GCCGTGGTCA TCAAGGCCGC GCTGGAGCGC GCCGGCGTCA
     AGCCGGAGCA

1101 GGTGAGCGAA GTCATCATGG GCCAGGTGCT GACCGCCGGT
     TCGGGCCAGA

1151 ACCCCGCACG CCAGGCCGCG ATCAAGGCCG GCCTGCCGGC
     GATGGTGCCG

1201 GCCATGACCA TCAACAAGGT GTGCGGCTCG GGCCTGAAGG
     CCGTGATGCT

1251 GGCCGCCAAC GCGATCATGG CGGGCGACGC CGAGATCGTG
     GTGGCCGGCG

1301 GCCAGGAAAA CATGAGCGCC GCCCCGCACG TGCTGCCGGG
     CTCGCGCGAT

1351 GGTTTCCGCA TGGGCGATGC CAAGCTGGTC GACACCATGA
     TCGTCGACGG

1401 CCTGTGGGAC GTGTACAACC AGTACCACAT GGGCATCACC
     GCCGAGAACG

1451 TGGCCAAGGA ATACGGCATC ACACGCGAGG CGCAGGATGA
     GTTCGCCGTC

1501 GGCTCGCAGA ACAAGGCCGA AGCCGCGCAG AAGGCCGGCA
     AGTTTGACGA

1551 AGAGATCGTC CCGGTGCTGA TCCCGCAGCG CAAGGGCGAC
     CCGGTGGCCT

1601 TCAAGACCGA CGAGTTCGTG CGCCAGGGCG CCACGCTGGA
     CAGCATGTCC

1651 GGCCTCAAGC CCGCCTTCGA CAAGGCCGGC ACGGTGACCG
     CGGCCAACGC

1701 CTCGGGCCTG AACGACGGCG CCGCCGCGGT GGTGGTGATG
     TCGGCGGCCA

1751 AGGCCAAGGA ACTGGGCCTG ACCCCGCTGG CCACGATCAA
     GAGCTATGCC

1801 AACGCCGGTG TCGATCCCAA GGTGATGGGC ATGGGCCCGG
     TGCCGGCCTC

1851 CAAGCGCGCC CTGTCGCGCG CCGAGTGGAC CCCGCAAGAC
     CTGGACCTGA

1901 TGGAGATCAA CGAGGCCTTT GCCGCGCAGG CGCTGGCGGT
     GCACCAGCAG

1951 ATGGGCTGGG ACACCTCCAA GGTCAATGTG AACGGCGGCG
     CCATCGCCAT

2001 CGGCCACCCG ATCGGCGCGT CGGGCTGCCG TATCCTGGTG
     ACGCTGCTGC

2051 ACGAGATGAA GCGCCGTGAC GCGAAGAAGG GCCTGGCCTC
     GCTGTGCATC

2101 GGCGGCGGCA TGGGCGTGGC GCTGGCAGTC GAGCGCAAAT
     AACTCGAGGC
```

-continued

```
2151 GGCCGCAGCC CTTTTTGTAT GTGCTACCCC ACTTTTGTCT
     TTTTGGCAAT

2201 AGTGCTAGCA ACCAATAAAT AATAATAATA ATAATGAATA
     AGAAAACAAA

2251 GGCTTTAGCT TGCCTTTTGT TCACTGTAAA ATAATAATGT
     AAGTACTCTC

2301 TATAATGAGT CACGAAACTT TTGCGGGAAT AAAAGGAGAA
     ATTCCAATGA

2351 GTTTTCTGTC AAATCTTCTT TTGTCTCTCT CTCTCTCTCT
     TTTTTTTTTT

2401 TCTTTCTTCT GAGCTTCTTG CAAAACAAAA GGCAAACAAT
     AACGATTGGT

2451 CCAATGATAG TTAGCTTGAT CGATGATATC TTTAGGAAGT
     GTTGGCAGGA

2501 CAGGACATGA TGTAGAAGAC TAAAATTGAA AGTATTGCAG
     ACCCAATAGT

2551 TGAAGATTAA CTTTAAGAAT GAAGACGTCT TATCAGGTTC
     TTCATGACTT

2601 AAGCTTTAAG AGGAGTCCAC CATGGTAGAT CTGACTAGTA
     GAAGGTAATT

2651 ATCCAAGATG TAGCATCAAG AATCCAATGT TTACGGGAAA
     AACTATGGAA

2701 GTATTATGTG AGCTCAGCAA GAAGCAGATC AATATGCGGC
     ACATATGCAA

2751 CCTATGTTCA AAAATGAAGA ATGTACAGAT ACAAGATCCT
     ATACTGCCAG

2801 AATACGAAGA AGAATACGTA GAAATTGAAA AAGAAGAACC
     AGGCGAAGAA

2851 AAGAATCTTG AAGACGTAAG CACTGACGAC AACAATGAAA
     AGAAGAAGAT

2901 AAGGTCGGTG ATTGTGAAAG AGACATAGAG GACACATGTA
     AGGTGGAAAA

2951 TGTAAGGGCG GAAAGTAACC TTATCACAAA GGAATCTTAT
     CCCCCACTAC

3001 TTATCCTTTT ATATTTTTCC GTGTCATTTT TGCCCTTGAG
     TTTTCCTATA

3051 TAAGGAACCA AGTTCGGCAT TTGTGAAAAC AAGAAAAAAT
     TGGTGTAAGC

3101 TATTTTCTTT GAAGTACTGA GGATACAACT TCAGAGAAAT
     TTGTAAGAAA

3151 GTGGATCGAA ACCATGGCCT CCTCCGAGAA CGTCATCACC
     GAGTTCATGC

3201 GCTTCAAGGT GCGCATGGAG GGCACCGTGA ACGGCCACGA
     GTTCGAGATC

3251 GAGGGCGAGG GCGAGGGCCG CCCCTACGAG GGCCACAACA
     CCGTGAAGCT

3301 GAAGGTGACC AAGGGCGGCC CCCTGCCCTT CGCCTGGGAC
     ATCCTGTCCC

3351 CCCAGTTCCA GTACGGCTCC AAGGTGTACG TGAAGCACCC
     CGCCGACATC

3401 CCCGACTACA AGAAGCTGTC CTTCCCCGAG GGCTTCAAGT
     GGGAGCGCGT

3451 GATGAACTTC GAGGACGGCG GCGTGGCGAC CGTGACCCAG
     GACTCCTCCC
```

-continued

3501 TGCAGGACGG CTGCTTCATC TACAAGGTGA AGTTCATCGG CGTGAACTTC

3551 CCCTCCGACG GCCCCGTGAT GCAGAAGAAG ACCATGGGCT GGGAGGCCTC

3601 CACCGAGCGC CTGTACCCCC GCGACGGCGT GCTGAAGGGC GAGACCCACA

3651 AGGCCCTGAA GCTGAAGGAC GGCGGCCACT ACCTGGTGGA GTTCAAGTCC

3701 ATCTACATGG CCAAGAAGCC CGTGCAGCTG CCCGGCTACT ACTACGTGGA

3751 CGCCAAGCTG GACATCACCT CCCACAACGA GGACTACACC ATCGTGGAGC

3801 AGTACGAGCG CACCGAGGGC CGCCACCACC TGTTCCTGGT ACCAATGAGC

3851 TCTGTCCAAC AGTCTCAGGG TTAATGTCTA TGTATCTTAA ATAATGTTGT

3901 CGGCGATCGT TCAAACATTT GGCAATAAAG TTTCTTAAGA TTGAATCCTG

3951 TTGCCGGTCT TGCGATGATT ATCATATAAT TTCTGTTGAA TTACGTTAAG

4001 CATGTAATAA TTAACATGTA ATGCATGACG TTATTTATGA GATGGGTTTT

4051 TATGATTAGA GTCCCGCAAT TATACATTTA ATACGCGATA GAAAACAAAA

4101 TATAGCGCGC AAACTAGGAT AAATTATCGC GCGCGGTGTC ATCTATGTTA

4151 CTAGATCGGG AATTAAACTA TCAGTGTTTG ACAGGATATA TTGGCGGGTA

4201 AACCTAAGAG AAAAGAGCGT TTATTAGAAT AACGGATATT TAAAAGGGCG

4251 TGAAAAGGTT TATCCGTTCG TCCATTTGTA TGTGCATGCC AACCACAGGG

4301 TTCCCCTCGG GATCAAAGTA CTTTGATCCA ACCCCTCCGC TGCTATAGTG

4351 CAGTCGGCTT CTGACGTTCA GTGCAGCCGT CTTCTGAAAA CGACATGTCG

4401 CACAAGTCCT AAGTTACGCG ACAGGCTGCC GCCCTGCCCT TTTCCTGGCG

4451 TTTTCTTGTC GCGTGTTTTA GTCGCATAAA GTAGAATACT TGCGACTAGA

4501 ACCGGAGACA TTACGCCATG AACAAGAGCG CCGCCGCTGG CCTGCTGGGC

4551 TATGCCCGCG TCAGCACCGA CGACCAGGAC TTGACCAACC AACGGGCCGA

4601 ACTGCACGCG GCCGGCTGCA CCAAGCTGTT TTCCGAGAAG ATCACCGGCA

4651 CCAGGCGCGA CCGCCCGGAG CTGGCCAGGA TGCTTGACCA CCTACGCCCT

4701 GGCGACGTTG TGACAGTGAC CAGGCTAGAC CGCCTGGCCC GCAGCACCCG

4751 CGACCTACTG GACATTGCCG AGCGCATCCA GGAGGCCGGC GCGGGCCTGC

4801 GTAGCCTGGC AGAGCCGTGG GCCGACACCA CCACGCCGGC CGGCCGCATG

-continued

4851 GTGTTGACCG TGTTCGCCGG CATTGCCGAG TTCGAGCGTT CCCTAATCAT

4901 CGACCGCACC CGGAGCGGGC GCGAGGCCGC CAAGGCCCGA GGCGTGAAGT

4951 TTGGCCCCCG CCCTACCCTC ACCCCGGCAC AGATCGCGCA CGCCCGCGAG

5001 CTGATCGACC AGGAAGGCCG CACCGTGAAA GAGGCGGCTG CACTGCTTGG

5051 CGTGCATCGC TCGACCCTGT ACCGCGCACT TGAGCGCAGC GAGGAAGTGA

5101 CGCCCACCGA GGCCAGGCGG CGCGGTGCCT TCCGTGAGGA CGCATTGACC

5151 GAGGCCGACG CCCTGGCGGC CGCCGAGAAT GAACGCCAAG AGGAACAAGC

5201 ATGAAACCGC ACCAGGACGG CCAGGACGAA CCGTTTTTCA TTACCGAAGA

5251 GATCGAGGCG GAGATGATCG CGGCCGGGTA CGTGTTCGAG CCGCCCGCGC

5301 ACGTCTCAAC CGTGCAGCTG CATGAAATCC TGGCCGGTTT GTCTGATGCC

5351 AAGCTGGCGG CCTGGCCGGC CAGCTTGGCC GCTGAAGAAA CCGAGCGCCG

5401 CCGTCTAAAA AGGTGATGTG TATTTGAGTA AAACAGCTTG CGTCATGCGG

5451 TCGCTGCGTA TATGATGCGA TGAGTAAATA AACAAATACG CAAGGGGAAC

5501 GCATGAAGGT TATCGCTGTA CTTAACCAGA AAGGCGGGTC AGGCAAGACG

5551 ACCATCGCAA CCCATCTAGC CCGCGCCCTG CAACTCGCCG GGGCCGATGT

5601 TCTGTTAGTC GATTCCGATC CCCAGGGCAG TGCCCGCGAT TGGGCGGCCG

5651 TGCGGGAAGA TCAACCGCTA ACCGTTGTCG GCATCGACCG CCCGACGATT

5701 GACCGCGACG TGAAGGCCAT CGGCCGGCGC GACTTCGTAG TGATCGACGG

5751 AGCGCCCCAG GCGGCGGACT TGGCTGTGTC CGCGATCAAG GCAGCCGACT

5801 TCGTGCTGAT TCCGGTGCAG CCAAGCCCTT ACGACATATG GGCCACCGCC

5851 GACCTGGTGG AGCTGGTTAA GCAGCGCATT GAGGTCACGG ATGGAAGGCT

5901 ACAAGCGGCC TTTGTCGTGT CGCGGGCGAT CAAAGGCACG CGCATCGGCG

5951 GTGAGGTTGC CGAGGCGCTG GCCGGGTACG AGCTGCCCAT TCTTGAGTCC

6001 CGTATCACGC AGCGCGTGAG CTACCCAGGC ACTGCCGCCG CCGGCACAAC

6051 CGTTCTTGAA TCAGAACCCG AGGGCGACGC TGCCCGCGAG GTCCAGGCGC

6101 TGGCCGCTGA AATTAAATCA AAACTCATTT GAGTTAATGA GGTAAAGAGA

6151 AAATGAGCAA AAGCACAAAC ACGCTAAGTG CCGGCCGTCC GAGCGCACGC

-continued

```
6201 AGCAGCAAGG CTGCAACGTT GGCCAGCCTG GCAGACACGC
     CAGCCATGAA

6251 GCGGGTCAAC TTTCAGTTGC CGGCGGAGGA TCACACCAAG
     CTGAAGATGT

6301 ACGCGGTACG CCAAGGCAAG ACCATTACCG AGCTGCTATC
     TGAATACATC

6351 GCGCAGCTAC CAGAGTAAAT GAGCAAATGA ATAAATGAGT
     AGATGAATTT

6401 TAGCGGCTAA AGGAGGCGGC ATGGAAAATC AAGAACAACC
     AGGCACCGAC

6451 GCCGTGGAAT GCCCCATGTG TGGAGGAACG GGCGGTTGGC
     CAGGCGTAAG

6501 CGGCTGGGTT GTCTGCCGGC CCTGCAATGG CACTGGAACC
     CCCAAGCCCG

6551 AGGAATCGGC GTGACGGTCG CAAACCATCC GGCCCGGTAC
     AAATCGGCGC

6601 GGCGCTGGGT GATGACCTGG TGGAGAAGTT GAAGGCCGCG
     CAGGCCGCCC

6651 AGCGGCAACG CATCGAGGCA GAAGCACGCC CCGGTGAATC
     GTGGCAAGCG

6701 GCCGCTGATC GAATCCGCAA AGAATCCCGG CAACCGCCGG
     CAGCCGGTGC

6751 GCCGTCGATT AGGAAGCCGC CCAAGGGCGA CGAGCAACCA
     GATTTTTTCG

6801 TTCCGATGCT CTATGACGTG GGCACCCGCG ATAGTCGCAG
     CATCATGGAC

6851 GTGGCCGTTT TCCGTCTGTC GAAGCGTGAC CGACGAGCTG
     GCGAGGTGAT

6901 CCGCTACGAG CTTCCAGACG GGCACGTAGA GGTTTCCGCA
     GGGCCGGCCG

6951 GCATGGCCAG TGTGTGGGAT TACGACCTGG TACTGATGGC
     GGTTTCCCAT

7001 CTAACCGAAT CCATGAACCG ATACCGGGAA GGGAAGGGAG
     ACAAGCCCGG

7051 CCGCGTGTTC CGTCCACACG TTGCGGACGT ACTCAAGTTC
     TGCCGGCGAG

7101 CCGATGGCGG AAAGCAGAAA GACGACCTGG TAGAAACCTG
     CATTCGGTTA

7151 AACACCACGC ACGTTGCCAT GCAGCGTACG AAGAAGGCCA
     AGAACGGCCG

7201 CCTGGTGACG GTATCCGAGG GTGAAGCCTT GATTAGCCGC
     TACAAGATCG

7251 TAAAGAGCGA AACCGGGCGG CCGGAGTACA TCGAGATCGA
     GCTAGCTGAT

7301 TGGATGTACC GCGAGATCAC AGAAGGCAAG AACCCGGACG
     TGCTGACGGT

7351 TCACCCCGAT TACTTTTTGA TCGATCCCGG CATCGGCCGT
     TTTCTCTACC

7401 GCCTGGCACG CCGCGCCGCA GGCAAGGCAG AAGCCAGATG
     GTTGTTCAAG

7451 ACGATCTACG AACGCAGTGG CAGCGCCGGA GAGTTCAAGA
     AGTTCTGTTT

7501 CACCGTGCGC AAGCTGATCG GGTCAAATGA CCTGCCGGAG
     TACGATTTGA

7551 AGGAGGAGGC GGGGCAGGCT GGCCCGATCC TAGTCATGCG
     CTACCGCAAC

7601 CTGATCGAGG GCGAAGCATC CGCCGGTTCC TAATGTACGG
     AGCAGATGCT

7651 AGGGCAAATT GCCCTAGCAG GGGAAAAAGG TCGAAAAGGT
     CTCTTTCCTG

7701 TGGATAGCAC GTACATTGGG AACCCAAAGC CGTACATTGG
     GAACCGGAAC

7751 CCGTACATTG GGAACCCAAA GCCGTACATT GGGAACCGGT
     CACACATGTA

7801 AGTGACTGAT ATAAAAGAGA AAAAAGGCGA TTTTTCCGCC
     TAAAACTCTT

7851 TAAAACTTAT TAAAACTCTT AAAACCCGCC TGGCCTGTGC
     ATAACTGTCT

7901 GGCCAGCGCA CAGCCGAAGA GCTGCAAAAA GCGCCTACCC
     TTCGGTCGCT

7951 GCGCTCCCTA CGCCCCGCCG CTTCGCGTCG GCCTATCGCG
     GCCGCTGGCC

8001 GCTCAAAAAT GGCTGGCCTA CGGCCAGGCA ATCTACCAGG
     GCGCGGACAA

8051 GCCGCGCCGT CGCCACTCGA CCGCCGGCGC CCACATCAAG
     GCACCCTGCC

8101 TCGCGCGTTT CGGTGATGAC GGTGAAAACC TCTGACACAT
     GCAGCTCCCG

8151 GAGACGGTCA CAGCTTGTCT GTAAGCGGAT GCCGGGAGCA
     GACAAGCCCG

8201 TCAGGGCGCG TCAGCGGGTG TTGGCGGGTG TCGGGGCGCA
     GCCATGACCC

8251 AGTCACGTAG CGATAGCGGA GTGTATACTG GCTTAACTAT
     GCGGCATCAG

8301 AGCAGATTGT ACTGAGAGTG CACCATATGC GGTGTGAAAT
     ACCGCACAGA

8351 TGCGTAAGGA GAAAATACCG CATCAGGCGC TCTTCCGCTT
     CCTCGCTCAC

8401 TGACTCGCTG CGCTCGGTCG TTCGGCTGCG GCGAGCGGTA
     TCAGCTCACT

8451 CAAAGGCGGT AATACGGTTA TCCACAGAAT CAGGGGATAA
     CGCAGGAAAG

8501 AACATGTGAG CAAAAGGCCA GCAAAAGGCC AGGAACCGTA
     AAAAGGCCGC

8551 GTTGCTGGCG TTTTTCCATA GGCTCCGCCC CCCTGACGAG
     CATCACAAAA

8601 ATCGACGCTC AAGTCAGAGG TGGCGAAACC CGACAGGACT
     ATAAAGATAC

8651 CAGGCGTTTC CCCCTGGAAG CTCCCTCGTG CGCTCTCCTG
     TTCCGACCCT

8701 GCCGCTTACC GGATACCTGT CCGCCTTTCT CCCTTCGGGA
     AGCGTGGCGC

8751 TTTCTCATAG CTCACGCTGT AGGTATCTCA GTTCGGTGTA
     GGTCGTTCGC

8801 TCCAAGCTGG GCTGTGTGCA CGAACCCCCC GTTCAGCCCG
     ACCGCTGCGC

8851 CTTATCCGGT AACTATCGTC TTGAGTCCAA CCCGGTAAGA
     CACGACTTAT
```

-continued

8901 CGCCACTGGC AGCAGCCACT GGTAACAGGA TTAGCAGAGC GAGGTATGTA

8951 GGCGGTGCTA CAGAGTTCTT GAAGTGGTGG CCTAACTACG GCTACACTAG

9001 AAGGACAGTA TTTGGTATCT GCGCTCTGCT GAAGCCAGTT ACCTTCGGAA

9051 AAAGAGTTGG TAGCTCTTGA TCCGGCAAAC AAACCACCGC TGGTAGCGGT

9101 GGTTTTTTTG TTTGCAAGCA GCAGATTACG CGCAGAAAAA AAGGATCTCA

9151 AGAAGATCCT TTGATCTTTT CTACGGGGTC TGACGCTCAG TGGAACGAAA

9201 ACTCACGTTA AGGGATTTTG GTCATGCATT CTAGGTACTA AAACAATTCA

9251 TCCAGTAAAA TATAATATTT TATTTTCTCC CAATCAGGCT TGATCCCCAG

9301 TAAGTCAAAA AATAGCTCGA CATACTGTTC TTCCCCGATA TCCTCCCTGA

9351 TCGACCGGAC GCAGAAGGCA ATGTCATACC ACTTGTCCGC CCTGCCGCTT

9401 CTCCCAAGAT CAATAAAGCC ACTTACTTTG CCATCTTTCA CAAAGATGTT

9451 GCTGTCTCCC AGGTCGCCGT GGGAAAAGAC AAGTTCCTCT TCGGGCTTTT

9501 CCGTCTTTAA AAAATCATAC AGCTCGCGCG GATCTTTAAA TGGAGTGTCT

9551 TCTTCCCAGT TTTCGCAATC CACATCGGCC AGATCGTTAT TCAGTAAGTA

9601 ATCCAATTCG GCTAAGCGGC TGTCTAAGCT ATTCGTATAG GGACAATCCG

9651 ATATGTCGAT GGAGTGAAAG AGCCTGATGC ACTCCGCATA CAGCTCGATA

9701 ATCTTTTCAG GGCTTTGTTC ATCTTCATAC TCTTCCGAGC AAAGGACGCC

9751 ATCGGCCTCA CTCATGAGCA GATTGCTCCA GCCATCATGC CGTTCAAAGT

9801 GCAGGACCTT TGGAACAGGC AGCTTTCCTT CCAGCCATAG CATCATGTCC

9851 TTTTCCCGTT CCACATCATA GGTGGTCCCT TTATACCGGC TGTCCGTCAT

9901 TTTTAAATAT AGGTTTTCAT TTTCTCCCAC CAGCTTATAT ACCTTAGCAG

9951 GAGACATTCC TTCCGTATCT TTTACGCAGC GGTATTTTTC GATCAGTTTT

10001 TTCAATTCCG GTGATATTCT CATTTTAGCC ATTTATTATT TCCTTCCTCT

10051 TTTCTACAGT ATTTAAAGAT ACCCCAAGAA GCTAATTATA ACAAGACGAA

10101 CTCCAATTCA CTGTTCCTTG CATTCTAAAA CCTTAAATAC CAGAAAACAG

10151 CTTTTTCAAA GTTGTTTTCA AAGTTGGCGT ATAACATAGT ATCGACGGAG

10201 CCGATTTTGA AACCGCGGTG ATCACAGGCA GCAACGCTCT GTCATCGTTA

-continued

10251 CAATCAACAT GCTACCCTCC GCGAGATCAT CCGTGTTTCA AACCCGGCAG

10301 CTTAGTTGCC GTTCTTCCGA ATAGCATCGG TAACATGAGC AAAGTCTGCC

10351 GCCTTACAAC GGCTCTCCCG CTGACGCCGT CCCGGACTGA TGGGCTGCCT

10401 GTATCGAGTG GTGATTTTGT GCCGAGCTGC CGGTCGGGGA GCTGTTGGCT

10451 GGCTGGTGGC AGGATATATT GTGGTGTAAA CAAATTGACG CTTAGACAAC

10501 TTAATAACAC ATTGCGGACG TTTTTAATGT ACTGAATTAA CGCCGAATTA

10551 ATTCCTAGGC CACCATGTTG GGCCCGGGGC GCGCCGTACG TAGTGTTTAT

10601 CTTTGTTGCT TTTCTGAACA ATTTATTTAC TATGTAAATA TATTATCAAT

10651 GTTTAATCTA TTTTAATTTG CACATGAATT TTCATTTTAT TTTTACTTTA

10701 CAAAACAAAT AAATATATAT GCAAAAAAAT TTACAAACGA TGCACGGGTT

10751 ACAAACTAAT TTCATTAAAT GCTAATGCAG ATTTTGTGAA GTAAAACTCC

10801 AATTATGATG AAAAATACCA CCAACACCAC CTGCGAAACT GTATCCCAAC

10851 TGTCCTTAAT AAAAATGTTA AAAAGTATAT TATTCTCATT TGTCTGTCAT

10901 AATTTATGTA CCCCACTTTA ATTTTTCTGA TGTACTAAAC CGAGGGCAAA

10951 CTGAAACCTG TTCCTCATGC AAAGCCCCTA CTCACCATGT ATCATGTACG

11001 TGTCATCACC CAACAACTCC ACTTTTGCTA TATAACAACA CCCCCGTCAC

11051 ACTCTCCCTC TCTAACACAC ACCCCACTAA CAATTCCTTC ACTTGCAGCA

11101 CTGTTGCATC ATCATCTTCA TTGCAAAACC CTAAACTTCA CCTTCAACCG

11151 CGGCCGCATG GCTTCTATGA TATCCTCTTC CGCTGTGACA ACAGTCAGCC

11201 GTGCCTCTAG GGGGCAATCC GCCGCAGTGG CTCCATTCGG CGGCCTCAAA

11251 TCCATGACTG GATTCCCAGT GAAGAAGGTC AACACTGACA TTACTTCCAT

11301 TACAAGCAAT GGTGGAAGAG TAAAGTGCAT GCAGGTGTGG CCTCCAATTG

11351 GAAAGAAGAA GTTTGAGACT CTTTCCTATT TGCCACCATT GACGAGAGAT

11401 TCTAGAGTGA GTAACAAGAA CAACGATGAG CTGCAGTGGC AATCCTGGTT

11451 CAGCAAGGCG CCCACCACCG AGGCGAACCC GATGGCCACC ATGTTGCAGG

11501 ATATCGGCGT TGCGCTCAAA CCGGAAGCGA TGGAGCAGCT GAAAAACGAT

11551 TATCTGCGTG ACTTCACCGC GTTGTGGCAG GATTTTTTGG CTGGCAAGGC

-continued

11601 GCCAGCCGTC AGCGACCGCC GCTTCAGCTC GGCAGCCTGG CAGGGCAATC

11651 CGATGTCGGC CTTCAATGCC GCATCTTACC TGCTCAACGC CAAATTCCTC

11701 AGTGCCATGG TGGAGGCGGT GGACACCGCA CCCCAGCAAA AGCAGAAAAT

11751 ACGCTTTGCC GTGCAGCAGG TGATTGATGC CATGTCGCCC GCGAACTTCC

11801 TCGCCACCAA CCCGGAAGCG CAGCAAAAAC TGATTGAAAC CAAGGGCGAG

11851 AGCCTGACGC GTGGCCTGGT CAATATGCTG GGCGATATCA ACAAGGGCCA

11901 TATCTCGCTG TCGGACGAAT CGGCCTTTGA AGTGGGCCGC AACCTGGCCA

11951 TTACCCCGGG CACCGTGATT TACGAAAATC CGCTGTTCCA GCTGATCCAG

12001 TACACGCCGA CCACGCCGAC GGTCAGCCAG CGCCCGCTGT TGATGGTGCC

12051 GCCGTGCATC AACAAGTTCT ACATCCTCGA CCTGCAACCG GAAAATTCGC

12101 TGGTGCGCTA CGCGGTGGAG CAGGGCAACA CCGTGTTCCT GATCTCGTGG

12151 AGCAATCCGG ACAAGTCGCT GGCCGGCACC ACCTGGGACG ACTACGTGGA

12201 GCAGGGCGTG ATCGAAGCGA TCCGCATCGT CCAGGACGTC AGCGGCCAGG

12251 ACAAGCTGAA CATGTTCGGC TTCTGCGTGG GCGGCACCAT CGTTGCCACC

12301 GCACTGGCGG TACTGGCGGC GCGTGGCCAG CACCCGGCGG CCAGCCTGAC

12351 CCTGCTGACC ACCTTCCTCG ACTTCAGCGA CACCGGCGTG CTCGACGTCT

12401 TCGTCGATGA AACCCAGGTC GCGCTGCGTG AACAGCAATT GCGCGATGGC

12451 GGCCTGATGC CGGGCCGTGA CCTGGCCTCG ACCTTCTCGA GCCTGCGTCC

12501 GAACGACCTG GTATGGAACT ATGTGCAGTC GAACTACCTC AAAGGCAATG

12551 AGCCGGCGGC GTTTGACCTG CTGTTCTGGA ATTCGGACAG CACCAATTTG

12601 CCGGGCCCGA TGTTCTGCTG GTACCTGCGC AACACCTACC TGGAAAACAG

12651 CCTGAAAGTG CCGGGCAAGC TGACGGTGGC CGGCGAAAAG ATCGACCTCG

12701 GCCTGATCGA CGCCCCGGCC TTCATCTACG GTTCGCGCGA AGACCACATC

12751 GTGCCGTGGA TGTCGGCGTA CGGTTCGCTC GACATCCTCA ACCAGGGCAA

12801 GCCGGGCGCC AACCGCTTCG TGCTGGGCGC GTCCGGCCAT ATCGCCGGCG

12851 TGATCAACTC GGTGGCCAAG AACAAGCGCA GCTACTGGAT CAACGACGGT

12901 GGCGCCGCCG ATGCCCAGGC CTGGTTCGAT GGCGCGCAGG AAGTGCCGGG

-continued

12951 CAGCTGGTGG CCGCAATGGG CCGGGTTCCT GACCCAGCAT GGCGGCAAGA

13001 AGGTCAAGCC CAAAACCAAG CCCGGCAACG CCCGCTACAC CGCGATCGAG

13051 GCGGCGCCCG GCCGTTACGT CAAAGCCAAG GGCTGAGCGG CCGCTGAGTA

13101 ATTCTGATAT TAGAGGGAGC ATTAATGTGT TGTTGTGATG TGGTTTATAT

13151 GGGGAAATTA AATAAATGAT GTATGTACCT CTTGCCTATG TAGGTTTGTG

13201 TGTTTTGTTT TGTTGTCTAG CTTTGGTTAT TAAGTAGTAG GGACGTTCGT

13251 TCGTGTCTCA AAAAAAGGGG TACTACCACT CTGTAGTGTA TATGGATGCT

13301 GGAAATCAAT GTGTTTTGTA TTTGTTCACC TCCATTGTTG AATTCAATGT

13351 CAAATGTGTT TTGCGTTGGT TATGTGTAAA ATTACTATCT TTCTCGTCCG

13401 ATGATCAAAG TTTTAAGCAA CAAAACCAAG GGTGAAATTT AAACTGTGCT

13451 TTGTTGAAGA TTCTTTTATC ATATTGAAAA TCAAATTACT AGCAGCAGAT

13501 TTTACCTAGC ATGAAATTTT ATCAACAGTA CAGCACTCAC TAACCAAGTT

13551 CCAAACTAAG ATGCGCCATT AACATCAGCC AATAGGCATT TTCAGCAAGG

13601 CGCGCCCGCG CCGATGTATG TGACAACCCT CGGGATTGTT GATTTATTTC

13651 AAAACTAAGA GTTTTTGTCT TATTGTTCTC GTCTATTTTG GATATCAATC

13701 TTAGTTTTAT ATCTTTTCTA GTTCTCTACG TGTTAAATGT TCAACACACT

13751 AGCAATTTGG CCTGCCAGCG TATGGATTAT GGAACTATCA AGTCTGTGAC

13801 GCGCCGTACG TAGTGTTTAT CTTTGTTGCT TTTCTGAACA ATTTATTTAC

13851 TATGTAAATA TATTATCAAT GTTTAATCTA TTTTAATTTG CACATGAATT

13901 TTCATTTTAT TTTTACTTTA CAAAACAAAT AAATATATAT GCAAAAAAAT

13951 TTACAAACGA TGCACGGGTT ACAAACTAAT TTCATTAAAT GCTAATGCAG

14001 ATTTTGTGAA GTAAAACTCC AATTATGATG AAAAATACCA CCAACACCAC

14051 CTGCGAAACT GTATCCCAAC TGTCCTTAAT AAAAATGTTA AAAAGTATAT

14101 TATTCTCATT TGTCTGTCAT AATTTATGTA CCCCACTTTA ATTTTTCTGA

14151 TGTACTAAAC CGAGGGCAAA CTGAAACCTG TTCCTCATGC AAAGCCCCTA

14201 CTCACCATGT ATCATGTACG TGTCATCACC CAACAACTCC ACTTTTGCTA

14251 TATAACAACA CCCCCGTCAC ACTCTCCCTC TCTAACACAC ACCCCACTAA

-continued

```
14301 CAATTCCTTC ACTTGCAGCA CTGTTGCATC ATCATCTTCA
      TTGCAAAACC

14351 CTAAACTTCA CCTTCAACCG CGGCCGCATG GCTTCTATGA
      TATCCTCTTC

14401 CGCTGTGACA ACAGTCAGCC GTGCCTCTAG GGGGCAATCC
      GCCGCAGTGG

14451 CTCCATTCGG CGGCCTCAAA TCCATGACTG GATTCCCAGT
      GAAGAAGGTC

14501 AACACTGACA TTACTTCCAT TACAAGCAAT GGTGGAAGAG
      TAAAGTGCAT

14551 GCAGGTGTGG CCTCCAATTG GAAAGAAGAA GTTTGAGACT
      CTTTCCTATT

14601 TGCCACCATT GACGAGAGAT TCTAGAGTGA CTCAGCGCAT
      TGCGTATGTG

14651 ACCGGCGGCA TGGGTGGTAT CGGAACCGCC ATTTGCCAGC
      GGCTGGCCAA

14701 GGATGGCTTT CGTGTGGTGG CCGGTTGCGG CCCCAACTCG
      CCGCGCCGCG

14751 AAAAGTGGCT GGAGCAGCAG AAGGCCCTGG GCTTCGATTT
      CATTGCCTCG

14801 GAAGGCAATG TGGCTGACTG GGACTCGACC AAGACCGCAT
      TCGACAAGGT

14851 CAAGTCCGAG GTCGGCGAGG TTGATGTGCT GATCAACAAC
      GCCGGTATCA

14901 CCCGCGACGT GGTGTTCCGC AAGATGACCC GCGCCGACTG
      GGATGCGGTG

14951 ATCGACACCA ACCTGACCTC GCTGTTCAAC GTCACCAAGC
      AGGTGATCGA

15001 CGGCATGGCC GACCGTGGCT GGGGCCGCAT CGTCAACATC
      TCGTCGATGA

15051 ACGGGCAGAA GGGCCAGTTC GGCCAGACCA ACTACTCCAC
      CGCCAAGGCC

15101 GGCCTGCATG GCTTCACCAT GGCACTGGCG CAGGAAGTGG
      CGACCAAGGG

15151 CGTGACCGTC AACACGGTCT CTCCGGGCTA TATCGCCACC
      GACATGGTCA

15201 AGGCGATCCG CCAGGACGTG CTCGACAAGA TCGTCGCGAC
      GATCCCGGTC

15251 AAGCGCCTGG GCCTGCCGGA AGAGATCGCC TCGATCTGCG
      CCTGGTTGTC

15301 GTCGGAGGAG TCCGGTTTCT CGACCGGCGC CGACTTCTCG
      CTCAACGGCG

15351 GCCTGCATAT GGGCTGAGCG GCCGCTGAGT AATTCTGATA
      TTAGAGGGAG

15401 CATTAATGTG TTGTTGTGAT GTGGTTTATA TGGGGAAATT
      AAATAAATGA

15451 TGTATGTACC TCTTGCCTAT GTAGGTTTGT GTGTTTTGTT
      TTGTTGTCTA

15501 GCTTTGGTTA TTAAGTAGTA GGGACGTTCG TTCGTGTCTC
      AAAAAAAGGG

15551 GTACTACCAC TCTGTAGTGT ATATGGATGC TGGAAATCAA
      TGTGTTTTGT

15601 ATTTGTTCAC CTCCATTGTT GAATTCAATG TCAAATGTGT
      TTTGCGTTGG
```

-continued

```
15651 TTATGTGTAA AATTACTATC TTTCTCGTCC GATGATCAAA
      GTTTTAAGCA

15701 ACAAAACCAA GGGTGAAATT TAAACTGTGC TTTGTTGAAG
      ATTCTTTTAT

15751 CATATTGAAA ATCAAATTAC TAGCAGCAGA TTTTACCTAG
      CATGAAATTT

15801 TATCAACAGT ACAGCACTCA CTAACCAAGT TCCAAACTAA
      GATGCGCCAT

15851 TAACATCAGC CAATAGGCAT TTTCAGCAAG GCGCGTAA
```

pMBXS364

(SEQ ID NO: 2)

```
   1 CATGCCAACC ACAGGGTTCC CCTCGGGATC AAAGTACTTT
     GATCCAACCC

  51 CTCCGCTGCT ATAGTGCAGT CGGCTTCTGA CGTTCAGTGC
     AGCCGTCTTC

 101 TGAAAACGAC ATGTCGCACA AGTCCTAAGT TACGCGACAG
     GCTGCCGCCC

 151 TGCCCTTTTC CTGGCGTTTT CTTGTCGCGT GTTTTAGTCG
     CATAAAGTAG

 201 AATACTTGCG ACTAGAACCG GAGACATTAC GCCATGAACA
     AGAGCGCCGC

 251 CGCTGGCCTG CTGGGCTATG CCCGCGTCAG CACCGACGAC
     CAGGACTTGA

 301 CCAACCAACG GGCCGAACTG CACGCGGCCG GCTGCACCAA
     GCTGTTTTCC

 351 GAGAAGATCA CCGGCACCAG GCGCGACCGC CCGGAGCTGG
     CCAGGATGCT

 401 TGACCACCTA CGCCCTGGCG ACGTTGTGAC AGTGACCAGG
     CTAGACCGCC

 451 TGGCCCGCAG CACCCGCGAC CTACTGGACA TTGCCGAGCG
     CATCCAGGAG

 501 GCCGGCGCGG GCCTGCGTAG CCTGGCAGAG CCGTGGGCCG
     ACACCACCAC

 551 GCCGGCCGGC CGCATGGTGT TGACCGTGTT CGCCGGCATT
     GCCGAGTTCG

 601 AGCGTTCCCT AATCATCGAC CGCACCCGGA GCGGGCGCGA
     GGCCGCCAAG

 651 GCCCGAGGCG TGAAGTTTGG CCCCCGCCCT ACCCTCACCC
     CGGCACAGAT

 701 CGCGCACGCC CGCGAGCTGA TCGACCAGGA AGGCCGCACC
     GTGAAAGAGG

 751 CGGCTGCACT GCTTGGCGTG CATCGCTCGA CCCTGTACCG
     CGCACTTGAG

 801 CGCAGCGAGG AAGTGACGCC CACCGAGGCC AGGCGGCGCG
     GTGCCTTCCG

 851 TGAGGACGCA TTGACCGAGG CCGACGCCCT GGCGGCCGCC
     GAGAATGAAC

 901 GCCAAGAGGA ACAAGCATGA AACCGCACCA GGACGGCCAG
     GACGAACCGT

 951 TTTTCATTAC CGAAGAGATC GAGGCGGAGA TGATCGCGGC
     CGGGTACGTG

1001 TTCGAGCCGC CCGCGCACGT CTCAACCGTG CGGCTGCATG
     AAATCCTGGC

1051 CGGTTTGTCT GATGCCAAGC TGGCGGCCTG GCCGGCCAGC
     TTGGCCGCTG
```

-continued

1101 AAGAAACCGA GCGCCGCCGT CTAAAAAGGT GATGTGTATT TGAGTAAAAC

1151 AGCTTGCGTC ATGCGGTCGC TGCGTATATG ATGCGATGAG TAAATAAACA

1201 AATACGCAAG GGGAACGCAT GAAGGTTATC GCTGTACTTA ACCAGAAAGG

1251 CGGGTCAGGC AAGACGACCA TCGCAACCCA TCTAGCCCGC GCCCTGCAAC

1301 TCGCCGGGGC CGATGTTCTG TTAGTCGATT CCGATCCCCA GGGCAGTGCC

1351 CGCGATTGGG CGGCCGTGCG GGAAGATCAA CCGCTAACCG TTGTCGGCAT

1401 CGACCGCCCG ACGATTGACC GCGACGTGAA GGCCATCGGC CGGCGCGACT

1451 TCGTAGTGAT CGACGGAGCG CCCCAGGCGG CGGACTTGGC TGTGTCCGCG

1501 ATCAAGGCAG CCGACTTCGT GCTGATTCCG GTGCAGCCAA GCCCTTACGA

1551 CATATGGGCC ACCGCCGACC TGGTGGAGCT GGTTAAGCAG CGCATTGAGG

1601 TCACGGATGG AAGGCTACAA GCGGCCTTTG TCGTGTCGCG GGCGATCAAA

1651 GGCACGCGCA TCGGCGGTGA GGTTGCCGAG GCGCTGGCCG GGTACGAGCT

1701 GCCCATTCTT GAGTCCCGTA TCACGCAGCG CGTGAGCTAC CCAGGCACTG

1751 CCGCCGCCGG CACAACCGTT CTTGAATCAG AACCCGAGGG CGACGCTGCC

1801 CGCGAGGTCC AGGCGCTGGC CGCTGAAATT AAATCAAAAC TCATTTGAGT

1851 TAATGAGGTA AAGAGAAAAT GAGCAAAAGC ACAAACACGC TAAGTGCCGG

1901 CCGTCCGAGC GCACGCAGCA GCAAGGCTGC AACGTTGGCC AGCCTGGCAG

1951 ACACGCCAGC CATGAAGCGG GTCAACTTTC AGTTGCCGGC GGAGGATCAC

2001 ACCAAGCTGA AGATGTACGC GGTACGCCAA GGCAAGACCA TTACCGAGCT

2051 GCTATCTGAA TACATCGCGC AGCTACCAGA GTAAATGAGC AAATGAATAA

2101 ATGAGTAGAT GAATTTTAGC GGCTAAAGGA GGCGGCATGG AAAATCAAGA

2151 ACAACCAGGC ACCGACGCCG TGGAATGCCC CATGTGTGGA GGAACGGGCG

2201 GTTGGCCAGG CGTAAGCGGC TGGGTTGTCT GCCGGCCCTG CAATGGCACT

2251 GGAACCCCCA AGCCCGAGGA ATCGGCGTGA CGGTCGCAAA CCATCCGGCC

2301 CGGTACAAAT CGGCGCGGCG CTGGGTGATG ACCTGGTGGA GAAGTTGAAG

2351 GCCGCGCAGG CCGCCCAGCG GCAACGCATC GAGGCAGAAG CACGCCCCGG

2401 TGAATCGTGG CAAGCGGCCG CTGATCGAAT CCGCAAAGAA TCCCGGCAAC

-continued

2451 CGCCGGCAGC CGGTGCGCCG TCGATTAGGA AGCCGCCCAA GGGCGACGAG

2501 CAACCAGATT TTTTCGTTCC GATGCTCTAT GACGTGGGCA CCCGCGATAG

2551 TCGCAGCATC ATGGACGTGG CCGTTTTCCG TCTGTCGAAG CGTGACCGAC

2601 GAGCTGGCGA GGTGATCCGC TACGAGCTTC CAGACGGGCA CGTAGAGGTT

2651 TCCGCAGGGC CGGCCGGCAT GGCCAGTGTG TGGGATTACG ACCTGGTACT

2701 GATGGCGGTT TCCCATCTAA CCGAATCCAT GAACCGATAC CGGGAAGGGA

2751 AGGGAGACAA GCCCGGCCGC GTGTTCCGTC CACACGTTGC GGACGTACTC

2801 AAGTTCTGCC GGCGAGCCGA TGGCGGAAAG CAGAAAGACG ACCTGGTAGA

2851 AACCTGCATT CGGTTAAACA CCACGCACGT TGCCATGCAG CGTACGAAGA

2901 AGGCCAAGAA CGGCCGCCTG GTGACGGTAT CCGAGGGTGA AGCCTTGATT

2951 AGCCGCTACA AGATCGTAAA GAGCGAAACC GGGCGGCCGG AGTACATCGA

3001 GATCGAGCTA GCTGATTGGA TGTACCGCGA GATCACAGAA GGCAAGAACC

3051 CGGACGTGCT GACGGTTCAC CCCGATTACT TTTTGATCGA TCCCGGCATC

3101 GGCCGTTTTC TCTACCGCCT GGCACGCCGC GCCGCAGGCA AGGCAGAAGC

3151 CAGATGGTTG TTCAAGACGA TCTACGAACG CAGTGGCAGC GCCGGAGAGT

3201 TCAAGAAGTT CTGTTTCACC GTGCGCAAGC TGATCGGGTC AAATGACCTG

3251 CCGGAGTACG ATTTGAAGGA GGAGGCGGGG CAGGCTGGCC CGATCCTAGT

3301 CATGCGCTAC CGCAACCTGA TCGAGGGCGA AGCATCCGCC GGTTCCTAAT

3351 GTACGGAGCA GATGCTAGGG CAAATTGCCC TAGCAGGGGA AAAAGGTCGA

3401 AAAGGTCTCT TTCCTGTGGA TAGCACGTAC ATTGGGAACC CAAAGCCGTA

3451 CATTGGGAAC CGGAACCCGT ACATTGGGAA CCCAAAGCCG TACATTGGGA

3501 ACCGGTCACA CATGTAAGTG ACTGATATAA AAGAGAAAAA AGGCGATTTT

3551 TCCGCCTAAA ACTCTTTAAA ACTTATTAAA ACTCTTAAAA CCCGCCTGGC

3601 CTGTGCATAA CTGTCTGGCC AGCGCACAGC CGAAGAGCTG CAAAAAGCGC

3651 CTACCCTTCG GTCGCTGCGC TCCCTACGCC CCGCCGCTTC GCGTCGGCCT

3701 ATCGCGGCCG CTGGCCGCTC AAAAATGGCT GGCCTACGGC CAGGCAATCT

3751 ACCAGGGCGC GGACAAGCCG CGCCGTCGCC ACTCGACCGC CGGCGCCCAC

-continued

3801 ATCAAGGCAC CCTGCCTCGC GCGTTTCGGT GATGACGGTG
AAAACCTCTG

3851 ACACATGCAG CTCCCGGAGA CGGTCACAGC TTGTCTGTAA
GCGGATGCCG

3901 GGAGCAGACA AGCCCGTCAG GGCGCGTCAG CGGGTGTTGG
CGGGTGTCGG

3951 GGCGCAGCCA TGACCCAGTC ACGTAGCGAT AGCGGAGTGT
ATACTGGCTT

4001 AACTATGCGG CATCAGAGCA GATTGTACTG AGAGTGCACC
ATATGCGGTG

4051 TGAAATACCG CACAGATGCG TAAGGAGAAA ATACCGCATC
AGGCGCTCTT

4101 CCGCTTCCTC GCTCACTGAC TCGCTGCGCT CGGTCGTTCG
GCTGCGGCGA

4151 GCGGTATCAG CTCACTCAAA GGCGGTAATA CGGTTATCCA
CAGAATCAGG

4201 GGATAACGCA GGAAAGAACA TGTGAGCAAA AGGCCAGCAA
AAGGCCAGGA

4251 ACCGTAAAAA GGCCGCGTTG CTGGCGTTTT TCCATAGGCT
CCGCCCCCCT

4301 GACGAGCATC ACAAAAATCG ACGCTCAAGT CAGAGGTGGC
GAAACCCGAC

4351 AGGACTATAA AGATACCAGG CGTTTCCCCC TGGAAGCTCC
CTCGTGCGCT

4401 CTCCTGTTCC GACCCTGCCG CTTACCGGAT ACCTGTCCGC
CTTTCTCCCT

4451 TCGGGAAGCG TGGCGCTTTC TCATAGCTCA CGCTGTAGGT
ATCTCAGTTC

4501 GGTGTAGGTC GTTCGCTCCA AGCTGGGCTG TGTGCACGAA
CCCCCCGTTC

4551 AGCCCGACCG CTGCGCCTTA TCCGGTAACT ATCGTCTTGA
GTCCGCCCTG

4601 GTAAGACACG ACTTATCGCC ACTGGCAGCA GCCACTGGTA
ACAGGATTAG

4651 CAGAGCGAGG TATGTAGGCG GTGCTACAGA GTTCTTGAAG
TGGTGGCCTA

4701 ACTACGGCTA CACTAGAAGG ACAGTATTTG GTATCTGCGC
TCTGCTGAAG

4751 CCAGTTACCT TCGGAAAAAG AGTTGGTAGC TCTTGATCCG
GCAAACAAAC

4801 CACCGCTGGT AGCGGTGGTT TTTTTGTTTG CAAGCAGCAG
ATTACGCGCA

4851 GAAAAAAAGG ATCTCAAGAA GATCCTTTGA TCTTTTCTAC
GGGGTCTGAC

4901 GCTCAGTGGA ACGAAAACTC ACGTTAAGGG ATTTTGGTCA
TGCATTCTAG

4951 GTACTAAAAC AATTCATCCA GTAAAATATA ATATTTTATT
TTCTCCCAAT

5001 CAGGCTTGAT CCCCAGTAAG TCAAAAAATA GCTCGACATA
CTGTTCTTCC

5051 CCGATATCCT CCCTGATCGA CCGGACGCAG AAGGCAATGT
CATACCACTT

5101 GTCCGCCCTG CCGCTTCTCC CAAGATCAAT AAAGCCACTT
ACTTTGCCAT

-continued

5151 CTTTCACAAA GATGTTGCTG TCTCCCAGGT CGCCGTGGGA
AAAGACAAGT

5201 TCCTCTTCGG GCTTTTCCGT CTTTAAAAAA TCATACAGCT
CGCGCGGATC

5251 TTTAAATGGA GTGTCTTCTT CCCAGTTTTC GCAATCCACA
TCGGCCAGAT

5301 CGTTATTCAG TAAGTAATCC AATTCGGCTA AGCGGCTGTC
TAAGCTATTC

5351 GTATAGGGAC AATCCGATAT GTCGATGGAG TGAAAGAGCC
TGATGCACTC

5401 CGCATACAGC TCGATAATCT TTTCAGGGCT TTGTTCATCT
TCATACTCTT

5451 CCGAGCAAAG GACGCCATCG GCCTCACTCA TGAGCAGATT
GCTCCAGCCA

5501 TCATGCCGTT CAAAGTGCAG GACCTTTGGA ACAGGCAGCT
TTCCTTCCAG

5551 CCATAGCATC ATGTCCTTTT CCCGTTCCAC ATCATAGGTG
GTCCCTTTAT

5601 ACCGGCTGTC CGTCATTTTT AAATATAGGT TTTCATTTTC
TCCCACCAGC

5651 TTATATACCT TAGCAGGAGA CATTCCTTCC GTATCTTTTA
CGCAGCGGTA

5701 TTTTTCGATC AGTTTTTTCA ATTCCGGTGA TATTCTCATT
TTAGCCATTT

5751 ATTATTTCCT TCCTCTTTTC TACAGTATTT AAAGATACCC
CAAGAAGCTA

5801 ATTATAACAA GACGAACTCC AATTCACTGT TCCTTGCATT
CTAAAACCTT

5851 AAATACCAGA AAACAGCTTT TTCAAAGTTG TTTTCAAAGT
TGGCGTATAA

5901 CATAGTATCG ACGGAGCCGA TTTTGAAACC GCGGTGATCA
CAGGCAGCAA

5951 CGCTCTGTCA TCGTTACAAT CAACATGCTA CCCTCCGCGA
GATCATCCGT

6001 GTTTCAAACC CGGCAGCTTA GTTGCCGTTC TTCCGAATAG
CATCGGTAAC

6051 ATGAGCAAAG TCTGCCGCCT TACAACGGCT CTCCCGCTGA
CGCCGTCCCG

6101 GACTGATGGG CTGCCTGTAT CGAGTGGTGA TTTTGTGCCG
AGCTGCCGGT

6151 CGGGGAGCTG TTGGCTGGCT GGTGGCAGGA TATATTGTGG
TGTAAACAAA

6201 TTGACGCTTA GACAACTTAA TAACACATTG CGGACGTTTT
TAATGTACTG

6251 AATTAACGCC GAATTAATTC GGGGGATCTG GATTTTAGTA
CTGGATTTTG

6301 GTTTTAGGAA TTAGAAATTT TATTGATAGA AGTATTTTAC
AAATACAAAT

6351 ACATACTAAG GGTTTCTTAT ATGCTCAACA CATGAGCGAA
ACCCTATAGG

6401 AACCCTAATT CCCTTATCTG GGAACTACTC ACACATTATT
ATGGAGAAAC

6451 TCGAGTTAAC CCTGAGACTG TTGGACAGAG CTCATTGGTA
CCAGGAACAG

-continued

6501 GTGGTGGCGG CCCTCGGTGC GCTCGTACTG CTCCACGATG GTGTAGTCCT

6551 CGTTGTGGGA GGTGATGTCC AGCTTGGCGT CCACGTAGTA GTAGCCGGGC

6601 AGCTGCACGG GCTTCTTGGC CATGTAGATG GACTTGAACT CCACCAGGTA

6651 GTGGCCGCCG TCCTTCAGCT TCAGGGCCTT GTGGGTCTCG CCCTTCAGCA

6701 CGCCGTCGCG GGGGTAGAGG CGCTCGGTGG AGGCCTCCCA GCCCATGGTC

6751 TTCTTCTGCA TCACGGGGCC GTCGGAGGGG AAGTTCACGC CGATGAACTT

6801 CACCTTGTAG ATGAAGCAGC CGTCCTGCAG GGAGGAGTCC TGGGTCACGG

6851 TCGCCACGCC GCCGTCCTCG AAGTTCATCA CGCGCTCCCA CTTGAAGCCC

6901 TCGGGGAAGG ACAGCTTCTT GTAGTCGGGG ATGTCGGCGG GGTGCTTCAC

6951 GTACACCTTG GAGCCGTACT GGAACTGGGG GGACAGGATG TCCCAGGCGA

7001 AGGGCAGGGG GCCGCCCTTG GTCACCTTCA GCTTCACGGT GTTGTGGCCC

7051 TCGTAGGGGC GGCCCTCGCC CTCGCCCTCG ATCTCGAACT CGTGGCCGTT

7101 CACGGTGCCC TCCATGCGCA CCTTGAAGCG CATGAACTCG GTGATGACGT

7151 TCTCGGAGGA GGCCATTTTG GTAGACTCGA GAGAGATAGA TTTGTAGAGA

7201 GAGACTGGTG ATTTCAGCGT GTCCTCTCCA AATGAAATGA ACTTCCTTAT

7251 ATAGAGGAAG GTCTTGCGAA GGATAGTGGG ATTGTGCGTC ATCCCTTACG

7301 TCAGTGGAGA TATCACATCA ATCCACTTGC TTTGAAGACG TGGTTGGAAC

7351 GTCTTCTTTT TCCACGATGC TCCTCGTGGG TGGGGGTCCA TCTTTGGGAC

7401 CACTGTCGGC AGAGGCATCT TGAACGATAG CCTTTCCTTT ATCGCAATGA

7451 TGGCATTTGT AGGTGCCACC TTCCTTTTCT ACTGTCCTTT TGATGAAGTG

7501 ACAGATAGCT GGGCAATGGA ATCCGAGGAG GTTTCCCGAT ATTACCCTTT

7551 GTTGAAAAGT CTCAATAGCC CTTTGGTCTT CTGAGACTGT ATCTTTGATA

7601 TTCTTGGAGT AGACGAGAGT GTCGTGCTCC ACCATGTTAT CACATCAATC

7651 CACTTGCTTT GAAGACGTGG TTGGAACGTC TTCTTTTTCC ACGATGCTCC

7701 TCGTGGGTGG GGGTCCATCT TTGGGACCAC TGTCGGCAGA GGCATCTTGA

7751 ACGATAGCCT TTCCTTTATC GCAATGATGG CATTTGTAGG TGCCACCTTC

-continued

7801 CTTTTCTACT GTCCTTTTGA TGAAGTGACA GATAGCTGGG CAATGGAATC

7851 CGAGGAGGTT TCCCGATATT ACCCTTTGTT GAAAAGTCTC AATAGCCCTT

7901 TGGTCTTCTG AGACTGTATC TTTGATATTC TTGGAGTAGA CGAGAGTGTC

7951 GTGCTCCACC ATGTTGGCAA GCTGCTCTAG CCAATACGCA AACCGCCTCT

8001 CCCCGCGCGT TGGCCGATTC ATTAATGCAG CTGGCACGAC AGGTTTCCCG

8051 ACTGGAAAGC GGGCAGTGAG CGCAACGCAA TTAATGTGAG TTAGCTCACT

8101 CATTAGGCAC CCCAGGCTTT ACACTTTATG CTTCCGGCTC GTATGTTGTG

8151 TGGAATTGTG AGCGGATAAC AATTTCACAC AGGAAACAGC TATGACCATG

8201 ATTACGAATT CAGGTACCAT TTAAATCCTG CAGGGTTTAA ACAGTGTTTT

8251 ACTCCTCATA TTAACTTCGG TCATTAGAGG CCACGATTTG ACACATTTTT

8301 ACTCAAAACA AAATGTTTGC ATATCTCTTA TAATTTCAAA TTCAACACAC

8351 AACAAATAAG AGAAAAAACA AATAATATTA ATTTGAGAAT GAACAAAAGG

8401 ACCATATCAT TCATTAACTC TTCTCCATCC ATTTCCATTT CACAGTTCGA

8451 TAGCGAAAAC CGAATAAAAA ACACAGTAAA TTACAAGCAC AACAAATGGT

8501 ACAAGAAAAA CAGTTTTCCC AATGCCATAA TACTCGAACG GCGCGCCTCA

8551 GCCCATATGC AGGCCGCCGT TGAGCGAGAA GTCGGCGCCG GTCGAGAAAC

8601 CGGACTCCTC CGACGACAAC CAGGCGCAGA TCGAGGCGAT CTCTTCCGGC

8651 AGGCCCAGGC GCTTGACCGG GATCGTCGCG ACGATCTTGT CGAGCACGTC

8701 CTGGCGGATC GCCTTGACCA TGTCGGTGGC GATATAGCCC GGAGAGACCG

8751 TGTTGACGGT CACGCCCTTG GTCGCCACTT CCTGCGCCAG TGCCATGGTG

8801 AAGCCATGCA GGCCGGCCTT GGCGGTGGAG TAGTTGGTCT GGCCGAACTG

8851 GCCCTTCTGC CCGTTCACCG ACGAGATGTT GACGATGCGG CCCCAGCCAC

8901 GGTCGGCCAT GCCGTCGATC ACCTGCTTGG TGACGTTGAA CAGCGAGGTC

8951 AGGTTGGTGT CGATCACCGC ATCCCAGTCG GCGCGGGTCA TCTTGCGGAA

9001 CACCACGTCG CGGGTGATAC CGGCGTTGTT GATCAGCACA TCAACCTCGC

9051 CGACCTCGGA CTTGACCTTG TCGAATGCGG TCTTGGTCGA GTCCCAGTCA

9101 GCCACATTGC CTTCCGAGGC AATGAAATCG AAGCCCAGGG CCTTCTGCTG

-continued

9151 CTCCAGCCAC TTTTCGCGGC GCGGCGAGTT GGGGCCGCAA CCGGCCACCA

9201 CACGAAAGCC ATCCTTGGCC AGCCGCTGGC AAATGGCGGT TCCGATACCA

9251 CCCATGCCGC CGGTCACATA CGCAATGCGC TGAGTCACTC TAGAATCTCT

9301 CGTCAATGGT GGCAAATAGG AAAGAGTCTC AAACTTCTTC TTTCCAATTG

9351 GAGGCCACAC CTGCATGCAC TTTACTCTTC CACCATTGCT TGTAATGGAA

9401 GTAATGTCAG TGTTGACCTT CTTCACTGGG AATCCAGTCA TGGATTTGAG

9451 GCCGCCGAAT GGAGCCACTG CGGCGGATTG CCCCCTAGAG GCACGGCTGA

9501 CTGTTGTCAC AGCGGAAGAG GATATCATAG AAGCCATTTT ACTAGTAAGA

9551 AGCTGAAAAT ATCAAAAGAA GGAACAGTCA TTAATCTATT GCATGTACTA

9601 GATTTAGAT ATGAGTGGTC AAAAAAAACT TACGTTAATA ACGATGAAGA

9651 AGACAATGAT CCTCAGCACA ATCTCTCTCT CTCTCTCTTG GCTTCTCTTC

9701 TGGTGAATAG CACGAGAGAG GGTTTAAATG GAAGGCTCGT GGGTCCAAAA

9751 TGGGTGGCGG AGGAAATAGG AGAAGTAGGC AGTGACAAGT AATGTAGTAT

9801 TTAGTATTTG ATGAATGACA CATTTTCATT TCAGCATCAT CACCAACCAT

9851 CCTTTTGTTC CTTTGCTTCA ACTGTCACTT TCAATTGACA AAATTTTTTA

9901 TGTTTTCATG AGAAAACTAA ATTCTTATAA AGATTCATCT TCTTGAGTAT

9951 TATACGTGTA GTTTATGAAC AACACGTGTT GTTCCTATAT TTTTGTTCTG

10001 TTACCTCTAG AATAAAGTTG TCACCATTTC ATGAGTTCAA TTTTTCTTTA

10051 ATAGCCCCAA AAACAAAAGA TGATTCACAA GAAAGATGCG AATATTTTGC

10101 TATGAATCTT TTCTTAAGAG AAGCAATTAC ATTTTCACAA TAAAATTAGA

10151 TCCACGACTT AACCTAGTTT ATGTTGATTA TTTCTAGTGT TAGTATTAAG

10201 CAAAAATAAA ACTTATGAAT ACGAAGGCCT TTAAAGGAAA CTAAAGAAAG

10251 GACAAGGTAT AAACGTCCTA GAAAGTTCTA GGGTTTAGGC TTAGGGTCTA

10301 AGATATATGC TTTGAGTTTT ATGGCTTAGT AACACATTTT TGTAACACTT

10351 CTTTGTAACA TTTCTTGATA TGTTGGAGAA GTAACTCGTC TGGACAATAG

10401 TTATTTCCCA TATATAGGAA AAACGGCCTA AACAATAGCC GACGGGGACA

10451 AATACATCAT AAACAAAAAA TCCCGGTTAC AAACTTCCTA AAAAGCCATT

-continued

10501 CGGTCCACTC CGTTAAGCCT GAACTGTGCC TCCGTTATGC AAAAACGCCG

10551 TTGACCATCC GTAACCTAGT TGACTGACGG ATTATGGATT TAATCCGTTT

10601 TAAGGCCGTT AATAACACCA AAACGACGTC GTTTTGGTGT TTTAATTTTT

10651 TTTAACAACA ATTAAACCAA ACGACGTCGT TTTGGTTTAA TTAAATTTTT

10701 TTATCAAAAA CCCAAGCCCA AGCCCAAAAC TCTTAACAAA AGATAAAGCC

10751 CATCTCTATT TTTTCTAATT AAAACGCACA GCATTATGTT TCTTCTCTAA

10801 CGGATATATT TTCAATCTCA TAAATTGGGG ATTAGGGTTC TTATTTCCCA

10851 ATTCTCAATC TCTCAAAATT CTCCAAAATT CTCTGAAATT GATAATGCCT

10901 TCTTCTTCTT CAAACTCGTT TTTCTCTTTT GACAGTGAGC TTGAAGATGA

10951 TAACCATCGT GGTTTTCCTA AGACCTGTCG ATTTGGATGT CGTGTTGTGA

11001 TCAGAACCTC AAGAACTCCA AAAAACCTAG GTAGATTATT CCATACCTGT

11051 GAGAAAAATT TCAAAAGAGG AGGATTCCAC ACCTGGAAGT GGACTGATGT

11101 GTCTTTAGTA GAAGAAGTAG AGGACATAAA GGCTTACATT CATAACCGTG

11151 AGAAGTGTCA CGATGAAGAA ATGTTATTAT TGAAGGCTCA GATTCGTGGC

11201 TGTGAGAAGA TGATTGAAGG CTTGAAAGGA GAAGCAAAAC GTATGAAGCT

11251 AATTGTTGTT GCCGGAATAG TTGTGTTTGG TTGCTTTTTG TGTCTCTCTA

11301 AGTGATGTAT GAGATGAATG TTTGTGTATG TGATGTTGTT TTGTCTCAAT

11351 AATTAGTCAC TGATGTTGTA TGTAATGTTG TGTTTTGCAT CTCTAATTAG

11401 TTAATAATGA ATGTTGTTCT TATGTAATGT TTGATTTAAT CAATGGCTTT

11451 TGCAAATAAA TCCATAACAG AACNTATTCA ATATTTTCGA AAACATAACA

11501 AAGGTTTCAA AAGAAATTGC ATTAGCATTA GCTGAGTTTT CAAACAAAAT

11551 GCATTACATA GACAGACCCT GCTTCATAAT CCCCAAAACA CAAAAGAGAA

11601 GCATGCTAAT AACCGCAACT AATATCCAAA GACAGCTTCA TAATCCCAAA

11651 ACACAAAAAA AGAAGATTCA TAACCGATCC TTCATGTATT TAAAGAAAAT

11701 CAGACAACAA GCAAAGACTT AATCTTCCTG AGTAACTGAT GAGCTCAAGT

11751 CGACGTTTAA ACAGTGTTTT ACTCCTCATA TTAACTTCGG TCATTAGAGG

11801 CCACGATTTG ACACATTTTT ACTCAAAACA AATGTTTGC ATATCTCTTA

-continued

11851 TAATTTCAAA TTCAACACAC AACAAATAAG AGAAAAAACA AATAATATTA

11901 ATTTGAGAAT GAACAAAAGG ACCATATCAT TCATTAACTC TTCTCCATCC

11951 ATTTCCATTT CACAGTTCGA TAGCGAAAAC CGAATAAAAA ACACAGTAAA

12001 TTACAAGCAC AACAAATGGT ACAAGAAAAA CAGTTTTCCC AATGCCATAA

12051 TACTCGAACT ACGTATTATT TGCGCTCGAC TGCCAGCGCC ACGCCCATGC

12101 CGCCGCCGAT GCACAGCGAG GCCAGGCCCT TCTTCGCGTC ACGGCGCTTC

12151 ATCTCGTGCA GCAGCGTCAC CAGGATACGG CAGCCCGACG CGCCGATCGG

12201 GTGGCCGATG GCGATGGCGC CGCCGTTCAC ATTGACCTTG GAGGTGTCCC

12251 AGCCCATCTG CTGGTGCACC GCCAGCGCCT GCGCGGCAAA GGCCTCGTTG

12301 ATCTCCATCA GGTCCAGGTC TTGCGGGGTC CACTCGGCGC GCGACAGGGC

12351 GCGCTTGGAG GCCGGCACCG GGCCCATGCC CATCACCTTG GGATCGACAC

12401 CGGCGTTGGC ATAGCTCTTG ATCGTGGCCA GCGGGGTCAG GCCCAGTTCC

12451 TTGGCCTTGG CCGCCGACAT CACCACCACC GCGGCGGCGC CGTCGTTCAG

12501 GCCCGAGGCG TTGGCCGCGG TCACCGTGCC GGCCTTGTCG AAGGCGGGCT

12551 TGAGGCCGGA CATGCTGTCC AGCGTGGCGC CCTGGCGCAC GAACTCGTCG

12601 GTCTTGAAGG CCACCGGGTC GCCCTTGCGC TGCGGGATCA GCACCGGGAC

12651 GATCTCTTCG TCAAACTTGC CGGCCTTCTG CGCGGCTTCG GCCTTGTTCT

12701 GCGAGCCGAC GGCGAACTCA TCCTGCGCCT CGCGTGTGAT GCCGTATTCC

12751 TTGGCCACGT TCTCGGCGGT GATGCCCATG TGGTACTGGT TGTACACGTC

12801 CCACAGGCCG TCGACGATCA TGGTGTCGAC CAGCTTGGCA TCGCCCATGC

12851 GGAAACCATC GCGCGAGCCC GGCAGCACGT GCGGGGCGGC GCTCATGTTT

12901 TCCTGGCCGC CGGCCACCAC GATCTCGGCG TCGCCCGCCA TGATCGCGTT

12951 GGCGGCCAGC ATCACGGCCT TCAGGCCCGA GCCGCACACC TTGTTGATGG

13001 TCATGGCCGG CACCATCGCC GGCAGGCCGG CCTTGATCGC GGCCTGGCGT

13051 GCGGGGTTCT GGCCCGAACC GGCGGTCAGC ACCTGGCCCA TGATGACTTC

13101 GCTCACCTGC TCCGGCTTGA CGCCGGCGCG CTCCAGCGCG GCCTTGATGA

13151 CCACGGCACC CAGTTCCGGT GCCGGGATCT TGGCCAGCGA GCCGCCAAAC

-continued

13201 TTGCCGACCG CGGTGCGGGC GGCGGATACG ATGACAACGT CAGTCACTCT

13251 AGAATCTCTC GTCAATGGTG GCAAATAGGA AAGAGTCTCA AACTTCTTCT

13301 TTCCAATTGG AGGCCACACC TGCATGCACT TTACTCTTCC ACCATTGCTT

13351 GTAATGGAAG TAATGTCAGT GTTGACCTTC TTCACTGGGA ATCCAGTCAT

13401 GGATTTGAGG CCGCCGAATG GAGCCACTGC GGCGGATTGC CCCCTAGAGG

13451 CACGGCTGAC TGTTGTCACA GCGGAAGAGG ATATCATAGA AGCCATTTTG

13501 GATCCAAGAA GCTGAAAATA TCAAAAGAAG GAACAGTCAT TAATCTATTG

13551 CATGTACTAG ATTTTAGATA TGAGTGGTCA AAAAAAACTT ACGTTAATAA

13601 CGATGAAGAA GACAATGATC CTCAGCACAA TCTCTCTCTC TCTCTCTTGG

13651 CTTCTCTTCT GGTGAATAGC ACGAGAGAGG GTTTAAATGG AAGGCTCGTG

13701 GGTCCAAAAT GGGTGGCGGA GGAAATAGGA GAAGTAGGCA GTGACAAGTA

13751 ATGTAGTATT TAGTATTTGA TGAATGACAC ATTTTCATTT CAGCATCATC

13801 ACCAACCATC CTTTTGTTCC TTTGCTTCAA CTGTCACTTT CAATTGACAA

13851 AATTTTTTAT GTTTTCATGA GAAAACTAAA TTCTTATAAA GATTCATCTT

13901 CTTGAGTATT ATACGTGTAG TTTATGAACA ACACGTGTTG TTCCTATATT

13951 TTTGTTCTGT TACCTCTAGA ATAAAGTTGT CACCATTTCA TGAGTTCAAT

14001 TTTTCTTTAA TAGCCCCAAA AACAAAAGAT GATTCACAAG AAAGATGCGA

14051 ATATTTTGCT ATGAATCTTT TCTTAAGAGA AGCAATTACA TTTTCACAAT

14101 AAAATTAGAT CCACGACTTA ACCTAGTTTA TGTTGATTAT TTCTAGTGTT

14151 AGTATTAAGC AAAAATAAAA CTTATGAATA CGAAGGCCTT TAAAGGAAAC

14201 TAAAGAAAGG ACAAGGTATA AACGTCCTAG AAAGTTCTAG GGTTTAGGCT

14251 TAGGGTCTAA GATATATGCT TTGAGTTTTA TGGCTTAGTA ACACATTTTT

14301 GTAACACTTC TTTGTAACAT TTCTTGATAT GTTGGAGAAG TAACTCGTCT

14351 GGACAATAGT TATTTCCAAT ATATAGGAAA AACGGCCTAA ACAATAGCCG

14401 ACGGGGACAA ATACATCATA AACAAAAAAT CCCGGTTACA AACGGCCTAA

14451 AAAGCCATTC GGTCCACTCC GTTAAGCCTG AACTGTGCCT CCGTTATGCA

14501 AAAACGCCGT TGACCATCCG TAACCTAGTT GACTGACGGA TTATGGATTT

-continued

14551 AATCCGTTTT AAGGCCGTTA ATAACACCAA AACGACGTCG TTTTGGTGTT

14601 TTAATTTTTT TTAACAACAA TTAAACCAAA CGACGTCGTT TTGGTTTAAT

14651 TAAATTTTTT TATCAAAAAC CCAAGCCCAA GCCCAAAACT CTTAACAAAA

14701 GATAAAGCCC ATCTCTATTT TTTCTAATTA AAACGCACAG CATTATGTTT

14751 CTTCTCTAAC GGATATATTT TCAATCTCAT AAATTGGGGA TTAGGGTTCT

14801 TATTTCCCAA TTCTCAATCT CTCAAAATTC TCCAAAATTC TCTGAAATTG

14851 ATAATGCCTT CTTCTTCTTC AAACTCGTTT TTCTCTTTTG ACAGTGAGCT

14901 TGAAGATGAT AACCATCGTG GTTTTCCTAA GACCTGTCGA TTTGGATGTC

14951 GTGTTGTGAT CAGAACCTCA AGAACTCCAA AAAACCTAGG TAGATTATTC

15001 CATACCTGTG AGAAAAATTT CAAAAGAGGA GGATTCCACA CCTGGAAGTG

15051 GACTGATGTG TCTTTAGTAG AAGAAGTAGA GGACATAAAG GCTTACATTC

15101 ATAACCGTGA GAAGTGTCAC GATGAAGAAA TGTTATTATT GAAGGCTCAG

15151 ATTCGTGGCT GTGAGAAGAT GATTGAAGGC TTGAAAGGAG AAGCAAAACG

15201 TATGAAGCTA ATTGTTGTTG CCGGAATAGT TGTGTTTGGT TGCTTTTTGT

15251 GTCTCTCTAA GTGATGTATG AGATGAATGT TTGTGTATGT GATGTTGTTT

15301 TGTCTCAATA ATTAGTCACT GATGTTGTAT GTAATGTTGT GTTTTGCATC

15351 TCTAATTAGT TAATAATGAA TGTTGTTCTT ATGTAATGTT TGATTTAATC

15401 AATGGCTTTT GCAAATAAAT CCATAACAGA ACNTATTCAA TATTTTCGAA

15451 AACATAACAA AGGTTTCAAA AGAAATTGCA TTAGCATTAG CTGAGTTTTC

15501 AAACAAAATG CATTACATAG ACAGACCCTG CTTCATAATC CCCAAAACAC

15551 AAAAGAGAAG CATGCTAATA ACCGCAACTA ATATCCAAAG ACAGCTTCAT

15601 AATCCCAAAA CACAAAAAAA GAAGATTCAT AACCGATCCT TCATGTATTT

15651 AAAGAAAATC AGACAACAAG CAAAGACTTA ATCTTCCTGA GTAACTGATG

15701 AGCTCAACTG CAGGTTTAAA CAGTGTTTTA CTCCTCATAT TAACTTCGGT

15751 CATTAGAGGC CACGATTTGA CACATTTTTA CTCAAAACAA AATGTTTGCA

15801 TATCTCTTAT AATTTCAAAT TCAACACACA ACAAATAAGA GAAAAAACAA

15851 ATAATATTAA TTTGAGAATG AACAAAAGGA CCATATCATT CATTAACTCT

-continued

15901 TCTCCATCCA TTTCCATTTC ACAGTTCGAT AGCGAAAACC GAATAAAAAA

15951 CACAGTAAAT TACAAGCACA ACAAATGGTA CAAGAAAAAC AGTTTTCCCA

16001 ATGCCATAAT ACTCGAACGC GATCGCTCAG CCCTTGGCTT TGACGTAACG

16051 GCCGGGCGCC GCCTCGATCG CGGTGTAGCG GGCGTTGCCG GGCTTGGCCT

16101 TGGGCTTGAC CTTCTTGCCG CCATGCTGGG TCAGGAACCC GGCCCATTGC

16151 GGCCACCAGC TGCCCGGCAC TTCCTGCGCG CCATCGAACC AGGCCTGGGC

16201 ATCGGCGGCG CCACCGTCGT TGATCCAGTA GCTGCGCTTG TTCTTGGCCA

16251 CCGAGTTGAT CACGCCGGCG ATATGGCCGG ACGCGCCCAG CACGAAGCGG

16301 TTGGCGCCCG GCTTGCCCTG GTTGAGGATG TCGAGCGAAC CGTACGCCGA

16351 CATCCACGGC ACGATGTGGT CTTCGCGCGA ACCGTAGATG AAGGCCGGGG

16401 CGTCGATCAG GCCGAGGTCG ATCTTTTCGC CGGCCACCGT CAGCTTGCCC

16451 GGCACTTTCA GGCTGTTTTC CAGGTAGGTG TTGCGCAGGT ACCAGCAGAA

16501 CATCGGGCCC GGCAAATTGG TGCTGTCCGA ATTCCAGAAC AGCAGGTCAA

16551 ACGCCGCCGG CTCATTGCCT TTGAGGTAGT TCGACTGCAC ATAGTTCCAT

16601 ACCAGGTCGT TCGGACGCAG GCTCGAGAAG GTCGAGGCCA GGTCACGGCC

16651 CGGCATCAGG CCGCCATCGC GCAATTGCTG TTCACGCAGC GCGACCTGGG

16701 TTTCATCGAC GAAGACGTCG AGCACGCCGG TGTCGCTGAA GTCGAGGAAG

16751 GTGGTCAGCA GGGTCAGGCT GGCCGCCGGG TGCTGGCCAC GCGCCGCCAG

16801 TACCGCCAGT GCGGTGGCAA CGATGGTGCC GCCCACGCAG AAGCCGAACA

16851 TGTTCAGCTT GTCCTGGCCG CTGACGTCCT GGACGATGCG GATCGCTTCG

16901 ATCACGCCCT GCTCCACGTA GTCGTCCCAG GTGGTGCCGG CCAGCGACTT

16951 GTCCGGATTG CTCCACGAGA TCAGGAACAC GGTGTTGCCC TGCTCCACCG

17001 CGTAGCGCAC CAGCGAATTT TCCGGTTGCA GGTCGAGGAT GTAGAACTTG

17051 TTGATGCACG GCGGCACCAT CAACAGCGGG CGCTGGCTGA CCGTCGGCGT

17101 GGTCGGCGTG TACTGGATCA GCTGGAACAG CGGATTTTCG TAAATCACGG

17151 TGCCCGGGGT AATGGCCAGG TTGCGGCCCA CTTCAAAGGC CGATTCGTCC

17201 GACAGCGAGA TATGGCCCTT GTTGATATCG CCCAGCATAT TGACCAGGCC

-continued

17251 ACGCGTCAGG CTCTCGCCCT TGGTTTCAAT CAGTTTTTGC TGCGCTTCCG

17301 GGTTGGTGGC GAGGAAGTTC GCGGGCGACA TGGCATCAAT CACCTGCTGC

17351 ACGGCAAAGC GTATTTTCTG CTTTTGCTGG GGTGCGGTGT CCACCGCCTC

17401 CACCATGGCA CTGAGGAATT TGGCGTTGAG CAGGTAAGAT GCGGCATTGA

17451 AGGCCGACAT CGGATTGCCC TGCCAGGCTG CCGAGCTGAA GCGGCGGTCG

17501 CTGACGGCTG GCGCCTTGCC AGCCAAAAAA TCCTGCCACA ACGCGGTGAA

17551 GTCACGCAGA TAATCGTTTT TCAGCTGCTC CATCGCTTCC GGTTTGAGCG

17601 CAACGCCGAT ATCCTGCAAC ATGGTGGCCA TCGGGTTCGC CTCGGTGGTG

17651 GGCGCCTTGC TGAACCAGGA TTGCCACTGC AGCTCATCGT TGTTCTTGTT

17701 ACTCACTCTA GAATCTCTCG TCAATGGTGG CAAATAGGAA AGAGTCTCAA

17751 ACTTCTTCTT TCCAATTGGA GGCCACACCT GCATGCACTT TACTCTTCCA

17801 CCATTGCTTG TAATGGAAGT AATGTCAGTG TTGACCTTCT TCACTGGGAA

17851 TCCAGTCATG GATTTGAGGC CGCCGAATGG AGCCACTGCG GCGGATTGCC

17901 CCCTAGAGGC ACGGCTGACT GTTGTCACAG CGGAAGAGGA TATCATAGAA

17951 GCCATTTTTG TACAAAGAAG CTGAAAATAT CAAAAGAAGG AACAGTCATT

18001 AATCTATTGC ATGTACTAGA TTTTAGATAT GAGTGGTCAA AAAAAACTTA

18051 CGTTAATAAC GATGAAGAAG ACAATGATCC TCAGCACAAT CTCTCTCTCT

18101 CTCTCTTGGC TTCTCTTCTG GTGAATAGCA CGAGAGAGGG TTTAAATGGA

18151 AGGCTCGTGG GTCCAAAATG GGTGGCGGAG GAAATAGGAG AAGTAGGCAG

18201 TGACAAGTAA TGTAGTATTT AGTATTTGAT GAATGACACA TTTTCATTTC

18251 AGCATCATCA CCAACCATCC TTTTGTTCCT TTGCTTCAAC TGTCACTTTC

18301 AATTGACAAA ATTTTTTATG TTTTCATGAG AAAACTAAAT TCTTATAAAG

18351 ATTCATCTTC TTGAGTATTA TACGTGTAGT TTATGAACAA CACGTGTTGT

18401 TCCTATATTT TTGTTCTGTT ACCTCTAGAA TAAAGTTGTC ACCATTTCAT

18451 GAGTTCAATT TTTCTTTAAT AGCCCCAAAA ACAAAAGATG ATTCACAAGA

18501 AAGATGCGAA TATTTTGCTA TGAATCTTTT CTTAAGAGAA GCAATTACAT

18551 TTTCACAATA AAATTAGATC CACGACTTAA CCTAGTTTAT GTTGATTATT

-continued

18601 TCTAGTGTTA GTATTAAGCA AAAATAAAAC TTATGAATAC GAAGGCCTTT

18651 AAAGGAAACT AAAGAAAGGA CAAGGTATAA ACGTCCTAGA AAGTTCTAGG

18701 GTTTAGGCTT AGGGTCTAAG ATATATGCTT TGAGTTTTAT GGCTTAGTAA

18751 CACATTTTTG TAACACTTCT TTGTAACATT TCTTGATATG TTGGAGAAGT

18801 AACTCGTCTG GACAATAGTT ATTTCCAATA TATAGGAAAA ACGGCCTAAA

18851 CAATAGCCGA CGGGGACAAA TACATCATAA ACAAAAAATC CCGGTTACAA

18901 ACTTCCTAAA AAGCCATTCG GTCCACTCCG TTAAGCCTGA ACTGTGCCTC

18951 CGTTATGCAA AAACGCCGTT GACCATCCGT AACCTAGTTG ACTGACGGAT

19001 TATGGATTTA ATCCGTTTTA AGGCCGTTAA TAACACCAAA ACGACGTCGT

19051 TTTGGTGTTT TAATTTTTTT TAACAACAAT TAAACCAAAC GACGTCGTTT

19101 TGGTTTAATT AAATTTTTTT ATCAAAAACC CAAGCCCAAG CCCAAAACTC

19151 TTAACAAAAG ATAAAGCCCA TCTCTATTTT TTCTAATTAA AACGCACAGC

19201 ATTATGTTTC TTCTCTAACG GATATATTTT CAATCTCATA AATTGGGGAT

19251 TAGGGTTCTT ATTTCCCAAT TCTCAATCTC TCAAAATTCT CCAAAATTCT

19301 CTGAAATTGA TAATGCCTTC TTCTTCTTCA AACTCGTTTT TCTCTTTTGA

19351 CAGTGAGCTT GAAGATGATA ACCATCGTGG TTTTCCTAAG ACCTGTCGAT

19401 TTGGATGTCG TGTTGTGATC AGAACCTCAA GAACTCCAAA AAACCTAGGT

19451 AGATTATTCC ATACCTGTGA GAAAAATTTC AGAAGTAGAG GATTCCACAC

19501 CTGGAAGTGG ACTGATGTGT CTTTAGTAGA AGAAGTAGAG GACATAAAGG

19551 CTTACATTCA TAACCGTGAG AAGTGTCACG ATGAAGAAAT GTTATTATTG

19601 AAGGCTCAGA TTCGTGGCTG TGAGAAGATG ATTGAAGGCT TGAAAGGAGA

19651 AGCAAAACGT ATGAAGCTAA TTGTTGTTGC CGGAATAGTT GTGTTTGGTT

19701 GCTTTTTGTG TCTCTCTAAG TGATGTATGA GATGAATGTT TGTGTATGTG

19751 ATGTTGTTTT GTCTCAATAA TTAGTCACTG ATGTTGTATG TAATGTTGTG

19801 TTTTGCATCT CTAATTAGTT AATAATGAAT GTTGTTCTTA TGTAATGTTT

19851 GATTTAATCA ATGGCTTTTG CAAATAAATC CATAACAGAA CNTATTCAAT

19901 ATTTTCGAAA ACATAACAAA GGTTTCAAAA GAAATTGCAT TAGCATTAGC

-continued

19951 TGAGTTTTCA AACAAAATGC ATTACATAGA CAGACCCTGC TTCATAATCC

20001 CCAAAACACA AAAGAGAAGC ATGCTAATAA CCGCAACTAA TATCCAAAGA

20051 CAGCTTCATA ATCCCAAAAC ACAAAAAAAG AAGATTCATA ACCGATCCTT

20101 CATGTATTTA AAGAAAATCA GACAACAAGC AAAGACTTAA TCTTCCTGAG

20151 TAACTGATGA GCTCAAAAGC TTGGCACTGG CCGTCGTTTT ACGACGTCGT

20201 GACTGGGAAA ACCCTGGCGT TACCCAACTT AATCGCCTTG CAGCACATCC

20251 CCCTTTCGCC AGCTGGCGTA ATAGCGAAGA GGCCCGCACC GATCGCCCTT

20301 CCCAACAGTT GCGCAGCCTG AATGGCGAAT GCTAGAGCAG CTTGAGCTTG

20351 GATCAGATTG TCGTTTCCCG CCTTCAGTTT AAACTATCAG TGTTTGACAG

20401 GATATATTGG CGGGTAAACC TAAGAGAAAA GAGCGTTTAT TAGAATAACG

20451 GATATTTAAA AGGGCGTGAA AAGGTTTATC CGTTCGTCCA TTTGTATGTG

Vector: pPhaA-RNAi/35S (SEQ ID NO: 3)

1 GTCCGTGACC ATGATTACGC CAAGCTTCGA CTGTACAGGA TGTTCTAGCT

51 ACTCGAGTAG CTAGAACATC CTGTACAGTC GAGTAGCTAG AACATCCTGT

101 ACAGTCGACT AGCTAGAACA TCCTGTACAG TCGAGTAGCT AGAACATCCT

151 GTACAGTCGA GTAGCTAGAC ATCCTGTACA GGATCCCTAT ATAAGGAAGT

201 TCATTTCATT TGGAGAGAAC ACGGGGGATC GGGTATCGTT AATTAAGTTT

251 ATCAACAAGT TTGTACAAAA AAGCAGGCTC CGCGGCCGCC CCCTTCACCA

301 TGATCGTCGA CGGCCTGTGG GACGTGTACA ACCAGTACCA CATGGGCATC

351 ACCGCCGAGA ACGTGGCCAA GGAATACGGC ATCACACGCG AGGCGCAGGA

401 TGAGTTCGCC GTCGGCTCGC AGAACAAGGC CGAAGCCGCG CAGAAGGCCG

451 GCAAGTTTGA CGAAGAGATC GTCCCGGTGC TGATCCCGCA GCGCAAGGGC

501 GACCCGGTGG CCTTCAAGAC CGACGAGTTC GTGCGCCAGG GCGCCACGCT

551 GGACAGCATG TCCGGCCTCA AGCCCGCCTT CGACAAGGCC GGCACGGTGA

601 CCGCGGCCAA CGCCTCGGGC CTGAACGACG GCGCCGCCGC GGTGGTGGTG

651 ATGTCGGCGG CCAAGGCCAA GGAACTGGGC CTGACCCCGC TGGCCACGAT

701 CAAGAGCTAT GCCAACGCCG GTGTCGATCC CAAGGTGATG GGCATGGGCC

-continued

751 CGGTGCCGGC CTCCAAGCGC GCCCTGTCGC GCGCCGAGTG GACCCCGCAA

801 GACCTGGACC TGATGGAGAT CAACGAGGCC TTTGCCGCGC AGGCGCTGGC

851 GGTGCACCAG CAGATGGGCT GGGACACCTC CAAGGTCAAT GTGAAAGGGT

901 GGGCGCGCCG ACCCAGCTTT CTTGTACAAA GTGGTTGATC CTGCAGGGTC

951 CGTCGCTTCT CTTCCATTTC TTCTCATTTT CGATTTTGAT TCTTATTTCT

1001 TTCCAGTAGC TCCTGCTCTG TGAATTTCTC CGCTCACGAT AGATCTGCTT

1051 ATACTCCTTA CATTCAACCT TAGATCTGGT CTCGATTCTC TGTTTCTCTG

1101 TTTTTTTCTT TTGGTCGAGA ATCTGATGTT TGTTTATGTT CTGTCACCAT

1151 TAATAATAAT GAACTCTCTC ATTCATACAA TGATTAGTTT CTCTCGTCTA

1201 CAAAACGATA TGTTGCATTT TCACTTTTCT TCTTTTTTTC TAAGATGATT

1251 TGCTTTGACC AATTTGTTTA GATCTTTATT CTATTTTATT TTCTGGTGGG

1301 TTGGTGGAAA TTGAAAAAAA AAAAACAGCA TAAATTGTTA TTTGTTAATG

1351 TATTCATTTT TTGGCTATTT GTTCTGGGTA AAAATCTGCT TCTACTATTG

1401 AATCTTTCCT GGATTTTTTA CTCCTATTGG GTTTTTATAG TAAAAATACA

1451 TAATAAAAGG AAAACAAAAG TTTTATAGAT TCTCTTAAAC CCCTTACGAT

1501 AAAAGTTGGA ATCAAAATAA TTCAGGATCA GATGCTCTTT GATTGATTCA

1551 GATGCGATTA CAGTTGCATG GCAAATTTTC TAGATCCGTC GTCACATTTT

1601 ATTTTCTGTT TAAATATCTA AATCTGATAT ATGATGTCGA CAAATTCTGG

1651 TGGCTTATAC ATCACTTCAA CTGTTTTCTT TTGGCTTTGT TTGTCAACTT

1701 GGTTTTCAAT ACGATTTGTG ATTTCGATCG CTGAATTTTT AATACAAGCA

1751 AACTGATGTT AACCACAAGC AAGAGATGTG ACCTGCCTTA TTAACATCGT

1801 ATTACTTACT ACTAGTCGTA TTCTCAACGC AATCGTTTTT GTATTTCTCA

1851 CATTATGCCG CTTCTCTACT CTTTATTCCT TTTGGTCCAC GCATTTTCTA

1901 TTTGTGGCAA TCCCTTTCAC AACCTGATTT CCCACTTTGG ATCATTTGTC

1951 TGAAGACTCT CTTGAATCGT TACCACTTGT TTCTTGTGCA TGCTCTGTTT

2001 TTTAGAATTA ATGATAAAAC TATTCCATAG TCTTGAGTTT TCAGCTTGTT

2051 GATTCTTTTG CTTTTGGTTT TCTGCAGGTT TAAACATCAA CCACTTTGTA

-continued

```
2101 CAAGAAAGCT GGGTCGGCGC GCCCACCCTT TCACATTGAC
     CTTGGAGGTG

2151 TCCCAGCCCA TCTGCTGGTG CACCGCCAGC GCCTGCGCGG
     CAAAGGCCTC

2201 GTTGATCTCC ATCAGGTCCA GGTCTTGCGG GGTCCACTCG
     GCGCGCGACA

2251 GGGCGCGCTT GGAGGCCGGC ACCGGGCCCA TGCCCATCAC
     CTTGGGATCG

2301 ACACCGGCGT TGGCATAGCT CTTGATCGTG GCCAGCGGGG
     TCAGGCCCAG

2351 TTCCTTGGCC TTGGCCGCCG ACATCACCAC CACCGCGGCG
     GCGCCGTCGT

2401 TCAGGCCCGA GGCGTTGGCC GCGGTCACCG TGCCGGCCTT
     GTCGAAGGCG

2451 GGCTTGAGGC CGGACATGCT GTCCAGCGTG GCGCCCTGGC
     GCACGAACTC

2501 GTCGGTCTTG AAGGCCACCG GGTCGCCCTT GCGCTGCGGG
     ATCAGCACCG

2551 GGACGATCTC TTCGTCAAAC TTGCCGGCCT TCTGCGCGGC
     TTCGGCCTTG

2601 TTCTGCGAGC CGACGGCGAA CTCATCCTGC GCCTCGCGTG
     TGATGCCGTA

2651 TTCCTTGGCC ACGTTCTCGG CGGTGATGCC CATGTGGTAC
     TGGTTGTACA

2701 CGTCCCACAG GCCGTCGACG ATCATGGTGA AGGGGGCGGC
     CGCGGAGCCT

2751 GCTTTTTTGT ACAAACTTGT TGATCTCGAG CGGCGCGCCG
     TTCGAGTATT

2801 ATGGCATTGG GAAAACTGTT TTTCTTGTAC CATTTGTTGT
     GCTTGTAATT

2851 TACTGTGTTT TTTATTCGGT TTTCGCTATC GAACTGTGAA
     ATGGAAATGG

2901 ATGGAGAAGA GTTAATGAAT GATATGGTCC TTTTGTTCAT
     TCTCAAATTA

2951 ATATTATTTG TTTTTTCTCT TATTTGTTGT GTGTTGAATT
     TGAAATTATA

3001 AGAGATATGC AAACATTTTG TTTTGAGTAA AAATGTGTCA
     AATCGTGGCC

3051 TCTAATGACC GAAGTTAATA TGAGGAGTAA AACACTGTTT
     AAACCCTGCA

3101 GGATTTAAAT AGAAGGTAAT TATCCAAGAT GTAGCATCAA
     GAATCCAATG

3151 TTTACGGGAA AAACTATGGA AGTATTATGT GAGCTCAGCA
     AGAAGCAGAT

3201 CAATATGCGG CACATATGCA ACCTATGTTC AAAAATGAAG
     AATGTACAGA

3251 TACAAGATCC TATACTGCCA GAATACGAAG AAGAATACGT
     AGAAATTGAA

3301 AAAGAAGAAC CAGGCGAAGA AAAGAATCTT GAAGACGTAA
     GCACTGACGA

3351 CAACAATGAA AAGAAGAAGA TAAGGTCGGT GATTGTGAAA
     GAGACATAGA

3401 GGACACATGT AAGGTGGAAA ATGTAAGGGC GGAAAGTAAC
     CTTATCACAA
```

-continued

```
3451 AGGAATCTTA TCCCCCACTA CTTATCCTTT TATATTTTTC
     CGTGTCATTT

3501 TTGCCCTTGA GTTTTCCTAT ATAAGGAACC AAGTTCGGCA
     TTTGTGAAAA

3551 CAAGAAAAAA TTGGTGTAAG CTATTTTCTT TGAAGTACTG
     AGGATACAAC

3601 TTCAGAGAAA TTTGTAAGAA AGTGGATCGA AACCATGGCC
     TCCTCCGAGA

3651 ACGTCATCAC CGAGTTCATG CGCTTCAAGG TGCGCATGGA
     GGGCACCGTG

3701 AACGGCCACG AGTTCGAGAT CGAGGGCGAG GGCGAGGGCC
     GCCCCTACGA

3751 GGGCCACAAC ACCGTGAAGC TGAAGGTGAC CAAGGGCGGC
     CCCCTGCCCT

3801 TCGCCTGGGA CATCCTGTCC CCCCAGTTCC AGTACGGCTC
     CAAGGTGTAC

3851 GTGAAGCACC CCGCCGACAT CCCCGACTAC AAGAAGCTGT
     CCTTCCCCGA

3901 GGGCTTCAAG TGGGAGCGCG TGATGAACTT CGAGGACGGC
     GGCGTGGCGA

3951 CCGTGACCCA GGACTCCTCC CTGCAGGACG GCTGCTTCAT
     CTACAAGGTG

4001 AAGTTCATCG GCGTGAACTT CCCCTCCGAC GGCCCCGTGA
     TGCAGAAGAA

4051 GACCATGGGC TGGGAGGCCT CCACCGAGCG CCTGTACCCC
     CGCGACGGCG

4101 TGCTGAAGGG CGAGACCCAC AAGGCCCTGA AGCTGAAGGA
     CGGCGGCCAC

4151 TACCTGGTGG AGTTCAAGTC CATCTACATG GCCAAGAAGC
     CCGTGCAGCT

4201 GCCCGGCTAC TACTACGTGG ACGCCAAGCT GGACATCACC
     TCCCACAACG

4251 AGGACTACAC CATCGTGGAG CAGTACGAGC GCACCGAGGG
     CCGCCACCAC

4301 CTGTTCCTGG TACCAATGAG CTCTGTCCAA CAGTCTCAGG
     GTTAATGTCT

4351 ATGTATCTTA AATAATGTTG TCGGCGATCG TTCAAACATT
     TGGCAATAAA

4401 GTTTCTTAAG ATTGAATCCT GTTGCCGGTC TTGCGATGAT
     TATCATATAA

4451 TTTCTGTTGA ATTACGTTAA GCATGTAATA ATTAACATGT
     AATGCATGAC

4501 GTTATTTATG AGATGGGTTT TTATGATTAG AGTCCCGCAA
     TTATACATTT

4551 AATACGCGAT AGAAAACAAA ATATACCGCG CAAACTAGGA
     TAAATTATCG

4601 CGCGCGGTGT CATCTATGTT ACTAGATCGG GAATTAAACT
     ATCAGTGTTT

4651 GACAGGATAT ATTGGCGGGT AAACCTAAGA GAAAAGAGCG
     TTTATTAGAA

4701 TAACGGATAT TTAAAAGGGC GTGAAAAGGT TTATCCGTTC
     GTCCATTTGT

4751 ATGTGCATGC CAACCACAGG GTTCCCCTCG GGATCAAAGT
     ACTTTGATCC
```

-continued

4801 AACCCCTCCG CTGCTATAGT GCAGTCGGCT TCTGACGTTC AGTGCAGCCG

4851 TCTTCTGAAA ACGACATGTC GCACAAGTCC TAAGTTACGC GACAGGCTGC

4901 CGCCCTGCCC TTTTCCTGGC GTTTTCTTGT CGCGTGTTTT AGTCGCATAA

4951 AGTAGAATAC TTGCGACTAG AACCGGAGAC ATTACGCCAT GAACAAGAGC

5001 GCCGCCGCTG GCCTGCTGGG CTATGCCCGC GTCAGCACCG ACGACCAGGA

5051 CTTGACCAAC CAACGGGCCG AACTGCACGC GGCCGGCTGC ACCAAGCTGT

5101 TTTCCGAGAA GATCACCGGC ACCAGGCGCG ACCGCCCGGA GCTGGCCAGG

5151 ATGCTTGACC ACCTACGCCC TGGCGACGTT GTGACAGTGA CCAGGCTAGA

5201 CCGCCTGGCC CGCAGCACCC GCGACCTACT GGACATTGCC GAGCGCATCC

5251 AGGAGGCCGG CGCGGGCCTG CAGAGCCGTG CAGAGCCGTG GGCCGACACC

5301 ACCACGCCGG CCGGCCGCAT GGTGTTGACC GTGTTCGCCG GCATTGCCGA

5351 GTTCGAGCGT TCCCTAATCA TCGACCGCAC CCGGAGCGGG CGCGAGGCCG

5401 CCAAGGCCCG AGGCGTGAAG TTTGGCCCCC GCCCTACCCT CACCCCGGCA

5451 CAGATCGCGC ACGCCCGCGA GCTGATCGAC CAGGAAGGCC GCACCGTGAA

5501 AGAGGCGGCT GCACTGCTTG GCGTGCATCG CTCGACCCTG TACCGCGCAC

5551 TTGAGCGCAG CGAGGAAGTG ACGCCCACCG AGGCCAGGCG GCGCGGTGCC

5601 TTCCGTGAGG ACGCATTGAC CGAGGCCGAC GCCCTGGCGG CCGCCGAGAA

5651 TGAACGCCAA GAGGAACAAG CATGAAACCG CACCAGGACG GCCAGGACGA

5701 ACCGTTTTTC ATTACCGAAG AGATCGAGGC GGAGATGATC GCGGCCGGGT

5751 ACGTGTTCGA GCCGCCCGCG CACGTCTCAA CCGTGCGGCT GCATGAAATC

5801 CTGGCCGGTT TGTCTGATGC CAAGCTGGCG GCCTGGCCGG CCAGCTTGGC

5851 CGCTGAAGAA ACCGAGCGCC GCCGTCTAAA AAGGTGATGT GTATTTGAGT

5901 AAAACAGCTT GCGTCATGCG GTCGCTGCGT ATATGATGCG ATGAGTAAAT

5951 AAACAAATAC GCAAGGGGAA CGCATGAAGG TTATCGCTGT ACTTAACCAG

6001 AAAGGCGGGT CAGGCAAGAC GACCATCGCA ACCCATCTAG CCCGCGCCCT

6051 GCAACTCGCC GGGGCCGATG TTCTGTTAGT CGATTCCGAT CCCCAGGGCA

6101 GTGCCCGCGA TTGGGCGGCC GTGCGGGAAG ATCAACCGCT AACCGTTGTC

6151 GGCATCGACC GCCCGACGAT TGACCGCGAC GTGAAGGCCA TCGGCCGGCG

6201 CGACTTCGTA GTGATCGACG GAGCGCCCCA GGCGGCGGAC TTGGCTGTGT

6251 CCGCGATCAA GGCAGCCGAC TTCGTGCTGA TTCCGGTGCA GCCAAGCCCT

6301 TACGACATAT GGGCCACCGC CGACCTGGTG GAGCTGGTTA AGCAGCGCAT

6351 TGAGGTCACG GATGGAAGGC TACAAGCGGC CTTTGTCGTG TCGCGGGCGA

6401 TCAAAGGCAC GCGCATCGGC GGTGAGGTTG CCGAGGCGCT GGCCGGGTAC

6451 GAGCTGCCCA TTCTTGAGTC CCGTATCACG CAGCGCGTGA GCTACCCAGG

6501 CACTGCCGCC GCCGGCACAA CCGTTCTTGA ATCAGAACCC GAGGGCGACG

6551 CTGCCCGCGA GGTCCAGGCG CTGGCCGCTG AAATTAAATC AAAACTCATT

6601 TGAGTTAATG AGGTAAAGAG AAAATGAGCA AAAGCACAAA CACGCTAAGT

6651 GCCGGCCGTC CGAGCGCACG CAGCAGCAAG GCTGCAACGT TGGCCAGCCT

6701 GGCAGACACG CCAGCCATGA AGCGGGTCAA CTTTCAGTTG CCGGCGGAGG

6751 ATCACACCAA GCTGAAGATG TACGCGGTAC GCCAAGGCAA GACCATTACC

6801 GAGCTGCTAT CTGAATACAT CGCGCAGCTA CCAGAGTAAA TGAGCAAATG

6851 AATAAATGAG TAGATGAATT TTAGCGGCTA AAGGAGGCGG CATGGAAAAT

6901 CAAGAACAAC CAGGCACCGA CGCCGTGGAA TGCCCCATGT GTGGAGGAAC

6951 GGGCGGTTGG CCAGGCGTAA GCGGCTGGGT TGTCTGCCGG CCCTGCAATG

7001 GCACTGGAAC CCCCAAGCCC GAGGAATCGG CGTGACGGTC GCAAACCATC

7051 CGGCCCGGTA CAAATCGGCG CGGCGCTGGG TGATGACCTG GTGGAGAAGT

7101 TGAAGGCCGC GCAGGCCGCC CAGCGGCAAC GCATCGAGGC AGAAGCACGC

7151 CCCGGTGAAT CGTGGCAAGC GGCCGCTGAT CGAATCCGCA AAGAATCCCG

7201 GCAACCGCCG GCAGCCGGTG CGCCGTCGAT TAGGAAGCCG CCCAAGGGCG

7251 ACGAGCAACC AGATTTTTTC GTTCCGATGC TCTATGACGT GGGCACCCGC

7301 GATAGTCGCA GCATCATGGA CGTGGCCGTT TTCCGTCTGT CGAAGCGTGA

7351 CCGACGAGCT GGCGAGGTGA TCCGCTACGA GCTTCCAGAC GGGCACGTAG

7401 AGGTTTCCGC AGGGCCGGCC GGCATGGCCA GTGTGTGGGA TTACGACCTG

7451 GTACTGATGG CGGTTTCCCA TCTAACCGAA TCCATGAACC GATACCGGGA

-continued

7501 AGGGAAGGGA GACAAGCCCG GCCGCGTGTT CCGTCCACAC GTTGCGGACG

7551 TACTCAAGTT CTGCCGGCGA GCCGATGGCG GAAAGCAGAA AGACGACCTG

7601 GTAGAAACCT GCATTCGGTT AAACACCACG CACGTTGCCA TGCAGCGTAC

7651 GAAGAAGGCC AAGAACGGCC GCCTGGTGAC GGTATCCGAG GGTGAAGCCT

7701 TGATTAGCCG CTACAAGATC GTAAAGAGCG AAACCGGGCG GCCGGAGTAC

7751 ATCGAGATCG AGCTAGCTGA TTGGATGTAC CGCGAGATCA CAGAAGGCAA

7801 GAACCCGGAC GTGCTGACGG TTCACCCCGA TTACTTTTTG ATCGATCCCG

7851 GCATCGGCCG TTTTCTCTAC CGCCTGGCAC GCCGCGCCGC AGGCAAGGCA

7901 GAAGCCAGAT GGTTGTTCAA GACGATCTAC GAACGCAGTG GCAGCGCCGG

7951 AGAGTTCAAG AAGTTCTGTT TCACCGTGCG CAAGCTGATC GGGTCAAATG

8001 ACCTGCCGGA GTACGATTTG AAGGAGGAGG CGGGGCAGGC TGGCCCGATC

8051 CTAGTCATGC GCTACCGCAA CCTGATCGAG GGCGAAGCAT CCGCCGGTTC

8101 CTAATGTACG GAGCAGATGC TAGGGCAAAT TGCCCTAGCA GGGGAAAAAG

8151 GTCGAAAAGG TCTCTTTCCT GTGGATAGCA CGTACATTGG GAACCCAAAG

8201 CCGTACATTG GGAACCGGAA CCCGTACATT GGGAACCCAA AGCCGTACAT

8251 TGGGAACCGG TCACACATGT AAGTGACTGA TATAAAAGAG AAAAAAGGCG

8301 ATTTTTCCGC CTAAAACTCT TTAAAACTTA TTAAAACTCT TAAAACCCGC

8351 CTGGCCTGTG CATAACTGTC TGGCCAGCGC ACAGCCGAAG AGCTGCAAAA

8401 AGCGCCTACC CTTCGGTCGC TGCGCTCCCT ACGCCCCGCC GCTTCGCGTC

8451 GGCCTATCGC GGCCGCTGGC CGCTCAAAAA TGGCTGGCCT ACGGCCAGGC

8501 AATCTACCAG GGCGCGGACA AGCCGCGCCG TCGCCACTCG ACCGCCGGCG

8551 CCCACATCAA GGCACCCTGC CTCGCGCGTT TCGGTGATGA CGGTGAAAAC

8601 CTCTGACACA TGCAGCTCCC GGAGACGGTC ACAGCTTGTC TGTAAGCGGA

8651 TGCCGGGAGC AGACAAGCCC GTCAGGGCGC GTTGGCGGGT GTTGGCGGGT

8701 GTCGGGGCGC AGCCATGACC CAGTCACGTA GCGATAGCGG AGTGTATACT

8751 GGCTTAACTA TGCGGCATCA GAGCAGATTG TACTGAGAGT GCACCATATG

8801 CGGTGTGAAA TACCGCACAG ATGCGTAAGG AGAAAATACC GCATCAGGCG

-continued

8851 CTCTTCCGCT TCCTCGCTCA CTGACTCGCT GCGCTCGGTC GTTCGGCTGC

8901 GGCGAGCGGT ATCAGCTCAC TCAAAGGCGG TAATACGGTT ATCCACAGAA

8951 TCAGGGGATA ACGCAGGAAA GAACATGTGA GCAAAAGGCC AGCAAAAGGC

9001 CAGGAACCGT AAAAAGGCCG CGTTGCTGGC GTTTTTCCAT AGGCTCCGCC

9051 CCCCTGACGA GCATCACAAA AATCGACGCT CAAGTCAGAG GTGGCGAAAC

9101 CCGACAGGAC TATAAAGATA CCAGGCGTTT CCCCCTGGAA GCTCCCTCGT

9151 GCGCTCTCCT GTTCCGACCC TGCCGCTTAC CGGATACCTG TCCGCCTTTC

9201 TCCCTTCGGG AAGCGTGGCG CTTTCTCATA GCTCACGCTG TAGGTATCTC

9251 AGTTCGGTGT AGGTCGTTCG CTCCAAGCTG GGCTGTGTGC ACGAACCCCC

9301 CGTTCAGCCC GACCGCTGCG CCTTATCCGG TAACTATCGT CTTGAGTCCA

9351 ACCCGGTAAG ACACGACTTA TCGCCACTGG CAGCAGCCAC TGGTAACAGG

9401 ATTAGCAGAG CGAGGTATGT AGGCGGTGCT ACAGAGTTCT TGAAGTGGTG

9451 GCCTAACTAC GGCTACACTA GAAGGACAGT ATTTGGTATC TGCGCTCTGC

9501 TGAAGCCAGT TACCTTCGGA AAAAGAGTTG GTAGCTCTTG ATCCGGCAAA

9551 CAAACCACCG CTGGTAGCGG TGGTTTTTTT GTTTGCAAGC AGCAGATTAC

9601 GCGCAGAAAA AAAGGATCTC AAGAAGATCC TTTGATCTTT TCTACGGGGT

9651 CTGACGCTCA GTGGAACGAA AACTCACGTT AAGGGATTTT GGTCATGCAT

9701 TCTAGGTACT AAAACAATTC ATCCAGTAAA ATATAATATT TTATTTTCTC

9751 CCAATCAGGC TTGATCCCCA GTAAGTCAAA AAATAGCTCG ACATACTGTT

9801 CTTCCCCGAT ATCCTCCCTG ATCGACCGGA CGCAGAAGGC AATGTCATAC

9851 CACTTGTCCG CCCTGCCGCT TCTCCCAAGA TCAATAAAGC CACTTACTTT

9901 GCCATCTTTC ACAAAGATGT TGCTGTCTCC CAGGTCGCCG TGGGAAAAGA

9951 CAAGTTCCTC TTCGGGCTTT TCCGTCTTTA AAAAATCATA CAGCTCGCGC

10001 GGATCTTTAA ATGGAGTGTC TTCTTCCCAG TTTTCGCAAT CCACATCGGC

10051 CAGATCGTTA TTCAGTAAGT AATCCAATTC GGCTAAGCGG CTGTCTAAGC

10101 TATTCGTATA GGGACAATCC GATATGTCGA TGGAGTGAAA GAGCCTGATG

10151 CACTCCGCAT ACAGCTCGAT AATCTTTTCA GGGCTTTGTT CATCTTCATA

-continued

10201 CTCTTCCGAG CAAAGGACGC CATCGGCCTC ACTCATGAGC AGATTGCTCC

10251 AGCCATCATG CCGTTCAAAG TGCAGGACCT TTGGAACAGG CAGCTTTCCT

10301 TCCAGCCATA GCATCATGTC CTTTTCCCGT TCCACATCAT AGGTGGTCCC

10351 TTTATACCGG CTGTCCGTCA TTTTTAAATA TAGGTTTTCA TTTTCTCCCA

10401 CCAGCTTATA TACCTTAGCA GGAGACATTC CTTCCGTATC TTTTACGCAG

10451 CGGTATTTTT CGATCAGTTT TTTCAATTCC GGTGATATTC TCATTTTAGC

10501 CATTTATTAT TTCCTTCCTC TTTTCTACAG TATTTAAAGA TACCCCAAGA

10551 AGCTAATTAT AACAAGACGA ACTCCAATTC ACTGTTCCTT GCATTCTAAA

10601 ACCTTAAATA CCAGAAAACA GCTTTTTCAA AGTTGTTTTC AAAGTTGGCG

10651 TATAACATAG TATCGACGGA GCCGATTTTG AAACCGCGGT GATCACAGGC

10701 AGCAACGCTC TGTCATCGTT ACAATCAACA TGCTACCCTC CGCGAGATCA

10751 TCCGTGTTTC AAACCCGGCA GCTTAGTTGC CGTTCTTCCG AATAGCATCG

10801 GTAACATGAG CAAAGTCTGC CGCCTTACAA CGGCTCTCCC GCTGACGCCG

10851 TCCCGGACTG ATGGGCTGCC TGTATCGAGT GGTGATTTTG TGCCGAGCTG

10901 CCGGTCGGGG AGCTGTTGGC TGGCTGGTGG CAGGATATAT TGTGGTGTAA

10951 ACAAATTGAC GCTTAGACAA CTTAATAACA CATTGCGGAC GTTTTTAATG

11001 TACTGAATTA ACGCCGAATT AATTCCTAGG CCACCATGTT GGGCCCGGGG

11051 CGCGCCGTAC GTAGTGTTTA TCTTTGTTGC TTTTCTGAAC AATTTATTTA

11101 CTATGTAAAT ATATTATCAA TGTTTAATCT ATTTTAATTT GCACATGAAT

11151 TTTCATTTTA TTTTTACTTT ACAAAACAAA TAAATATATA TGCAAAAAAA

11201 TTTACAAACG ATGCACGGGT TACAAACTAA TTTCATTAAA TGCTAATGCA

11251 GATTTTGTGA AGTAAAACTC CAATTATGAT GAAAAATACC ACCAACACCA

11301 CCTGCGAAAC TGTATCCCAA CTGTCCTTAA TAAAAATGTT AAAAAGTATA

11351 TTATTCTCAT TTGTCTGTCA TAATTTATGT ACCCCACTTT AATTTTTCTG

11401 ATGTACTAAA CCGAGGGCAA ACTGAAACCT GTTCCTCATG CAAAGCCCCT

11451 ACTCACCATG TATCATGTAC GTGTCATCAC CCAACAACTC CACTTTTGCT

11501 ATATAACAAC ACCCCCGTCA CACTCTCCCT CTCTAACACA CACCCCACTA

-continued

11551 ACAATTCCTT CACTTGCAGC ACTGTTGCAT CATCATCTTC ATTGCAAAAC

11601 CCTAAACTTC ACCTTCAACC GCGGCCGCAT GGCTTCTATG ATATCCTCTT

11651 CCGCTGTGAC AACAGTCAGC CGTGCCTCTA GGGGGCAATC CGCCGCAGTG

11701 GCTCCATTCG GCGGCCTCAA ATCCATGACT GGATTCCCAG TGAAGAAGGT

11751 CAACACTGAC ATTACTTCCA TTACAAGCAA TGGTGGAAGA GTAAAGTGCA

11801 TGCAGGTGTG GCCTCCAATT GGAAAGAAGA AGTTTGAGAC TCTTTCCTAT

11851 TTGCCACCAT TGACGAGAGA TTCTAGAGTG AGTAACAAGA ACAACGATGA

11901 GCTGCAGTGG CAATCCTGGT TCAGCAAGGC GCCCACCACC GAGGCGAACC

11951 CGATGGCCAC CATGTTGCAG GATATCGGCG TTGCGCTCAA ACCGGAAGCG

12001 ATGGAGCAGC TGAAAAACGA TTATCTGCGT GACTTCACCG CGTTGTGGCA

12051 GGATTTTTTG GCTGGCAAGG CGCCAGCCGT CAGCGACCGC CGCTTCAGCT

12101 CGGCAGCCTG GCAGGGCAAT CCGATGTCGG CCTTCAATGC CGCATCTTAC

12151 CTGCTCAACG CCAAATTCCT CAGTGCCATG GTGGAGGCGG TGGACACCGC

12201 ACCCCAGCAA AAGCAGAAAA TACGCTTTGC CGTGCAGCAG GTGATTGATG

12251 CCATGTCGCC CGCGAACTTC CTCGCCACCA ACCCGGAAGC GCAGCAAAAA

12301 CTGATTGAAA CCAAGGGCGA GAGCCTGACG CGTGGCCTGG TCAATATGCT

12351 GGGCGATATC AACAAGGGCC ATATCTCGCT GTCGGACGAA TCGGCCTTTG

12401 AAGTGGGCCG CAACCTGGCC ATTACCCCGG GCACCGTGAT TTACGAAAAT

12451 CCGCTGTTCC AGCTGATCCA GTACACGCCG ACCACGCCGA CGGTCAGCCA

12501 GCGCCCGCTG TTGATGGTGC CGCCGTGCAT CAACAAGTTC TACATCCTCG

12551 ACCTGCAACC GGAAAATTCG CTGGTGCGCT ACGCGGTGGA GCAGGGCAAC

12601 ACCGTGTTCC TGATCTCGTG GAGCAATCCG GACAAGTCGC TGGCCGGCAC

12651 CACCTGGGAC GACTACGTGG AGCAGGGCGT GATCGAAGCG ATCCGCATCG

12701 TCCAGGACGT CAGCGGCCAG GACAAGCTGA ACATGTTCGG CTTCTGCGTG

12751 GGCGGCACCA TCGTTGCCAC CGCACTGGCG GTACTGGCGG CGCGTGGCCA

12801 GCACCCGGCG GCCAGCCTGA CCCTGCTGAC CACCTTCCTC GACTTCAGCG

12851 ACACCGGCGT GCTCGACGTC TTCGTCGATG AAACCCAGGT CGCGCTGCGT

-continued

12901 GAACAGCAAT TGCGCGATGG CGGCCTGATG CCGGGCCGTG ACCTGGCCTC

12951 GACCTTCTCG AGCCTGCGTC CGAACGACCT GGTATGGAAC TATGTGCAGT

13001 CGAACTACCT CAAAGGCAAT GAGCCGGCGG CGTTTGACCT GCTGTTCTGG

13051 AATTCGGACA GCACCAATTT GCCGGGCCCG ATGTTCTGCT GGTACCTGCG

13101 CAACACCTAC CTGGAAAACA GCCTGAAAGT GCCGGGCAAG CTGACGGTGG

13151 CCGGCGAAAA GATCGACCTC GGCCTGATCG ACGCCCCGGC CTTCATCTAC

13201 GGTTCGCGCG AAGACCACAT CGTGCCGTGG ATGTCGGCGT ACGGTTCGCT

13251 CGACATCCTC AACCAGGGCA AGCCGGGCGC CAACCGCTTC GTGCTGGGCG

13301 CGTCCGGCCA TATCGCCGGC GTGATCAACT CGGTGGCCAA GAACAAGCGC

13351 AGCTACTGGA TCAACGACGG TGGCGCCGCC GATGCCCAGG CCTGGTTCGA

13401 TGGCGCGCAG GAAGTGCCGG GCAGCTGGTG GCCGCAATGG GCCGGGTTCC

13451 TGACCCAGCA TGGCGGCAAG AAGGTCAAGC CCAAGGCCAA GCCCGGCAAC

13501 GCCCGCTACA CCGCGATCGA GGCGGCGCCC GGCCGTTACG TCAAAGCCAA

13551 GGGCTGAGCG GCCGCTGAGT AATTCTGATA TTAGAGGGAG CATTAATGTG

13601 TTGTTGTGAT GTGGTTTATA TGGGGAAATT AAATAAATGA TGTATGTACC

13651 TCTTGCCTAT GTAGGTTTGT GTGTTTTGTT TTGTTGTCTA GCTTTGGTTA

13701 TTAAGTAGTA GGGACGTTCG TTCGTGTCTC AAAAAAAGGG GTACTACCAC

13751 TCTGTAGTGT ATATGGATGC TGGAAATCAA TGTGTTTTGT ATTTGTTCAC

13801 CTCCATTGTT GAATTCAATG TCAAATGTGT TTTGCGTTGG TTATGTGTAA

13851 AATTACTATC TTTCTCGTCC GATGATCAAA GTTTTAAGCA ACAAAACCAA

13901 GGGTGAAATT TAAACTGTGC TTTGTTGAAG ATTCTTTTAT CATATTGAAA

13951 ATCAAATTAC TAGCAGCAGA TTTTACCTAG CATGAAATTT TATCAACAGT

14001 ACAGCACTCA CTAACCAAGT TCCAAACTAA GATGCGCCAT TAACATCAGC

14051 CAATAGGCAT TTTCAGCAAG GCGCGCCCGC GCCGATGTAT GTGACAACCC

14101 TCGGGATTGT TGATTTATTT CAAAACTAAG AGTTTTTGTC TTATTGTTCT

14151 CGTCTATTTT GGATATCAAT CTTAGTTTTA TATCTTTTCT AGTTCTCTAC

14201 GTGTTAAATG TTCAACACAC TAGCAATTTG GCCTGCCAGC GTATGGATTA

-continued

14251 TGGAACTATC AAGTCTGTGA CGCGCCGTAC GTAGTGTTTA TCTTTGTTGC

14301 TTTTCTGAAC AATTTATTTA CTATGTAAAT ATATTATCAA TGTTTAATCT

14351 ATTTTAATTT GCACATGAAT TTTCATTTTA TTTTTACTTT ACAAAACAAA

14401 TAAATATATA TGCAAAAAAA TTTACAAACG ATGCACGGGT TACAAACTAA

14451 TTTCATTAAA TGCTAATGCA GATTTTGTGA AGTAAAACTC CAATTATGAT

14501 GAAAAATACC ACCAACACCA CCTGCGAAAC TGTATCCCAA CTGTCCTTAA

14551 TAAAAATGTT AAAAAGTATA TTATTCTCAT TTGTCTCTCA TAATTTATGT

14601 ACCCCACTTT AATTTTTCTG ATGTACTAAA CCGAGGGCAA ACTGAAACCT

14651 GTTCCTCATG CAAAGCCCCT ACTCACCATG TATCATGTAC GTGTCATCAC

14701 CCAACAACTC CACTTTTGCT ATATAACAAC ACCCCCGTCA CACTCTCCCT

14751 CTCTAACACA CACCCCACTA ACAATTCCTT CACTTGCAGC ACTGTTGCAT

14801 CATCATCTTC ATTGCAAAAC CCTAAACTTC ACCTTCAACC GCGGCCGCAT

14851 GGCTTCTATG ATATCCTCTT CCGCTGTGAC AACAGTCAGC CGTGCCTCTA

14901 GGGGGCAATC CGCCGCAGTG GCTCCATTCG GCGGCCTCAA ATCCATGACT

14951 GGATTCCCAG TGAAGAAGGT CAACACTGAC ATTACTTCCA TTACAAGCAA

15001 TGGTGGAAGA GTAAAGTGCA TGCAGGTGTG GCCTCCAATT GGAAAGAAGA

15051 AGTTTGAGAC TCTTTCCTAT TTGCCACCAT TGACGAGAGA TTCTAGAGTG

15101 ACTCAGCGCA TTGCGTATGT GACCGGCGGC ATGGGTGGTA TCGGAACCGC

15151 CATTTGCCAG CGGCTGGCCA AGGATGGCTT TCGTGTGGTG GCCGGTTGCG

15201 GCCCCAACTC GCCGCGCCGC GAAAAGTGGC TGGAGCAGCA GAAGGCCCTG

15251 GGCTTCGATT TCATTGCCTC GGAAGGCAAT GTGGCTGACT GGGACTCGAC

15301 CAAGACCGCA TTCGACAAGG TCAAGTCCGA GGTCGGCGAG GTTGATGTGC

15351 TGATCAACAA CGCCGGTATC ACCCGCGACG TGGTGTTCCG CAAGATGACC

15401 CGCGCCGACT GGGATGCGGT GATCGACACC AACCTGACCT CGCTGTTCAA

15451 CGTCACCAAG CAGGTGATCG ACGGCATGGC CGACCGTGGC TGGGGCCGCA

15501 TCGTCAACAT CTCGTCGGTG AACGGGCAGA AGGGCCAGTT CGGCCAGACC

15551 AACTACTCCA CCGCCAAGGC CGGCCTGCAT GGCTTCACCA TGGCACTGGC

-continued

15601 GCAGGAAGTG GCCGCCAAGG GCGTGACCGT CAACACGGTC TCTCCGGGCT

15651 ATATCGCCAC CGACATGGTC AAGGCGATCC GCCAGGACGT GCTCGACAAG

15701 ATCGTCGCGA CGATCCCGGT CAAGCGCCTG GGCCTGCCGG AAGAGATCGC

15751 CTCGATCTGC GCCTGGTTGT CGTCGGAGGA GTCCGGTTTC TCGACCGGCG

15801 CCGACTTCTC GCTCAACGGC GGCCTGCATA TGGGCTGAGC GGCCGCTGAG

15851 TAATTCTGAT ATTAGAGGGA GCATTAATGT GTTGTTGTGA TGTGGTTTAT

15901 ATGGGGAAAT TAAATAAATG ATGTATGTAC CTCTTGCCTA TGTAGGTTTG

15951 TGTGTTTTGT TTTGTTGTCT AGCTTTGGTT ATTAAGTAGT AGGGACGTTC

16001 GTTCGTGTCT CAAAAAAAGG GGTACTACCA CTCTGTAGTG TATATGGATG

16051 CTGGAAATCA ATGTGTTTTG TATTTGTTCA CCTCCATTGT TGAATTCAAT

16101 GTCAAATGTG TTTTGCGTTG GTTATGTGTA AAATTACTAT CTTTCTCGTC

16151 CGATGATCAA AGTTTTAAGC AACAAAACCA AGGGTGAAAT TTAAACTGTG

16201 CTTTGTTGAA GATTCTTTTA TCATATTGAA AATCAAATTA CTAGCAGCAG

16251 ATTTTACCTA GCATGAAATT TTATCAACAG TACAGCACTC ACTAACCAAG

16301 TTCCAAACTA AGATGCGCCA TTAACATCAG CCAATAGGCA TTTTCAGCAA

16351 GGCGCGTAAG GGGATCCGTA CGTAAGTACG TACTCAAAAT GCCAACAAAT

16401 AAAAAAAAAG TTGCTTTAAT AATGCCAAAA CAAATTAATA AAACACTTAC

16451 AACACCGGAT TTTTTTTAAT TAAAATGTGC CATTTAGGAT AAATAGTTAA

16501 TATTTTTAAT AATTATTTAA AAAGCCGTAT CTACTAAAAT GATTTTTATT

16551 TGGTTGAAAA TATTAATATG TTTAAATCAA CACAATCTAT CAAAATTAAA

16601 CTAAAAAAAA AATAAGTGTA CGTGGTTAAC ATTAGTACAG TAATATAAGA

16651 GGAAAATGAG AAATTAAGAA ATTGAAAGCG AGTCTAATTT TTAAATTATG

16701 AACCTGCATA TATAAAAGGA AAGAAAGAAT CCAGGAAGAA AAGAAATGAA

16751 ACCATGCATG GTCCCCTCGT CATCACGAGT TTCTGCCATT TGCAATAGAA

16801 ACACTGAAAC ACCTTTCTCT TTGTCACTTA ATTGAGATGC CGAAGCCACC

16851 TCACACCATG AACTTCATGA GGTGTAGCAC CCAAGGCTTC CATAGCCATG

16901 CATACTGAAG AATGTCTCAA GCTCAGCACC CTACTTCTGT GACGTGTCCC

-continued

16951 TCATTCACCT TCCTCTCTTC CCTATAAATA ACCACGCCTC AGGTTCTCCG

17001 CTTCACAACT CAAACATTCT CTCCATTGGT CCTTAAACAC TCATCAGTCA

17051 TCACCGCGGC CGCGGAATTC ATGGCTTCTA TGATATCCTC TTCCGCTGTG

17101 ACAACAGTCA GCCGTGCCTC TAGGGGGCAA TCCGCCGCAG TGGCTCCATT

17151 CGGCGGCCTC AAATCCATGA CTGGATTCCC AGTGAAGAAG GTCAACACTG

17201 ACATTACTTC CATTACAAGC AATGGTGGAA GAGTAAAGTG CATGCAGGTG

17251 TGGCCTCCAA TTGGAAAGAA GAAGTTTGAG ACTCTTTCCT ATTTGCCACC

17301 ATTGACGAGA GATTCTAGAG TGACTGACGT TGTCATCGTA TCCGCCGCCC

17351 GCACCGCGGT CGGCAAGTTT GGCGGCTCGC TGGCCAAGAT CCCGGCACCG

17401 GAACTGGGTG CCGTGGTCAT CAAGGCCGCG CTGGAGCGCG CCGGCGTCAA

17451 GCCGGAGCAG GTGAGCGAAG TCATCATGGG CCAGGTGCTG ACCGCCGGTT

17501 CGGGCCAGAA CCCCGCACGC CAGGCCGCGA TCAAGGCCGG CCTGCCCGCG

17551 ATGGTGCCGG CCATGACCAT CAACAAGGTG TGCGGCTCGG GCCTGAAGGC

17601 CGTGATGCTG GCCGCCAACG CGATCATGGC GGGCGACGCC GAGATCGTGG

17651 TGGCCGGCGG CCAGGAAAAC ATGAGCGCCG CCCCGCACGT GCTGCCGGGC

17701 TCGCGCGATG GTTTCCGCAT GGGCGATGCC AAGCTGGTCG ACACCATGAT

17751 CGTCGACGGC CTGTGGGACG TGTACAACCA GTACCACATG GGCATCACCG

17801 CCGAGAACGT GGCCAAGGAA TACGGCATCA CACGCGAGGC GCAGGATGAG

17851 TTCGCCGTCG GCTCGCAGAA CAAGGCCGAA GCCGCGCAGA AGGCCGGCAA

17901 GTTTGACGAA GAGATCGTCC CGGTGCTGAT CCCGCAGCGC AAGGGCGACC

17951 CGGTGGCCTT CAAGACCGAC GAGTTCGTGC GCCAGGGCGC CACGCTGGAC

18001 AGCATGTCCG GCCTCAAGCC CGCCTTCGAC AAGGCCGGCA CGGTGACCGC

18051 GGCCAACGCC TCGGGCCTGA ACGACGGCGC CGCCGCGGTG GTGGTGATGT

18101 CGGCGGCCAA GGCCAAGGAA CTGGGCCTGA CCCCGCTGGC CACGATCAAG

18151 AGCTATGCCA ACGCCGGTGT CGATCCCAAG GTGATGGGCA TGGGCCCGGT

18201 GCCGGCCTCC AAGCGCGCCC TGTCGCGCGC CGAGTGGACC CCGCAAGACC

18251 TGGACCTGAT GGAGATCAAC GAGGCCTTTG CCGCGCAGGC GCTGGCGGTG

-continued

18301 CACCAGCAGA TGGGCTGGGA CACCTCCAAG GTCAATGTGA ACGGCGGCGC

18351 CATCGCCATC GGCCACCCGA TCGGCGCGTC GGGCTGCCGT ATCCTGGTGA

18401 CGCTGCTGCA CGAGATGAAG CGCCGTGACG CGAAGAAGGG CCTGGCCTCG

18451 CTGTGCATCG GCGGCGGCAT GGGCGTGGCG CTGGCAGTCG AGCGCAAATA

18501 ACTCGAGGCG GCCGCAGCCC TTTTTGTATG TGCTACCCCA CTTTTGTCTT

18551 TTTGGCAATA GTGCTAGCAA CCAATAAATA ATAATAATAA TAATGAATAA

18601 GAAAACAAAG GCTTTAGCTT GCCTTTTGTT CACTGTAAAA TAATAATGTA

18651 AGTACTCTCT ATAATGAGTC ACGAAACTTT TGCGGGAATA AAAGGAGAAA

18701 TTCCAATGAG TTTTCTGTCA AATCTTCTTT TGTCTCTCTC TCTCTCTCTT

18751 TTTTTTTTTT CTTTCTTCTG AGCTTCTTGC AAAACAAAAG GCAAACAATA

18801 ACGATTGGTC CAATGATAGT TAGCTTGATC GATGATATCT TTAGGAAGTG

18851 TTGGCAGGAC AGGACATGAT GTAGAAGACT AAAATTGAAA GTATTGCAGA

18901 CCCAATAGTT GAAGATTAAC TTTAAGAATG AAGACGTCTT ATCAGGTTCT

18951 TCATGACTTA AGCTTTAAGA GGAGTCCACC ATGGTAGATC TGACTAGTAA

19001 CGGCCGCCAG TGTGCTGGAA TTCTGCAGAT GTGGAGCACG ACACTCTCGT

19051 CTACTCCAAG AATATCAAAG ATACAGTCTC AGAAGACCAA AGGGCTATTG

19101 AGACTTTTCA ACAAAGGGTA ATATCGGGAA ACCTCCTCGG ATTCCATTGC

19151 CCAGCTATCT GTCACTTCAT CAAAAGGACA GTAGAAAAGG AAGGTGGCAC

19201 CTACAAATGC CATCATTGCG ATAAAGGAAA GGCTATCGTT CAAGATGCCT

19251 CTGCCGACAG TGGTCCCAAA GATGGACCCC CACCCACGAG GAGCATCGTG

19301 GAAAAAGAAG ACGTTCCAAC CACGTCTTCA AAGCAAGTGG ATTGATGTGA

19351 TAACATGGTG GAGCACGACA CTCTCGTCTA CTCCAAGAAT ATCAAAGATA

19401 CAGTCTCAGA AGACCAAAGG GCTATTGAGA CTTTTCAACA AAGGGTAATA

19451 TCGGGAAACC TCCTCGGATT CCATTGCCCA GCTATCTGTC ACTTCATCAA

19501 AAGGACAGTA GAAAAGGAAG GTGGCACCTA CAAATGCCAT CATTGCGATA

19551 AAGGAAAGGC TATCGTTCAA GATGCCTCTG CCGACAGTGG TCCCAAAGAT

19601 GGACCCCCAC CCACGAGGAG CATCGTGGAA AAAGAAGACG TTCCAACCAC

19651 GTCTTCAAAG CAAGTGGATT GATGTGATAT CTCCACTGAC GTAAGGGATG

19701 ACGCACAATC CCACTATCCT TCGCAAGACC TTCCTCTATA TAAGGAAGTT

19751 CATTTCATTT GGAGAGGACA CGCTGAAATC ACCAGTCTCT CTCTACAAAT

19801 CTATCTCTCT CGAGCTTTCG CAGATCTGTC GATCGACCAT GGACTCCAAA

19851 GAATCATTAA CTCCTGGTAG AGAAGAAAAC CCCAGCAGTG TGCTTGCTCA

19901 GGAGAGGGGA GATGTGATGG ACTTCTATAA AACCCTAAGA GGAGGAGCTA

19951 CTGTGAAGGT TTCTGCGTCT TCACCCTCAC TGGCTGTCGC TTCTCAATCA

20001 GACTCCAAGC AGCGAAGACT TTTGGTTGAT TTTCCAAAAG GCTCAGTAAG

20051 CAATGCGCAG CAGCCAGATC TGTCCAAAGC AGTTTCACTC TCAATGGGAC

20101 TGTATATGGG AGAGACAGAA ACAAAAGTGA TGGGAAATGA CCTGGGATTC

20151 CCACAGCAGG GCCAAATCAG CCTTTCCTCG GGGGAAACAG ACTTAAAGCT

20201 TTTGGAAGAA AGCATTGCAA ACCTCAATAG GTCGACCAGT GTTCCAGAGA

20251 ACCCCAAGAG TTCAGCATCC ACTGCTGTGT CTGCTGCCCC CACAGCTAGT

20301 TCTGCGGCCC CCCCGACCGA TGTCAGCCTG GGGGACGAGC TCCACTTAGA

20351 CGGCGAGGAC GTGGCGATGG CGCATGCCGA CGCGCTAGAC GATTTCGATC

20401 TGGACATGTT GGGGGACGGG GATTCCCCGG GTCCGGGATT TACCCCCCAC

20451 GACTCCGCCC CCTACGGCGC TCTGGATATG GCCGACTTCG AGTTTGAGCA

20501 GATGTTTACC GATGCCCTTG GAATTGACGA GTACGGTGGG ACTAGCTCCA

20551 GCTCCTCAAC AGCAACAACA GGACCACCTC CCAAACTCTG CCTGGTGTGC

20601 TCTGATGAAG CTTCAGGATG TCATTATGGA GTCTTAACTT GTGGAAGCTG

20651 TAAAGTTTTC TTCAAAAGAG CAGTGGAAGG ACAGCACAAT TACCTATGTG

20701 CTGGAAGGAA TGATTGCATC ATCGATAAAA TTCGAAGAAA AAACTGCCCA

20751 GCATGCCGCT ATCGAAAATG TCTTCAGGCT GGAATGAACC TGGAAGCTCG

20801 AAAAACAAAG AAAAAAATAA AAGGAATTGC TCGACAAAGG CCCGAGTGCG

20851 TGGTGCCGGA GAACCAGTGT GCAATGAAAC GGAAAGAGAA AAAGGCGCAG

20901 AGGGAAAAAG ACAAATTGCC CGTCAGTACG ACGACAGTAG ACGATCACAT

20951 GCCTCCCATC ATGCAATGTG ACCCTCCGCC CCCAGAGGCC GCTAGAATTC

-continued

21001 TGGAATGTTT GCAGCACGAG GTGGTGCCAC GATTCCTGAA TGAGAAGCTA

21051 ATGGAACAGA ACAGATTGAA GAACGTGCCC CCCCTCACTG CCAATCAGAA

21101 GTCGTTGATC GCAAGGCTCG TGTGGTACCA GGAAGGCTAT GAACAACCTT

21151 CCGAGGAAGA CCTGAAGAGG GTTACACAGT CGGACGAGGA CGACGAAGAC

21201 TCGGATATGC CGTTCCGTCA GATTACCGAG ATGACGATTC TCACAGTGCA

21251 GCTCATCGTA GAATTCGCTA AGGGCCTCCC GGGCTTCGCC AAGATCTCGC

21301 AGTCGGACCA GATCACGTTA TTAAAGGCGT GCTCAAGTGA GGTGATGATG

21351 CTCCGAGTGG CTCGGCGGTA TGACGCGGCC ACCGACAGCG TACTGTTCGC

21401 GAACAACCAG GCGTACACTC GCGACAACTA CCGCAAGGCA GGCATGGCGT

21451 ACGTCATCGA GGACCTGCTG CACTTCTGTC GGTGCATGTA CTCCATGATG

21501 ATGGATAACG TGCATTATGC GCTGCTTACA GCCATTGTCA TCTTCTCAGA

21551 CCGGCCCGGG CTTGAGCAAC CCCTGTTGGT GGAGGAGATC CAGAGATATT

21601 ACCTGAACAC GCTACGGGTG TACATCCTGA ACCAGAACAG CGCGTCGCCC

21651 CGCTGCGCCG TCATCTTCGG CAAGATCCTG GGCATACTGA CGGAGATCCG

21701 CACGCTGGGC ATGCAGAACT CCAACATGTG CATCTCCCTC AAGCTGAAGA

21751 ACAGGAAGCT GCCGCCGTTC CTCGAGGAGA TCTGGGACGT GGCGGACGTG

21801 GCGACGACGG CGACGCCGGT GGCGGCGGAG GCGCCGGCGC TCTAGCCCCC

21851 GCGCCGCCCG CCCGGCCGCG CGCACGTCTA GCGCGCCTCA GGAGAGAACG

21901 CTCATAGACT GGCTAGTTTT AGTGAAGTGC ACGGACACTG ACGTCGGACG

21951 TGATCAACCT ATTTATAAGG ACTGCGAATT TTACCACTTA AGAGGGCACA

22001 CCCGTACCCG ATTTCGTACG GGAATTCCTG CAGCCCGGGG GATCCTTAAT

22051 TAACTCGAGG AATTCATCGA TTCCGCGGGT ACCGAGCTCG ATCCGTCGAC

22101 CTGCAGATCG TTCAAACATT TGGCAATAAA GTTTCTTAAG ATTGAATCCT

22151 GTTGCCGGTC TTGCGATGAT TATCATATAA TTTCTGTTGA ATTACGTTAA

22201 GCATGTAATA ATTAACATGT AATGCATGAC GTTATTTATG AGATGGGTTT

22251 TTATGATTAG AGTCCCGCAA TTATACATTT AATACGCGAT AGAAAACAAA

22301 ATATAGCGCG CAAACTAGGA TAAATTATCG CGCGCGGTGT CATCTATGTT

-continued

22351 ACTAGATCTG GCGCGCCCCT AGGTCTAGAG TCGACTGTTT AAACG

Vector: pPhaC-RNAi/35S (SEQ ID NO: 4)

1 AAATAGAAGG TAATTATCCA AGATGTAGCA TCAAGAATCC AATGTTTACG

51 GGAAAAACTA TGGAAGTATT ATGTGAGCTC AGCAAGAAGC AGATCAATAT

101 GCGGCACATA TGCAACCTAT GTTCAAAAAT GAAGAATGTA CAGATACAAG

151 ATCCTATACT GCCAGAATAC GAAGAAGAAT ACGTAGAAAT TGAAAAAGAA

201 GAACCAGGCG AAGAAAAGAA TCTTGAAGAC GTAAGCACTG ACGACAACAA

251 TGAAAAGAAG AAGATAAGGT CGGTGATTGT GAAAGAGACA TAGAGGACAC

301 ATGTAAGGTG GAAAATGTAA GGGCGGAAAG TAACCTTATC ACAAAGGAAT

351 CTTATCCCCC ACTACTTATC CTTTTATATT TTTCCGTGTC ATTTTTGCCC

401 TTGAGTTTTC CTATATAAGG AACCAAGTTC GGCATTTGTG AAAACAAGAA

451 AAAATTGGTG TAAGCTATTT TCTTTGAAGT ACTGAGGATA CAACTTCAGA

501 GAAATTTGTA AGAAAGTGGA TCGAAACCAT GGCCTCCTCC GAGAACGTCA

551 TCACCGAGTT CATGCGCTTC AAGGTGCGCA TGGAGGGCAC CGTGAACGGC

601 CACGAGTTCG AGATCGAGGG CGAGGGCGAG GGCCGCCCCT ACGAGGGCCA

651 CAACACCGTG AAGCTGAAGG TGACCAAGGG CGGCCCCCTG CCCTTCGCCT

701 GGGACATCCT GTCCCCCCAG TTCCAGTACG GCTCCAAGGT GTACGTGAAG

751 CACCCCGCCG ACATCCCCGA CTACAAGAAG CTGTCCTTCC CCGAGGGCTT

801 CAAGTGGGAG CGCGTGATGA ACTTCGAGGA CGGCGGCGTG GCGACCGTGA

851 CCCAGGACTC CTCCCTGCAG GACGGCTGCT TCATCTACAA GGTGAAGTTC

901 ATCGGCGTGA ACTTCCCCTC CGACGGCCCC GTGATGCAGA AGAAGACCAT

951 GGGCTGGGAG GCCTCCACCG AGCGCCTGTA CCCCCGCGAC GGCGTGCTGA

1001 AGGGCGAGAC CCACAAGGCC CTGAAGCTGA AGGACGGCGG CCACTACCTG

1051 GTGGAGTTCA AGTCCATCTA CATGGCCAAG AAGCCCGTGC AGCTGCCCGG

1101 CTACTACTAC GTGGACGCCA AGCTGGACAT CACCTCCCAC AACGAGGACT

1151 ACACCATCGT GGAGCAGTAC GAGCGCACCG AGGGCCGCCA CCACCTGTTC

1201 CTGGTACCAA TGAGCTCTGT CCAACAGTCT CAGGGTTAAT GTCTATGTAT

-continued

1251 CTTAAATAAT GTTGTCGGCG ATCGTTCAAA CATTTGGCAA TAAAGTTTCT

1301 TAAGATTGAA TCCTGTTGCC GGTCTTGCGA TGATTATCAT ATAATTTCTG

1351 TTGAATTACG TTAAGCATGT AATAATTAAC ATGTAATGCA TGACGTTATT

1401 TATGAGATGG GTTTTTATGA TTAGAGTCCC GCAATTATAC ATTTAATACG

1451 CGATAGAAAA CAAAATATAG CGCGCAAACT AGGATAAATT ATCGCGCGCG

1501 GTGTCATCTA TGTTACTAGA TCGGGAATTA AACTATCAGT GTTTGACAGG

1551 ATATATTGGC GGGTAAACCT AAGAGAAAAG AGCGTTTATT AGAATAACGG

1601 ATATTTAAAA GGGCGTGAAA AGGTTTATCC GTTCGTCCAT TTGTATGTGC

1651 ATGCCAACCA CAGGGTTCCC CTCGGGATCA AAGTACTTTG ATCCAACCCC

1701 TCCGCTGCTA TAGTGCAGTC GGCTTCTGAC GTTCAGTGCA GCCGTCTTCT

1751 GAAAACGACA TGTCGCACAA GTCCTAAGTT ACGCGACAGG CTGCCGCCCT

1801 GCCCTTTTCC TGGCGTTTTC TTGTCGCGTG TTTTAGTCGC ATAAAGTAGA

1851 ATACTTGCGA CTAGAACCGG AGACATTACG CCATGAACAA GAGCGCCGCC

1901 GCTGGCCTGC TGGGCTATGC CCGCGTCAGC ACCGACGACC AGGACTTGAC

1951 CAACCAACGG GCCGAACTGC ACGCGGCCGG CTGCACCAGG CTGTTTTCCG

2001 AGAAGATCAC CGGCACCAGG CGCGACCGCC CGGAGCTGGC CAGGATGCTT

2051 GACCACCTAC GCCCTGGCGA CGTTGTGACA GTGACCAGGC TAGACCGCCT

2101 GGCCCGCAGC ACCCGCGACC TACTGGACAT TGCCGAGCGC ATCCAGGAGG

2151 CCGGCGCGGG CCTGCGTAGC CTGGCAGAGC CGTGGGCCGA CACCACCACG

2201 CCGGCCGGCC GCATGGTGTT GACCGTGTTC GCCGGCATTG CCGAGTTCGA

2251 GCGTTCCCTA ATCATCGACC GCACCCGGAG CGGGCGCGAG GCCGCCAAGG

2301 CCCGAGGCGT GAAGTTTGGC CCCCGCCCTA CCCTCACCCC GGCACAGATC

2351 GCGCACGCCC GCGAGCTGAT CGACCAGGAA GGCCGCACCG TGAAAGAGGC

2401 GGCTGCACTG CTTGGCGTGC ATCGCTCGAC CCTGTACCGC GCACTTGAGC

2451 GCAGCGAGGA AGTGACGCCC ACCGAGGCCA GGCGGCGCGG TGCCTTCCGT

2501 GAGGACGCAT TGACCGAGGC CGACGCCCTG GCGGCCGCCG AGAATGAACG

2551 CCAAGAGGAA CAAGCATGAA ACCGCACCAG GACGGCCAGG ACGAACCGTT

-continued

2601 TTTCATTACC GAAGAGATCG AGGCGGAGAT GATCGCGGCC GGGTACGTGT

2651 TCGAGCCGCC CGCGCACGTC TCAACCGTGC GGCTGCATGA AATCCTGGCC

2701 GGTTTGTCTG ATGCCAAGCT GGCGGCCTGG CCGGCCAGCT TGGCCGCTGA

2751 AGAAACCGAG CGCCGCCGTC TAAAAAGGTG ATGTGTATTT GAGTAAAACA

2801 GCTTGCGTCA TGCGGTCGCT GCGTATATGA TGCGATGAGT AAATAAACAA

2851 ATACGCAAGG GGAACGCATG AAGGTTATCG CTGTACTTAA CCAGAAAGGC

2901 GGGTCAGGCA AGACGACCAT CGCAACCCAT CTAGCCCGCG CCCTGCAACT

2951 CGCCGGGGCC GATGTTCTGT TAGTCGATTC CGATCCCCAG GGCAGTGCCC

3001 GCGATTGGGC GGCCGTGCGG GAAGATCAAC CGCTAACCGT TGTCGGCATC

3051 GACCGCCCGA CGATTGACCG CGACGTGAAG GCCATCGGCC GGCGCGACTT

3101 CGTAGTGATC GACGGAGCGC CCCAGGCGGC GGACTTGGCT GTGTCCGCGA

3151 TCAAGGCAGC CGACTTCGTG CTGATTCCGG TGCAGCCAAG CCCTTACGAC

3201 ATATGGGCCA CCGCCGACCT GGTGGAGCTG GTTAAGCAGC GCATTGAGGT

3251 CACGGATGGA AGGCTACAAG CGGCCTTTGT CGTGTCGCGG GCGATCAAAG

3301 GCACGCGCAT CGGCGGTGAG GTTGCCGAGG CGCTGGCCGG GTACGAGCTG

3351 CCCATTCTTG AGTCCCGTAT CACGCAGCGC GTGAGCTACC CAGGCACTGC

3401 CGCCGCCGGC ACAACCGTTC TTGAATCAGA ACCCGAGGGC GACGCTGCCC

3451 GCGAGGTCCA GGCGCTGGCC GCTGAAATTA AATCAAAACT CATTTGAGTT

3501 AATGAGGTAA AGAGAAAATG AGCAAAAGCA CAAACACGCT AAGTGCCGGC

3551 CGTCCGAGCG CACGCAGCAG CAAGGCTGCA ACGTTGGCCA GCCTGGCAGA

3601 CACGCCAGCC ATGAAGCGGG TCAACTTTCA GTTGCCGGCG GAGGATCACA

3651 CCAAGCTGAA GATGTACGCG GTACGCCAAG GCAAGACCAT TACCGAGCTG

3701 CTATCTGAAT ACATCGCGCA GCTACCAGAG TAAATGAGCA AATGAATAAA

3751 TGAGTAGATG AATTTTAGCG GCTAAAGGAG GCGGCATGGA AAATCAAGAA

3801 CAACCAGGCA CCGACGCCGT GGAATGCCCC ATGTGTGGAG GAACGGGCGG

3851 TTGGCCAGGC GTAAGCGGCT GGGTTGTCTG CCGGCCCTGC AATGGCACTG

3901 GAACCCCCAA GCCCGAGGAA TCGGCGTGAC GGTCGCAAAC CATCCGGCCC

-continued

```
3951 GGTACAAATC GGCGCGGCGC TGGGTGATGA CCTGGTGGAG
     AAGTTGAAGG

4001 CCGCGCAGGC CGCCCAGCGG CAACGCATCG AGGCAGAAGC
     ACGCCCCGGT

4051 GAATCGTGGC AAGCGGCCGC TGATCGAATC CGCAAAGAAT
     CCCGGCAACC

4101 GCCGGCAGCC GGTGCGCCGT CGATTAGGAA GCCGCCCAAG
     GGCGACGAGC

4151 AACCAGATTT TTTCGTTCCG ATGCTCTATG ACGTGGGCAC
     CCGCGATAGT

4201 CGCAGCATCA TGGACGTGGC CGTTTTCCGT CTGTCGAAGC
     GTGACCGACG

4251 AGCTGGCGAG GTGATCCGCT ACGAGCTTCC AGACGGGCAC
     GTAGAGGTTT

4301 CCGCAGGGCC GGCCGGCATG GCCAGTGTGT GGGATTACGA
     CCTGGTACTG

4351 ATGGCGGTTT CCCATCTAAC CGAATCCATG AACCGATACC
     GGGAAGGGAA

4401 GGGAGACAAG CCCGGCCGCG TGTTCCGTCC ACACGTTGCG
     GACGTACTCA

4451 AGTTCTGCCG GCGAGCCGAT GGCGGAAAGC AGAAAGACGA
     CCTGGTAGAA

4501 ACCTGCATTC GGTTAAACAC CACGCACGTT GCCATGCAGC
     GTACGAAGAA

4551 GGCCAAGAAC GGCCGCCTGG TGACGGTATC CGAGGGTGAA
     GCCTTGATTA

4601 GCCGCTACAA GATCGTAAAG AGCGAAACCG GGCGGCCGGA
     GTACATCGAG

4651 ATCGAGCTAG CTGATTGGAT GTACCGCGAG ATCACAGAAG
     GCAAGAACCC

4701 GGACGTGCTG ACGGTTCACC CCGATTACTT TTTGATCGAT
     CCCGGCATCG

4751 GCCGTTTTCT CTACCGCCTG GCACGCCGCG CCGCAGGCAA
     GGCAGAAGCC

4801 AGATGGTTGT TCAAGACGAT CTACGAACGC AGTGGCAGCG
     CCGGAGAGTT

4851 CAAGAAGTTC TGTTTCACCG TGCGCAAGCT GATCGGGTCA
     AATGACCTGC

4901 CGGAGTACGA TTTGAAGGAG GAGGCGGGGC AGGCTGGCCC
     GATCCTAGTC

4951 ATGCGCTACC GCAACCTGAT CGAGGGCGAA GCATCCGCCG
     GTTCCTAATG

5001 TACGGAGCAG ATGCTAGGGC AAATTGCCCT AGCAGGGGAA
     AAAGGTCGAA

5051 AAGGTCTCTT TCCTGTGGAT AGCACGTACA TTGGGAACCC
     AAAGCCGTAC

5101 ATTGGGAACC GGAACCCGTA CATTGGGAAC CCAAAGCCGT
     ACATTGGGAA

5151 CCGGTCACAC ATGTAAGTGA CTGATATAAA AGAGAAAAAA
     GGCGATTTTT

5201 CCGCCTAAAA CTCTTTAAAA CTTATTAAAA CTCTTAAAAC
     CCGCCTGGCC

5251 TGTGCATAAC TGTCTGGCCA GCGCACAGCC GAAGAGCTGC
     AAAAAGCGCC

5301 TACCCTTCGG TCGCTGCGCT CCCTACGCCC CGCCGCTTCG
     CGTCGGCCTA

5351 TCGCGGCCGC TGGCCGCTCA AAAATGGCTG GCCTACGGCC
     AGGCAATCTA

5401 CCAGGGCGCG GACAAGCCGC GCCGTCGCCA CTCGACCGCC
     GGCGCCCACA

5451 TCAAGGCACC CTGCCTCGCG CGTTTCGGTG ATGACGGTGA
     AAACCTCTGA

5501 CACATGCAGC TCCCGGAGAC GGTCACAGCT TGTCTGTAAG
     CGGATGCCGG

5551 GAGCAGACAA GCCCGTCAGG GCGCGTCAGC GGGTGTTGGC
     GGGTGTCGGG

5601 GCGCAGCCAT GACCCAGTCA CGTAGCGATA GCGGAGTGTA
     TACTGGCTTA

5651 ACTATGCGGC ATCAGAGCAG ATTGTACTGA GAGTGCACCA
     TATGCGGTGT

5701 GAAATACCGC ACAGATGCGT AAGGAGAAAA TACCGCATCA
     GGCGCTCTTC

5751 CGCTTCCTCG CTCACTGACT CGCTGCGCTC GGTCGTTCGG
     CTGCGGCGAG

5801 CGGTATCAGC TCACTCAAAG GCGGTAATAC GGTTATCCAC
     AGAATCAGGG

5851 GATAACGCAG GAAAGAACAT GTGAGCAAAA GGCCAGCAAA
     AGGCCAGGAA

5901 CCGTAAAAAG GCCGCGTTGC TGGCGTTTTT CCATAGGCTC
     CGCCCCCCTG

5951 ACGAGCATCA CAAAAATCGA CGCTCAAGTC AGAGGTGGCG
     AAACCCGACA

6001 GGACTATAAA GATACCAGGC GTTTCCCCCT GGAAGCTCCC
     TCGTGCGCTC

6051 TCCTGTTCCG ACCCTGCCGC TTACCGGATA CCTGTCCGCC
     TTTCTCCCTT

6101 CGGGAAGCGT GGCGCTTTCT CATAGCTCAC GCTGTAGGTA
     TCTCAGTTCG

6151 GTGTAGGTCG TTCGCTCCAA GCTGGGCTGT GTGCACGAAC
     CCCCCGTTCA

6201 GCCCGACCGC TGCGCCTTAT CCGGTAACTA TCGTCTTGAG
     TCCAACCCGG

6251 TAAGACACGA CTTATCGCCA CTGGCAGCAG CCACTGGTAA
     CAGGATTAGC

6301 AGAGCGAGGT ATGTAGGCGG TGCTACAGAG TTCTTGAAGT
     GGTGGCCTAA

6351 CTACGGCTAC ACTAGAAGGA CAGTATTTGG TATCTGCGCT
     CTGCTGAAGC

6401 CAGTTACCTT CGGAAAAAGA GTTGGTAGCT CTTGATCCGG
     CAAACAAACC

6451 ACCGCTGGTA GCGGTGGTTT TTTTGTTTGC AAGCAGCAGA
     TTACGCGCAG

6501 AAAAAAAGGA TCTCAAGAAG ATCCTTTGAT CTTTTCTACG
     GGGTCTGACG

6551 CTCAGTGGAA CGAAAACTCA CGTTAAGGGA TTTTGGTCAT
     GCATTCTAGG

6601 TACTAAAACA ATTCATCCAG TAAAATATAA TATTTTATTT
     TCTCCCAATC
```

-continued

6651 AGGCTTGATC CCCAGTAAGT CAAAAAATAG CTCGACATAC TGTTCTTCCC

6701 CGATATCCTC CCTGATCGAC CGGACGCAGA AGGCAATGTC ATACCACTTG

6751 TCCGCCCTGC CGCTTCTCCC AAGATCAATA AAGCCACTTA CTTTGCCATC

6801 TTTCACAAAG ATGTTGCTGT CTCCCAGGTC GCCGTGGGAA AAGACAAGTT

6851 CCTCTTCGGG CTTTTCCGTC TTTAAAAAAT CATACAGCTC GCGCGGATCT

6901 TTAAATGGAG TGTCTTCTTC CCAGTTTTCG CAATCCACAT CGGCCAGATC

6951 GTTATTCAGT AAGTAATCCA ATTCGGCTAA GCGGCTGTCT AAGCTATTCG

7001 TATAGGGACA ATCCGATATG TCGATGGAGT GAAAGAGCCT GATGCACTCC

7051 GCATACAGCT CGATAATCTT TTCAGGGCTT TGTTCATCTT CATACTCTTC

7101 CGAGCAAAGG ACGCCATCGG CCTCACTCAT GAGCAGATTG CTCCAGCCAT

7151 CATGCCGTTC AAAGTGCAGG ACCTTTGGAA CAGGCAGCTT TCCTTCCAGC

7201 CATAGCATCA TGTCCTTTTC CCGTTCCACA TCATAGGTGG TCCCTTTATA

7251 CCGGCTGTCC GTCATTTTTA AATATAGGTT TTCATTTTCT CCCACCAGCT

7301 TATATACCTT AGCAGGAGAC ATTCCTTCCG TATCTTTTAC GCAGCGGTAT

7351 TTTTCGATCA GTTTTTTCAA TTCCGGTGAT ATTCTCATTT TAGCCATTTA

7401 TTATTTCCTT CCTCTTTTCT ACAGTATTTA AAGATACCCC AAGAAGCTAA

7451 TTATAACAAG ACGAACTCCA ATTCACTGTT CCTTGCATTC TAAAACCTTA

7501 AATACCAGAA AACAGCTTTT TCAAAGTTGT TTTCAAAGTT GGCGTATAAC

7551 ATAGTATCGA CGGAGCCGAT TTTGAAACCG CGGTGATCAC AGGCAGCAAC

7601 GCTCTGTCAT CGTTACAATC AACATGCTAC CCTCCGCGAG ATCATCCGTG

7651 TTTCAAACCC GGCAGCTTAG TTGCCGTTCT TCCGAATAGC ATCGGTAACA

7701 TGAGCAAAGT CTGCCGCCTT ACAACGGCTC TCCCGCTGAC GCCGTCCCGG

7751 ACTGATGGGC TGCCTGTATC GAGTGGTGAT TTTGTGCCGA GCTGCCGGTC

7801 GGGGAGCTGT TGGCTGGCTG GTGGCAGGAT ATATTGTGGT GTAAACAAAT

7851 TGACGCTTAG ACAACTTAAT AACACATTGC GGACGTTTTT AATGTACTGA

7901 ATTAACGCCG AATTAATTCC TAGGCCACCA TGTTGGGCCC GGGGCGCGCC

7951 GTACGTAGTG TTTATCTTTG TTGCTTTTCT GAACAATTTA TTTACTATGT

-continued

8001 AAATATATTA TCAATGTTTA ATCTATTTTA ATTTGCACAT GAATTTTCAT

8051 TTTATTTTTA CTTTACAAAA CAAATAAATA TATATGCAAA AAAATTTACA

8101 AACGATGCAC GGGTTACAAA CTAATTTCAT TAAATGCTAA TGCAGATTTT

8151 GTGAAGTAAA ACTCCAATTA TGATGAAAAA TACCACCAAC ACCACCTGCG

8201 AAACTGTATC CCAACTGTCC TTAATAAAAA TGTTAAAAAG TATATTATTC

8251 TCATTTGTCT GTCATAATTT ATGTACCCCA CTTTAATTTT TCTGATGTAC

8301 TAAACCGAGG GCAAACTGAA ACCTGTTCCT CATGCAAAGC CCCTACTCAC

8351 CATGTATCAT GTACGTGTCA TCACCCAACA ACTCCACTTT TGCTATATAA

8401 CAACACCCCC GTCACACTCT CCCTCTCTAA CACACACCCC ACTAACAATT

8451 CCTTCACTTG CAGCACTGTT GCATCATCAT CTTCATTGCA AAACCCTAAA

8501 CTTCACCTTC AACCGCGGCC GCATGGCTTC TATGATATCC TCTTCCGCTG

8551 TGACAACAGT CAGCCGTGCC TCTAGGGGGC AATCCGCCGC AGTGGCTCCA

8601 TTCGGCGGCC TCAAATCCAT GACTGGATTC CCAGTGAAGA AGGTCAACAC

8651 TGACATTACT TCCATTACAA GCAATGGTGG AAGAGTAAAG TGCATGCAGG

8701 TGTGGCCTCC AATTGGAAAG AAGAAGTTTG AGACTCTTTC CTATTTGCCA

8751 CCATTGACGA GAGATTCTAG AGTGAGTAAC AAGAACAACG ATGAGCTGCA

8801 GTGGCAATCC TGGTTCAGCA AGGCGCCCAC CACCGAGGCG AACCCGATGG

8851 CCACCATGTT GCAGGATATC GGCGTTGCGC TCAAACCGGA AGCGATGGAG

8901 CAGCTGAAAA ACGATTATCT GCGTGACTTC ACCGCGTTGT GGCAGGATTT

8951 TTTGGCTGGC AAGGCGCCAG CCGTCAGCGA CCGCCGCTTC AGCTCGGCAG

9001 CCTGGCAGGG CAATCCGATG TCGGCCTTCA ATGCCGCATC TTACCTGCTC

9051 AACGCCAAAT TCCTCAGTGC CATGGTGGAG GCGGTGGACA CCGCACCCCA

9101 GCAAAAGCAG AAAATACGCT TTGCCGTGCA GCAGGTGATT GATGCCATGT

9151 CGCCCGCGAA CTTCCTCGCC ACCAACCCGG AAGCGCAGCA AAAACTGATT

9201 GAAACCAAGG GCGAGAGCCT GACGCGTGGC CTGGTCAATA TGCTGGGCGA

9251 TATCAACAAG GGCCATATCT CGCTGTCGGA CGAATCGGCC TTTGAAGTGG

9301 GCCGCAACCT GGCCATTACC CCGGGCACCG TGATTTACGA AATCCGCTG

-continued

```
9351 TTCCAGCTGA TCCAGTACAC GCCGACCACG CCGACGGTCA
     GCCAGCACCC

9401 GCTGTTGATG GTGCCGCCGT GCATCAACAA GTTCTACATC
     CTCGACCTGC

9451 AACCGGAAAA TTCGCTGGTG CGCTACGCGG TGGAGCAGGG
     CAACACCGTG

9501 TTCCTGATCT CGTGGAGCAA TCCGGACAAG TCGCTGGCCG
     GCACCACCTG

9551 GGACGACTAC GTGGAGCAGG GCGTGATCGA AGCGATCCGC
     ATCGTCCAGG

9601 ACGTCAGCGG CCAGGACAAG CTGAACATGT TCGGCTTCTG
     CGTGGGCGGC

9651 ACCATCGTTG CCACCGCACT GGCGGTACTG GCGGCGCGTG
     GCCAGCACCC

9701 GGCGGCCAGC CTGACCCTGC TGACCACCTT CCTCGACTTC
     AGCGACACCG

9751 GCGTGCTCGA CGTCTTCGTC GATGAAACCC AGGTCGCGCT
     GCGTGAACAG

9801 CAATTGCGCG ATGGCGGCCT GATGCCGGGC CGTGACCTGG
     CCTCGACCTT

9851 CTCGAGCCTG CGTCCGAACG ACCTGGTATG GAACTATGTG
     CAGTCGAACT

9901 ACCTCAAAGG CAATGAGCCG GCGGCGTTTG ACCTGCTGTT
     CTGGAATTCG

9951 GACAGCACCA ATTTGCCGGG CCCGATGTTC TGCTGGTACC
     TGCGCAACAC

10001 CTACCTGGAA AACAGCCTGA AAGTGCCGGG CAAGCTGACG
      GTGGCCGGCG

10051 AAAAGATCGA CCTCGGCCTG ATCGACGCCC CGGCCTTCAT
      CTACGGTTCG

10101 CGCGAAGACC ACATCGTGCC GTGGATGTCG GCGTACGGTT
      CGCTCGACAT

10151 CCTCAACCAG GGCAAGCCGG GCGCCAACCG CTTCGTGCTG
      GGCGCGTCCG

10201 GCCATATCGC CGGCGTGATC AACTCGGTGG CCAAGAACAA
      GCGCAGCTAC

10251 TGGATCAACG ACGGTGGCGC CGCCGATGCC CAGGCCTGGT
      TCGATGGCGC

10301 GCAGGAAGTG CCGGGCAGCT GGTGGCCGCA ATGGGCCGGG
      TTCCTGACCC

10351 AGCATGGCGG CAAGAAGGTC AAGCCCAAGG CCAAGCCCGG
      CAACGCCCGC

10401 TACACCGCGA TCGAGGCGGC GCCCGGCCGT TACGTCAAAG
      CCAAGGGCTG

10451 AGCGGCCGCT GAGTAATTCT GATATTAGAG GGAGCATTAA
      TGTGTTGTTG

10501 TGATGTGGTT TATATGGGGA AATTAAATAA ATGATGTATG
      TACCTCTTGC

10551 CTATGTAGGT TTGTGTGTTT TGTTTTGTTG TCTAGCTTTG
      GTTATTAAGT

10601 AGTAGGGACG TTCGTTCGTG TCTCAAAAAA AGGGGTACTA
      CCACTCTGTA

10651 GTGTATATGG ATGCTGGAAA TCAATGTGTT TTGTATTTGT
      TCACCTCCAT

10701 TGTTGAATTC AATGTCAAAT GTGTTTTGCG TTGTATTTGT
      GTAAAATTAC

10751 TATCTTTCTC GTCCGATGAT CAAAGTTTTA AGCAACAAAA
      CCAAGGGTGA

10801 AATTTAAACT GTGCTTTGTT GAAGATTCTT TTATCATATT
      GAAAATCAAA

10851 TTACTAGCAG CAGATTTTAC CTAGCATGAA ATTTTATCAA
      CAGTACAGCA

10901 CTCACTAACC AAGTTCCAAA CTAAGATGCG CCATTAACAT
      CAGCCAATAG

10951 GCATTTTCAG CAAGGCGCGC CCGCGCCGAT GTATGTGACA
      ACCCTCGGGA

11001 TTGTTGATTT ATTTCAAAAC TAAGAGTTTT TGTCTTATTG
      TTCTCGTCTA

11051 TTTTGGATAT CAATCTTAGT TTTATATCTT TTCTAGTTCT
      CTACGTGTTA

11101 AATGTTCAAC ACACTAGCAA TTTGGCCTGC CAGCGTATGG
      ATTATGGAAC

11151 TATCAAGTCT GTGACGCGCC GTACGTAGTG TTTATCTTTG
      TTGCTTTTCT

11201 GAACAATTTA TTTACTATGT AAATATATTA TCAATGTTTA
      ATCTATTTTA

11251 ATTTGCACAT GAATTTTCAT TTTATTTTTA CTTTACAAAA
      CAAATAAATA

11301 TATATGCAAA AAAATTTACA AACGATGCAC GGGTTACAAA
      CTAATTTCAT

11351 TAAATGCTAA TGCAGATTTT GTGAAGTAAA ACTCCAATTA
      TGATGAAAAA

11401 TACCACCAAC ACCACCTGCG AAACTGTATC CCAACTGTCC
      TTAATAAAAA

11451 TGTTAAAAAG TATATTATTC TCATTTGTCT GTCATAATTT
      ATGTACCCCA

11501 CTTTAATTTT TCTGATGTAC TAAACCGAGG GCAAACTGAA
      ACCTGTTCCT

11551 CATGCAAAGC CCCTACTCAC CATGTATCAT GTACGTGTCA
      TCACCCAACA

11601 ACTCCACTTT TGCTATATAA CAACACCCCC GTCACACTCT
      CCCTCTCTAA

11651 CACACACCCC ACTAACAATT CCTTCACTTG CAGCACTGTT
      GCATCATCAT

11701 CTTCATTGCA AAACCCTAAA CTTCACCTTC AACCGCGGCC
      GCATGGCTTC

11751 TATGATATCC TCTTCCGCTG TGACAACAGT CAGCCGTGCC
      TCTAGGGGGC

11801 AATCCGCCGC AGTGGCTCCA TTCGGCGGCC TCAAATCCAT
      GACTGGATTC

11851 CCAGTGAAGA AGGTCAACAC TGACATTACT TCCATTACAA
      GCAATGGTGG

11901 AAGAGTAAAG TGCATGCAGG TGTGGCCTCC AATTGGAAAG
      AAGAAGTTTG

11951 AGACTCTTTC CTATTTGCCA CCATTGACGA GAGATTCTAG
      AGTGACTCAG

12001 CGCATTGCGT ATGTGACCGG CGGCATGGGT GGTATCGGAA
      CCGCCATTTG
```

-continued

12051 CCAGCGGCTG GCCAAGGATG GCTTTCGTGT GGTGGCCGGT TGCGGCCCCA

12101 ACTCGCCGCG CCGCGAAAAG TGGCTGGAGC AGCAGAAGGC CCTGGGCTTC

12151 GATTTCATTG CCTCGGAAGG CAATGTGGCT GACTGGGACT CGACCAAGAC

12201 CGCATTCGAC AAGGTCAAGT CCGAGGTCGG CGAGGTTGAT GTGCTGATCA

12251 ACAACGCCGG TATCACCCGC GACGTGGTGT TCCGCAAGAT GACCCGCGCC

12301 GACTGGGATG CGGTGATCGA CACCAACCTG ACCTCGCTGT TCAACGTCAC

12351 CAAGCAGGTG ATCGACGGCA TGGCCGACCG TGGCTGGGGC CGCATCGTCA

12401 ACATCTCGTC GGTGAACGGG CAGAAGGGCC AGTTCGGCCA GACCAACTAC

12451 TCCACCGCCA AGGCCGGCCT GCATGGCTTC ACCATGGCAC TGGCGCAGGA

12501 AGTGGCGACC AAGGGCGTGA CCGTCAACAC GGTCTCTCCG GGCTATATCG

12551 CCACCGACAT GGTCAAGGCG ATCCGCCAGG ACGTGCTCGA CAAGATCGTC

12601 GCGACGATCC CGGTCAAGCG CCTGGGCCTG CCGGAAGAGA TCGCCTCGAT

12651 CTGCGCCTGG TTGTCGTCGG AGGAGTCCGG TTTCTCGACC GGCGCCGACT

12701 TCTCGCTCAA CGGCGGCCTG CATATGGGCT GAGCGGCCGC TGAGTAATTC

12751 TGATATTAGA GGGAGCATTA ATGTGTTGTT GTGATGTGGT TTATATGGGG

12801 AAATTAAATA AATGATGTAT GTACCTCTTG CCTATGTAGG TTTGTGTGTT

12851 TTGTTTTGTT GTCTAGCTTT GGTTATTAAG TAGTAGGGAC GTTCGTTCGT

12901 GTCTCAAAAA AAGGGGTACT ACCACTCTGT AGTGTATATG GATGCTGGAA

12951 ATCAATGTGT TTTGTATTTG TTCACCTCCA TTGTTGAATT CAATGTCAAA

13001 TGTGTTTTGC GTTGGTTATG TGTAAAATTA CTATCTTTCT CGTCCGATGA

13051 TCAAAGTTTT AAGCAACAAA ACCAAGGGTG AAATTTAAAC TGTGCTTTGT

13101 TGAAGATTCT TTTATCATAT TGAAAATCAA ATTACTAGCA GCAGATTTTA

13151 CCTAGCATGA AATTTTATCA ACAGTACAGC ACTCACTAAC CAAGTTCCAA

13201 ACTAAGATGC GCCATTAACA TCACCCAACA GGCATTTTCA GCAAGGCGCG

13251 TAAGGGGATC CGTACGTAAG TACGTACTCA AAATGCCAAC AAATAAAAAA

13301 AAAGTTGCTT TAATAATGCC AAAACAAATT AATAAAACAC TTACAACACC

13351 GGATTTTTTT TAATTAAAAT GTGCCATTTA GGATAAATAG TTAATATTTT

-continued

13401 TAATAATTAT TTAAAAAGCC GTATCTACTA AAATGATTTT TATTTGGTTG

13451 AAAATATTAA TATGTTTAAA TCAACACAAT CTATCAAAAT TAAACTAAAA

13501 AAAAAATAAG TGTACGTGGT TAACATTAGT ACAGTAATAT AAGCAACAAA

13551 TGAGAAATTA AGAAATTGAA AGCGAGTCTA ATTTTTAAAT TATGAACCTG

13601 CATATATAAA AGAAAAGAAA GAATCCAGGA AGAAAAGAAA TGAAACCATG

13651 CATGGTCCCC TCGTCATCAC GAGTTTCTGC CATTTGCAAT AGAAACACTG

13701 AAACACCTTT CTCTTTGTCA CTTAATTGAG ATGCCGAAGC CACCTCACAC

13751 CATGAACTTC ATGAGGTGTA GCACCCAAGG CTTCCATAGC CATGCATACT

13801 GAAGAATGTC TCAAGCTCAG CACCCTACTT CTGTGACGTG TCCCTCATTC

13851 ACCTTCCTCT CTTCCCTATA AATAACCACG CCTCAGGTTC TCCGCTTCAC

13901 AACTCAAACA TTCTCTCCAT TGGTCCTTAA ACACTCATCA GTCATCACCG

13951 CGGCCGCGGA ATTCATGGCT TCTATGATAT CCTCTTCCGC TGTGACAACA

14001 GTCAGCCGTG CCTCTAGGGG GCAATCCGCC GCAGTGGCTC CATTCGGCGG

14051 CCTCAAATCC ATGACTGGAT TCCCAGTGAA GAAGGTCAAC ACTGACATTA

14101 CTTCCATTAC AAGCAATGGT GGAAGAGTAA AGTGCATGCA GGTGTGGCCT

14151 CCAATTGGAA AGAAGAAGTT TGAGACTCTT TCCTATTTGC CACCATTGAC

14201 GAGAGATTCT AGAGTGACTG ACGTTGTCAT CGTATCCGCC GCCCGCACCG

14251 CGGTCGGCAA GTTTGGCGGC TCGCTGGCCA AGATCCCGGC ACCGGAACTG

14301 GGTGCCGTGG TCATCAAGGC CGCGCTGGAG CGCGCCGGCG TCAAGCCGGA

14351 GCAGGTGAGC GAAGTCATCA TGGGCCAGGT GCTGACCGCC GGTTCGGGCC

14401 AGAACCCCGC ACGCCAGGCC GCGATCAAGG CCGGCCTGCC GGCGATGGTG

14451 CCGGCCATGA CCATCAACAA GGTGTGCGGC TCGGGCCTGA AGGCCGTGAT

14501 GCTGGCCGCC AACGCGATCA TGGCGGGCGA CGCCGAGATC GTGGTGGCCG

14551 GCGGCCAGGA AAACATGAGC GCCGCCCCGC ACGTGCTGCC GGGCTCGCGC

14601 GATGGTTTCC GCATGGGCGA TGCCAAGCTG GTCGACACCA TGATCGTCGA

14651 CGGCCTGTGG GACGTGTACA ACCAGTACCA CATGGGCATC ACCGCCGAGA

14701 ACGTGGCCAA GGAATACGGC ATCACACGCG AGGCGCAGGA TGAGTTCGCC

-continued

14751 GTCGGCTCGC AGAACAAGGC CGAAGCCGCG CAGAAGGCCG GCAAGTTTGA

14801 CGAAGAGATC GTCCCGGTGC TGATCCCGCA GCGCAAGGGC GACCCGGTGG

14851 CCTTCAAGAC CGACGAGTTC GTGCGCCAGG GCGCCACGCT GGACAGCATG

14901 TCCGGCCTCA AGCCCGCCTT CGACAAGGCC GGCACGGTGA CCGCGGCCAA

14951 CGCCTCGGGC CTGAACGACG GCGCCGCCGC GGTGGTGGTG ATGTCGGCGG

15001 CCAAGGCCAA GGAACTGGGC CTGACCCCGC TGGCCACGAT CAAGAGCTAT

15051 GCCAACGCCG GTGTCGATCC CAAGGTGATG GGCATGGGCC CGGTGCCGGC

15101 CTCCAAGCGC GCCCTGTCGC GCGCCGAGTG GACCCCGCAA GACCTGGACC

15151 TGATGGAGAT CAACGAGGCC TTTGCCGCGC AGGCGCTGGC GGTGCACCAG

15201 CAGATGGGCT GGGACACCTC CAAGGTCAAT GTGAACGGCG GCGCCATCGC

15251 CATCGGCCAC CCGATCGGCG CGTCGGGCTG CCGTATCCTG GTGACGCTGC

15301 TGCACGAGAT GAAGCGCCGT GACGCGAAGA AGGGCCTGGC CTCGCTGTGC

15351 ATCGGCGGCG GCATGGGCGT GGCGCTGGCA GTCGAGCGCA AATAACTCGA

15401 GGCGGCCGCA GCCCTTTTTG TATGTGCTAC CCCACTTTTG TCTTTTTGGC

15451 AATAGTGCTA GCAACCAATA AATAATAATA ATAATAATGA ATAAGAAAAC

15501 AAAGGCTTTA GCTTGCCTTT TGTTCACTGT AAAATAATAA TGTAAGTACT

15551 CTCTATAATG AGTCACGAAA CTTTTGCGGG AATAAAAGGA GAAATTCCAA

15601 TGAGTTTTCT GTCAAATCTT CTTTTGTCTC TCTCTCTCTC TCTTTTTTTT

15651 TTTTCTTTCT TCTGAGCTTC TTGCAAAACA AAAGGCAAAC AATAACGATT

15701 GGTCCAATGA TAGTTAGCTT GATCGATGAT ATCTTTAGGA AGTGTTGGCA

15751 GGACAGGACA TGATGTAGAA GACTAAAATT GAAAGTATTG CAGACCCAAT

15801 AGTTGAAGAT TAACTTTAAG AATGAAGACG TCTTATCAGG TTCTTCATGA

15851 CTTAAGCTTT AAGAGGAGTC CACCATGGTA GATCTGACTA GTAACGGCCG

15901 CCAGTGTGCT GGAATTCTGC AGATGTGGAG CACGACACTC TCGTCTACTC

15951 CAAGAATATC AAAGATACAG TCTCAGAAGA CCAAAGGGCT ATTGAGACTT

16001 TTCAACAAAG GGTAATATCG GGAAACCTCC TCGGATTCCA TTGCCCAGCT

16051 ATCTGTCACT TCATCAAAAG GACAGTAGAA AAGGAAGGTG GCACCTACAA

-continued

16101 ATGCCATCAT TGCGATAAAG GAAAGGCTAT CGTTCAAGAT GCCTCTGCCG

16151 ACAGTGGTCC CAAAGAATCA CCCCCACCCA CGAGGAGCAT CGTGGAAAAA

16201 GAAGACGTTC CAACCACGTC TTCAAAGCAA GTGGATTGAT GTGATAACAT

16251 GGTGGAGCAC GACACTCTCG TCTACTCCAA GAATATCAAA GATACAGTCT

16301 CAGAAGACCA AAGGGCTATT GAGACTTTTC AACAAAGGGT AATATCGGGA

16351 AACCTCCTCG GATTCCATTG CCCAGCTATC TGTCACTTCA TCAAAAGGAC

16401 AGTAGAAAAG GAAGGTGGCA CCTACAAATG CCATCATTGC GATAAAGGAA

16451 AGGCTATCGT TCAAGATGCC TCTGCCGACA GTGGTCCCAA AGATGGACCC

16501 CCACCCACGA GGAGCATCGT GGAAAAAGAA GACGTTCCAA CCACGTCTTC

16551 AAAGCAAGTG GATTGATGTG ATATCTCCAC TGACGTAAGG GATGACGCAC

16601 AATCCCACTA TCCTTCGCAA GACCTTCCTC TATATAAGGA AGTTCATTTC

16651 ATTTGGAGAG GACACGCTGA AATCACCAGT CTCTCTCTAC AAATCTATCT

16701 CTCTCGAGCT TTCGCAGATC TGTCGATCGA CCATGGACTC CAAAGAATCA

16751 TTAACTCCTG GTAGAGAAGA AAACCCCAGC AGTGTGCTTG CTCAGGAGAG

16801 GGGAGATGTG ATGGACTTCT ATAAAACCCT AAGAGGAGGA GCTACTGTGA

16851 AGGTTTCTGC GTCTTCACCC TCACTGGCTG TCGCTTCTCA ATCAGACTCC

16901 AAGCAGCGAA GACTTTTGGT TGATTTTCCA AAAGGCTCAG TAAGCAATGC

16951 GCAGCAGCCA GATCTGTCCA AAGCAGTTTC ACTCTCAATG GGACTGTATA

17001 TGGGAGAGAC AGAAACAAAA GTGATGGGAA ATGACCTGGG ATTCCCACAG

17051 CAGGGCCAAA TCAGCCTTTC CTCGGGGGAA ACAGACTTAA AGCTTTTGGA

17101 AGAAAGCATT GCAAACCTCA ATAGGTCGAC CAGTGTTCCA GAGAACCCCA

17151 AGAGTTCAGC ATCCACTGCT GTGTCTGCTG CCCCCACAGC TAGTTCTGCG

17201 GCCCCCCCGA CCGATGTCAG CCTGGGGGAC GAGCTCCACT TAGACGGCGA

17251 GGACGTGGCG ATGGCGCATG CCGACGCGCT AGACGATTTC GATCTGGACA

17301 TGTTGGGGGA CGGGGATTCC CCGGGTCCGG GATTTACCCC CCACGACTCC

17351 GCCCCCTACG GCGCTCTGGA TATGGCCGAC TTCGAGTTTG AGCAGATGTT

17401 TACCGATGCC CTTGGAATTG ACGAGTACGG TGGGACTAGC TCCAGCTCCT

-continued

17451 CAACAGCAAC AACAGGACCA CCTCCCAAAC TCTGCCTGGT GTGCTCTGAT

17501 GAAGCTTCAG GATGTCATTA TGGAGTCTTA ACTTGTGGAA GCTGTAAAGT

17551 TTTCTTCAAA AGAGCAGTGG AAGGACAGCA CAATTACCTA TGTGCTGGAA

17601 GGAATGATTG CATCATCGAT AAAATTCGAA GAAAAAACTG CCCAGCATGC

17651 CGCTATCGAA AATGTCTTCA GGCTGGAATG AACCTGGAAG CTCGAAAAAC

17701 AAAGAAAAAA ATAAAAGGAA TTGCTCGACA AAGGCCCGAG TGCGTGGTGC

17751 CGGAGAACCA GTGTGCAATG AAACGGAAAG AGAAAAAGGC GCAGAGGGAA

17801 AAAGACAAAT TGCCCGTCAG TACGACGACA GTAGACGATC ACATGCCTCC

17851 CATCATGCAA TGTGACCCTC CGCCCCCAGA GGCCGCTAGA ATTCTGGAAT

17901 GTTTGCAGCA CGAGGTGGTG CCACGATTCC TGAATGAGAA GCTAATGGAA

17951 CAGAACAGAT TGAAGAACGT GCCCCCCCTC ACTGCCAATC AGAAGTCGTT

18001 GATCGCAAGG CTCGTGTGGT ACCAGGAAGG CTATGAACAA CCTTCCGAGG

18051 AAGACCTGAA GAGGGTTACA CAGTCGGACG AGGACGACGA AGACTCGGAT

18101 ATGCCGTTCC GTCAGATTAC CGAGATGACG ATTCTCACAG TGCAGCTCAT

18151 CGTAGAATTC GCTAAGGGCC TCCCGGGCTT CGCCAAGATC TCGCAGTCGG

18201 ACCAGATCAC GTTATTAAAG GCGTGCTCAA GTGAGGTGAT GATGCTCCGA

18251 GTGGCTCGGC GGTATGACGC GGCCACCGAC AGCGTACTGT TCGCGAACAA

18301 CCAGGCGTAC ACTCGCGACA ACTACCGCAA GGCAGGCATG GCGTACGTCA

18351 TCGAGGACCT GCTGCACTTC TGTCGGTGCA TGTACTCCAT GATGATGGAT

18401 AACGTGCATT ATGCGCTGCT TACAGCCATT GTCATCTTCT CAGACCGGCC

18451 CGGGCTTGAG CAACCCCTGT TGGTGGAGGA GATCCAGAGA TATTACCTGA

18501 ACACGCTACG GGTGTACATC CTGAACCAGA ACAGCGCGTC GCCCCGCTGC

18551 GCCGTCATCT TCGGCAAGAT CCTGGGCATA CTGACGGAGA TCCGCACGCT

18601 GGGCATGCAG AACTCCAACA TGTGCATCTC CCTCAAGCTG AAGAACAGGA

18651 AGCTGCCGCC GTTCCTCGAG GAGATCTGGG ACGTGGCGGA CGTGGCGACG

18701 ACGGCGACGC CGGTGGCGGC GGAGGCGCCG GCGCTCTAGC CCCCGCGCCG

18751 CCCGCCCGGC CGCGCGCACG TCTAGCGCGC CTCAGGAGAG AACGCTCATA

-continued

18801 GACTGGCTAG TTTTAGTGAA GTGCACGGAC ACTGACGTCG GACGTGATCA

18851 ACCTATTTAT AAGGACTGCG AATTTTACCA CTTAAGAGGG CACACCCGTA

18901 CCCGATTTCG TACGGGAATT CCTGCAGCCC GGGGGATCCT TAATTAACTC

18951 GAGGAATTCA TCGATTCCGC GGGTACCGAG CTCGATCCGT CGACCTGCAG

19001 ATCGTTCAAA CATTTGGCAA TAAAGTTTCT TAAGATTGAA TCCTGTTGCC

19051 GGTCTTGCGA TGATTATCAT ATAATTTCTG TTGAATTACG TTAAGCATGT

19101 AATAATTAAC ATGTAATGCA TGACGTTATT TATGAGATGG GTTTTTATGA

19151 TTAGAGTCCC GCAATTATAC ATTTAATACG CGATAGAAAA CAAAATATAG

19201 CGCGCAAACT AGGATAAATT ATCGCGCGCG GTGTCATCTA TGTTACTAGA

19251 TCTGGCGCGC CCCTAGGTCT AGAGTCGACT GTTTAAACGG TCCGTGACCA

19301 TGATTACGCC AAGCTTCGAC TGTACAGGAT GTTCTAGCTA CTCGAGTAGC

19351 TAGAACATCC TGTACAGTCG AGTAGCTAGA ACATCCTGTA CAGTCGACTA

19401 GCTAGAACAT CCTGTACAGT CGAGTAGCTA GAACATCCTG TACAGTCGAG

19451 TAGCTAGACA TCCTGTACAG GATCCCTATA TAAGGAAGTT CATTTCATTT

19501 GGAGAGAACA CGGGGGATCG GGTATCGTTA ATTAAGTTTA TCAACAAGTT

19551 TGTACAAAAA AGCAGGCTCC GCGGCCGCCC CCTTCACCTT CCTCGACTTC

19601 AGCGACACCG GCGTGCTCGA CGTCTTCGTC GATGAAACCC AGGTCGCGCT

19651 GCGTGAACAG CAATTGCGCG ATGGCGGCCT GATGCCGGGC CGTGACCTGG

19701 CCTCGACCTT CTCGAGCCTG CGTCCGAACG ACCTGGTATG GAACTATGTG

19751 CAGTCGAACT ACCTCAAAGG CAATGAGCCG GCGGCGTTTG ACCTGCTGTT

19801 CTGGAATTCG GACAGCACCA ATTTGCCGGG CCCGATGTTC TGCTGGTACC

19851 TGCGCAACAC CTACCTGGAA AACAGCCTGA AAGTGCCGGG CAAGCTGACG

19901 GTGGCCGGCG AAAAGATCGA CCTCGGCCTG ATCGACGCCC CGGCCTTCAT

19951 CTACGGTTCG CGCGAAGACC ACATCGTGCC GTGGATGTCG GCGTACGGTT

20001 CGCTCGACAT CCTCAACCAG GGCAAGCCGG GCGCCAACCG CTTCGTGCTG

20051 GGCGCGTCCG GCCATATCGC CGGCGTGATC AACTCGGTGG CCAAGAACAA

20101 GCGCAGCTAC TGGATCAACG ACGGTGGCGC CGCCGATGCC CAGGCCTGGT

-continued

```
20151 TCGATGGCGC GCAGGAAGTG CCGGGCAGCT GGTGGCCGCA
      ATGGGCCGGG

20201 TTCCTGACCC AGCATGGCGG CAAGAAGGTC AAGCCCAAGG
      CCAAAAGGGT

20251 GGGCGCGCCG ACCCAGCTTT CTTGTACAAA GTGGTTGATC
      CTGCAGGGTC

20301 CGTCGCTTCT CTTCCATTTC TTCTCATTTT CGATTTTGAT
      TCTTATTTCT

20351 TTCCAGTAGC TCCTGCTCTG TGAATTTCTC CGCTCACGAT
      AGATCTGCTT

20401 ATACTCCTTA CATTCAACCT TAGATCTGGT CTCGATTCTC
      TGTTTCTCTG

20451 TTTTTTTCTT TTGGTCGAGA ATCTGATGTT TGTTTATGTT
      CTGTCACCAT

20501 TAATAATAAT GAACTCTCTC ATTCATACAA TGATTAGTTT
      CTCTCGTCTA

20551 CAAAACGATA TGTTGCATTT TCACTTTTCT TCTTTTTTTC
      TAAGATGATT

20601 TGCTTTGACC AATTTGTTTA GATCTTTATT CTATTTTATT
      TTCTGGTGGG

20651 TTGGTGGAAA TTGAAAAAAA AATACAAGCA TAAATTGTTA
      TTTGTTAATG

20701 TATTCATTTT TTGGCTATTT GTTCTGGGTA AAAATCTGCT
      TCTACTATTG

20751 AATCTTTCCT GGATTTTTTA CTCCTATTGG GTTTTTATAG
      TAAAAATACA

20801 TAATAAAAGG AAAACAAAAG TTTTATAGAT TCTCTTAAAC
      CCCTTACGAT

20851 AAAAGTTGGA ATCAAAATAA TTCAGGATCA GATGCTCTTT
      GATTGATTCA

20901 GATGCGATTA CAGTTGCATG GCAAATTTTC TAGATCCGTC
      GTCACATTTT

20951 ATTTTCTGTT TAAATATCTA AATCTGATAT ATGATGTCGA
      CAAATTCTGG

21001 TGGCTTATAC ATCACTTCAA CTGTTTTCTT TTGGCTTTGT
      TTGTCAACTT

21051 GGTTTTCAAT ACGATTTGTG ATTTCGATCG CTGAATTTTT
      AATACAAGCA

21101 AACTGATGTT AACCACAAGC AAGAGATGTG ACCTGCCTTA
      TTAACATCGT

21151 ATTACTTACT ACTAGTCGTA TTCTCAACGC AATCGTTTTT
      GTATTTCTCA

21201 CATTATGCCG CTTCTCTACT CTTTATTCCT TTTGGTCCAC
      GCATTTTCTA

21251 TTTGTGGCAA TCCCTTTCAC AACCTGATTT CCCACTTTGG
      ATCATTTGTC

21301 TGAAGACTCT CTTGAATCGT TACCACTTGT TTCTTGTGCA
      TGCTCTGTTT

21351 TTTAGAATTA ATGATAAAAC TATTCCATAG TCTTGAGTTT
      TCAGCTTGTT

21401 GATTCTTTTG CTTTTGGTTT TCTGCAGGTT TAAACATCAA
      CCACTTTGTA

21451 CAAGAAAGCT GGGTCGGCGC GCCCACCCTT TTGGCCTTGG
      GCTTGACCTT

21501 CTTGCCGCCA TGCTGGGTCA GGAACCCGGC CCATTGCGGC
      CACCAGCTGC

21551 CCGGCACTTC CTGCGCGCCA TCGAACCAGG CCTGGGCATC
      GGCGGCGCCA

21601 CCGTCGTTGA TCCAGTAGCT GCGCTTGTTC TTGGCCACCG
      AGTTGATCAC

21651 GCCGGCGATA TGGCCGGACG CGCCCAGCAC GAAGCGGTTG
      GCGCCCGGCT

21701 TGCCCTGGTT GAGGATGTCG AGCGAACCGT ACGCCGACAT
      CCACGGCACG

21751 ATGTGGTCTT CGCGCGAACC GTAGATGAAG GCCGGGGCGT
      CGATCAGGCC

21801 GAGGTCGATC TTTTCGCCGG CCACCGTCAG CTTGCCCGGC
      ACTTTCAGGC

21851 TGTTTTCCAG GTAGGTGTTG CGCAGGTACC AGCAGAACAT
      CGGGCCCGGC

21901 AAATTGGTGC TGTCCGAATT CCAGAACAGC AGGTCAAACG
      CCGCCGGCTC

21951 ATTGCCTTTG AGGTAGTTCG ACTGCACATA GTTCCATACC
      AGGTCGTTCG

22001 GACGCAGGCT CGAGAAGGTC GAGGCCAGGT CACGGCCCGG
      CATCAGGCCG

22051 CCATCGCGCA ATTGCTGTTC ACGCAGCGCG ACCTGGGTTT
      CATCGACGAA

22101 GACGTCGAGC ACGCCGGTGT CGCTGAAGTC GAGGAAGGTG
      AAGGGGGCGG

22151 CCGCGGAGCC TGCTTTTTTG TACAAACTTG TTGATCTCGA
      GCGGCGCGCC

22201 GTTCGAGTAT TATGGCATTG GGAAAACTGT TTTTCTTGTA
      CCATTTGTTG

22251 TGCTTGTAAT TTACTGTGTT TTTTATTCGG TTTTCGCTAT
      CGAACTGTGA

22301 AATGGAAATG GATGGAGAAG AGTTAATGAA TGATATGGTC
      CTTTTGTTCA

22351 TTCTCAAATT AATATTATTT GTTTTTTCTC TTATTTGTTG
      TGTGTTGAAT

22401 TTGAAATTAT AAGAGATATG CAAACATTTT GTTTTGAGTA
      AAAATGTGTC

22451 AAATCGTGGC CTCTAATGAC CGAAGTTAAT ATGAGGAGTA
      AAACACTGTT

22501 TAAACCCTGC AGGATTT
```

Vector: pPhaA-RNAi/glyP (SEQ ID NO: 5)

```
  1 AAATAGAAGG TAATTATCCA AGATGTAGCA TCAAGAATCC
    AATGTTTACG

 51 GGAAAAACTA TGGAAGTATT ATGTGAGCTC AGCAAGAAGC
    AGATCAATAT

101 GCGGCACATA TGCAACCTAT GTTCAAAAAT GAAGAATGTA
    CAGATACAAG

151 ATCCTATACT GCCAGAATAC GAAGAAGAAT ACGTAGAAAT
    TGAAAAAGAA

201 GAACCAGGCG AAGAAAAGAA TCTTGAAGAC GTAAGCACTG
    ACGACAACAA

251 TGAAAAGAAG AAGATAAGGT CGGTGATTGT GAAAGAGACA
    TAGAGGACAC
```

-continued

301 ATGTAAGGTG GAAAATGTAA GGGCGGAAAG TAACCTTATC ACAAAGGAAT

351 CTTATCCCCC ACTACTTATC CTTTTATATT TTTCCGTGTC ATTTTTGCCC

401 TTGAGTTTTC CTATATAAGG AACCAAGTTC GGCATTTGTG AAAACAAGAA

451 AAAATTGGTG TAAGCTATTT TCTTTGAAGT ACTGAGGATA CAACTTCAGA

501 GAAATTTGTA AGAAAGTGGA TCGAAACCAT GGCCTCCTCC GAGAACGTCA

551 TCACCGAGTT CATGCGCTTC AAGGTGCGCA TGGAGGGCAC CGTGAACGGC

601 CACGAGTTCG AGATCGAGGG CGAGGGCGAG GGCCGCCCCT ACGAGGGCCA

651 CAACACCGTG AAGCTGAAGG TGACCAAGGG CGGCCCCCTG CCCTTCGCCT

701 GGGACATCCT GTCCCCCCAG TTCCAGTACG GCTCCAAGGT GTACGTGAAG

751 CACCCCGCCG ACATCCCCGA CTACAAGAAG CTGTCCTTCC CCGAGGGCTT

801 CAAGTGGGAG CGCGTGATGA ACTTCGAGGA CGGCGGCGTG GCGACCGTGA

851 CCCAGGACTC CTCCCTGCAG GACGGCTGCT TCATCTACAA GGTGAAGTTC

901 ATCGGCGTGA ACTTCCCCTC CGACGGCCCC GTGATGCAGA AGAAGACCAT

951 GGGCTGGGAG GCCTCCACCG AGCGCCTGTA CCCCCGCGAC GGCGTGCTGA

1001 AGGGCGAGAC CCACAAGGCC CTGAAGCTGA AGGACGGCGG CCACTACCTG

1051 GTGGAGTTCA AGTCCATCTA CATGGCCAAG AAGCCCGTGC AGCTGCCCGG

1101 CTACTACTAC GTGGACGCCA AGCTGGACAT CACCTCCCAC AACGAGGACT

1151 ACACCATCGT GGAGCAGTAC GAGCGCACCG AGGGCCGCCA CCACCTGTTC

1201 CTGGTACCAA TGAGCTCTGT CCAACAGTCT CAGGGTTAAT GTCTATGTAT

1251 CTTAAATAAT GTTGTCGGCG ATCGTTCAAA CATTTGGCAA TAAAGTTTCT

1301 TAAGATTGAA TCCTGTTGCC GGTCTTGCGA TGATTATCAT ATAATTTCTG

1351 TTGAATTACG TTAAGCATGT AATAATTAAC ATGTAATGCA TGACGTTATT

1401 TATGAGATGG GTTTTTATGA TTAGAGTCCC GCAATTATAC ATTTAATACG

1451 CGATAGAAAA CAAAATATAG CGCGCAAACT AGGATAAATT ATCGCGCGCG

1501 GTGTCATCTA TGTTACTAGA TCGGGAATTA AACTATCAGT GTTTGACAGG

1551 ATATATTGGC GGGTAAACCT AAGAGAAAAG AGCGTTTATT AGAATAACGG

1601 ATATTTAAAA GGGCGTGAAA AGGTTTATCC GTTCGTCCAT TTGTATGTGC

-continued

1651 ATGCCAACCA CAGGGTTCCC CTCGGGATCA AAGTACTTTG ATCCAACCCC

1701 TCCGCTGCTA TAGTGCAGTC GGCTTCTGAC GTTCAGTGCA GCCGTCTTCT

1751 GAAAACGACA TGTCGCACAA GTCCTAAGTT ACGCGACAGG CTGCCGCCCT

1801 GCCCTTTTCC TGGCGTTTTC TTGTCGCGTG TTTTAGTCGC ATAAAGTAGA

1851 ATACTTGCGA CTAGAACCGG AGACATTACG CCATGAACAA GAGCGCCGCC

1901 GCTGGCCTGC TGGGCTATGC CCGCGTCAGC ACCGACGACC AGGACTTGAC

1951 CAACCAACGG GCCGAACTGC ACGCGGCCGG CTGCACCAAG CTGTTTTCCG

2001 AGAAGATCAC CGGCACCAGG CGCGACCGCC CGGAGCTGGC CAGGATGCTT

2051 GACCACCTAC GCCCTGGCGA CGTTGTGACA GTGACCAGGC TAGACCGCCT

2101 GGCCCGCAGC ACCCGCGACC TACTGGACAT TGCCGAGCGC ATCCAGGAGG

2151 CCGGCGCGGG CCTGCGTAGC CTGGCAGAGC CGTGGGCCGA CACCACCACG

2201 CCGGCCGGCC GCATGGTGTT GACCGTGTTC GCCGGCATTG CCGAGTTCGA

2251 GCGTTCCCTA ATCATCGACC GCACCCGGAG CGGGCGCGAG GCCGCCAAGG

2301 CCCGAGGCGT GAAGTTTGGC CCCCGCCCTA CCCTCACCCC GGCACAGATC

2351 GCGCACGCCC GCGAGCTGAT CGACCAGGAA GGCCGCACCG TGAAAGAGGC

2401 GGCTGCACTG CTTGGCGTGC ATCGCTCGAC CCTGTACCGC GCACTTGAGC

2451 GCAGCGAGGA AGTGACGCCC ACCGAGGCCA GGCGGCGCGG TGCCTTCCGT

2501 GAGGACGCAT TGACCGAGGC CGACGCCCTG GCGGCCGCCG AGAATGAACG

2551 CCAAGAGGAA CAAGCATGAA ACCGCACCAG GACGGCCAGG ACGAACCGTT

2601 TTTCATTACC GAAGAGATCG AGGCGGAGAT GATCGCGGCC GGGTACGTGT

2651 TCGAGCCGCC CGCGCACGTC TCAACCGTGC GGCTGCATGA AATCCTGGCC

2701 GGTTTGTCTG ATGCCAAGCT GGCGGCCTGG CCGGCCAGCT TGGCCGCTGA

2751 AGAAACCGAG CGCCGCCGTC TAAAAAGGTG ATGTGTATTT GAGTAAAACA

2801 GCTTGCGTCA TGCGGTCGCT GCGTATATGA TGCGATGAGT AAATAAACAA

2851 ATACGCAAGG GGAACGCATG AAGGTTATCG CTGTACTTAA CCAGAAAGGC

2901 GGGTCAGGCA AGACGACCAT CGCAACCCAT CTAGCCCGCG CCCTGCAACT

2951 CGCCGGGGCC GATGTTCTGT TAGTCGATTC CGATCCCCAG GGCAGTGCCC

-continued

```
3001 GCGATTGGGC GGCCGTGCGG GAAGATCAAC CGCTAACCGT
     TGTCGGCATC

3051 GACCGCCCGA CGATTGACCG CGACGTGAAG GCCATCGGCC
     GGCGCGACTT

3101 CGTAGTGATC GACGGAGCGC CCCAGGCGGC GGACTTGGCT
     GTGTCCGCGA

3151 TCAAGGCAGC CGACTTCGTG CTGATTCCGG TGCAGCCAAG
     CCCTTACGAC

3201 ATATGGGCCA CCGCCGACCT GGTGGAGCTG GTTAAGCAGC
     GCATTGAGGT

3251 CACGGATGGA AGGCTACAAG CGGCCTTTGT CGTGTCGCGG
     GCGATCAAAG

3301 GCACGCGCAT CGGCGGTGAG GTTGCCGAGG CGCTGGCCGG
     GTACGAGCTG

3351 CCCATTCTTG AGTCCCGTAT CACGCAGCGC GTGAGCTACC
     CAGGCACTGC

3401 CGCCGCCGGC ACAACCGTTC TTGAATCAGA ACCCGAGGGC
     GACGCTGCCC

3451 GCGAGGTCCA GGCGCTGGCC GCTGAAATTA AATCAAAACT
     CATTTGAGTT

3501 AATGAGGTAA AGAGAAAATG AGCAAAAGCA CAAACACGCT
     AAGTGCCGGC

3551 CGTCCGAGCG CACGCAGCAG CAAGGCTGCA ACGTTGGCCA
     GCCTGGCAGA

3601 CACGCCAGCC ATGAAGCGGG TCAACTTTCA GTTGCCGGCG
     GAGGATCACA

3651 CCAAGCTGAA GATGTACGCG GTACGCCAAG GCAAGACCAT
     TACCGAGCTG

3701 CTATCTGAAT ACATCGCGCA GCTACCAGAG TAAATGAGCA
     AATGAATAAA

3751 TGAGTAGATG AATTTTAGCG GCTAAAGGAG GCGGCATGGA
     AAATCAAGAA

3801 CAACCAGGCA CCGACGCCGT GGAATGCCCC ATGTGTGGAG
     GAACGGGCGG

3851 TTGGCCAGGC GTAAGCGGCT GGGTTGTCTG CCGGCCCTGC
     AATGGCACTG

3901 GAACCCCCAA GCCCGAGGAA TCGGCGTGAC GGTCGCAAAC
     CATCCGGCCC

3951 GGTACAAATC GGCGCGGCGC TGGGTGATGA CCTGGTGGAG
     AAGTTGAAGG

4001 CCGCGCAGGC CGCCCAGCGG CAACGCATCG AGGCAGAAGC
     ACGCCCCGGT

4051 GAATCGTGGC AAGCGGCCGC TGATCGAATC CGCAAAGAAT
     CCCGGCAACC

4101 GCCGGCAGCC GGTGCGCCGT CGATTAGGAA GCCGCCCAAG
     GGCGACGAGC

4151 AACCAGATTT TTTCGTTCCG ATGCTCTATG ACGTGGGCAC
     CCGCGATAGT

4201 CGCAGCATCA TGGACGTGGC CGTTTTCCGT CTGTCGAAGC
     GTGACCGACG

4251 AGCTGGCGAG GTGATCCGCT ACGAGCTTCC AGACGGGCAC
     GTAGAGGTTT

4301 CCGCAGGGCC GGCCGGCATG GCCAGTGTGT GGGATTACGA
     CCTGGTACTG
```

-continued

```
4351 ATGGCGGTTT CCCATCTAAC CGAATCCATG AACCGATACC
     GGGAAGGGAA

4401 GGGAGACAAG CCCGGCCGCG TGTTCCGTCC ACACGTTGCG
     GACGTACTCA

4451 AGTTCTGCCG GCGAGCCGAT GGCGGAAAGC AGAAAGACGA
     CCTGGTAGAA

4501 ACCTGCATTC GGTTAAACAC CACGCACGTT GCCATGCAGC
     GTACGAAGAA

4551 GGCCAAGAAC GGCCGCCTGG TGACGGTATC CGAGGGTGAA
     GCCTTGATTA

4601 GCCGCTACAA GATCGTAAAG AGCGAAACCG GGCGGCCGGA
     GTACATCGAG

4651 ATCGAGCTAG CTGATTGGAT GTACCGCGAG ATCACAGAAG
     GCAAGAACCC

4701 GGACGTGCTG ACGGTTCACC CCGATTACTT TTTGATCGAT
     CCCGGCATCG

4751 GCCGTTTTCT CTACCGCCTG GCACGCCGCG CCGCAGGCAA
     GGCAGAAGCC

4801 AGATGGTTGT TCAAGACGAT CTACGAACGC AGTGGCAGCG
     CCGGAGAGTT

4851 CAAGAAGTTC TGTTTCACCG TGCGCAAGCT GATCGGGTCA
     AATGACCTGC

4901 CGGAGTACGA TTTGAAGGAG GAGGCGGGGC AGGCTGGCCC
     GATCCTAGTC

4951 ATGCGCTACC GCAACCTGAT CGAGGGCGAA GCATCCGCCG
     GTTCCTAATG

5001 TACGGAGCAG ATGCTAGGGC AAATTGCCCT AGCAGGGGAA
     AAAGGTCGAA

5051 AAGGTCTCTT TCCTGTGGAT AGCACGTACA TTGGGAACCC
     AAAGCCGTAC

5101 ATTGGGAACC GGAACCCGTA CATTGGGAAC CCAAAGCCGT
     ACATTGGGAA

5151 CCGGTCACAC ATGTAAGTGA CTGATATAAA AGAGAAAAAA
     GGCGATTTTT

5201 CCGCCTAAAA CTCTTTAAAA CTTATTAAAA CTCTTAAAAC
     CCGCCTGGCC

5251 TGTGCATAAC TGTCTGGCCA GCGCACAGCC GAAGAGCTGC
     AAAAAGCGCC

5301 TACCCTTCGG TCGCTGCGCT CCCTACGCCC CGCCGCTTCG
     CGTCGGCCTA

5351 TCGCGGCCGC TGGCCGCTCA AAAATGGCTG GCCTACGGCC
     AGGCAATCTA

5401 CCAGGGCGCG GACAAGCCGC GCCGTCGCCA CTCGACCGCC
     GGCGCCCACA

5451 TCAAGGCACC CTGCCTCGCG CGTTTCGGTG ATGACGGTGA
     AAACCTCTGA

5501 CACATGCAGC TCCCGGAGAC GGTCACAGCT TGTCTGTAAG
     CGGATGCCGG

5551 GAGCAGACAA GCCCGTCAGG GCGCGTCAGC GGGTGTTGGC
     GGGTGTCGGG

5601 GCGCAGCCAT GACCCAGTCA CGTAGCGATA GCGGAGTGTA
     TACTGGCTTA

5651 ACTATGCGGC ATCAGAGCAG ATTGTACTGA GAGTGCACCA
     TATGCGGTGT
```

-continued

```
5701 GAAATACCGC ACAGATGCGT AAGGAGAAAA TACCGCATCA
     GGCGCTCTTC

5751 CGCTTCCTCG CTCACTGACT CGCTGCGCTC GGTCGTTCGG
     CTGCGGCGAG

5801 CGGTATCAGC TCACTCAAAG GCGGTAATAC GGTTATCCAC
     AGAATCAGGG

5851 GATAACGCAG GAAAGAACAT GTGAGCAAAA GGCCAGCAAA
     AGGCCAGGAA

5901 CCGTAAAAAG GCCGCGTTGC TGGCGTTTTT CCATAGGCTC
     CGCCCCCCTG

5951 ACGAGCATCA CAAAAATCGA CGCTCAAGTC AGAGGTGGCG
     AAACCCGACA

6001 GGACTATAAA GATACCAGGC GTTTCCCCCT GGAAGCTCCC
     TCGTGCGCTC

6051 TCCTGTTCCG ACCCTGCCGC TTACCGGATA CCTGTCCGCC
     TTTCTCCCTT

6101 CGGGAAGCGT GGCGCTTTCT CATAGCTCAC GCTGTAGGTA
     TCTCAGTTCG

6151 GTGTAGGTCG TTCGCTCCAA GCTGGGCTGT GTGCACGAAC
     CCCCCGTTCA

6201 GCCCGACCGC TGCGCCTTAT CCGGTAACTA TCGTCTTGAG
     TCCAACCCGG

6251 TAAGACACGA CTTATCGCCA CTGGCAGCAG CCACTGGTAA
     CAGGATTAGC

6301 AGAGCGAGGT ATGTAGGCGG TGCTACAGAG TTCTTGAAGT
     GGTGGCCTAA

6351 CTACGGCTAC ACTAGAAGGA CAGTATTTGG TATCTGCGCT
     CTGCTGAAGC

6401 CAGTTACCTT CGGAAAAAGA GTTGGTAGCT CTTGATCCGG
     CAAACAAACC

6451 ACCGCTGGTA GCGGTGGTTT TTTTGTTTGC AAGCAGCAGA
     TTACGCGCAG

6501 AAAAAAAGGA TCTCAAGAAG ATCCTTTGAT CTTTTCTACG
     GGGTCTGACG

6551 CTCAGTGGAA CGAAAACTCA CGTTAAGGGA TTTTGGTCAT
     GCATTCTAGG

6601 TACTAAAACA ATTCATCCAG TAAAATATAA TATTTTATTT
     TCTCCCAATC

6651 AGGCTTGATC CCCAGTAAGT CAAAAAATAG CTCGACATAC
     TGTTCTTCCC

6701 CGATATCCTC CCTGATCGAC CGGACGCAGA AGGCAATGTC
     ATACCACTTG

6751 TCCGCCCTGC CGCTTCTCCC AAGATCAATA AAGCCACTTA
     CTTTGCCATC

6801 TTTCACAAAG ATGTTGCTGT CTCCCAGGTC GCCGTGGGAA
     AAGACAAGTT

6851 CCTCTTCGGG CTTTTCCGTC TTTAAAAAAT CATACAGCTC
     GCGCGGATCT

6901 TTAAATGGAG TGTCTTCTTC CCAGTTTTCG CAATCCACAT
     CGGCCAGATC

6951 GTTATTCAGT AAGTAATCCA ATTCGGCTAA GCGGCTGTCT
     AAGCTATTCG

7001 TATAGGGACA ATCCGATATG TCGATGGAGT GAAAGAGCCT
     GATGCACTCC
```

-continued

```
7051 GCATACAGCT CGATAATCTT TTCAGGGCTT TGTTCATCTT
     CATACTCTTC

7101 CGAGCAAAGG ACGCCATCGG CCTCACTCAT GAGCAGATTG
     CTCCAGCCAT

7151 CATGCCGTTC AAAGTGCAGG ACCTTTGGAA CAGGCAGCTT
     TCCTTCCAGC

7201 CATAGCATCA TGTCCTTTTC CCGTTCCACA TCATAGGTGG
     TCCCTTTATA

7251 CCGGCTGTCC GTCATTTTTA AATATAGGTT TTCATTTTCT
     CCCACCAGCT

7301 TATATACCTT AGCAGGAGAC ATTCCTTCCG TATCTTTTAC
     GCAGCGGTAT

7351 TTTTCGATCA GTTTTTTCAA TTCCGGTGAT ATTCTCATTT
     TAGCCATTTA

7401 TTATTTCCTT CCTCTTTTCT ACAGTATTTA AAGATACCCC
     AAGAAGCTAA

7451 TTATAACAAG ACGAACTCCA ATTCACTGTT CCTTGCATTC
     TAAAACCTTA

7501 AATACCAGAA AACAGCTTTT TCAAAGTTGT TTTCAAAGTT
     GGCGTATAAC

7551 ATAGTATCGA CGGAGCCGAT TTTGAAACCG CGGTGATCAC
     AGGCAGCAAC

7601 GCTCTGTCAT CGTTACAATC AACATGCTAC CCTCCGCGAG
     ATCATCCGTG

7651 TTTCAAACCC GGCAGCTTAG TTGCCGTTCT TCCGAATAGC
     ATCGGTAACA

7701 TGAGCAAAGT CTGCCGCCTT ACAACGGCTC TCCCGCTGAC
     GCCGTCCCGG

7751 ACTGATGGGC TGCCTGTATC GAGTGGTGAT TTTGTGCCGA
     GCTGCCGGTC

7801 GGGGAGCTGT TGGCTGGCTG GTGGCAGGAT ATATTGTGGT
     GTAAACAAAT

7851 TGACGCTTAG ACAACTTAAT AACACATTGC GGACGTTTTT
     AATGTACTGA

7901 ATTAACGCCG AATTAATTCC TAGGCCACCA TGTTGGGCCC
     GGGGCGCGCC

7951 GTACGTAGTG TTTATCTTTG TTGCTTTTCT GAACAATTTA
     TTTACTATGT

8001 AAATATATTA TCAATGTTTA ATCTATTTTA ATTTGCACAT
     GAATTTTCAT

8051 TTTATTTTTA CTTTACAAAA CAAATAAATA TATATGCAAA
     AAAATTTACA

8101 AACGATGCAC GGGTTACAAA CTAATTTCAT TAAATGCTAA
     TGCAGATTTT

8151 GTGAAGTAAA ACTCCAATTA TGATGAAAAA TACCACCAAC
     ACCACCTGCG

8201 AAACTGTATC CCAACTGTCC TTAATAAAAA TGTTAAAAAG
     TATATTATTC

8251 TCATTTGTCT GTCATAATTT ATGTACCCCA CTTTAATTTT
     TCTGATGTAC

8301 TAAACCGAGG GCAAACTGAA ACCTGTTCCT CATGCAAAGC
     CCCTACTCAC

8351 CATGTATCAT GTACGTGTCA TCACCCAACA ACTCCACTTT
     TGCTATATAA
```

-continued

8401 CAACACCCCC GTCACACTCT CCCTCTCTAA CACACACCCC ACTAACAATT

8451 CCTTCACTTG CAGCACTGTT GCATCATCAT CTTCATTGCA AAACCCTAAA

8501 CTTCACCTTC AACCGCGGCC GCATGGCTTC TATGATATCC TCTTCCGCTG

8551 TGACAACAGT CAGCCGTGCC TCTAGGGGGC AATCCGCCGC AGTGGCTCCA

8601 TTCGGCGGCC TCAAATCCAT GACTGGATTC CCAGTGAAGA AGGTCAACAC

8651 TGACATTACT TCCATTACAA GCAATGGTGG AAGAGTAAAG TGCATGCAGG

8701 TGTGGCCTCC AATTGGAAAG AAGAAGTTTG AGACTCTTTC CTATTTGCCA

8751 CCATTGACGA GAGATTCTAG AGTGAGTAAC AAGAACAACG ATGAGCTGCA

8801 GTGGCAATCC TGGTTCAGCA AGGCGCCCAC CACCGAGGCG AACCCGATGG

8851 CCACCATGTT GCAGGATATC GGCGTTGCGC TCAAACCGGA AGCGATGGAG

8901 CAGCTGAAAA ACGATTATCT GCGTGACTTC ACCGCGTTGT GGCAGGATTT

8951 TTTGGCTGGC AAGGCGCCAG CCGTCAGCGA CCGCCGCTTC AGCTCGGCAG

9001 CCTGGCAGGG CAATCCGATG TCGGCCTTCA ATGCCGCATC TTACCTGCTC

9051 AACGCCAAAT TCCTCAGTGC CATGGTGGAG GCGGTGGACA CCGCACCCCA

9101 GCAAAAGCAG AAAATACGCT TTGCCGTGCA GCAGGTGATT GATGCCATGT

9151 CGCCCGCGAA CTTCCTCGCC ACCAACCCGG AAGCGCAGCA AAAACTGATT

9201 GAAACCAAGG GCGAGAGCCT GACGCGTGGC CTGGTCAATA TGCTGGGCGA

9251 TATCAACAAG GGCCATATCT CGCTGTCGGA CGAATCGGCC TTTGAAGTGG

9301 GCCGCAACCT GGCCATTACC CCGGGCACCG TGATTTACGA AAATCCGCTG

9351 TTCCAGCTGA TCCAGTACAC GCCGACCACG CCGACGGTCA GCCAGCGCCC

9401 GCTGTTGATG GTGCCGCCGT GCATCAACAA GTTCTACATC CTCGACCTGC

9451 AACCGGAAAA TTCGCTGGTG CGCTACGCGG TGGAGCAGGG CAACACCGTG

9501 TTCCTGATCT CGTGGAGCAA TCCGGACAAG TCGCTGGCCG GCACCACCTG

9551 GGACGACTAC GTGGAGCAGG GCGTGATCGA AGCGATCCGC ATCGTCCAGG

9601 ACGTCAGCGG CCAGGACAAG CTGAACATGT TCGGCTTCTG CGTGGGCGGC

9651 ACCATCGTTG CCACCGCACT GGCGGTACTG GCGGCGCGTG GCCAGCACCC

9701 GGCGGCCAGC CTGACCCTGC TGACCACCTT CCTCGACTTC AGCGACACCG

-continued

9751 GCGTGCTCGA CGTCTTCGTC GATGAAACCC AGGTCGCGCT GCGTGAACAG

9801 CAATTGCGCG ATGGCGGCCT GATGCCGGGC CGTGACCTGG CCTCGACCTT

9851 CTCGAGCCTG CGTCCGAACG ACCTGGTATG GAACTATGTG CAGTCGAACT

9901 ACCTCAAAGG CAATGAGCCG GCGGCGTTTG ACCTGCTGTT CTGGAATTCG

9951 GACAGCACCA ATTTGCCGGG CCCGATGTTC TGCTGGTACC TGCGCAACAC

10001 CTACCTGGAA AACAGCCTGA AAGTGCCGGG CAAGCTGACG GTGGCCGGCG

10051 AAAAGATCGA CCTCGGCCTG ATCGACGCCC CGGCCTTCAT CTACGGTTCG

10101 CGCGAAGACC ACATCGTGCC GTGGATGTCG GCGTACGGTT CGCTCGACAT

10151 CCTCAACCAG GGCAAGCCGG GCGCCAACCG CTTCGTGCTG GGCGCGTCCG

10201 GCCATATCGC CGGCGTGATC AACTCGGTGG CCAAGAACAA GCGCAGCTAC

10251 TGGATCAACG ACGGTGGCGC CGCCGATGCC CAGGCCTGGT TCGATGGCGC

10301 GCAGGAAGTG CCGGGCAGCT GGTGGCCGCA ATGGGCCGGG TTCCTGACCC

10351 AGCATGGCGG CAAGAAGGTC AAGCCCAAGG CCAAGCCCGG CAACGCCCGC

10401 TACACCGCGA TCGAGGCGGC GCCCGGCCGT TACGTCAAAG CCAAGGGCTG

10451 AGCGGCCGCT GAGTAATTCT GATATTAGAG GGAGCATTAA TGTGTTGTTG

10501 TGATGTGGTT TATATGGGGA AATTAAATAA ATGATGTATG TACCTCTTGC

10551 CTATGTAGGT TTGTGTGTTT TGTTTTGTTG TCTAGCTTTG GTTATTAAGT

10601 AGTAGGGACG TTCGTTCGTG TCTCAAAAAA AGGGGTACTA CCACTCTGTA

10651 GTGTATATGG ATGCTGGAAA TCAATGTGTT TTGTATTTGT TCACCTCCAT

10701 TGTTGAATTC AATGTCAAAT GTGTTTTGCG TTGGTTATGT GTAAAATTAC

10751 TATCTTTCTC GTCCGATGAT CAAAGTTTTA AGCAACAAAA CCAAGGGTGA

10801 AATTTAAACT GTGCTTTGTT GAAGATTCTT TTATCATATT GAAAATCAAA

10851 TTACTAGCAG CAGATTTTAC CTAGCATGAA ATTTTATCAA CAGTACAGCA

10901 CTCACTAACC AAGTTCCAAA CTAAGATGCG CCATTAACAT CAGCCAATAG

10951 GCATTTTCAG CAAGGCGCGC CCGCGCCGAT GTATGTGACA ACCCTCGGGA

11001 TTGTTGATTT ATTTCAAAAC TAAGAGTTTT TGTCTTATTG TTCTCGTCTA

11051 TTTTGGATAT CAATCTTAGT TTTATATCTT TTCTAGTTCT CTACGTGTTA

-continued

11101 AATGTTCAAC ACACTAGCAA TTTGGCCTGC CAGCGTATGG ATTATGGAAC

11151 TATCAAGTCT GTGACGCGCC GTACGTAGTG TTTATCTTTG TTGCTTTTCT

11201 GAACAATTTA TTTACTATGT AAATATATTA TCAATGTTTA ATCTATTTTA

11251 ATTTGCACAT GAATTTTCAT TTTATTTTTA CTTTACAAAA CAAATAAATA

11301 TATATGCAAA AAAATTTACA AACGATGCAC GGGTTACAAA CTAATTTCAT

11351 TAAATGCTAA TGCAGATTTT GTGAAGTAAA ACTCCAATTA TGATGAAAAA

11401 TACCACCAAC ACCACCTGCG AAACTGTATC CCAACTGTCC TTAATAAAAA

11451 TGTTAAAAAG TATATTATTC TCATTTGTCT GTCATAATTT ATGTACCCCA

11501 CTTTAATTTT TCTGATGTAC TAAACCGAGG GCAAACTGAA ACCTGTTCCT

11551 CATGCAAAGC CCCTACTCAC CATGTATCAT GTACGTGTCA TCACCCAACA

11601 ACTCCACTTT TGCTATATAA CAACACCCCC GTCACACTCT CCCTCTCTAA

11651 CACACACCCC ACTAACAATT CCTTCACTTG CAGCACTGTT GCATCATCAT

11701 CTTCATTGCA AAACCCTAAA CTTCACCTTC AACCGCGGCC GCATGGCTTC

11751 TATGATATCC TCTTCCGCTG TGACAACAGT CAGCCGTGCC TCTAGGGGGC

11801 AATCCGCCGC AGTGGCTCCA TTCGGCGGCC TCAAATCCAT GACTGGATTC

11851 CCAGTGAAGA AGGTCAACAC TGACATTACT TCCATTACAA GCAATGGTGG

11901 AAGAGTAAAG TGCATGCAGG TGTGGCCTCC AATTGGAAAG AAGAAGTTTG

11951 AGACTCTTTC CTATTTGCCA CCATTGACGA GAGATTCTAG AGTGACTCAG

12001 CGCATTGCGT ATGTGACCGG CGGCATGGGT GGTATCGGAA CCGCCATTTG

12051 CCAGCGGCTG GCCAAGGATG GCTTTCGTGT GGTGGCCGGT TGCGGCCCCA

12101 ACTCGCCGCG CCGCGAAAAG TGGCTGGAGC AGCAGAAGGC CCTGGGCTTC

12151 GATTTCATTG CCTCGGAAGG CAATGTGGCT GACTGGGACT CGACCAAGAC

12201 CGCATTCGAC AAGGTCAAGT CCGAGGTCGG CGAGGTTGAT GTGCTGATCA

12251 ACAACGCCGG TATCACCCGC GACGTGGTGT TCCGCAAGAT GACCCGCGCC

12301 GACTGGGATG CGGTGATCGA CACCAACCTG ACCTCGCTGT TCAACGTCAC

12351 CAAGCAGGTG ATCGACGGCA TGGCCGACCG TGGCTGGGGC CGCATCGTCA

12401 ACATCTCGTC GGTGAACGGG CAGAAGGGCC AGTTCGGCCA GACCAACTAC

12451 TCCACCGCCA AGGCCGGCCT GCATGGCTTC ACCATGGCAC TGGCGCAGGA

12501 AGTGGCGACC AAGGGCGTGA CCGTCAACAC GGTCTCTCCG GGCTATATCG

12551 CCACCGACAT GGTCAAGGCG ATCCGCCAGG ACGTGCTCGA CAAGATCGTC

12601 GCGACGATCC CGGTCAAGCG CCTGGGCCTG CCGGAAGAGA TCGCCTCGAT

12651 CTGCGCCTGG TTGTCGTCGG AGGAGTCCGG TTTCTCGACC GGCGCCGACT

12701 TCTCGCTCAA CGGCGGCCTG CATATGGGCT GAGCGGCCGC TGAGTAATTC

12751 TGATATTAGA GGGAGCATTA ATGTGTTGTT GTGATGTGGT TTATATGGGG

12801 AAATTAAATA AATGATGTAT GTACCTCTTG CCTATGTAGG TTTGTGTGTT

12851 TTGTTTTGTT GTCTAGCTTT GGTTATTAAG TAGTAGGGAC GTTCGTTCGT

12901 GTCTCAAAAA AAGGGGTACT ACCACTCTGT AGTGTATATG GATGCTGGAA

12951 ATCAATGTGT TTTGTATTTG TTCACCTCCA TTGTTGAATT CAATGTCAAA

13001 TGTGTTTTGC GTTGGTTATG TGTAAAATTA CTATCTTTCT CGTCCGATGA

13051 TCAAAGTTTT AAGCAACAAA ACCAAGGGTG AAATTTAAAC TGTGCTTTGT

13101 TGAAGATTCT TTTATCATAT TGAAAATCAA ATTACTAGCA GCAGATTTTA

13151 CCTAGCATGA AATTTTATCA ACAGTACAGC ACTCACTAAC CAAGTTCCAA

13201 ACTAAGATGC GCCATTAACA TCAGCCAATA GGCATTTTCA GCAAGGCGCG

13251 TAAGGGGATC CGTACGTAAG TACGTACTCA AAATGCCAAC AAATAAAAAA

13301 AAAGTTGCTT TAATAATGCC AAAACAAATT AATAAAACAC TTACAACACC

13351 GGATTTTTTT TAATTAAAAT GTGCCATTTA GGATAAATAG TTAATATTTT

13401 TAATAATTAT TTAAAAAGCC GTATCTACTA AAATGATTTT TATTTGGTTG

13451 AAAATATTAA TATGTTTAAA TCAACACAAT CTATCAAAAT TAAACTAAAA

13501 AAAAAATAAG TGTACGTGGT TAACATTAGT ACAGTAATAT AAGAGGAAAA

13551 TGAGAAATTA AGAAATTGAA AGCGAGTCTA ATTTTTAAAT TATGAACCTG

13601 CATATATAAA AGGAAAGAAA GAATCCAGGA AGAAAAGAAA TGAAACCATG

13651 CATGGTCCCC TCGTCATCAC GAGTTTCTGC CATTTGCAAT AGAAACACTG

13701 AAACACCTTT CTCTTTGTCA CTTAATTGAG ATGCCGAAGC CACCTCACAC

13751 CATGAACTTC ATGAGGTGTA GCACCCAAGG CTTCCATAGC CATGCATACT

-continued

13801 GAAGAATGTC TCAAGCTCAG CACCCTACTT CTGTGACGTG TCCCTCATTC

13851 ACCTTCCTCT CTTCCCTATA AATAACCACG CCTCAGGTTC TCCGCTTCAC

13901 AACTCAAACA TTCTCTCCAT TGGTCCTTAA ACACTCATCA GTCATCACCG

13951 CGGCCGCGGA ATTCATGGCT TCTATGATAT CCTCTTCCGC TGTGACAACA

14001 GTCAGCCGTG CCTCTAGGGG GCAATCCGCC GCAGTGGCTC CATTCGGCGG

14051 CCTCAAATCC ATGACTGGAT TCCCAGTGAA GAAGGTCAAC ACTGACATTA

14101 CTTCCATTAC AAGCAATGGT GGAAGAGTAA AGTGCATGCA GGTGTGGCCT

14151 CCAATTGGAA AGAAGAAGTT TGAGACTCTT TCCTATTTGC CACCATTGAC

14201 GAGAGATTCT AGAGTGACTG ACGTTGTCAT CGTATCCGCC GCCCGCACCG

14251 CGGTCGGCAA GTTTGGCGGC TCGCTGGCCA AGATCCCGGC ACCGGAACTG

14301 GGTGCCGTGG TCATCAAGGC CGCGCTGGAG CGCGCCGGCG TCAAGCCGGA

14351 GCAGGTGAGC GAAGTCATCA TGGGCCAGGT GCTGACCGCC GGTTCGGGCC

14401 AGAACCCCGC ACGCCAGGCC GCGATCAAGG CCGGCCTGCC GGCGATGGTG

14451 CCGGCCATGA CCATCAACAA GGTGTGCGGC TCGGGCCTGA AGGCCGTGAT

14501 GCTGGCCGCC AACGCGATCA TGGCGGGCGA CGCCGAGATC GTGGTGGCCG

14551 GCGGCCAGGA AAACATGAGC GCCGCCCCGC ACGTGCTGCC GGGCTCGCGC

14601 GATGGTTTCC GCATGGGCGA TGCCAAGCTG GTCGACACCA TGATCGTCGA

14651 CGGCCTGTGG GACGTGTACA ACCAGTACCA CATGGGCATC ACCGCCGAGA

14701 ACGTGGCCAA GGAATACGGC ATCACACGCG AGGCGCAGGA TGAGTTCGCC

14751 GTCGGCTCGC AGAACAAGGC CGAAGCCGCG CAGAAGGCCG GCAAGTTTGA

14801 CGAAGAGATC GTCCCGGTGC TGATCCCGCA GCGCAAGGGC GACCCGGTGG

14851 CCTTCAAGAC CGACGAGTTC GTGCGCCAGG GCGCCACGCT GGACAGCATG

14901 TCCGGCCTCA AGCCCGCCTT CGACAAGGCC GGCACGGTGA CCGCGGCCAA

14951 CGCCTCGGGC CTGAACGACG GCGCCGCCGC GGTGGTGGTG ATGTCGGCGG

15001 CCAAGGCCAA GGAACTGGGC CTGACCCCGC TGGCCACGAT CAAGAGCTAT

15051 GCCAACGCCG GTGTCGATCC CAAGGTGATG GGCATGGGCC CGGTGCCGGC

15101 CTCCAAGCGC GCCCTGTCGC GCGCCGAGTG GACCCCGCAA GACCTGGACC

15151 TGATGGAGAT CAACGAGGCC TTTGCCGCGC AGGCGCTGGC GGTGCACCAG

15201 CAGATGGGCT GGGACACCTC CAAGGTCAAT GTGAACGGCG GCGCCATCGC

15251 CATCGGCCAC CCGATCGGCG CGTCGGGCTG CCGTATCCTG GTGACGCTGC

15301 TGCACGAGAT GAAGCGCCGT GACGCGAAGA AGGGCCTGGC CTCGCTGTGC

15351 ATCGGCGGCG GCATGGGCGT GGCGCTGGCA GTCGAGCGCA AATAACTCGA

15401 GGCGGCCGCA GCCCTTTTTG TATGTGCTAC CCCACTTTTG TCTTTTTGGC

15451 AATAGTGCTA GCAACCAATA AATAATAATA ATAATAATGA ATAAGAAAAC

15501 AAAGGCTTTA GCTTGCCTTT TGTTCACTGT AAAATAATAA TGTAAGTACT

15551 CTCTATAATG AGTCACGAAA CTTTTGCGGG AATAAAAGGA GAAATTCCAA

15601 TGAGTTTTCT GTCAAATCTT CTTTTGTCTC TCTCTCTCTC TCTTTTTTTT

15651 TTTTCTTTCT TCTGAGCTTC TTGCAAAACA AAAGGCAAAC AATAACGATT

15701 GGTCCAATGA TAGTTAGCTT GATCGATGAT ATCTTTAGGA AGTGTTGGCA

15751 GGACAGGACA TGATGTAGAA GACTAAAATT GAAAGTATTG CAGACCCAAT

15801 AGTTGAAGAT TAACTTTAAG AATGAAGACG TCTTATCAGG TTCTTCATGA

15851 CTTAAGCTTT AAGAGGAGTC CACCATGGTA GATCTGACTA GTGATCCGTA

15901 CGTAAGTACG TACTCAAAAT GCCAACAAAT AAAAAAAAAG TTGCTTTAAT

15951 AATGCCAAAA CAAATTAATA AAACACTTAC AACACCGGAT TTTTTTTAAT

16001 TAAAATGTGC CATTTAGGAT AAATAGTTAA TATTTTTAAT AATTATTTAA

16051 AAAGCCGTAT CTACTAAAAT GATTTTTATT TGGTTGAAAA TATTAATATG

16101 TTTAAATCAA CACAATCTAT CAAAATTAAA CTAAAAAAAA AATAAGTGTA

16151 CGTGGTTAAC ATTAGTACAG TAATATAAGA GGAAAATGAG AAATTAAGAA

16201 ATTGAAAGCG AGTCTAATTT TTAAATTATG AACCTGCATA TATAAAAGGA

16251 AAGAAAGAAT CCAGGAAGAA AAGAAATGAA ACCATGCATG GTCCCCTCGT

16301 CATCACGAGT TTCTGCCATT TGCAATAGAA ACACTGAAAC ACCTTTCTCT

16351 TTGTCACTTA ATTGAGATGC CGAAGCCACC TCACACCATG AACTTCATGA

16401 GGTGTAGCAC CCAAGGCTTC CATAGCCATG CATACTGAAG AATGTCTCAA

16451 GCTCAGCACC CTACTTCTGT GACGTGTCCC TCATTCACCT TCCTCTCTTC

-continued

16501 CCTATAAATA ACCACGCCTC AGGTTCTCCG CTTCACAACT CAAACATTCT

16551 CTCCATTGGT CCTTAAACAC TCATCAGTCA TCACCATGGA CTCCAAAGAA

16601 TCATTAACTC CTGGTAGAGA AGAAAACCCC AGCAGTGTGC TTGCTCAGGA

16651 GAGGGGAGAT GTGATGGACT TCTATAAAAC CCTAAGAGGA GGAGCTACTG

16701 TGAAGGTTTC TGCGTCTTCA CCCTCACTGG CTGTCGCTTC TCAATCAGAC

16751 TCCAAGCAGC GAAGACTTTT GGTTGATTTT CCAAAAGGCT CAGTAAGCAA

16801 TGCGCAGCAG CCAGATCTGT CCAAAGCAGT TTCACTCTCA ATGGGACTGT

16851 ATATGGGAGA GACAGAAACA AAAGTGATGG GAAATGACCT GGGATTCCCA

16901 CAGCAGGGCC AAATCAGCCT TTCCTCGGGG GAAACAGACT TAAAGCTTTT

16951 GGAAGAAAGC ATTGCAAACC TCAATAGGTC GACCAGTGTT CCAGAGAACC

17001 CCAAGAGTTC AGCATCCACT GCTGTGTCTG CTGCCCCCAC AGCTAGTTCT

17051 GCGGCCCCCC CGACCGATGT CAGCCTGGGG GACGAGCTCC ACTTAGACGG

17101 CGAGGACGTG GCGATGGCGC ATGCCGACGC GCTAGACGAT TTCGATCTGG

17151 ACATGTTGGG GGACGGGGAT TCCCCGGGTC CGGGATTTAC CCCCCACGAC

17201 TCCGCCCCCT ACGGCGCTCT GGATATGGCC GACTTCGAGT TTGAGCAGAT

17251 GTTTACCGAT GCCCTTGGAA TTGACGAGTA CGGTGGGACT AGCTCCAGCT

17301 CCTCAACAGC AACAACAGGA CCACCTCCCA AACTCTGCCT GGTGTGCTCT

17351 GATGAAGCTT CAGGATGTCA TTATGGAGTC TTAACTTGTG GAAGCTGTAA

17401 AGTTTTCTTC AAAAGAGCAG TGGAAGGACA GCACAATTAC CTATGTGCTG

17451 GAAGGAATGA TTGCATCATC GATAAAATTC GAAGAAAAAA CTGCCCAGCA

17501 TGCCGCTATC GAAAATGTCT TCAGGCTGGA ATGAACCTGG AAGCTCGAAA

17551 AACAAAGAAA AAAATAAAAG GAATTGCTCG ACAAAGGCCC GAGTGCGTGG

17601 TGCCGGAGAA CCAGTGTGCA ATGAAACGGA AAGAGAAAAA GGCGCAGAGG

17651 GAAAAAGACA AATTGCCCGT CAGTACGACG ACAGTAGACG ATCACATGCC

17701 TCCCATCATG CAATGTGACC CTCCGCCCCC AGAGGCCGCT AGAATTCTGG

17751 AATGTTTGCA GCACGAGGTG GTGCCACGAT TCCTGAATGA GAAGCTAATG

17801 GAACAGAACA GATTGAAGAA CGTGCCCCCC CTCACTGCCA ATCAGAAGTC

17851 GTTGATCGCA AGGCTCGTGT GGTACCAGGA AGGCTATGAA CAACCTTCCG

17901 AGGAAGACCT GAAGAGGGTT ACACAGTCGG ACGAGGACGA CGAAGACTCG

17951 GATATGCCGT TCCGTCAGAT TACCGAGATG ACGATTCTCA CAGTGCAGCT

18001 CATCGTAGAA TTCGCTAAGG GCCTCCCGGG CTTCGCCAAG ATCTCGCAGT

18051 CGGACCAGAT CACGTTATTA AAGGCGTGCT CAAGTGAGGT GATGATGCTC

18101 CGAGTGGCTC GGCGGTATGA CGCGGCCACC GACAGCGTAC TGTTCGCGAA

18151 CAACCAGGCG TACACTCGCG ACAACTACCG CAAGGCAGGC ATGGCGTACG

18201 TCATCGAGGA CCTGCTGCAC TTCTGTCGGT GCATGTACTC CATGATGATG

18251 GATAACGTGC ATTATGCGCT GCTTACAGCC ATTGTCATCT TCTCAGACCG

18301 GCCCGGGCTT GAGCAACCCC TGTTGGTGGA GGAGATCCAG AGATATTACC

18351 TGAACACGCT ACGGGTGTAC ATCCTGAACC AGAACAGCGC GTCGCCCCGC

18401 TGCGCCGTCA TCTTCGGCAA GATCCTGGGC ATACTGACGG AGATCCGCAC

18451 GCTGGGCATG CAGAACTCCA ACATGTGCAT CTCCCTCAAG CTGAAGAACA

18501 GGAAGCTGCC GCCGTTCCTC GAGGAGATCT GGGACGTGGC GGACGTGGCG

18551 ACGACGGCGA CGCCGGTGGC GGCGGAGGCG CCGGCGCTCT AGCCCCCGCG

18601 CCGCCCGCCC GGCCGCGCGC ACGTCTAGCG CGCCTCAGGA GAGAACGCTC

18651 ATAGACTGGC TAGTTTTAGT GAAGTGCACG GACACTGACG TCGGACGTGA

18701 TCAACCTATT TATAAGGACT GCGAATTTTA CCACTTAAGA GGGCACACCC

18751 GTACCCGATT TCGTACGGGA ATTCCTGCAG CCCGGGGGAT CCTTAATTAA

18801 CTCGAGGAAT TCATCGATTC CGCGGGTACC GAGCTCGATC CGTCGACCTG

18851 CAGATCGTTC AAACATTTGG CAATAAAGTT TCTTAAGATT GAATCCTGTT

18901 GCCGGTCTTG CGATGATTAT CATATAATTT CTGTTGAATT AGGTTAAGCA

18951 TGTAATAATT AACATGTAAT GCATGACGTT ATTTATGAGA TGGGTTTTTA

19001 TGATTAGAGT CCCGCAATTA TACATTTAAT ACGCGATAGA AAACAAAATA

19051 TAGCGCGCAA ACTAGGATAA ATTATCGCGC GCGGTGTCAT CTATGTTACT

19101 AGATCTGGCG CGCCCCTAGG TCTAGAGTCG ACTGTTTAAA CGGTCCGTGA

19151 CCATGATTAC GCCAAGCTTC GACTGTACAG GATGTTCTAG CTACTCGAGT

-continued

19201 AGCTAGAACA TCCTGTACAG TCGAGTAGCT AGAACATCCT GTACAGTCGA

19251 CTAGCTAGAA CATCCTGTAC AGTCGAGTAG CTAGAACATC CTGTACAGTC

19301 GAGTAGCTAG ACATCCTGTA CAGGATCCCT ATATAAGGAA GTTCATTTCA

19351 TTTGGAGAGA ACACGGGGGA TCGGGTATCG TTAATTAAGT TTATCAACAA

19401 GTTTGTACAA AAAAGCAGGC TCCGCGGCCG CCCCCTTCAC CATGATCGTC

19451 GACGGCCTGT GGGACGTGTA CAACCAGTAC CACATGGGCA TCACCGCCGA

19501 GAACGTGGCC AAGGAATACG GCATCACACG CGAGGCGCAG GATGAGTTCG

19551 CCGTCGGCTC GCAGAACAAG GCCGAAGCCG CGCAGAAGGC CGGCAAGTTT

19601 GACGAAGAGA TCGTCCCGGT GCTGATCCCG CAGCGCAAGG GCGACCCGGT

19651 GGCCTTCAAG ACCGACGAGT TCGTGCGCCA GGGCGCCACG CTGGACAGCA

19701 TGTCCGGCCT CAAGCCCGCC TTCGACAAGG CCGGCACGGT GACCGCGGCC

19751 AACGCCTCGG GCCTGAACGA CGGCGCCGCC GCGGTGGTGG TGATGTCGGC

19801 GGCCAAGGCC AAGGAACTGG GCCTGACCCC GCTGGCCACG ATCAAGAGCT

19851 ATGCCAACGC CGGTGTCGAT CCCAAGGTGA TGGGCATGGG CCCGGTGCCG

19901 GCCTCCAAGC GCGCCCTGTC GCGCGCCGAG TGGACCCCGC AAGACCTGGA

19951 CCTGATGGAG ATCAACGAGG CCTTTGCCGC GCAGGCGCTG GCGGTGCACC

20001 AGCAGATGGG CTGGGACACC TCCAAGGTCA ATGTGAAAGG GTGGGCGCGC

20051 CGACCCAGCT TTCTTGTACA AAGTGGTTGA TCCTGCAGGG TCCGTCGCTT

20101 CTCTTCCATT TCTTCTCATT TTCGATTTTG ATTCTTATTT CTTTCCAGTA

20151 GCTCCTGCTC TGTGAATTTC TCCGCTCACG ATAGATCTGC TTATACTCCT

20201 TACATTCAAC CTTAGATCTG GTCTCGATTC TCTGTTTCTC TGTTTTTTTC

20251 TTTTGGTCGA GAATCTGATG TTTGTTTATG TTCTGTCACC ATTAATAATA

20301 ATGAACTCTC TCATTCATAC AATGATTAGT TTCTCTCGTC TACAAAACGA

20351 TATGTTGCAT TTTCACTTTT CTTCTTTTTT TCTAAGATGA TTTGCTTTGA

20401 CCAATTTGTT TAGATCTTTA TTCTATTTTA TTTTCTGGTG GGTTGGTGGA

20451 AATTGAAAAA AAAAAAACAG CATAAATTGT TATTTGTTAA TGTATTCATT

20501 TTTTGGCTAT TTGTTCTGGG TAAAAATCTG CTTCTACTAT TGAATCTTTC

-continued

20551 CTGGATTTTT TACTCCTATT GGGTTTTTAT AGTAAAAATA CATAATAAAA

20601 GGAAAACAAA AGTTTTATAG ATTCTCTTAA ACCCCTTACG ATAAAAGTTG

20651 GAATCAAAAT AATTCAGGAT CAGATGCTCT TTGATTGATT CAGATGCGAT

20701 TACAGTTGCA TGGCAAATTT TCTAGATCCG TCGTCACATT TTATTTTCTG

20751 TTTAAATATC TAAATCTGAT ATATGATGTC GACAAATTCT GGTGGCTTAT

20801 ACATCACTTC AACTGTTTTC TTTTGGCTTT GTTTGTCAAC TTGGTTTTCA

20851 ATACGATTTG TGATTTCGAT CGCTGAATTT TTAATACAAG CAAACTGATG

20901 TTAACCACAA GCAAGAGATG TGACCTGCCT TATTAACATC GTATTACTTA

20951 CTACTAGTCG TATTCTCAAC GCAATCGTTT TTGTATTTCT CACATTATGC

21001 CGCTTCTCTA CTCTTTATTC CTTTTGGTCC ACGCATTTTC TATTTGTGGC

21051 AATCCCTTTC ACAACCTGAT TTCCCACTTT GGATCATTTG TCTGAAGACT

21101 CTCTTGAATC GTTACCACTT GTTTCTTGTG CATGCTCTGT TTTTTAGAAT

21151 TAATGATAAA ACTATTCCAT AGTCTTGAGT TTTCAGCTTG TTGATTCTTT

21201 TGCTTTTGGT TTTCTGCAGG TTTAAACATC AACCACTTTG TACAAGAAAG

21251 CTGGGTCGGC GCGCCCACCC TTTCACATTG ACCTTGGAGG TGTCCCAGCC

21301 CATCTGCTGG TGCACCGCCA GCGCCTGCGC GGCAAAGGCC TCGTTGATCT

21351 CCATCAGGTC CAGGTCTTGC GGGGTCCACT CGGCGCGCGA CAGGGCGCGC

21401 TTGGAGGCCG GCACCGGGCC CATGCCCATC ACCTTGGGAT CGACACCGGC

21451 GTTGGCATAG CTCTTGATCG TGGCCAGCGG GGTCAGGCCC AGTTCCTTGG

21501 CCTTGGCCGC CGACATCACC ACCACCGCGG CGGCGCCGTC GTTCAGGCCC

21551 GAGGCGTTGG CCGCGGTCAC CGTGCCGGCC TTGTCGAAGG CGGGCTTGAG

21601 GCCGGACATG CTGTCCAGCG TGGCGCCCTG GCGCACGAAC TCGTCGGTCT

21651 TGAAGGCCAC CGGGTCGCCC TTGCGCTGCG GGATCAGCAC CGGGACGATC

21701 TCTTCGTCAA ACTTGCCGGC CTTCTGCGCG GCTTCGGCCT TGTTCTGCGA

21751 GCCGACGGCG AACTCATCCT GCGCCTCGCG TGTGATGCCG TATTCCTTGG

21801 CCACGTTCTC GGCGGTGATG CCCATGTGGT ACTGGTTGTA CACGTCCCAC

21851 AGGCCGTCGA CGATCATGGT GAAGGGGGCG GCCGCGGAGC CTGCTTTTTT

-continued

21901 GTACAAACTT GTTGATCTCG AGCGGCGCGC CGTTCGAGTA TTATGGCATT

21951 GGGAAAACTG TTTTTCTTGT ACCATTTGTT GTGCTTGTAA TTTACTGTGT

22001 TTTTTATTCG GTTTTCGCTA TCGAACTGTG AAATGGAAAT GGATGGAGAA

22051 GAGTTAATGA ATGATATGGT CCTTTTGTTC ATTCTCAAAT TAATATTATT

22101 TGTTTTTTCT CTTATTTGTT GTGTGTTGAA TTTGAAATTA TAAGAGATAT

22151 GCAAACATTT TGTTTTGAGT AAAAATGTGT CAAATCGTGG CCTCTAATGA

22201 CCGAAGTTAA TATGAGGAGT AAAACACTGT TTAAACCCTG CAGGATTT

Vector: pPhaC-RNAi/glyP (SEQ ID NO: 6)

1 GTCCGTGACC ATGATTACGC CAAGCTTCGA CTGTACAGGA TGTTCTAGCT

51 ACTCGAGTAG CTAGAACATC CTGTACAGTC GAGTAGCTAG AACATCCTGT

101 ACAGTCGACT AGCTAGAACA TCCTGTACAG TCGAGTAGCT AGAACATCCT

151 GTACAGTCGA GTAGCTAGAC ATCCTGTACA GGATCCCTAT ATAAGGAAGT

201 TCATTTCATT TGGAGAGAAC ACGGGGGATC GGGTATCGTT AATTAAGTTT

251 ATCAACAAGT TTGTACAAAA AAGCAGGCTC CGCGGCCGCC CCCTTCACCT

301 TCCTCGACTT CAGCGACACC GGCGTGCTCG ACGTCTTCGT CGATGAAACC

351 CAGGTCGCGC TGCGTGAACA GCAATTGCGC GATGGCGGCC TGATGCCGGG

401 CCGTGACCTG GCCTCGACCT TCTCGAGCCT GCGTCCGAAC GACCTGGTAT

451 GGAACTATGT GCAGTCGAAC TACCTCAAAG GCAATGAGCC GGCGGCGTTT

501 GACCTGCTGT TCTGGAATTC GGACAGCACC AATTTGCCGG GCCCGATGTT

551 CTGCTGGTAC CTGCGCAACA CCTACCTGGA AAACAGCCTG AAAGTGCCGG

601 GCAAGCTGAC GGTGGCCGGC GAAAAGATCG ACCTCGGCCT GATCGACGCC

651 CCGGCCTTCA TCTACGGTTC GCGCGAAGAC CACATCGTGC CGTGGATGTC

701 GGCGTACGGT TCGCTCGACA TCCTCAACCA GGGCAAGCCG GGCGCCAACC

751 GCTTCGTGCT GGGCGCGTCC GGCCATATCG CCGGCGTGAT CAACTCGGTG

801 GCCAAGAACA AGCGCAGCTA CTGGATCAAC GACGGTGGCG CCGCCGATGC

851 CCAGGCCTGG TTCGATGGCG CGCAGGAAGT GCCGGGCAGC TGGTGGCCGC

901 AATGGGCCGG GTTCCTGACC CAGCATGGCG GCAAGAAGGT CAAGCCCAAG

-continued

951 GCCAAAAGGG TGGGCGCGCC GACCCAGCTT TCTTGTACAA AGTGGTTGAT

1001 CCTGCAGGGT CCGTCGCTTC TCTTCCATTT CTTCTCATTT TCGATTTTGA

1051 TTCTTATTTC TTTCCAGTAG CTCCTGCTCT GTGAATTTCT CCGCTCACGA

1101 TAGATCTGCT TATACTCCTT ACATTCAACC TTAGATCTGG TCTCGATTCT

1151 CTGTTTCTCT GTTTTTTTCT TTTGGTCGAG AATCTGATGT TTGTTTATGT

1201 TCTGTCACCA TTAATAATAA TGAACTCTCT CATTCATACA ATGATTAGTT

1251 TCTCTCGTCT ACAAAACGAT ATGTTGCATT TTCACTTTTC TTCTTTTTTT

1301 CTAAGATGAT TTGCTTTGAC CAATTTGTTT AGATCTTTAT TCTATTTTAT

1351 TTTCTGGTGG GTTGGTGGAA ATTGAAAAAA AAAAAACAGC ATAAATTGTT

1401 ATTTGTTAAT GTATTCATTT TTTGGCTATT TGTTCTGGGT AAAAATCTGC

1451 TTCTACTATT GAATCTTTCC TGGATTTTTT ACTCCTATTG GGTTTTTATA

1501 GTAAAAATAC ATAATAAAAG GAAAACAAAA GTTTTATAGA TTCTCTTAAA

1551 CCCCTTACGA TAAAAGTTGG AATCAAAATA ATTCAGGATC AGATGCTCTT

1601 TGATTGATTC AGATGCGATT ACAGTTGCAT GGCAAATTTT CTAGATCCGT

1651 CGTCACATTT TATTTTCTGT TTAAATATCT AAATCTGATA TATGATGTCG

1701 ACAAATTCTG GTGGCTTATA CATCACTTCA ACTGTTTTCT TTTGGCTTTG

1751 TTTGTCAACT TGGTTTTCAA TACGATTTGT GATTTCGATC GCTGAATTTT

1801 TAATACAAGC AAACTGATGT TAACCACAAG CAAGAGATGT GACCTGCCTT

1851 ATTAACATCG TATTACTTAC TACTAGTCGT ATTCTCAACG CAATCGTTTT

1901 TGTATTTCTC ACATTATGCC GCTTCTCTAC TCTTTATTCC TTTTGGTCCA

1951 CGCATTTTCT ATTTGTGGCA ATCCCTTTCA CAACCTGATT TCCCACTTTG

2001 GATCATTTGT CTGAAGACTC TCTTGAATCG TTACCACTTG TTTCTTGTGC

2051 ATGCTCTGTT TTTTAGAATT AATGATAAAA CTATTCCATA GTCTTGAGTT

2101 TTCAGCTTGT TGATTCTTTT GCTTTTGGTT TTCTGCAGGT TTAAACATCA

2151 ACCACTTTGT ACAAGAAAGC TGGGTCGGCG CGCCCACCCT TTTGGCCTTG

2201 GGCTTGACCT TCTTGCCGCC ATGCTGGGTC AGGAACCCGG CCCATTGCGG

2251 CCACCAGCTG CCCGGCACTT CCTGCGCGCC ATCGAACCAG GCCTGGGCAT

-continued

2301 CGGCGGCGCC ACCGTCGTTG ATCCAGTAGC TGCGCTTGTT
CTTGGCCACC

2351 GAGTTGATCA CGCCGGCGAT ATGGCCGGAC GCGCCCAGCA
CGAAGCGGTT

2401 GGCGCCCGGC TTGCCCTGGT TGAGGATGTC GAGCGAACCG
TACGCCGACA

2451 TCCACGGCAC GATGTGGTCT TCGCGCGAAC CGTAGATGAA
GGCCGGGGCG

2501 TCGATCAGGC CGAGGTCGAT CTTTTCGCCG GCCACCGTCA
GCTTGCCCGG

2551 CACTTTCAGG CTGTTTTCCA GGTAGGTGTT GCGCAGGTAC
CAGCAGAACA

2601 TCGGGCCCGG CAAATTGGTG CTGTCCGAAT TCCAGAACAG
CAGGTCAAAC

2651 GCCGCCGGCT CATTGCCTTT GAGGTAGTTC GACTGCACAT
AGTTCCATAC

2701 CAGGTCGTTC GGACGCAGGC TCGAGAAGGT CGAGGCCAGG
TCACGGCCCG

2751 GCATCAGGCC GCCATCGCGC AATTTCTGTT CACGCAGCGC
GACCTGGGTT

2801 TCATCGACGA AGACGTCGAG CACGCCGGTG TCGCTGAAGT
CGAGGAAGGT

2851 GAAGGGGGCG GCCGCGGAGC CTGCTTTTTT GTACAAACTT
GTTGATCTCG

2901 AGCGGCGCGC CGTTCGAGTA TTATGGCATT GGGAAAACTG
TTTTTCTTGT

2951 ACCATTTGTT GTGCTTGTAA TTTACTGTGT TTTTTATTCG
GTTTTCGCTA

3001 TCGAACTGTG AAATGGAAAT GGATGGAGAA GAGTTAATGA
ATGATATGGT

3051 CCTTTTGTTC ATTCTCAAAT TAATATTATT TGTTTTTTCT
CTTATTTGTT

3101 GTGTGTTGAA TTTGAAATTA TAAGAGATAT GCAAACATTT
TGTTTTGAGT

3151 AAAAATGTGT CAAATCGTGG CCTCTAATGA CCGAAGTTAA
TATGAGGAGT

3201 AAAACACTGT TTAAACCCTG CAGGATTTAA ATAGAAGGTA
ATTATCCAAG

3251 ATGTAGCATC AAGAATCCAA TGTTTACGGG AAAAACTATG
GAAGTATTAT

3301 GTGAGCTCAG CAAGAAGGAG ATCAATATGC GGCACATATG
CAACCTATGT

3351 TCAAAAATGA AGAATGTACA GATACAAGAT CCTATACTGC
CAGAATACGA

3401 AGAAGAATAC GTAGAAATTG AAAAAGAAGA ACCAGGCGAA
GAAAAGAATC

3451 TTGAAGACGT AAGCACTGAC GACAACAATG AAAAGAAGAA
GATAAGGTCG

3501 GTGATTGTGA AAGAGACATA GAGGACACAT GTAAGGTGGA
AAATGTAAGG

3551 GCGGAAAGTA ACCTTATCAC AAAGGAATCT TATCCCCCAC
TACTTATCCT

3601 TTTATATTTT TCCGTGTCAT TTTTGCCCTT GAGTTTTCCT
ATATAAGGAA

-continued

3651 CCAAGTTCGG CATTTGTGAA AACAAGAAAA AATTGGTGTA
AGCTATTTTC

3701 TTTGAAGTAC TGAGGATACA ACTTCAGAGA AATTTGTAAG
AAAGTGGATC

3751 GAAACCATGG CCTCCTCCGA GAACGTCATC ACCGAGTTCA
TGCGCTTCAA

3801 GGTGCGCATG GAGGGCACCG TGAACGGCCA CGAGTTCGAG
ATCGAGGGCG

3851 AGGGCGAGGG CCGCCCCTAC GAGGGCCACA ACACCGTGAA
GCTGAAGGTG

3901 ACCAAGGGCG GCCCCCTGCC CTTCGCCTGG GACATCCTGT
CCCCCCAGTT

3951 CCAGTACGGC TCCAAGGTGT ACGTGAAGCA CCCCGCCGAC
ATCCCCGACT

4001 ACAAGAAGCT GTCCTTCCCC GAGGGCTTCA AGTGGGAGCG
CGTGATGAAC

4051 TTCGAGGACG GCGGCGTGGC GACCGTGACC CAGGACTCCT
CCCTGCAGGA

4101 CGGCTGCTTC ATCTACAAGG TGAAGTTCAT CGGCGTGAAC
TTCCCCTCCG

4151 ACGGCCCCGT GATGCAGAAG AAGACCATGG GCTGGGAGGC
CTCCACCGAG

4201 CGCCTGTACC CCCGCGACGG CGTGCTGAAG GGCGAGACCC
ACAAGGCCCT

4251 GAAGCTGAAG GACGGCGGCC ACTACCTGGT GGAGTTCAAG
TCCATCTACA

4301 TGGCCAAGAA GCCCGTGCAG CTGCCCGGCT ACTACTACGT
GGACGCCAAG

4351 CTGGACATCA CCTCCCACAA CGAGGACTAC ACCATCGTGG
AGCAGTACGA

4401 GCGCACCGAG GGCCGCCACC ACCTGTTCCT GGTACCAATG
AGCTCTGTCC

4451 AACAGTCTCA GGGTTAATGT CTATGTATCT TAAATAATGT
TGTCGGCGAT

4501 CGTTCAAACA TTTGGCAATA AAGTTTCTTA AGATTGAATC
CTGTTGCCGG

4551 TCTTGCGATG ATTATCATAT AATTTCTGTT GAATTACGTT
AAGCATGTAA

4601 TAATTAACAT GTAATGCATG ACGTTATTTA TGAGATGGGT
TTTTATGATT

4651 AGAGTCCCGC AATTATACAT TTAATACGCG ATAGAAAACA
AAATATAGCG

4701 CGCAAACTAG GATAAATTAT CGCGCGCGGT GTCATCTATG
TTACTAGATC

4751 GGGAATTAAA CTATCAGTGT TTGACAGGAT ATATTGGCGG
GTAAACCTAA

4801 GAGAAAAGAG CGTTTATTAG AATAACGGAT ATTTAAAAGG
GCGTGAAAAG

4851 GTTTATCCGT TCGTCCATTT GTATGTGCAT GCCAACCACA
GGGTTCCCCT

4901 CGGGATCAAA GTACTTTGAT CCAACCCCTC CGCTGCTATA
GTGCAGTCGG

4951 CTTCTGACGT TCAGTGCAGC CGTCTTCTGA AAACGACATG
TCGCACAAGT

-continued

5001 CCTAAGTTAC GCGACAGGCT GCCGCCCTGC CCTTTTCCTG GCGTTTTCTT

5051 GTCGCGTGTT TTAGTCGCAT AAAGTAGAAT ACTTGCGACT AGAACCGGAG

5101 ACATTACGCC ATGAACAAGA GCGCCGCCGC TGGCCTGCTG GGCTATGCCC

5151 GCGTCAGCAC CGACGACCAG GACTTGACCA ACCAACGGGC CGAACTGCAC

5201 GCGGCCGGCT GCACCAAGCT GTTTTCCGAG AAGATCACCG GCACCAGGCG

5251 CGACCGCCCG GAGCTGGCCA GGATGCTTGA CCACCTACGC CCTGGCGACG

5301 TTGTGACAGT GACCAGGCTA GACCGCCTGG CCCGCAGCAC CCGCGACCTA

5351 CTGGACATTG CCGAGCGCAT CCAGGAGGCC GGCGCGGGCC TGCGTAGCCT

5401 GGCAGAGCCG TGGGCCGACA CCACCACGCC GGCCGGCCGC ATGGTGTTGA

5451 CCGTGTTCGC CGGCATTGCC GATTACGACC GTTCCCTAAT CATCGACCGC

5501 ACCCGGAGCG GGCGCGAGGC CGCCAAGGCC CGAGGCGTGA AGTTTGGCCC

5551 CCGCCCTACC CTCACCCCGG CACAGATCGC GCACGCCCGC GAGCTGATCG

5601 ACCAGGAAGG CCGCACCGTG AAAGAGGCGG CTGCACTGCT TGGCGTGCAT

5651 CGCTCGACCC TGTACCGCGC ACTTGAGCGC AGCGAGGAAG TGACGCCCAC

5701 CGAGGCCAGG CGGCGCGGTG CCTTCCGTGA GGACGCATTG ACCGAGGCCG

5751 ACGCCCTGGC GGCCGCCGAG AATGAACGCC AAGAGGAACA AGCATGAAAC

5801 CGCACCAGGA CGGCCAGGAC GAACCGTTTT TCATTACCGA AGAGATCGAG

5851 GCGGAGATGA TCGCGGCCGG GTACGTGTTC GAGCCGCCCG CGCACGTCTC

5901 AACCGTGCGG CTGCATGAAA TCCTGGCCGG TTTGTCTGAT GCCAAGCTGG

5951 CGGCCTGGCC GGCCAGCTTG GCCGCTGAAG AAACCGAGCG CCGCCGTCTA

6001 AAAAGGTGAT GTGTATTTGA GTAAAACAGC TTGCGTCATG CGGTCGCTGC

6051 GTATATGATG CGATGAGTAA ATAAACAAAT ACGCAAGGGG AACGCATGAA

6101 GGTTATCGCT GTACTTAACC AGAAAGGCGG GTCAGGCAAG ACGACCATCG

6151 CAACCCATCT AGCCCGCGCC CTGCAACTCG CCGGGGCCGA TGTTCTGTTA

6201 GTCGATTCCG ATCCCCAGGG CAGTGCCCGC GATTGGGCGG CCGTGCGGGA

6251 AGATCAACCG CTAACCGTTG TCGGCATCGA CCGCCCGACG ATTGACCGCG

6301 ACGCCAAGGC CATCGGCCGG CGCGACTTCG TAGTGATCGA CGGAGCGCCC

6351 CAGGCGGCGG ACTTGGCTGT GTCCGCGATC AAGGCAGCCG ACTTCGTGCT

6401 GATTCCGGTG CAGCCAAGCC CTTACGACAT ATGGGCCACC GCCGACCTGG

6451 TGGAGCTGGT TAAGCAGCGC ATTGAGGTCA CGGATGGAAG GCTACAAGCG

6501 GCCTTTGTCG TGTCGCGGGC GATCAAAGGC ACGCGCATCG GCGGTGAGGT

6551 TGCCGAGGCG CTGGCCGGGT ACGAGCTGCC CATTCTTGAG TCCCGTATCA

6601 CGCAGCGCGT GAGCTACCCA GGCACTGCCG CCGCCGGCAC AACCGTTCTT

6651 GAATCAGAAC CCGAGGGCGA CGCTGCCCGC GAGGTCCAGG CGCTGGCCGC

6701 TGAAATTAAA TCAAAACTCA TTTGAGTTAA TGAGGTAAAG AGAAAATGAG

6751 CAAAAGCACA AACACGCTAA GTGCCGGCCG TCCGAGCGCA CGCAGCAGCA

6801 AGGCTGCAAC GTTGGCCAGC CTGGCAGACA CGCCAGCCAT GAAGCGGGTC

6851 AACTTTCAGT TGCCGGCGGA GGATCACACC AAGCTGAAGA TGTACGCGGT

6901 ACGCCAAGGC AAGACCATTA CCGAGCTGCT ATCTGAATAC ATCGCGCAGC

6951 TACCAGAGTA AATGAGCAAA TGAATAAATG AGTAGATGAA TTTTAGCGGC

7001 TAAAGGAGGC GGCATGGAAA ATCAAGAACA ACCAGGCACC GACGCCGTGG

7051 AATGCCCCAT GTGTGGAGGA ACGGGCGGTT GGCCAGGCGT AAGCGGCTGG

7101 GTTGTCTGCC GGCCCTGCAA TGGCACTGGA ACCCCCAAGC CCGAGGAATC

7151 GGCGTGACGG TCGCAAACCA TCCGGCCCGG TACAAATCGG CGCGGCGCTG

7201 GGTGATGACC TGGTGGAGAA GTTGAAGGCC GCGCAGGCCG CCCAGCGGCA

7251 ACGCATCGAG GCAGAAGCAC GCCCCGGTGA ATCGTGGCAA GCGGCCGCTG

7301 ATCGAATCCG CAAAGAATCC CGGCAACCGC CGGCAGCCGG TGCGCCGTCG

7351 ATTAGGAAGC CGCCCAAGGG CGACGAGCAA CCAGATTTTT TCGTTCCGAT

7401 GCTCTATGAC GTGGGCACCC GCGATAGTCG CAGCATCATG GACGTGGCCG

7451 TTTTCCGTCT GTCGAAGCGT GACCGACGAG CTGGCGAGGT GATCCGCTAC

7501 GAGCTTCCAG ACGGGCACGT AGAGGTTTCC GCAGGGCCGG CCGGCATGGC

7551 CAGTGTGTGG GATTACGACC TGGTACTGAT GGCGGTTTCC CATCTAACCG

7601 AATCCATGAA CCGATACCGG GAAGGGAAGG GAGACAAGCC CGGCCGCGTG

7651 TTCCGTCCAC ACGTTGCGGA CGTACTCAAG TTCTGCCGGC GAGCCGATGG

-continued

```
7701 CGGAAAGCAG AAAGACGACC TGGTAGAAAC CTGCATTCGG
     TTAAACACCA

7751 CGCACGTTGC CATGCAGCGT ACGAAGAAGG CCAAGAACGG
     CCGCCTGGTG

7801 ACGGTATCCG AGGGTGAAGC CTTGATTAGC CGCTACAAGA
     TCGTAAAGAG

7851 CGAAACCGGG CGGCCGGAGT ACATCGAGAT CGAGCTAGCT
     GATTGGATGT

7901 ACCGCGAGAT CACAGAAGGC AAGAACCCGG ACGTGCTGAC
     GGTTCACCCC

7951 GATTACTTTT TGATCGATCC CGGCATCGGC CGTTTTCTCT
     ACCGCCTGGC

8001 ACGCCGCGCC GCAGGCAAGG CAGAAGCCAG ATGGTTGTTC
     AAGACGATCT

8051 ACGAACGCAG TGGCAGCGCC GGAGAGTTCA AGAAGTTCTG
     TTTCACCGTG

8101 CGCAAGCTGA TCGGGTCAAA TGACCTGCCG GAGTACGATT
     TGAAGGAGGA

8151 GGCGGGGCAG GCTGGCCCGA TCCTAGTCAT GCGCTACCGC
     AACCTGATCG

8201 AGGGCGAAGC ATCCGCCGGT TCCTAATGTA CGGAGCAGAT
     GCTAGGGCAA

8251 ATTGCCCTAG CAGGGGAAAA AGGTCGAAAA GGTCTCTTTC
     CTGTGGATAG

8301 CACGTACATT GGGAACCCAA AGCCGTACAT TGGGAACCGG
     AACCCGTACA

8351 TTGGGAACCC AAAGCCGTAC ATTGGGAACC GGTCACACAT
     GTAAGTGACT

8401 GATATAAAAG AGAAAAAAGG CGATTTTTCC GCCTAAAACT
     CTTTAAAACT

8451 TATTAAAACT CTTAAAACCC GCCTGGCCTG TGCATAACTG
     TCTGGCCAGC

8501 GCACAGCCGA AGAGCTGCAA AAAGCGCCTA CCCTTCGGTC
     GCTGCGCTCC

8551 CTACGCCCCG CCGCTTCGCG TCGGCCTATC GCGGCCGCTG
     GCCGCTCAAA

8601 AATGGCTGGC CTACGGCCAG GCAATCTACC AGGGCGCGGA
     CAAGCCGCGC

8651 CGTCGCCACT CGACCGCCGG CGCCCACATC AAGGCACCCT
     GCCTCGCGCG

8701 TTTCGGTGAT GACGGTGAAA ACCTCTGACA CATGCAGCTC
     CCGGAGACGG

8751 TCACAGCTTG TCTGTAAGCG GATGCCGGGA GCAGACAAGC
     CCGTCAGGGC

8801 GCGTCAGCGG GTGTTGGCGG GTGTCGGGGC GCAGCCATGA
     CCCAGTCACG

8851 TAGCGATAGC GGAGTGTATA CTGGCTTAAC TATGCGGCAT
     CAGAGCAGAT

8901 TGTACTGAGA GTGCACCATA TGCGGTGTGA AATACCGCAC
     AGATGCGTAA

8951 GGAGAAAATA CCGCATCAGG CGCTCTTCCG CTTCCTCGCT
     CACTGACTCG

9001 CTGCGCTCGG TCGTTCGGCT GCGGCGAGCG GTATCAGCTC
     ACTCAAAGGC
```

-continued

```
9051 GGTAATACGG TTATCCACAG AATCAGGGGA TAACGCAGGA
     AAGAACATGT

9101 GAGCAAAAGG CCAGCAAAAG GCCAGGAACC GTAAAAAGGC
     CGCGTTGCTG

9151 GCGTTTTTCC ATAGGCTCCG CCCCCCTGAC GAGCATCACA
     AAAATCGACG

9201 CTCAAGTCAG AGGTGGCGAA ACCCGACAGG ACTATAAAGA
     TACCAGGCGT

9251 TTCCCCCTGG AAGCTCCCTC GTGCGCTCTC CTGTTCCGAC
     CCTGCCGCTT

9301 ACCGGATACC TGTCCGCCTT TCTCCCTTCG GGAAGCGTGG
     CGCTTTCTCA

9351 TAGCTCACGC TGTAGGTATC TCAGTTCGGT GTAGGTCGTT
     CGCTCCAAGC

9401 TGGGCTGTGT GCACGAACCC CCCGTTCAGC CCGACCGCTG
     CGCCTTATCC

9451 GGTAACTATC GTCTTGAGTC CAACCCGGTA AGACACGACT
     TATCGCCACT

9501 GGCAGCAGCC ACTGGTAACA GGATTAGCAG AGCGAGGTAT
     GTAGGCGGTG

9551 CTACAGAGTT CTTGAAGTGG TGGCCTAACT ACGGCTACAC
     TAGAAGGACA

9601 GTATTTGGTA TCTGCGCTCT GCTGAAGCCA GTTACCTTCG
     GAAAAAGAGT

9651 TGGTAGCTCT TGATCCGGCA AACAAACCAC CGCTGGTAGC
     GGTGGTTTTT

9701 TTGTTTGCAA GCAGCAGATT ACGCGCAGAA AAAAAGGATC
     TCAAGAAGAT

9751 CCTTTGATCT TTTCTACGGG GTCTGACGCT CAGTGGAACG
     AAAACTCACG

9801 TTAAGGGATT TTGGTCATGC ATTCTAGGTA CTAAAACAAT
     TCATCCAGTA

9851 AAATATAATA TTTTATTTTC TCCCAATCAG GCTTGATCCC
     CAGTAAGTCA

9901 AAAAATAGCT CGACATACTG TTCTTCCCCG ATATCCTCCC
     TGATCGACCG

9951 GACGCAGAAG GCAATGTCAT ACCACTTGTC CGCCCTGCCG
     CTTCTCCCAA

10001 GATCAATAAA GCCACTTACT TTGCCATCTT TCACAAAGAT
      GTTGCTGTCT

10051 CCCAGGTCGC CGTGGGAAAA GACAAGTTCC TCTTCGGGCT
      TTTCCGTCTT

10101 TAAAAAATCA TACAGCTCGC GCGGATCTTT AAATGGAGTG
      TCTTCTTCCC

10151 AGTTTTCGCA ATCCACATCG GCCAGATCGT TATTCAGTAA
      GTAATCCAAT

10201 TCGGCTAAGC GGCTGTCTAA GCTATTCGTA TAGGGACAAT
      CCGATATGTC

10251 GATGGAGTGA AAGAGCCTGA TGCACTCCGC ATACAGCTCG
      ATAATCTTTT

10301 CAGGGCTTTG TTCATCTTCA TACTCTTCCG AGCAAAGGAC
      GCCATCGGCC

10351 TCACTCATGA GCAGATTGCT CCAGCCATCA TGCCGTTCAA
      AGTGCAGGAC
```

-continued

```
10401 CTTTGGAACA GGCAGCTTTC CTTCCAGCCA TAGCATCATG
      TCCTTTTCCC

10451 GTTCCACATC ATAGGTGGTC CCTTTATACC GGCTGTCCGT
      CATTTTTAAA

10501 TATAGGTTTT CATTTTCTCC CACCAGCTTA TATACCTTAG
      CAGGAGACAT

10551 TCCTTCCGTA TCTTTTACGC AGCGGTATTT TTCGATCAGT
      TTTTTCAATT

10601 CCGGTGATAT TCTCATTTTA GCCATTTATT ATTTCCTTCC
      TCTTTTCTAC

10651 AGTATTTAAA GATACCCCAA GAAGCTAATT ATAACAAGAC
      GAACTCCAAT

10701 TCACTGTTCC TTGCATTCTA AAACCTTAAA TACCAGAAAA
      CAGCTTTTTC

10751 AAAGTTGTTT TCAAAGTTGG CGTATAACAT AGTATCGACG
      GAGCCGATTT

10801 TGAAACCGCG GTGATCACAG GCAGCAACGC TCTGTCATCG
      TTACAATCAA

10851 CATGCTACCC TCCGCGAGAT CATCCGTGTT TCAAACCCGG
      CAGCTTAGTT

10901 GCCGTTCTTC CGAATAGCAT CGGTAACATG AGCAAAGTCT
      GCCGCCTTAC

10951 AACGGCTCTC CCGCTGACGC CGTCCCGGAC TGATGGGCTG
      CCTGTATCGA

11001 GTGGTGATTT TGTGCCGAGC TGCCGGTCGG GGAGCTGTTG
      GCTGGCTGGT

11051 GGCAGGATAT ATTGTGGTGT AAACAAATTG ACGCTTAGAC
      AACTTAATAA

11101 CACATTGCGG ACGTTTTTAA TGTACTGAAT TAACGCCGAA
      TTAATTCCTA

11151 GGCCACCATG TTGGGCCCGG GGCGCGCCGT ACGTAGTGTT
      TATCTTTGTT

11201 GCTTTTCTGA ACAATTTATT TACTATGTAA ATATATTATC
      AATGTTTAAT

11251 CTATTTTAAT TTGCACATGA ATTTTCATTT TATTTTTACT
      TTACAAAACA

11301 AATAAATATA TATGCAAAAA AATTTACAAA CGATGCACGG
      GTTACAAACT

11351 AATTTCATTA AATGCTAATG CAGATTTTGT GAAGTAAAAC
      TCCAATTATG

11401 ATGAAAAATA CCACCAACAC CACCTGCGAA ACTGTATCCC
      AACTGTCCTT

11451 AATAAAAATG TTAAAAAGTA TATTATTCTC ATTTGTCTGT
      CATAATTTAT

11501 GTACCCCACT TTAATTTTTC TGATGTACTA AACCGAGGGC
      AAACTGAAAC

11551 CTGTTCCTCA TGCAAAGCCC CTACTCACCA TGTATCATGT
      ACGTGTCATC

11601 ACCCAACAAC TCCACTTTTG CTATATAACA ACACCCCCGT
      CACACTCTCC

11651 CTCTCTAACA CACACCCCAC TAACAATTCC TTCACTTGCA
      GCACTGTTGC

11701 ATCATCATCT TCATTGCAAA ACCCTAAACT TCACCTTCAA
      CCGCGGCCGC
```

-continued

```
11751 ATGGCTTCTA TGATATCCTC TTCCGCTGTG ACAACAGTCA
      GCCGTGCCTC

11801 TAGGGGGCAA TCCGCCGCAG TGGCTCCATT CGGCGGCCTC
      AAATCCATGA

11851 CTGGATTCCC AGTGAAGAAG GTCAACACTG ACATTACTTC
      CATTACAAGC

11901 AATGGTGGAA GAGTAAAGTG CATGCAGGTG TGGCCTCCAA
      TTGGAAAGAA

11951 GAAGTTTGAG ACTCTTTCCT ATTTGCCACC ATTGACGAGA
      GATTCTAGAG

12001 TGAGTAACAA GAACAACGAT GAGCTGCAGT GGCAATCCTG
      GTTCAGCAAG

12051 GCGCCCACCA CCGAGGCGAA CCCGATGGCC ACCATGTTGC
      AGGATATCGG

12101 CGTTGCGCTC AAACCGGAAG CGATGGAGCA GCTGAAAAAC
      GATTATCTGC

12151 GTGACTTCAC CGCGTTGTGG CAGGATTTTT TGGCTGGCAA
      GGCGCCAGCC

12201 GTCAGCGACC GCCGCTTCAG CTCGGCAGCC TGGCAGGGCA
      ATCCGATGTC

12251 GGCCTTCAAT GCCGCATCTT ACCTGCTCAA CGCCAAATTC
      CTCAGTGCCA

12301 TGGTGGAGGC GGTGGACACC GCACCCCAGC AAAAGCAGAA
      AATACGCTTT

12351 GCCGTGCAGC AGGTGATTGA TGCCATGTCG CCCGCGAACT
      TCCTCGCCAC

12401 CAACCCGGAA GCGCAGCAAA AACTGATTGA AACCAAGGGC
      GAGAGCCTGA

12451 CGCGTGGCCT GGTCAATATG CTGGGCGATA TCAACAAGGG
      CCATATCTCG

12501 CTGTCGGACG AATCGGCCTT TGAAGTGGGC CGCAACCTGG
      CCATTACCCC

12551 GGGCACCGTG ATTTACGAAA ATCCGCTGTT CCAGCTGATC
      CAGTACACGC

12601 CGACCACGCC GACGGTCAGC CAGCGCCCGC TGTTGATGGT
      GCCGCCGTGC

12651 ATCAACAAGT TCTACATCCT CGACCTGCAA CCGGAAAATT
      CGCTGGTGCG

12701 CTACGCGGTG GAGCAGGGCA ACACCGTGTT CCTGATCTCG
      TGGAGCAATC

12751 CGGACAAGTC GCTGGCCGGC ACCACCTGGG ACGACTACGT
      GGAGCAGGGC

12801 GTGATCGAAG CGATCCGCAT CGTCCAGGAC GTCAGCGGCC
      AGGACAAGCT

12851 GAACATGTTC GGCTTCTGCG TGGGCGGCAC CATCGTTGCC
      ACCGCACTGG

12901 CGGTACTGGC GGCGCGTGGC CAGCACCCGG CGGCCAGCCT
      GACCCTGCTG

12951 ACCACCTTCC TCGACTTCAG CGACACCGGC GTGCTCGACG
      TCTTCGTCGA

13001 TGAAACCCAG GTCGCGCTGC GTGAACAGCA ATTGCGCGAT
      GGCGGCCTGA

13051 TGCCGGGCCG TGACCTGGCC TCGACCTTCT CGAGCCTGCG
      TCCGAACGAC
```

-continued

13101 CTGGTATGGA ACTATGTGCA GTCGAACTAC CTCAAAGGCA ATGAGCCGGC

13151 GGCGTTTGAC CTGCTGTTCT GGAATTCGGA CAGCACCAAT TTGCCGGGCC

13201 CGATGTTCTG CTGGTACCTG CGCAACACCT ACCTGGAAAA CAGCCTGAAA

13251 GTGCCGGGCA AGCTGACGGT GGCCGGCGAA AAGATCGACC TCGGCCTGAT

13301 CGACGCCCCG GCCTTCATCT ACGGTTCGCG CGAAGACCAC ATCGTGCCGT

13351 GGATGTCGGC GTACGGTTCG CTCGACATCC TCAACCAGGG CAAGCCGGGC

13401 GCCAACCGCT TCGTGCTGGG CGCGTCCGGC CATATCGCCG GCGTGATCAA

13451 CTCGGTGGCC AAGAACAAGC GCAGCTACTG GATCAACGAC GGTGGCGCCG

13501 CCGATGCCCA GGCCTGGTTC GATGGCGCGC AGGAAGTGCC GGGCAGCTGG

13551 TGGCCGCAAT GGGCCGGGTT CCTGACCCAG CATGGCGGCA AGAAGGTCAA

13601 GCCCAAGGCC AAGCCCGGCA ACGCCCGCTA CACCGCGATC GAGGCGGCGC

13651 CCGGCCGTTA CGTCAAAGCC AAGGGCTGAG CGGCCGCTGA GTAATTCTGA

13701 TATTAGAGGG AGCATTAATG TGTTGTTGTG ATGTGGTTTA TATGGGGAAA

13751 TTAAATAAAT GATGTATGTA CCTCTTGCCT ATGTAGGTTT GTGTGTTTTG

13801 TTTTGTTGTC TAGCTTTGGT TATTAAGTAG TAGGGACGTT CGTTCGTGTC

13851 TCAAAAAAAG GGGTACTACC ACTCTGTAGT GTATATGGAT GCTGGAAATC

13901 AATGTGTTTT GTATTTGTTC ACCTCCATTG TTGAATTCAA TGTCAAATGT

13951 GTTTTGCGTT GGTTATGTGT AAAATTACTA TCTTTCTCGT CCGATGATCA

14001 AAGTTTTAAG CAACAAAACC AAGGGTGAAA TTTAAACTGT GCTTTGTTGA

14051 AGATTCTTTT ATCATATTGA AAATCAAATT ACTAGCAGCA GATTTTACCT

14101 AGCATGAAAT TTTATCAACA GTACAGCACT CACTAACCAA GTTCCAAACT

14151 AAGATGCGCC ATTAACATCA GCCAATAGGC ATTTTCAGCA AGGCGCGCCC

14201 GCGCCGATGT ATGTGACAAC CCTCGGGATT GTTGATTTAT TTCAAAACTA

14251 AGAGTTTTTG TCTTATTGTT CTCGTCTATT TTGGATATCA ATCTTAGTTT

14301 TATATCTTTT CTAGTTCTCT ACGTGTTAAA TGTTCAACAC ACTAGCAATT

14351 TGGCCTGCCA GCGTATGGAT TATGGAACTA TCAAGTCTGT GACGCGCCGT

14401 ACGTAGTGTT TATCTTTGTT GCTTTTCTGA ACAATTTATT TACTATGTAA

-continued

14451 ATATATTATC AATGTTTAAT CTATTTTAAT TTGCACATGA ATTTTCATTT

14501 TATTTTTACT TTACAAAACA AATAAATATA TATGCAAAAA AATTTACAAA

14551 CGATGCACGG GTTACAAACT AATTTCATTA AATGCTAATG CAGATTTTGT

14601 GAAGTAAAAC TCCAATTATG ATGAAAAATA CCACCAACAC CACCTGCGAA

14651 ACTGTATCCC AACTGTCCTT AATAAAAATG TTAAAAAGTA TATTATTCTC

14701 ATTTGTCTGT CATAATTTAT GTACCCCACT TTAATTTTTC TGATGTACTA

14751 AACCGAGGGC AAACTGAAAC CTGTTCCTCA TGCAAAGCCC CTACTCACCA

14801 TGTATCATGT ACGTGTCATC ACCCAACAAC TCCACTTTTG CTATATAACA

14851 ACACCCCCGT CACACTCTCC CTCTCTAACA CACACCCCAC TAACAATTCC

14901 TTCACTTGCA GCACTGTTGC ATCATCATCT TCATTGCAAA ACCCTAAACT

14951 TCACCTTCAA CCGCGGCCGC ATGGCTTCTA TGATATCCTC TTCCGCTGTG

15001 ACAACAGTCA GCCGTGCCTC TAGGGGGCAA TCCGCCGCAG TGGCTCCATT

15051 CGGCGGCCTC AAATCCATGA CTGGATTCCC AGTGAAGAAG GTCAACACTG

15101 ACATTACTTC CATTACAAGC AATGGTGGAA GAGTAAAGTG CATGCAGGTG

15151 TGGCCTCCAA TTGGAAAGAA GAAGTTTGAG ACTCTTTCCT ATTTGCCACC

15201 ATTGACGAGA GATTCTAGAG TGACTCAGCG CATTGCGTAT GTGACCGGCG

15251 GCATGGGTGG TATCGGAACC GCCATTTGCC AGCGGCTGGC CAAGGATGGC

15301 TTTCGTGTGG TGGCCGGTTG CGGCCCCAAC TCGCCGCGCC GCGAAAAGTG

15351 GCTGGAGCAG CAGAAGGCCC TGGGCTTCGA TTTCATTGCC TCGGAAGGCA

15401 ATGTGGCTGA CTGGGACTCG ACCAAGACCG CATTCGACAA GGTCAAGTCC

15451 GAGGTCGGCG AGGTTGATGT GCTGATCAAC AACGCCGGTA TCACCCGCGA

15501 CGTGGTGTTC CGCAAGATGA CCCGCGCCGA CTGGGATGCG GTGATCGACA

15551 CCAACCTGAC CTCGCTGTTC AACGTCACCA AGCAGGTGAT CGACGGCATG

15601 GCCGACCGTG GCTGGGGCCG CATCGTCAAC ATCTCGTCGG TGAACGGGCA

15651 GAAGGGCCAG TTCGGCCAGA CCAACTACTC CACCGCCAAG GCCGGCCTGC

15701 ATGGCTTCAC CATGGCACTG GCGCAGGAAG TGGCGACCAA GGGCGTGACC

15751 GTCAACACGG TCTCTCCGGG CTATATCGCC ACCGACATGG TCAAGGCGAT

-continued

15801 CCGCCAGGAC GTGCTCGACA AGATCGTCGC GACGATCCCG GTCAAGCGCC

15851 TGGGCCTGCC GGAAGAGATC GCCTCGATCT GCGCCTGGTT GTCGTCGGAG

15901 GAGTCCGGTT TCTCGACCGG CGCCGACTTC TCGCTCAACG GCGGCCTGCA

15951 TATGGGCTGA GCGGCCGCTG AGTAATTCTG ATATTAGAGG GAGCATTAAT

16001 GTGTTGTTGT GATGTGGTTT ATATGGGGAA ATTAAATAAA TGATGTATGT

16051 ACCTCTTGCC TATGTAGGTT TGTGTGTTTT GTTTTGTTGT CTAGCTTTGG

16101 TTATTAAGTA GTAGGGACGT TCGTTCGTGT CTCAAAAAAA GGGGTACTAC

16151 CACTCTGTAG TGTATATGGA TGCTGGAAAT CAATGTGTTT TGTATTTGTT

16201 CACCTCCATT GTTGAATTCA ATGTCAAATG TGTTTTGCGT TGGTTATGTG

16251 TAAAATTACT ATCTTTCTCG TCCGATGATC AAAGTTTTAA GCAACAAAAC

16301 CAAGGGTGAA ATTTAAACTG TGCTTTGTTG AAGATTCTTT TATCATATTG

16351 AAAATCAAAT TACTAGCAGC AGATTTTACC TAGCATGAAA TTTTATCAAC

16401 AGTACAGCAC TCACTAACCA AGTTCCAAAC TAAGATGCGC CATTAACATC

16451 AGCCAATAGG CATTTTCAGC AAGGCGCGTA AGGGGATCCG TACGTAAGTA

16501 CGTACTCAAA ATGCCAACAA ATAAAAAAAA AGTTGCTTTA ATAATGCCAA

16551 AACAAATTAA TAAAACACTT ACAACACCGG ATTTTTTTTA ATTAAAATGT

16601 GCCATTTAGG ATAAATAGTT ATTTTTTTTA ATAATTATTT AAAAAGCCGT

16651 ATCTACTAAA ATGATTTTTA TTTGGTTGAA AATATTAATA TGTTTAAATC

16701 AACACAATCT ATCAAAATTA AACTAAAAAA AAAATAAGTG TACGTGGTTA

16751 ACATTAGTAC AGTAATATAA GAGGAAAATG AGAAATTAAG AAATTGAAAG

16801 CGAGTCTAAT TTTTAAATTA TGAACCTGCA TATATAAAAG GAAAGAAAGA

16851 ATCCAGGAAG AAAAGAAATG AAACCATGCA TGGTCCCCTC GTCATCACGA

16901 GTTTCTGCCA TTTGCAATAG AAACACTGAA ACACCTTTCT CTTTGTCACT

16951 TAATTGAGAT GCCGAAGCCA CCTCACACCA TGAACTTCAT GAGGTGTAGC

17001 ACCCAAGGCT TCCATAGCCA TGCATACTGA AGAATGTCTC AAGCTCAGCA

17051 CCCTACTTCT GTGACGTGTC CCTCATTCAC CTTCCTCTCT TCCCTATAAA

17101 TAACCACGCC TCAGGTTCTC CGCTTCACAA CTCAAACATT CTCTCCATTG

-continued

17151 GTCCTTAAAC ACTCATCAGT CATCACCGCG GCCGCGGAAT TCATGGCTTC

17201 TATGATATCC TCTTCCGCTG TGACAACAGT CAGCCGTGCC TCTAGGGGGC

17251 AATCCGCCGC AGTGGCTCCA TTCGGCGGCC TCAAATCCAT GACTGGATTC

17301 CCAGTGAAGA AGGTCAACAC TGACATTACT TCCATTACAA GCAATGGTGG

17351 AAGAGTAAAG TGCATGCAGG TGTGGCCTCC AATTGGAAAG AAGAAGTTTG

17401 AGACTCTTTC CTATTTGCCA CCATTGACGA GAGATTCTAG AGTGACTGAC

17451 GTTGTCATCG TATCCGCCGC CCGCACCGCG GTCGGCAAGT TTGGCGGCTC

17501 GCTGGCCAAG ATCCCGGCAC CGGAACTGGG TGCCGTGGTC ATCAAGGCCG

17551 CGCTGGAGCG CGCCGGCGTC AAGCCGGAGC AGGTGAGCGA AGTCATCATG

17601 GGCCAGGTGC TGACCGCCGG TTCGGGCCAG AACCCCGCAC GCCAGGCCGC

17651 GATCAAGGCC GGCCTGCCGG CGATGGTGCC GGCCATGACC ATCAACAAGG

17701 TGTGCGGCTC GGGCCTGAAG GCCGTGATGC TGGCCGCCAA CGCGATCATG

17751 GCGGGCGACG CCGAGATCGT GGTGGCCGGC GGCCAGGAAA ACATGAGCGC

17801 CGCCCCGCAC GTGCTGCCGG GCTCGCGCGA TGGTTTCCGC ATGGGCGATG

17851 CCAAGCTGGT CGACACCATG ATCGTCGACG GCCTGTGGGA CGTGTACAAC

17901 CAGTACCACA TGGGCATCAC CGCCGAGAAC GTGGCCAAGG AATACGGCAT

17951 CACACGCGAG GCGCAGGATG AGTTCGCCGT CGGCTCGCAG AACAAGGCCG

18001 AAGCCGCGCA GAAGGCCGGC AAGTTTGACG AAGAGATCGT CCCGGTGCTG

18051 ATCCCGCAGC GCAAGGGCGA CCCGGTGGCC TTCAAGACCG ACGAGTTCGT

18101 GCGCCAGGGC GCCACGCTGG ACAGCATGTC CGGCCTCAAG CCCGCCTTCG

18151 ACAAGGCCGG CACGGTGACC GCGGCCAACG CCTCGGGCCT GAACGACGGC

18201 GCCGCCGCGG TGGTGGTGAT GTCGGCGGCC AAGGCCAAGG AACTGGGCCT

18251 GACCCCGCTG GCCACGATCA AGAGCTATGC CAACGCCGGT GTCGATCCCA

18301 AGGTGATGGG CATGGGCCCG GTGCCGGCCT CCAAGCGCGC CCTGTCGCGC

18351 GCCGAGTGGA CCCCGCAAGA CCTGGACCTG ATGGAGATCA ACGAGGCCTT

18401 TGCCGCGCAG GCGCTGGCGG TGCACCAGCA GATGGGCTGG GACACCTCCA

18451 AGGTCAATGT GAACGGCGGC GCCATCGCCA TCGGCCACCC GATCGGCGCG

-continued

18501 TCGGGCTGCC GTATCCTGGT GACGCTGCTG CACGAGATGA AGCGCCGTGA

18551 CGCGAAGAAG GGCCTGGCCT CGCTGTGCAT CGGCGGCGGC ATGGGCGTGG

18601 CGCTGGCAGT CGAGCGCAAA TAACTCGAGG CGGCCGCAGC CCTTTTTGTA

18651 TGTGCTACCC CACTTTTGTC TTTTTGGCAA TAGTGCTAGC AACCAATAAA

18701 TAATAATAAT AATAATGAAT AAGAAAACAA AGGCTTTAGC TTGCCTTTTG

18751 TTCACTGTAA AATAATAATG TAAGTACTCT CTATAATGAG TCACGAAACT

18801 TTTGCGGGAA TAAAAGGAGA AATTCCAATG AGTTTTCTGT CAAATCTTCT

18851 TTTGTCTCTC TCTCTCTCTC TTTTTTTTTT TTCTTTCTTC TGAGCTTCTT

18901 GCAAAACAAA AGGCAAACAA TAACGATTGG TCCAATGATA GTTAGCTTGA

18951 TCGATGATAT CTTTAGGAAG TGTTGGCAGG ACAGGACATG ATGTAGAAGA

19001 CTAAAATTGA AAGTATTGCA GACCCAATAG TTGAAGATTA ACTTTAAGAA

19051 TGAAGACGTC TTATCAGGTT CTTCATGACT TAAGCTTTAA GAGGAGTCCA

19101 CCATGGTAGA TCTGACTAGT GATCCGTACG TAAGTACGTA CTCAAAATGC

19151 CAACAAATAA AAAAAAAGTT GCTTTAATAA TGCCAAAACA AATTAATAAA

19201 ACACTTACAA CACCGGATTT TTTTTAATTA AAATGTGCCA TTTAGGATAA

19251 ATAGTTAATA TTTTTAATAA TTATTTAAAA AGCCGTATCT ACTAAAATGA

19301 TTTTTATTTG GTTGAAAATA TTAATATGTT TAAATCAACA CAATCTATCA

19351 AAATTAAACT AAAAAAAAAA TAAGTGTACG TGGTTAACAT TAGTACAGTA

19401 ATATAAGAGG AAAATGAGAA ATTAAGAAAT TGAAAGCGAG TCTAATTTTT

19451 AAATTATGAA CCTGCATATA TAAAAGGAAA GAAAGAATCC AGGAAGAAAA

19501 GAAATGAAAC CATGCATGGT CCCCTCGTCA TCACGAGTTT CTGCCATTTG

19551 CAATAGAAAC ACTGAAACAC CTTTCTCTTT GTCACTTAAT TGAGATGCCG

19601 AAGCCACCTC ACACCATGAA CTTCATGAGG TGTAGCACCC AAGGCTTCCA

19651 TAGCCATGCA TACTGAAGAA TGTCTCAAGC TCAGCACCCT ACTTCTGTGA

19701 CGTGTCCCTC ATTCACCTTC CTCTCTTCCC TATAAATAAC CACGCCTCAG

19751 GTTCTCCGCT TCACAACTCA AACATTCTCT CCATTGGTCC TTAAACACTC

19801 ATCAGTCATC ACCATGGACT CCAAAGAATC ATTAACTCCT GGTAGAGAAG

-continued

19851 AAAACCCCAG CAGTGTGCTT GCTCAGGAGA GGGGAGATGT GATGGACTTC

19901 TATAAAACCC TAAGAGGAGG AGCTACTGTG AAGGTTTCTG CGTCTTCACC

19951 CTCACTGGCT GTCGCTTCTC AATCAGACTC CAAGCAGCGA AGACTTTTGG

20001 TTGATTTTCC AAAAGGCTCA GTAAGCAATG CGCAGCAGCC AGATCTGTCC

20051 AAAGCAGTTT CACTCTCAAT GGGACTGTAT ATGGGAGAGA CAGAAACAAA

20101 AGTGATGGGA AATGACCTGG GATTCCCACA GCAGGGCCAA ATCAGCCTTT

20151 CCTCGGGGGA AACAGACTTA AAGCTTTTGG AAGAAAGCAT TGCAAACCTC

20201 AATAGGTCGA CCAGTGTTCC AGAGAACCCC AAGAGTTCAG CATCCACTGC

20251 TGTGTCTGCT GCCCCCACAG CTAGTTCTGC GGCCCCCCCG ACCGATGTCA

20301 GCCTGGGGGA CGAGCTCCAC TTAGACGGCG AGGACGTGGC GATGGCGCAT

20351 GCCGACGCGC TAGACGATTT CGATCTGGAC ATGTTGGGGG ACGGGGATTC

20401 CCCGGGTCCG GGATTTACCC CCCACGACTC CGCCCCCTAC GGCGCTCTGG

20451 ATATGGCCGA CTTCGAGTTT GAGCAGATGT TTACCGATGC CCTTGGAATT

20501 GACGAGTACG GTGGGACTAG CTCCAGCTCC TCAACAGCAA CAACAGGACC

20551 ACCTCCCAAA CTCTGCCTGG TGTGCTCTGA TGAAGCTTCA GGATGTCATT

20601 ATGGAGTCTT AACTTGTGGA AGCTGTAAAG TTTTCTTCAA AAGAGCAGTG

20651 GAAGGACAGC ACAATTACCT ATGTGCTGGA AGGAATGATT GCATCATCGA

20701 TAAAATTCGA AGAAAAAACT GCCCAGCATG CCGCTATCGA AAATGTCTTC

20751 AGGCTGGAAT GAACCTGGAA GCTCGAAAAA CAAAGAAAAA AATAAAAGGA

20801 ATTGCTCGAC AAAGGCCCGA GTGCGTGGTG CCGGAGAACC AGTGTGCAAT

20851 GAAACGGAAA GAGAAAAAGG CGCAGAGGGA AAAAGACAAA TTGCCCGTCA

20901 GTACGACGAC AGTAGACGAT CACATGCCTC CCATCATGCA ATGTGACCCT

20951 CCGCCCCCAG AGGCCGCTAG AATTCTGGAA TGTTTGCAGC ACGAGGTGGT

21001 GCCACGATTC CTGAATGAGA AGCTAATGGA ACAGAACAGA TTGAAGAACG

21051 TGCCCCCCCT CACTGCCAAT CAGAAGTCGT TGATCGCAAG GCTCGTGTGG

21101 TACCAGGAAG GCTATGAACA ACCTTCCGAG GAAGACCTGA AGAGGGTTAC

21151 ACAGTCGGAC GAGGACGACG AAGACTCGGA TATGCCGTTC CGTCAGATTA

-continued

21201 CCGAGATGAC GATTCTCACA GTGCAGCTCA TCGTAGAATT CGCTAAGGGC

21251 CTCCCGGGCT TCGCCAAGAT CTCGCAGTCG GACCAGATCA CGTTATTAAA

21301 GGCGTGCTCA AGTGAGGTGA TGATGCTCCG AGTGGCTCGG CGGTATGACG

21351 CGGCCACCGA CAGCGTACTG TTCGCGAACA ACCAGGCGTA CACTCGCGAC

21401 AACTACCGCA AGGCAGGCAT GGCGTACGTC ATCGAGGACC TGCTGCACTT

21451 CTGTCGGTGC ATGTACTCCA TGATGATGGA TAACGTGCAT TATGCGCTGC

21501 TTACAGCCAT TGTCATCTTC TCAGACCGGC CCGGGCTTGA GCAACCCCTG

21551 TTGGTGGAGG AGATCCAGAG ATATTACCTG AACACGCTAC GGGTGTACAT

21601 CCTGAACCAG AACAGCGCGT CGCCCCGCTG CGCCGTCATC TTCGGCAAGA

21651 TCCTGGGCAT ACTGACGGAG ATCCGCACGC TGGGCATGCA GAACTCCAAC

21701 ATGTGCATCT CCCTCAAGCT GAAGAACAGG AAGCTGCCGC CGTTCCTCGA

21751 GGAGATCTGG GACGTGGCGG ACGTGGCGAC GACGGCGACG CCGGTGGCGG

21801 CGGAGGCGCC GGCGCTCTAG CCCCCGCGCC GCCCGCCCGG CCGCGCGCAC

21851 GTCTAGCGCG CCTCAGGAGA GAACGCTCAT AGACTGGCTA GTTTTAGTGA

21901 AGTGCACGGA CACTGACGTC GGACGTGATC AACCTATTTA TAAGGACTGC

21951 GAATTTTACC ACTTAAGAGG GCACACCCGT ACCCGATTTC GTACGGGAAT

22001 TCCTGCAGCC CGGGGGATCC TTAATTAACT CGAGGAATTC ATCGATTCCG

22051 CGGGTACCGA GCTCGATCCG TCGACCTGCA GATCGTTCAA ACATTTGGCA

22101 ATAAAGTTTC TTAAGATTGA ATCCTGTTGC CGGTCTTGCG ATGATTATCA

22151 TATAATTTCT GTTGAATTAC GTTAAGCATG TAATAATTAA CATGTAATGC

22201 ATGACGTTAT TTATGAGATG GGTTTTTATG ATTAGAGTCC CGCAATTATA

22251 CATTTAATAC GCGATAGAAA ACAAAATATA GCGCGCAAAC TAGGATAAAT

22301 TATCGCGCGC GGTGTCATCT ATGTTACTAG ATCTGGCGCG CCCCTAGGTC

22351 TAGAGTCGAC TGTTTAAACG

Vector pMBXVT1

(SEQ ID NO: 7)

1 GGGGATCCGT ACGTAAGTAC GTACTCAAAA TGCCAACAAA TAAAAAAAAA

51 GTTGCTTTAA TAATGCCAAA ACAAATTAAT AAAACACTTA CAACACCGGA

101 TTTTTTTTAA TTAAAATGTG CCATTTAGGA TAAATAGTTA ATATTTTTAA

-continued

151 TAATTATTTA AAAAGCCGTA TCTACTAAAA TGATTTTTAT TTGGTTGAAA

201 ATATTAATAT GTTTAAATCA ACACAATCTA TCAAAATTAA ACTAAAAAAA

251 AAATAAGTGT ACGTGGTTAA CATTAGTACA GTAATATAAG AGGAAAATGA

301 GAAATTAAGA AATTGAAAGC GAGTCTAATT TTTAAATTAT GAACCTGCAT

351 ATATAAAAGG AAAGAAAGAA TCCAGGAAGA AAAGAAATGA AACCATGCAT

401 GGTCCCCTCG TCATCACGAG TTTCTGCCAT TTGCAATAGA AACACTGAAA

451 CACCTTTCTC TTTGTCACTT AATTGAGATG CCGAAGCCAC CTCACACCAT

501 GAACTTCATG AGGTGTAGCA CCCAAGGCTT CCATAGCCAT GCATACTGAA

551 GAATGTCTCA AGCTCAGCAC CCTACTTCTG TGACGTGTCC CTCATTCACC

601 TTCCTCTCTT CCCTATAAAT AACCACGCCT CAGGTTCTCC GCTTCACAAC

651 TCAAACATTC TCTCCATTGG TCCTTAAACA CTCATCAGTC ATCACCGCGG

701 CCGCGGAATT CATGGCTTCT ATGATATCCT CTTCCGCTGT GACAACAGTC

751 AGCCGTGCCT CTAGGGGGCA ATCCGCCGCA GTGGCTCCAT TCGGCGGCCT

801 CAAATCCATG ACTGGATTCC CAGTGAAGAA GGTCAACACT GACATTACTT

851 CCATTACAAG CAATGGTGGA AGAGTAAAGT GCATGCAGGT GTGGCCTCCA

901 ATTGGAAAGA AGAAGTTTGA GACTCTTTCC TATTTGCCAC CATTGACGAG

951 AGATTCTAGA GTGACTGACG TTGTCATCGT ATCCGCCGCC CGCACCGCGG

1001 TCGGCAAGTT TGGCGGCTCG CTGGCCAAGA TCCCGGCACC GGAACTGGGT

1051 GCCGTGGTCA TCAAGGCCGC GCTGGAGCGC GCCGGCGTCA AGCCGGAGCA

1101 GGTGAGCGAA GTCATCATGG GCCAGGTGCT GACCGCCGGT TCGGGCCAGA

1151 ACCCCGCACG CCAGGCCGCG ATCAAGGCCG GCCTGCCGGC GATGGTGCCG

1201 GCCATGACCA TCAACAAGGT GTGCGGCTCG GGCCTGAAGG CCGTGATGCT

1251 GGCCGCCAAC GCGATCATGG CGGGCGACGC CGAGATCGTG GTGGCCGGCG

1301 GCCAGGAAAA CATGAGCGCC GCCCCGCACG TGCTGCCGGG CTCGCGCGAT

1351 GGTTTCCGCA TGGGCGATGC CAAGCTGGTC GACACCATGA TCGTCGACGG

1401 CCTGTGGGAC GTGTACAACC AGTACCACAT GGGCATCACC GCCGAGAACG

1451 TGGCCAAGGA ATACGGCATC ACACGCGAGG CGCAGGATGA GTTCGCCGTC

-continued

```
1501 GGCTCGCAGA ACAAGGCCGA AGCCGCGCAG AAGGCCGGCA
     AGTTTGACGA

1551 AGAGATCGTC CCGGTGCTGA TCCCGCAGCG CAAGCGCGAC
     CCGGTGGCCT

1601 TCAAGACCGA CGAGTTCGTG CGCCAGGGCG CCACGCTGGA
     CAGCATGTCC

1651 GGCCTCAAGC CCGCCTTCGA CAAGGCCGGC ACGGTGACCG
     CGGCCAACGC

1701 CTCGGGCCTG AACGACGGCG CCGCCGCGGT GGTGGTGATG
     TCGGCGGCCA

1751 AGGCCAAGGA ACTGGGCCTG ACCCCGCTGG CCACGATCAA
     GAGCTATGCC

1801 AACGCCGGTG TCGATCCCAA GGTGATGGGC ATGGGCCCGG
     TGCCGGCCTC

1851 CAAGCGCGCC CTGTCGCGCG CCGAGTGGAC CCCGCAAGAC
     CTGGACCTGA

1901 TGGAGATCAA CGAGGCCTTT GCCGCGCAGG CGCTGGCGGT
     GCACCAGCAG

1951 ATGGGCTGGG ACACCTCCAA GGTCAATGTG AACGGCGGCG
     CCATCGCCAT

2001 CGGCCACCCG ATCGGCGCGT CGGGCTGCCG TATCCTGGTG
     ACGCTGCTGC

2051 ACGAGATGAA GCGCCGTGAC GCGAAGAAGG GCCTGGCCTC
     GCTGTGCATC

2101 GGCGGCGGCA TGGGCGTGGC GCTGGCAGTC GAGCGCAAAT
     AACTCGAGGC

2151 GGCCGCAGCC CTTTTTGTAT GTGCTACCCC ACTTTTGTCT
     TTTTGGCAAT

2201 AGTGCTAGCA ACCAATAAAT AATAATAATA ATAATGAATA
     AGAAAACAAA

2251 GGCTTTAGCT TGCCTTTTGT TCACTGTAAA ATAATAATGT
     AAGTACTCTC

2301 TATAATGAGT CACGAAACTT TTGCGGGAAT AAAAGGAGAA
     ATTCCAATGA

2351 GTTTTCTGTC AAATCTTCTT TTGTCTCTCT CTCTCTCTCT
     TTTTTTTTTT

2401 TCTTTCTTCT GAGCTTCTTG CAAAACAAAA GGCAAACAAT
     AACGATTGGT

2451 CCAATGATAG TTAGCTTGAT CGATGATATC TTTAGGAAGT
     GTTGGCAGGA

2501 CAGGACATGA TGTAGAAGAC TAAAATTGAA AGTATTGCAG
     ACCCAATAGT

2551 TGAAGATTAA CTTTAAGAAT GAAGACGTCT TATCAGGTTC
     TTCATGACTT

2601 AAGCTTAACT TTTGAGGCAG AGCTTGTAAA TTGTAACAGG
     TGAGGTAGAA

2651 AGACGGAAAG TACTTTTAAT AATAAAAGGT TTGAAAAATT
     AAGAAAAGAA

2701 GAAGAAAATA TTTTGTGAGT GCACGCGATG GATCTAATCC
     TTCCATGAAA

2751 AAGAATATCA AGAATAACAA AAATTGACAA AATCAGCGAA
     TACTTCACCC

2801 AAAAGTCTAC ACAATAATAA ATGCTAAATC ACATATAATT
     TGTGATGCAT
```

-continued

```
2851 AACGCATTAC GCTATCGTAA TCCTTTACAA CAAGCAAGAA
     CGTCATCCCA

2901 GAATCTCAAC TCAAATCAAA ACCGTTCATT CATAAATAAA
     AAATATTCTT

2951 ACATTCTTTT GCAAATAGAA CCTTTGCCAA ATTGAAATAA
     CAAACTCTAG

3001 GTATTTGTCA AATTAACTTA CCAACTTCTC GTTATATAAT
     TTTAGATTTA

3051 TAATCATGTC TATAAATTAT TTCTATACAC TCTCTCTCAA
     ATTTGACCTT

3101 TACATTCTGT GATTTATTTG AACAGAATAA ATCACTGTAA
     AACTAAACAA

3151 CTCTTTAAAA AAGGTAAATT AGGAAAAGTC GAAATCAATA
     AATTATAAAT

3201 CAATCCCTAG AAAACTGCAA GATAATATTC TTACCAAAAT
     CATTTAAATA

3251 AATTTGTAAG TTTTTTCTTT ATACCAATTT TCTGAGACCC
     AGAGACATTC

3301 TTAAATTCAT AACAACGGTT TTAAGTATCA GAGTATAACA
     TCTTTGTATA

3351 AATAGATTTT TGAACGTTCA ATAACTAACA CGTCAGTTTT
     TGTTTCCACG

3401 TTGTACGTTT AATAACAATA AATGCGTGAG TTAGATTACT
     AATCAGAAGT

3451 TAGAAGTGTA CAAGACTAAC TTTATACAGA AATATATTGT
     TTCAGACTGC

3501 ACTTTATGGT GCGTAGCACC TCAAAACTCT TACCTTTCGC
     ATACATTTTC

3551 ACACTTCATC CAAACCTTTC GAAAAGTCAC TTCCCTTATA
     TTAAAGGACT

3601 ATGATATAAA AAAGACTATA TGTGTTACTA ATTTATTGGT
     TTGTATATTT

3651 GTAATAAATC GTTCCATCAA GAGGAGCTAT CACATATTGA
     GAACAGTAAA

3701 AAAAAAAAAA AGTTGGTAAA AAAACATTTT CTTATATTAT
     ATCATAAAAT

3751 CAGTTACCAT AGTATTTTAG AGTTTTCAGA ATAATGCTTC
     ACCCAACTTG

3801 CAACTCATTG TGCCTCAAAA CAGGACGTAA CCATGTTACT
     CACTCTCCTG

3851 CACAACCCCT TGTTAAACTG ATAGCGTGAT CAGCATGCAA
     GAGAAAGATG

3901 ATTCTTGAAG CATACGATAA CAGATTGAAT GTGACAAAAA
     GTTTGTGTCT

3951 CAGCTTCAGG GTCGGCACCT AATACAAAAG GAAAATTTGT
     CAGGTTTCCT

4001 TCCGTAGTTT CATTCACTAT TATTGAATCC TTTGGCTACC
     ATTCTTGAGA

4051 AACACAAACA CTTCTTATAT CTGTTCTACA CAATTCTCTG
     AGTGCGTGCC

4101 ACAGTTTGGT ATCTTCATGA TTGCTCATTG TTCATGCCCA
     TAAGGAACAT

4151 GTAACTTCCT CATTTATTTA TTATTGCTTT TGTTTTCTTC
     TCACTAGTTA
```

-continued

4201 ACTTTCGTTT CCCTATATAA ACCCTCCTTT GTTCCCTTCC CTTCCCATCT

4251 TCCATTTATT GATTCCAAAC ACAAACCTCG AGAAAATGGC TTCTATGATA

4301 TCCTCTTCCG CTGTGACAAC AGTCAGCCGT GCCTCTAGGG GGCAATCCGC

4351 CGCAGTGGCT CCATTCGGCG GCCTCAAATC CATGACTGGA TTCCCAGTGA

4401 AGAAGGTCAA CACTGACATT ACTTCCATTA CAAGCAATGG TGGAAGAGTA

4451 AAGTGCATGC AGGTGTGGCC TCCAATTGGA AAGAAGAAGT TTGAGACTCT

4501 TTCCTATTTG CCACCATTGA CGAGAGATTC TAGAGTGCTC TACCAATTGC

4551 ATGAGTTCCA GCGCTCGATC CTGCACCCGC TGACCGCGTG GGCCCAGGCG

4601 ACCGCCAAGA CCTTCACCAA CCCCCTCAGC CCGCTCTCGC TGGTTCCCGG

4651 CGCACCCCGC CTGGCTGCCG GCTATGAACT GCTGTACCGG CTCGGCAAGG

4701 AATACGAAAA GCCGGCATTC GACATCAAGT CGGTGCGCTC CAACGGGCGC

4751 GACATCCCCA TCGTCGAGCA GACCGTGCTT GAAAAGCCGT TCTGCAAGCT

4801 GGTGCGCTTC AAGCGCTATG CCGACGACCC GGAGACCATC AAGCTGCTCA

4851 AGGATGAGCC GGTGGTGCTG GTGGCCGCGC CGCTGTCGGG CCACCATGCC

4901 ACGCTGCTGC GCGACACGGT GCGCACGCTG CTCCAGGACC ACAAGGTCTA

4951 CGTCACCGAC TGGATCGACG CACGCATGGT GCCGGTCGAG GAAGGCGCGT

5001 TCCACCTGTC GGACTACATC TACTACATCC AGGAGTTCAT CCGCCATATC

5051 GGCGCCGAGA ACCTGCATGT GATCTCGGTA TGCCAGCCCA CCGTGCCGGT

5101 GCTGGCCGCG ATCTCGCTGA TGGCCTCGGC CGGCGAGAAG ACGCCGCGCA

5151 CCATGACCAT GATGGGCGGC CCGATCGACG CCCGCAAGAG CCCCACGGCG

5201 GTCAACTCGC TGGCGACCAA CAAGTCGTTC GAGTGGTTCG AGAACAACGT

5251 CATCTACACC GTGCCGGCCA ACTACCCCGG CCACGGCCGC CGCGTCTACC

5301 CAGGCTTTTT GCAGCATGCC GGTTTCGTGG CGATGAACCC GGACCGGCAC

5351 CTTTCCTCGC ACTATGACTT CTACCTGAGC CTGGTCGAGG GCGATGCGGA

5401 TGACGCCGAA GCCCACGTGC GCTTCTACGA CGAATACAAC GCGGTGCTCG

5451 ACATGGCCGC CGAGTACTAC CTCGACACCA TCCGCGAGGT GTTCCAGGAG

5501 TTCCGCCTGG CCAACGGCAC CTGGGCCATC GACGGCAATC CGGTCCGGCC

5551 GCAGGACATC AAGAGCACCG CGCTGATGAC CGTCGAGGGC GAACTGGACG

5601 ACATCTCGGG CGCGGGCCAG ACCGCAGCGG CGCACGACCT GTGCGCCGGC

5651 ATCCCGAAAA TCCGCAAGCA GCACCTGAAC GCGGCACACT GCGGCCACTA

5701 CGGCATCTTC TCGGGCCGGC GCTGGCGCGA AGAGATATAC CCGCAGCTGC

5751 GCGACTTTAT CCGCAAGTAC CACCAGGCCT CGGCCACCAG GTAAGAGCTC

5801 GAATTGATCC TCTAGAGCTT TCGTTCGTAT CATCGGTTTC GACAACGTTC

5851 GTCAAGTTCA ATGCATCAGT TTCATTGCGC ACACACCAGA ATCCTACTGA

5901 GTTCGAGTAT TATGGCATTG GGAAAACTGT TTTTCTTGTA CCATTTGTTG

5951 TGCTTGTAAT TTACTGTGTT TTTTATTCGG TTTTCGCTAT CGAACTGTGA

6001 AATGGAAATG GATGGAGAAG AGTTAATGAA TGATATGGTC CTTTTGTTCA

6051 TTCTCAAATT AATATTATTT GTTTTTTCTC TTATTTGTTG TGTGTTGAAT

6101 TTGAAATTAT AAGAGATATG CAAACATTTT GTTTTGAGTA AAAATGTGTC

6151 AAATCGTGGC CTCTAATGAC CGAAGTTAAT ATGAGGAGTA AAACACTTGT

6201 AGTTGTACCA TTATGCTTAT TCACTAGGCA ACAAATATAT TTTCAGACCT

6251 AGAAAAGCTG CAAATGTTAC TGAATACAAG TATGTCCTCT TGTGTTTTAG

6301 ACATTTATGA ACTTTCCTTT ATGTAATTTT CCAGAATCCT TGTCAGATTC

6351 TAATCATTGC TTTATAATTA TAGTTATACT CATGGATTTG TAGTTGAGTA

6401 TGAAAATATT TTTTAATGCA TTTTATGACT TGCCAATTGA TTGACAACAT

6451 GCATCAGTCG ACCTGAGGTA ATTATAACCC GGGCCCTATA TATGGATCCA

6501 ACTTTTGAGG CAGAGCTTGT AAATTGTAAC ACCTGAGGTA GAAAGACGGA

6551 AAGTACTTTT AATAATAAAA GGTTTGAAAA ATTAAGAAAA GAAGAAGAAA

6601 ATATTTTGTG AGTGCACGCG ATGGATCTAA TCCTTCCATG AAAAAGAATA

6651 TCAAGAATAA CAAAAATTGA CAAAATCAGC GAATACTTCA CCCAAAAGTC

6701 TACACAATAA TAAATGCTAA ATCACATATA ATTTGTGATG CATAACGCAT

6751 TACGCTATCG TAATCCTTTA CAACAAGCAA GAACGTCATC CCAGAATCTC

6801 AACTCAAATC AAAACCGTTC ATTCATAAAT AAAAAATATT CTTACATTCT

6851 TTTGCAAATA GAACCTTTGC CAAATTGAAA TAACAAACTC TAGGTATTTG

-continued

6901 TCAAATTAAC TTACCAACTT CTCGTTATAT AATTTTAGAT TTATAATCAT

6951 GTCTATAAAT TATTTCTATA CACTCTCTCT CAAATTTGAC CTTTACATTC

7001 TGTGATTTAT TTGAACAGAA TAAATCACTG TAAAACTAAA CAACTCTTTA

7051 AAAAAGGTAA ATTAGGAAAA GTCGAAATCA ATAAATTATA AATCAATCCC

7101 TAGAAAACTG CAAGATAATA TTCTTACCAA AATCATTTAA ATAAATTTGT

7151 AAGTTTTTTC TTTATACCAA TTTTCTGAGA CCCAGAGACA TTCTTAAATT

7201 CATAACAACG GTTTTAAGTA TCAGAGTATA ACATCTTTGT ATAAATAGAT

7251 TTTTGAACGT TCAATAACTA ACACGTCAGT TTTTGTTTCC ACGTTGTACG

7301 TTTAATAACA ATAAATGCGT GAGTTAGATT ACTAATCAGA AGTTAGAAGT

7351 GTACAAGACT AACTTTATAC AGAAATATAT TGTTTCAGAC TGCACTTTAT

7401 GGTGCGTAGC ACCTCAAAAC TCTTACCTTT CGCATACATT TTCACACTTC

7451 ATCCAAACCT TTCGAAAAGT CACTTCCCTT ATATTAAAGG ACTATGATAT

7501 AAAAAAGACT ATATGTGTTA CTAATTTATT GGTTTGTATA TTTGTAATAA

7551 ATCGTTCCAT CAAGAGGAGC TATCACATAT TGAGAACAGT AAAAAAAAAA

7601 AAAAGTTGGT AAAAAAACAT TTTCTTATAT TATATCATAA AATCAGTTAC

7651 CATAGTATTT TAGAGTTTTC AGAATAATGC TTCACCCAAC TTGCAACTCA

7701 TTGTGCCTCA AAACAGGACG TAACCATGTT ACTCACTCTC CTGCACAACC

7751 CCTTGTTAAA CTGATAGCGT GATCAGCATG CAAGAGAAAG ATGATTCTTG

7801 AAGCATACGA TAACAGATTG AATGTGACAA AAAGTTTGTG TCTCAGCTTC

7851 AGGGTCGGCA CCTAATACAA AAGGAAAATT TGTCAGGTTT CCTTCCGTAG

7901 TTTCATTCAC TATTATTGAA TCCTTTGGCT ATGATTCTTG AGAAACACAA

7951 ACACTTCTTA TATCTGTTCT ACACAATTCT CTGAGTGCGT GCCACAGTTT

8001 GAATACTTCA TGATTGCTCA TTGTTCATGC CCATAAGGAA CATGTAACTT

8051 CCTCATTTAT TTATTATTGC TTTTGTTTTC TTCTCACTAG TTAACTTTCG

8101 TTTCCCTATA TAAACCCTCC TTTGTTCCCT TCCCTTCCCA TCTTCCATTT

8151 ATTGATTCCA AACACAAACC TCGAGAAAAT GGCTTCTATG ATATCCTCTT

8201 CCGCTGTGAC AACAGTCAGC CGTGCCTCTA GGGGGCAATC CGCCGCAGTG

8251 GCTCCATTCG GCGGCCTCAA ATCCATGACT GGATTCCCAG TGAAGAAGGT

8301 CAACACTGAC ATTACTTCCA TTACAAGCAA TGGTGGAAGA GTAAAGTGCA

8351 TGCAGGTGTG GCCTCCAATT GGAAAGAAGA AGTTTGAGAC TCTTTCCTAT

8401 TTGCCACCAT TGACGAGAGA TTCTAGAGTG CTCAAAGGAA AAGTCGCAGT

8451 CGTCACCGGT TCCACCAGCG GGATCGGCCT GGGTATCGCC ACCGCGCTGG

8501 CCGCGCAGGG CGCCGATATC GTCCTGAACG GCTTCGGCGA CGCCGCCGAG

8551 ATCGAAAAGG TGCGCGCCGG CCTGGCCGCC CAGCATGGCG TCAAGGTGCT

8601 GTACGACGGC GCCGACCTGT CCAAGGGCGA GGCCGTGCGC GGCCTGGTGG

8651 ACAACGCGGT GCGCCAGATG GGCCGCATCG ACATCCTGGT CAACAACGCC

8701 GGCATCCAGC ACACCGCGCT GATCGAGGAC TTTCCCACCG AAAAATGGGA

8751 CGCCATCCTG GCGCTGAACC TGTCGGCCGT GTTCCACGGC ACCGCCGCCG

8801 CGCTGCCGCA CATGAAGAAG CAGGGCTTCG GCCGCATCAT CAACATCGCC

8851 TCGGCGCACG GCCTGGTGGC CTCGGCCAAC AAGTCGGCCT ACGTCGCCGC

8901 CAAGCACGGC GTGGTGGGCT TCACCAAGGT GACCGCGCTG GAAACCGCCG

8951 GCCAGGGCAT CACCGCCAAC GCCATCTGCC CAGGCTGGGT GCGCACTCCG

9001 CTGGTCGAAA AGCAGATATC GGCGCTGGCC GAAAAGAACG GCGTGGACCA

9051 GGAAACCGCC GCGCGCGAAC TGCTCAGCGA AAAGCAGCCG TCGCTGCAAT

9101 TCGTCACGCC CGAACAACTG GGCGGCACGG CCGTCTTCCT GGCCTCCGAT

9151 GCCGCCGCGC AAATCACCGG CACGACCGTC TCCGTCGATG GCGGCTGGAC

9201 GGCGCGCTGA GAGCTCGCTT TCGTTCGTAT CATCGGTTTC GACAACGTTC

9251 GTCAAGTTCA ATGCATCAGT TTCATTGCGC ACACACCAGA ATCCTACTGA

9301 GTTCGAGTAT TATGGCATTG GGAAAACTGT TTTTCTTGTA CCATTTGTTG

9351 TGCTTGTAAT TTACTGTGTT TTTTATTCGG TTTTCGCTAT CGAACTGTGA

9401 AATGGAAATG GATGGAGAAG AGTTAATGAA TGATATGGTC CTTTTGTTCA

9451 TTCTCAAATT AATATTATTT GTTTTTTCTC TTATTTGTTG TGTGTTGAAT

9501 TTGAAATTAT AAGAGATATG CAAACATTTT GTTTTGAGTA AAAATGTGTC

9551 AAATCGTGGC CTCTAATGAC CGAAGTTAAT ATGAGGAGTA AAACACTTGT

-continued

```
9601 AGTTGTACCA TTATGCTTAT TCACTAGGCA ACAAATATAT
     TTTCAGACCT

9651 AGAAAAGCTG CAAATGTTAC TGAATACAAG TATGTCCTCT
     TGTGTTTTAG

9701 ACATTTATGA ACTTTCCTTT ATGTAATTTT CCAGAATCCT
     TGTCAGATTC

9751 TAATCATTGC TTTATAATTA TAGTTATACT CATGGATTTG
     TAGTTGAGTA

9801 TGAAAATATT TTTTAATGCA TTTTATGACT TGCCAATTGA
     TTGACAACAT

9851 GCATCAGCTA GTAGAAGGTA ATTATCCAAG ATGTAGCATC
     AAGAATCCAA

9901 TGTTTACGGG AAAAACTATG GAAGTATTAT GTGAGCTCAG
     CAAGAAGCAG

9951 ATCAATATGC GGCACATATG CAACCTATGT TCAAAAATGA
     AGAATGTACA

10001 GATACAAGAT CCTATACTGC CAGAATACGA AGAAGAATAC
      GTAGAAATTG

10051 AAAAAGAAGA ACCAGGCGAA GAAAAGAATC TTGAAGACGT
      AAGCACTGAC

10101 GACAACAATG AAAAGAAGAA GATAAGGTCG GTGATTGTGA
      AAGAGACATA

10151 GAGGACACAT GTAAGGTGGA AAATGTAAGG GCGGAAAGTA
      ACCTTATCAC

10201 AAAGGAATCT TATCCCCCAC TACTTATCCT TTTATATTTT
      TCCGTGTCAT

10251 TTTTGCCCTT GAGTTTTCCT ATATAAGGAA CCAAGTTCGG
      CATTTGTGAA

10301 AACAAGAAAA AATTGGTGTA AGCTATTTTC TTTGAAGTAC
      TGAGGATACA

10351 ACTTCAGAGA AATTTGTAAG AAAGTGGATC GAAACCATGG
      CCTCCTCCGA

10401 GAACGTCATC ACCGAGTTCA TGCCCTTCAA GGTGCGCATG
      CAGGGCACCG

10451 TGAACGGCCA CGAGTTCGAG ATCGAGGGCG AGGGCGAGGG
      CCGCCCCTAC

10501 GAGGGCCACA ACACCGTGAA GCTGAAGGTG ACCAAGGGCG
      GCCCCCTGCC

10551 CTTCGCCTGG GACATCCTGT CCCCCCAGTT CCAGTACGGC
      TCCAAGGTGT

10601 ACGTGAAGCA CCCCGCCGAC ATCCCCGACT ACAAGAAGCT
      GTCCTTCCCC

10651 GAGGGCTTCA AGTGGGAGCG CGTGATGAAC TTCGAGGACG
      GCGGCGTGGC

10701 GACCGTGACC CAGGACTCCT CCCTGCAGGA CGGCTGCTTC
      ATCTACAAGG

10751 TGAAGTTCAT CGGCGTGAAC TTCCCCTCCG ACGGCCCCGT
      GATGCAGAAG

10801 AAGACCATGG GCTGGGAGGC CTCCACCGAG CGCCTGTACC
      CCCGCGACGG

10851 CGTGCTGAAG GGCGAGACCC ACAAGGCCCT GAAGCTGAAG
      GACGGCGGCC

10901 ACTACCTGGT GGAGTTCAAG TCCATCTACA TGGCCAAGAA
      GCCCGTGCAG
```

-continued

```
10951 CTGCCCGGCT ACTACTACGT GGACGCCAAG CTGGACATCA
      CCTCCCACAA

11001 CGAGGACTAC ACCATCGTGG AGCAGTACGA GCGCACCGAG
      GGCCGCCACC

11051 ACCTGTTCCT GGTACCAATG AGCTCTGTCC AACAGTCTCA
      GGGTTAATGT

11101 CTATGTATCT TAAATAATGT TGTCGGCGAT CGTTCAAACA
      TTTGGCAATA

11151 AAGTTTCTTA AGATTGAATC CTGTTGCCGG TCTTGCGATG
      ATTATCATAT

11201 AATTTCTGTT GAATTACGTT AAGCATGTAA TAATTAACAT
      GTAATGCATG

11251 ACGTTATTTA TGAGATGGGT TTTTATGATT AGAGTCCCGC
      AATTATACAT

11301 TTAATACGCG ATAGAAAACA AAATATAGCG CGCAAACTAG
      GATAAATTAT

11351 CGCGCGCGGT GTCATCTATG TTACTAGATC GGGAATTAAA
      CTATCAGTGT

11401 TTGACAGGAT ATATTGGCGG GTAAACCTAA GAGAAAAGAG
      CGTTTATTAG

11451 AATAACGGAT ATTTAAAAGG GCGTGAAAAG GTTTATCCGT
      TCGTCCATTT

11501 GTATGTGCAT GCCAACCACA GGGTTCCCCT CGGGATCAAA
      GTACTTTGAT

11551 CCAACCCCTC CGCTGCTATA GTGCAGTCGG CTTCTGACGT
      TCAGTGCAGC

11601 CGTCTTCTGA AAACGACATG TCGCACAAGT CCTAAGTTAC
      GCGACAGGCT

11651 GCCGCCCTGC CCTTTTCCTG GCGTTTTCTT GTCGCGTGTT
      TTAGTCGCAT

11701 AAAGTAGAAT ACTTGCGACT AGAACCGGAG ACATTACGCC
      ATGAACAAGA

11751 GCGCCGCCGC TGGCCTGCTG GGCTATGCCC GCGTCAGCAC
      CGACGACCAG

11801 GACTTGACCA ACCAACGGGC CGAACTGCAC GCGGCCGGCT
      GCACCAAGCT

11851 GTTTTCCGAG AAGATCACCG GCACCAGGCG CGACCGCCCG
      GAGCTGGCCA

11901 GGATGCTTGA CCACCTACGC CCTGGCGACG TTGTGACAGT
      GACCAGGCTA

11951 GACCGCCTGG CCCGCAGCAC CCGCGACCTA CTGGACATTG
      CCGAGCGCAT

12001 CCAGGAGGCC GGCGCGGGCC TGCGTAGCCT GGCAGAGCCG
      TGGGCCGACA

12051 CCACCACGCC GGCCGGCCGC ATGGTGTTGA CCGTGTTCGC
      CGGCATTGCC

12101 GAGTTCGAGC GTTCCCTAAT CATCGACCGC ACCCGGAGCG
      GGCGCGAGGC

12151 CGCCAAGGCC CGAGGCGTGA AGTTTGGCCC CCGCCCTACC
      CTCACCCCGG

12201 CACAGATCGC GCACGCCCGC GAGCTGATCG ACCAGGAAGG
      CCGCACCGTG

12251 AAAGAGGCGG CTGCACTGCT TGGCGTGCAT CGCTCGACCC
      TGTACCGCGC
```

-continued

12301 ACTTGAGCGC AGCGAGGAAG TGACCCCCAC CGAGGCCAGG CGGCGCGGTG

12351 CCTTCCGTGA GGACGCATTG ACCGAGGCCG ACGCCCTGGC GGCCGCCGAG

12401 AATGAACGCC AAGAGGAACA AGCATGAAAC CGCACCAGGA CGGCCAGGAC

12451 GAACCGTTTT TCATTACCGA AGAGATCGAG GCGGAGATGA TCGCGGCCGG

12501 GTACGTGTTC GAGCCGCCCG CGCACGTCTC AACCGTGCGG CTGCATGAAA

12551 TCCTGGCCGG TTTGTCTGAT GCCAAGCTGG CGGCCTGGCC GGCCAGCTTG

12601 GCCGCTGAAG AAACCGAGCG CCGCCGTCTA AAAAGGTGAT GTGTATTTGA

12651 GTAAAACAGC TTGCGTCATG CGGTCGCTGC GTATATGATG CGATGAGTAA

12701 ATAAACAAAT ACGCAAGGGG AACGCATGAA GGTTATCGCT GTACTTAACC

12751 AGAAAGGCGG GTCAGGCAAG ACGACCATCG CAACCCATCT AGCCCGCGCC

12801 CTGCAACTCG CCGGGGCCGA TGTTCTGTTA GTCGATTCCG ATCCCCAGGG

12851 CAGTGCCCGC GATTGGGCGG CCGTGCGGGA AGATCAACCG CTAACCGTTG

12901 TCGGCATCGA CCGCCCGACG ATTGACCGCG ACGTGAAGGC CATCGGCCGG

12951 CGCGACTTCG TCGGCATCGA CGGAGCGCCC CAGGCGGCGG ACTTGGCTGT

13001 GTCCGCGATC AAGGCAGCCG ACTTCGTGCT GATTCCGGTG CAGCCAAGCC

13051 CTTACGACAT ATGGGCCACC GCCGACCTGG TGGAGCTGGT TAAGCAGCGC

13101 ATTGAGGTCA CGGATGGAAG GCTACAAGCG GCCTTTGTCG TGTCGCGGGC

13151 GATCAAAGGC ACGCGCATCG GCGGTGAGGT TGCCGAGGCG CTGGCCGGGT

13201 ACGAGCTGCC CATTCTTGAG TCCCGTATCA CGCAGCGCGT GAGCTACCCA

13251 GGCACTGCCG CCGCCGGCAC AACCGTTCTT GAATCAGAAC CCGAGGGCGA

13301 CGCTGCCCGC GAGGTCCAGG CGCTGGCCGC TGAAATTAAA TCAAAACTCA

13351 TTTGAGTTAA TGAGGTAAAG AGAAAATGAG CAAAAGCACA AACACGCTAA

13401 GTGCCGGCCG TCCGAGCGCA CGCAGCAGCA AGGCTGCAAC GTTGGCCAGC

13451 CTGGCAGACA CGCCAGCCAT GAAGCGGGTC AACTTTCAGT TGCCGGCGGA

13501 GGATCACACC AAGCTGAAGA TGTACGCGGT ACGCCAAGGC AAGACCATTA

13551 CCGAGCTGCT ATCTGAATAC ATCGCGCAGC TACCAGAGTA AATGAGCAAA

13601 TGAATAAATG AGTAGATGAA TTTTAGCGGC TAAAGGAGGC GGCATGGAAA

-continued

13651 ATCAAGAACA ACCAGGCACC GACGCCGTGG AATGCCCCAT GTGTGGAGGA

13701 ACGGGCGGTT GGCCAGGCGT AAGCGGCTGG GTTGTCTGCC GGCCCTGCAA

13751 TGGCACTGGA ACCCCCAAGC CCGAGGAATC GGCGTGACGG TCGCAAACCA

13801 TCCGGCCCGG TACAAATCGG CGCGGCGCTG GGTGATGACC TGGTGGAGAA

13851 GTTGAAGGCC GCGCAGGCCG CCCAGCGGCA ACGCATCGAG GCAGAAGCAC

13901 GCCCCGGTGA ATCGTGGCAA GCGGCCGCTG ATCGAATCCG CAAAGAATCC

13951 CGGCAACCGC CGGCAGCCGG TGCGCCGTCG ATTAGGAAGC CGCCCAAGGG

14001 CGACGAGCAA CCAGATTTTT TCGTTCCGAT GCTCTATGAC GTGGGCACCC

14051 GCGATAGTCG CAGCATCATG GACGTGGCCG TTTTCCGTCT GTCGAAGCGT

14101 GACCGACGAG CTGGCGAGGT GATCCGCTAC GAGCTTCCAG ACGGGCACGT

14151 AGAGGTTTCC GCAGGGCCGG CCGGCATGGC CAGTGTGTGG GATTACGACC

14201 TGGTACTGAT GGCGGTTTCC CATCTAACCG AATCCATGAA CCGATACCGG

14251 GAAGGGAAGG GAGACAAGCC CGGCCGCGTG TTCCGTCCAC ACGTTGCGGA

14301 CGTACTCAAG TTCTGCCGGC GAGCCGATGG CGGAAAGCAG AAAGACGACC

14351 TGGTAGAAAC CTGCATTCGG TTAAACACCA CGCACGTTGC CATGCAGCGT

14401 ACGAAGAAGG CCAAGAACGG CCGCCTGGTG ACGGTATCCG AGGGTGAAGC

14451 CTTGATTAGC CGCTACAAGA TCGTAAAGAG CGAAACCGGG CGGCCCGAGT

14501 ACATCGAGAT CGAGCTAGCT GATTGGATGT ACCGCGAGAT CACAGAAGGC

14551 AAGAACCCGG ACGTGCTGAC GGTTCACCCC GATTACTTTT TGATCGATCC

14601 CGGCATCGGC CGTTTTCTCT ACCGCCTGGC ACGCCGCGCC GCAGGCAAGG

14651 CAGAAGCCAG ATGGTTGTTC AAGACGATCT ACGAACGCAG TGGCAGCGCC

14701 GGAGAGTTCA AGAAGTTCTG TTTCACCGTG CGCAAGCTGA TCGGGTCAAA

14751 TGACCTGCCG GAGTACGATT TGAAGGAGGA GGCGGGGCAG GCTGGCCCGA

14801 TCCTAGTCAT GCGCTACCGC AACCTGATCG AGGGCGAAGC ATCCGCCGGT

14851 TCCTAATGTA CGGAGCAGAT GCTAGGGCAA ATTGCCCTAG CAGGGGAAAA

14901 AGGTCGAAAA GGTCTCTTTC CTGTGGATAG CACGTACATT GGGAACCCAA

14951 AGCCGTACAT TGGGAACCGG AACCCGTACA TTGGGAACCC AAAGCCGTAC

-continued

15001 ATTGGGAACC GGTCACACAT GTAAGTGACT GATATAAAAG AGAAAAAAGG

15051 CGATTTTTCC GCCTAAAACT CTTTAAAACT TATTAAAACT CTTAAAACCC

15101 GCCTGGCCTG TGCATAACTG TCTGGCCAGC GCACAGCCGA AGAGCTGCAA

15151 AAAGCGCCTA CCCTTCGGTC GCTGCGCTCC CTACGCCCCG CCGCTTCGCG

15201 TCGGCCTATC GCGGCCGCTG GCCGCTCAAA AATGGCTGGC CTACGGCCAG

15251 GCAATCTACC AGGGCGCGGA CAAGCCGCGC CGTCGCCACT CGACCGCCGG

15301 CGCCCACATC AAGGCACCCT GCCTCGCGCG TTTCGGTGAT GACGGTGAAA

15351 ACCTCTGACA CATGCAGCTC CCGGAGACGG TCACAGCTTG TCTGTAAGCG

15401 GATGCCGGGA GCAGACAAGC CCGTCAGGGC GCGTCAGCGG GTGTTGGCGG

15451 GTGTCGGGGC GCAGCCATGA CCCAGTCACG TAGCGATAGC GGAGTGTATA

15501 CTGGCTTAAC TATGCGGCAT CAGAGCAGAT TGTACTGAGA GTGCACCATA

15551 TGCGGTGTGA AATACCGCAC AGATGCGTAA GGAGAAAATA CCGCATCAGG

15601 CGCTCTTCCG CTTCCTCGCT CACTGACTCG CTGCGCTCGG TCGTTCGGCT

15651 GCGGCGAGCG GTATCAGCTC ACGCCAAGGC GGTAATACGG TTATCCACAG

15701 AATCAGGGGA TAACGCAGGA AAGAACATGT GAGCAAAAGG CCAGCAAAAG

15751 GCCAGGAACC GTAAAAAGGC CGCGTTGCTG GCGTTTTTCC ATAGGCTCCG

15801 CCCCCCTGAC GAGCATCACA AAAATCGACG CTCAAGTCAG AGGTGGCGAA

15851 ACCCGACAGG ACTATAAAGA TACCAGGCGT TTCCCCCTGG AAGCTCCCTC

15901 GTGCGCTCTC CTGTTCCGAC CCTGCCGCTT ACCGGATACC TGTCCGCCTT

15951 TCTCCCTTCG GGAAGCGTGG CGCTTTCTCA TAGCTCACGC TGTAGGTATC

16001 TCAGTTCGGT GTAGGTCGTT CGCTCCAAGC TGGGCTGTGT GCACGAACCC

16051 CCCGTTCAGC CCGACCGCTG CGCCTTATCC GGTAACTATC GTCTTGAGTC

16101 CAACCCGGTA AGACACGACT TATCGCCACT GGCAGCAGCC ACTGGTAACA

16151 GGATTAGCAG AGCGAGGTAT GTAGGCGGTG CTACAGAGTT CTTGAAGTGG

16201 TGGCCTAACT ACGGCTACAC TAGAAGGACA GTATTTGGTA TCTGCGCTCT

16251 GCTGAAGCCA GTTACCTTCG GAAAAAGAGT TGGTAGCTCT TGATCCGGCA

16301 AACAAACCAC CGCTGGTAGC GGTGGTTTTT TTGTTTGCAA GCAGCAGATT

-continued

16351 ACGCGCAGAA AAAAAGGATC TCAAGAAGAT CCTTTGATCT TTTCTACGGG

16401 GTCTGACGCT CAGTGGAACG AAAACTCACG TTAAGGGATT TTGGTCATGC

16451 ATTCTAGGTA CTAAAACAAT TCATCCAGTA AAATATAATA TTTTATTTTC

16501 TCCCAATCAG GCTTGATCCC CAGTAAGTCA AAAAATAGCT CGACATACTG

16551 TTCTTCCCCG ATATCCTCCC TGATCGACCG GACGCAGAAG GCAATGTCAT

16601 ACCACTTGTC CGCCCTGCCG CTTCTCCCAA GATCAATAAA GCCACTTACT

16651 TTGCCATCTT TCACAAAGAT GTTGCTGTCT CCCAGGTCGC CGTGGGAAAA

16701 GACAAGTTCC TCTTCGGGCT TTTCCGTCTT TAAAAAATCA TACAGCTCGC

16751 GCGGATCTTT AAATGGAGTG TCTTCTTCCC AGTTTTCGCA ATCCACATCG

16801 GCCAGATCGT TATTCAGTAA GTAATCCAAT TCGGCTAAGC GGCTGTCTAA

16851 GCTATTCGTA TAGGGACAAT CCGATATGTC GATGGAGTGA AAGAGCCTGA

16901 TGCACTCCGC ATACAGCTCG ATAATCTTTT CAGGGCTTTG TTCATCTTCA

16951 TACTCTTCCG AGCAAAGGAC GCCATCGGCC TCACTCATGA GCAGATTGCT

17001 CCAGCCATCA TGCCGTTCAA AGTGCAGGAC CTTTGGAACA GGCAGCTTTC

17051 CTTCCAGCCA TAGCATCATG TCCTTTTCCC GTTCCACATC ATAGGTGGTC

17101 CCTTTATACC GGCTGTCCGT CATTTTTAAA TATAGGTTTT CATTTTCTCC

17151 CACCAGCTTA TATACCTTAG CAGGAGACAT TCCTTCCGTA TCTTTTACGC

17201 AGCGGTATTT TTCGATCAGT TTTTTCAATT CCGGTGATAT TCTCATTTTA

17251 GCCATTTATT ATTTCCTTCC TCTTTTCTAC AGTATTTAAA GATACCCCAA

17301 GAAGCTAATT ATAACAAGAC GAACTCCAAT TCACTGTTCC TTGCATTCTA

17351 AAACCTTAAA TACCAGAAAA CAGCTTTTTC AAAGTTGTTT TCAAAGTTGG

17401 CGTATAACAT AGTATCGACG GAGCCGATTT TGAAACCGCG GTGATCACAG

17451 GCAGCAACGC TCTGTCATCG TTACAATCAA CATGCTACCC TCCGCGAGAT

17501 CATCCGTGTT TCAAACCCGG CAGCTTAGTT GCCGTTCTTC CGAATAGCAT

17551 CGGTAACATG AGCAAAGTCT GCCGCCTTAC AACGGCTCTC CCGCTGACGC

17601 CGTCCCGGAC TGATGGGCTG CCTGTATCGA GTGGTGATTT TGTGCCGAGC

17651 TGCCGGTCGG GGAGCTGTTG GCTGGCTGGT GGCAGGATAT ATTGTGGTGT

-continued

17701 AAACAAATTG ACGCTTAGAC AACTTAATAA CACATTGCGG ACGTTTTTAA

17751 TGTACTGAAT TAACGCCGAA TTAATTCCTA GGCCACCATG TTGGGCCCGG

17801 GGCGCGCCGT ACGTAGTGTT TATCTTTGTT GCTTTTCTGA ACAATTTATT

17851 TACTATGTAA ATATATTATC AATGTTTAAT CTATTTTAAT TTGCACATGA

17901 ATTTTCATTT TATTTTTACT TTACAAAACA AATAAATATA TATGCAAAAA

17951 AATTTACAAA CGATGCACGG GTTACAAACT AATTTCATTA AATGCTAATG

18001 CAGATTTTGT GAAGTAAAAC TCCAATTATG ATGAAAAATA CCACCAACAC

18051 CACCTGCGAA ACTGTATCCC AACTGTCCTT AATAAAAATG TTAAAAAGTA

18101 TATTATTCTC ATTTGTCTGT CATAATTTAT GTACCCCACT TTAATTTTTC

18151 TGATGTACTA AACCGAGGGC AAACTGAAAC CTGTTCCTCA TGCAAAGCCC

18201 CTACTCACCA TGTATCATGT ACGTGTCATC ACCCAACAAC TCCACTTTTG

18251 CTATATAACA ACACCCCCGT CACACTCTCC CTCTCTAACA CACACCCCAC

18301 TAACAATTCC TTCACTTGCA GCACTGTTGC ATCATCATCT TCATTGCAAA

18351 ACCCTAAACT TCACCTTCAA CCGCGGCCGC ATGGCTTCTA TGATATCCTC

18401 TTCCGCTGTG ACAACAGTCA GCCGTGCCTC TAGGGGGCAA TCCGCCGCAG

18451 TGGCTCCATT CGGCGGCCTC AAATCCATGA CTGGATTCCC AGTGAAGAAG

18501 GTCAACACTG ACATTACTTC CATTACAAGC AATGGTGGAA GAGTAAAGTG

18551 CATGCAGGTG TGGCCTCCAA TTGGAAAGAA GAAGTTTGAG ACTCTTTCCT

18601 ATTTGCCACC ATTGACGAGA GATTCTAGAG TGAGTAACAA GAACAACGAT

18651 GAGCTGCAGT GGCAATCCTG GTTCAGCAAG GCGCCCACCA CCGAGGCGAA

18701 CCCGATGGCC ACCATGTTGC AGGATATCGG CGTTGCGCTC AAACCGGAAG

18751 CGATGGAGCA GCTGAAAAAC GATTATCTGC GTGACTTCAC CGCGTTGTGG

18801 CAGGATTTTT TGGCTGGCAA GGCGCCAGCC GTCAGCGACC GCCGCTTCAG

18851 CTCGGCAGCC TGGCAGGGCA ATCCGATGTC GGCCTTCAAT GCCGCATCTT

18901 ACCTGCTCAA CGCCAAATTC CTCAGTGCCA TGGTGGAGGC GGTGGACACC

18951 GCACCCCAGC AAAAGCAGAA AATACGCTTT GCCGTGCAGC AGGTGATTGA

19001 TGCCATGTCG CCCGCGAACT TCCTCGCCAC CAACCCGGAA GCGCAGCAAA

-continued

19051 AACTGATTGA AACCAAGGGC GAGAGCCTGA CGCGTGGCCT GGTCAATATG

19101 CTGGGCGATA TCAACAAGGG CCATATCTCG CTGTCGGACG AATCGGCCTT

19151 TGAAGTGGGC CGCAACCTGG CCATTACCCC GGGCACCGTG ATTTACGAAA

19201 ATCCGCTGTT CCAGCTGATC CAGTACACGC CGACCACGCC GACGGTCAGC

19251 CAGCGCCCGC TGTTGATGGT GCCGCCGTGC ATCAACAAGT TCTACATCCT

19301 CGACCTGCAA CCGGAAAATT CGCTGGTGCG CTACGCGGTG GAGCAGGGCA

19351 ACACCGTGTT CCTGATCTCG TGGAGCAATC CGGACAAGTC GCTGGCCGGC

19401 ACCACCTGGG ACGACTACGT GGAGCAGGGC GTGATCGAAG CGATCCGCAT

19451 CGTCCAGGAC GTCAGCGGCC AGGACAAGCT GAACATGTTC GGCTTCTGCG

19501 TGGGCGGCAC CATCGTTGCC ACCGCACTGG CGGTACTGGC GGCGCGTGGC

19551 CAGCACCCGG CGGCCAGCCT GACCCTGCTG ACCACCTTCC TCGACTTCAG

19601 CGACACCGGC GTGCTCGACG TCTTCGTCGA TGAAACCCAG GTCGCGCTGC

19651 GTGAACAGCA ATTGCGCGAT GGCGGCCTGA TGCCGGGCCG TGACCTGGCC

19701 TCGACCTTCT CGAGCCTGCG TCCGAACGAC CTGGTATGGA ACTATGTGCA

19751 GTCGAACTAC CTCAAAGGCA ATGAGCCGGC GGCGTTTGAC CTGCTGTTCT

19801 GTAATTCGGA CAGCACCAAT TTGCCGGGCC CGATGTTCTG CTGGTACCTG

19851 CGCAACACCT ACCTGGAAAA CAGCCTGAAA GTGCCGGGCA AGCTGACGGT

19901 GGCCGGCGAA AAGATCGACC TCGGCCTGAT CGACGCCCCG GCCTTCATCT

19951 ACGGTTCGCG CGAAGACCAC ATCGTGCCGT GGATGTCGGC GTACGGTTCG

20001 CTCGACATCC TCAACCAGGG CAAGCCGGGC GCCAACCGCT TCGTGCTGGG

20051 CGCGTCCGGC CATATCGCCG GCGTGATCAA CTCGGTGGCC AAGAACAAGC

20101 GCAGCTACTG GATCAACGAC GGTGGCGCCG CCGATGCCCA GGCCTGGTTC

20151 GATGCCGCGC AGGAAGTGCC GGGCAGCTGG TGGCCGCAAT GGGCCGGGTT

20201 CCTGACCCAG CATGGCGGCA AGAAGGTCAA GCCCAAGGCC AAGCCCGGCA

20251 ACGCCCGCTA CACCGCGATC GAGGCGGCGC CCGGCCGTTA CGTCAAAGCC

20301 AAGGGCTGAG CGGCCGCTGA GTAATTCTGA TATTAGAGGG AGCATTAATG

20351 TGTTGTTGTG ATGTGGTTTA TATGGGGAAA TTAAATAAAT GATGTATGTA

-continued

20401 CCTCTTGCCT ATGTAGGTTT GTGTGTTTTG TTTTGTTGTC TAGCTTTGGT

20451 TATTAAGTAG TAGGGACGTT CGTTCGTGTC TCAAAAAAAG GGGTACTACC

20501 ACTCTGTAGT GTATATGGAT GCTGGAAATC AATGTGTTTT GTATTTGTTC

20551 ACCTCCATTG TTGAATTCAA TGTCAAATGT GTTTTGCGTT GGTTATGTGT

20601 AAAATTACTA TCTTTCTCGT CCGATGATCA AAGTTTTAAG CAACAAAACC

20651 AAGGGTGAAA TTTAAACTGT GCTTTGTTGA AGATTCTTTT ATCATATTGA

20701 AAATCAAATT ACTAGCAGCA GATTTTACCT AGCATGAAAT TTTATCAACA

20751 GTACAGCACT CACTAACCAA GTTCCAAACT AAGATGCGCC ATTAACATCA

20801 GCCAATAGGC ATTTTCAGCA AGGCGCGCCC GCGCCGATGT ATGTGACAAC

20851 CCTCGGGATT GTTGATTTAT TTCAAAACTA AGAGTTTTTG TCTTATTGTT

20901 CTCGTCTATT TTGGATATCA ATCTTAGTTT TATATCTTTT CTAGTTCTCT

20951 ACGTGTTAAA TGTTCAACAC ACTAGCAATT TGGCCTGCCA GCGTATGGAT

21001 TATGGAACTA TCAAGTCTGT GACGCGCCGT ACGTAGTGTT TATCTTTGTT

21051 GCTTTTCTGA ACAATTTATT TACTATGTAA ATATATTATC AATGTTTAAT

21101 CTATTTTAAT TTGCACATGA ATTTTCATTT TATTTTTACT TTACAAAACA

21151 AATAAATATA TATGCAAAAA AATTTACAAA CGATGCACGG GTTACAAACT

21201 AATTTCATTA AATGCTAATG CAGATTTTGT GAAGTAAAAC TCCAATTATG

21251 ATGAAAAATA CCACCAACAC CACCTGCGAA ACTGTATCCC AACTGTCCTT

21301 AATAAAAATG TTAAAAAGTA TATTATTCTC ATTTGTCTGT CATAATTTAT

21351 GTACCCCACT TTAATTTTTC TGATGTACTA AACCGAGGGC AAACTGAAAC

21401 CTGTTCCTCA TGCAAAGCCC CTACTCACCA TGTATCATGT ACGTGTCATC

21451 ACCCAACAAC TCCACTTTTG CTATATAACA ACACCCCCGT CACACTCTCC

21501 CTCTCTAACA CACACCCCAC TAACAATTCC TTCACTTGCA GCACTGTTGC

21551 ATCATCATCT TCATTGCAAA ACCCTAAACT TCACCTTCAA CCGCGGCCGC

21601 ATGGCTTCTA TGATATCCTC TTCCGCTGTG ACAACAGTCA GCCGTGCCTC

21651 TAGGGGGCAA TCCGCCGCAG TGGCTCCATT CGGCGGCCTC AAATCCATGA

21701 CTGGATTCCC AGTGAAGAAG GTCAACACTG ACATTACTTC CATTACAAGC

-continued

21751 AATGGTGGAA GAGTAAAGTG CATGCAGGTG TGGCCTCCAA TTGGAAAGAA

21801 GAAGTTTGAG ACTCTTTCCT ATTTGCCACC ATTGACGAGA GATTCTAGAG

21851 TGACTCAGCG CATTGCGTAT GTGACCGGCG GCATGGGTGG TATCGGAACC

21901 GCCATTTGCC AGCGGCTGGC CAAGGATGGC TTTCGTGTGG TGGCCGGTTG

21951 CGGCCCCAAC TCGCCGCGCC GCGAAAAGTG GCTGGAGCAG CAGAAGGCCC

22001 TGGGCTTCGA TTTCATTGCC TCGGAAGGCA ATGTGGCTGA CTGGGACTCG

22051 ACCAAGACCG CATTCGACAA GGTCAAGTCC GAGGTCGGCG AGGTTGATGT

22101 GCTGATCAAC AACGCCGGTA TCACCCGCGA CGTGGTGTTC CGCAAGATGA

22151 CCCGCGCCGA CTGGGATGCG GTGATCGACA CCAACCTGAC CTCGCTGTTC

22201 AACGTCACCA AGCAGGTGAT CGACGGCATG GCCGACCGTG GCTGGGGCCG

22251 CATCGTCAAC ATCTCGTCGG TGAACGGGCA GAAGGGCCAG TTCGGCCAGA

22301 CCAACTACTC CACCGCCAAG GCCGGCCTGC ATGGCTTCAC CATGGCACTG

22351 GCGCAGGAAG TGGCGACCAA GGGCGTGACC GTCAACACGG TCTCTCCGGG

22401 CTATATCGCC ACCGACATGG TCAAGGCGAT CCGCCAGGAC GTGCTCGACA

22451 AGATCGTCGC GACGATCCCG GTCAAGCGCC TGGGCCTGCC GGAAGAGATC

22501 GCCTCGATCT GCGCCTGGTT GTCGTCGGAG GAGTCCGGTT TCTCGACCGG

22551 CGCCGACTTC TCGCTCAACG GCGGCCTGCA TATGGGCTGA GCGGCCGCTG

22601 AGTAATTCTG ATATTAGAGG GAGCATTAAT GTGTTGTTGT GATGTGGTTT

22651 ATATGGGGAA ATTAAATAAA TGATGTATGT ACCTCTTGCC TATGTAGGTT

22701 TGTGTGTTTT GTTTTGTTGT CTAGCTTTGG TTATTAAGTA GTAGGGACGT

22751 TCGTTCGTGT CTCAAAAAAA GGGGTACTAC CACTCTGTAG TGTATATGGA

22801 TGCTGGAAAT CAATGTGTTT TGTATTTGTT CACCTCCATT GTTGAATTCA

22851 ATGTCAAATG TGTTTTGCGT TGGTTATGTG TAAAATTACT ATCTTTCTCG

22901 TCCGATGATC AAAGTTTTAA GCAACAAAAC CAAGGGTGAA ATTTAAACTG

22951 TGCTTTGTTG AAGATTCTTT TATCATATTG AAAATCAAAT TACTAGCAGC

23001 AGATTTTACC TAGCATGAAA TTTTATCAAC AGTACAGCAC TCACTAACCA

-continued

23051 AGTTCCAAAC TAAGATGCGC CATTAACATC AGCCAATAGG CATTTTCAGC

23101 AAGGCGCGTA A pMBXVT3

(SEQ ID NO: 8)

1 GGGGATCCGT ACGTAAGTAC GTACTCAAAA TGCCAACAAA TAAAAAAAAA

51 GTTGCTTTAA TAATGCCAAA ACAAATTAAT AAAACACTTA CAACACCGGA

101 TTTTTTTTAA TTAAAATGTG CCATTTAGGA TAAATAGTTA ATATTTTTAA

151 TAATTATTTA AAAAGCCGTA TCTACTAAAA TGATTTTTAT TTGGTTGAAA

201 ATATTAATAT GTTTAAATCA ACACAATCTA TCAAAATTAA ACTAAAAAAA

251 AAATAAGTGT ACGTGGTTAA CATTAGTACA GTAATATAAG AGGAAAATGA

301 GAAATTAAGA AATTGAAAGC GAGTCTAATT TTTAAATTAT GAACCTGCAT

351 ATATAAAAGG AAAGAAAGAA TCCAGGAAGA AAAGAAATGA AACCATGCAT

401 GGTCCCCTCG TCATCACGAG TTTCTGCCAT TTGCAATAGA AACACTGAAA

451 CACCTTTCTC TTTGTCACTT AATTGAGATG CCGAAGCCAC CTCACACCAT

501 GAACTTCATG AGGTGTAGCA CCCAAGGCTT CCATAGCCAT GCATACTGAA

551 GAATGTCTCA AGCTCAGCAC CCTACTTCTG TGACGTGTCC CTCATTCACC

601 TTCCTCTCTT CCCTATAAAT AACCACGCCT CAGGTTCTCC GCTTCACAAC

651 TCAAACATTC TCTCCATTGG TCCTTAAACA CTCATCAGTC ATCACCGCGG

701 CCGCGGAATT CATGGCTTCT ATGATATCCT CTTCCGCTGT GACAACAGTC

751 AGCCGTGCCT CTAGGGGGCA ATCCGCCGCA GTGGCTCCAT TCGGCGGCCT

801 CAAATCCATG ACTGGATTCC CAGTGAAGAA GGTCAACACT GACATTACTT

851 CCATTACAAG CAATGGTGGA AGAGTAAAGT GCATGCAGGT GTGGCCTCCA

901 ATTGGAAAGA AGAAGTTTGA GACTCTTTCC TATTTGCCAC CATTGACGAG

951 AGATTCTAGA GTGACTGACG TTGTCATCGT ATCCGCCGCC CGCACCGCGG

1001 TCGGCAAGTT TGGCGGCTCG CTGGCCAAGA TCCCGGCACC GGAACTGGGT

1051 GCCGTGGTCA TCAAGGCCGC GCTGGAGCGC GCCGGCGTCA AGCCGGAGCA

1101 GGTGAGCGAA GTCATCATGG GCCAGGTGCT GACCGCCGGT TCGGGCCAGA

1151 ACCCCGCACG CCAGGCCGCG ATCAAGGCCG GCCTGCCGGC GATGGTGCCG

1201 GCCATGACCA TCAACAAGGT GTGCGGCTCG GGCCTGAAGG CCGTGATGCT

-continued

1251 GGCCGCCAAC GCGATCATGG CGGGCGACGC CGAGATCGTG GTGGCCGGCG

1301 GCCAGGAAAA CATGAGCGCC GCCCCGCACG TGCTGCCGGG CTCGCGCGAT

1351 GGTTTCCGCA TGGGCGATGC CAAGCTGGTC GACACCATGA TCGTCGACGG

1401 CCTGTGGGAC GTGTACAACC AGTACCACAT GGGCATCACC GCCGAGAACG

1451 TGGCCAAGGA ATACGGCATC ACACGCGAGG CGCAGGATGA GTTCGCCGTC

1501 GGCTCGCAGA ACAAGGCCGA AGCCGCGCAG AAGGCCGGCA AGTTTGACGA

1551 AGAGATCGTC CCGGTGCTGA TCCCGCAGCG CAAGGGCGAC CCGGTGGCCT

1601 TCAAGACCGA CGAGTTCGTG CGCCAGGGCG CCACGCTGGA CAGCATGTCC

1651 GGCCTCAAGC CCGCCTTCGA CAAGGCCGGC ACGGTGACCG CGGCCAACGC

1701 CTCGGGCCTG AACGACGGCG CCGCCGCGGT GGTGGTGATG TCGGCGGCCA

1751 AGGCCAAGGA ACTGGGCCTG ACCCCGCTGG CCACGATCAA GAGCTATGCC

1801 AACGCCGGTG TCGATCCCAA GGTGATGGGC ATGGGCCCGG TGCCGGCCTC

1851 CAAGCGCGCC CTGTCGCGCG CCGAGTGGAC CCCGCAAGAC CTGGACCTGA

1901 TGGAGATCAA CGAGGCCTTT GCCGCGCAGG CGCTGGCGGT GCACCAGCAG

1951 ATGGGCTGGG ACACCTCCAA GGTCAATGTG AACGGCGGCG CCATCGCCAT

2001 CGGCCACCCG ATCGGCGCGT CGGGCTGCCG TATCCTGGTG ACGCTGCTGC

2051 ACGAGATGAA GCGCCGTGAC GCGAAGAAGG GCCTGGCCTC GCTGTGCATC

2101 GGCGGCGGCA TGGGCGTGGC GCTGGCAGTC GAGCGCAAAT AACTCGAGGC

2151 GGCCGCAGCC CTTTTTGTAT GTGCTACCCC ACTTTTGTCT TTTTGGCAAT

2201 AGTGCTAGCA ACCAATAAAT AATAATAATA ATAATGAATA AGAAAACAAA

2251 GGCTTTAGCT TGCCTTTTGT TCACTGTAAA ATAATAATGT AAGTACTCTC

2301 TATAATGAGT CACGAAACTT TTGCGGGAAT AAAAGGAGAA ATTCCAATGA

2351 GTTTTCTGTC AAATCTTCTT TTGTCTCTCT CTCTCTCTCT TTTTTTTTTT

2401 TCTTTCTTCT GAGCTTCTTG CAAAACAAAA GGCAAACAAT AACGATTGGT

2451 CCAATGATAG TTAGCTTGAT CGATGATATC TTTAGGAAGT GTTGGCAGGA

2501 CAGGACATGA TGTAGAAGAC TAAAATTGAA AGTATTGCAG ACCCAATAGT

2551 TGAAGATTAA CTTTAAGAAT GAAGACGTCT TATCAGGTTC TTCATGACTT

-continued

2601 AAGCTTCTGC AGGGAGTACT GTCCTCCGAG CGGAGTACTG TCCTCCGAGC

2651 GGAGTACTGT CCTCCGAGCG GAGTACTGTC CTCCGAGCGG AGTACTGTCC

2701 TCCGAGCGGA GACTCTAGTG CAAGACCCTT CCTCTATATA AGGAAGTTCA

2751 TTTCATTTGG AGAGGACACG CTGAAATCAC CAGTCTCTCT CTAAGCTAGC

2801 TTGGATCCTC GAGAAAATGG CTTCTATGAT ATCCTCTTCC GCTGTGACAA

2851 CAGTCAGCCG TGCCTCTAGG GGGCAATCCG CCGCAGTGGC TCCATTCGGC

2901 GGCCTCAAAT CCATGACTGG ATTCCCAGTG AAGAAGGTCA ACACTGACAT

2951 TACTTCCATT ACAAGCAATG GTGGAAGAGT AAAGTGCATG CAGGTGTGGC

3001 CTCCAATTGG AAAGAAGAAG TTTGAGACTC TTTCCTATTT GCCACCATTG

3051 ACGAGAGATT CTAGAGTGCT CTACCAATTG CATGAGTTCC AGCGCTCGAT

3101 CCTGCACCCG CTGACCGCGT GGGCCCAGGC GACCGCCAAG ACCTTCACCA

3151 ACCCCCTCAG CCCGCTCTCG CTGGTTCCCG GCGCACCCCG CCTGGCTGCC

3201 GGCTATGAAC TGCTGTACCG GCTCGGCAAG GAATACGAAA AGCCGGCATT

3251 CGACATCAAG TCGGTGCGCT CCAACGGGCG CGACATCCCC ATCGTCGAGC

3301 AGACCGTGCT TGAAAAGCCG TTCTGCAAGC TGGTGCGCTT CAAGCGCTAT

3351 GCCGACGACC CGGAGACCAT CAAGCTGCTC AAGGATGAGC CGGTGGTGCT

3401 GGTGGCCGCG CCGCTGTCGG GCCACCATGC CACGCTGCTG CGCGACACGG

3451 TGCGCACGCT GCTCCAGGAC CACAAGGTCT ACGTCACCGA CTGGATCGAC

3501 GCACGCATGG TGCCGGTCGA GGAAGGCGCG TTCCACCTGT CGGACTACAT

3551 CTACTACATC CAGGAGTTCA TCCGCCATAT CGGCGCCGAG AACCTGCATG

3601 TGATCTCGGT ATGCCAGCCC ACCGTGCCGG TGCTGGCCGC GATCTCGCTG

3651 ATGGCCTCGG CCGGCGAGAA GACGCCGCGC ACCATGACCA TGATGGGCGG

3701 CCCGATCGAC GCCCGCAAGA GCCCCACGGC GGTCAACTCG CTGGCGACCA

3751 ACAAGTCGTT CGAGTGGTTC GAGAACAACG TCATCTACAC CGTGCCGGCC

3801 AACTACCCCG GCCACGGCCG CCGCGTCTAC CCAGGCTTTT TGCAGCATGC

3851 CGGTTTCGTG GCGATGAACC CGGACCGGCA CCTTTCCTCG CACTATGACT

3901 TCTACCTGAG CCTGGTCGAG GGCGATGCGG ATGACGCCGA AGCCCACGTG

-continued

3951 CGCTTCTACG ACGAATACAA CGCGGTGCTC GACATGGCCG CCGAGTACTA

4001 CCTCGACACC ATCCGCGAGG TGTTCCAGGA GTTCCGCCTG GCCAACGGCA

4051 CCTGGGCCAT CGACGGCAAT CCGGTCCGGC CGCAGGACAT CAAGAGCACC

4101 GCGCTGATGA CCGTCGAGGG CGAACTGGAC GACATCTCGG GCGCGGGCCA

4151 GACCGCAGCG GCGCACGACC TGTGCGCCGG CATCCCGAAA ATCCGCAAGC

4201 AGCACCTGAA CGCGGCACAC TGCGGCCACT ACGGCATCTT CTCGGGCCGG

4251 CGCTGGCGCG AAGAGATATA CCCGCAGCTG CGCGACTTTA TCCGCAAGTA

4301 CCACCAGGCC TCGGCCACCA GGTAAGAGCT CGAATTGATC CTCTAGAGCT

4351 TTCGTTCGTA TCATCGGTTT CGACAACGTT CGTCAAGTTC AATGCATCAG

4401 TTTCATTGCG CACACACCAG AATCCTACTG AGTTCGAGTA TTATGGCATT

4451 GGGAAAACTG TTTTTCTTGT ACCATTTGTT GTGCTTGTAA TTTACTGTGT

4501 TTTTTATTCG GTTTTCGCTA TCGAACTGTG AAATGGAAAT GGATGGAGAA

4551 GAGTTAATGA ATGATATGGT CCTTTTGTTC ATTCTCAAAT TAATATTATT

4601 TGTTTTTTCT CTTATTTGTT GTGTGTTGAA TTTGAAATTA TAAGAGATAT

4651 GCAAACATTT TGTTTTGAGT AAAAATGTGT CAAATCGTGG CCTCTAATGA

4701 CCGAAGTTAA TATGAGGAGT AAAACACTTG TAGTTGTACC ATTATGCTTA

4751 TTCACTAGGC AACAAATATA TTTTCAGACC TAGAAAAGCT GCAAATGTTA

4801 CTGAATACAA GTATGTCCTC TTGTGTTTTA GACATTTATG AACTTTCCTT

4851 TATGTAATTT TCCAGAATCC TTGTCAGATT CTAATCATTG CTTTATAATT

4901 ATAGTTATAC TCATGGATTT GTAGTTGAGT ATGAAAATAT TTTTTAATGC

4951 ATTTTATGAC TTGCCAATTG ATTGACAACA TGCATCAGTC GAGGGAGTAC

5001 TGTCCTCCGA GCGGAGTACT GTCCTCCGAG CGGAGTACTG TCCTCCGAGC

5051 GGAGTACTGT CCTCCGAGCG GAGTACTGTC CTCCGAGCGG AGACTCTAGT

5101 GCAAGACCCT TCCTCTATAT AAGGAAGTTC ATTTCATTTG GAGAGGACAC

5151 GCTGAAATCA CCAGTCTCTC TCTAAGCTAG CTTGGATCCT CGAGAAAATG

5201 GCTTCTATGA TATCCTCTTC CGCTGTGACA ACAGTCAGCC GTGCCTCTAG

5251 GGGGCAATCC GCCGCAGTGG CTCCATTCGG CGGCCTCAAA TCCATGACTG

-continued

5301 GATTCCCAGT GAAGAAGGTC AACACTGACA TTACTTCCAT TACAAGCAAT

5351 GGTGGAAGAG TAAAGTGCAT GCAGGTGTGG CCTCCAATTG GAAAGAAGAA

5401 GTTTGAGACT CTTTCCTATT TGCCACCATT GACGAGAGAT TCTAGAGTGC

5451 TCAAAGGAAA AGTCGCAGTC GTCACCGGTT CCACCAGCGG GATCGGCCTG

5501 GGTATCGCCA CCGCGCTGGC CGCGCAGGGC GCCGATATCG TCCTGAACGG

5551 CTTCGGCGAC GCCGCCGAGA TCGAAAAGGT GCGCGCCGGC CTGGCCGCCC

5601 AGCATGGCGT CAAGGTGCTG TACGACGGCG CCGACCTGTC CAAGGGCGAG

5651 GCCGTGCGCG GCCTGGTGGA CAACGCGGTG CGCCAGATGG GCCGCATCGA

5701 CATCCTGGTC AACAACGCCG GCATCCAGCA CACCGCGCTG ATCGAGGACT

5751 TTCCCACCGA AAAATGGGAC GCCATCCTGG CGCTGAACCT GTCGGCCGTG

5801 TTCCACGGCA CCGCCGCCGC GCTGCCGCAC ATGAAGAAGC AGGGCTTCGG

5851 CCGCATCATC AACATCGCCT CGGCGCACGG CCTGGTGGCC TCGGCCAACA

5901 AGTCGGCCTA CGTCGCCGCC AAGCACGGCG TGGTGGGCTT CACCAAGGTG

5951 ACCGCGCTGG AAACCGCCGG CCAGGGCATC ACCGCCAACG CCATCTGCCC

6001 AGGCTGGGTG CGCACTCCGC TGGTCGAAAA GCAGATATCG GCGCTGGCCG

6051 AAAAGAACGG CGTGGACCAG GAAACCGCCG CGCGCGAACT GCTCAGCGAA

6101 AAGCAGCCGT CGCTGCAATT CGTCACGCCC GAACAACTGG GCGGCACGGC

6151 CGTCTTCCTG GCCTCCGATG CCGCCGCGCA AATCACCGGC ACGACCGTCT

6201 CCGTCGATGG CGGCTGGACG GCGCGCTGAG AGCTCGAATT GATCCTCTAG

6251 AGCTTTCGTT CGTATCATCG GTTTCGACAA CGTTCGTCAA GTTCAATGCA

6301 TCAGTTTCAT TGCGCACACA CCAGAATCCT ACTGAGTTCG AGTATTATGG

6351 CATTGGGAAA ACTGTTTTTC TTGTACCATT TGTTGTGCTT GTAATTTACT

6401 GTGTTTTTTA TTCGGTTTTC GCTATCGAAC TGTGAAATGG AAATGGATGG

6451 AGAAGAGTTA ATGAATGATA TGGTCCTTTT GTTCATTCTC AAATTAATAT

6501 TATTTGTTTT TTCTCTTATT TGTTGTGTGT TGAATTTGAA ATTATAAGAG

6551 ATATGCAAAC ATTTTGTTTT GAGTAAAAAT GTGTCAAATC GTGGCCTCTA

6601 ATGACCGAAG TTAATATGAG GAGTAAAACA CTTGTAGTTG TACCATTATG

6651 CTTATTCACT AGGCAACAAA TATATTTTCA GACCTAGAAA AGCTGCAAAT

6701 GTTACTGAAT ACAAGTATGT CCTCTTGTGT TTTAGACATT TATGAACTTT

6751 CCTTTATGTA ATTTTCCAGA ATCCTTGTCA GATTCTAATC ATTGCTTTAT

6801 AATTATAGTT ATACTCATGG ATTTGTAGTT GAGTATGAAA ATATTTTTTA

6851 ATGCATTTTA TGACTTGCCA ATTGATTGAC AACATGCATC AACTAGTAGA

6901 AGGTAATTAT CCAAGATGTA GCATCAAGAA TCCAATGTTT ACGGGAAAAA

6951 CTATGGAAGT ATTATGTGAG CTCAGCAAGA AGCAGATCAA TATGCGGCAC

7001 ATATGCAACC TATGTTCAAA AATGAAGAAT GTACAGATAC AAGATCCTAT

7051 ACTGCCAGAA TACGAAGAAG AATACGTAGA AATTGAAAAA GAAGAACCAG

7101 GCGAAGAAAA GAATCTTGAA GACGTAAGCA CTGACGACAA CAATGAAAAG

7151 AAGAAGATAA GGTCGGTGAT TGTGAAAGAG ACATAGAGGA CACATGTAAG

7201 GTGGAAAATG TAAGGGCGGA AAGTAACCTT ATCACAAAGG AATCTTATCC

7251 CCCACTACTT ATCCTTTTAT ATTTTTCCGT GTCATTTTTG CCCTTGAGTT

7301 TTCCTATATA AGGAACCAAG TTCGGCATTT GTGAAAACAA GAAAAAATTG

7351 GTGTAAGCTA TTTTCTTTGA AGTACTGAGG ATACAACTTC AGAGAAATTT

7401 GTAAGAAAGT GGATCGAAAC CATGGCCTCC TCCGAGAACG TCATCACCGA

7451 GTTCATGCGC TTCAAGGTGC GCATGGAGGG CACCGTGAAC GGCCACGAGT

7501 TCGAGATCGA GGGCGAGGGC GAGGGCCGCC CCTACGAGGG CCACAACACC

7551 GTGAAGCTGA AGGTGACCAA GGGCGGCCCC CTGCCCTTCG CCTGGGACAT

7601 CCTGTCCCCC CAGTTCCAGT ACGGCTCCAA GGTGTACGTG AAGCACCCCG

7651 CCGACATCCC CGACTACAAG AAGCTGTCCT TCCCCGAGGG CTTCAAGTGG

7701 GAGCGCGTGA TGAACTTCGA GGACGGCGGC GTGGCGACCG TGACCCAGGA

7751 CTCCTCCCTG CAGGACGGCT GCTTCATCTA CAAGGTGAAG TTCATCGGCG

7801 TGAACTTCCC CTCCGACGGC CCCGTGATGC AGAAGAAGAC CATGGGCTGG

7851 GAGGCCTCCA CCGAGCGCCT GTACCCCCGC GACGGCGTGC TGAAGGGCGA

7901 GACCCACAAG GCCCTGAAGC TGAAGGACGG CGGCCACTAC CTGGTGGAGT

7951 TCAAGTCCAT CTACATGGCC AAGAAGCCCG TGCAGCTGCC CGGCTACTAC

-continued

8001 TACGTGGACG CCAAGCTGGA CATCACCTCC CACAACGAGG ACTACACCAT

8051 CGTGGAGCAG TACGAGCGCA CCGAGGGCCG CCACCACCTG TTCCTGGTAC

8101 CAATGAGCTC TGTCCAACAG TCTCAGGGTT AATGTCTATG TATCTTAAAT

8151 AATGTTGTCG GCGATCGTTC AAACATTTGG CAATAAAGTT TCTTAAGATT

8201 GAATCCTGTT GCCGGTCTTG CGATGATTAT CATATAATTT CTGTTGAATT

8251 ACGTTAAGCA TGTAATAATT AACATGTAAT GCATGACGTT ATTTATGAGA

8301 TGGGTTTTTA TGATTAGAGT CCCGCAATTA TACATTTAAT ACGCGATAGA

8351 AAACAAAATA TAGCGCGCAA ACTAGGATAA ATTATCGCGC GCGGTGTCAT

8401 CTATGTTACT AGATCGGGAA TTAAACTATC AGTGTTTGAC AGGATATATT

8451 GGCGGGTAAA CCTAAGAGAA AAGAGCGTTT ATTAGAATAA CGGATATTTA

8501 AAAGGGCGTG AAAAGGTTTA TCCGTTCGTC CATTTGTATG TGCATGCCAA

8551 CCACAGGGTT CCCCTCGGGA TCAAAGTACT TTGATCCAAC CCCTCCGCTG

8601 CTATAGTGCA GTCGGCTTCT GACGTTCAGT GCAGCCGTCT TCTGAAAACG

8651 ACATGTCGCA CAAGTCCTAA GTTACGCGAC AGGCTGCCGC CCTGCCCTTT

8701 TCCTGGCGTT TTCTTGTCGC GTGTTTTAGT CGCATAAAGT AGAATACTTG

8751 CGACTAGAAC CGGAGACATT ACGCCATGAA CAAGAGCGCC GCCGCTGGCC

8801 TGCTGGGCTA TGCCCGCGTC AGCACCGACG ACCAGGACTT GACCAACCAA

8851 CGGGCCGAAC TGCACGCGGC CGGCTGCACC AAGCTGTTTT CCGAGAAGAT

8901 CACCGGCACC AGGCGCGACC GCCCGGAGCT GGCCAGGATG CTTGACCACC

8951 TACGCCCTGG CGACGTTGTG ACAGTGACCA GGCTAGACCG CCTGGCCCGC

9001 AGCACCCGCG ACCTACTGGA CATTGCCGAG CGCATCCAGG AGGCCGGCGC

9051 GGGCCTGCGT AGCCTGGCAG AGCCGTGGGC CGACACCACC ACGCCGGCCG

9101 GCCGCATGGT GTTGACCGTG TTCGCCGGCA TTGCCGAGTT CGAGCGTTCC

9151 CTAATCATCG ACCGCACCCG GAGCGGGCGC GAGGCCGCCA AGGCCCGAGG

9201 CGTGAAGTTT GGCCCCCGCC CTACCCTCAC CCCGGCACAG ATCGCGCACG

9251 CGCGCGAGCT GATCGACCAG GAAGGCCGCA CCGTGAAAGA GGCGGCTGCA

9301 CTGCTTGGCG TGCATCGCTC GACCCTGTAC CGCGCACTTG AGCGCAGCGA

9351 GGAAGTGACG CCCACCGAGG CCAGGCGGCG CGGTGCCTTC CGTGAGGACG

9401 CATTGACCGA GGCCGACGCC CTGGCGGCCG CCGAGAATGA ACGCCAAGAG

9451 GAACAAGCAT GAAACCGCAC CAGGACGGCC AGGACGAACC GTTTTTCATT

9501 ACCGAAGAGA TCGAGGCGGA GATGATCGCG GCCGGGTACG TGTTCGAGCC

9551 GCCCGCGCAC GTCTCAACCG TGCGGCTGCA TGAAATCCTG GCCGGTTTGT

9601 CTGATGCCAA GCTGGCGGCC TGGCCGGCCA GCTTGGCCGC TGAAGAAACC

9651 GAGCGCCGCC GTCTAAAAAG GTGATGTGTA TTTGAGTAAA ACAGCTTGCG

9701 TCATGCGGTC GCTGCGTATA TGATGCGATG AGTAAATAAA CAAATACGCA

9751 AGGGGAACGC ATGAAGGTTA TCGCTGTACT TAACCAGAAA GGCGGGTCAG

9801 GCAAGACGAC CATCGCAACC CATCTAGCCC GCGCCCTGCA ACTCGCCGGG

9851 GCCGATGTTC TGTTAGTCGA TTCCGATCCC CAGGGCAGTG CCCGCGATTG

9901 GGCGGCCGTG CGGGAAGATC AACCGCTAAC CGTTGTCGGC ATCGACCGCC

9951 CGACGATTGA CCGCGACGTG AAGGCCATCG GCCGGCGCGA CTTCGTAGTG

10001 ATCGACGGAG CGCCCCAGGC GGCGGACTTG GCTGTGTCCG CGATCAAGGC

10051 AGCCGACTTC GTGCTGATTC CGGTGCAGCC AAGCCCTTAC GACATATGGG

10101 CCACCGCCGA CCTGGTGGAG CTGGTTAAGC AGCGCATTGA GGTCACGGAT

10151 GGAAGGCTAC AAGCGGCCTT TGTCGTGTCG CGGGCGATCA AAGGCACGCG

10201 CATCGGCGGT GAGGTTGCCG AGGCGCTGGC CGGGTACGAG CTGCCCATTC

10251 TTGAGTCCCG TATCACGCAG CGCGTGAGCT ACCCAGGCAC TGCCGCCGCC

10301 GGCACAACCG TTCTTGAATC AGAACCCGAG GGCGACGCTG CCCGCGAGGT

10351 CCAGGCGCTG GCCGCTGAAA TTAAATCAAA ACTCATTTGA GTTAATGAGG

10401 TAAAGAGAAA ATGAGCAAAA GCACAAACAC GCTAAGTGCC GGCCGTCCGA

10451 GCGCACGCAG CAGCAAGGCT GCAACGTTGG CCAGCCTGGC AGACACGCCA

10501 GCCATGAAGC GGGTCAACTT TCAGTTGCCG GCGGAGGATC ACACCAAGCT

10551 GAAGATGTAC GCGGTACGCC AAGGCAAGAC CATTACCGAG CTGCTATCTG

10601 AATACATCGC GCAGCTACCA GAGTAAATGA GCAAATGAAT AAATGAGTAG

10651 ATGAATTTTA GCGGCTAAAG GAGGCGGCAT GGAAAATCAA GAACAACCAG

-continued

10701 GCACCGACGC CGTGGAATGC CCCATGTGTG GAGGAACGGG CGGTTGGCCA

10751 GGCGTAAGCG GCTGGGTTGT CTGCCGGCCC TGCAATGGCA CTGGAACCCC

10801 CAAGCCCGAG GAATCGGCGT GACGGTCGCA AACCATCCGG CCCGGTACAA

10851 ATCGGCGCGG CGCTGGGTGA TGACCTGGTG GAGAAGTTGA AGGCCGCGCA

10901 GGCCGCCCAG CGGCAACGCA TCGAGGCAGA AGCACGCCCC GGTGAATCGT

10951 GGCAAGCGGC CGCTGATCGA ATCCGCAAAG AATCCCGGCA ACCGCCGGCA

11001 GCCGGTGCGC CGTCGATTAG GAAGCCGCCC AAGGGCGACG AGCAACCAGA

11051 TTTTTTCGTT CCGATGCTCT ATGACGTGGG CACCCGCGAT AGTCGCAGCA

11101 TCATGGACGT GGCCGTTTTC CGTCTGTCGA AGCGTGACCG ACGAGCTGGC

11151 GAGGTGATCC GCTACGAGCT TCCAGACGGG CACGTAGAGG TTTCCGCAGG

11201 GCCGGCCGGC ATGGCCAGTG TGTGGGATTA CGACCTGGTA CTGATGGCGG

11251 TTTCCCATCT AACCGAATCC ATGAACCGAT ACCGGGAAGG GAAGGGAGAC

11301 AAGCCCGGCC GCGTGTTCCG TCCACACGTT GCGGACGTAC TCAAGTTCTG

11351 CCGGCGAGCC GATGGCGGAA AGCAGAAAGA CGACCTGGTA GAAACCTGCA

11401 TTCGGTTAAA CACCACGCAC GTTGCCATGC AGCGTACGAA GAAGGCCAAG

11451 AACGGCCGCC TGGTGACGGT ATCCGAGGGT GAAGCCTTGA TTAGCCGCTA

11501 CAAGATCGTA AAGAGCGAAA CCGGGCGGCC GGAGTACATC GAGATCGAGC

11551 TAGCTGATTG GATGTACCGC GAGATCACAG AAGGCAAGAA CCCGGACGTG

11601 CTGACGGTTC ACCCCGATTA CTTTTTGATC GATCCCGGCA TCGGCCGTTT

11651 TCTCTACCGC CTGGCACGCC GCGCCGCAGG CAAGGCAGAA GCCAGATGGT

11701 TGTTCAAGAC GATCTACGAA CGCAGTGGCA GCGCCGGAGA GTTCAAGAAG

11751 TTCTGTTTCA CCGTGCGCAA GCTGATCGGG TCAAATGACC TGCCGGAGTA

11801 CGATTTGAAG GAGGAGGCGG GGCAGGCTGG CCCGATCGTA GTCATGCGCT

11851 ACCGCAACCT GATCGAGGGC GAAGCATCCG CCGGTTCCTA ATGTACGGAG

11901 CAGATGCTAG GGCAAATTGC CCTAGCAGGG GAAAAAGGTC GAAAAGGTCT

11951 CTTTCCTGTG GATAGCACGT ACATTGGGAA CCCAAAGCCG TACATTGGGA

12001 ACCGGAACCC GTACATTGGG AACCCAAAGC CGTACATTGG GAACCGGTCA

12051 CACATGTAAG TGACTGATAT AAAAGAGAAA AAAGGCGATT TTTCCGCCTA

12101 AAACTCTTTA AAACTTATTA AAACTCTTAA AACCCGCCTG GCCTGTGCAT

12151 AACTGTCTGG CCAGCGCACA GCCGAAGAGC TGCAAAAAGC GCCTACCCTT

12201 CGGTCGCTGC GCTCCCTACG CCCCGCCGCT TCGCGTCGGC CTATCGCGGC

12251 CGCTGGCCGC TCAAAAATGG CTGGCCTACG GCCAGGCAAT CTACCAGGGC

12301 GCGGACAAGC CGCGCCGTCG CCACTCGACC GCCGGCGCCC ACATCAAGGC

12351 ACCCTGCCTC GCGCGTTTCG GTGATGACGG TGAAAACCTC TGACACATGC

12401 AGCTCCCGGA GACGGTCACA GCTTGTCTGT AAGCGGATGC CGGGAGCAGA

12451 CAAGCCCGTC AGGGCGCGTC AGCGGGTGTT GGCGGGTGTC GGGGCGCAGC

12501 CATGACCCAG TCACGTAGCG ATAGCGGAGT GTATACTGGC TTAACTATGC

12551 GGCATCAGAG CAGATTGTAC TGAGAGTGCA CCATATGCGG TGTGAAATAC

12601 CGCACAGATG CGTAAGGAGA AAATACCGCA TCAGGCGCTC TTCCGCTTCC

12651 TCGCTCACTG ACTCGCTGCG CTCGGTCGTT CGGCTGCGGC GAGCGGTATC

12701 AGCTCACTCA AAGGCGGTAA TACGGTTATC CACAGAATCA GGGGATAACG

12751 CAGGAAAGAA CATGTGAGCA AAAGGCCAGC AAAAGGCCAG GAACCGTAAA

12801 AAGGCCGCGT TGCTGGCGTT TTTCCATAGG CTCCGCCCCC CTGACGAGCA

12851 TCACAAAAAT CGACGCTCAA GTCAGAGGTG GCGAAACCCG ACAGGACTAT

12901 AAAGATACCA GGCGTTTCCC CCTGGAAGCT CCCTCGTGCG CTCTCCTGTT

12951 CCGACCCTGC CGCTTACCGG ATACCTGTCC GCCTTTCTCC CTTCGGGAAG

13001 CGTGGCGCTT TCTCATAGCT CACGCTGTAG GTATCTCAGT TCGGTGTAGG

13051 TCGTTCGCTC CAAGCTGGGC TGTGTGCACG AACCCCCCGT TCAGCCCGAC

13101 CGCTGCGCCT TATCCGGTAA CTATCGTCTT GAGTCCAACC CGGTAAGACA

13151 CGACTTATCG CCACTGGCAG CAGCCACTGG TAACAGGATT AGCAGAGCGA

13201 GGTATGTAGG CGGTGCTACA GAGTTCTTGA AGTGGTGGCC TAACTACGGC

13251 TACACTAGAA GGACAGTATT TGGTATCTGC GCTCTGCTGA AGCCAGTTAC

13301 CTTCGGAAAA AGAGTTGGTA GCTCTTGATC CGGCAAACAA ACCACCGCTG

13351 GTAGCGGTGG TTTTTTTGTT TGCAAGCAGC AGATTACGCG CAGAAAAAAA

-continued

13401 GGATCTCAAG AAGATCCTTT GATCTTTTCT ACGGGGTCTG ACGCTCAGTG

13451 GAACGAAAAC TCACGTTAAG GGATTTTGGT CATGCATTCT AGGTACTAAA

13501 ACAATTCATC CAGTAAAATA TAATATTTTA TTTTCTCCCA ATCAGGCTTG

13551 ATCCCCAGTA AGTCAAAAAA TAGCTCGACA TACTGTTCTT CCCCGATATC

13601 CTCCCTGATC GACCGGACGC AGAAGGCAAT GTCATACCAC TTGTCCGCCC

13651 TGCCGCTTCT CCCAAGATCA ATAAAGCCAC TTACTTTGCC ATCTTTCACA

13701 AAGATGTTGC TGTCTCCCAG GTCGCCGTGG GAAAAGACAA GTTCCTCTTC

13751 GGGCTTTTCC GTCTTTAAAA AATCATACAG CTCGCGCGGA TCTTTAAATG

13801 GAGTGTCTTC TTCCCAGTTT TCGCAATCCA CATCGGCCAG ATCGTTATTC

13851 AGTAAGTAAT CCAATTCGGC TAAGCGGCTG TCTAAGCTAT TCGTATAGGG

13901 ACAATCCGAT ATGTCGATGG AGTGAAAGAG CCTGATGCAC TCCGCATACA

13951 GCTCGATAAT CTTTTCAGGG CTTTGTTCAT CTTCATACTC TTCCGAGCAA

14001 AGGACGCCAT CGGCCTCACT CATGAGCAGA TTGCTCCAGC CATCATGCCG

14051 TTCAAAGTGC AGGACCTTTG GAACAGGCAG CTTTCCTTCC AGCCATAGCA

14101 TCATGTCCTT TTCCCGTTCC ACATCATAGG TGGTCCCTTT ATACCGGCTG

14151 TCCGTCATTT TTAAATATAG GTTTTCATTT TCTCCCACCA GCTTATATAC

14201 CTTAGCAGGA GACATTCCTT CCGTATCTTT TACGCAGCGG TATTTTTCGA

14251 TCAGTTTTTT CAATTCCGGT GATATTCTCA TTTTAGCCAT TTATTATTTC

14301 CTTCCTCTTT TCTACAGTAT TTAAAGATAC CCCAAGAAGC TAATTATAAC

14351 AAGACGAACT CCAATTCACT GTTCCTTGCA TTCTAAAACC TTAAATACCA

14401 GAAAACAGCT TTTTCAAAGT TGTTTTCAAA GTTGGCGTAT AACATAGTAT

14451 CGACGGAGCC GATTTTGAAA CCGCGGTGAT CACAGGCAGC AACGCTCTGT

14501 CATCGTTACA ATCAACATGC TACCCTCCGC GAGATCATCC GTGTTTCAAA

14551 CCCGGCAGCT TAGTTGCCGT TCTTCCGAAT AGCATCGGTA ACATGAGCAA

14601 AGTCTGCCGC CTTACAACGG CTCTCCCGCT GACGCCGTCC CGGACTGATG

14651 GGCTGCCTGT ATCGAGTGGT GATTTTGTGC CGAGCTGCCG GTCGGGGAGC

14701 TGTTGGCTGG CTGGTGGCAG GATATATTGT GGTGTAAACA AATTGACGCT

-continued

14751 TAGACAACTT AATAACACAT TGCGGACGTT TTTAATGTAC TGAATTAACG

14801 CCGAATTAAT TCCTAGTCCA ATACTCAACT TCAAGGAATC TCACCCATGC

14851 GCGCCGGCGG GGAACCGGAG TTCCCTTCAG TGAACGTTAT TAGTTCGCCG

14901 CTCGGTGTGT CGTAGATACT AGCCCCTGGG GCCTTTTGAA ATTTGAATAA

14951 GATTTATGTA ATCAGTCTTT TAGGTTTGAC CGGTTCTGCC GCTTTTTTTA

15001 AAATTGGATT TGTAATAATA AAACGCAATT GTTTGTTATT GTGGCGCTCT

15051 ATCATAGATG TCGCTATAAA CCTATTCAGC ACAATATATT GTTTTCATTT

15101 TAATATTGTA CATATAAGTA GTAGGGTACA ATCAGTAAAT TGAACGGAGA

15151 ATATTATTCA TAAAAATACG ATAGTAACGG GTGATATATT CATTCATTAG

15201 AATGAACCGA AACCGGCGGT AAGGATCTGA GCTACACATG CTCAGGTTTT

15251 TTACAACGTG CACAACAGAA TTGAAAGCAA ATATCATGCG ATCATAGGCG

15301 TCTCGCATAT CTCATTAAAG CAGCTGGAAG ATTTGATTCT AGATTAGAGA

15351 TTCGTGGGGG ACTCGAGATA GGCGGCGGTT GGGTGTGCGA CATGTCCTGC

15401 CACATCCCAG ATCTCCTCGA GGAAAGGCGG CAGCTTTCTG TTCTTGAGCT

15451 TGAGGGAGAT GCACATGTTG GAGTTTTGCA TGCCGAGCGT GCGTAGCTCA

15501 GAGAGGATTG AGAGGATCTT GCCGTATATG ACGGACGAAC GCGCCGACCC

15551 GCTCAGCTGG TTCAGGATAT AGATGCGGAG CGTATTCAGG TAGTACCGCT

15601 GGATTTCTTC CACCAGTTGC GGCTGCTCCA ACCCTGGCCG GTCAGAAAAG

15651 ATGACGACAG CCGTGAGCAG CGCGTAATGG ATGTTGTCCA ACGCCATAGA

15701 GTACATGCAC CGGCAGAAGT GCAGTAGATC CTCGATGACT TCGGCCATGC

15751 CAGCCTTGCG GTAGTTGTCG CGAGTGTACG CTTGGTTGTT CGGGAACAGA

15801 ATACTGTCTG AGGCCGCATC GTACTGCTGC GCGACTCGGA GCATCATTAC

15851 CTCACTTGAG CAAGCCTTAA GCAGCGTAAT TTGATCAGGC TGCGAGATCT

15901 TGGCGAACCC TGGCAATCCC TTCGCGAACT CCACGATAAG TTGGACCGTG

15951 AGGATAGTCA TCTCTACGAT CTGGCGGAAG GGAGTGTCAG ACTCTTCGTT

16001 TTCATCGTCC GCTTGCTGCC ACGTCTGCGT AATCCTCTTC AAATCTTCAT

16051 CAGAAGGCTG CTCGTACCCG TCCTGGTACC AGATGAGCCT GGCGATAAGG

-continued

16101 AACTGCTGGT TGGCTGTCAA CTGGGGGATG TTTTTCTGCC GGTTTGTCTC

16151 CAACAGCTTG TCGGAGAGAA ACCTTGGAAC CACTTCGTGA ATCCTTGCTG

16201 CTTCAGGAGG TGGAGGTTCA CACTGCATAA TGGGCGGCAT GTGGTCGTCC

16251 ACCGTCGTCG TGCTGACAGG CAGTTTGTCC TTCTCCTTCT GTGCTTTCTT

16301 CTCTTTCCGC TTCATGGCGC ACTGAGTCTC GGGTACTACG CACTCAGGCC

16351 TGATCCCCGG GAATTCCGGC GATACAGTCA ACTGTCTTTG ACCTTTGTTA

16401 CTACTCTCTT CCGATGATGA TGTCGCACTT ATTCTATGCT GTCTCAATGT

16451 TAGAGGCATA TCAGTCTCCA CTGAAGCCAA TCTATCTGTG ACGGCATCTT

16501 TATTCACATT ATCTTGTACA AATAATCCTG TTAACAATGC TTTTATATCC

16551 TGTAAAGAAT CCATTTTCAA AATCATGTCA AGGTCTTCTC GAGGAAAAAT

16601 CAGTAGAAAT AGCTGTTCCA GTCTTTCTAG CCTTGATTCC ACTTCTGTCA

16651 GATGTGCCCT AGTCAGCGGA GACCTTTTGG TTTTGGGAGA GTAGCGACAC

16701 TCCCAGTTGT TCTTCAGACA CTTGGCGCAC TTCGGTTTTT CTTTGGAGCA

16751 CTTGAGCTTT TTAAGTCGGC AAATATCGCA TGCTTGTTCG ATAGAAGACA

16801 GTAGCTTCAG TCGACGGATC CCTGGCGATC CCGGACCCGG GGAATCCCCG

16851 TCCCCCAACA TGTCCAGATC GAAATCGTCT AGCGCGTCGG CATGCGCCAT

16901 CGCCACGTCC TCGCCGTCTA AGTGGAGCTC GTCCCCCAGG CTGACATCGG

16951 TCGGGGGGGC CGTCGAGATC CCCGGGAATT CATCTACCTT TCTCTTCTTT

17001 TTTGGGCATG CTTGTTCGAT AGAAGACAGT AGCTTCATCT TTCAGGAGGC

17051 TTGCTTCAAG CTGGCTAGAC TCGAGAGATG AGAGATTTCG ATTCCGATTT

17101 TGATTTCGAT TCCGATTTTG ATTTCGATTG ATCTCTTCCT TCTGATTTGT

17151 GTTCCTTATA TAAGGAAATT CTTGTGGGAT TAGACGTCAT GGCTTACGTC

17201 ATTTCCTTCG TCCTGTTGCT CACTGATTGA GCTGTGAGTG GAGGGACCAC

17251 TGGAAGATGC TTCACTAATT TTCTTAGTGG AGGGACCGGC TTCACATGCT

17301 TCACACAAGT GGCTGTCGGG CATCATCTTT TTTAGCTTTT GACAAAGCAA

17351 TGTTTTAGTG GTGGCTCCCA CTCTTATCTT CAACATTATT ATCTTATCTT

17401 CAAAGGACGA TAAGATGTTG ATGTCTGTGG ACGAAGTTGG GATTAGACGT

17451 CATGGCTTAC GTCATTTCCT TCGTCCTGTT GCTCACTGAT TGAGCTGTGA

17501 GTGGAGGGAC CACTGGAAGA TGCTTCACTA ATTTTCTTAG TGGAGGGACC

17551 GGCTTCACAT GCTTCACACA AGTGGCTGTC GGGCATCATC TTTTTTAGCT

17601 TTTGACAAAG CAATGTTTTA GTGGTGGCTC CCACTCTTAT CTTCAACATT

17651 ATTATCTTAT CTTCAAAGGA CGATAAGATG TTGATGTCTG TGGACGAAGT

17701 TGACGAATTC CTGCAGGCGG CCGCCATATG CATCCTAGGC CACCATGTTG

17751 GGCCCGGGGC GCGCCGTACG TAGTGTTTAT CTTTGTTGCT TTTCTGAACA

17801 ATTTATTTAC TATGTAAATA TATTATCAAT GTTTAATCTA TTTTAATTTG

17851 CACATGAATT TTCATTTTAT TTTTACTTTA CAAAACAAAT AAATATATAT

17901 GCAAAAAAAT TTACAAACGA TGCACGGGTT ACAAACTAAT TTCATTAAAT

17951 GCTAATGCAG ATTTTGTGAA GTAAAACTCC AATTATGATG AAAAATACCA

18001 CCAACACCAC CTGCGAAACT GTATCCCAAC TGTCCTTAAT AAAAATGTTA

18051 AAAAGTATAT TATTCTCATT TGTCTGTCAT AATTTATGTA CCCCACTTTA

18101 ATTTTTCTGA TGTACTAAAC CGAGGGCAAA CTGAAACCTG TTCCTCATGC

18151 AAAGCCCCTA CTCACCATGT ATCATGTACG TGTCATCACC CAACAACTCC

18201 ACTTTTGCTA TATAACAACA CCCCCGTCAC ACTCTCCCTC TCTAACACAC

18251 ACCCCACTAA CAATTCCTTC ACTTGCAGCA CTGTTGCATC ATCATCTTCA

18301 TTGCAAAACC CTAAACTTCA CCTTCAACCG CGGCCGCATG GCTTCTATGA

18351 TATCCTCTTC CGCTGTGACA ACAGTCAGCC GTGCCTCTAG GGGGCAATCC

18401 GCCGCAGTGG CTCCATTCGG CGGCCTCAAA TCCATGACTG GATTCCCAGT

18451 GAAGAAGGTC AACACTGACA TTACTTCCAT TACAAGCAAT GGTGGAAGAG

18501 TAAAGTGCAT GCAGGTGTGG CCTCCAATTG GAAAGAAGAA GTTTGAGACT

18551 CTTTCCTATT TGCCACCATT GACGAGAGAT TCTAGAGTGA GTAACAAGAA

18601 CAACGATGAG CTGCAGTGGC AATCCTGGTT CAGCAAGGCG CCCACCACCG

18651 AGGCGAACCC GATGGCCACC ATGTTGCAGG ATATCGGCGT TGCGCTCAAA

18701 CCGGAAGCGA TGGAGCAGCT GAAAAACGAT TATCTGCGTG ACTTCACCGC

18751 GTTGTGGCAG GATTTTTTGG CTGGCAAGGC GCCAGCCGTC AGCGACCGCC

-continued

18801 GCTTCAGCTC GGCAGCCTGG CAGGGCAATC CGATGTCGGC CTTCAATGCC

18851 GCATCTTACC TGCTCAACGC CAAATTCCTC AGTGCCATGG TGGAGGCGGT

18901 GGACACCGCA CCCCAGCAAA AGCAGAAAAT ACGCTTTGCC GTGCAGCAGG

18951 TGATTGATGC CATGTCGCCC GCGAACTTCC TCGCCACCAA CCCGGAAGCG

19001 CAGCAAAAAC TGATTGAAAC CAAGGGCGAG AGCCTGACGC GTGGCCTGGT

19051 CAATATGCTG GGCGATATCA ACAAGGGCCA TATCTCGCTG TCGGACGAAT

19101 CGGCCTTTGA AGTGGGCCGC AACCTGGCCA TTACCCCGGG CACCGTGATT

19151 TACGAAAATC CGCTGTTCCA GCTGATCCAG TACACGCCGA CCACGCCGAC

19201 GGTCAGCCAG CGCCCGCTGT TGATGGTGCC GCCGTGCATC AACAAGTTCT

19251 ACATCCTCGA CCTGCAACCG GAAAATTCGC TGGTGCGCTA CGCGGTGGAG

19301 CAGGGCAACA CCGTGTTCCT GATCTCGTGG AGCAATCCGG ACAAGTCGCT

19351 GGCCGGCACC ACCTGGGACG ACTACGTGGA GCAGGGCGTG ATCGAAGCGA

19401 TCCGCATCGT CCAGGACGTC AGCGGCCAGG ACAAGCTGAA CATGTTCGGC

19451 TTCTGCGTGG GCGGCACCAT CGTTGCCACC GCACTGGCGG TACTGGCGGC

19501 GCGTGGCCAG CACCCGGCGG CCAGCCTGAC CCTGCTGACC ACCTTCCTCG

19551 ACTTCAGCGA CACCGGCGTG CTCGACGTCT TCGTCGATGA AACCCAGGTC

19601 GCGCTGCGTG AACAGCAATT GCGCGATGGC GGCCTGATGC CGGGCCGTGA

19651 CCTGGCCTCG ACCTTCTCGA GCCTGCGTCC GAACGACCTG GTATGGAACT

19701 ATGTGCAGTC GAACTACCTC AAAGGCAATG AGCCGGCGGC GTTTGACCTG

19751 CTGTTCTGGA ATTCGGACAG CACCAATTTG CCGGGCCCGA TGTTCTGCTG

19801 GTACCTGCGC AACACCTACC TGGAAAACAG CCTGAAAGTG CCGGGCAAGC

19851 TGACGGTGGC CGGCGAAAAG ATCGACCTCG GCCTGATCGA CGCCCCGGCC

19901 TTCATCTACG GTTCGCGCGA AGACCACATC GTGCCGTGGA TGTCGGCGTA

19951 CGGTTCGCTC GACATCCTCA ACCAGGGCAA GCCGGGCGCC AACCGCTTCG

20001 TGCTGGGCGC GTCCGGCCAT ATCGCCGGCG TGATCAACTC GGTGGCCAAG

20051 AACAAGCGCA GCTACTGGAT CAACGACGGT GGCGCCGCCG ATGCCCAGGC

20101 CTGGTTCGAT GGCGCGCAGG AAGTGCCGGG CAGCTGGTGG CCGCAATGGG

-continued

20151 CCGGGTTCCT GACCCAGCAT GGCGGCAAGA AGGTCAAGCC CAAGGCCAAG

20201 CCCGGCAACG CCCGCTACAC CGCGATCGAG GCGGCGCCCG GCCGTTACGT

20251 CAAAGCCAAG GGCTGAGCGG CCGCTGAGTA ATTCTGATAT TAGAGGGAGC

20301 ATTAATGTGT TGTTGTGATG TGGTTTATAT GGGGAAATTA AATAAATGAT

20351 GTATGTACCT CTTGCCTATG TAGGTTTGTG TGTTTTGTTT TGTTGTCTAG

20401 CTTTGGTTAT TAAGTAGTAG GGACGTTCGT TCGTGTCTCA AAAAAAGGGG

20451 TACTACCACT CTGTAGTGTA TATGGATGCT GGAAATCAAT GTGTTTTGTA

20501 TTTGTTCACC TCCATTGTTG AATTCAATGT CAAATGTGTT TTGCGTTGGT

20551 TATGTGTAAA ATTACTATCT TTCTCGTCCG ATGATCAAAG TTTTAAGCAA

20601 CAAAACCAAG GGTGAAATTT AAACTGTGCT TTGTTGAAGA TTCTTTTATC

20651 ATATTGAAAA TCAAATTACT AGCAGCAGAT TTTACCTAGC ATGAAATTTT

20701 ATCAACAGTA CAGCACTCAC TAACCAAGTT CCAAACTAAG ATGCGCCATT

20751 AACATCAGCC AATAGGCATT TTCAGCAAGG CGCGCCCGCG CCGATGTATG

20801 TGACAACCCT CGGGATTGTT GATTTATTTC AAAACTAAGA GTTTTTGTCT

20851 TATTGTTCTC GTCTATTTTG GATATCAATC TTAGTTTTAT ATCTTTTCTA

20901 GTTCTCTACG TGTTAAATGT TCAACACACT AGCAATTTGG CCTGCCAGCG

20951 TATGGATTAT GGAACTATCA AGTCTGTGAC GCGCCGTACG TAGTGTTTAT

21001 CTTTGTTGCT TTTCTGAACA ATTTATTTAC TATGTAAATA TATTATCAAT

21051 GTTTAATCTA TTTTAATTTG CACATGAATT TTCATTTTAT TTTTACTTTA

21101 CAAAACAAAT AAATATATAT GCAAAAAAAT TTACAAACGA TGCACGGGTT

21151 ACAAACTAAT TTCATTAAAT GCTAATGCAG ATTTTGTGAA GTAAAACTCC

21201 AATTATGATG AAAAATACCA CCAACACCAC CTGCGAAACT GTATCCCAAC

21251 TGTCCTTAAT AAAAATGTTA AAAAGTATAT TATTCTCATT TGTCTGTCAT

21301 AATTTATGTA CCCCACTTTA ATTTTTCTGA TGTACTAAAC CGAGGGCAAA

21351 CTGAAACCTG TTCCTCATGC AAAGCCCCTA CTCACCATGT ATCATGTACG

21401 TGTCATCACC CAACAACTCC ACTTTTGCTA TATAACAACA CCCCCGTCAC

21451 ACTCTCCCTC TCTAACACAC ACCCCACTAA CAATTCCTTC ACTTGCAGCA

-continued

21501 CTGTTGCATC ATCATCTTCA TTGCAAAACC CTAAACTTCA
CCTTCAACCG

21551 CGGCCGCATG GCTTCTATGA TATCCTCTTC CGCTGTGACA
ACAGTCAGCC

21601 GTGCCTCTAG GGGGCAATCC GCCGCAGTGG CTCCATTCGG
CGGCCTCAAA

21651 TCCATGACTG GATTCCCAGT GAAGAAGGTC AACACTGACA
TTACTTCCAT

21701 TACAAGCAAT GGTGGAAGAG TAAAGTGCAT GCAGGTGTGG
CCTCCAATTG

21751 GAAAGAAGAA GTTTGAGACT CTTTCCTATT TGCCACCATT
GACGAGAGAT

21801 TCTAGAGTGA CTCAGCGCAT TGCGTATGTG ACCGGCGGCA
TGGGTGGTAT

21851 CGGAACCGCC ATTTGCCAGC GGCTGGCCAA GGATGGCTTT
CGTGTGGTGG

21901 CCGGTTGCGG CCCCAACTCG CCGCGCCGCG AAAAGTGGCT
GGAGCAGCAG

21951 AAGGCCCTGG GCTTCGATTT CATTGCCTCG GAAGGCAATG
TGGCTGACTG

22001 GGACTCGACC AAGACCGCAT TCGACAAGGT CAAGTCCGAG
GTCGGCGAGG

22051 TTGATGTGCT GATCAACAAC GCCGGTATCA CCCGCGACGT
GGTGTTCCGC

22101 AAGATGACCC GCGCCGACTG GGATGCGGTG ATCGACACCA
ACCTGACCTC

22151 GCTGTTCAAC GTCACCAAGC AGGTGATCGA CGGCATGGCC
GACCGTGGCT

22201 GGGGCCGCAT CGTCAACATC TCGTCGGTGA ACGGGCAGAA
GGGCCAGTTC

22251 GCCATGACCA ACTACTCCAC CGCCAAGGCC GGCCTGCATG
GCTTCACCAT

22301 GGCACTGGCG CAGGAAGTGG CGACCAAGGG CGTGACCGTC
AACACGGTCT

22351 CTCCGGGCTA TATCGCCACC GACATGGTCA AGGCGATCCG
CCAGGACGTG

22401 CTCGACAAGA TCGTCGCGAC GATCCCGGTC AAGCGCCTGG
GCCTGCCGGA

22451 AGAGATCGCC TCGATCTGCG CCTGGTTGTC GTCGGAGGAG
TCCGGTTTCT

22501 CGACCGGCGC CGACTTCTCG CTCAACGGCG GCCTGCATAT
GGGCTGAGCG

22551 GCCGCTGAGT AATTCTGATA TTAGAGGGAG CATTAATGTG
TTGTTGTGAT

22601 GTGGTTTATA TGGGGAAATT AAATAAATGA TGTATGTACC
TCTTGCCTAT

22651 GTAGGTTTGT GTGTTTTGTT TTGTTGTCTA GCTTTGGTTA
TTAAGTAGTA

22701 GGGACGTTCG TTCGTGTCTC AAAAAAAGGG GTACTACCAC
TCTGTAGTGT

22751 ATATGGATGC TGGAAATCAA TGTGTTTTGT ATTTGTTCAC
CTCCATTGTT

22801 GAATTCAATG TCAAATGTGT TTTGCGTTGG TTATGTGTAA
AATTACTATC

-continued

22851 TTTCTCGTCC GATGATCAAA GTTTTAAGCA ACAAAACCAA
GGGTGAAATT

22901 TAAACTGTGC TTTGTTGAAG ATTCTTTTAT CATATTGAAA
ATCAAATTAC

22951 TAGCAGCAGA TTTTACCTAG CATGAAATTT TATCAACAGT
ACAGCACTCA

23001 CTAACCAAGT TCCAAACTAA GATGCGCCAT TAACATCAGC
CAATAGGCAT

23051 TTTCAGCAAG GCGCGTAA

Vector: pMBXS407

(SEQ ID NO: 9)

1 GGGGATCCGT ACGTAAGTAC GTACTCAAAA TGCCAACAAA
TAAAAAAAAA

51 GTTGCTTTAA TAATGCCAAA ACAAATTAAT AAAACACTTA
CAACACCGGA

101 TTTTTTTTAA TTAAAATGTG CCATTTAGGA TAAATAGTTA
ATATTTTTAA

151 TAATTATTTA AAAAGCCGTA TCTACTAAAA TGATTTTTAT
TTGGTTGAAA

201 ATATTAATAT GTTTAAATCA ACACAATCTA TCAAAATTAA
ACTAAAAAAA

251 AAATAAGTGT ACGTGGTTAA CATTAGTACA GTAATATAAG
AGGAAAATGA

301 GAAATTAAGA AATTGAAAGC GAGTCTAATT TTTAAATTAT
GAACCTGCAT

351 ATATAAAAGG AAAGAAAGAA TCCAGGAAGA AAAGAAATGA
AACCATGCAT

401 GGTCCCCTCG TCATCACGAG TTTCTGCCAT TTGCAATAGA
AACACTGAAA

451 CACCTTTCTC TTTGTCACTT AATTGAGATG CCGAAGCCAC
CTCACACCAT

501 GAACTTCATG AGGTGTAGCA CCCAAGGCTT CCATAGCCAT
GCATACTGAA

551 GAATGTCTCA AGCTCAGCAC CCTACTTCTG TGACGTGTCC
CTCATTCACC

601 TTCCTCTCTT CCCTATAAAT AACCACGCCT CAGGTTCTCC
GCTTCACAAC

651 TCAAACATTC TCTCCATTGG TCCTTAAACA CTCATCAGTC
ATCACCGCGG

701 CCGCGGAATT CATGGCTTCT ATGATATCCT CTTCCGCTGT
GACAACAGTC

751 AGCCGTGCCT CTAGGGGGCA ATCCGCCGCA GTGGCTCCAT
TCGGCGGCCT

801 CAAATCCATG ACTGGATTCC CAGTGAAGAA GGTCAACACT
GACATTACTT

851 CCATTACAAG CAATGGTGGA AGAGTAAAGT GCATGCAGGT
GTGGCCTCCA

901 ATTGGAAAGA AGAAGTTTGA GACTCTTTCC TATTTGCCAC
CATTGACGAG

951 AGATTCTAGA GTGACTGACG TTGTCATCGT ATCCGCCGCC
CGCACCGCGG

1001 TCGGCAAGTT TGGCGGCTCG CTGGCCAAGA TCCCGGCACC
GGAACTGGGT

1051 GCCGTGGTCA TCAAGGCCGC GCTGGAGCGC GCCGGCGTCA
AGCCGGAGCA

-continued

1101 GGTGAGCGAA GTCATCATGG GCCAGGTGCT GACCGCCGGT TCGGGCCAGA

1151 ACCCCGCACG CCAGGCCGCG ATCAAGGCCG GCCTGCCGGC GATGGTGCCG

1201 GCCATGACCA TCAACAAGGT GTGCGGCTCG GGCCTGAAGG CCGTGATGCT

1251 GGCCGCCAAC GCGATCATGG CGGGCGACGC CGAGATCGTG GTGGCCGGCG

1301 GCCAGGAAAA CATGAGCGCC GCCCCGCACG TGCTGCCGGG CTCGCGCGAT

1351 GGTTTCCGCA TGGGCGATGC CAAGCTGGTC GACACCATGA TCGTCGACGG

1401 CCTGTGGGAC GTGTACAACC AGTACCACAT GGGCATCACC GCCGAGAACG

1451 TGGCCAAGGA ATACGGCATC ACACGCGAGG CGCAGGATGA GTTCGCCGTC

1501 GGCTCGCAGA ACAAGGCCGA AGCCGCGCAG AAGGCCGGCA AGTTTGACGA

1551 AGAGATCGTC CCGGTGCTGA TCCCGCAGCG CAAGGGCGAC CCGGTGGCCT

1601 TCAAGACCGA CGAGTTCGTG CGCCAGGGCG CCACGCTGGA CAGCATGTCC

1651 GGCCTCAAGC CCGCCTTCGA CAAGGCCGGC ACGGTGACCG CGGCCAACGC

1701 CTCGGGCCTG AACGACGGCG CCGCCGCGGT GGTGGTGATG TCGGCGGCCA

1751 AGGCCAAGGA ACTGGGCCTG ACCCCGCTGG CCACGATCAA GAGCTATGCC

1801 AACGCCGGTG TCGATCCCAA GGTGATGGGC ATGGGCCCGG TGCCGGCCTC

1851 CAAGCGCGCC CTGTCGCGCG CCGAGTGGAC CCCGCAAGAC CTGGACCTGA

1901 TGGAGATCAA CGAGGCCTTT GCCGCGCAGG CGCTGGCGGT GCACCAGCAG

1951 ATGGGCTGGG ACACCTCCAA GGTCAATGTG AACGGCGGCG CCATCGCCAT

2001 CGGCCACCCG ATCGGCGCGT CGGGCTGCCG TATCCTGGTG ACGCTGCTGC

2051 ACGAGATGAA GCGCCGTGAC GCGAAGAAGG GCCTGGCCTC GCTGTGCATC

2101 GGCGGCGGCA TGGGCGTGGC GCTGGCAGTC GAGCGCAAAT AACTCGAGGC

2151 GGCCGCAGCC CTTTTTGTAT GTGCTACCCC ACTTTTGTCT TTTTGGCAAT

2201 AGTGCTAGCA ACCAATAAAT AATAATAATA ATAATGAATA AGAAAACAAA

2251 GGCTTTAGCT TGCCTTTTGT TCACTGTAAA ATAATAATGT AAGTACTCTC

2301 TATAATGAGT CACGAAACTT TTGCGGGAAT AAAAGGAGAA ATTCCAATGA

2351 GTTTTCTGTC AAATCTTCTT TTGTCTCTCT CTCTCTCTCT TTTTTTTTTT

2401 TCTTTCTTCT GAGCTTCTTG CAAAACAAAA GGCAAACAAT AACGATTGGT

-continued

2451 CCAATGATAG TTAGCTTGAT CGATGATATC TTTAGGAAGT GTTGGCAGGA

2501 CAGGACATGA TGTAGAAGAC TAAAATTGAA AGTATTGCAG ACCCAATAGT

2551 TGAAGATTAA CTTTAAGAAT GAAGACGTCT TATCAGGTTC TTCATGACTT

2601 AAGCTTTAAG AGGAGTCCAC CATGGTAGAT CTGACTAGTA ACGGCCGCCA

2651 GTGTGCTGGA ATTCTGCAGA TGTGGAGCAC GACACTCTCG TCTACTCCAA

2701 GAATATCAAA GATACAGTCT CAGAAGACCA AAGGGCTATT GAGACTTTTC

2751 AACAAAGGGT AATATCGGGA AACCTCCTCG GATTCCATTG CCCAGCTATC

2801 TGTCACTTCA TCAAAAGGAC AGTAGAAAAG GAAGGTGGCA CCTACAAATG

2851 CCATCATTGC GATAAAGGAA AGGCTATCGT TCAAGATGCC TCTGCCGACA

2901 GTGGTCCCAA AGATGGACCC CCACCCACGA GGAGCATCGT GGAAAAAGAA

2951 GACGTTCCAA CCACGTCTTC AAAGCAAGTG GATTGATGTG ATAACATGGT

3001 GGAGCACGAC ACTCTCGTCT ACTCCAAGAA TATCAAAGAT ACAGTCTCAG

3051 AAGACCAAAG GGCTATTGAG ACTTTTCAAC AAAGGGTAAT ATCGGGAAAC

3101 CTCCTCGGAT TCCATTGCCC AGCTATCTGT CACTTCATCA AAAGGACAGT

3151 AGAAAAGGAA GGTGGCACCT ACAAATGCCA TCATTGCGAT AAAGGAAAGG

3201 CTATCGTTCA AGATGCCTCT GCCGACAGTG GTCCCAAAGA TGGACCCCCA

3251 CCCACGAGGA GCATCGTGGA AAAAGAAGAC GTTCCAACCA CGTCTTCAAA

3301 GCAAGTGGAT TGATGTGATA TCTCCACTGA CGTAAGGGAT GACGCACAAT

3351 CCCACTATCC TTCGCAAGAC CTTCCTCTAT ATAAGGAAGT TCATTTCATT

3401 TGGAGAGGAC ACGCTGAAAT CACCAGTCTC TCTCTACAAA TCTATCTCTC

3451 TCGAGTTAAT TAAAATGGCT TCTATGATAT CCTCTTCCGC TGTGACAACA

3501 GTCAGCCGTG CCTCTAGGGG GCAATCCGCC GCAGTGGCTC CATTCGGCGG

3551 CCTCAAATCC ATGACTGGAT TCCCAGTGAA GAAGGTCAAC ACTGACATTA

3601 CTTCCATTAC AAGCAATGGT GGAAGAGTAA AGTGCATGCA GGTGTGGCCT

3651 CCAATTGGAA AGAAGAAGTT TGAGACTCTT TCCTATTTGC CACCATTGAC

3701 GAGAGATTCT AGAGTGGAGA AGACGATCGG TCTCGAGATT ATTGAAGTTG

3751 TCGAGCAGGC AGCGATCGCC TCGGCCCGCC TGATGGGCAA AGGCGAAAAG

-continued

3801 AATGAAGCCG ATCGCGTCGC AGTAGAAGCG ATGCGGGTGC GGATGAACCA

3851 AGTGGAAATG CTGGGCCGCA TCGTCATCGG TGAAGGCGAG CGCGACGAAG

3901 CACCGATGCT CTATATCGGT GAAGAAGTGG GCATCTACCG CGATGCAGAC

3951 AAGCGGGCTG GCGTACCGGC TGGCAAGCTG GTGGAAATCG ACATCGCCGT

4001 TGACCCCTGC GAAGGCACCA ACCTCTGCGC CTACGGTCAG CCCGGCTCGA

4051 TGGCAGTTTT GGCCATCTCC GAGAAAGGCG GCCTGTTTGC AGCTCCCGAC

4101 TTCTACATGA AGAAACTGGC TGCACCCCCA GCTGCCAAAG GCAAAGTAGA

4151 CATCAATAAG TCCGCGACCG AAAACCTGAA AATTCTCTCG GAATGTCTCG

4201 ATCGCGCCAT CGATGAATTG GTGGTCGTGG TCATGGATCG TCCCCGCCAC

4251 AAAGAGCTAA TCCAAGAGAT CCGCCAAGCG GGTGCCCGCG TCCGTCTGAT

4301 CAGCGATGGT GACGTTTCGG CCGCGATCTC CTGCGGTTTT GCTGGCACCA

4351 ACACCCACGC CCTGATGGGC ATCGGTGCAG CTCCCGAGGG TGTGATTTCG

4401 GCAGCAGCAA TGCGTTGCCT CGGCGGTCAC TTCCAAGGCC AGCTGATCTA

4451 CGACCCAGAA GTGGTCAAAA CCGGCCTGAT CGGTGAAAGC CGTGAGAGCA

4501 ACATCGCTCG CCTGCAAGAA ATGGGCATCA CCGATCCCGA TCGCGTCTAC

4551 GACGCCAACG AACTGGCTTC GGGTCAAGAA GTGCTGTTTG CGGCTTGCGG

4601 TATCACCCCG GGCTTGCTGA TGGAAGGCGT GCGCTTCTTC AAAGGCGGCG

4651 CTCGCACCCA GAGCTTGGTG ATCTCCAGCC AGTCACGGAC GGCTCGCTTC

4701 GTTGACACCG TTCACATGTT CGACGATGTC AAAACGGTTA GCCTCCGTTA

4751 ATTCCTGATC CCAAATGGCG GCCGGAGCGG TAGGGCGCGC CATCGTTCAA

4801 ACATTTGGCA ATAAAGTTTC TTAAGATTGA ATCCTGTTGC CGGTCTTGCG

4851 ATGATTATCA TATAATTTCT GTTGAATTAC GTTAAGCATG TAATAATTAA

4901 CATGTAATGC ATGACGTTAT TTATGAGATG GGTTTTTATG ATTAGAGTCC

4951 CGCAATTATA CATTTAATAC GCGATAGAAA ACAAAATATA GCGCGCAAAC

5001 TAGGATAAAT TATCGCGCGC GGTGTCATCT ATGTTACTAG ATCCGATGAT

5051 AAGCTGTCAA ACATGAATTT AAATACTAGT AGAAGGTAAT TATCCAAGAT

5101 GTAGCATCAA GAATCCAATG TTTACGGGAA AAACTATGGA AGTATTATGT

-continued

5151 GAGCTCAGCA AGAAGCAGAT CAATATGCGG CACATATGCA ACCTATGTTC

5201 AAAAATGAAG AATGTACAGA TACAAGATCC TATACTGCCA GAATACGAAG

5251 AAGAATACGT AGAAATTGAA AAAGAAGAAC CAGGCGAAGA AAAGAATCTT

5301 GAAGACGTAA GCACTGACGA CAACAATGAA AAGAAGAAGA TAAGGTCGGT

5351 GATTGTGAAA GAGACATAGA GGACACATGT AAGGTGGAAA ATGTAAGGGC

5401 GGAAAGTAAC CTTATCACAA AGGAATCTTA TCCCCCACTA CTTATCCTTT

5451 TATATTTTTC CGTGTCATTT TTGCCCTTGA GTTTTCCTAT ATAAGGAACC

5501 AAGTTCGGCA TTTGTGAAAA CAAGAAAAAA TTGGTGTAAG CTATTTTCTT

5551 TGAAGTACTG AGGATACAAC TTCAGAGAAA TTTGTAAGAA AGTGGATCGA

5601 AACCATGGCC TCCTCCGAGA ACGTCATCAC CGAGTTCATG CGCTTCAAGG

5651 TGCGCATGGA GGGCACCGTG AACGGCCACG AGTTCGAGAT CGAGGGCGAG

5701 GGCGAGGGCC GCCCCTACGA GGGCCACAAC ACCGTGAAGC TGAAGGTGAC

5751 CAAGGGCGGC CCCCTGCCCT TCGCCTGGGA CATCCTGTCC CCCCAGTTCC

5801 AGTACGGCTC CAAGGTGTAC GTGAAGCACC CCGCCGACAT CCCCGACTAC

5851 AAGAAGCTGT CCTTCCCCGA GGGCTTCAAG TGGGAGCGCG TGATGAACTT

5901 CGAGGACGGC GGCGTGGCGA CCGTGACCCA GGACTCCTCC CTGCAGGACG

5951 GCTGCTTCAT CTACAAGGTG AAGTTCATCG GCGTGAACTT CCCCTCCGAC

6001 GGCCCCGTGA TGCAGAAGAA GACCATGGGC TGGGAGGCCT CCACCGAGCG

6051 CCTGTACCCC CGCGACGGCG TGCTGAAGGG CGAGACCCAC AAGGCCCTGA

6101 AGCTGAAGGA CGGCGGCCAC TACCTGGTGG AGTTCAAGTC CATCTACATG

6151 GCCAAGAAGC CCGTGCAGCT GCCCGGCTAC TACTACGTGG ACGCCAAGCT

6201 GGACATCACC TCCCACAACG AGGACTACAC CATCGTGGAG CAGTACGAGC

6251 GCACCGAGGG CCGCCACCAC CTGTTCCTGG TACCAATGAG CTCTGTCCAA

6301 CAGTCTCAGG GTTAATGTCT ATGTATCTTA AATAATGTTG TCGGCGATCG

6351 TTCAAACATT TGGCAATAAA GTTTCTTAAG ATTGAATCCT GTTGCCGGTC

6401 TTGCGATGAT TATCATATAA TTTCTGTTGA ATTACGTTAA GCATGTAATA

6451 ATTAACATGT AATGCATGAC GTTATTTATG AGATGGGTTT TTATGATTAG

-continued

6501 AGTCCCGCAA TTATACATTT AATACGCGAT AGAAAACAAA ATATAGCGCG

6551 CAAACTAGGA TAAATTATCG CGCGCGGTGT CATCTATGTT ACTAGATCGG

6601 GAATTAAACT ATCAGTGTTT GACAGGATAT ATTGGCGGGT AAACCTAAGA

6651 GAAAAGAGCG TTTATTAGAA TAACGGATAT TTAAAAGGGC GTGAAAAGGT

6701 TTATCCGTTC GTCCATTTGT ATGTGCATGC CAACCACAGG GTTCCCCTCG

6751 GGATCAAAGT ACTTTGATCC AACCCCTCCG CTGCTATAGT GCAGTCGGCT

6801 TCTGACGTTC AGTGCAGCCG TCTTCTGAAA ACGACATGTC GCACAAGTCC

6851 TAAGTTACGC GACAGGCTGC CGCCCTGCCC TTTTCCTGGC GTTTTCTTGT

6901 CGCGTGTTTT AGTCGCATAA AGTAGAATAC TTGCGACTAG AACCGGAGAC

6951 ATTACGCCAT GAACAAGAGC GCCGCCGCTG GCCTGCTGGG CTATGCCCGC

7001 GTCAGCACCG ACGACCAGGA CTTGACCAAC CAACGGGCCG AACTGCACGC

7051 GGCCGGCTGC ACCAAGCTGT TTTCCGAGAA GATCACCGGC ACCAGGCGCG

7101 ACCGCCCGGA GCTGGCCAGG ATGCTTGACC ACCTACGCCC TGGCGACGTT

7151 GTGACAGTGA CCAGGCTAGA CCGCCTGGCC CGCAGCACCC GCGACCTACT

7201 GGACATTGCC GAGCGCATCC AGGAGGCCGG CGCGGGCCTG CGTAGCCTGG

7251 CAGAGCCGTG GGCCGACACC ACCACGCCGG CCGGCCGCAT GGTGTTGACC

7301 GTGTTCGCCG GCATTGCCGA GTTCGAGCGT TCCCTAATCA TCGACCGCAC

7351 CCGGAGCGGG CGCGAGGCCG CCAAGGCCCG AGGCGTGAAG TTTGGCCCCC

7401 GCCCTACCCT CACCCCGGCA CAGATCGCGC ACGCCCGCGA GCTGATCGAC

7451 CAGGAAGGCC GCACCGTGAA AGAGGCGGCT GCACTGCTTG GCGTGCATCG

7501 CTCGACCCTG TACCGCGCAC TTGAGCGCAG CGAGGAAGTG ACGCCCACCG

7551 AGGCCAGGCG GCGCGGTGCC TTCCGTGAGG ACGCATTGAC CGAGGCCGAC

7601 GCCCTGGCGG CCGCCGAGAA TGAACGCCAA GAGGAACAAG CATGAAACCG

7651 CACCAGGACG GCCAGGACGA ACCGTTTTTC ATTACCGAAG AGATCGAGGC

7701 GGAGATGATC GCGGCCGGGT ACGTGTTCGA GCCGCCCGCG CACGTCTCAA

7751 CCGTGCGGCT GCATGAAATC CTGGCCGGTT TGTCTGATGC CAAGCTGGCG

7801 GCCTGGCCGG CCAGCTTGGC CGCTGAAGAA ACCGAGCGCC GCCGTCTAAA

-continued

7851 AAGGTGATGT GTATTTGAGT AAAACAGCTT GCGTCATGCG GTCGCTGCGT

7901 ATATGATGCG ATGAGTAAAT AAACAAATAC GCAAGGGGAA CGCATGAAGG

7951 TTATCGCTGT ACTTAACCAG AAAGGCGGGT CAGGCAAGAC GACCATCGCA

8001 ACCCATCTAG CCCGCGCCCT GCAACTCGCC GGGGCCGATG TTCTGTTAGT

8051 CGATTCCGAT CCCCAGGGCA GTGCCCGCGA TTGGGCGGCC GTGCGGGAAG

8101 ATCAACCGCT AACCGTTGTC GGCATCGACC GCCCGACGAT TGACCGCGAC

8151 GTGAAGGCCA TCGGCCGGCG CGACTTCGTA GTGATCGACG GAGCGCCCCA

8201 GGCGGCGGAC TTGGCTGTGT CCGCGATCAA GGCAGCCGAC TTCGTGCTGA

8251 TTCCGGTGCA GCCAAGCCCT TACGACATAT GGGCCACCGC CGACCTGGTG

8301 GAGCTGGTTA AGCAGCGCAT TGAGGTCACG GATGGAAGGC TACAAGCGGC

8351 CTTTGTCGTG TCGCGGGCGA TCAAAGGCAC GCGCATCGGC GGTGAGGTTG

8401 CCGAGGCGCT GGCCGGGTAC GAGCTGCCCA TTCTTGAGTC CCGTATCACG

8451 CAGCGCGTGA GCTACCCAGG CACTGCCGCC GCCGGCACAA CCGTTCTTGA

8501 ATCAGAACCC GAGGGCGACG CTGCCCGCGA GGTCCAGGCG CTGGCCGCTG

8551 AAATTAAATC AAAACTCATT TGAGTTAATG AGGTAAAGAG AAAATGAGCA

8601 AAAGCACAAA CACGCTAAGT GCCGGCCGTC CGAGCGCACG CAGCAGCAAG

8651 GCTGCAACGT TGGCCAGCCT GGCAGACACG CCAGCCATGA AGCGGGTCAA

8701 CTTTCAGTTG CCGGCGGAGG ATCACACCAA GCTGAAGATG TACGCGGTAC

8751 GCCAAGGCAA GACCATTACC GAGCTGCTAT CTGAATACAT CGCGCAGCTA

8801 CCAGAGTAAA TGAGCAAATG AATAAATGAG TAGATGAATT TTAGCGGCTA

8851 AAGGAGGCGG CATGGAAAAT CAAGAACAAC CAGGCACCGA CGCCGTGGAA

8901 TGCCCCATGT GTGGAGGAAC GGGCGGTTGG CCAGGCGTAA GCGGCTGGGT

8951 TGTCTGCCGG CCCTGCAATG GCACTGGAAC CCCCAAGCCC GAGGAATCGG

9001 CGTGACGGTC GCAAACCATC CGGCCCGGTA CAAATCGGCG CGGCGCTGGG

9051 TGATGACCTG GTGGAGAAGT TGAAGGCCGC GCAGGCCGCC CAGCGGCAAC

9101 GCATCGAGGC AGAAGCACGC CCCGGTGAAT CGTGGCAAGC GGCCGCTGAT

9151 CGAATCCGCA AAGAATCCCG GCAACCGCCG GCAGCCGGTG CGCCGTCGAT

-continued

9201 TAGGAAGCCG CCCAAGGGCG ACGAGCAACC AGATTTTTTC GTTCCGATGC

9251 TCTATGACGT GGGCACCCGC GATAGTCGCA GCATCATGGA CGTGGCCGTT

9301 TTCCGTCTGT CGAAGCGTGA CCGACGAGCT GGCGAGGTGA TCCGCTACGA

9351 GCTTCCAGAC GGGCACGTAG AGGTTTCCGC AGGGCCGGCC GGCATGGCCA

9401 GTGTGTGGGA TTACGACCTG GTACTGATGG CGGTTTCCCA TCTAACCGAA

9451 TCCATGAACC GATACCGGGA AGGGAAGGGA GACAAGCCCG GCCGCGTGTT

9501 CCGTCCACAC GTTGCGGACG TACTCAAGTT CTGCCGGCGA GCCGATGGCG

9551 GAAAGCAGAA AGACGACCTG GTAGAAACCT GCATTCGGTT AAACACCACG

9601 CACGTTGCCA TGCAGCGTAC GAAGAAGGCC AAGAACGGCC GCCTGGTGAC

9651 GGTATCCGAG GGTGAAGCCT TGATTAGCCG CTACAAGATC GTAAAGAGCG

9701 AAACCGGGCG GCCGGAGTAC ATCGAGATCG AGCTAGCTGA TTGGATGTAC

9751 CGCGAGATCA CAGAAGGCAA GAACCCGGAC GTGCTGACGG TTCACCCCGA

9801 TTACTTTTTG ATCGATCCCG GCATCGGCCG TTTTCTCTAC CGCCTGGCAC

9851 GCCGCGCCGC AGGCAAGGCA GAAGCCAGAT GGTTGTTCAA GACGATCTAC

9901 GAACGCAGTG GCAGCGCCGG AGAGTTCAAG AAGTTCTGTT TCACCGTGCG

9951 CAAGCTGATC GGGTCAAATG ACCTGCCGGA GTACGATTTG AAGGAGGAGG

10001 CGGGGCAGGC TGGCCCGATC CTAGTCATGC GCTACCGCAA CCTGATCGAG

10051 GGCGAAGCAT CCGCCGGTTC CTAATGTACG GAGCAGATGC TAGGGCAAAT

10101 TGCCCTAGCA GGGGAAAAAG GTCGAAAAGG TCTCTTTCCT GTGGATAGCA

10151 CGTACATTGG GAACCCAAAG CCGTACATTG GGAACCGGAA CCCGTACATT

10201 GGGAACCCAA AGCCGTACAT TGGGAACCGG TCACACATGT AAGTGACTGA

10251 TATAAAAGAG AAAAAAGGCG ATTTTTCCGC CTAAAACTCT TTAAAACTTA

10301 TTAAAACTCT TAAAACCCGC CTGGCCTGTG CATAACTGTC TGGCCAGCGC

10351 ACAGCCGAAG AGCTGCAAAA AGCGCCTACC CTTCGGTCGC TGCGCTCCCT

10401 ACGCCCCGCC GCTTCGCGTC GGCCTATCGC GGCCGCTGGC CGCTCAAAAA

10451 TGGCTGGCCT ACGGCCAGGC AATCTACCAG GGCGCGGACA AGCCGCGCCG

10501 TCGCCACTCG ACCGCCGGCG CCCACATCAA GGCACCCTGC CTCGCGCGTT

-continued

10551 TCGGTGATGA CGGTGAAAAC CTCTGACACA TGCAGCTCCC GGAGACGGTC

10601 ACAGCTTGTC TGTAAGCGGA TGCCGGGAGC AGACAAGCCC GTCAGGGCGC

10651 GTCAGCGGGT GTTGGCGGGT GTCGGGGCGC AGCCATGACC CAGTCACGTA

10701 GCGATAGCGG AGTGTATACT GGCTTAACTA TGCGGCATCA GAGCAGATTG

10751 TACTGAGAGT GCACCATATG CGGTGTGAAA TACCGCACAG ATGCGTAAGG

10801 AGAAAATACC GCATCAGGCG CTCTTCCGCT TCCTCGCTCA CTGACTCGCT

10851 GCGCTCGGTC GTTCGGCTGC GGCGAGCGGT ATCAGCTCAC TCAAAGGCGG

10901 TAATACGGTT ATCCACAGAA TCAGGGGATA ACGCAGGAAA GAACATGTGA

10951 GCAAAAGGCC AGCAAAAGGC CAGGAACCGT AAAAAGGCCG CGTTGCTGGC

11001 GTTTTTCCAT AGGCTCCGCC CCCCTGACGA GCATCACAAA AATCGACGCT

11051 CAAGTCAGAG GTGGCGAAAC CCGACAGGAC TATAAAGATA CCAGGCGTTT

11101 CCCCCTGGAA GCTCCCTCGT GCGCTCTCCT GTTCCGACCC TGCCGCTTAC

11151 CGGATACCTG TCCGCCTTTC TCCCTTCGGG AAGCGTGGCG CTTTCTCATA

11201 GCTCACGCTG TAGGTATCTC AGTTCGGTGT AGGTCGTTCG CTCCAAGCTG

11251 GGCTGTGTGC ACGAACCCCC CGTTCAGCCC GACCGCTGCG CCTTATCCGG

11301 TAACTATCGT CTTGAGTCCA ACCCGGTAAG ACACGACTTA TCGCCACTGG

11351 CAGCAGCCAC TGGTAACAGG ATTAGCAGAG CGAGGTATGT AGGCGGTGCT

11401 ACAGAGTTCT TGAAGTGGTG GCCTAACTAC GGCTACACTA GAAGGACAGT

11451 ATTTGGTATC TGCGCTCTGC TGAAGCCAGT TACCTTCGGA AAAAGAGTTG

11501 GTAGCTCTTG ATCCGGCAAA CAAACCACCG CTGGTAGCGG TGGTTTTTTT

11551 GTTTGCAAGC AGCAGATTAC GCGCAGAAAA AAAGGATCTC AAGAAGATCC

11601 TTTGATCTTT TCTACGGGGT CTGACGCTCA GTGGAACGAA AACTCACGTT

11651 AAGGGATTTT GGTCATGCAT TCTAGGTACT AAAACAATTC ATCCAGTAAA

11701 ATATAATATT TTATTTTCTC CCAATCAGGC TTGATCCCCA GTAAGTCAAA

11751 AAATAGCTCG ACATACTGTT CTTCCCCGAT ATCCTCCCTG ATCGACCGGA

11801 CGCAGAAGGC AATGTCATAC CACTTGTCCG CCCTGCCGCT TCTCCCAAGA

11851 TCAATAAAGC CACTTACTTT GCCATCTTTC ACAAAGATGT TGCTGTCTCC

-continued

11901 CAGGTCGCCG TGGGAAAAGA CAAGTTCCTC TTCGGGCTTT TCCGTCTTTA

11951 AAAAATCATA CAGCTCGCGC GGATCTTTAA ATGGAGTGTC TTCTTCCCAG

12001 TTTTCGCAAT CCACATCGGC CAGATCGTTA TTCAGTAAGT AATCCAATTC

12051 GGCTAAGCGG CTGTCTAAGC TATTCGTATA GGGACAATCC GATATGTCGA

12101 TGGAGTGAAA GAGCCTGATG CACTCCGCAT ACAGCTCGAT AATCTTTTCA

12151 GGGCTTTGTT CATCTTCATA CTCTTCCGAG CAAAGGACGC CATCGGCCTC

12201 ACTCATGAGC AGATTGCTCC AGCCATCATG CCGTTCAAAG TGCAGGACCT

12251 TTGGAACAGG CAGCTTTCCT TCCAGCCATA GCATCATGTC CTTTTCCCGT

12301 TCCACATCAT AGGTGGTCCC TTTATACCGG CTGTCCGTCA TTTTTAAATA

12351 TAGGTTTTCA TTTTCTCCCA CCAGCTTATA TACCTTAGCA GGAGACATTC

12401 CTTCCGTATC TTTTACGCAG CGGTATTTTT CGATCAGTTT TTTCAATTCC

12451 GGTGATATTC TCATTTTAGC CATTTATTAT TTCCTTCCTC TTTTCTACAG

12501 TATTTAAAGA TACCCCAAGA AGCTAATTAT AACAAGACGA ACTCCAATTC

12551 ACTGTTCCTT GCATTCTAAA ACCTTAAATA CCAGAAAACA GCTTTTTCAA

12601 AGTTGTTTTC AAAGTTGGCG TATAACATAG TATCGACGGA GCCGATTTTG

12651 AAACCGCGGT GATCACAGGC AGCAACGCTC TGTCATCGTT ACAATCAACA

12701 TGCTACCCTC CGCGAGATCA TCCGTGTTTC AAACCCGGCA GCTTAGTTGC

12751 CGTTCTTCCG AATAGCATCG GTAACATGAG CAAAGTCTGC CGCCTTACAA

12801 CGGCTCTCCC GCTGACGCCG TCCCGGACTG ATGGGCTGCC TGTATCGAGT

12851 GGTGATTTTG TGCCGAGCTG CCGGTCGGGG AGCTGTTGGC TGGCTGGTGG

12901 CAGGATATAT TGTGGTGTAA ACAAATTGAC GCTTAGACAA CTTAATAACA

12951 CATTGCGGAC GTTTTTAATG TACTGAATTA ACGCCGAATT AATTCCTAGG

13001 CCACCATGTT GGGCCCGGGG CGCGCCGTAC GTAGTGTTTA TCTTTGTTGC

13051 TTTTCTGAAC AATTTATTTA CTATGTAAAT ATATTATCAA TGTTTAATCT

13101 ATTTTAATTT GCACATGAAT TTTCATTTTA TTTTTACTTT ACAAAACAAA

13151 TAAATATATA TGCAAAAAAA TTTACAAACG ATGCACGGGT TACAAACTAA

13201 TTTCATTAAA TGCTAATGCA GATTTTGTGA AGTAAAACTC CAATTATGAT

-continued

13251 GAAAAATACC ACCAACACCA CCTGCGAAAC TGTATCCCAA CTGTCCTTAA

13301 TAAAAATGTT AAAAAGTATA TTATTCTCAT TTGTCTGTCA TAATTTATGT

13351 ACCCCACTTT AATTTTTCTG ATGTACTAAA CCGAGGGCAA ACTGAAACCT

13401 GTTCCTCATG CAAAGCCCCT ACTCACCATG TATCATGTAC GTGTCATCAC

13451 CCAACAACTC CACTTTTGCT ATATAACAAC ACCCCCGTCA CACTCTCCCT

13501 CTCTAACACA CACCCCACTA ACAATTCCTT CACTTGCAGC ACTGTTGCAT

13551 CATCATCTTC ATTGCAAAAC CCTAAACTTC ACCTTCAACC GCGGCCGCAT

13601 GGCTTCTATG ATATCCTCTT CCGCTGTGAC AACAGTCAGC CGTGCCTCTA

13651 GGGGGCAATC CGCCGCAGTG GCTCCATTCG GCGGCCTCAA ATCCATGACT

13701 GGATTCCCAG TGAAGAAGGT CAACACTGAC ATTACTTCCA TTACAAGCAA

13751 TGGTGGAAGA GTAAAGTGCA TGCAGGTGTG GCCTCCAATT GGAAAGAAGA

13801 AGTTTGAGAC TCTTTCCTAT TTGCCACCAT TGACGAGAGA TTCTAGAGTG

13851 AGTAACAAGA ACAACGATGA GCTGCAGTGG CAATCCTGGT TCAGCAAGGC

13901 GCCCACCACC GAGGCGAACC CGATGGCCAC CATGTTGCAG GATATCGGCG

13951 TTGCGCTCAA ACCGGAAGCG ATGGAGCAGC TGAAAAACGA TTATCTGCGT

14001 GACTTCACCG CGTTGTGGCA GGATTTTTTG GCTGGCAAGG CGCCAGCCGT

14051 CAGCGACCGC CGCTTCAGCT CGGCAGCCTG GCAGGGCAAT CCGATGTCGG

14101 CCTTCAATGC CGCATCTTAC CTGCTCAACG CCAAATTCCT CAGTGCCATG

14151 GTGGAGGCGG TGGACACCGC ACCCCAGCAA AAGCAGAAAA TACGCTTTGC

14201 CGTGCAGCAG GTGATTGATG CCATGTCGCC CGCGAACTTC CTCGCCACCA

14251 ACCCGGAAGC GCAGCAAAAA CTGATTGAAA CCAAGGGCGA GAGCCTGACG

14301 CGTGGCCTGG TCAATATGCT GGGCGATATC AACAAGGGCC ATATCTCGCT

14351 GTCGGACGAA TCGGCCTTTG AAGTGGGCCG CAACCTGGCC ATTACCCCGG

14401 GCACCGTGAT TTACGAAAAT CCGCTGTTCC AGCTGATCCA GTACACGCCG

14451 ACCACGCCGA CGGTCAGCCA GCGCCCGCTG TTGATGGTGC CGCCGTGCAT

14501 CAACAAGTTC TACATCCTCG ACCTGCAACC GGAAAATTCG CTGGTGCGCT

14551 ACGCGGTGGA GCAGGGCAAC ACCGTGTTCC TGATCTCGTG GAGCAATCCG

-continued

14601 GACAAGTCGC TGGCCGGCAC CACCTGGGAC GACTACGTGG AGCAGGGCGT

14651 GATCGAAGCG ATCCGCATCG TCCAGGACGT CAGCGGCCAG GACAAGCTGA

14701 ACATGTTCGG CTTCTGCGTG GGCGGCACCA TCGTTGCCAC CGCACTGGCG

14751 GTACTGGCGG CGCGTGGCCA GCACCCGGCG GCCAGCCTGA CCCTGCTGAC

14801 CACCTTCCTC GACTTCAGCG ACACCGGCGT GCTCGACGTC TTCGTCGATG

14851 AAACCCAGGT CGCGCTGCGT GAACAGCAAT TGCGCGATGG CGGCCTGATG

14901 CCGGGCCGTG ACCTGGCCTC GACCTTCTCG AGCCTGCGTC CGAACGACCT

14951 GGTATGGAAC TATGTGCAGT CGAACTACCT CAAAGGCAAT GAGCCGGCGG

15001 CGTTTGACCT GCTGTTCTGG AATTCGGACA GCACCAATTT GCCGGGCCCG

15051 ATGTTCTGCT GGTACCTGCG CAACACCTAC CTGGAAAACA GCCTGAAAGT

15101 GCCGGGCAAG CTGACGGTGG CCGGCGAAAA GATCGACCTC GGCCTGATCG

15151 ACGCCCCGGC CTTCATCTAC GGTTCGCGCG AAGACCACAT CGTGCCGTGG

15201 ATGTCGGCGT ACGGTTCGCT CGACATCCTC AACCAGGGCA AGCCGGGCGC

15251 CAACCGCTTC GTGCTGGGCG CGTCCGGCCA TATCGCCGGC GTGATCAACT

15301 CGGTGGCCAA GAACAAGCGC AGCTACTGGA TCAACGACGG TGGCGCCGCC

15351 GATGCCCAGG CCTGGTTCGA TGGCGCGCAG GAAGTGCCGG GCAGCTGGTG

15401 GCCGCAATGG GCCGGGTTCC TGACCCAGCA TGGCGGCAAG AAGGTCAAGC

15451 CCAAGGCCAA GCCCGGCAAC GCCCGCTACA CCGCGATCGA GGCGGCGCCC

15501 GGCCGTTACG TCAAAGCCAA GGGCTGAGCG GCCGCTGAGT AATTCTGATA

15551 TTAGAGGGAG CATTAATGTG TTGTTGTGAT GTGGTTTATA TGGGGAAATT

15601 AAATAAATGA TGTATGTACC TCTTGCCTAT GTAGGTTTGT GTGTTTTGTT

15651 TTGTTGTCTA GCTTTGGTTA TTAAGTAGTA GGGACGTTCG TTCGTGTCTC

15701 AAAAAAAGGG GTACTACCAC TCTGTAGTGT ATATGGATGC TGGAAATCAA

15751 TGTGTTTTGT ATTTGTTCAC CTCCATTGTT GAATTCAATG TCAAATGTGT

15801 TTTGCGTTGG TTATGTGTAA AATTACTATC TTTCTCGTCC GATGATCAAA

15851 GTTTTAAGCA ACAAAACCAA GGGTGAAATT TAAACTGTGC TTTGTTGAAG

15901 ATTCTTTTAT CATATTGAAA ATCAAATTAC TAGCAGCAGA TTTTACCTAG

-continued

15951 CATGAAATTT TATCAACAGT ACAGCACTCA CTAACCAAGT TCCAAACTAA

16001 GATGCGCCAT TAACATCAGC CAATAGGCAT TTTCAGCAAG GCGCGCCCGC

16051 GCCGATGTAT GTGACAACCC TCGGGATTGT TGATTTATTT CAAAACTAAG

16101 AGTTTTTGTC TTATTGTTCT CGTCTATTTT GGATATCAAT CTTAGTTTTA

16151 TATCTTTTCT AGTTCTCTAC GTGTTAAATG TTCAACACAC TAGCAATTTG

16201 GCCTGCCAGC GTATGGATTA TGGAACTATC AAGTCTGTGA CGCGCCGTAC

16251 GTAGTGTTTA TCTTTGTTGC TTTTCTGAAC AATTTATTTA CTATGTAAAT

16301 ATATTATCAA TGTTTAATCT ATTTTAATTT GCACATGAAT TTTCATTTTA

16351 TTTTTACTTT ACAAAACAAA TAAATATATA TGCAAAAAAA TTTACAAACG

16401 ATGCACGGGT TACAAACTAA TTTCATTAAA TGCTAATGCA GATTTTGTGA

16451 AGTAAAACTC CAATTATGAT GAAAAATACC ACCAACACCA CCTGCGAAAC

16501 TGTATCCCAA CTGTCCTTAA TAAAAATGTT AAAAAGTATA TTATTCTCAT

16551 TTGTCTGTCA TAATTTATGT ACCCCACTTT AATTTTTCTG ATGTACTAAA

16601 CCGAGGGCAA ACTGAAACCT GTTCCTCATG CAAAGCCCCT ACTCACCATG

16651 TATCATGTAC GTGTCATCAC CCAACAACTC CACTTTTGCT ATATAACAAC

16701 ACCCCCGTCA CACTCTCCCT CTCTAACACA CACCCCACTA ACAATTCCTT

16751 CACTTGCAGC ACTGTTGCAT CATCATCTTC ATTGCAAAAC CCTAAACTTC

16801 ACCTTCAACC GCGGCCGCAT GGCTTCTATG ATATCCTCTT CCGCTGTGAC

16851 AACAGTCAGC CGTGCCTCTA GGGGGCAATC CGCCGCAGTG GCTCCATTCG

16901 GCGGCCTCAA ATCCATGACT GGATTCCCAG TGAAGAAGGT CAACACTGAC

16951 ATTACTTCCA TTACAAGCAA TGGTGGAAGA GTAAAGTGCA TGCAGGTGTG

17001 GCCTCCAATT GGAAAGAAGA AGTTTGAGAC TCTTTCCTAT TTGCCACCAT

17051 TGACGAGAGA TTCTAGAGTG ACTCAGCGCA TTGCGTATGT GACCGGCGGC

17101 ATGGGTGGTA TCGGAACCGC CATTTGCCAG CGGCTGGCCA AGGATGGCTT

17151 TCGTGTGGTG GCCGGTTGCG GCCCCAACTC GCCGCGCCGC GAAAAGTGGC

17201 TGGAGCAGCA GAAGGCCCTG GGCTTCGATT TCATTGCCTC GGAAGGCAAT

17251 GTGGCTGACT GGGACTCGAC CAAGACCGCA TTCGACAAGG TCAAGTCCGA

-continued

17301 GGTCGGCGAG GTTGATGTGC TGATCAACAA CGCCGGTATC ACCCGCGACG

17351 TGGTGTTCCG CAAGATGACC CGCGCCGACT GGGATGCGGT GATCGACACC

17401 AACCTGACCT CGCTGTTCAA CGTCACCAAG CAGGTGATCG ACGGCATGGC

17451 CGACCGTGGC TGGGGCCGCA TCGTCAACAT CTCGTCGGTG AACGGGCAGA

17501 AGGGCCAGTT CGGCCAGACC AACTACTCCA CCGCCAAGGC CGGCCTGCAT

17551 GGCTTCACCA TGGCACTGGC GCAGGAAGTG GCGACCAAGG GCGTGACCGT

17601 CAACACGGTC TCTCCGGGCT ATATCGCCAC CGACATGGTC AAGGCGATCC

17651 GCCAGGACGT GCTCGACAAG ATCGTCGCGA CGATCCCGGT CAAGCGCCTG

17701 GGCCTGCCGG AAGAGATCGC CTCGATCTGC GCCTGGTTGT CGTCGGAGGA

17751 GTCCGGTTTC TCGACCGGCG CCGACTTCTC GCTCAACGGC GGCCTGCATA

17801 TGGGCTGAGC GGCCGCTGAG TAATTCTGAT ATTAGAGGGA GCATTAATGT

17851 GTTGTTGTGA TGTGGTTTAT ATGGGGAAAT TAAATAAATG ATGTATGTAC

17901 CTCTTGCCTA TGTAGGTTTG TGTGTTTTGT TTTGTTGTCT AGCTTTGGTT

17951 ATTAAGTAGT AGGGACGTTC GTTCGTGTCT CAAAAAAAGG GGTACTACCA

18001 CTCTGTAGTG TATATGGATG CTGGAAATCA ATGTGTTTTG TATTTGTTCA

18051 CCTCCATTGT TGAATTCAAT GTCAAATGTG TTTTGCGTTG GTTATGTGTA

18101 AAATTACTAT CTTTCTCGTC CGATGATCAA AGTTTTAAGC AACAAAACCA

18151 AGGGTGAAAT TTAAACTGTG CTTTGTTGAA GATTCTTTTA TCATATTGAA

18201 AATCAAATTA CTAGCAGCAG ATTTTACCTA GCATGAAATT TTATCAACAG

18251 TACAGCACTC ACTAACCAAG TTCCAAACTA AGATGCGCCA TTAACATCAG

18301 CCAATAGGCA TTTTCAGCAA GGCGCGTAA

We claim:

1. A transgenic plant comprising:

(a) one or more nucleotide sequences encoding one or more enzymes for producing polyhydroxyalkanoate (PHA) in the transgenic plant, and (b) one or more nucleotide sequences selected from the group consisting of:

(i) a nucleotide sequence encoding a small interfering RNA (siRNA) specific for the one or more nucleotide sequences encoding the one or more enzymes for producing PHA in the transgenic plant wherein the expression of the nucleotide sequences encoding the siRNA is under the control of an inducible regulatory element, and (ii) a nucleotide sequence encoding one or more PHA degradation enzymes, wherein the expression of the one or more PHA degradation enzymes is under the control of an inducible regulatory element or germination specific regulatory element.

2. The transgenic plant of claim 1 wherein the transgenic plant produces seeds.

3. The transgenic plant of claim 2 wherein the seeds comprise oilseeds.

4. The transgenic plant of claim 1 wherein one or more of the nucleotide sequences encoding the one or more enzymes for producing polyhydroxyalkanoate (PHA) is under the control of a seed specific promoter.

5. The transgenic plant of claim 1 wherein the siRNA inhibits expression of phaA, phaB or phaC in the transgenic plant.

6. A transgenic plant or seed comprising a nucleotide sequence of a vector selected from the group consisting of phaA-RNAi/35S; phaC-RNAi/35S; phaA-RNAi/gly; and phaC-RNAi/gly.

7. The transgenic plant of claim 1 wherein seeds of the transgenic plant produce PHA.

8. The transgenic plant of claim 7 wherein one or more seeds produced by the plant comprise up to 12.32% PHA dry weight of the seed.

9. The transgenic plant of claim 1 wherein one or more seeds produced by the transgenic plant are capable of germinating.

10. The transgenic plant of claim 1 further comprising one or more transgenes selected from the group consisting of sedoheptulose 1,7-bisphosphatase (SBPase, EC 3.1.3.37), fructose 1,6-bisphosphatase (FBPase, EC 3.1.3.11), and a bi-functional enzyme encoding both SBPase and FBPase, that increase carbon flow through the Calvin cycle.

11. The transgenic plant claim 10 wherein the bifunctional enzyme is isolated from an organism selected from the group consisting of *Ralstonia eutropha* H16, Synechococcus elongatus PCC 7942, Synechococcus sp. WH 7805, *Butyrivibrio crossotus* DSM 2876, *Rothia mucilaginosa* DY-18, *Thiobacillus denitrificans* ATCC 25259, *Methylacidiphilum* infernorum V4, *Nitrosomonas europaea* ATCC 19718, *Vibrio vulnificus* CMCP6, and *Methanohalophilus mahii* DSM 5219.

12. A method for producing transgenic plants engineered to produce PHA comprising:

(a) genetically engineering the transgenic plant to express a nucleotide sequence under the control of an inducible regulatory element or germination specific regulatory element, wherein the nucleotide sequence is selected from the group consisting of: (i) a nucleotide sequence encoding siRNA for one or more genes encoding enzymes for producing PHA in the transgenic plant, and (ii) a nucleotide sequence encoding one or more PHA degradation enzymes, and (b) inducing expression of the nucleotide sequences during germination.

13. A nucleic acid construct comprising a nucleotide sequence of a vector selected from the group consisting of phaA-RNAi/35S; phaC-RNAi/35S; phaA-RNAi/gly; and phaC-RNAi/gly.

14. The transgenic plant of claim 1 wherein the plant is selected from the group consisting of *B. napus, B. rappa, B. carinata, B. juncea, Camelina sativa*, Crambe, jatropha, castor, *Cuphea, Calendula, Arabidopsis thaliana*, maize, soybean, cottonseed, sunflower, palm, coconut, safflower, peanut, *Sinapis alba*, sugarcane and flax.

15. The transgenic plant of claim 1 further comprising a transketolase (EC 2.2.1.1).

16. The transgenic plant of claim 1 further comprising an aldolase (EC 4.1.2.13).

17. The method of claim 12 wherein siRNA expression is induced by soaking seeds of the transgenic plant in an inducing agent.

* * * * *

SEQUENCE LISTING

<160> NUMBER OF SEQ ID NOS: 11

<210> SEQ ID NO 1
<211> LENGTH: 15888
<212> TYPE: DNA
<213> ORGANISM: Artificial Sequence
<220> FEATURE:
<223> OTHER INFORMATION: Synthetic Vector

<400> SEQUENCE: 1
ggggatccgt acgtaagtac gtactcaaaa tgccaacaaa taaaaaaaaa gttgctttaa 60
taatgccaaa acaaattaat aaaacactta caacaccgga ttttttttaa ttaaaatgtg 120
ccatttagga taaatagtta atatttttaa taattattta aaaagccgta tctactaaaa 180
tgatttttat ttggttgaaa atattaatat gtttaaatca acacaatcta tcaaaattaa 240
actaaaaaaa aaataagtgt acgtggttaa cattagtaca gtaatataag aggaaaatga 300
gaaattaaga aattgaaagc gagtctaatt tttaaattat gaacctgcat atataaaagg 360
aaagaaagaa tccaggaaga aaagaaatga aaccatgcat ggtcccctcg tcatcacgag 420
tttctgccat ttgcaataga aacactgaaa cacctttctc tttgtcactt aattgagatg 480
ccgaagccac ctcacaccat gaacttcatg aggtgtagca cccaaggctt ccatagccat 540
gcatactgaa gaatgtctca agctcagcac cctacttctg tgacgtgtcc ctcattcacc 600
ttcctctctt ccctataaat aaccacgcct caggttctcc gcttcacaac tcaaacattc 660
tctccattgg tccttaaaca ctcatcagtc atcaccgcgg ccgcggaatt catggcttct 720
atgatatcct cttccgctgt gacaacagtc agccgtgcct ctagggggca atccgccgca 780
gtggctccat tcggcggcct caaatccatg actggattcc cagtgaagaa ggtcaacact 840
gacattactt ccattacaag caatggtgga agagtaaagt gcatgcaggt gtggcctcca 900
attggaaaga agaagtttga gactctttcc tatttgccac cattgacgag agattctaga 960

-continued

```
gtgactgacg ttgtcatcgt atccgccgcc cgcaccgcgg tcggcaagtt tggcggctcg   1020
ctggccaaga tcccggcacc ggaactgggt gccgtggtca tcaaggccgc gctggagcgc   1080
gccggcgtca agccggagca ggtgagcgaa gtcatcatgg gccaggtgct gaccgccggt   1140
tcgggccaga accccgcacg ccaggccgcg atcaaggccg gcctgccggc gatggtgccg   1200
gccatgacca tcaacaaggt gtgcggctcg ggcctgaagg ccgtgatgct ggccgccaac   1260
gcgatcatgg cgggcgacgc cgagatcgtg gtggccggcg gccaggaaaa catgagcgcc   1320
gccccgcacg tgctgccggg ctcgcgcgat ggtttccgca tgggcgatgc caagctggtc   1380
gacaccatga tcgtcgacgg cctgtgggac gtgtacaacc agtaccacat gggcatcacc   1440
gccgagaacg tggccaagga atacggcatc acacgcgagg cgcaggatga gttcgccgtc   1500
ggctcgcaga acaaggccga agccgcgcag aaggccggca agtttgacga agagatcgtc   1560
ccggtgctga tcccgcagcg caagggcgac ccggtggcct tcaagaccga cgagttcgtg   1620
cgccagggcg ccacgctgga cagcatgtcc ggcctcaagc ccgccttcga caaggccggc   1680
acggtgaccg cggccaacgc ctcgggcctg aacgacggcg ccgccgcggt ggtggtgatg   1740
tcggcggcca aggccaagga actgggcctg accccgctgg ccacgatcaa gagctatgcc   1800
aacgccggtg tcgatcccaa ggtgatgggc atgggcccgg tgccggcctc caagcgcgcc   1860
ctgtcgcgcg ccgagtggac cccgcaagac ctggacctga tggagatcaa cgaggccttt   1920
gccgcgcagg cgctggcggt gcaccagcag atgggctggg acacctccaa ggtcaatgtg   1980
aacggcggcg ccatcgccat cggccacccg atcggcgcgt cgggctgccg tatcctggtg   2040
acgctgctgc acgagatgaa gcgccgtgac gcgaagaagg gcctggcctc gctgtgcatc   2100
ggcggcggca tgggcgtggc gctggcagtc gagcgcaaat aactcgaggc ggccgcagcc   2160
ctttttgtat gtgctacccc acttttgtct tttggcaat agtgctagca accaataaat   2220
aataataata ataatgaata agaaaacaaa ggctttagct tgccttttgt tcactgtaaa   2280
ataataatgt aagtactctc tataatgagt cacgaaactt ttgcgggaat aaaaggagaa   2340
attccaatga gttttctgtc aaatcttctt ttgtctctct ctctctctct ttttttttt   2400
tctttcttct gagcttcttg caaaacaaaa ggcaaacaat aacgattggt ccaatgatag   2460
ttagcttgat cgatgatatc tttaggaagt gttggcagga caggacatga tgtagaagac   2520
taaaattgaa agtattgcag acccaatagt tgaagattaa ctttaagaat gaagacgtct   2580
tatcaggttc ttcatgactt aagctttaag aggagtccac catggtagat ctgactagta   2640
gaaggtaatt atccaagatg tagcatcaag aatccaatgt ttacgggaaa aactatggaa   2700
gtattatgtg agctcagcaa gaagcagatc aatatgcggc acatatgcaa cctatgttca   2760
aaaatgaaga atgtacagat acaagatcct atactgccag aatacgaaga agaatacgta   2820
gaaattgaaa aagaagaacc aggcgaagaa aagaatcttg aagacgtaag cactgacgac   2880
aacaatgaaa agaagaagat aaggtcggtg attgtgaaag agacatagag gacacatgta   2940
aggtggaaaa tgtaagggcg gaaagtaacc ttatcacaaa ggaatcttat cccccactac   3000
ttatcctttt atatttttcc gtgtcatttt tgcccttgag ttttcctata taaggaacca   3060
agttcggcat ttgtgaaaac aagaaaaaat tggtgtaagc tattttcttt gaagtactga   3120
ggatacaact tcagagaaat ttgtaagaaa gtggatcgaa accatggcct cctccgagaa   3180
cgtcatcacc gagttcatgc gcttcaaggt gcgcatggag ggcaccgtga acggccacga   3240
gttcgagatc gagggcgagg gcgagggccg cccctacgag ggccacaaca ccgtgaagct   3300
gaaggtgacc aagggcggcc ccctgccctt cgcctgggac atcctgtccc cccagttcca   3360
```

-continued

```
gtacggctcc aaggtgtacg tgaagcaccc cgccgacatc cccgactaca agaagctgtc   3420
cttccccgag ggcttcaagt gggagcgcgt gatgaacttc gaggacggcg gcgtggcgac   3480
cgtgacccag gactcctccc tgcaggacgg ctgcttcatc tacaaggtga agttcatcgg   3540
cgtgaacttc ccctccgacg gccccgtgat gcagaagaag accatgggct gggaggcctc   3600
caccgagcgc ctgtaccccc gcgacggcgt gctgaagggc gagacccaca aggccctgaa   3660
gctgaaggac ggcggccact acctggtgga gttcaagtcc atctacatgg ccaagaagcc   3720
cgtgcagctg cccggctact actacgtgga cgccaagctg gacatcacct cccacaacga   3780
ggactacacc atcgtggagc agtacgagcg caccgagggc cgccaccacc tgttcctggt   3840
accaatgagc tctgtccaac agtctcaggg ttaatgtcta tgtatcttaa ataatgttgt   3900
cggcgatcgt tcaaacattt ggcaataaag tttcttaaga ttgaatcctg ttgccggtct   3960
tgcgatgatt atcatataat ttctgttgaa ttacgttaag catgtaataa ttaacatgta   4020
atgcatgacg ttatttatga gatgggtttt tatgattaga gtcccgcaat tatacattta   4080
atacgcgata gaaaacaaaa tatagcgcgc aaactaggat aaattatcgc gcgcggtgtc   4140
atctatgtta ctagatcggg aattaaacta tcagtgtttg acaggatata ttggcgggta   4200
aacctaagag aaaagagcgt ttattagaat aacggatatt taaaagggcg tgaaaaggtt   4260
tatccgttcg tccatttgta tgtgcatgcc aaccacaggg ttcccctcgg gatcaaagta   4320
ctttgatcca acccctccgc tgctatagtg cagtcggctt ctgacgttca gtgcagccgt   4380
cttctgaaaa cgacatgtcg cacaagtcct aagttacgcg acaggctgcc gccctgccct   4440
tttcctggcg ttttcttgtc gcgtgtttta gtcgcataaa gtagaatact tgcgactaga   4500
accggagaca ttacgccatg aacaagagcg ccgccgctgg cctgctgggc tatgcccgcg   4560
tcagcaccga cgaccaggac ttgaccaacc aacgggccga actgcacgcg gccggctgca   4620
ccaagctgtt ttccgagaag atcaccggca ccaggcgcga ccgcccggag ctggccagga   4680
tgcttgacca cctacgccct ggcgacgttg tgacagtgac caggctagac cgcctggccc   4740
gcagcacccg cgacctactg gacattgccg agcgcatcca ggaggccggc gcgggcctgc   4800
gtagcctggc agagccgtgg gccgacacca ccacgccggc cggccgcatg gtgttgaccg   4860
tgttcgccgg cattgccgag ttcgagcgtt ccctaatcat cgaccgcacc cggagcgggc   4920
gcgaggccgc caaggcccga ggcgtgaagt ttggcccccg ccctaccctc accccggcac   4980
agatcgcgca cgcccgcgag ctgatcgacc aggaaggccg caccgtgaaa gaggcggctg   5040
cactgcttgg cgtgcatcgc tcgaccctgt accgcgcact tgagcgcagc gaggaagtga   5100
cgcccaccga ggccaggcgg cgcggtgcct tccgtgagga cgcattgacc gaggccgacg   5160
ccctggcggc cgccgagaat gaacgccaag aggaacaagc atgaaaccgc accaggacgg   5220
ccaggacgaa ccgtttttca ttaccgaaga gatcgaggcg gagatgatcg cggccgggta   5280
cgtgttcgag ccgcccgcgc acgtctcaac cgtgcggctg catgaaatcc tggccggttt   5340
gtctgatgcc aagctggcgg cctggccggc cagcttggcc gctgaagaaa ccgagcgccg   5400
ccgtctaaaa aggtgatgtg tatttgagta aaacagcttg cgtcatgcgg tcgctgcgta   5460
tatgatgcga tgagtaaata aacaaatacg caaggggaac gcatgaaggt tatcgctgta   5520
cttaaccaga aaggcgggtc aggcaagacg accatcgcaa cccatctagc ccgcgccctg   5580
caactcgccg gggccgatgt tctgttagtc gattccgatc cccagggcag tgcccgcgat   5640
tgggcggccg tgcgggaaga tcaaccgcta accgttgtcg gcatcgaccg cccgacgatt   5700
```

-continued

```
gaccgcgacg tgaaggccat cggccggcgc gacttcgtag tgatcgacgg agcgccccag   5760
gcggcggact tggctgtgtc cgcgatcaag gcagccgact tcgtgctgat tccggtgcag   5820
ccaagccctt acgacatatg ggccaccgcc gacctggtgg agctggttaa gcagcgcatt   5880
gaggtcacgg atggaaggct acaagcggcc tttgtcgtgt cgcgggcgat caaaggcacg   5940
cgcatcggcg gtgaggttgc cgaggcgctg gccgggtacg agctgcccat tcttgagtcc   6000
cgtatcacgc agcgcgtgag ctacccaggc actgccgccg ccggcacaac cgttcttgaa   6060
tcagaacccg agggcgacgc tgcccgcgag gtccaggcgc tggccgctga aattaaatca   6120
aaactcattt gagttaatga ggtaaagaga aaatgagcaa aagcacaaac acgctaagtg   6180
ccggccgtcc gagcgcacgc agcagcaagg ctgcaacgtt ggccagcctg gcagacacgc   6240
cagccatgaa gcgggtcaac tttcagttgc cggcggagga tcacaccaag ctgaagatgt   6300
acgcggtacg ccaaggcaag accattaccg agctgctatc tgaatacatc gcgcagctac   6360
cagagtaaat gagcaaatga ataaatgagt agatgaattt tagcggctaa aggaggcggc   6420
atggaaaatc aagaacaacc aggcaccgac gccgtggaat gccccatgtg tggaggaacg   6480
ggcggttggc caggcgtaag cggctgggtt gtctgccggc cctgcaatgg cactggaacc   6540
cccaagcccg aggaatcggc gtgacggtcg caaaccatcc ggcccggtac aaatcggcgc   6600
ggcgctgggt gatgacctgg tggagaagtt gaaggccgcg caggccgccc agcggcaacg   6660
catcgaggca gaagcacgcc ccggtgaatc gtggcaagcg gccgctgatc gaatccgcaa   6720
agaatcccgg caaccgccgg cagccggtgc gccgtcgatt aggaagccgc ccaagggcga   6780
cgagcaacca gatttttttcg ttccgatgct ctatgacgtg ggcacccgcg atagtcgcag   6840
catcatggac gtggccgttt tccgtctgtc gaagcgtgac cgacgagctg gcgaggtgat   6900
ccgctacgag cttccagacg ggcacgtaga ggtttccgca gggccggccg gcatggccag   6960
tgtgtgggat tacgacctgg tactgatggc ggtttcccat ctaaccgaat ccatgaaccg   7020
ataccgggaa gggaagggag acaagcccgg ccgcgtgttc cgtccacacg ttgcggacgt   7080
actcaagttc tgccggcgag ccgatggcgg aaagcagaaa gacgacctgg tagaaacctg   7140
cattcggtta aacaccacgc acgttgccat gcagcgtacg aagaaggcca agaacggccg   7200
cctggtgacg gtatccgagg gtgaagcctt gattagccgc tacaagatcg taaagagcga   7260
aaccgggcgg ccggagtaca tcgagatcga gctagctgat tggatgtacc gcgagatcac   7320
agaaggcaag aacccggacg tgctgacggt tcaccccgat tactttttga tcgatcccgg   7380
catcggccgt tttctctacc gcctggcacg ccgcgccgca ggcaaggcag aagccagatg   7440
gttgttcaag acgatctacg aacgcagtgg cagcgccgga gagttcaaga agttctgttt   7500
caccgtgcgc aagctgatcg ggtcaaatga cctgccggag tacgatttga aggaggaggc   7560
ggggcaggct ggcccgatcc tagtcatgcg ctaccgcaac ctgatcgagg gcgaagcatc   7620
cgccggttcc taatgtacgg agcagatgct agggcaaatt gccctagcag gggaaaaagg   7680
tcgaaaaggt ctctttcctg tggatagcac gtacattggg aacccaaagc cgtacattgg   7740
gaaccggaac ccgtacattg ggaacccaaa gccgtacatt gggaaccggt cacacatgta   7800
agtgactgat ataaaagaga aaaaaggcga tttttccgcc taaaactctt taaaacttat   7860
taaaactctt aaaacccgcc tggcctgtgc ataactgtct ggccagcgca cagccgaaga   7920
gctgcaaaaa gcgcctaccc ttcggtcgct gcgctcccta cgccccgccg cttcgcgtcg   7980
gcctatcgcg gccgctggcc gctcaaaaat ggctggccta cggccaggca atctaccagg   8040
gcgcggacaa gccgcgccgt cgccactcga ccgccggcgc ccacatcaag gcaccctgcc   8100
```

-continued

```
tcgcgcgttt cggtgatgac ggtgaaaacc tctgacacat gcagctcccg gagacggtca   8160
cagcttgtct gtaagcggat gccgggagca gacaagcccg tcagggcgcg tcagcgggtg   8220
ttggcgggtg tcggggcgca gccatgaccc agtcacgtag cgatagcgga gtgtatactg   8280
gcttaactat gcggcatcag agcagattgt actgagagtg caccatatgc ggtgtgaaat   8340
accgcacaga tgcgtaagga gaaaataccg catcaggcgc tcttccgctt cctcgctcac   8400
tgactcgctg cgctcggtcg ttcggctgcg gcgagcggta tcagctcact caaaggcggt   8460
aatacggtta tccacagaat caggggataa cgcaggaaag aacatgtgag caaaaggcca   8520
gcaaaaggcc aggaaccgta aaaaggccgc gttgctggcg tttttccata ggctccgccc   8580
ccctgacgag catcacaaaa atcgacgctc aagtcagagg tggcgaaacc cgacaggact   8640
ataaagatac caggcgtttc cccctggaag ctccctcgtg cgctctcctg ttccgaccct   8700
gccgcttacc ggatacctgt ccgcctttct cccttcggga agcgtggcgc tttctcatag   8760
ctcacgctgt aggtatctca gttcggtgta ggtcgttcgc tccaagctgg gctgtgtgca   8820
cgaacccccc gttcagcccg accgctgcgc cttatccggt aactatcgtc ttgagtccaa   8880
cccggtaaga cacgacttat cgccactggc agcagccact ggtaacagga ttagcagagc   8940
gaggtatgta ggcggtgcta cagagttctt gaagtggtgg cctaactacg gctacactag   9000
aaggacagta tttggtatct gcgctctgct gaagccagtt accttcggaa aaagagttgg   9060
tagctcttga tccggcaaac aaaccaccgc tggtagcggt ggtttttttg tttgcaagca   9120
gcagattacg cgcagaaaaa aaggatctca agaagatcct ttgatctttt ctacggggtc   9180
tgacgctcag tggaacgaaa actcacgtta agggattttg gtcatgcatt ctaggtacta   9240
aaacaattca tccagtaaaa tataatattt tattttctcc caatcaggct tgatccccag   9300
taagtcaaaa aatagctcga catactgttc ttccccgata tcctccctga tcgaccggac   9360
gcagaaggca atgtcatacc acttgtccgc cctgccgctt ctcccaagat caataaagcc   9420
acttactttg ccatctttca caaagatgtt gctgtctccc aggtcgccgt gggaaaagac   9480
aagttcctct tcgggctttt ccgtctttaa aaaatcatac agctcgcgcg gatctttaaa   9540
tggagtgtct tcttcccagt tttcgcaatc cacatcggcc agatcgttat tcagtaagta   9600
atccaattcg gctaagcggc tgtctaagct attcgtatag ggacaatccg atatgtcgat   9660
ggagtgaaag agcctgatgc actccgcata cagctcgata atcttttcag ggctttgttc   9720
atcttcatac tcttccgagc aaaggacgcc atcggcctca ctcatgagca gattgctcca   9780
gccatcatgc cgttcaaagt gcaggacctt tggaacaggc agctttcctt ccagccatag   9840
catcatgtcc ttttcccgtt ccacatcata ggtggtccct ttataccggc tgtccgtcat   9900
ttttaaatat aggttttcat tttctcccac cagcttatat accttagcag gagacattcc   9960
ttccgtatct tttacgcagc ggtatttttc gatcagtttt ttcaattccg gtgatattct  10020
cattttagcc atttattatt tccttcctct tttctacagt atttaaagat accccaagaa  10080
gctaattata acaagacgaa ctccaattca ctgttccttg cattctaaaa ccttaaatac  10140
cagaaaacag ctttttcaaa gttgttttca aagttggcgt ataacatagt atcgacggag  10200
ccgattttga aaccgcggtg atcacaggca gcaacgctct gtcatcgtta caatcaacat  10260
gctaccctcc gcgagatcat ccgtgtttca aacccggcag cttagttgcc gttcttccga  10320
atagcatcgg taacatgagc aaagtctgcc gccttacaac ggctctcccg ctgacgccgt  10380
cccggactga tgggctgcct gtatcgagtg gtgattttgt gccgagctgc cggtcgggga  10440
```

-continued

```
gctgttggct ggctggtggc aggatatatt gtggtgtaaa caaattgacg cttagacaac  10500
ttaataacac attgcggacg tttttaatgt actgaattaa cgccgaatta attcctaggc  10560
caccatgttg ggcccggggc gcgccgtacg tagtgtttat ctttgttgct tttctgaaca  10620
atttatttac tatgtaaata tattatcaat gtttaatcta ttttaatttg cacatgaatt  10680
ttcattttat ttttacttta caaaacaaat aaatatatat gcaaaaaaat ttacaaacga  10740
tgcacgggtt acaaactaat ttcattaaat gctaatgcag attttgtgaa gtaaaactcc  10800
aattatgatg aaaaatacca ccaacaccac ctgcgaaact gtatcccaac tgtccttaat  10860
aaaaatgtta aaaagtatat tattctcatt tgtctgtcat aatttatgta ccccacttta  10920
atttttctga tgtactaaac cgagggcaaa ctgaaacctg ttcctcatgc aaagccccta  10980
ctcaccatgt atcatgtacg tgtcatcacc caacaactcc acttttgcta tataacaaca  11040
cccccgtcac actctccctc tctaacacac accccactaa caattccttc acttgcagca  11100
ctgttgcatc atcatcttca ttgcaaaacc ctaaacttca ccttcaaccg cggccgcatg  11160
gcttctatga tatcctcttc cgctgtgaca acagtcagcc gtgcctctag gggggcaatcc  11220
gccgcagtgg ctccattcgg cggcctcaaa tccatgactg gattcccagt gaagaaggtc  11280
aacactgaca ttacttccat tacaagcaat ggtggaagag taaagtgcat gcaggtgtgg  11340
cctccaattg gaaagaagaa gtttgagact ctttcctatt tgccaccatt gacgagagat  11400
tctagagtga gtaacaagaa caacgatgag ctgcagtggc aatcctggtt cagcaaggcg  11460
cccaccaccg aggcgaaccc gatggccacc atgttgcagg atatcggcgt tgcgctcaaa  11520
ccggaagcga tggagcagct gaaaaacgat tatctgcgtg acttcaccgc gttgtggcag  11580
gatttttttgg ctggcaaggc gccagccgtc agcgaccgcc gcttcagctc ggcagcctgg  11640
cagggcaatc cgatgtcggc cttcaatgcc gcatcttacc tgctcaacgc caaattcctc  11700
agtgccatgg tggaggcggt ggacaccgca ccccagcaaa agcagaaaat acgctttgcc  11760
gtgcagcagg tgattgatgc catgtcgccc gcgaacttcc tcgccaccaa cccggaagcg  11820
cagcaaaaac tgattgaaac caagggcgag agcctgacgc gtggcctggt caatatgctg  11880
ggcgatatca acaagggcca tatctcgctg tcggacgaat cggcctttga agtgggccgc  11940
aacctggcca ttaccccggg caccgtgatt tacgaaaatc cgctgttcca gctgatccag  12000
tacacgccga ccacgccgac ggtcagccag cgcccgctgt tgatggtgcc gccgtgcatc  12060
aacaagttct acatcctcga cctgcaaccg gaaaattcgc tggtgcgcta cgcggtggag  12120
cagggcaaca ccgtgttcct gatctcgtgg agcaatccgg acaagtcgct ggccggcacc  12180
acctgggacg actacgtgga gcagggcgtg atcgaagcga tccgcatcgt ccaggacgtc  12240
agcggccagg acaagctgaa catgttcggc ttctgcgtgg gcggcaccat cgttgccacc  12300
gcactggcgg tactggcggc gcgtggccag cacccggcgg ccagcctgac cctgctgacc  12360
accttcctcg acttcagcga caccggcgtg ctcgacgtct tcgtcgatga aacccaggtc  12420
gcgctgcgtg aacagcaatt gcgcgatggc ggcctgatgc cgggccgtga cctggcctcg  12480
accttctcga gcctgcgtcc gaacgacctg gtatggaact atgtgcagtc gaactacctc  12540
aaaggcaatg agccggcggc gtttgacctg ctgttctgga attcggacag caccaatttg  12600
ccgggcccga tgttctgctg gtacctgcgc aacacctacc tggaaaacag cctgaaagtg  12660
ccgggcaagc tgacggtggc cggcgaaaag atcgacctcg gcctgatcga cgccccggcc  12720
ttcatctacg gttcgcgcga agaccacatc gtgccgtgga tgtcggcgta cggttcgctc  12780
gacatcctca accagggcaa gccgggcgcc aaccgcttcg tgctgggcgc gtccggccat  12840
```

```
atcgccggcg tgatcaactc ggtggccaag aacaagcgca gctactggat caacgacggt  12900
ggcgccgccg atgcccaggc ctggttcgat ggcgcgcagg aagtgccggg cagctggtgg  12960
ccgcaatggg ccgggttcct gacccagcat ggcggcaaga aggtcaagcc caaggccaag  13020
cccggcaacg cccgctacac cgcgatcgag gcggcgcccg gccgttacgt caaagccaag  13080
ggctgagcgg ccgctgagta attctgatat tagagggagc attaatgtgt tgttgtgatg  13140
tggtttatat ggggaaatta aataaatgat gtatgtacct cttgcctatg taggtttgtg  13200
tgttttgttt tgttgtctag ctttggttat taagtagtag ggacgttcgt tcgtgtctca  13260
aaaaaagggg tactaccact ctgtagtgta tatggatgct ggaaatcaat gtgttttgta  13320
tttgttcacc tccattgttg aattcaatgt caaatgtgtt ttgcgttggt tatgtgtaaa  13380
attactatct ttctcgtccg atgatcaaag ttttaagcaa caaaaccaag ggtgaaattt  13440
aaactgtgct ttgttgaaga ttcttttatc atattgaaaa tcaaattact agcagcagat  13500
tttacctagc atgaaatttt atcaacagta cagcactcac taaccaagtt ccaaactaag  13560
atgcgccatt aacatcagcc aataggcatt ttcagcaagg cgcgcccgcg ccgatgtatg  13620
tgacaaccct cgggattgtt gatttatttc aaaactaaga gtttttgtct tattgttctc  13680
gtctattttg gatatcaatc ttagttttat atcttttcta gttctctacg tgttaaatgt  13740
tcaacacact agcaatttgg cctgccagcg tatggattat ggaactatca agtctgtgac  13800
gcgccgtacg tagtgtttat ctttgttgct tttctgaaca atttatttac tatgtaaata  13860
tattatcaat gtttaatcta ttttaatttg cacatgaatt ttcattttat ttttacttta  13920
caaaacaaat aaatatatat gcaaaaaaat ttacaaacga tgcacgggtt acaaactaat  13980
ttcattaaat gctaatgcag attttgtgaa gtaaaactcc aattatgatg aaaaatacca  14040
ccaacaccac ctgcgaaact gtatcccaac tgtccttaat aaaaatgtta aaaagtatat  14100
tattctcatt tgtctgtcat aatttatgta ccccacttta atttttctga tgtactaaac  14160
cgagggcaaa ctgaaacctg ttcctcatgc aaagccccta ctcaccatgt atcatgtacg  14220
tgtcatcacc caacaactcc acttttgcta tataacaaca cccccgtcac actctccctc  14280
tctaacacac accccactaa caattccttc acttgcagca ctgttgcatc atcatcttca  14340
ttgcaaaacc ctaaacttca ccttcaaccg cggccgcatg gcttctatga tatcctcttc  14400
cgctgtgaca acagtcagcc gtgcctctag ggggcaatcc gccgcagtgg ctccattcgg  14460
cggcctcaaa tccatgactg gattcccagt gaagaaggtc aacactgaca ttacttccat  14520
tacaagcaat ggtggaagag taaagtgcat gcaggtgtgg cctccaattg gaaagaagaa  14580
gtttgagact ctttcctatt tgccaccatt gacgagagat tctagagtga ctcagcgcat  14640
tgcgtatgtg accggcggca tgggtggtat cggaaccgcc atttgccagc ggctggccaa  14700
ggatggcttt cgtgtggtgg ccggttgcgg ccccaactcg ccgcgccgcg aaaagtggct  14760
ggagcagcag aaggccctgg gcttcgattt cattgcctcg gaaggcaatg tggctgactg  14820
ggactcgacc aagaccgcat tcgacaaggt caagtccgag gtcggcgagg ttgatgtgct  14880
gatcaacaac gccggtatca cccgcgacgt ggtgttccgc aagatgaccc gcgccgactg  14940
ggatgcggtg atcgacacca acctgacctc gctgttcaac gtcaccaagc aggtgatcga  15000
cggcatggcc gaccgtggct ggggccgcat cgtcaacatc tcgtcggtga acgggcagaa  15060
gggccagttc ggccagacca actactccac cgccaaggcc ggcctgcatg gcttcaccat  15120
ggcactggcg caggaagtgg cgaccaaggg cgtgaccgtc aacacggtct ctccgggcta  15180
```

| | | | | |
|---|---|---|---|---|
| tatcgccacc | gacatggtca | aggcgatccg | ccaggacgtg | ctcgacaaga tcgtcgcgac | 15240 |
| gatcccggtc | aagcgcctgg | gcctgccgga | agagatcgcc | tcgatctgcg cctggttgtc | 15300 |
| gtcggaggag | tccggtttct | cgaccggcgc | cgacttctcg | ctcaacggcg gcctgcatat | 15360 |
| gggctgagcg | gccgctgagt | aattctgata | ttagagggag | cattaatgtg ttgttgtgat | 15420 |
| gtggtttata | tggggaaatt | aaataaatga | tgtatgtacc | tcttgcctat gtaggtttgt | 15480 |
| gtgttttgtt | ttgttgtcta | gctttggtta | ttaagtagta | gggacgttcg ttcgtgtctc | 15540 |
| aaaaaaaggg | gtactaccac | tctgtagtgt | atatggatgc | tggaaatcaa tgtgttttgt | 15600 |
| atttgttcac | ctccattgtt | gaattcaatg | tcaaatgtgt | tttgcgttgg ttatgtgtaa | 15660 |
| aattactatc | tttctcgtcc | gatgatcaaa | gttttaagca | acaaaaccaa gggtgaaatt | 15720 |
| taaactgtgc | tttgttgaag | attcttttat | catattgaaa | atcaaattac tagcagcaga | 15780 |
| ttttacctag | catgaaattt | tatcaacagt | acagcactca | ctaaccaagt tccaaactaa | 15840 |
| gatgcgccat | taacatcagc | caataggcat | tttcagcaag | gcgcgtaa | 15888 |

```
<210> SEQ ID NO 2
<211> LENGTH: 20500
<212> TYPE: DNA
<213> ORGANISM: Artificial Sequence
<220> FEATURE:
<223> OTHER INFORMATION: Synthetic Vector
<220> FEATURE:
<221> NAME/KEY: misc_feature
<222> LOCATION: (11474)..(11474)
<223> OTHER INFORMATION: n is a, c, g, or t
<220> FEATURE:
<221> NAME/KEY: misc_feature
<222> LOCATION: (15433)..(15433)
<223> OTHER INFORMATION: n is a, c, g, or t
<220> FEATURE:
<221> NAME/KEY: misc_feature
<222> LOCATION: (19892)..(19892)
<223> OTHER INFORMATION: n is a, c, g, or t

<400> SEQUENCE: 2
```

| | | | | |
|---|---|---|---|---|
| catgccaacc | acagggttcc | cctcgggatc | aaagtacttt | gatccaaccc ctccgctgct | 60 |
| atagtgcagt | cggcttctga | cgttcagtgc | agccgtcttc | tgaaaacgac atgtcgcaca | 120 |
| agtcctaagt | tacgcgacag | gctgccgccc | tgcccttttc | ctggcgtttt cttgtcgcgt | 180 |
| gttttagtcg | cataaagtag | aatacttgcg | actagaaccg | gagacattac gccatgaaca | 240 |
| agagcgccgc | cgctggcctg | ctgggctatg | cccgcgtcag | caccgacgac caggacttga | 300 |
| ccaaccaacg | ggccgaactg | cacgcggccg | gctgcaccaa | gctgttttcc gagaagatca | 360 |
| ccggcaccag | gcgcgaccgc | ccggagctgg | ccaggatgct | tgaccaccta cgccctggcg | 420 |
| acgttgtgac | agtgaccagg | ctagaccgcc | tggcccgcag | cacccgcgac ctactggaca | 480 |
| ttgccgagcg | catccaggag | gccggcgcgg | gcctgcgtag | cctggcagag ccgtgggccg | 540 |
| acaccaccac | gccggccggc | cgcatggtgt | tgaccgtgtt | cgccggcatt gccgagttcg | 600 |
| agcgttccct | aatcatcgac | cgcacccgga | gcgggcgcga | ggccgccaag gcccgaggcg | 660 |
| tgaagtttgg | cccccgccct | accctcaccc | cggcacagat | cgcgcacgcc cgcgagctga | 720 |
| tcgaccagga | aggccgcacc | gtgaaagagg | cggctgcact | gcttggcgtg catcgctcga | 780 |
| ccctgtaccg | cgcacttgag | cgcagcgagg | aagtgacgcc | caccgaggcc aggcggcgcg | 840 |
| gtgccttccg | tgaggacgca | ttgaccgagg | ccgacgccct | ggcggccgcc gagaatgaac | 900 |
| gccaagagga | acaagcatga | aaccgcacca | ggacggccag | gacgaaccgt ttttcattac | 960 |
| cgaagagatc | gaggcggaga | tgatcgcggc | cgggtacgtg | ttcgagccgc ccgcgcacgt | 1020 |

```
ctcaaccgtg cggctgcatg aaatcctggc cggtttgtct gatgccaagc tggcggcctg   1080
gccggccagc ttggccgctg aagaaaccga gcgccgccgt ctaaaaaggt gatgtgtatt   1140
tgagtaaaac agcttgcgtc atgcggtcgc tgcgtatatg atgcgatgag taaataaaca   1200
aatacgcaag gggaacgcat gaaggttatc gctgtactta accagaaagg cgggtcaggc   1260
aagacgacca tcgcaaccca tctagcccgc gccctgcaac tcgccggggc cgatgttctg   1320
ttagtcgatt ccgatcccca gggcagtgcc cgcgattggg cggccgtgcg ggaagatcaa   1380
ccgctaaccg ttgtcggcat cgaccgcccg acgattgacc gcgacgtgaa ggccatcggc   1440
cggcgcgact tcgtagtgat cgacggagcg ccccaggcgg cggacttggc tgtgtccgcg   1500
atcaaggcag ccgacttcgt gctgattccg gtgcagccaa gcccttacga catatgggcc   1560
accgccgacc tggtggagct ggttaagcag cgcattgagg tcacggatgg aaggctacaa   1620
gcggcctttg tcgtgtcgcg ggcgatcaaa ggcacgcgca tcggcggtga ggttgccgag   1680
gcgctggccg ggtacgagct gcccattctt gagtcccgta tcacgcagcg cgtgagctac   1740
ccaggcactg ccgccgccgg cacaaccgtt cttgaatcag aacccgaggg cgacgctgcc   1800
cgcgaggtcc aggcgctggc cgctgaaatt aaatcaaaac tcatttgagt taatgaggta   1860
aagagaaaat gagcaaaagc acaaacacgc taagtgccgg ccgtccgagc gcacgcagca   1920
gcaaggctgc aacgttggcc agcctggcag acacgccagc catgaagcgg gtcaactttc   1980
agttgccggc ggaggatcac accaagctga agatgtacgc ggtacgccaa ggcaagacca   2040
ttaccgagct gctatctgaa tacatcgcgc agctaccaga gtaaatgagc aaatgaataa   2100
atgagtagat gaattttagc ggctaaagga ggcggcatgg aaaatcaaga acaaccaggc   2160
accgacgccg tggaatgccc catgtgtgga ggaacgggcg gttggccagg cgtaagcggc   2220
tgggttgtct gccggccctg caatggcact ggaaccccca agcccgagga atcggcgtga   2280
cggtcgcaaa ccatccggcc cggtacaaat cggcgcggcg ctgggtgatg acctggtgga   2340
gaagttgaag gccgcgcagg ccgcccagcg gcaacgcatc gaggcagaag cacgccccgg   2400
tgaatcgtgg caagcggccg ctgatcgaat ccgcaaagaa tcccggcaac cgccggcagc   2460
cggtgcgccg tcgattagga agccgcccaa gggcgacgag caaccagatt ttttcgttcc   2520
gatgctctat gacgtgggca cccgcgatag tcgcagcatc atggacgtgg ccgttttccg   2580
tctgtcgaag cgtgaccgac gagctggcga ggtgatccgc tacgagcttc cagacgggca   2640
cgtagaggtt tccgcagggc cggccggcat ggccagtgtg tgggattacg acctggtact   2700
gatggcggtt tcccatctaa ccgaatccat gaaccgatac cgggaaggga agggagacaa   2760
gcccggccgc gtgttccgtc cacacgttgc ggacgtactc aagttctgcc ggcgagccga   2820
tggcggaaag cagaaagacg acctggtaga aacctgcatt cggttaaaca ccacgcacgt   2880
tgccatgcag cgtacgaaga aggccaagaa cggccgcctg gtgacggtat ccgagggtga   2940
agccttgatt agccgctaca agatcgtaaa gagcgaaacc gggcggccgg agtacatcga   3000
gatcgagcta gctgattgga tgtaccgcga gatcacagaa ggcaagaacc cggacgtgct   3060
gacggttcac cccgattact tttgatcga tcccggcatc ggccgttttc tctaccgcct   3120
ggcacgccgc gccgcaggca aggcagaagc cagatggttg ttcaagacga tctacgaacg   3180
cagtggcagc gccggagagt tcaagaagtt ctgtttcacc gtgcgcaagc tgatcgggtc   3240
aaatgacctg ccggagtacg atttgaagga ggaggcgggg caggctggcc cgatcctagt   3300
catgcgctac cgcaacctga tcgagggcga agcatccgcc ggttcctaat gtacggagca   3360
```

-continued

```
gatgctaggg caaattgccc tagcagggga aaaaggtcga aaaggtctct ttcctgtgga   3420
tagcacgtac attgggaacc caaagccgta cattgggaac cggaacccgt acattgggaa   3480
cccaaagccg tacattggga accggtcaca catgtaagtg actgatataa aagagaaaaa   3540
aggcgatttt tccgcctaaa actctttaaa acttattaaa actcttaaaa cccgcctggc   3600
ctgtgcataa ctgtctggcc agcgcacagc cgaagagctg caaaaagcgc ctacccttcg   3660
gtcgctgcgc tccctacgcc ccgccgcttc gcgtcggcct atcgcggccg ctggccgctc   3720
aaaaatggct ggcctacggc caggcaatct accagggcgc ggacaagccg cgccgtcgcc   3780
actcgaccgc cggcgcccac atcaaggcac cctgcctcgc gcgtttcggt gatgacggtg   3840
aaaacctctg acacatgcag ctcccggaga cggtcacagc ttgtctgtaa gcggatgccg   3900
ggagcagaca agcccgtcag ggcgcgtcag cgggtgttgg cgggtgtcgg ggcgcagcca   3960
tgacccagtc acgtagcgat agcggagtgt atactggctt aactatgcgg catcagagca   4020
gattgtactg agagtgcacc atatgcggtg tgaaataccg cacagatgcg taaggagaaa   4080
ataccgcatc aggcgctctt ccgcttcctc gctcactgac tcgctgcgct cggtcgttcg   4140
gctgcggcga gcggtatcag ctcactcaaa ggcggtaata cggttatcca cagaatcagg   4200
ggataacgca ggaaagaaca tgtgagcaaa aggccagcaa aaggccagga accgtaaaaa   4260
ggccgcgttg ctggcgtttt tccataggct ccgcccccct gacgagcatc acaaaaatcg   4320
acgctcaagt cagaggtggc gaaacccgac aggactataa agataccagg cgtttccccc   4380
tggaagctcc ctcgtgcgct ctcctgttcc gaccctgccg cttaccggat acctgtccgc   4440
ctttctccct tcgggaagcg tggcgctttc tcatagctca cgctgtaggt atctcagttc   4500
ggtgtaggtc gttcgctcca agctgggctg tgtgcacgaa ccccccgttc agcccgaccg   4560
ctgcgcctta tccggtaact atcgtcttga gtccaacccg gtaagacacg acttatcgcc   4620
actggcagca gccactggta acaggattag cagagcgagg tatgtaggcg gtgctacaga   4680
gttcttgaag tggtggccta actacggcta cactagaagg acagtatttg gtatctgcgc   4740
tctgctgaag ccagttacct tcggaaaaag agttggtagc tcttgatccg gcaaacaaac   4800
caccgctggt agcggtggtt tttttgtttg caagcagcag attacgcgca gaaaaaaagg   4860
atctcaagaa gatcctttga tcttttctac ggggtctgac gctcagtgga acgaaaactc   4920
acgttaaggg attttggtca tgcattctag gtactaaaac aattcatcca gtaaaatata   4980
atattttatt ttctcccaat caggcttgat ccccagtaag tcaaaaaata gctcgacata   5040
ctgttcttcc ccgatatcct ccctgatcga ccggacgcag aaggcaatgt cataccactt   5100
gtccgccctg ccgcttctcc caagatcaat aaagccactt actttgccat ctttcacaaa   5160
gatgttgctg tctcccaggt cgccgtggga aaagacaagt tcctcttcgg gcttttccgt   5220
ctttaaaaaa tcatacagct cgcgcggatc tttaaatgga gtgtcttctt cccagttttc   5280
gcaatccaca tcggccagat cgttattcag taagtaatcc aattcggcta agcggctgtc   5340
taagctattc gtatagggac aatccgatat gtcgatggag tgaaagagcc tgatgcactc   5400
cgcatacagc tcgataatct tttcagggct ttgttcatct tcatactctt ccgagcaaag   5460
gacgccatcg gcctcactca tgagcagatt gctccagcca tcatgccgtt caaagtgcag   5520
gacctttgga acaggcagct ttccttccag ccatagcatc atgtcctttt cccgttccac   5580
atcataggtg gtccctttat accggctgtc cgtcattttt aaatataggt tttcattttc   5640
tcccaccagc ttatatacct tagcaggaga cattccttcc gtatctttta cgcagcggta   5700
tttttcgatc agtttttca attccggtga tattctcatt ttagccattt attatttcct   5760
```

-continued

```
tcctcttttc tacagtattt aaagataccc caagaagcta attataacaa gacgaactcc   5820
aattcactgt tccttgcatt ctaaaacctt aaataccaga aaacagcttt ttcaaagttg   5880
ttttcaaagt tggcgtataa catagtatcg acggagccga ttttgaaacc gcggtgatca   5940
caggcagcaa cgctctgtca tcgttacaat caacatgcta ccctccgcga gatcatccgt   6000
gtttcaaacc cggcagctta gttgccgttc ttccgaatag catcggtaac atgagcaaag   6060
tctgccgcct tacaacggct ctcccgctga cgccgtcccg gactgatggg ctgcctgtat   6120
cgagtggtga ttttgtgccg agctgccggt cggggagctg ttggctggct ggtggcagga   6180
tatattgtgg tgtaaacaaa ttgacgctta gacaacttaa taacacattg cggacgtttt   6240
taatgtactg aattaacgcc gaattaattc gggggatctg gattttagta ctggattttg   6300
gttttaggaa ttagaaattt tattgataga agtattttac aaatacaaat acatactaag   6360
ggtttcttat atgctcaaca catgagcgaa accctatagg aaccctaatt cccttatctg   6420
ggaactactc acacattatt atggagaaac tcgagttaac cctgagactg ttggacagag   6480
ctcattggta ccaggaacag gtggtggcgg ccctcggtgc gctcgtactg ctccacgatg   6540
gtgtagtcct cgttgtggga ggtgatgtcc agcttggcgt ccacgtagta gtagccgggc   6600
agctgcacgg gcttcttggc catgtagatg gacttgaact ccaccaggta gtggccgccg   6660
tccttcagct tcagggcctt gtgggtctcg cccttcagca cgccgtcgcg ggggtacagg   6720
cgctcggtgg aggcctccca gcccatggtc ttcttctgca tcacggggcc gtcggagggg   6780
aagttcacgc cgatgaactt caccttgtag atgaagcagc cgtcctgcag ggaggagtcc   6840
tgggtcacgg tcgccacgcc gccgtcctcg aagttcatca cgcgctccca cttgaagccc   6900
tcggggaagg acagcttctt gtagtcgggg atgtcggcgg ggtgcttcac gtacaccttg   6960
gagccgtact ggaactgggg ggacaggatg tcccaggcga agggcagggg gccgcccttg   7020
gtcaccttca gcttcacggt gttgtggccc tcgtaggggc ggccctcgcc ctcgccctcg   7080
atctcgaact cgtggccgtt cacggtgccc tccatgcgca ccttgaagcg catgaactcg   7140
gtgatgacgt tctcggagga ggccattttg gtagactcga gagagataga tttgtagaga   7200
gagactggtg atttcagcgt gtcctctcca aatgaaatga acttccttat atagaggaag   7260
gtcttgcgaa ggatagtggg attgtgcgtc atcccttacg tcagtggaga tatcacatca   7320
atccacttgc tttgaagacg tggttggaac gtcttctttt tccacgatgc tcctcgtggg   7380
tgggggtcca tctttgggac cactgtcggc agaggcatct tgaacgatag cctttccttt   7440
atcgcaatga tggcatttgt aggtgccacc ttccttttct actgtccttt tgatgaagtg   7500
acagatagct gggcaatgga atccgaggag gtttcccgat attacccttt gttgaaaagt   7560
ctcaatagcc ctttggtctt ctgagactgt atctttgata ttcttggagt agacgagagt   7620
gtcgtgctcc accatgttat cacatcaatc cacttgcttt gaagacgtgg ttggaacgtc   7680
ttctttttcc acgatgctcc tcgtgggtgg gggtccatct ttgggaccac tgtcggcaga   7740
ggcatcttga acgatagcct ttcctttatc gcaatgatgg catttgtagg tgccaccttc   7800
cttttctact gtccttttga tgaagtgaca gatagctggg caatggaatc cgaggaggtt   7860
tcccgatatt accctttgtt gaaaagtctc aatagccctt tggtcttctg agactgtatc   7920
tttgatattc ttggagtaga cgagagtgtc gtgctccacc atgttggcaa gctgctctag   7980
ccaatacgca aaccgcctct ccccgcgcgt tggccgattc attaatgcag ctggcacgac   8040
aggtttcccg actggaaagc gggcagtgag cgcaacgcaa ttaatgtgag ttagctcact   8100
```

```
cattaggcac cccaggcttt acactttatg cttccggctc gtatgttgtg tggaattgtg   8160
agcggataac aatttcacac aggaaacagc tatgaccatg attacgaatt caggtaccat   8220
ttaaatcctg cagggtttaa acagtgtttt actcctcata ttaacttcgg tcattagagg   8280
ccacgatttg acacattttt actcaaaaca aaatgtttgc atatctctta taatttcaaa   8340
ttcaacacac aacaaataag agaaaaaaca aataatatta atttgagaat gaacaaaagg   8400
accatatcat tcattaactc ttctccatcc atttccattt cacagttcga tagcgaaaac   8460
cgaataaaaa acacagtaaa ttacaagcac aacaaatggt acaagaaaaa cagttttccc   8520
aatgccataa tactcgaacg gcgcgcctca gcccatatgc aggccgccgt tgagcgagaa   8580
gtcggcgccg gtcgagaaac cggactcctc cgacgacaac caggcgcaga tcgaggcgat   8640
ctcttccggc aggcccaggc gcttgaccgg gatcgtcgcg acgatcttgt cgagcacgtc   8700
ctggcggatc gccttgacca tgtcggtggc gatatagccc ggagagaccg tgttgacggt   8760
cacgcccttg gtcgccactt cctgcgccag tgccatggtg aagccatgca ggccggcctt   8820
ggcggtggag tagttggtct ggccgaactg gcccttctgc ccgttcaccg acgagatgtt   8880
gacgatgcgg ccccagccac ggtcggccat gccgtcgatc acctgcttgg tgacgttgaa   8940
cagcgaggtc aggttggtgt cgatcaccgc atcccagtcg gcgcgggtca tcttgcggaa   9000
caccacgtcg cgggtgatac cggcgttgtt gatcagcaca tcaacctcgc cgacctcgga   9060
cttgaccttg tcgaatgcgg tcttggtcga gtcccagtca gccacattgc cttccgaggc   9120
aatgaaatcg aagcccaggg ccttctgctg ctccagccac ttttcgcggc gcggcgagtt   9180
ggggccgcaa ccggccacca cacgaaagcc atccttggcc agccgctggc aaatggcggt   9240
tccgatacca cccatgccgc cggtcacata cgcaatgcgc tgagtcactc tagaatctct   9300
cgtcaatggt ggcaaatagg aaagagtctc aaacttcttc tttccaattg gaggccacac   9360
ctgcatgcac tttactcttc caccattgct tgtaatggaa gtaatgtcag tgttgacctt   9420
cttcactggg aatccagtca tggatttgag gccgccgaat ggagccactg cggcggattg   9480
ccccctagag gcacggctga ctgttgtcac agcggaagag gatatcatag aagccatttt   9540
actagtaaga agctgaaaat atcaaaagaa ggaacagtca ttaatctatt gcatgtacta   9600
gattttagat atgagtggtc aaaaaaaact tacgttaata acgatgaaga agacaatgat   9660
cctcagcaca atctctctct ctctctcttg gcttctcttc tggtgaatag cacgagagag   9720
ggtttaaatg gaaggctcgt gggtccaaaa tgggtggcgg aggaaatagg agaagtaggc   9780
agtgacaagt aatgtagtat ttagtatttg atgaatgaca cattttcatt tcagcatcat   9840
caccaaccat ccttttgttc ctttgcttca actgtcactt tcaattgaca aaattttta    9900
tgttttcatg agaaaactaa attcttataa agattcatct tcttgagtat tatacgtgta   9960
gtttatgaac aacacgtgtt gttcctatat ttttgttctg ttacctctag aataaagttg  10020
tcaccatttc atgagttcaa tttttcttta atagccccaa aaacaaaaga tgattcacaa  10080
gaaagatgcg aatattttgc tatgaatctt ttcttaagag aagcaattac attttcacaa  10140
taaaattaga tccacgactt aacctagttt atgttgatta tttctagtgt tagtattaag  10200
caaaaataaa acttatgaat acgaaggcct ttaaaggaaa ctaaagaaag gacaaggtat  10260
aaacgtccta gaaagttcta gggtttaggc ttagggtcta agatatatgc tttgagtttt  10320
atggcttagt aacacatttt tgtaacactt ctttgtaaca tttcttgata tgttggagaa  10380
gtaactcgtc tggacaatag ttatttccaa tatataggaa aaacggccta aacaatagcc  10440
gacggggaca aatacatcat aaacaaaaaa tcccggttac aaacttccta aaaagccatt  10500
```

cggtccactc cgttaagcct gaactgtgcc tccgttatgc aaaaacgccg ttgaccatcc 10560
gtaacctagt tgactgacgg attatggatt taatccgttt taaggccgtt aataacacca 10620
aaacgacgtc gttttggtgt tttaattttt tttaacaaca attaaaccaa acgacgtcgt 10680
tttggtttaa ttaaattttt ttatcaaaaa cccaagccca agcccaaaac tcttaacaaa 10740
agataaagcc catctctatt ttttctaatt aaaacgcaca gcattatgtt tcttctctaa 10800
cggatatatt ttcaatctca taaattgggg attagggttc ttatttccca attctcaatc 10860
tctcaaaatt ctccaaaatt ctctgaaatt gataatgcct tcttcttctt caaactcgtt 10920
tttctctttt gacagtgagc ttgaagatga taaccatcgt ggttttccta agacctgtcg 10980
atttggatgt cgtgttgtga tcagaacctc aagaactcca aaaaacctag gtagattatt 11040
ccatacctgt gagaaaaatt tcaaaagagg aggattccac acctggaagt ggactgatgt 11100
gtctttagta gaagaagtag aggacataaa ggcttacatt cataaccgtg agaagtgtca 11160
cgatgaagaa atgttattat tgaaggctca gattcgtggc tgtgagaaga tgattgaagg 11220
cttgaaagga gaagcaaaac gtatgaagct aattgttgtt gccggaatag ttgtgtttgg 11280
ttgctttttg tgtctctcta agtgatgtat gagatgaatg tttgtgtatg tgatgttgtt 11340
ttgtctcaat aattagtcac tgatgttgta tgtaatgttg tgttttgcat ctctaattag 11400
ttaataatga atgttgttct tatgtaatgt ttgatttaat caatggcttt tgcaaataaa 11460
tccataacag aacntattca atattttcga aaacataaca aaggtttcaa aagaaattgc 11520
attagcatta gctgagtttt caaacaaaat gcattacata gacagaccct gcttcataat 11580
ccccaaaaca caaaagagaa gcatgctaat aaccgcaact aatatccaaa gacagcttca 11640
taatcccaaa acacaaaaaa agaagattca taaccgatcc ttcatgtatt taaagaaaat 11700
cagacaacaa gcaaagactt aatcttcctg agtaactgat gagctcaagt cgacgtttaa 11760
acagtgtttt actcctcata ttaacttcgg tcattagagg ccacgatttg acacattttt 11820
actcaaaaca aaatgtttgc atatctctta taatttcaaa ttcaacacac aacaaataag 11880
agaaaaaaca aataatatta atttgagaat gaacaaaagg accatatcat tcattaactc 11940
ttctccatcc atttccattt cacagttcga tagcgaaaac cgaataaaaa acacagtaaa 12000
ttacaagcac aacaaatggt acaagaaaaa cagttttccc aatgccataa tactcgaact 12060
acgtattatt tgcgctcgac tgccagcgcc acgcccatgc cgccgccgat gcacagcgag 12120
gccaggccct tcttcgcgtc acggcgcttc atctcgtgca gcagcgtcac caggatacgg 12180
cagcccgacg cgccgatcgg gtggccgatg gcgatggcgc cgccgttcac attgaccttg 12240
gaggtgtccc agcccatctg ctggtgcacc gccagcgcct gcgcggcaaa ggcctcgttg 12300
atctccatca ggtccaggtc ttgcggggtc cactcggcgc gcgacagggc gcgcttggag 12360
gccggcaccg ggcccatgcc catcaccttg ggatcgacac cggcgttggc atagctcttg 12420
atcgtggcca gcggggtcag gcccagttcc ttggccttgg ccgccgacat caccaccacc 12480
gcggcggcgc cgtcgttcag gcccgaggcg ttggccgcgg tcaccgtgcc ggccttgtcg 12540
aaggcgggct tgaggccgga catgctgtcc agcgtggcgc cctggcgcac gaactcgtcg 12600
gtcttgaagg ccaccgggtc gcccttgcgc tgcgggatca gcaccgggac gatctcttcg 12660
tcaaacttgc cggccttctg cgcggcttcg gccttgttct gcgagccgac ggcgaactca 12720
tcctgcgcct cgcgtgtgat gccgtattcc ttggccacgt tctcggcggt gatgcccatg 12780
tggtactggt tgtacacgtc ccacaggccg tcgacgatca tggtgtcgac cagcttggca 12840
tcgcccatgc ggaaaccatc gcgcgagccc ggcagcacgt gcggggcggc gctcatgttt 12900
tcctggccgc cggccaccac gatctcggcg tcgcccgcca tgatcgcgtt ggcggccagc 12960
atcacggcct tcaggcccga gccgcacacc ttgttgatgg tcatggccgg caccatcgcc 13020
ggcaggccgg ccttgatcgc ggcctggcgt gcggggttct ggcccgaacc ggcggtcagc 13080
acctggccca tgatgacttc gctcacctgc tccggcttga cgccggcgcg ctccagcgcg 13140
gccttgatga ccacggcacc cagttccggt gccgggatct tggccagcga gccgccaaac 13200
ttgccgaccg cggtgcgggc ggcggatacg atgacaacgt cagtcactct agaatctctc 13260
gtcaatggtg gcaaatagga aagagtctca aacttcttct ttccaattgg aggccacacc 13320
tgcatgcact ttactcttcc accattgctt gtaatggaag taatgtcagt gttgaccttc 13380
ttcactggga atccagtcat ggatttgagg ccgccgaatg gagccactgc ggcggattgc 13440
cccctagagg cacggctgac tgttgtcaca gcggaagagg atatcataga agccattttg 13500
gatccaagaa gctgaaaata tcaaaagaag gaacagtcat taatctattg catgtactag 13560
atttagata tgagtggtca aaaaaaactt acgttaataa cgatgaagaa gacaatgatc 13620
ctcagcacaa tctctctctc tctctcttgg cttctcttct ggtgaatagc acgagagagg 13680
gtttaaatgg aaggctcgtg ggtccaaaat gggtggcgga ggaaatagga gaagtaggca 13740
gtgacaagta atgtagtatt tagtatttga tgaatgacac attttcattt cagcatcatc 13800
accaaccatc cttttgttcc tttgcttcaa ctgtcacttt caattgacaa aattttttat 13860
gttttcatga gaaaactaaa ttcttataaa gattcatctt cttgagtatt atacgtgtag 13920
tttatgaaca acacgtgttg ttcctatatt tttgttctgt tacctctaga ataaagttgt 13980
caccatttca tgagttcaat ttttctttaa tagccccaaa aacaaaagat gattcacaag 14040
aaagatgcga atattttgct atgaatcttt tcttaagaga agcaattaca ttttcacaat 14100
aaaattagat ccacgactta acctagttta tgttgattat ttctagtgtt agtattaagc 14160
aaaaataaaa cttatgaata cgaaggcctt taaaggaaac taaagaaagg acaaggtata 14220
aacgtcctag aaagttctag ggtttaggct tagggtctaa gatatatgct ttgagtttta 14280
tggcttagta acacattttt gtaacacttc tttgtaacat ttcttgatat gttggagaag 14340
taactcgtct ggacaatagt tatttccaat atataggaaa aacggcctaa acaatagccg 14400
acggggacaa atacatcata aacaaaaaat cccggttaca aacttcctaa aaagccattc 14460
ggtccactcc gttaagcctg aactgtgcct ccgttatgca aaaacgccgt tgaccatccg 14520
taacctagtt gactgacgga ttatggattt aatccgtttt aaggccgtta ataacaccaa 14580
aacgacgtcg ttttggtgtt ttaatttttt ttaacaacaa ttaaaccaaa cgacgtcgtt 14640
ttggtttaat taaatttttt tatcaaaaac ccaagcccaa gcccaaaact cttaacaaaa 14700
gataaagccc atctctattt tttctaatta aaacgcacag cattatgttt cttctctaac 14760
ggatatattt tcaatctcat aaattgggga ttagggttct tatttcccaa ttctcaatct 14820
ctcaaaattc tccaaaattc tctgaaattg ataatgcctt cttcttcttc aaactcgttt 14880
ttctcttttg acagtgagct tgaagatgat aaccatcgtg gttttcctaa gacctgtcga 14940
tttggatgtc gtgttgtgat cagaacctca agaactccaa aaaacctagg tagattattc 15000
catacctgtg agaaaaattt caaaagagga ggattccaca cctggaagtg gactgatgtg 15060
tctttagtag aagaagtaga ggacataaag gcttacattc ataaccgtga gaagtgtcac 15120
gatgaagaaa tgttattatt gaaggctcag attcgtggct gtgagaagat gattgaaggc 15180
ttgaaaggag aagcaaaacg tatgaagcta attgttgttg ccggaatagt tgtgtttggt 15240
tgctttttgt gtctctctaa gtgatgtatg agatgaatgt ttgtgtatgt gatgttgttt 15300
tgtctcaata attagtcact gatgttgtat gtaatgttgt gttttgcatc tctaattagt 15360
taataatgaa tgttgttctt atgtaatgtt tgatttaatc aatggctttt gcaaataaat 15420
ccataacaga acntattcaa tattttcgaa aacataacaa aggtttcaaa agaaattgca 15480
ttagcattag ctgagttttc aaacaaaatg cattacatag acagaccctg cttcataatc 15540
cccaaaacac aaaagagaag catgctaata accgcaacta atatccaaag acagcttcat 15600
aatcccaaaa cacaaaaaaa gaagattcat aaccgatcct tcatgtattt aaagaaaatc 15660
agacaacaag caaagactta atcttcctga gtaactgatg agctcaactg caggtttaaa 15720
cagtgtttta ctcctcatat taacttcggt cattagaggc cacgatttga cacattttta 15780
ctcaaaacaa aatgtttgca tatctcttat aatttcaaat tcaacacaca acaaataaga 15840
gaaaaaacaa ataatattaa tttgagaatg aacaaaagga ccatatcatt cattaactct 15900
tctccatcca tttccatttc acagttcgat agcgaaaacc gaataaaaaa cacagtaaat 15960
tacaagcaca acaaatggta caagaaaaac agttttccca atgccataat actcgaacgc 16020
gatcgctcag cccttggctt tgacgtaacg gccgggcgcc gcctcgatcg cggtgtagcg 16080
ggcgttgccg ggcttggcct tgggcttgac cttcttgccg ccatgctggg tcaggaaccc 16140
ggcccattgc ggccaccagc tgcccggcac ttcctgcgcg ccatcgaacc aggcctgggc 16200
atcggcggcg ccaccgtcgt tgatccagta gctgcgcttg ttcttggcca ccgagttgat 16260
cacgccggcg atatggccgg acgcgcccag cacgaagcgg ttggcgcccg gcttgccctg 16320
gttgaggatg tcgagcgaac cgtacgccga catccacggc acgatgtggt cttcgcgcga 16380
accgtagatg aaggccgggg cgtcgatcag gccgaggtcg atcttttcgc cggccaccgt 16440
cagcttgccc ggcactttca ggctgttttc caggtaggtg ttgcgcaggt accagcagaa 16500
catcgggccc ggcaaattgg tgctgtccga attccagaac agcaggtcaa acgccgccgg 16560
ctcattgcct ttgaggtagt tcgactgcac atagttccat accaggtcgt tcggacgcag 16620
gctcgagaag gtcgaggcca ggtcacggcc cggcatcagg ccgccatcgc gcaattgctg 16680
ttcacgcagc gcgacctggg tttcatcgac gaagacgtcg agcacgccgg tgtcgctgaa 16740
gtcgaggaag gtggtcagca gggtcaggct ggccgccggg tgctggccac gcgccgccag 16800
taccgccagt gcggtggcaa cgatggtgcc gcccacgcag aagccgaaca tgttcagctt 16860
gtcctggccg ctgacgtcct ggacgatgcg gatcgcttcg atcacgccct gctccacgta 16920
gtcgtcccag gtggtgccgg ccagcgactt gtccggattg ctccacgaga tcaggaacac 16980
ggtgttgccc tgctccaccg cgtagcgcac cagcgaattt tccggttgca ggtcgaggat 17040
gtagaacttg ttgatgcacg gcggcaccat caacagcggg cgctggctga ccgtcggcgt 17100
ggtcggcgtg tactggatca gctggaacag cggattttcg taaatcacgg tgcccggggt 17160
aatggccagg ttgcggccca cttcaaaggc cgattcgtcc gacagcgaga tatggccctt 17220
gttgatatcg cccagcatat tgaccaggcc acgcgtcagg ctctcgccct tggtttcaat 17280
cagtttttgc tgcgcttccg ggttggtggc gaggaagttc gcgggcgaca tggcatcaat 17340
cacctgctgc acggcaaagc gtattttctg cttttgctgg ggtgcggtgt ccaccgcctc 17400
caccatggca ctgaggaatt tggcgttgag caggtaagat gcggcattga aggccgacat 17460
cggattgccc tgccaggctg ccgagctgaa gcggcggtcg ctgacggctg gcgccttgcc 17520
agccaaaaaa tcctgccaca acgcggtgaa gtcacgcaga taatcgtttt tcagctgctc 17580
catcgcttcc ggtttgagcg caacgccgat atcctgcaac atggtggcca tcgggttcgc 17640
ctcggtggtg ggcgccttgc tgaaccagga ttgccactgc agctcatcgt tgttcttgtt 17700
actcactcta gaatctctcg tcaatggtgg caaataggaa agagtctcaa acttcttctt 17760
tccaattgga ggccacacct gcatgcactt tactcttcca ccattgcttg taatggaagt 17820
aatgtcagtg ttgaccttct tcactgggaa tccagtcatg gatttgaggc cgccgaatgg 17880
agccactgcg gcggattgcc ccctagaggc acggctgact gttgtcacag cggaagagga 17940
tatcatagaa gccatttttg tacaaagaag ctgaaaatat caaaagaagg aacagtcatt 18000
aatctattgc atgtactaga ttttagatat gagtggtcaa aaaaaactta cgttaataac 18060
gatgaagaag acaatgatcc tcagcacaat ctctctctct ctctcttggc ttctcttctg 18120
gtgaatagca cgagagaggg tttaaatgga aggctcgtgg gtccaaaatg ggtggcggag 18180
gaaataggag aagtaggcag tgacaagtaa tgtagtattt agtatttgat gaatgacaca 18240
ttttcatttc agcatcatca ccaaccatcc ttttgttcct ttgcttcaac tgtcactttc 18300
aattgacaaa atttttatg ttttcatgag aaaactaaat tcttataaag attcatcttc 18360
ttgagtatta tacgtgtagt ttatgaacaa cacgtgttgt tcctatattt ttgttctgtt 18420
acctctagaa taaagttgtc accatttcat gagttcaatt tttctttaat agccccaaaa 18480
acaaaagatg attcacaaga aagatgcgaa tattttgcta tgaatctttt cttaagagaa 18540
gcaattacat tttcacaata aaattagatc cacgacttaa cctagtttat gttgattatt 18600
tctagtgtta gtattaagca aaaataaaac ttatgaatac gaaggccttt aaaggaaact 18660
aaagaaagga caaggtataa acgtcctaga aagttctagg gtttaggctt agggtctaag 18720
atatatgctt tgagttttat ggcttagtaa cacatttttg taacacttct ttgtaacatt 18780
tcttgatatg ttggagaagt aactcgtctg gacaatagtt atttccaata tataggaaaa 18840
acggcctaaa caatagccga cggggacaaa tacatcataa acaaaaaatc ccggttacaa 18900
acttcctaaa aagccattcg gtccactccg ttaagcctga actgtgcctc cgttatgcaa 18960
aaacgccgtt gaccatccgt aacctagttg actgacggat tatggattta atccgtttta 19020
aggccgttaa taacaccaaa acgacgtcgt tttggtgttt taattttttt taacaacaat 19080
taaaccaaac gacgtcgttt tggtttaatt aaattttttt atcaaaaacc caagcccaag 19140
cccaaaactc ttaacaaaag ataaagccca tctctatttt ttctaattaa aacgcacagc 19200
attatgtttc ttctctaacg gatatatttt caatctcata aattggggat tagggttctt 19260
atttcccaat tctcaatctc tcaaaattct ccaaaattct ctgaaattga taatgccttc 19320
ttcttcttca aactcgtttt tctcttttga cagtgagctt gaagatgata accatcgtgg 19380
ttttcctaag acctgtcgat ttggatgtcg tgttgtgatc agaacctcaa gaactccaaa 19440
aaacctaggt agattattcc atacctgtga gaaaaaattc aaaagaggag gattccacac 19500
ctggaagtgg actgatgtgt ctttagtaga agaagtagag gacataaagg cttacattca 19560
taaccgtgag aagtgtcacg atgaagaaat gttattattg aaggctcaga ttcgtggctg 19620
tgagaagatg attgaaggct tgaaaggaga agcaaaacgt atgaagctaa ttgttgttgc 19680
cggaatagtt gtgtttggtt gctttttgtg tctctctaag tgatgtatga gatgaatgtt 19740
tgtgtatgtg atgttgtttt gtctcaataa ttagtcactg atgttgtatg taatgttgtg 19800
ttttgcatct ctaattagtt aataatgaat gttgttctta tgtaatgttt gatttaatca 19860
atggcttttg caaataaatc cataacagaa cntattcaat attttcgaaa acataacaaa 19920
ggtttcaaaa gaaattgcat tagcattagc tgagttttca aacaaaatgc attacataga 19980
cagaccctgc ttcataatcc ccaaaacaca aaagagaagc atgctaataa ccgcaactaa 20040
tatccaaaga cagcttcata atcccaaaac acaaaaaaag aagattcata accgatcctt 20100
catgtattta aagaaaatca gacaacaagc aaagacttaa tcttcctgag taactgatga 20160
gctcaaaagc ttggcactgg ccgtcgtttt acaacgtcgt gactgggaaa accctggcgt 20220
tacccaactt aatcgccttg cagcacatcc ccctttcgcc agctggcgta atagcgaaga 20280
ggcccgcacc gatcgccctt cccaacagtt gcgcagcctg aatggcgaat gctagagcag 20340
cttgagcttg gatcagattg tcgtttcccg ccttcagttt aaactatcag tgtttgacag 20400
gatatattgg cgggtaaacc taagagaaaa gagcgtttat tagaataacg gatatttaaa 20460
agggcgtgaa aaggtttatc cgttcgtcca tttgtatgtg 20500

<210> SEQ ID NO 3
<211> LENGTH: 22395
<212> TYPE: DNA
<213> ORGANISM: Artificial Sequence
<220> FEATURE:
<223> OTHER INFORMATION: Synthetic Vector

<400> SEQUENCE: 3
gtccgtgacc atgattacgc caagcttcga ctgtacagga tgttctagct actcgagtag 60
ctagaacatc ctgtacagtc gagtagctag aacatcctgt acagtcgact agctagaaca 120
tcctgtacag tcgagtagct agaacatcct gtacagtcga gtagctagac atcctgtaca 180
ggatccctat ataaggaagt tcatttcatt tggagagaac acgggggatc gggtatcgtt 240
aattaagttt atcaacaagt ttgtacaaaa aagcaggctc cgcggccgcc cccttcacca 300
tgatcgtcga cggcctgtgg gacgtgtaca accagtacca catgggcatc accgccgaga 360
acgtggccaa ggaatacggc atcacacgcg aggcgcagga tgagttcgcc gtcggctcgc 420
agaacaaggc cgaagccgcg cagaaggccg gcaagtttga cgaagagatc gtcccggtgc 480
tgatcccgca gcgcaagggc gacccggtgg ccttcaagac cgacgagttc gtgcgccagg 540
gcgccacgct ggacagcatg tccggcctca agcccgcctt cgacaaggcc ggcacggtga 600
ccgcggccaa cgcctcgggc ctgaacgacg gcgccgccgc ggtggtggtg atgtcggcgg 660
ccaaggccaa ggaactgggc ctgaccccgc tggccacgat caagagctat gccaacgccg 720
gtgtcgatcc caaggtgatg ggcatgggcc cggtgccggc ctccaagcgc gccctgtcgc 780
gcgccgagtg gaccccgcaa gacctggacc tgatggagat caacgaggcc tttgccgcgc 840
aggcgctggc ggtgcaccag cagatgggct gggacacctc caaggtcaat gtgaaagggt 900
gggcgcgccg acccagcttt cttgtacaaa gtggttgatc ctgcagggtc cgtcgcttct 960
cttccatttc ttctcatttt cgattttgat tcttatttct ttccagtagc tcctgctctg 1020
tgaatttctc cgctcacgat agatctgctt atactcctta cattcaacct tagatctggt 1080
ctcgattctc tgtttctctg tttttttctt ttggtcgaga atctgatgtt tgtttatgtt 1140
ctgtcaccat taataataat gaactctctc attcatacaa tgattagttt ctctcgtcta 1200
caaaacgata tgttgcattt tcacttttct tcttttttc taagatgatt tgctttgacc 1260
aatttgttta gatctttatt ctattttatt ttctggtggg ttggtggaaa ttgaaaaaaa 1320
aaaaacagca taaattgtta tttgttaatg tattcatttt ttggctattt gttctgggta 1380
aaaatctgct tctactattg aatctttcct ggatttttta ctcctattgg gtttttatag 1440
taaaaataca taataaaagg aaaacaaaag ttttatagat tctcttaaac cccttacgat 1500

```
aaaagttgga atcaaaataa ttcaggatca gatgctcttt gattgattca gatgcgatta   1560
cagttgcatg gcaaattttc tagatccgtc gtcacatttt attttctgtt taaatatcta   1620
aatctgatat atgatgtcga caaattctgg tggcttatac atcacttcaa ctgttttctt   1680
ttggctttgt ttgtcaactt ggttttcaat acgatttgtg atttcgatcg ctgaattttt   1740
aatacaagca aactgatgtt aaccacaagc aagagatgtg acctgcctta ttaacatcgt   1800
attacttact actagtcgta ttctcaacgc aatcgttttt gtatttctca cattatgccg   1860
cttctctact ctttattcct tttggtccac gcattttcta tttgtggcaa tccctttcac   1920
aacctgattt cccactttgg atcatttgtc tgaagactct cttgaatcgt taccacttgt   1980
ttcttgtgca tgctctgttt tttagaatta atgataaaac tattccatag tcttgagttt   2040
tcagcttgtt gattcttttg cttttggttt tctgcaggtt taaacatcaa ccactttgta   2100
caagaaagct gggtcggcgc gcccaccctt tcacattgac cttggaggtg tcccagccca   2160
tctgctggtg caccgccagc gcctgcgcgg caaaggcctc gttgatctcc atcaggtcca   2220
ggtcttgcgg ggtccactcg gcgcgcgaca gggcgcgctt ggaggccggc accgggccca   2280
tgcccatcac cttgggatcg acaccggcgt tggcatagct cttgatcgtg gccagcgggg   2340
tcaggcccag ttccttggcc ttggccgccg acatcaccac caccgcggcg gcgccgtcgt   2400
tcaggcccga ggcgttggcc gcggtcaccg tgccggcctt gtcgaaggcg ggcttgaggc   2460
cggacatgct gtccagcgtg gcgccctggc gcacgaactc gtcggtcttg aaggccaccg   2520
ggtcgccctt gcgctgcggg atcagcaccg ggacgatctc ttcgtcaaac ttgccggcct   2580
tctgcgcggc ttcggccttg ttctgcgagc cgacggcgaa ctcatcctgc gcctcgcgtg   2640
tgatgccgta ttccttggcc acgttctcgg cggtgatgcc catgtggtac tggttgtaca   2700
cgtcccacag gccgtcgacg atcatggtga agggggcggc cgcggagcct gctttttttgt   2760
acaaacttgt tgatctcgag cggcgcgccg ttcgagtatt atggcattgg gaaaactgtt   2820
tttcttgtac catttgttgt gcttgtaatt tactgtgttt tttattcggt tttcgctatc   2880
gaactgtgaa atggaaatgg atggagaaga gttaatgaat gatatggtcc ttttgttcat   2940
tctcaaatta atattatttg ttttttctct tatttgttgt gtgttgaatt tgaaattata   3000
agagatatgc aaacattttg ttttgagtaa aaatgtgtca aatcgtggcc tctaatgacc   3060
gaagttaata tgaggagtaa aacactgttt aaaccctgca ggatttaaat agaaggtaat   3120
tatccaagat gtagcatcaa gaatccaatg tttacgggaa aaactatgga agtattatgt   3180
gagctcagca agaagcagat caatatgcgg cacatatgca acctatgttc aaaaatgaag   3240
aatgtacaga tacaagatcc tatactgcca gaatacgaag aagaatacgt agaaattgaa   3300
aaagaagaac caggcgaaga aaagaatctt gaagacgtaa gcactgacga caacaatgaa   3360
aagaagaaga taaggtcggt gattgtgaaa gagacataga ggacacatgt aaggtggaaa   3420
atgtaagggc ggaaagtaac cttatcacaa aggaatctta tcccccacta cttatccttt   3480
tatatttttc cgtgtcattt ttgcccttga gttttcctat ataaggaacc aagttcggca   3540
tttgtgaaaa caagaaaaaa ttggtgtaag ctattttctt tgaagtactg aggatacaac   3600
ttcagagaaa tttgtaagaa agtggatcga aaccatggcc tcctccgaga acgtcatcac   3660
cgagttcatg cgcttcaagg tgcgcatgga gggcaccgtg aacggccacg agttcgagat   3720
cgagggcgag ggcgagggcc gcccctacga gggccacaac accgtgaagc tgaaggtgac   3780
caagggcggc cccctgccct tcgcctggga catcctgtcc ccccagttcc agtacggctc   3840
caaggtgtac gtgaagcacc ccgccgacat ccccgactac aagaagctgt ccttccccga   3900
```

```
gggcttcaag tgggagcgcg tgatgaactt cgaggacggc ggcgtggcga ccgtgaccca   3960
ggactcctcc ctgcaggacg gctgcttcat ctacaaggtg aagttcatcg gcgtgaactt   4020
cccctccgac ggccccgtga tgcagaagaa gaccatgggc tgggaggcct ccaccgagcg   4080
cctgtacccc cgcgacggcg tgctgaaggg cgagacccac aaggccctga agctgaagga   4140
cggcggccac tacctggtgg agttcaagtc catctacatg gccaagaagc ccgtgcagct   4200
gcccggctac tactacgtgg acgccaagct ggacatcacc tcccacaacg aggactacac   4260
catcgtggag cagtacgagc gcaccgaggg ccgccaccac ctgttcctgg taccaatgag   4320
ctctgtccaa cagtctcagg gttaatgtct atgtatctta aataatgttg tcggcgatcg   4380
ttcaaacatt tggcaataaa gtttcttaag attgaatcct gttgccggtc ttgcgatgat   4440
tatcatataa tttctgttga attacgttaa gcatgtaata attaacatgt aatgcatgac   4500
gttatttatg agatgggttt ttatgattag agtcccgcaa ttatacattt aatacgcgat   4560
agaaaacaaa atatagcgcg caaactagga taaattatcg cgcgcggtgt catctatgtt   4620
actagatcgg gaattaaact atcagtgttt gacaggatat attggcgggt aaacctaaga   4680
gaaaagagcg tttattagaa taacggatat ttaaaagggc gtgaaaaggt ttatccgttc   4740
gtccatttgt atgtgcatgc caaccacagg gttcccctcg ggatcaaagt actttgatcc   4800
aacccctccg ctgctatagt gcagtcggct tctgacgttc agtgcagccg tcttctgaaa   4860
acgacatgtc gcacaagtcc taagttacgc gacaggctgc cgccctgccc ttttcctggc   4920
gttttcttgt cgcgtgtttt agtcgcataa agtagaatac ttgcgactag aaccggagac   4980
attacgccat gaacaagagc gccgccgctg gcctgctggg ctatgcccgc gtcagcaccg   5040
acgaccagga cttgaccaac caacgggccg aactgcacgc ggccggctgc accaagctgt   5100
tttccgagaa gatcaccggc accaggcgcg accgcccgga gctggccagg atgcttgacc   5160
acctacgccc tggcgacgtt gtgacagtga ccaggctaga ccgcctggcc cgcagcaccc   5220
gcgacctact ggacattgcc gagcgcatcc aggaggccgg cgcgggcctg cgtagcctgg   5280
cagagccgtg ggccgacacc accacgccgg ccggccgcat ggtgttgacc gtgttcgccg   5340
gcattgccga gttcgagcgt tccctaatca tcgaccgcac ccggagcggg cgcgaggccg   5400
ccaaggcccg aggcgtgaag tttggccccc gccctaccct caccccggca cagatcgcgc   5460
acgcccgcga gctgatcgac caggaaggcc gcaccgtgaa agaggcggct gcactgcttg   5520
gcgtgcatcg ctcgaccctg taccgcgcac ttgagcgcag cgaggaagtg acgcccaccg   5580
aggccaggcg gcgcggtgcc ttccgtgagg acgcattgac cgaggccgac gccctggcgg   5640
ccgccgagaa tgaacgccaa gaggaacaag catgaaaccg caccaggacg gccaggacga   5700
accgtttttc attaccgaag agatcgaggc ggagatgatc gcggccgggt acgtgttcga   5760
gccgcccgcg cacgtctcaa ccgtgcggct gcatgaaatc ctggccggtt tgtctgatgc   5820
caagctggcg gcctggccgg ccagcttggc cgctgaagaa accgagcgcc gccgtctaaa   5880
aaggtgatgt gtatttgagt aaaacagctt gcgtcatgcg gtcgctgcgt atatgatgcg   5940
atgagtaaat aaacaaatac gcaaggggaa cgcatgaagg ttatcgctgt acttaaccag   6000
aaaggcgggt caggcaagac gaccatcgca acccatctag cccgcgccct gcaactcgcc   6060
ggggccgatg ttctgttagt cgattccgat ccccagggca gtgcccgcga ttgggcggcc   6120
gtgcgggaag atcaaccgct aaccgttgtc ggcatcgacc gcccgacgat tgaccgcgac   6180
gtgaaggcca tcggccggcg cgacttcgta gtgatcgacg gagcgcccca ggcggcggac   6240
```

-continued ttggctgtgt ccgcgatcaa ggcagccgac ttcgtgctga ttccggtgca gccaagccct 6300
tacgacatat gggccaccgc cgacctggtg gagctggtta agcagcgcat tgaggtcacg 6360
gatggaaggc tacaagcggc ctttgtcgtg tcgcgggcga tcaaaggcac gcgcatcggc 6420
ggtgaggttg ccgaggcgct ggccgggtac gagctgccca ttcttgagtc ccgtatcacg 6480
cagcgcgtga gctacccagg cactgccgcc gccggcacaa ccgttcttga atcagaaccc 6540
gagggcgacg ctgcccgcga ggtccaggcg ctggccgctg aaattaaatc aaaactcatt 6600
tgagttaatg aggtaaagag aaaatgagca aaagcacaaa cacgctaagt gccggccgtc 6660
cgagcgcacg cagcagcaag gctgcaacgt tggccagcct ggcagacacg ccagccatga 6720
agcgggtcaa ctttcagttg ccggcggagg atcacaccaa gctgaagatg tacgcggtac 6780
gccaaggcaa gaccattacc gagctgctat ctgaatacat cgcgcagcta ccagagtaaa 6840
tgagcaaatg aataaatgag tagatgaatt ttagcggcta aaggaggcgg catggaaaat 6900
caagaacaac caggcaccga cgccgtggaa tgccccatgt gtggaggaac gggcggttgg 6960
ccaggcgtaa gcggctgggt tgtctgccgg ccctgcaatg gcactggaac ccccaagccc 7020
gaggaatcgg cgtgacggtc gcaaaccatc cggcccggta caaatcggcg cggcgctggg 7080
tgatgacctg gtggagaagt tgaaggccgc gcaggccgcc cagcggcaac gcatcgaggc 7140
agaagcacgc cccggtgaat cgtggcaagc ggccgctgat cgaatccgca aagaatcccg 7200
gcaaccgccg gcagccggtg cgccgtcgat taggaagccg cccaagggcg acgagcaacc 7260
agattttttc gttccgatgc tctatgacgt gggcacccgc gatagtcgca gcatcatgga 7320
cgtggccgtt ttccgtctgt cgaagcgtga ccgacgagct ggcgaggtga tccgctacga 7380
gcttccagac gggcacgtag aggtttccgc agggccggcc ggcatggcca gtgtgtggga 7440
ttacgacctg gtactgatgg cggtttccca tctaaccgaa tccatgaacc gataccggga 7500
agggaaggga gacaagcccg gccgcgtgtt ccgtccacac gttgcggacg tactcaagtt 7560
ctgccggcga gccgatggcg gaaagcagaa agacgacctg gtagaaacct gcattcggtt 7620
aaacaccacg cacgttgcca tgcagcgtac gaagaaggcc aagaacggcc gcctggtgac 7680
ggtatccgag ggtgaagcct tgattagccg ctacaagatc gtaaagagcg aaaccgggcg 7740
gccggagtac atcgagatcg agctagctga ttggatgtac cgcgagatca cagaaggcaa 7800
gaacccggac gtgctgacgg ttcaccccga ttactttttg atcgatcccg gcatcggccg 7860
ttttctctac cgcctggcac gccgcgccgc aggcaaggca gaagccagat ggttgttcaa 7920
gacgatctac gaacgcagtg gcagcgccgg agagttcaag aagttctgtt tcaccgtgcg 7980
caagctgatc gggtcaaatg acctgccgga gtacgatttg aaggaggagg cggggcaggc 8040
tggcccgatc ctagtcatgc gctaccgcaa cctgatcgag ggcgaagcat ccgccggttc 8100
ctaatgtacg gagcagatgc tagggcaaat tgccctagca ggggaaaaag gtcgaaaagg 8160
tctctttcct gtggatagca cgtacattgg gaacccaaag ccgtacattg ggaaccggaa 8220
cccgtacatt gggaacccaa agccgtacat tgggaaccgg tcacacatgt aagtgactga 8280
tataaaagag aaaaaaggcg atttttccgc ctaaaactct ttaaaactta ttaaaactct 8340
taaaacccgc ctggcctgtg cataactgtc tggccagcgc acagccgaag agctgcaaaa 8400
agcgcctacc cttcggtcgc tgcgctccct acgccccgcc gcttcgcgtc ggcctatcgc 8460
ggccgctggc cgctcaaaaa tggctggcct acggccaggc aatctaccag ggcgcggaca 8520
agccgcgccg tcgccactcg accgccggcg cccacatcaa ggcaccctgc ctcgcgcgtt 8580
tcggtgatga cggtgaaaac ctctgacaca tgcagctccc ggagacggtc acagcttgtc 8640
tgtaagcgga tgccgggagc agacaagccc gtcagggcgc gtcagcgggt gttggcgggt 8700
gtcggggcgc agccatgacc cagtcacgta gcgatagcgg agtgtatact ggcttaacta 8760
tgcggcatca gagcagattg tactgagagt gcaccatatg cggtgtgaaa taccgcacag 8820
atgcgtaagg agaaaatacc gcatcaggcg ctcttccgct tcctcgctca ctgactcgct 8880
gcgctcggtc gttcggctgc ggcgagcggt atcagctcac tcaaaggcgg taatacggtt 8940
atccacagaa tcaggggata acgcaggaaa gaacatgtga gcaaaaggcc agcaaaaggc 9000
caggaaccgt aaaaaggccg cgttgctggc gtttttccat aggctccgcc cccctgacga 9060
gcatcacaaa aatcgacgct caagtcagag gtggcgaaac ccgacaggac tataaagata 9120
ccaggcgttt ccccctggaa gctccctcgt gcgctctcct gttccgaccc tgccgcttac 9180
cggatacctg tccgcctttc tcccttcggg aagcgtggcg ctttctcata gctcacgctg 9240
taggtatctc agttcggtgt aggtcgttcg ctccaagctg ggctgtgtgc acgaaccccc 9300
cgttcagccc gaccgctgcg ccttatccgg taactatcgt cttgagtcca acccggtaag 9360
acacgactta tcgccactgg cagcagccac tggtaacagg attagcagag cgaggtatgt 9420
aggcggtgct acagagttct tgaagtggtg gcctaactac ggctacacta gaaggacagt 9480
atttggtatc tgcgctctgc tgaagccagt taccttcgga aaaagagttg gtagctcttg 9540
atccggcaaa caaaccaccg ctggtagcgg tggttttttt gtttgcaagc agcagattac 9600
gcgcagaaaa aaaggatctc aagaagatcc tttgatcttt tctacggggt ctgacgctca 9660
gtggaacgaa aactcacgtt aagggatttt ggtcatgcat tctaggtact aaaacaattc 9720
atccagtaaa atataatatt ttattttctc ccaatcaggc ttgatcccca gtaagtcaaa 9780
aaatagctcg acatactgtt cttccccgat atcctccctg atcgaccgga cgcagaaggc 9840
aatgtcatac cacttgtccg ccctgccgct tctcccaaga tcaataaagc cacttacttt 9900
gccatctttc acaaagatgt tgctgtctcc caggtcgccg tgggaaaaga caagttcctc 9960
ttcgggcttt tccgtcttta aaaaatcata cagctcgcgc ggatctttaa atggagtgtc 10020
ttcttcccag ttttcgcaat ccacatcggc cagatcgtta ttcagtaagt aatccaattc 10080
ggctaagcgg ctgtctaagc tattcgtata gggacaatcc gatatgtcga tggagtgaaa 10140
gagcctgatg cactccgcat acagctcgat aatcttttca gggctttgtt catcttcata 10200
ctcttccgag caaaggacgc catcggcctc actcatgagc agattgctcc agccatcatg 10260
ccgttcaaag tgcaggacct ttggaacagg cagctttcct tccagccata gcatcatgtc 10320
cttttcccgt tccacatcat aggtggtccc tttataccgg ctgtccgtca tttttaaata 10380
taggttttca ttttctccca ccagcttata taccttagca ggagacattc cttccgtatc 10440
ttttacgcag cggtattttt cgatcagttt tttcaattcc ggtgatattc tcattttagc 10500
catttattat ttccttcctc ttttctacag tatttaaaga taccccaaga agctaattat 10560
aacaagacga actccaattc actgttcctt gcattctaaa accttaaata ccagaaaaca 10620
gctttttcaa agttgttttc aaagttggcg tataacatag tatcgacgga gccgattttg 10680
aaaccgcggt gatcacaggc agcaacgctc tgtcatcgtt acaatcaaca tgctaccctc 10740
cgcgagatca tccgtgtttc aaacccggca gcttagttgc cgttcttccg aatagcatcg 10800
gtaacatgag caaagtctgc cgccttacaa cggctctccc gctgacgccg tcccggactg 10860
atgggctgcc tgtatcgagt ggtgattttg tgccgagctg ccggtcgggg agctgttggc 10920
tggctggtgg caggatatat tgtggtgtaa acaaattgac gcttagacaa cttaataaca 10980
cattgcggac gtttttaatg tactgaatta acgccgaatt aattcctagg ccaccatgtt 11040
gggcccgggg cgcgccgtac gtagtgttta tctttgttgc ttttctgaac aatttattta 11100
ctatgtaaat atattatcaa tgtttaatct attttaattt gcacatgaat tttcatttta 11160
tttttacttt acaaaacaaa taaatatata tgcaaaaaaa tttacaaacg atgcacgggt 11220
tacaaactaa tttcattaaa tgctaatgca gattttgtga agtaaaactc caattatgat 11280
gaaaaatacc accaacacca cctgcgaaac tgtatcccaa ctgtccttaa taaaaatgtt 11340
aaaaagtata ttattctcat ttgtctgtca taatttatgt accccacttt aatttttctg 11400
atgtactaaa ccgagggcaa actgaaacct gttcctcatg caaagcccct actcaccatg 11460
tatcatgtac gtgtcatcac ccaacaactc cacttttgct atataacaac acccccgtca 11520
cactctccct ctctaacaca caccccacta acaattcctt cacttgcagc actgttgcat 11580
catcatcttc attgcaaaac cctaaacttc accttcaacc gcggccgcat ggcttctatg 11640
atatcctctt ccgctgtgac aacagtcagc cgtgcctcta gggggcaatc cgccgcagtg 11700
gctccattcg gcggcctcaa atccatgact ggattcccag tgaagaaggt caacactgac 11760
attacttcca ttacaagcaa tggtggaaga gtaaagtgca tgcaggtgtg gcctccaatt 11820
ggaaagaaga agtttgagac tctttcctat ttgccaccat tgacgagaga ttctagagtg 11880
agtaacaaga acaacgatga gctgcagtgg caatcctggt tcagcaaggc gcccaccacc 11940
gaggcgaacc cgatggccac catgttgcag gatatcggcg ttgcgctcaa accggaagcg 12000
atggagcagc tgaaaaacga ttatctgcgt gacttcaccg cgttgtggca ggatttttg 12060
gctggcaagg cgccagccgt cagcgaccgc cgcttcagct cggcagcctg gcagggcaat 12120
ccgatgtcgg ccttcaatgc cgcatcttac ctgctcaacg ccaaattcct cagtgccatg 12180
gtggaggcgg tggacaccgc accccagcaa aagcagaaaa tacgctttgc cgtgcagcag 12240
gtgattgatg ccatgtcgcc cgcgaacttc ctcgccacca acccggaagc gcagcaaaaa 12300
ctgattgaaa ccaagggcga gagcctgacg cgtggcctgg tcaatatgct gggcgatatc 12360
aacaagggcc atatctcgct gtcggacgaa tcggcctttg aagtgggccg caacctggcc 12420
attaccccgg gcaccgtgat ttacgaaaat ccgctgttcc agctgatcca gtacacgccg 12480
accacgccga cggtcagcca gcgcccgctg ttgatggtgc cgccgtgcat caacaagttc 12540
tacatcctcg acctgcaacc ggaaaattcg ctggtgcgct acgcggtgga gcagggcaac 12600
accgtgttcc tgatctcgtg gagcaatccg gacaagtcgc tggccggcac cacctgggac 12660
gactacgtgg agcagggcgt gatcgaagcg atccgcatcg tccaggacgt cagcggccag 12720
gacaagctga acatgttcgg cttctgcgtg ggcggcacca tcgttgccac cgcactggcg 12780
gtactggcgg cgcgtggcca gcacccggcg gccagcctga ccctgctgac caccttcctc 12840
gacttcagcg acaccggcgt gctcgacgtc ttcgtcgatg aaacccaggt cgcgctgcgt 12900
gaacagcaat tgcgcgatgg cggcctgatg ccgggccgtg acctggcctc gaccttctcg 12960
agcctgcgtc cgaacgacct ggtatggaac tatgtgcagt cgaactacct caaaggcaat 13020
gagccggcgg cgtttgacct gctgttctgg aattcggaca gcaccaattt gccgggcccg 13080
atgttctgct ggtacctgcg caacacctac ctggaaaaca gcctgaaagt gccgggcaag 13140
ctgacggtgg ccggcgaaaa gatcgacctc ggcctgatcg acgccccggc cttcatctac 13200
ggttcgcgcg aagaccacat cgtgccgtgg atgtcggcgt acggttcgct cgacatcctc 13260
aaccagggca agccgggcgc caaccgcttc gtgctgggcg cgtccggcca tatcgccggc 13320
gtgatcaact cggtggccaa gaacaagcgc agctactgga tcaacgacgg tggcgccgcc 13380
gatgcccagg cctggttcga tggcgcgcag gaagtgccgg gcagctggtg gccgcaatgg 13440
gccgggttcc tgacccagca tggcggcaag aaggtcaagc ccaaggccaa gcccggcaac 13500
gcccgctaca ccgcgatcga ggcggcgccc ggccgttacg tcaaagccaa gggctgagcg 13560
gccgctgagt aattctgata ttagagggag cattaatgtg ttgttgtgat gtggtttata 13620
tggggaaatt aaataaatga tgtatgtacc tcttgcctat gtaggtttgt gtgttttgtt 13680
ttgttgtcta gctttggtta ttaagtagta gggacgttcg ttcgtgtctc aaaaaaaggg 13740
gtactaccac tctgtagtgt atatggatgc tggaaatcaa tgtgttttgt atttgttcac 13800
ctccattgtt gaattcaatg tcaaatgtgt tttgcgttgg ttatgtgtaa aattactatc 13860
tttctcgtcc gatgatcaaa gttttaagca acaaaaccaa gggtgaaatt taaactgtgc 13920
tttgttgaag attcttttat catattgaaa atcaaattac tagcagcaga ttttacctag 13980
catgaaattt tatcaacagt acagcactca ctaaccaagt tccaaactaa gatgcgccat 14040
taacatcagc caataggcat tttcagcaag gcgcgcccgc gccgatgtat gtgacaaccc 14100
tcgggattgt tgatttattt caaaactaag agtttttgtc ttattgttct cgtctatttt 14160
ggatatcaat cttagtttta tatcttttct agttctctac gtgttaaatg ttcaacacac 14220
tagcaatttg gcctgccagc gtatggatta tggaactatc aagtctgtga cgcgccgtac 14280
gtagtgttta tctttgttgc ttttctgaac aatttattta ctatgtaaat atattatcaa 14340
tgtttaatct attttaattt gcacatgaat tttcatttta tttttacttt acaaaacaaa 14400
taaatatata tgcaaaaaaa tttacaaacg atgcacgggt tacaaactaa tttcattaaa 14460
tgctaatgca gattttgtga agtaaaactc caattatgat gaaaaatacc accaacacca 14520
cctgcgaaac tgtatcccaa ctgtccttaa taaaaatgtt aaaaagtata ttattctcat 14580
ttgtctgtca taatttatgt accccacttt aatttttctg atgtactaaa ccgagggcaa 14640
actgaaacct gttcctcatg caaagcccct actcaccatg tatcatgtac gtgtcatcac 14700
ccaacaactc cacttttgct atataacaac acccccgtca cactctccct ctctaacaca 14760
caccccacta acaattcctt cacttgcagc actgttgcat catcatcttc attgcaaaac 14820
cctaaacttc accttcaacc gcggccgcat ggcttctatg atatcctctt ccgctgtgac 14880
aacagtcagc cgtgcctcta gggggcaatc cgccgcagtg gctccattcg gcggcctcaa 14940
atccatgact ggattcccag tgaagaaggt caacactgac attacttcca ttacaagcaa 15000
tggtggaaga gtaaagtgca tgcaggtgtg gcctccaatt ggaaagaaga agtttgagac 15060
tctttcctat ttgccaccat tgacgagaga ttctagagtg actcagcgca ttgcgtatgt 15120
gaccggcggc atgggtggta tcggaaccgc catttgccag cggctggcca aggatggctt 15180
tcgtgtggtg gccggttgcg gccccaactc gccgcgccgc gaaaagtggc tggagcagca 15240
gaaggccctg ggcttcgatt tcattgcctc ggaaggcaat gtggctgact gggactcgac 15300
caagaccgca ttcgacaagg tcaagtccga ggtcggcgag gttgatgtgc tgatcaacaa 15360
cgccggtatc acccgcgacg tggtgttccg caagatgacc cgcgccgact gggatgcggt 15420
gatcgacacc aacctgacct cgctgttcaa cgtcaccaag caggtgatcg acggcatggc 15480
cgaccgtggc tggggccgca tcgtcaacat ctcgtcggtg aacgggcaga agggccagtt 15540
cggccagacc aactactcca ccgccaaggc cggcctgcat ggcttcacca tggcactggc 15600
gcaggaagtg gcgaccaagg gcgtgaccgt caacacggtc tctccgggct atatcgccac 15660
cgacatggtc aaggcgatcc gccaggacgt gctcgacaag atcgtcgcga cgatcccggt 15720

-continued caagcgcctg ggcctgccgg aagagatcgc ctcgatctgc gcctggttgt cgtcggagga 15780
gtccggtttc tcgaccggcg ccgacttctc gctcaacggc ggcctgcata tgggctgagc 15840
ggccgctgag taattctgat attagaggga gcattaatgt gttgttgtga tgtggtttat 15900
atggggaaat taaataaatg atgtatgtac ctcttgccta tgtaggtttg tgtgttttgt 15960
tttgttgtct agctttggtt attaagtagt agggacgttc gttcgtgtct caaaaaaagg 16020
ggtactacca ctctgtagtg tatatggatg ctggaaatca atgtgttttg tatttgttca 16080
cctccattgt tgaattcaat gtcaaatgtg ttttgcgttg gttatgtgta aaattactat 16140
ctttctcgtc cgatgatcaa agttttaagc aacaaaacca agggtgaaat ttaaactgtg 16200
ctttgttgaa gattctttta tcatattgaa aatcaaatta ctagcagcag attttaccta 16260
gcatgaaatt ttatcaacag tacagcactc actaaccaag ttccaaacta agatgcgcca 16320
ttaacatcag ccaataggca ttttcagcaa ggcgcgtaag gggatccgta cgtaagtacg 16380
tactcaaaat gccaacaaat aaaaaaaaag ttgctttaat aatgccaaaa caaattaata 16440
aaacacttac aacaccggat tttttttaat taaaatgtgc catttaggat aaatagttaa 16500
tatttttaat aattatttaa aaagccgtat ctactaaaat gatttttatt tggttgaaaa 16560
tattaatatg tttaaatcaa cacaatctat caaaattaaa ctaaaaaaaa aataagtgta 16620
cgtggttaac attagtacag taatataaga ggaaaatgag aaattaagaa attgaaagcg 16680
agtctaattt ttaaattatg aacctgcata tataaaagga aagaaagaat ccaggaagaa 16740
aagaaatgaa accatgcatg gtcccctcgt catcacgagt ttctgccatt tgcaatagaa 16800
acactgaaac acctttctct ttgtcactta attgagatgc cgaagccacc tcacaccatg 16860
aacttcatga ggtgtagcac ccaaggcttc catagccatg catactgaag aatgtctcaa 16920
gctcagcacc ctacttctgt gacgtgtccc tcattcacct tcctctcttc cctataaata 16980
accacgcctc aggttctccg cttcacaact caaacattct ctccattggt ccttaaacac 17040
tcatcagtca tcaccgcggc cgcggaattc atggcttcta tgatatcctc ttccgctgtg 17100
acaacagtca gccgtgcctc tagggggcaa tccgccgcag tggctccatt cggcggcctc 17160
aaatccatga ctggattccc agtgaagaag gtcaacactg acattacttc cattacaagc 17220
aatggtggaa gagtaaagtg catgcaggtg tggcctccaa ttggaaagaa gaagtttgag 17280
actctttcct atttgccacc attgacgaga gattctagag tgactgacgt tgtcatcgta 17340
tccgccgccc gcaccgcggt cggcaagttt ggcggctcgc tggccaagat cccggcaccg 17400
gaactgggtg ccgtggtcat caaggccgcg ctggagcgcg ccggcgtcaa gccggagcag 17460
gtgagcgaag tcatcatggg ccaggtgctg accgccggtt cgggccagaa ccccgcacgc 17520
caggccgcga tcaaggccgg cctgccggcg atggtgccgg ccatgaccat caacaaggtg 17580
tgcggctcgg gcctgaaggc cgtgatgctg gccgccaacg cgatcatggc gggcgacgcc 17640
gagatcgtgg tggccggcgg ccaggaaaac atgagcgccg ccccgcacgt gctgccgggc 17700
tcgcgcgatg gtttccgcat gggcgatgcc aagctggtcg acaccatgat cgtcgacggc 17760
ctgtgggacg tgtacaacca gtaccacatg ggcatcaccg ccgagaacgt ggccaaggaa 17820
tacggcatca cacgcgaggc gcaggatgag ttcgccgtcg gctcgcagaa caaggccgaa 17880
gccgcgcaga aggccggcaa gtttgacgaa gagatcgtcc cggtgctgat cccgcagcgc 17940
aagggcgacc cggtggcctt caagaccgac gagttcgtgc gccagggcgc cacgctggac 18000
agcatgtccg gcctcaagcc cgccttcgac aaggccggca cggtgaccgc ggccaacgcc 18060
tcgggcctga acgacggcgc cgccgcggtg gtggtgatgt cggcggccaa ggccaaggaa 18120
ctgggcctga ccccgctggc cacgatcaag agctatgcca acgccggtgt cgatcccaag 18180
gtgatgggca tgggcccggt gccggcctcc aagcgcgccc tgtcgcgcgc cgagtggacc 18240
ccgcaagacc tggacctgat ggagatcaac gaggcctttg ccgcgcaggc gctggcggtg 18300
caccagcaga tgggctggga cacctccaag gtcaatgtga acggcggcgc catcgccatc 18360
ggccacccga tcggcgcgtc gggctgccgt atcctggtga cgctgctgca cgagatgaag 18420
cgccgtgacg cgaagaaggg cctggcctcg ctgtgcatcg gcggcggcat gggcgtggcg 18480
ctggcagtcg agcgcaaata actcgaggcg gccgcagccc tttttgtatg tgctacccca 18540
cttttgtctt tttggcaata gtgctagcaa ccaataaata ataataataa taatgaataa 18600
gaaaacaaag gctttagctt gccttttgtt cactgtaaaa taataatgta agtactctct 18660
ataatgagtc acgaaacttt tgcgggaata aaaggagaaa ttccaatgag ttttctgtca 18720
aatcttcttt tgtctctctc tctctctctt ttttttttt ctttcttctg agcttcttgc 18780
aaaacaaaag gcaaacaata acgattggtc caatgatagt tagcttgatc gatgatatct 18840
ttaggaagtg ttggcaggac aggacatgat gtagaagact aaaattgaaa gtattgcaga 18900
cccaatagtt gaagattaac tttaagaatg aagacgtctt atcaggttct tcatgactta 18960
agctttaaga ggagtccacc atggtagatc tgactagtaa cggccgccag tgtgctggaa 19020
ttctgcagat gtggagcacg acactctcgt ctactccaag aatatcaaag atacagtctc 19080
agaagaccaa agggctattg agacttttca acaaagggta atatcgggaa acctcctcgg 19140
attccattgc ccagctatct gtcacttcat caaaaggaca gtagaaaagg aaggtggcac 19200
ctacaaatgc catcattgcg ataaaggaaa ggctatcgtt caagatgcct ctgccgacag 19260
tggtcccaaa gatggacccc cacccacgag gagcatcgtg gaaaaagaag acgttccaac 19320
cacgtcttca aagcaagtgg attgatgtga taacatggtg gagcacgaca ctctcgtcta 19380
ctccaagaat atcaaagata cagtctcaga agaccaaagg gctattgaga cttttcaaca 19440
aagggtaata tcgggaaacc tcctcggatt ccattgccca gctatctgtc acttcatcaa 19500
aaggacagta gaaaaggaag gtggcaccta caaatgccat cattgcgata aaggaaaggc 19560
tatcgttcaa gatgcctctg ccgacagtgg tcccaaagat ggacccccac ccacgaggag 19620
catcgtggaa aaagaagacg ttccaaccac gtcttcaaag caagtggatt gatgtgatat 19680
ctccactgac gtaagggatg acgcacaatc ccactatcct tcgcaagacc ttcctctata 19740
taaggaagtt catttcattt ggagaggaca cgctgaaatc accagtctct ctctacaaat 19800
ctatctctct cgagctttcg cagatctgtc gatcgaccat ggactccaaa gaatcattaa 19860
ctcctggtag agaagaaaac cccagcagtg tgcttgctca ggagaggga gatgtgatgg 19920
acttctataa aaccctaaga ggaggagcta ctgtgaaggt ttctgcgtct tcaccctcac 19980
tggctgtcgc ttctcaatca gactccaagc agcgaagact tttggttgat tttccaaaag 20040
gctcagtaag caatgcgcag cagccagatc tgtccaaagc agtttcactc tcaatgggac 20100
tgtatatggg agagacagaa acaaaagtga tgggaaatga cctgggattc ccacagcagg 20160
gccaaatcag cctttcctcg ggggaaacag acttaaagct tttggaagaa agcattgcaa 20220
acctcaatag gtcgaccagt gttccagaga accccaagag ttcagcatcc actgctgtgt 20280
ctgctgcccc cacagctagt tctgcggccc ccccgaccga tgtcagcctg ggggacgagc 20340
tccacttaga cggcgaggac gtggcgatgg cgcatgccga cgcgctagac gatttcgatc 20400
tggacatgtt gggggacggg gattccccgg gtccgggatt taccccccac gactccgccc 20460

```
cctacggcgc tctggatatg gccgacttcg agtttgagca gatgtttacc gatgcccttg  20520
gaattgacga gtacggtggg actagctcca gctcctcaac agcaacaaca ggaccacctc  20580
ccaaactctg cctggtgtgc tctgatgaag cttcaggatg tcattatgga gtcttaactt  20640
gtggaagctg taaagttttc ttcaaaagag cagtggaagg acagcacaat tacctatgtg  20700
ctggaaggaa tgattgcatc atcgataaaa ttcgaagaaa aaactgccca gcatgccgct  20760
atcgaaaatg tcttcaggct ggaatgaacc tggaagctcg aaaaacaaag aaaaaaataa  20820
aaggaattgc tcgacaaagg cccgagtgcg tggtgccgga gaaccagtgt gcaatgaaac  20880
ggaaagagaa aaaggcgcag agggaaaaag acaaattgcc cgtcagtacg acgacagtag  20940
acgatcacat gcctcccatc atgcaatgtg accctccgcc cccagaggcc gctagaattc  21000
tggaatgttt gcagcacgag gtggtgccac gattcctgaa tgagaagcta atggaacaga  21060
acagattgaa gaacgtgccc cccctcactg ccaatcagaa gtcgttgatc gcaaggctcg  21120
tgtggtacca ggaaggctat gaacaacctt ccgaggaaga cctgaagagg gttacacagt  21180
cggacgagga cgacgaagac tcggatatgc cgttccgtca gattaccgag atgacgattc  21240
tcacagtgca gctcatcgta gaattcgcta agggcctccc gggcttcgcc aagatctcgc  21300
agtcggacca gatcacgtta ttaaaggcgt gctcaagtga ggtgatgatg ctccgagtgg  21360
ctcggcggta tgacgcggcc accgacagcg tactgttcgc gaacaaccag gcgtacactc  21420
gcgacaacta ccgcaaggca ggcatggcgt acgtcatcga ggacctgctg cacttctgtc  21480
ggtgcatgta ctccatgatg atggataacg tgcattatgc gctgcttaca gccattgtca  21540
tcttctcaga ccggcccggg cttgagcaac ccctgttggt ggaggagatc cagagatatt  21600
acctgaacac gctacgggtg tacatcctga accagaacag cgcgtcgccc cgctgcgccg  21660
tcatcttcgg caagatcctg ggcatactga cggagatccg cacgctgggc atgcagaact  21720
ccaacatgtg catctccctc aagctgaaga acaggaagct gccgccgttc ctcgaggaga  21780
tctgggacgt ggcggacgtg gcgacgacgg cgacgccggt ggcggcggag gcgccggcgc  21840
tctagccccc gcgccgcccg cccggccgcg cgcacgtcta gcgcgcctca ggagagaacg  21900
ctcatagact ggctagtttt agtgaagtgc acggacactg acgtcggacg tgatcaacct  21960
atttataagg actgcgaatt ttaccactta agagggcaca cccgtacccg atttcgtacg  22020
ggaattcctg cagcccgggg gatccttaat taactcgagg aattcatcga ttccgcgggt  22080
accgagctcg atccgtcgac ctgcagatcg ttcaaacatt tggcaataaa gtttcttaag  22140
attgaatcct gttgccggtc ttgcgatgat tatcatataa tttctgttga attacgttaa  22200
gcatgtaata attaacatgt aatgcatgac gttatttatg agatgggttt ttatgattag  22260
agtcccgcaa ttatacattt aatacgcgat agaaaacaaa atatagcgcg caaactagga  22320
taaattatcg cgcgcggtgt catctatgtt actagatctg gcgcgcccct aggtctagag  22380
tcgactgttt aaacg                                                   22395
```

<210> SEQ ID NO 4
<211> LENGTH: 22517
<212> TYPE: DNA
<213> ORGANISM: Artificial Sequence
<220> FEATURE:
<223> OTHER INFORMATION: Synthetic Vector

<400> SEQUENCE: 4

```
aaatagaagg taattatcca agatgtagca tcaagaatcc aatgtttacg ggaaaaacta     60
tggaagtatt atgtgagctc agcaagaagc agatcaatat gcggcacata tgcaacctat    120
```

-continued

```
gttcaaaaat gaagaatgta cagatacaag atcctatact gccagaatac gaagaagaat    180
acgtagaaat tgaaaaagaa gaaccaggcg aagaaaagaa tcttgaagac gtaagcactg    240
acgacaacaa tgaaaagaag aagataaggt cggtgattgt gaaagagaca tagaggacac    300
atgtaaggtg gaaaatgtaa gggcggaaag taaccttatc acaaaggaat cttatccccc    360
actacttatc cttttatatt tttccgtgtc atttttgccc ttgagttttc ctatataagg    420
aaccaagttc ggcatttgtg aaaacaagaa aaaattggtg taagctattt tctttgaagt    480
actgaggata caacttcaga gaaatttgta agaaagtgga tcgaaaccat ggcctcctcc    540
gagaacgtca tcaccgagtt catgcgcttc aaggtgcgca tggagggcac cgtgaacggc    600
cacgagttcg agatcgaggg cgagggcgag ggccgcccct acgagggcca caacaccgtg    660
aagctgaagg tgaccaaggg cggccccctg cccttcgcct gggacatcct gtccccccag    720
ttccagtacg gctccaaggt gtacgtgaag caccccgccg acatccccga ctacaagaag    780
ctgtccttcc ccgagggctt caagtgggag cgcgtgatga acttcgagga cggcggcgtg    840
gcgaccgtga cccaggactc ctccctgcag gacggctgct tcatctacaa ggtgaagttc    900
atcggcgtga acttcccctc cgacggcccc gtgatgcaga agaagaccat gggctgggag    960
gcctccaccg agcgcctgta cccccgcgac ggcgtgctga agggcgagac ccacaaggcc   1020
ctgaagctga aggacggcgg ccactacctg gtggagttca agtccatcta catggccaag   1080
aagcccgtgc agctgcccgg ctactactac gtggacgcca agctggacat cacctcccac   1140
aacgaggact acaccatcgt ggagcagtac gagcgcaccg agggccgcca ccacctgttc   1200
ctggtaccaa tgagctctgt ccaacagtct cagggttaat gtctatgtat cttaaataat   1260
gttgtcggcg atcgttcaaa catttggcaa taaagtttct taagattgaa tcctgttgcc   1320
ggtcttgcga tgattatcat ataatttctg ttgaattacg ttaagcatgt aataattaac   1380
atgtaatgca tgacgttatt tatgagatgg gtttttatga ttagagtccc gcaattatac   1440
atttaatacg cgatagaaaa caaaatatag cgcgcaaact aggataaatt atcgcgcgcg   1500
gtgtcatcta tgttactaga tcgggaatta aactatcagt gtttgacagg atatattggc   1560
gggtaaacct aagagaaaag agcgtttatt agaataacgg atatttaaaa gggcgtgaaa   1620
aggtttatcc gttcgtccat ttgtatgtgc atgccaacca cagggttccc ctcgggatca   1680
aagtactttg atccaacccc tccgctgcta tagtgcagtc ggcttctgac gttcagtgca   1740
gccgtcttct gaaaacgaca tgtcgcacaa gtcctaagtt acgcgacagg ctgccgccct   1800
gccctttcc tggcgttttc ttgtcgcgtg ttttagtcgc ataaagtaga atacttgcga   1860
ctagaaccgg agacattacg ccatgaacaa gagcgccgcc gctggcctgc tgggctatgc   1920
ccgcgtcagc accgacgacc aggacttgac caaccaacgg gccgaactgc acgcggccgg   1980
ctgcaccaag ctgttttccg agaagatcac cggcaccagg cgcgaccgcc cggagctggc   2040
caggatgctt gaccacctac gccctggcga cgttgtgaca gtgaccaggc tagaccgcct   2100
ggcccgcagc acccgcgacc tactggacat tgccgagcgc atccaggagg ccggcgcggg   2160
cctgcgtagc ctggcagagc cgtgggccga caccaccacg ccggccggcc gcatggtgtt   2220
gaccgtgttc gccggcattg ccgagttcga gcgttcccta atcatcgacc gcacccggag   2280
cgggcgcgag gccgccaagg cccgaggcgt gaagtttggc ccccgcccta ccctcacccc   2340
ggcacagatc gcgcacgccc gcgagctgat cgaccaggaa ggccgcaccg tgaaagaggc   2400
ggctgcactg cttggcgtgc atcgctcgac cctgtaccgc gcacttgagc gcagcgagga   2460
```

```
agtgacgccc accgaggcca ggcggcgcgg tgccttccgt gaggacgcat tgaccgaggc   2520
cgacgccctg gcggccgccg agaatgaacg ccaagaggaa caagcatgaa accgcaccag   2580
gacggccagg acgaaccgtt tttcattacc gaagagatcg aggcggagat gatcgcggcc   2640
gggtacgtgt tcgagccgcc cgcgcacgtc tcaaccgtgc ggctgcatga aatcctggcc   2700
ggtttgtctg atgccaagct ggcggcctgg ccggccagct tggccgctga agaaaccgag   2760
cgccgccgtc taaaaaggtg atgtgtattt gagtaaaaca gcttgcgtca tgcggtcgct   2820
gcgtatatga tgcgatgagt aaataaacaa atacgcaagg ggaacgcatg aaggttatcg   2880
ctgtacttaa ccagaaaggc gggtcaggca agacgaccat cgcaacccat ctagcccgcg   2940
ccctgcaact cgccggggcc gatgttctgt tagtcgattc cgatccccag ggcagtgccc   3000
gcgattgggc ggccgtgcgg gaagatcaac cgctaaccgt tgtcggcatc gaccgcccga   3060
cgattgaccg cgacgtgaag gccatcggcc ggcgcgactt cgtagtgatc gacggagcgc   3120
cccaggcggc ggacttggct gtgtccgcga tcaaggcagc cgacttcgtg ctgattccgg   3180
tgcagccaag cccttacgac atatgggcca ccgccgacct ggtggagctg gttaagcagc   3240
gcattgaggt cacggatgga aggctacaag cggcctttgt cgtgtcgcgg gcgatcaaag   3300
gcacgcgcat cggcggtgag gttgccgagg cgctggccgg gtacgagctg cccattcttg   3360
agtcccgtat cacgcagcgc gtgagctacc caggcactgc cgccgccggc acaaccgttc   3420
ttgaatcaga acccgagggc gacgctgccc gcgaggtcca ggcgctggcc gctgaaatta   3480
aatcaaaact catttgagtt aatgaggtaa agagaaaatg agcaaaagca caaacacgct   3540
aagtgccggc cgtccgagcg cacgcagcag caaggctgca acgttggcca gcctggcaga   3600
cacgccagcc atgaagcggg tcaactttca gttgccggcg gaggatcaca ccaagctgaa   3660
gatgtacgcg gtacgccaag gcaagaccat taccgagctg ctatctgaat acatcgcgca   3720
gctaccagag taaatgagca aatgaataaa tgagtagatg aattttagcg gctaaaggag   3780
gcggcatgga aaatcaagaa caaccaggca ccgacgccgt ggaatgcccc atgtgtggag   3840
gaacgggcgg ttggccaggc gtaagcggct gggttgtctg ccggccctgc aatggcactg   3900
gaacccccaa gcccgaggaa tcggcgtgac ggtcgcaaac catccggccc ggtacaaatc   3960
ggcgcggcgc tgggtgatga cctggtggag aagttgaagg ccgcgcaggc cgcccagcgg   4020
caacgcatcg aggcagaagc acgccccggt gaatcgtggc aagcggccgc tgatcgaatc   4080
cgcaaagaat cccggcaacc gccggcagcc ggtgcgccgt cgattaggaa gccgcccaag   4140
ggcgacgagc aaccagattt tttcgttccg atgctctatg acgtgggcac ccgcgatagt   4200
cgcagcatca tggacgtggc cgttttccgt ctgtcgaagc gtgaccgacg agctggcgag   4260
gtgatccgct acgagcttcc agacgggcac gtagaggttt ccgcagggcc ggccggcatg   4320
gccagtgtgt gggattacga cctggtactg atggcggttt cccatctaac cgaatccatg   4380
aaccgatacc gggaagggaa gggagacaag cccggccgcg tgttccgtcc acacgttgcg   4440
gacgtactca agttctgccg gcgagccgat ggcggaaagc agaaagacga cctggtagaa   4500
acctgcattc ggttaaacac cacgcacgtt gccatgcagc gtacgaagaa ggccaagaac   4560
ggccgcctgg tgacggtatc cgagggtgaa gccttgatta gccgctacaa gatcgtaaag   4620
agcgaaaccg ggcggccgga gtacatcgag atcgagctag ctgattggat gtaccgcgag   4680
atcacagaag gcaagaaccc ggacgtgctg acggttcacc ccgattactt tttgatcgat   4740
cccggcatcg gccgttttct ctaccgcctg gcacgccgcg ccgcaggcaa ggcagaagcc   4800
agatggttgt tcaagacgat ctacgaacgc agtggcagcg ccggagagtt caagaagttc   4860
```

-continued

```
tgtttcaccg tgcgcaagct gatcgggtca aatgacctgc cggagtacga tttgaaggag   4920
gaggcggggc aggctggccc gatcctagtc atgcgctacc gcaacctgat cgagggcgaa   4980
gcatccgccg gttcctaatg tacggagcag atgctagggc aaattgccct agcaggggaa   5040
aaaggtcgaa aaggtctctt tcctgtggat agcacgtaca ttgggaaccc aaagccgtac   5100
attgggaacc ggaacccgta cattgggaac ccaaagccgt acattgggaa ccggtcacac   5160
atgtaagtga ctgatataaa agagaaaaaa ggcgattttt ccgcctaaaa ctctttaaaa   5220
cttattaaaa ctcttaaaac ccgcctggcc tgtgcataac tgtctggcca gcgcacagcc   5280
gaagagctgc aaaaagcgcc tacccttcgg tcgctgcgct ccctacgccc cgccgcttcg   5340
cgtcggccta tcgcggccgc tggccgctca aaaatggctg gcctacggcc aggcaatcta   5400
ccagggcgcg gacaagccgc gccgtcgcca ctcgaccgcc ggcgcccaca tcaaggcacc   5460
ctgcctcgcg cgtttcggtg atgacggtga aaacctctga cacatgcagc tcccggagac   5520
ggtcacagct tgtctgtaag cggatgccgg gagcagacaa gcccgtcagg gcgcgtcagc   5580
gggtgttggc gggtgtcggg gcgcagccat gacccagtca cgtagcgata gcggagtgta   5640
tactggctta actatgcggc atcagagcag attgtactga gagtgcacca tatgcggtgt   5700
gaaataccgc acagatgcgt aaggagaaaa taccgcatca ggcgctcttc cgcttcctcg   5760
ctcactgact cgctgcgctc ggtcgttcgg ctgcggcgag cggtatcagc tcactcaaag   5820
gcggtaatac ggttatccac agaatcaggg gataacgcag gaaagaacat gtgagcaaaa   5880
ggccagcaaa aggccaggaa ccgtaaaaag gccgcgttgc tggcgttttt ccataggctc   5940
cgcccccctg acgagcatca caaaaatcga cgctcaagtc agaggtggcg aaacccgaca   6000
ggactataaa gataccaggc gtttccccct ggaagctccc tcgtgcgctc tcctgttccg   6060
accctgccgc ttaccggata cctgtccgcc tttctccctt cgggaagcgt ggcgctttct   6120
catagctcac gctgtaggta tctcagttcg gtgtaggtcg ttcgctccaa gctgggctgt   6180
gtgcacgaac cccccgttca gcccgaccgc tgcgccttat ccggtaacta tcgtcttgag   6240
tccaacccgg taagacacga cttatcgcca ctggcagcag ccactggtaa caggattagc   6300
agagcgaggt atgtaggcgg tgctacagag ttcttgaagt ggtggcctaa ctacggctac   6360
actagaagga cagtatttgg tatctgcgct ctgctgaagc cagttacctt cggaaaaaga   6420
gttggtagct cttgatccgg caaacaaacc accgctggta gcggtggttt ttttgtttgc   6480
aagcagcaga ttacgcgcag aaaaaaagga tctcaagaag atcctttgat cttttctacg   6540
gggtctgacg ctcagtggaa cgaaaactca cgttaaggga ttttggtcat gcattctagg   6600
tactaaaaca attcatccag taaaatataa tattttattt tctcccaatc aggcttgatc   6660
cccagtaagt caaaaaatag ctcgacatac tgttcttccc cgatatcctc cctgatcgac   6720
cggacgcaga aggcaatgtc ataccacttg tccgccctgc cgcttctccc aagatcaata   6780
aagccactta ctttgccatc tttcacaaag atgttgctgt ctcccaggtc gccgtgggaa   6840
aagacaagtt cctcttcggg cttttccgtc tttaaaaaat catacagctc gcgcggatct   6900
ttaaatggag tgtcttcttc ccagttttcg caatccacat cggccagatc gttattcagt   6960
aagtaatcca attcggctaa gcggctgtct aagctattcg tatagggaca atccgatatg   7020
tcgatggagt gaaagagcct gatgcactcc gcatacagct cgataatctt ttcagggctt   7080
tgttcatctt catactcttc cgagcaaagg acgccatcgg cctcactcat gagcagattg   7140
ctccagccat catgccgttc aaagtgcagg acctttggaa caggcagctt tccttccagc   7200
```

```
catagcatca tgtccttttc ccgttccaca tcataggtgg tccctttata ccggctgtcc   7260
gtcattttta aatataggtt ttcattttct cccaccagct tatatacctt agcaggagac   7320
attccttccg tatcttttac gcagcggtat ttttcgatca gtttttttcaa ttccggtgat   7380
attctcattt tagccattta ttatttcctt cctcttttct acagtattta aagatacccc   7440
aagaagctaa ttataacaag acgaactcca attcactgtt ccttgcattc taaaacctta   7500
aataccagaa aacagctttt tcaaagttgt tttcaaagtt ggcgtataac atagtatcga   7560
cggagccgat tttgaaaccg cggtgatcac aggcagcaac gctctgtcat cgttacaatc   7620
aacatgctac cctccgcgag atcatccgtg tttcaaaccc ggcagcttag ttgccgttct   7680
tccgaatagc atcggtaaca tgagcaaagt ctgccgcctt acaacggctc tcccgctgac   7740
gccgtcccgg actgatgggc tgcctgtatc gagtggtgat tttgtgccga gctgccggtc   7800
ggggagctgt tggctggctg gtggcaggat atattgtggt gtaaacaaat tgacgcttag   7860
acaacttaat aacacattgc ggacgttttt aatgtactga attaacgccg aattaattcc   7920
taggccacca tgttgggccc ggggcgcgcc gtacgtagtg tttatctttg ttgctttttct   7980
gaacaattta tttactatgt aaatatatta tcaatgttta atctatttta atttgcacat   8040
gaattttcat tttatttttta ctttacaaaa caaataaata tatatgcaaa aaaatttaca   8100
aacgatgcac gggttacaaa ctaatttcat taaatgctaa tgcagatttt gtgaagtaaa   8160
actccaatta tgatgaaaaa taccaccaac accacctgcg aaactgtatc ccaactgtcc   8220
ttaataaaaa tgttaaaaag tatattattc tcatttgtct gtcataattt atgtacccca   8280
ctttaatttt tctgatgtac taaaccgagg gcaaactgaa acctgttcct catgcaaagc   8340
ccctactcac catgtatcat gtacgtgtca tcacccaaca actccacttt tgctatataa   8400
caacaccccc gtcacactct ccctctctaa cacacacccc actaacaatt ccttcacttg   8460
cagcactgtt gcatcatcat cttcattgca aaaccctaaa cttcaccttc aaccgcggcc   8520
gcatggcttc tatgatatcc tcttccgctg tgacaacagt cagccgtgcc tctagggggc   8580
aatccgccgc agtggctcca ttcggcggcc tcaaatccat gactggattc ccagtgaaga   8640
aggtcaacac tgacattact tccattacaa gcaatggtgg aagagtaaag tgcatgcagg   8700
tgtggcctcc aattggaaag aagaagtttg agactctttc ctatttgcca ccattgacga   8760
gagattctag agtgagtaac aagaacaacg atgagctgca gtggcaatcc tggttcagca   8820
aggcgcccac caccgaggcg aacccgatgg ccaccatgtt gcaggatatc ggcgttgcgc   8880
tcaaaccgga agcgatggag cagctgaaaa acgattatct gcgtgacttc accgcgttgt   8940
ggcaggattt tttggctggc aaggcgccag ccgtcagcga ccgccgcttc agctcggcag   9000
cctggcaggg caatccgatg tcggccttca atgccgcatc ttacctgctc aacgccaaat   9060
tcctcagtgc catggtggag gcggtggaca ccgcaccccca gcaaaagcag aaaatacgct   9120
ttgccgtgca gcaggtgatt gatgccatgt cgcccgcgaa cttcctcgcc accaacccgg   9180
aagcgcagca aaaactgatt gaaaccaagg gcgagagcct gacgcgtggc ctggtcaata   9240
tgctgggcga tatcaacaag ggccatatct cgctgtcgga cgaatcggcc tttgaagtgg   9300
gccgcaacct ggccattacc ccgggcaccg tgatttacga aaatccgctg ttccagctga   9360
tccagtacac gccgaccacg ccgacggtca gccagcgccc gctgttgatg gtgccgccgt   9420
gcatcaacaa gttctacatc ctcgacctgc aaccggaaaa ttcgctggtg cgctacgcgg   9480
tggagcaggg caacaccgtg ttcctgatct cgtggagcaa tccggacaag tcgctggccg   9540
gcaccacctg ggacgactac gtggagcagg gcgtgatcga agcgatccgc atcgtccagg   9600
```

-continued

```
acgtcagcgg ccaggacaag ctgaacatgt tcggcttctg cgtgggcggc accatcgttg   9660
ccaccgcact ggcggtactg gcggcgcgtg gccagcaccc ggcggccagc ctgaccctgc   9720
tgaccacctt cctcgacttc agcgacaccg gcgtgctcga cgtcttcgtc gatgaaaccc   9780
aggtcgcgct gcgtgaacag caattgcgcg atggcggcct gatgccgggc cgtgacctgg   9840
cctcgacctt ctcgagcctg cgtccgaacg acctggtatg gaactatgtg cagtcgaact   9900
acctcaaagg caatgagccg gcggcgtttg acctgctgtt ctggaattcg gacagcacca   9960
atttgccggg cccgatgttc tgctggtacc tgcgcaacac ctacctggaa aacagcctga  10020
aagtgccggg caagctgacg gtggccggcg aaaagatcga cctcggcctg atcgacgccc  10080
cggccttcat ctacggttcg cgcgaagacc acatcgtgcc gtggatgtcg gcgtacggtt  10140
cgctcgacat cctcaaccag ggcaagccgg gcgccaaccg cttcgtgctg ggcgcgtccg  10200
gccatatcgc cggcgtgatc aactcggtgg ccaagaacaa gcgcagctac tggatcaacg  10260
acggtggcgc cgccgatgcc caggcctggt tcgatggcgc gcaggaagtg ccgggcagct  10320
ggtggccgca atgggccggg ttcctgaccc agcatggcgg caagaaggtc aagcccaagg  10380
ccaagcccgg caacgcccgc tacaccgcga tcgaggcggc gcccggccgt tacgtcaaag  10440
ccaagggctg agcggccgct gagtaattct gatattagag ggagcattaa tgtgttgttg  10500
tgatgtggtt tatatgggga aattaaataa atgatgtatg tacctcttgc ctatgtaggt  10560
ttgtgtgttt tgttttgttg tctagctttg gttattaagt agtagggacg ttcgttcgtg  10620
tctcaaaaaa aggggtacta ccactctgta gtgtatatgg atgctggaaa tcaatgtgtt  10680
ttgtatttgt tcacctccat tgttgaattc aatgtcaaat gtgttttgcg ttggttatgt  10740
gtaaaattac tatctttctc gtccgatgat caaagtttta agcaacaaaa ccaagggtga  10800
aatttaaact gtgctttgtt gaagattctt ttatcatatt gaaaatcaaa ttactagcag  10860
cagattttac ctagcatgaa attttatcaa cagtacagca ctcactaacc aagttccaaa  10920
ctaagatgcg ccattaacat cagccaatag gcattttcag caaggcgcgc ccgcgccgat  10980
gtatgtgaca accctcggga ttgttgattt atttcaaaac taagagtttt tgtcttattg  11040
ttctcgtcta ttttggatat caatcttagt tttatatctt ttctagttct ctacgtgtta  11100
aatgttcaac acactagcaa tttggcctgc cagcgtatgg attatggaac tatcaagtct  11160
gtgacgcgcc gtacgtagtg tttatctttg ttgcttttct gaacaattta tttactatgt  11220
aaatatatta tcaatgttta atctatttta atttgcacat gaattttcat tttattttta  11280
ctttacaaaa caaataaata tatatgcaaa aaaatttaca aacgatgcac gggttacaaa  11340
ctaatttcat taaatgctaa tgcagatttt gtgaagtaaa actccaatta tgatgaaaaa  11400
taccaccaac accacctgcg aaactgtatc ccaactgtcc ttaataaaaa tgttaaaaag  11460
tatattattc tcatttgtct gtcataattt atgtacccca ctttaatttt tctgatgtac  11520
taaaccgagg gcaaactgaa acctgttcct catgcaaagc ccctactcac catgtatcat  11580
gtacgtgtca tcacccaaca actccacttt tgctatataa caacaccccc gtcacactct  11640
ccctctctaa cacacacccc actaacaatt ccttcacttg cagcactgtt gcatcatcat  11700
cttcattgca aaaccctaaa cttcaccttc aaccgcggcc gcatggcttc tatgatatcc  11760
tcttccgctg tgacaacagt cagccgtgcc tctagggggc aatccgccgc agtggctcca  11820
ttcggcggcc tcaaatccat gactggattc ccagtgaaga aggtcaacac tgacattact  11880
tccattacaa gcaatggtgg aagagtaaag tgcatgcagg tgtggcctcc aattggaaag  11940
```

-continued

```
aagaagtttg agactctttc ctatttgcca ccattgacga gagattctag agtgactcag  12000
cgcattgcgt atgtgaccgg cggcatgggt ggtatcggaa ccgccatttg ccagcggctg  12060
gccaaggatg gctttcgtgt ggtggccggt tgcggcccca actcgccgcg ccgcgaaaag  12120
tggctggagc agcagaaggc cctgggcttc gatttcattg cctcggaagg caatgtggct  12180
gactgggact cgaccaagac cgcattcgac aaggtcaagt ccgaggtcgg cgaggttgat  12240
gtgctgatca acaacgccgg tatcacccgc gacgtggtgt tccgcaagat gacccgcgcc  12300
gactgggatg cggtgatcga caccaacctg acctcgctgt tcaacgtcac caagcaggtg  12360
atcgacggca tggccgaccg tggctggggc cgcatcgtca acatctcgtc ggtgaacggg  12420
cagaagggcc agttcggcca gaccaactac tccaccgcca aggccggcct gcatggcttc  12480
accatggcac tggcgcagga agtggcgacc aagggcgtga ccgtcaacac ggtctctccg  12540
ggctatatcg ccaccgacat ggtcaaggcg atccgccagg acgtgctcga caagatcgtc  12600
gcgacgatcc cggtcaagcg cctgggcctg ccggaagaga tcgcctcgat ctgcgcctgg  12660
ttgtcgtcgg aggagtccgg tttctcgacc ggcgccgact tctcgctcaa cggcggcctg  12720
catatgggct gagcggccgc tgagtaattc tgatattaga gggagcatta atgtgttgtt  12780
gtgatgtggt ttatatgggg aaattaaata aatgatgtat gtacctcttg cctatgtagg  12840
tttgtgtgtt ttgttttgtt gtctagcttt ggttattaag tagtagggac gttcgttcgt  12900
gtctcaaaaa aaggggtact accactctgt agtgtatatg gatgctggaa atcaatgtgt  12960
tttgtatttg ttcacctcca ttgttgaatt caatgtcaaa tgtgttttgc gttggttatg  13020
tgtaaaatta ctatctttct cgtccgatga tcaaagtttt aagcaacaaa accaagggtg  13080
aaatttaaac tgtgctttgt tgaagattct tttatcatat tgaaaatcaa attactagca  13140
gcagatttta cctagcatga aattttatca acagtacagc actcactaac caagttccaa  13200
actaagatgc gccattaaca tcagccaata ggcattttca gcaaggcgcg taaggggatc  13260
cgtacgtaag tacgtactca aaatgccaac aaataaaaaa aaagttgctt taataatgcc  13320
aaaacaaatt aataaaacac ttacaacacc ggattttttt taattaaaat gtgccattta  13380
ggataaatag ttaatatttt taataattat ttaaaaagcc gtatctacta aaatgatttt  13440
tatttggttg aaaatattaa tatgtttaaa tcaacacaat ctatcaaaat taaactaaaa  13500
aaaaaataag tgtacgtggt taacattagt acagtaatat aagaggaaaa tgagaaatta  13560
agaaattgaa agcgagtcta atttttaaat tatgaacctg catatataaa aggaaagaaa  13620
gaatccagga agaaaagaaa tgaaaccatg catggtcccc tcgtcatcac gagtttctgc  13680
catttgcaat agaaacactg aaacaccttt ctctttgtca cttaattgag atgccgaagc  13740
cacctcacac catgaacttc atgaggtgta gcacccaagg cttccatagc catgcatact  13800
gaagaatgtc tcaagctcag caccctactt ctgtgacgtg tccctcattc accttcctct  13860
cttccctata aataaccacg cctcaggttc tccgcttcac aactcaaaca ttctctccat  13920
tggtccttaa acactcatca gtcatcaccg cggccgcgga attcatggct tctatgatat  13980
cctcttccgc tgtgacaaca gtcagccgtg cctctagggg gcaatccgcc gcagtggctc  14040
cattcggcgg cctcaaatcc atgactggat tcccagtgaa gaaggtcaac actgacatta  14100
cttccattac aagcaatggt ggaagagtaa agtgcatgca ggtgtggcct ccaattggaa  14160
agaagaagtt tgagactctt tcctatttgc caccattgac gagagattct agagtgactg  14220
acgttgtcat cgtatccgcc gcccgcaccg cggtcggcaa gtttggcggc tcgctggcca  14280
agatcccggc accggaactg ggtgccgtgg tcatcaaggc cgcgctggag cgcgccggcg  14340
```

tcaagccgga gcaggtgagc gaagtcatca tgggccaggt gctgaccgcc ggttcgggcc 14400
agaaccccgc acgccaggcc gcgatcaagg ccggcctgcc ggcgatggtg ccggccatga 14460
ccatcaacaa ggtgtgcggc tcgggcctga aggccgtgat gctggccgcc aacgcgatca 14520
tggcgggcga cgccgagatc gtggtggccg gcggccagga aaacatgagc gccgccccgc 14580
acgtgctgcc gggctcgcgc gatggtttcc gcatgggcga tgccaagctg gtcgacacca 14640
tgatcgtcga cggcctgtgg gacgtgtaca accagtacca catgggcatc accgccgaga 14700
acgtggccaa ggaatacggc atcacacgcg aggcgcagga tgagttcgcc gtcggctcgc 14760
agaacaaggc cgaagccgcg cagaaggccg gcaagtttga cgaagagatc gtcccggtgc 14820
tgatcccgca gcgcaagggc gacccggtgg ccttcaagac cgacgagttc gtgcgccagg 14880
gcgccacgct ggacagcatg tccggcctca agcccgcctt cgacaaggcc ggcacggtga 14940
ccgcggccaa cgcctcgggc ctgaacgacg gcgccgccgc ggtggtggtg atgtcggcgg 15000
ccaaggccaa ggaactgggc ctgaccccgc tggccacgat caagagctat gccaacgccg 15060
gtgtcgatcc caaggtgatg ggcatgggcc cggtgccggc ctccaagcgc gccctgtcgc 15120
gcgccgagtg gaccccgcaa gacctggacc tgatggagat caacgaggcc tttgccgcgc 15180
aggcgctggc ggtgcaccag cagatgggct gggacacctc caaggtcaat gtgaacggcg 15240
gcgccatcgc catcggccac ccgatcggcg cgtcgggctg ccgtatcctg gtgacgctgc 15300
tgcacgagat gaagcgccgt gacgcgaaga agggcctggc ctcgctgtgc atcggcggcg 15360
gcatgggcgt ggcgctggca gtcgagcgca aataactcga ggcggccgca gccctttttg 15420
tatgtgctac cccacttttg tctttttggc aatagtgcta gcaaccaata aataataata 15480
ataataatga ataagaaaac aaaggcttta gcttgccttt tgttcactgt aaaataataa 15540
tgtaagtact ctctataatg agtcacgaaa cttttgcggg aataaaagga gaaattccaa 15600
tgagttttct gtcaaatctt cttttgtctc tctctctctc tctttttttt ttttctttct 15660
tctgagcttc ttgcaaaaca aaaggcaaac aataacgatt ggtccaatga tagttagctt 15720
gatcgatgat atctttagga agtgttggca ggacaggaca tgatgtagaa gactaaaatt 15780
gaaagtattg cagacccaat agttgaagat taactttaag aatgaagacg tcttatcagg 15840
ttcttcatga cttaagcttt aagaggagtc caccatggta gatctgacta gtaacggccg 15900
ccagtgtgct ggaattctgc agatgtggag cacgacactc tcgtctactc caagaatatc 15960
aaagatacag tctcagaaga ccaaagggct attgagactt ttcaacaaag ggtaatatcg 16020
ggaaacctcc tcggattcca ttgcccagct atctgtcact tcatcaaaag gacagtagaa 16080
aaggaaggtg gcacctacaa atgccatcat tgcgataaag gaaaggctat cgttcaagat 16140
gcctctgccg acagtggtcc caaagatgga cccccaccca cgaggagcat cgtggaaaaa 16200
gaagacgttc caaccacgtc ttcaaagcaa gtggattgat gtgataacat ggtggagcac 16260
gacactctcg tctactccaa gaatatcaaa gatacagtct cagaagacca aagggctatt 16320
gagacttttc aacaaagggt aatatcggga aacctcctcg gattccattg cccagctatc 16380
tgtcacttca tcaaaaggac agtagaaaag gaaggtggca cctacaaatg ccatcattgc 16440
gataaaggaa aggctatcgt tcaagatgcc tctgccgaca gtggtcccaa agatggaccc 16500
ccacccacga ggagcatcgt ggaaaaagaa gacgttccaa ccacgtcttc aaagcaagtg 16560
gattgatgtg atatctccac tgacgtaagg gatgacgcac aatcccacta tccttcgcaa 16620
gaccttcctc tatataagga agttcatttc atttggagag gacacgctga aatcaccagt 16680

-continued

```
ctctctctac aaatctatct ctctcgagct ttcgcagatc tgtcgatcga ccatggactc  16740
caaagaatca ttaactcctg gtagagaaga aaaccccagc agtgtgcttg ctcaggagag  16800
gggagatgtg atggacttct ataaaaccct aagaggagga gctactgtga aggtttctgc  16860
gtcttcaccc tcactggctg tcgcttctca atcagactcc aagcagcgaa gacttttggt  16920
tgattttcca aaaggctcag taagcaatgc gcagcagcca gatctgtcca aagcagtttc  16980
actctcaatg ggactgtata tgggagagac agaaacaaaa gtgatgggaa atgacctggg  17040
attcccacag cagggccaaa tcagcctttc ctcgggggaa acagacttaa agcttttgga  17100
agaaagcatt gcaaacctca ataggtcgac cagtgttcca gagaacccca agagttcagc  17160
atccactgct gtgtctgctg cccccacagc tagttctgcg gcccccccga ccgatgtcag  17220
cctgggggac gagctccact tagacggcga ggacgtggcg atggcgcatg ccgacgcgct  17280
agacgatttc gatctggaca tgttggggga cggggattcc ccgggtccgg gatttacccc  17340
ccacgactcc gccccctacg gcgctctgga tatggccgac ttcgagtttg agcagatgtt  17400
taccgatgcc cttggaattg acgagtacgg tgggactagc tccagctcct caacagcaac  17460
aacaggacca cctcccaaac tctgcctggt gtgctctgat gaagcttcag gatgtcatta  17520
tggagtctta acttgtggaa gctgtaaagt tttcttcaaa agagcagtgg aaggacagca  17580
caattaccta tgtgctggaa ggaatgattg catcatcgat aaaattcgaa gaaaaaactg  17640
cccagcatgc cgctatcgaa aatgtcttca ggctggaatg aacctggaag ctcgaaaaac  17700
aaagaaaaaa ataaaaggaa ttgctcgaca aaggcccgag tgcgtggtgc cggagaacca  17760
gtgtgcaatg aaacggaaag agaaaaaggc gcagagggaa aaagacaaat tgcccgtcag  17820
tacgacgaca gtagacgatc acatgcctcc catcatgcaa tgtgaccctc cgcccccaga  17880
ggccgctaga attctggaat gtttgcagca cgaggtggtg ccacgattcc tgaatgagaa  17940
gctaatggaa cagaacagat tgaagaacgt gcccccccctc actgccaatc agaagtcgtt  18000
gatcgcaagg ctcgtgtggt accaggaagg ctatgaacaa ccttccgagg aagacctgaa  18060
gagggttaca cagtcggacg aggacgacga agactcggat atgccgttcc gtcagattac  18120
cgagatgacg attctcacag tgcagctcat cgtagaattc gctaagggcc tcccgggctt  18180
cgccaagatc tcgcagtcgg accagatcac gttattaaag gcgtgctcaa gtgaggtgat  18240
gatgctccga gtggctcggc ggtatgacgc ggccaccgac agcgtactgt tcgcgaacaa  18300
ccaggcgtac actcgcgaca actaccgcaa ggcaggcatg gcgtacgtca tcgaggacct  18360
gctgcacttc tgtcggtgca tgtactccat gatgatggat aacgtgcatt atgcgctgct  18420
tacagccatt gtcatcttct cagaccggcc cgggcttgag caacccctgt tggtggagga  18480
gatccagaga tattacctga acacgctacg ggtgtacatc ctgaaccaga acagcgcgtc  18540
gccccgctgc gccgtcatct tcggcaagat cctgggcata ctgacggaga tccgcacgct  18600
gggcatgcag aactccaaca tgtgcatctc cctcaagctg aagaacagga agctgccgcc  18660
gttcctcgag gagatctggg acgtggcgga cgtggcgacg acggcgacgc cggtggcggc  18720
ggaggcgccg gcgctctagc cccgcgccg cccgcccggc cgcgcgcacg tctagcgcgc  18780
ctcaggagag aacgctcata gactggctag ttttagtgaa gtgcacggac actgacgtcg  18840
gacgtgatca acctatttat aaggactgcg aattttacca cttaagaggg cacacccgta  18900
cccgatttcg tacgggaatt cctgcagccc gggggatcct taattaactc gaggaattca  18960
tcgattccgc gggtaccgag ctcgatccgt cgacctgcag atcgttcaaa catttggcaa  19020
taaagtttct taagattgaa tcctgttgcc ggtcttgcga tgattatcat ataatttctg  19080
```

ttgaattacg ttaagcatgt aataattaac atgtaatgca tgacgttatt tatgagatgg 19140
gtttttatga ttagagtccc gcaattatac atttaatacg cgatagaaaa caaaatatag 19200
cgcgcaaact aggataaatt atcgcgcgcg gtgtcatcta tgttactaga tctggcgcgc 19260
ccctaggtct agagtcgact gtttaaacgg tccgtgacca tgattacgcc aagcttcgac 19320
tgtacaggat gttctagcta ctcgagtagc tagaacatcc tgtacagtcg agtagctaga 19380
acatcctgta cagtcgacta gctagaacat cctgtacagt cgagtagcta gaacatcctg 19440
tacagtcgag tagctagaca tcctgtacag gatccctata taaggaagtt catttcattt 19500
ggagagaaca cgggggatcg ggtatcgtta attaagttta tcaacaagtt tgtacaaaaa 19560
agcaggctcc gcggccgccc ccttcacctt cctcgacttc agcgacaccg gcgtgctcga 19620
cgtcttcgtc gatgaaaccc aggtcgcgct gcgtgaacag caattgcgcg atggcggcct 19680
gatgccgggc cgtgacctgg cctcgacctt ctcgagcctg cgtccgaacg acctggtatg 19740
gaactatgtg cagtcgaact acctcaaagg caatgagccg gcggcgtttg acctgctgtt 19800
ctggaattcg gacagcacca atttgccggg cccgatgttc tgctggtacc tgcgcaacac 19860
ctacctggaa aacagcctga aagtgccggg caagctgacg gtggccggcg aaaagatcga 19920
cctcggcctg atcgacgccc cggccttcat ctacggttcg cgcgaagacc acatcgtgcc 19980
gtggatgtcg gcgtacggtt cgctcgacat cctcaaccag ggcaagccgg gcgccaaccg 20040
cttcgtgctg ggcgcgtccg gccatatcgc cggcgtgatc aactcggtgg ccaagaacaa 20100
gcgcagctac tggatcaacg acggtggcgc cgccgatgcc caggcctggt tcgatggcgc 20160
gcaggaagtg ccgggcagct ggtggccgca atgggccggg ttcctgaccc agcatggcgg 20220
caagaaggtc aagcccaagg ccaaaagggt gggcgcgccg acccagcttt cttgtacaaa 20280
gtggttgatc ctgcagggtc cgtcgcttct cttccatttc ttctcatttt cgattttgat 20340
tcttatttct ttccagtagc tcctgctctg tgaatttctc cgctcacgat agatctgctt 20400
atactcctta cattcaacct tagatctggt ctcgattctc tgtttctctg tttttttctt 20460
ttggtcgaga atctgatgtt tgtttatgtt ctgtcaccat taataataat gaactctctc 20520
attcatacaa tgattagttt ctctcgtcta caaaacgata tgttgcattt tcacttttct 20580
tctttttttc taagatgatt tgctttgacc aatttgttta gatctttatt ctattttatt 20640
ttctggtggg ttggtggaaa ttgaaaaaaa aaaaacagca taaattgtta tttgttaatg 20700
tattcatttt ttggctattt gttctgggta aaaatctgct tctactattg aatctttcct 20760
ggatttttta ctcctattgg gtttttatag taaaaataca taataaaagg aaaacaaaag 20820
ttttatagat tctcttaaac cccttacgat aaaagttgga atcaaaataa ttcaggatca 20880
gatgctcttt gattgattca gatgcgatta cagttgcatg gcaaattttc tagatccgtc 20940
gtcacatttt attttctgtt taaatatcta aatctgatat atgatgtcga caaattctgg 21000
tggcttatac atcacttcaa ctgttttctt ttggctttgt ttgtcaactt ggttttcaat 21060
acgatttgtg atttcgatcg ctgaattttt aatacaagca aactgatgtt aaccacaagc 21120
aagagatgtg acctgcctta ttaacatcgt attacttact actagtcgta ttctcaacgc 21180
aatcgttttt gtatttctca cattatgccg cttctctact ctttattcct tttggtccac 21240
gcattttcta tttgtggcaa tccctttcac aacctgattt cccactttgg atcatttgtc 21300
tgaagactct cttgaatcgt taccacttgt ttcttgtgca tgctctgttt tttagaatta 21360
atgataaaac tattccatag tcttgagttt tcagcttgtt gattcttttg cttttggttt 21420
tctgcaggtt taaacatcaa ccactttgta caagaaagct gggtcggcgc gcccaccctt 21480
ttggccttgg gcttgacctt cttgccgcca tgctgggtca ggaacccggc ccattgcggc 21540
caccagctgc ccggcacttc ctgcgcgcca tcgaaccagg cctgggcatc ggcggcgcca 21600
ccgtcgttga tccagtagct gcgcttgttc ttggccaccg agttgatcac gccggcgata 21660
tggccggacg cgcccagcac gaagcggttg gcgcccggct tgccctggtt gaggatgtcg 21720
agcgaaccgt acgccgacat ccacggcacg atgtggtctt cgcgcgaacc gtagatgaag 21780
gccggggcgt cgatcaggcc gaggtcgatc ttttcgccgg ccaccgtcag cttgcccggc 21840
actttcaggc tgttttccag gtaggtgttg cgcaggtacc agcagaacat cgggcccggc 21900
aaattggtgc tgtccgaatt ccagaacagc aggtcaaacg ccgccggctc attgcctttg 21960
aggtagttcg actgcacata gttccatacc aggtcgttcg gacgcaggct cgagaaggtc 22020
gaggccaggt cacggcccgg catcaggccg ccatcgcgca attgctgttc acgcagcgcg 22080
acctgggttt catcgacgaa gacgtcgagc acgccggtgt cgctgaagtc gaggaaggtg 22140
aagggggcgg ccgcggagcc tgcttttttg tacaaacttg ttgatctcga gcggcgcgcc 22200
gttcgagtat tatggcattg ggaaaactgt ttttcttgta ccatttgttg tgcttgtaat 22260
ttactgtgtt ttttattcgg ttttcgctat cgaactgtga aatggaaatg gatggagaag 22320
agttaatgaa tgatatggtc cttttgttca ttctcaaatt aatattattt gtttttttctc 22380 ttatttgttg tgtgttgaat ttgaaattat aagagatatg caaacatttt gttttgagta 22440
aaaatgtgtc aaatcgtggc ctctaatgac cgaagttaat atgaggagta aaacactgtt 22500
taaaccctgc aggattt 22517

<210> SEQ ID NO 5
<211> LENGTH: 22248
<212> TYPE: DNA
<213> ORGANISM: Artificial Sequence
<220> FEATURE:
<223> OTHER INFORMATION: Synthetic Vector

<400> SEQUENCE: 5
aaatagaagg taattatcca agatgtagca tcaagaatcc aatgtttacg ggaaaaacta 60
tggaagtatt atgtgagctc agcaagaagc agatcaatat gcggcacata tgcaacctat 120
gttcaaaaat gaagaatgta cagatacaag atcctatact gccagaatac gaagaagaat 180
acgtagaaat tgaaaaagaa gaaccaggcg aagaaaagaa tcttgaagac gtaagcactg 240
acgacaacaa tgaaaagaag aagataaggt cggtgattgt gaaagagaca tagaggacac 300
atgtaaggtg gaaaatgtaa gggcggaaag taaccttatc acaaaggaat cttatccccc 360
actacttatc cttttatatt tttccgtgtc atttttgccc ttgagttttc ctatataagg 420
aaccaagttc ggcatttgtg aaaacaagaa aaaattggtg taagctattt tctttgaagt 480
actgaggata caacttcaga gaaatttgta agaaagtgga tcgaaaccat ggcctcctcc 540
gagaacgtca tcaccgagtt catgcgcttc aaggtgcgca tggagggcac cgtgaacggc 600
cacgagttcg agatcgaggg cgagggcgag ggccgcccct acgagggcca caacaccgtg 660
aagctgaagg tgaccaaggg cggcccccctg cccttcgcct gggacatcct gtccccccag 720
ttccagtacg gctccaaggt gtacgtgaag caccccgccg acatccccga ctacaagaag 780
ctgtccttcc ccgagggctt caagtgggag cgcgtgatga acttcgagga cggcggcgtg 840
gcgaccgtga cccaggactc ctccctgcag gacggctgct tcatctacaa ggtgaagttc 900
atcggcgtga acttcccctc cgacggcccc gtgatgcaga agaagaccat gggctgggag 960

-continued

```
gcctccaccg agcgcctgta cccccgcgac ggcgtgctga agggcgagac ccacaaggcc   1020
ctgaagctga aggacggcgg ccactacctg gtggagttca agtccatcta catggccaag   1080
aagcccgtgc agctgcccgg ctactactac gtggacgcca agctggacat cacctcccac   1140
aacgaggact acaccatcgt ggagcagtac gagcgcaccg agggccgcca ccacctgttc   1200
ctggtaccaa tgagctctgt ccaacagtct cagggttaat gtctatgtat cttaaataat   1260
gttgtcggcg atcgttcaaa catttggcaa taaagtttct taagattgaa tcctgttgcc   1320
ggtcttgcga tgattatcat ataatttctg ttgaattacg ttaagcatgt aataattaac   1380
atgtaatgca tgacgttatt tatgagatgg gtttttatga ttagagtccc gcaattatac   1440
atttaatacg cgatagaaaa caaaatatag cgcgcaaact aggataaatt atcgcgcgcg   1500
gtgtcatcta tgttactaga tcgggaatta aactatcagt gtttgacagg atatattggc   1560
gggtaaacct aagagaaaag agcgtttatt agaataacgg atatttaaaa gggcgtgaaa   1620
aggtttatcc gttcgtccat ttgtatgtgc atgccaacca cagggttccc ctcgggatca   1680
aagtactttg atccaacccc tccgctgcta tagtgcagtc ggcttctgac gttcagtgca   1740
gccgtcttct gaaaacgaca tgtcgcacaa gtcctaagtt acgcgacagg ctgccgccct   1800
gcccttttcc tggcgttttc ttgtcgcgtg ttttagtcgc ataaagtaga atacttgcga   1860
ctagaaccgg agacattacg ccatgaacaa gagcgccgcc gctggcctgc tgggctatgc   1920
ccgcgtcagc accgacgacc aggacttgac caaccaacgg gccgaactgc acgcggccgg   1980
ctgcaccaag ctgttttccg agaagatcac cggcaccagg cgcgaccgcc cggagctggc   2040
caggatgctt gaccacctac gccctggcga cgttgtgaca gtgaccaggc tagaccgcct   2100
ggcccgcagc acccgcgacc tactggacat tgccgagcgc atccaggagg ccggcgcggg   2160
cctgcgtagc ctggcagagc cgtgggccga caccaccacg ccggccggcc gcatggtgtt   2220
gaccgtgttc gccggcattg ccgagttcga gcgttcccta atcatcgacc gcacccggag   2280
cgggcgcgag gccgccaagg cccgaggcgt gaagtttggc ccccgcccta ccctcacccc   2340
ggcacagatc gcgcacgccc gcgagctgat cgaccaggaa ggccgcaccg tgaaagaggc   2400
ggctgcactg cttggcgtgc atcgctcgac cctgtaccgc gcacttgagc gcagcgagga   2460
agtgacgccc accgaggcca ggcggcgcgg tgccttccgt gaggacgcat tgaccgaggc   2520
cgacgccctg gcggccgccg agaatgaacg ccaagaggaa caagcatgaa accgcaccag   2580
gacggccagg acgaaccgtt tttcattacc gaagagatcg aggcggagat gatcgcggcc   2640
gggtacgtgt tcgagccgcc cgcgcacgtc tcaaccgtgc ggctgcatga aatcctggcc   2700
ggtttgtctg atgccaagct ggcggcctgg ccggccagct tggccgctga agaaaccgag   2760
cgccgccgtc taaaaaggtg atgtgtattt gagtaaaaca gcttgcgtca tgcggtcgct   2820
gcgtatatga tgcgatgagt aaataaacaa atacgcaagg ggaacgcatg aaggttatcg   2880
ctgtacttaa ccagaaaggc gggtcaggca agacgaccat cgcaacccat ctagcccgcg   2940
ccctgcaact cgccggggcc gatgttctgt tagtcgattc cgatccccag ggcagtgccc   3000
gcgattgggc ggccgtgcgg gaagatcaac cgctaaccgt tgtcggcatc gaccgcccga   3060
cgattgaccg cgacgtgaag gccatcggcc ggcgcgactt cgtagtgatc gacggagcgc   3120
cccaggcggc ggacttggct gtgtccgcga tcaaggcagc cgacttcgtg ctgattccgg   3180
tgcagccaag cccttacgac atatgggcca ccgccgacct ggtggagctg gttaagcagc   3240
gcattgaggt cacggatgga aggctacaag cggcctttgt cgtgtcgcgg gcgatcaaag   3300
```

-continued gcacgcgcat cggcggtgag gttgccgagg cgctggccgg gtacgagctg cccattcttg 3360
agtcccgtat cacgcagcgc gtgagctacc caggcactgc cgccgccggc acaaccgttc 3420
ttgaatcaga acccgagggc gacgctgccc gcgaggtcca ggcgctggcc gctgaaatta 3480
aatcaaaact catttgagtt aatgaggtaa agagaaaatg agcaaaagca caaacacgct 3540
aagtgccggc cgtccgagcg cacgcagcag caaggctgca acgttggcca gcctggcaga 3600
cacgccagcc atgaagcggg tcaactttca gttgccggcg gaggatcaca ccaagctgaa 3660
gatgtacgcg gtacgccaag gcaagaccat taccgagctg ctatctgaat acatcgcgca 3720
gctaccagag taaatgagca aatgaataaa tgagtagatg aattttagcg gctaaaggag 3780
gcggcatgga aaatcaagaa caaccaggca ccgacgccgt ggaatgcccc atgtgtggag 3840
gaacgggcgg ttggccaggc gtaagcggct gggttgtctg ccggccctgc aatggcactg 3900
gaacccccaa gcccgaggaa tcggcgtgac ggtcgcaaac catccggccc ggtacaaatc 3960
ggcgcggcgc tgggtgatga cctggtggag aagttgaagg ccgcgcaggc cgcccagcgg 4020
caacgcatcg aggcagaagc acgccccggt gaatcgtggc aagcggccgc tgatcgaatc 4080
cgcaaagaat cccggcaacc gccggcagcc ggtgcgccgt cgattaggaa gccgcccaag 4140
ggcgacgagc aaccagattt tttcgttccg atgctctatg acgtgggcac ccgcgatagt 4200
cgcagcatca tggacgtggc cgttttccgt ctgtcgaagc gtgaccgacg agctggcgag 4260
gtgatccgct acgagcttcc agacgggcac gtagaggttt ccgcagggcc ggccggcatg 4320
gccagtgtgt gggattacga cctggtactg atggcggttt cccatctaac cgaatccatg 4380
aaccgatacc gggaagggaa gggagacaag cccggccgcg tgttccgtcc acacgttgcg 4440
gacgtactca agttctgccg gcgagccgat ggcggaaagc agaaagacga cctggtagaa 4500
acctgcattc ggttaaacac cacgcacgtt gccatgcagc gtacgaagaa ggccaagaac 4560
ggccgcctgg tgacggtatc cgagggtgaa gccttgatta gccgctacaa gatcgtaaag 4620
agcgaaaccg ggcggccgga gtacatcgag atcgagctag ctgattggat gtaccgcgag 4680
atcacagaag gcaagaaccc ggacgtgctg acggttcacc ccgattactt tttgatcgat 4740
cccggcatcg gccgttttct ctaccgcctg gcacgccgcg ccgcaggcaa ggcagaagcc 4800
agatggttgt tcaagacgat ctacgaacgc agtggcagcg ccggagagtt caagaagttc 4860
tgtttcaccg tgcgcaagct gatcgggtca aatgacctgc cggagtacga tttgaaggag 4920
gaggcggggc aggctggccc gatcctagtc atgcgctacc gcaacctgat cgagggcgaa 4980
gcatccgccg gttcctaatg tacggagcag atgctagggc aaattgccct agcaggggaa 5040
aaaggtcgaa aaggtctctt tcctgtggat agcacgtaca ttgggaaccc aaagccgtac 5100
attgggaacc ggaacccgta cattgggaac ccaaagccgt acattgggaa ccggtcacac 5160
atgtaagtga ctgatataaa agagaaaaaa ggcgattttt ccgcctaaaa ctctttaaaa 5220
cttattaaaa ctcttaaaac ccgcctggcc tgtgcataac tgtctggcca gcgcacagcc 5280
gaagagctgc aaaaagcgcc tacccttcgg tcgctgcgct ccctacgccc cgccgcttcg 5340
cgtcggccta tcgcggccgc tggccgctca aaaatggctg gcctacggcc aggcaatcta 5400
ccagggcgcg gacaagccgc gccgtcgcca ctcgaccgcc ggcgcccaca tcaaggcacc 5460
ctgcctcgcg cgtttcggtg atgacggtga aaacctctga cacatgcagc tcccggagac 5520
ggtcacagct tgtctgtaag cggatgccgg gagcagacaa gcccgtcagg gcgcgtcagc 5580
gggtgttggc gggtgtcggg gcgcagccat gacccagtca cgtagcgata gcggagtgta 5640
tactggctta actatgcggc atcagagcag attgtactga gagtgcacca tatgcggtgt 5700

```
gaaataccgc acagatgcgt aaggagaaaa taccgcatca ggcgctcttc cgcttcctcg   5760
ctcactgact cgctgcgctc ggtcgttcgg ctgcggcgag cggtatcagc tcactcaaag   5820
gcggtaatac ggttatccac agaatcaggg gataacgcag gaaagaacat gtgagcaaaa   5880
ggccagcaaa aggccaggaa ccgtaaaaag gccgcgttgc tggcgttttt ccataggctc   5940
cgcccccctg acgagcatca caaaaatcga cgctcaagtc agaggtggcg aaacccgaca   6000
ggactataaa gataccaggc gtttccccct ggaagctccc tcgtgcgctc tcctgttccg   6060
accctgccgc ttaccggata cctgtccgcc tttctccctt cgggaagcgt ggcgctttct   6120
catagctcac gctgtaggta tctcagttcg gtgtaggtcg ttcgctccaa gctgggctgt   6180
gtgcacgaac cccccgttca gcccgaccgc tgcgccttat ccggtaacta tcgtcttgag   6240
tccaacccgg taagacacga cttatcgcca ctggcagcag ccactggtaa caggattagc   6300
agagcgaggt atgtaggcgg tgctacagag ttcttgaagt ggtggcctaa ctacggctac   6360
actagaagga cagtatttgg tatctgcgct ctgctgaagc cagttacctt cggaaaaaga   6420
gttggtagct cttgatccgg caaacaaacc accgctggta gcggtggttt ttttgtttgc   6480
aagcagcaga ttacgcgcag aaaaaaagga tctcaagaag atcctttgat cttttctacg   6540
gggtctgacg ctcagtggaa cgaaaactca cgttaaggga ttttggtcat gcattctagg   6600
tactaaaaca attcatccag taaaatataa tattttattt tctcccaatc aggcttgatc   6660
cccagtaagt caaaaaatag ctcgacatac tgttcttccc cgatatcctc cctgatcgac   6720
cggacgcaga aggcaatgtc ataccacttg tccgccctgc cgcttctccc aagatcaata   6780
aagccactta ctttgccatc tttcacaaag atgttgctgt ctcccaggtc gccgtgggaa   6840
aagacaagtt cctcttcggg cttttccgtc tttaaaaaat catacagctc gcgcggatct   6900
ttaaatggag tgtcttcttc ccagttttcg caatccacat cggccagatc gttattcagt   6960
aagtaatcca attcggctaa gcggctgtct aagctattcg tatagggaca atccgatatg   7020
tcgatggagt gaaagagcct gatgcactcc gcatacagct cgataatctt ttcagggctt   7080
tgttcatctt catactcttc cgagcaaagg acgccatcgg cctcactcat gagcagattg   7140
ctccagccat catgccgttc aaagtgcagg acctttggaa caggcagctt tccttccagc   7200
catagcatca tgtccttttc ccgttccaca tcataggtgg tccctttata ccggctgtcc   7260
gtcattttta aatataggtt ttcattttct cccaccagct tatatacctt agcaggagac   7320
attccttccg tatcttttac gcagcggtat ttttcgatca gtttttttcaa ttccggtgat   7380
attctcattt tagccattta ttatttcctt cctcttttct acagtattta aagataccc   7440
aagaagctaa ttataacaag acgaactcca attcactgtt ccttgcattc taaaacctta   7500
aataccagaa aacagctttt tcaaagttgt tttcaaagtt ggcgtataac atagtatcga   7560
cggagccgat tttgaaaccg cggtgatcac aggcagcaac gctctgtcat cgttacaatc   7620
aacatgctac cctccgcgag atcatccgtg tttcaaaccc ggcagcttag ttgccgttct   7680
tccgaatagc atcggtaaca tgagcaaagt ctgccgcctt acaacggctc tcccgctgac   7740
gccgtcccgg actgatgggc tgcctgtatc gagtggtgat tttgtgccga gctgccggtc   7800
ggggagctgt tggctggctg gtggcaggat atattgtggt gtaaacaaat tgacgcttag   7860
acaacttaat aacacattgc ggacgttttt aatgtactga attaacgccg aattaattcc   7920
taggccacca tgttgggccc ggggcgcgcc gtacgtagtg tttatctttg ttgcttttct   7980
gaacaattta tttactatgt aaatatatta tcaatgttta atctatttta atttgcacat   8040
```

-continued

```
gaattttcat tttattttta ctttacaaaa caaataaata tatatgcaaa aaaatttaca   8100
aacgatgcac gggttacaaa ctaatttcat taaatgctaa tgcagatttt gtgaagtaaa   8160
actccaatta tgatgaaaaa taccaccaac accacctgcg aaactgtatc ccaactgtcc   8220
ttaataaaaa tgttaaaaag tatattattc tcatttgtct gtcataattt atgtacccca   8280
ctttaatttt tctgatgtac taaaccgagg gcaaactgaa acctgttcct catgcaaagc   8340
ccctactcac catgtatcat gtacgtgtca tcacccaaca actccacttt tgctatataa   8400
caacaccccc gtcacactct ccctctctaa cacacacccc actaacaatt ccttcacttg   8460
cagcactgtt gcatcatcat cttcattgca aaaccctaaa cttcaccttc aaccgcggcc   8520
gcatggcttc tatgatatcc tcttccgctg tgacaacagt cagccgtgcc tctagggggc   8580
aatccgccgc agtggctcca ttcggcggcc tcaaatccat gactggattc ccagtgaaga   8640
aggtcaacac tgacattact tccattacaa gcaatggtgg aagagtaaag tgcatgcagg   8700
tgtggcctcc aattggaaag aagaagtttg agactctttc ctatttgcca ccattgacga   8760
gagattctag agtgagtaac aagaacaacg atgagctgca gtggcaatcc tggttcagca   8820
aggcgcccac caccgaggcg aacccgatgg ccaccatgtt gcaggatatc ggcgttgcgc   8880
tcaaaccgga agcgatggag cagctgaaaa acgattatct gcgtgacttc accgcgttgt   8940
ggcaggattt tttggctggc aaggcgccag ccgtcagcga ccgccgcttc agctcggcag   9000
cctggcaggg caatccgatg tcggccttca atgccgcatc ttacctgctc aacgccaaat   9060
tcctcagtgc catggtggag gcggtggaca ccgcacccca gcaaaagcag aaaatacgct   9120
ttgccgtgca gcaggtgatt gatgccatgt cgcccgcgaa cttcctcgcc accaacccgg   9180
aagcgcagca aaaactgatt gaaaccaagg gcgagagcct gacgcgtggc ctggtcaata   9240
tgctgggcga tatcaacaag ggccatatct cgctgtcgga cgaatcggcc tttgaagtgg   9300
gccgcaacct ggccattacc ccgggcaccg tgatttacga aaatccgctg ttccagctga   9360
tccagtacac gccgaccacg ccgacggtca gccagcgccc gctgttgatg gtgccgccgt   9420
gcatcaacaa gttctacatc ctcgacctgc aaccggaaaa ttcgctggtg cgctacgcgg   9480
tggagcaggg caacaccgtg ttcctgatct cgtggagcaa tccggacaag tcgctggccg   9540
gcaccacctg ggacgactac gtggagcagg gcgtgatcga agcgatccgc atcgtccagg   9600
acgtcagcgg ccaggacaag ctgaacatgt tcggcttctg cgtgggcggc accatcgttg   9660
ccaccgcact ggcggtactg gcggcgcgtg gccagcaccc ggcggccagc ctgaccctgc   9720
tgaccacctt cctcgacttc agcgacaccg gcgtgctcga cgtcttcgtc gatgaaaccc   9780
aggtcgcgct gcgtgaacag caattgcgcg atggcggcct gatgccgggc cgtgacctgg   9840
cctcgacctt ctcgagcctg cgtccgaacg acctggtatg gaactatgtg cagtcgaact   9900
acctcaaagg caatgagccg gcggcgtttg acctgctgtt ctggaattcg gacagcacca   9960
atttgccggg cccgatgttc tgctggtacc tgcgcaacac ctacctggaa aacagcctga  10020
aagtgccggg caagctgacg gtggccggcg aaaagatcga cctcggcctg atcgacgccc  10080
cggccttcat ctacggttcg cgcgaagacc acatcgtgcc gtggatgtcg gcgtacggtt  10140
cgctcgacat cctcaaccag ggcaagccgg gcgccaaccg cttcgtgctg ggcgcgtccg  10200
gccatatcgc cggcgtgatc aactcggtgg ccaagaacaa gcgcagctac tggatcaacg  10260
acggtggcgc cgccgatgcc caggcctggt tcgatggcgc gcaggaagtg ccgggcagct  10320
ggtggccgca atgggccggg ttcctgaccc agcatggcgg caagaaggtc aagcccaagg  10380
ccaagcccgg caacgcccgc tacaccgcga tcgaggcggc gcccggccgt tacgtcaaag  10440
```

```
ccaagggctg agcggccgct gagtaattct gatattagag ggagcattaa tgtgttgttg  10500
tgatgtggtt tatatgggga aattaaataa atgatgtatg tacctcttgc ctatgtaggt  10560
ttgtgtgttt tgttttgttg tctagctttg gttattaagt agtagggacg ttcgttcgtg  10620
tctcaaaaaa aggggtacta ccactctgta gtgtatatgg atgctggaaa tcaatgtgtt  10680
ttgtatttgt tcacctccat tgttgaattc aatgtcaaat gtgttttgcg ttggttatgt  10740
gtaaaattac tatctttctc gtccgatgat caaagtttta agcaacaaaa ccaagggtga  10800
aatttaaact gtgctttgtt gaagattctt ttatcatatt gaaaatcaaa ttactagcag  10860
cagattttac ctagcatgaa attttatcaa cagtacagca ctcactaacc aagttccaaa  10920
ctaagatgcg ccattaacat cagccaatag gcattttcag caaggcgcgc ccgcgccgat  10980
gtatgtgaca accctcggga ttgttgattt atttcaaaac taagagtttt tgtcttattg  11040
ttctcgtcta ttttggatat caatcttagt tttatatctt ttctagttct ctacgtgtta  11100
aatgttcaac acactagcaa tttggcctgc cagcgtatgg attatggaac tatcaagtct  11160
gtgacgcgcc gtacgtagtg tttatctttg ttgcttttct gaacaattta tttactatgt  11220
aaatatatta tcaatgttta atctatttta atttgcacat gaattttcat tttattttta  11280
ctttacaaaa caaataaata tatatgcaaa aaaatttaca aacgatgcac gggttacaaa  11340
ctaatttcat taaatgctaa tgcagatttt gtgaagtaaa actccaatta tgatgaaaaa  11400
taccaccaac accacctgcg aaactgtatc ccaactgtcc ttaataaaaa tgttaaaaag  11460
tatattattc tcatttgtct gtcataattt atgtacccca ctttaatttt tctgatgtac  11520
taaaccgagg gcaaactgaa acctgttcct catgcaaagc ccctactcac catgtatcat  11580
gtacgtgtca tcacccaaca actccacttt tgctatataa caacaccccc gtcacactct  11640
ccctctctaa cacacacccc actaacaatt ccttcacttg cagcactgtt gcatcatcat  11700
cttcattgca aaaccctaaa cttcaccttc aaccgcggcc gcatggcttc tatgatatcc  11760
tcttccgctg tgacaacagt cagccgtgcc tctagggggc aatccgccgc agtggctcca  11820
ttcggcggcc tcaaatccat gactggattc ccagtgaaga aggtcaacac tgacattact  11880
tccattacaa gcaatggtgg aagagtaaag tgcatgcagg tgtggcctcc aattggaaag  11940
aagaagtttg agactctttc ctatttgcca ccattgacga gagattctag agtgactcag  12000
cgcattgcgt atgtgaccgg cggcatgggt ggtatcggaa ccgccatttg ccagcggctg  12060
gccaaggatg gctttcgtgt ggtggccggt tgcggcccca actcgccgcg ccgcgaaaag  12120
tggctggagc agcagaaggc cctgggcttc gatttcattg cctcggaagg caatgtggct  12180
gactgggact cgaccaagac cgcattcgac aaggtcaagt ccgaggtcgg cgaggttgat  12240
gtgctgatca acaacgccgg tatcacccgc gacgtggtgt tccgcaagat gacccgcgcc  12300
gactgggatg cggtgatcga caccaacctg acctcgctgt tcaacgtcac caagcaggtg  12360
atcgacggca tggccgaccg tggctggggc cgcatcgtca acatctcgtc ggtgaacggg  12420
cagaagggcc agttcggcca gaccaactac tccaccgcca aggccggcct gcatggcttc  12480
accatggcac tggcgcagga agtggcgacc aagggcgtga ccgtcaacac ggtctctccg  12540
ggctatatcg ccaccgacat ggtcaaggcg atccgccagg acgtgctcga caagatcgtc  12600
gcgacgatcc cggtcaagcg cctgggcctg ccggaagaga tcgcctcgat ctgcgcctgg  12660
ttgtcgtcgg aggagtccgg tttctcgacc ggcgccgact tctcgctcaa cggcggcctg  12720
catatgggct gagcggccgc tgagtaattc tgatattaga gggagcatta atgtgttgtt  12780
```

-continued

```
gtgatgtggt ttatatgggg aaattaaata aatgatgtat gtacctcttg cctatgtagg  12840
tttgtgtgtt ttgttttgtt gtctagcttt ggttattaag tagtagggac gttcgttcgt  12900
gtctcaaaaa aaggggtact accactctgt agtgtatatg gatgctggaa atcaatgtgt  12960
tttgtatttg ttcacctcca ttgttgaatt caatgtcaaa tgtgttttgc gttggttatg  13020
tgtaaaatta ctatctttct cgtccgatga tcaaagtttt aagcaacaaa accaagggtg  13080
aaatttaaac tgtgctttgt tgaagattct tttatcatat tgaaaatcaa attactagca  13140
gcagatttta cctagcatga aattttatca acagtacagc actcactaac caagttccaa  13200
actaagatgc gccattaaca tcagccaata ggcattttca gcaaggcgcg taaggggatc  13260
cgtacgtaag tacgtactca aaatgccaac aaataaaaaa aaagttgctt taataatgcc  13320
aaaacaaatt aataaaacac ttacaacacc ggattttttt taattaaaat gtgccattta  13380
ggataaatag ttaatatttt taataattat ttaaaaagcc gtatctacta aaatgatttt  13440
tatttggttg aaaatattaa tatgtttaaa tcaacacaat ctatcaaaat taaactaaaa  13500
aaaaaataag tgtacgtggt taacattagt acagtaatat aagaggaaaa tgagaaatta  13560
agaaattgaa agcgagtcta atttttaaat tatgaacctg catatataaa aggaaagaaa  13620
gaatccagga agaaaagaaa tgaaaccatg catggtcccc tcgtcatcac gagtttctgc  13680
catttgcaat agaaacactg aaacaccttt ctctttgtca cttaattgag atgccgaagc  13740
cacctcacac catgaacttc atgaggtgta gcacccaagg cttccatagc catgcatact  13800
gaagaatgtc tcaagctcag caccctactt ctgtgacgtg tccctcattc accttcctct  13860
cttccctata aataaccacg cctcaggttc tccgcttcac aactcaaaca ttctctccat  13920
tggtccttaa acactcatca gtcatcaccg cggccgcgga attcatggct tctatgatat  13980
cctcttccgc tgtgacaaca gtcagccgtg cctctagggg gcaatccgcc gcagtggctc  14040
cattcggcgg cctcaaatcc atgactggat tcccagtgaa gaaggtcaac actgacatta  14100
cttccattac aagcaatggt ggaagagtaa agtgcatgca ggtgtggcct ccaattggaa  14160
agaagaagtt tgagactctt tcctatttgc caccattgac gagagattct agagtgactg  14220
acgttgtcat cgtatccgcc gcccgcaccg cggtcggcaa gtttggcggc tcgctggcca  14280
agatcccggc accggaactg ggtgccgtgg tcatcaaggc cgcgctggag cgcgccggcg  14340
tcaagccgga gcaggtgagc gaagtcatca tgggccaggt gctgaccgcc ggttcgggcc  14400
agaaccccgc acgccaggcc gcgatcaagg ccggcctgcc ggcgatggtg ccggccatga  14460
ccatcaacaa ggtgtgcggc tcgggcctga aggccgtgat gctggccgcc aacgcgatca  14520
tggcgggcga cgccgagatc gtggtggccg gcggccagga aaacatgagc gccgccccgc  14580
acgtgctgcc gggctcgcgc gatggtttcc gcatgggcga tgccaagctg gtcgacacca  14640
tgatcgtcga cggcctgtgg gacgtgtaca accagtacca catgggcatc accgccgaga  14700
acgtggccaa ggaatacggc atcacacgcg aggcgcagga tgagttcgcc gtcggctcgc  14760
agaacaaggc cgaagccgcg cagaaggccg gcaagtttga cgaagagatc gtcccggtgc  14820
tgatcccgca gcgcaagggc gacccggtgg ccttcaagac cgacgagttc gtgcgccagg  14880
gcgccacgct ggacagcatg tccggcctca agcccgcctt cgacaaggcc ggcacggtga  14940
ccgcggccaa cgcctcgggc ctgaacgacg gcgccgccgc ggtggtggtg atgtcggcgg  15000
ccaaggccaa ggaactgggc ctgaccccgc tggccacgat caagagctat gccaacgccg  15060
gtgtcgatcc caaggtgatg ggcatgggcc cggtgccggc ctccaagcgc gccctgtcgc  15120
gcgccgagtg gaccccgcaa gacctggacc tgatggagat caacgaggcc tttgccgcgc  15180
```

-continued aggcgctggc ggtgcaccag cagatgggct gggacacctc caaggtcaat gtgaacggcg 15240
gcgccatcgc catcggccac ccgatcggcg cgtcgggctg ccgtatcctg gtgacgctgc 15300
tgcacgagat gaagcgccgt gacgcgaaga agggcctggc ctcgctgtgc atcggcggcg 15360
gcatgggcgt ggcgctggca gtcgagcgca aataactcga ggcggccgca gcccttttg 15420
tatgtgctac cccactttg tcttttggc aatagtgcta gcaaccaata aataataata 15480
ataataatga ataagaaaac aaaggcttta gcttgccttt tgttcactgt aaaataataa 15540
tgtaagtact ctctataatg agtcacgaaa cttttgcggg aataaaagga gaaattccaa 15600
tgagttttct gtcaaatctt cttttgtctc tctctctctc tcttttttt ttttctttct 15660
tctgagcttc ttgcaaaaca aaaggcaaac aataacgatt ggtccaatga tagttagctt 15720
gatcgatgat atctttagga agtgttggca ggacaggaca tgatgtagaa gactaaaatt 15780
gaaagtattg cagacccaat agttgaagat taactttaag aatgaagacg tcttatcagg 15840
ttcttcatga cttaagcttt aagaggagtc caccatggta gatctgacta gtgatccgta 15900
cgtaagtacg tactcaaaat gccaacaaat aaaaaaaaag ttgctttaat aatgccaaaa 15960
caaattaata aaacacttac aacaccggat ttttttaat taaaatgtgc catttaggat 16020
aaatagttaa tatttttaat aattatttaa aaagccgtat ctactaaaat gatttttatt 16080
tggttgaaaa tattaatatg tttaaatcaa cacaatctat caaaattaaa ctaaaaaaaa 16140
aataagtgta cgtggttaac attagtacag taatataaga ggaaaatgag aaattaagaa 16200
attgaaagcg agtctaattt ttaaattatg aacctgcata tataaaagga aagaaagaat 16260
ccaggaagaa aagaaatgaa accatgcatg gtcccctcgt catcacgagt ttctgccatt 16320
tgcaatagaa acactgaaac acctttctct ttgtcactta attgagatgc cgaagccacc 16380
tcacaccatg aacttcatga ggtgtagcac ccaaggcttc catagccatg catactgaag 16440
aatgtctcaa gctcagcacc ctacttctgt gacgtgtccc tcattcacct tcctctcttc 16500
cctataaata accacgcctc aggttctccg cttcacaact caaacattct ctccattggt 16560
ccttaaacac tcatcagtca tcaccatgga ctccaaagaa tcattaactc ctggtagaga 16620
agaaaacccc agcagtgtgc ttgctcagga gaggggagat gtgatggact tctataaaac 16680
cctaagagga ggagctactg tgaaggtttc tgcgtcttca ccctcactgg ctgtcgcttc 16740
tcaatcagac tccaagcagc gaagactttt ggttgatttt ccaaaaggct cagtaagcaa 16800
tgcgcagcag ccagatctgt ccaaagcagt ttcactctca atgggactgt atatgggaga 16860
gacagaaaca aaagtgatgg gaaatgacct gggattccca cagcagggcc aaatcagcct 16920
ttcctcgggg gaaacagact taaagctttt ggaagaaagc attgcaaacc tcaataggtc 16980
gaccagtgtt ccagagaacc ccaagagttc agcatccact gctgtgtctg ctgcccccac 17040
agctagttct gcggcccccc cgaccgatgt cagcctgggg gacgagctcc acttagacgg 17100
cgaggacgtg gcgatggcgc atgccgacgc gctagacgat ttcgatctgg acatgttggg 17160
ggacggggat tccccgggtc cgggatttac cccccacgac tccgcccccct acggcgctct 17220
ggatatggcc gacttcgagt ttgagcagat gtttaccgat gcccttggaa ttgacgagta 17280
cggtgggact agctccagct cctcaacagc aacaacagga ccacctccca aactctgcct 17340
ggtgtgctct gatgaagctt caggatgtca ttatggagtc ttaacttgtg gaagctgtaa 17400
agttttcttc aaaagagcag tggaaggaca gcacaattac ctatgtgctg gaaggaatga 17460
ttgcatcatc gataaaattc gaagaaaaaa ctgcccagca tgccgctatc gaaaatgtct 17520

-continued tcaggctgga atgaacctgg aagctcgaaa aacaaagaaa aaaataaaag gaattgctcg 17580
acaaaggccc gagtgcgtgg tgccggagaa ccagtgtgca atgaaacgga aagagaaaaa 17640
ggcgcagagg gaaaaagaca aattgcccgt cagtacgacg acagtagacg atcacatgcc 17700
tcccatcatg caatgtgacc ctccgccccc agaggccgct agaattctgg aatgtttgca 17760
gcacgaggtg gtgccacgat tcctgaatga gaagctaatg gaacagaaca gattgaagaa 17820
cgtgcccccc ctcactgcca atcagaagtc gttgatcgca aggctcgtgt ggtaccagga 17880
aggctatgaa caaccttccg aggaagacct gaagagggtt acacagtcgg acgaggacga 17940
cgaagactcg gatatgccgt tccgtcagat taccgagatg acgattctca cagtgcagct 18000
catcgtagaa ttcgctaagg gcctcccggg cttcgccaag atctcgcagt cggaccagat 18060
cacgttatta aaggcgtgct caagtgaggt gatgatgctc cgagtggctc ggcggtatga 18120
cgcggccacc gacagcgtac tgttcgcgaa caaccaggcg tacactcgcg acaactaccg 18180
caaggcaggc atggcgtacg tcatcgagga cctgctgcac ttctgtcggt gcatgtactc 18240
catgatgatg gataacgtgc attatgcgct gcttacagcc attgtcatct tctcagaccg 18300
gcccgggctt gagcaacccc tgttggtgga ggagatccag agatattacc tgaacacgct 18360
acgggtgtac atcctgaacc agaacagcgc gtcgccccgc tgcgccgtca tcttcggcaa 18420
gatcctgggc atactgacgg agatccgcac gctgggcatg cagaactcca acatgtgcat 18480
ctccctcaag ctgaagaaca ggaagctgcc gccgttcctc gaggagatct gggacgtggc 18540
ggacgtggcg acgacggcga cgccggtggc ggcggaggcg ccggcgctct agccccccgcg 18600 ccgcccgccc ggccgcgcgc acgtctagcg cgcctcagga gagaacgctc atagactggc 18660
tagttttagt gaagtgcacg gacactgacg tcggacgtga tcaacctatt tataaggact 18720
gcgaatttta ccacttaaga gggcacaccc gtacccgatt tcgtacggga attcctgcag 18780
cccgggggat ccttaattaa ctcgaggaat tcatcgattc cgcgggtacc gagctcgatc 18840
cgtcgacctg cagatcgttc aaacatttgg caataaagtt tcttaagatt gaatcctgtt 18900
gccggtcttg cgatgattat catataattt ctgttgaatt acgttaagca tgtaataatt 18960
aacatgtaat gcatgacgtt atttatgaga tgggttttta tgattagagt cccgcaatta 19020
tacatttaat acgcgataga aaacaaaata tagcgcgcaa actaggataa attatcgcgc 19080
gcggtgtcat ctatgttact agatctggcg cgcccctagg tctagagtcg actgtttaaa 19140
cggtccgtga ccatgattac gccaagcttc gactgtacag gatgttctag ctactcgagt 19200
agctagaaca tcctgtacag tcgagtagct agaacatcct gtacagtcga ctagctagaa 19260
catcctgtac agtcgagtag ctagaacatc ctgtacagtc gagtagctag acatcctgta 19320
caggatccct atataaggaa gttcatttca tttggagaga acacggggga tcgggtatcg 19380
ttaattaagt ttatcaacaa gtttgtacaa aaaagcaggc tccgcggccg ccccccttcac 19440 catgatcgtc gacggcctgt gggacgtgta caaccagtac cacatgggca tcaccgccga 19500
gaacgtggcc aaggaatacg gcatcacacg cgaggcgcag gatgagttcg ccgtcggctc 19560
gcagaacaag gccgaagccg cgcagaaggc cggcaagttt gacgaagaga tcgtcccggt 19620
gctgatcccg cagcgcaagg gcgacccggt ggccttcaag accgacgagt tcgtgcgcca 19680
gggcgccacg ctggacagca tgtccggcct caagcccgcc ttcgacaagg ccggcacggt 19740
gaccgcggcc aacgcctcgg gcctgaacga cggcgccgcc gcggtggtgg tgatgtcggc 19800
ggccaaggcc aaggaactgg gcctgacccc gctggccacg atcaagagct atgccaacgc 19860
cggtgtcgat cccaaggtga tgggcatggg cccggtgccg gcctccaagc gcgccctgtc 19920

-continued

```
gcgcgccgag tggaccccgc aagacctgga cctgatggag atcaacgagg cctttgccgc  19980
gcaggcgctg gcggtgcacc agcagatggg ctgggacacc tccaaggtca atgtgaaagg  20040
gtgggcgcgc cgacccagct ttcttgtaca aagtggttga tcctgcaggg tccgtcgctt  20100
ctcttccatt tcttctcatt ttcgattttg attcttattt ctttccagta gctcctgctc  20160
tgtgaatttc tccgctcacg atagatctgc ttatactcct tacattcaac cttagatctg  20220
gtctcgattc tctgtttctc tgtttttttc ttttggtcga gaatctgatg tttgtttatg  20280
ttctgtcacc attaataata atgaactctc tcattcatac aatgattagt ttctctcgtc  20340
tacaaaacga tatgttgcat tttcactttt cttcttttt tctaagatga tttgctttga  20400
ccaatttgtt tagatcttta ttctatttta ttttctggtg ggttggtgga aattgaaaaa  20460
aaaaaaacag cataaattgt tatttgttaa tgtattcatt ttttggctat ttgttctggg  20520
taaaaatctg cttctactat tgaatctttc ctggattttt tactcctatt gggtttttat  20580
agtaaaaata cataataaaa ggaaaacaaa agttttatag attctcttaa accccttacg  20640
ataaaagttg gaatcaaaat aattcaggat cagatgctct ttgattgatt cagatgcgat  20700
tacagttgca tggcaaattt tctagatccg tcgtcacatt ttattttctg tttaaatatc  20760
taaatctgat atatgatgtc gacaaattct ggtggcttat acatcacttc aactgttttc  20820
ttttggcttt gtttgtcaac ttggttttca atacgatttg tgatttcgat cgctgaattt  20880
ttaatacaag caaactgatg ttaaccacaa gcaagagatg tgacctgcct tattaacatc  20940
gtattactta ctactagtcg tattctcaac gcaatcgttt ttgtatttct cacattatgc  21000
cgcttctcta ctctttattc cttttggtcc acgcattttc tatttgtggc aatccctttc  21060
acaacctgat ttcccacttt ggatcatttg tctgaagact ctcttgaatc gttaccactt  21120
gtttcttgtg catgctctgt tttttagaat taatgataaa actattccat agtcttgagt  21180
tttcagcttg ttgattcttt tgcttttggt tttctgcagg tttaaacatc aaccactttg  21240
tacaagaaag ctgggtcggc gcgcccaccc tttcacattg accttggagg tgtcccagcc  21300
catctgctgg tgcaccgcca gcgcctgcgc ggcaaaggcc tcgttgatct ccatcaggtc  21360
caggtcttgc ggggtccact cggcgcgcga cagggcgcgc ttggaggccg gcaccgggcc  21420
catgcccatc accttgggat cgacaccggc gttggcatag ctcttgatcg tggccagcgg  21480
ggtcaggccc agttccttgg ccttggccgc cgacatcacc accaccgcgg cggcgccgtc  21540
gttcaggccc gaggcgttgg ccgcggtcac cgtgccggcc ttgtcgaagg cgggcttgag  21600
gccggacatg ctgtccagcg tggcgccctg gcgcacgaac tcgtcggtct tgaaggccac  21660
cgggtcgccc ttgcgctgcg ggatcagcac cgggacgatc tcttcgtcaa acttgccggc  21720
cttctgcgcg gcttcggcct tgttctgcga gccgacggcg aactcatcct gcgcctcgcg  21780
tgtgatgccg tattccttgg ccacgttctc ggcggtgatg cccatgtggt actggttgta  21840
cacgtcccac aggccgtcga cgatcatggt gaagggggcg gccgcggagc ctgctttttt  21900
gtacaaactt gttgatctcg agcggcgcgc cgttcgagta ttatggcatt gggaaaactg  21960
tttttcttgt accatttgtt gtgcttgtaa tttactgtgt tttttattcg gttttcgcta  22020
tcgaactgtg aaatggaaat ggatggagaa gagttaatga atgatatggt ccttttgttc  22080
attctcaaat taatattatt tgttttttct cttatttgtt gtgtgttgaa tttgaaatta  22140
taagagatat gcaaacattt tgttttgagt aaaaatgtgt caaatcgtgg cctctaatga  22200
ccgaagttaa tatgaggagt aaaacactgt ttaaaccctg caggattt              22248
```

<210> SEQ ID NO 6
<211> LENGTH: 22370
<212> TYPE: DNA
<213> ORGANISM: Artificial Sequence
<220> FEATURE:
<223> OTHER INFORMATION: Synthetic Vector

<400> SEQUENCE: 6
gtccgtgacc atgattacgc caagcttcga ctgtacagga tgttctagct actcgagtag 60
ctagaacatc ctgtacagtc gagtagctag aacatcctgt acagtcgact agctagaaca 120
tcctgtacag tcgagtagct agaacatcct gtacagtcga gtagctagac atcctgtaca 180
ggatccctat ataaggaagt tcatttcatt tggagagaac acgggggatc gggtatcgtt 240
aattaagttt atcaacaagt ttgtacaaaa aagcaggctc cgcggccgcc cccttcacct 300
tcctcgactt cagcgacacc ggcgtgctcg acgtcttcgt cgatgaaacc caggtcgcgc 360
tgcgtgaaca gcaattgcgc gatggcggcc tgatgccggg ccgtgacctg gcctcgacct 420
tctcgagcct gcgtccgaac gacctggtat ggaactatgt gcagtcgaac tacctcaaag 480
gcaatgagcc ggcggcgttt gacctgctgt tctggaattc ggacagcacc aatttgccgg 540
gcccgatgtt ctgctggtac ctgcgcaaca cctacctgga aaacagcctg aaagtgccgg 600
gcaagctgac ggtggccggc gaaaagatcg acctcggcct gatcgacgcc ccggccttca 660
tctacggttc gcgcgaagac cacatcgtgc cgtggatgtc ggcgtacggt tcgctcgaca 720
tcctcaacca gggcaagccg ggcgccaacc gcttcgtgct gggcgcgtcc ggccatatcg 780
ccggcgtgat caactcggtg gccaagaaca agcgcagcta ctggatcaac gacggtggcg 840
ccgccgatgc ccaggcctgg ttcgatggcg cgcaggaagt gccgggcagc tggtggccgc 900
aatgggccgg gttcctgacc cagcatggcg gcaagaaggt caagcccaag gccaaaaggg 960
tgggcgcgcc gacccagctt tcttgtacaa agtggttgat cctgcagggt ccgtcgcttc 1020
tcttccattt cttctcattt tcgattttga ttcttatttc tttccagtag ctcctgctct 1080
gtgaatttct ccgctcacga tagatctgct tatactcctt acattcaacc ttagatctgg 1140
tctcgattct ctgtttctct gtttttttct tttggtcgag aatctgatgt ttgtttatgt 1200
tctgtcacca ttaataataa tgaactctct cattcataca atgattagtt tctctcgtct 1260
acaaaacgat atgttgcatt ttcacttttc ttcttttttt ctaagatgat ttgctttgac 1320
caatttgttt agatctttat tctattttat tttctggtgg gttggtggaa attgaaaaaa 1380
aaaaaacagc ataaattgtt atttgttaat gtattcattt tttggctatt tgttctgggt 1440
aaaaatctgc ttctactatt gaatctttcc tggatttttt actcctattg ggtttttata 1500
gtaaaaatac ataataaaag gaaaacaaaa gttttataga ttctcttaaa ccccttacga 1560
taaaagttgg aatcaaaata attcaggatc agatgctctt tgattgattc agatgcgatt 1620
acagttgcat ggcaaatttt ctagatccgt cgtcacattt tattttctgt ttaaatatct 1680
aaatctgata tatgatgtcg acaaattctg gtggcttata catcacttca actgttttct 1740
tttggctttg tttgtcaact tggttttcaa tacgatttgt gatttcgatc gctgaatttt 1800
taatacaagc aaactgatgt taaccacaag caagagatgt gacctgcctt attaacatcg 1860
tattacttac tactagtcgt attctcaacg caatcgtttt tgtatttctc acattatgcc 1920
gcttctctac tctttattcc ttttggtcca cgcattttct atttgtggca atccctttca 1980
caacctgatt tcccactttg gatcatttgt ctgaagactc tcttgaatcg ttaccacttg 2040
tttcttgtgc atgctctgtt ttttagaatt aatgataaaa ctattccata gtcttgagtt 2100

-continued

```
ttcagcttgt tgattctttt gcttttggtt ttctgcaggt ttaaacatca accactttgt   2160
acaagaaagc tgggtcggcg cgcccaccct tttggccttg ggcttgacct tcttgccgcc   2220
atgctgggtc aggaacccgg cccattgcgg ccaccagctg cccggcactt cctgcgcgcc   2280
atcgaaccag gcctgggcat cggcggcgcc accgtcgttg atccagtagc tgcgcttgtt   2340
cttggccacc gagttgatca cgccggcgat atggccggac gcgcccagca cgaagcggtt   2400
ggcgcccggc ttgccctggt tgaggatgtc gagcgaaccg tacgccgaca tccacggcac   2460
gatgtggtct tcgcgcgaac cgtagatgaa ggccggggcg tcgatcaggc cgaggtcgat   2520
cttttcgccg gccaccgtca gcttgcccgg cactttcagg ctgttttcca ggtaggtgtt   2580
gcgcaggtac cagcagaaca tcgggcccgg caaattggtg ctgtccgaat tccagaacag   2640
caggtcaaac gccgccggct cattgccttt gaggtagttc gactgcacat agttccatac   2700
caggtcgttc ggacgcaggc tcgagaaggt cgaggccagg tcacggcccg gcatcaggcc   2760
gccatcgcgc aattgctgtt cacgcagcgc gacctgggtt tcatcgacga agacgtcgag   2820
cacgccggtg tcgctgaagt cgaggaaggt gaagggggcg gccgcggagc ctgctttttt   2880
gtacaaactt gttgatctcg agcggcgcgc cgttcgagta ttatggcatt gggaaaactg   2940
tttttcttgt accatttgtt gtgcttgtaa tttactgtgt tttttattcg gttttcgcta   3000
tcgaactgtg aaatggaaat ggatggagaa gagttaatga atgatatggt ccttttgttc   3060
attctcaaat taatattatt tgtttttct cttatttgtt gtgtgttgaa tttgaaatta   3120
taagagatat gcaaacattt tgttttgagt aaaaatgtgt caaatcgtgg cctctaatga   3180
ccgaagttaa tatgaggagt aaaacactgt ttaaaccctg caggatttaa atagaaggta   3240
attatccaag atgtagcatc aagaatccaa tgtttacggg aaaaactatg gaagtattat   3300
gtgagctcag caagaagcag atcaatatgc ggcacatatg caacctatgt tcaaaaatga   3360
agaatgtaca gatacaagat cctatactgc cagaatacga agaagaatac gtagaaattg   3420
aaaaagaaga accaggcgaa gaaaagaatc ttgaagacgt aagcactgac gacaacaatg   3480
aaaagaagaa gataaggtcg gtgattgtga aagagacata gaggacacat gtaaggtgga   3540
aaatgtaagg gcggaaagta accttatcac aaaggaatct tatcccccac tacttatcct   3600
tttatatttt tccgtgtcat ttttgccctt gagttttcct atataaggaa ccaagttcgg   3660
catttgtgaa aacaagaaaa aattggtgta agctattttc tttgaagtac tgaggataca   3720
acttcagaga aatttgtaag aaagtggatc gaaaccatgg cctcctccga gaacgtcatc   3780
accgagttca tgcgcttcaa ggtgcgcatg gagggcaccg tgaacggcca cgagttcgag   3840
atcgagggcg agggcgaggg ccgcccctac gagggccaca acaccgtgaa gctgaaggtg   3900
accaagggcg gccccctgcc cttcgcctgg gacatcctgt ccccccagtt ccagtacggc   3960
tccaaggtgt acgtgaagca ccccgccgac atccccgact acaagaagct gtccttcccc   4020
gagggcttca agtgggagcg cgtgatgaac ttcgaggacg gcggcgtggc gaccgtgacc   4080
caggactcct ccctgcagga cggctgcttc atctacaagg tgaagttcat cggcgtgaac   4140
ttcccctccg acggccccgt gatgcagaag aagaccatgg gctgggaggc ctccaccgag   4200
cgcctgtacc cccgcgacgg cgtgctgaag ggcgagaccc acaaggccct gaagctgaag   4260
gacggcggcc actacctggt ggagttcaag tccatctaca tggccaagaa gcccgtgcag   4320
ctgcccggct actactacgt ggacgccaag ctggacatca cctcccacaa cgaggactac   4380
accatcgtgg agcagtacga gcgcaccgag ggccgccacc acctgttcct ggtaccaatg   4440
```

-continued

```
agctctgtcc aacagtctca gggttaatgt ctatgtatct taaataatgt tgtcggcgat   4500
cgttcaaaca tttggcaata aagtttctta agattgaatc ctgttgccgg tcttgcgatg   4560
attatcatat aatttctgtt gaattacgtt aagcatgtaa taattaacat gtaatgcatg   4620
acgttattta tgagatgggt ttttatgatt agagtcccgc aattatacat ttaatacgcg   4680
atagaaaaca aaatatagcg cgcaaactag gataaattat cgcgcgcggt gtcatctatg   4740
ttactagatc gggaattaaa ctatcagtgt ttgacaggat atattggcgg gtaaacctaa   4800
gagaaaagag cgtttattag aataacggat atttaaaagg gcgtgaaaag gtttatccgt   4860
tcgtccattt gtatgtgcat gccaaccaca gggttcccct cgggatcaaa gtactttgat   4920
ccaacccctc cgctgctata gtgcagtcgg cttctgacgt tcagtgcagc cgtcttctga   4980
aaacgacatg tcgcacaagt cctaagttac gcgacaggct gccgccctgc ccttttcctg   5040
gcgttttctt gtcgcgtgtt ttagtcgcat aaagtagaat acttgcgact agaaccggag   5100
acattacgcc atgaacaaga gcgccgccgc tggcctgctg ggctatgccc gcgtcagcac   5160
cgacgaccag gacttgacca accaacgggc cgaactgcac gcggccggct gcaccaagct   5220
gttttccgag aagatcaccg gcaccaggcg cgaccgcccg gagctggcca ggatgcttga   5280
ccacctacgc cctggcgacg ttgtgacagt gaccaggcta gaccgcctgg cccgcagcac   5340
ccgcgaccta ctggacattg ccgagcgcat ccaggaggcc ggcgcgggcc tgcgtagcct   5400
ggcagagccg tgggccgaca ccaccacgcc ggccggccgc atggtgttga ccgtgttcgc   5460
cggcattgcc gagttcgagc gttccctaat catcgaccgc acccggagcg ggcgcgaggc   5520
cgccaaggcc cgaggcgtga agtttggccc ccgccctacc ctcaccccgg cacagatcgc   5580
gcacgcccgc gagctgatcg accaggaagg ccgcaccgtg aaagaggcgg ctgcactgct   5640
tggcgtgcat cgctcgaccc tgtaccgcgc acttgagcgc agcgaggaag tgacgcccac   5700
cgaggccagg cggcgcggtg ccttccgtga ggacgcattg accgaggccg acgccctggc   5760
ggccgccgag aatgaacgcc aagaggaaca agcatgaaac cgcaccagga cggccaggac   5820
gaaccgtttt tcattaccga agagatcgag gcggagatga tcgcggccgg gtacgtgttc   5880
gagccgcccg cgcacgtctc aaccgtgcgg ctgcatgaaa tcctggccgg tttgtctgat   5940
gccaagctgg cggcctggcc ggccagcttg gccgctgaag aaaccgagcg ccgccgtcta   6000
aaaaggtgat gtgtatttga gtaaaacagc ttgcgtcatg cggtcgctgc gtatatgatg   6060
cgatgagtaa ataaacaaat acgcaagggg aacgcatgaa ggttatcgct gtacttaacc   6120
agaaaggcgg gtcaggcaag acgaccatcg caacccatct agcccgcgcc ctgcaactcg   6180
ccggggccga tgttctgtta gtcgattccg atccccaggg cagtgcccgc gattgggcgg   6240
ccgtgcggga agatcaaccg ctaaccgttg tcggcatcga ccgcccgacg attgaccgcg   6300
acgtgaaggc catcggccgg cgcgacttcg tagtgatcga cggagcgccc caggcggcgg   6360
acttggctgt gtccgcgatc aaggcagccg acttcgtgct gattccggtg cagccaagcc   6420
cttacgacat atgggccacc gccgacctgg tggagctggt taagcagcgc attgaggtca   6480
cggatggaag gctacaagcg gcctttgtcg tgtcgcgggc gatcaaaggc acgcgcatcg   6540
gcggtgaggt tgccgaggcg ctggccgggt acgagctgcc cattcttgag tcccgtatca   6600
cgcagcgcgt gagctaccca ggcactgccg ccgccggcac aaccgttctt gaatcagaac   6660
ccgagggcga cgctgcccgc gaggtccagg cgctggccgc tgaaattaaa tcaaaactca   6720
tttgagttaa tgaggtaaag agaaaatgag caaaagcaca aacacgctaa gtgccggccg   6780
tccgagcgca cgcagcagca aggctgcaac gttggccagc ctggcagaca cgccagccat   6840
```

gaagcgggtc aactttcagt tgccggcgga ggatcacacc aagctgaaga tgtacgcggt 6900
acgccaaggc aagaccatta ccgagctgct atctgaatac atcgcgcagc taccagagta 6960
aatgagcaaa tgaataaatg agtagatgaa ttttagcggc taaaggaggc ggcatggaaa 7020
atcaagaaca accaggcacc gacgccgtgg aatgccccat gtgtggagga acgggcggtt 7080
ggccaggcgt aagcggctgg gttgtctgcc ggccctgcaa tggcactgga acccccaagc 7140
ccgaggaatc ggcgtgacgg tcgcaaacca tccggcccgg tacaaatcgg cgcggcgctg 7200
ggtgatgacc tggtggagaa gttgaaggcc gcgcaggccg cccagcggca acgcatcgag 7260
gcagaagcac gccccggtga atcgtggcaa gcggccgctg atcgaatccg caaagaatcc 7320
cggcaaccgc cggcagccgg tgcgccgtcg attaggaagc cgcccaaggg cgacgagcaa 7380
ccagattttt tcgttccgat gctctatgac gtgggcaccc gcgatagtcg cagcatcatg 7440
gacgtggccg ttttccgtct gtcgaagcgt gaccgacgag ctggcgaggt gatccgctac 7500
gagcttccag acgggcacgt agaggtttcc gcagggccgg ccggcatggc cagtgtgtgg 7560
gattacgacc tggtactgat ggcggtttcc catctaaccg aatccatgaa ccgataccgg 7620
gaagggaagg gagacaagcc cggccgcgtg ttccgtccac acgttgcgga cgtactcaag 7680
ttctgccggc gagccgatgg cggaaagcag aaagacgacc tggtagaaac ctgcattcgg 7740
ttaaacacca cgcacgttgc catgcagcgt acgaagaagg ccaagaacgg ccgcctggtg 7800
acggtatccg agggtgaagc cttgattagc cgctacaaga tcgtaaagag cgaaaccggg 7860
cggccggagt acatcgagat cgagctagct gattggatgt accgcgagat cacagaaggc 7920
aagaacccgg acgtgctgac ggttcacccc gattactttt tgatcgatcc cggcatcggc 7980
cgttttctct accgcctggc acgccgcgcc gcaggcaagg cagaagccag atggttgttc 8040
aagacgatct acgaacgcag tggcagcgcc ggagagttca agaagttctg tttcaccgtg 8100
cgcaagctga tcgggtcaaa tgacctgccg gagtacgatt tgaaggagga ggcggggcag 8160
gctggcccga tcctagtcat gcgctaccgc aacctgatcg agggcgaagc atccgccggt 8220
tcctaatgta cggagcagat gctagggcaa attgccctag caggggaaaa aggtcgaaaa 8280
ggtctctttc ctgtggatag cacgtacatt gggaacccaa agccgtacat tgggaaccgg 8340
aacccgtaca ttgggaaccc aaagccgtac attgggaacc ggtcacacat gtaagtgact 8400
gatataaaag agaaaaaagg cgatttttcc gcctaaaact ctttaaaact tattaaaact 8460
cttaaaaccc gcctggcctg tgcataactg tctggccagc gcacagccga agagctgcaa 8520
aaagcgccta cccttcggtc gctgcgctcc ctacgccccg ccgcttcgcg tcggcctatc 8580
gcggccgctg gccgctcaaa aatggctggc ctacggccag gcaatctacc agggcgcgga 8640
caagccgcgc cgtcgccact cgaccgccgg cgcccacatc aaggcaccct gcctcgcgcg 8700
tttcggtgat gacggtgaaa acctctgaca catgcagctc ccggagacgg tcacagcttg 8760
tctgtaagcg gatgccggga gcagacaagc ccgtcagggc gcgtcagcgg gtgttggcgg 8820
gtgtcggggc gcagccatga cccagtcacg tagcgatagc ggagtgtata ctggcttaac 8880
tatgcggcat cagagcagat tgtactgaga gtgcaccata tgcggtgtga aataccgcac 8940
agatgcgtaa ggagaaaata ccgcatcagg cgctcttccg cttcctcgct cactgactcg 9000
ctgcgctcgg tcgttcggct gcggcgagcg gtatcagctc actcaaaggc ggtaatacgg 9060
ttatccacag aatcagggga taacgcagga aagaacatgt gagcaaaagg ccagcaaaag 9120
gccaggaacc gtaaaaaggc cgcgttgctg gcgtttttcc ataggctccg cccccctgac 9180

-continued

```
gagcatcaca aaaatcgacg ctcaagtcag aggtggcgaa acccgacagg actataaaga   9240
taccaggcgt ttccccctgg aagctccctc gtgcgctctc ctgttccgac cctgccgctt   9300
accggatacc tgtccgcctt tctcccttcg ggaagcgtgg cgctttctca tagctcacgc   9360
tgtaggtatc tcagttcggt gtaggtcgtt cgctccaagc tgggctgtgt gcacgaaccc   9420
cccgttcagc ccgaccgctg cgccttatcc ggtaactatc gtcttgagtc caacccggta   9480
agacacgact tatcgccact ggcagcagcc actggtaaca ggattagcag agcgaggtat   9540
gtaggcggtg ctacagagtt cttgaagtgg tggcctaact acggctacac tagaaggaca   9600
gtatttggta tctgcgctct gctgaagcca gttaccttcg gaaaaagagt tggtagctct   9660
tgatccggca aacaaaccac cgctggtagc ggtggttttt ttgtttgcaa gcagcagatt   9720
acgcgcagaa aaaaaggatc tcaagaagat cctttgatct tttctacggg gtctgacgct   9780
cagtggaacg aaaactcacg ttaagggatt ttggtcatgc attctaggta ctaaaacaat   9840
tcatccagta aaatataata ttttattttc tcccaatcag gcttgatccc cagtaagtca   9900
aaaaatagct cgacatactg ttcttccccg atatcctccc tgatcgaccg gacgcagaag   9960
gcaatgtcat accacttgtc cgccctgccg cttctcccaa gatcaataaa gccacttact  10020
ttgccatctt tcacaaagat gttgctgtct cccaggtcgc cgtgggaaaa gacaagttcc  10080
tcttcgggct tttccgtctt taaaaaatca tacagctcgc gcggatcttt aaatggagtg  10140
tcttcttccc agttttcgca atccacatcg gccagatcgt tattcagtaa gtaatccaat  10200
tcggctaagc ggctgtctaa gctattcgta tagggacaat ccgatatgtc gatggagtga  10260
aagagcctga tgcactccgc atacagctcg ataatctttt cagggctttg ttcatcttca  10320
tactcttccg agcaaaggac gccatcggcc tcactcatga gcagattgct ccagccatca  10380
tgccgttcaa agtgcaggac ctttggaaca ggcagctttc cttccagcca tagcatcatg  10440
tccttttccc gttccacatc ataggtggtc cctttatacc ggctgtccgt catttttaaa  10500
tataggtttt cattttctcc caccagctta tataccttag caggagacat tccttccgta  10560
tcttttacgc agcggtattt ttcgatcagt tttttcaatt ccggtgatat tctcatttta  10620
gccatttatt atttccttcc tcttttctac agtatttaaa gataccccaa gaagctaatt  10680
ataacaagac gaactccaat tcactgttcc ttgcattcta aaaccttaaa taccagaaaa  10740
cagctttttc aaagttgttt tcaaagttgg cgtataacat agtatcgacg gagccgattt  10800
tgaaaccgcg gtgatcacag gcagcaacgc tctgtcatcg ttacaatcaa catgctaccc  10860
tccgcgagat catccgtgtt tcaaacccgg cagcttagtt gccgttcttc cgaatagcat  10920
cggtaacatg agcaaagtct gccgccttac aacggctctc ccgctgacgc cgtcccggac  10980
tgatgggctg cctgtatcga gtggtgattt tgtgccgagc tgccggtcgg ggagctgttg  11040
gctggctggt ggcaggatat attgtggtgt aaacaaattg acgcttagac aacttaataa  11100
cacattgcgg acgtttttaa tgtactgaat taacgccgaa ttaattccta ggccaccatg  11160
ttgggcccgg ggcgcgccgt acgtagtgtt tatctttgtt gcttttctga acaatttatt  11220
tactatgtaa atatattatc aatgtttaat ctattttaat ttgcacatga attttcattt  11280
tatttttact ttacaaaaca aataaatata tatgcaaaaa aatttacaaa cgatgcacgg  11340
gttacaaact aatttcatta aatgctaatg cagattttgt gaagtaaaac tccaattatg  11400
atgaaaaata ccaccaacac cacctgcgaa actgtatccc aactgtcctt aataaaaatg  11460
ttaaaaagta tattattctc atttgtctgt cataatttat gtaccccact ttaatttttc  11520
tgatgtacta aaccgagggc aaactgaaac ctgttcctca tgcaaagccc ctactcacca  11580
```

-continued

```
tgtatcatgt acgtgtcatc acccaacaac tccacttttg ctatataaca acaccccegt  11640
cacactctcc ctctctaaca cacaccccac taacaattcc ttcacttgca gcactgttgc  11700
atcatcatct tcattgcaaa accctaaact tcaccttcaa ccgcggccgc atggcttcta  11760
tgatatcctc ttccgctgtg acaacagtca gccgtgcctc taggggggcaa tccgccgcag  11820
tggctccatt cggcggcctc aaatccatga ctggattccc agtgaagaag gtcaacactg  11880
acattacttc cattacaagc aatggtggaa gagtaaagtg catgcaggtg tggcctccaa  11940
ttggaaagaa gaagtttgag actctttcct atttgccacc attgacgaga gattctagag  12000
tgagtaacaa gaacaacgat gagctgcagt ggcaatcctg gttcagcaag gcgcccacca  12060
ccgaggcgaa cccgatggcc accatgttgc aggatatcgg cgttgcgctc aaaccggaag  12120
cgatggagca gctgaaaaac gattatctgc gtgacttcac cgcgttgtgg caggattttt  12180
tggctggcaa ggcgccagcc gtcagcgacc gccgcttcag ctcggcagcc tggcagggca  12240
atccgatgtc ggccttcaat gccgcatctt acctgctcaa cgccaaattc ctcagtgcca  12300
tggtggaggc ggtggacacc gcaccccagc aaaagcagaa aatacgcttt gccgtgcagc  12360
aggtgattga tgccatgtcg cccgcgaact tcctcgccac caacccggaa gcgcagcaaa  12420
aactgattga aaccaagggc gagagcctga cgcgtggcct ggtcaatatg ctgggcgata  12480
tcaacaaggg ccatatctcg ctgtcggacg aatcggcctt tgaagtgggc cgcaacctgg  12540
ccattacccc gggcaccgtg atttacgaaa atccgctgtt ccagctgatc cagtacacgc  12600
cgaccacgcc gacggtcagc cagcgcccgc tgttgatggt gccgccgtgc atcaacaagt  12660
tctacatcct cgacctgcaa ccggaaaatt cgctggtgcg ctacgcggtg gagcagggca  12720
acaccgtgtt cctgatctcg tggagcaatc cggacaagtc gctggccggc accacctggg  12780
acgactacgt ggagcagggc gtgatcgaag cgatccgcat cgtccaggac gtcagcggcc  12840
aggacaagct gaacatgttc ggcttctgcg tgggcggcac catcgttgcc accgcactgg  12900
cggtactggc ggcgcgtggc cagcacccgg cggccagcct gaccctgctg accaccttcc  12960
tcgacttcag cgacaccggc gtgctcgacg tcttcgtcga tgaaacccag gtcgcgctgc  13020
gtgaacagca attgcgcgat ggcggcctga tgccgggccg tgacctggcc tcgaccttct  13080
cgagcctgcg tccgaacgac ctggtatgga actatgtgca gtcgaactac ctcaaaggca  13140
atgagccggc ggcgtttgac ctgctgttct ggaattcgga cagcaccaat ttgccgggcc  13200
cgatgttctg ctggtacctg cgcaacacct acctggaaaa cagcctgaaa gtgccgggca  13260
agctgacggt ggccggcgaa aagatcgacc tcggcctgat cgacgccccg gccttcatct  13320
acggttcgcg cgaagaccac atcgtgccgt ggatgtcggc gtacggttcg ctcgacatcc  13380
tcaaccaggg caagccgggc gccaaccgct tcgtgctggg cgcgtccggc catatcgccg  13440
gcgtgatcaa ctcggtggcc aagaacaagc gcagctactg gatcaacgac ggtggcgccg  13500
ccgatgccca ggcctggttc gatggcgcgc aggaagtgcc gggcagctgg tggccgcaat  13560
gggccgggtt cctgacccag catggcggca agaaggtcaa gcccaaggcc aagcccggca  13620
acgcccgcta caccgcgatc gaggcggcgc ccggccgtta cgtcaaagcc aagggctgag  13680
cggccgctga gtaattctga tattagaggg agcattaatg tgttgttgtg atgtggttta  13740
tatggggaaa ttaaataaat gatgtatgta cctcttgcct atgtaggttt gtgtgttttg  13800
ttttgttgtc tagctttggt tattaagtag tagggacgtt cgttcgtgtc tcaaaaaaag  13860
ggtactacc actctgtagt gtatatggat gctggaaatc aatgtgtttt gtatttgttc  13920
```

acctccattg ttgaattcaa tgtcaaatgt gttttgcgtt ggttatgtgt aaaattacta 13980
tctttctcgt ccgatgatca aagttttaag caacaaaacc aagggtgaaa tttaaactgt 14040
gctttgttga agattctttt atcatattga aaatcaaatt actagcagca gattttacct 14100
agcatgaaat tttatcaaca gtacagcact cactaaccaa gttccaaact aagatgcgcc 14160
attaacatca gccaataggc attttcagca aggcgcgccc gcgccgatgt atgtgacaac 14220
cctcgggatt gttgatttat ttcaaaacta agagtttttg tcttattgtt ctcgtctatt 14280
ttggatatca atcttagttt tatatctttt ctagttctct acgtgttaaa tgttcaacac 14340
actagcaatt tggcctgcca gcgtatggat tatggaacta tcaagtctgt gacgcgccgt 14400
acgtagtgtt tatctttgtt gcttttctga acaatttatt tactatgtaa atatattatc 14460
aatgtttaat ctattttaat ttgcacatga attttcattt tatttttact ttacaaaaca 14520
aataaatata tatgcaaaaa aatttacaaa cgatgcacgg gttacaaact aatttcatta 14580
aatgctaatg cagattttgt gaagtaaaac tccaattatg atgaaaaata ccaccaacac 14640
cacctgcgaa actgtatccc aactgtcctt aataaaaatg ttaaaaagta tattattctc 14700
atttgtctgt cataatttat gtaccccact ttaatttttc tgatgtacta aaccgagggc 14760
aaactgaaac ctgttcctca tgcaaagccc ctactcacca tgtatcatgt acgtgtcatc 14820
acccaacaac tccacttttg ctatataaca acaccccgt cacactctcc ctctctaaca 14880
cacaccccac taacaattcc ttcacttgca gcactgttgc atcatcatct tcattgcaaa 14940
accctaaact tcaccttcaa ccgcggccgc atggcttcta tgatatcctc ttccgctgtg 15000
acaacagtca gccgtgcctc tagggggcaa tccgccgcag tggctccatt cggcggcctc 15060
aaatccatga ctggattccc agtgaagaag gtcaacactg acattacttc cattacaagc 15120
aatggtggaa gagtaaagtg catgcaggtg tggcctccaa ttggaaagaa gaagtttgag 15180
actctttcct atttgccacc attgacgaga gattctagag tgactcagcg cattgcgtat 15240
gtgaccggcg gcatgggtgg tatcggaacc gccatttgcc agcggctggc caaggatggc 15300
tttcgtgtgg tggccggttg cggccccaac tcgccgcgcc gcgaaaagtg gctggagcag 15360
cagaaggccc tgggcttcga tttcattgcc tcggaaggca atgtggctga ctgggactcg 15420
accaagaccg cattcgacaa ggtcaagtcc gaggtcggcg aggttgatgt gctgatcaac 15480
aacgccggta tcacccgcga cgtggtgttc cgcaagatga cccgcgccga ctgggatgcg 15540
gtgatcgaca ccaacctgac ctcgctgttc aacgtcacca agcaggtgat cgacggcatg 15600
gccgaccgtg gctggggccg catcgtcaac atctcgtcgg tgaacgggca gaagggccag 15660
ttcggccaga ccaactactc caccgccaag gccggcctgc atggcttcac catggcactg 15720
gcgcaggaag tggcgaccaa gggcgtgacc gtcaacacgg tctctccggg ctatatcgcc 15780
accgacatgg tcaaggcgat ccgccaggac gtgctcgaca agatcgtcgc gacgatcccg 15840
gtcaagcgcc tgggcctgcc ggaagagatc gcctcgatct gcgcctggtt gtcgtcggag 15900
gagtccggtt tctcgaccgg cgccgacttc tcgctcaacg gcggcctgca tatgggctga 15960
gcggccgctg agtaattctg atattagagg gagcattaat gtgttgttgt gatgtggttt 16020
atatggggaa attaaataaa tgatgtatgt acctcttgcc tatgtaggtt tgtgtgtttt 16080
gttttgttgt ctagctttgg ttattaagta gtagggacgt tcgttcgtgt ctcaaaaaaa 16140
ggggtactac cactctgtag tgtatatgga tgctggaaat caatgtgttt tgtatttgtt 16200
cacctccatt gttgaattca atgtcaaatg tgttttgcgt tggttatgtg taaaattact 16260
atctttctcg tccgatgatc aaagttttaa gcaacaaaac caagggtgaa atttaaactg 16320

-continued

```
tgctttgttg aagattcttt tatcatattg aaaatcaaat tactagcagc agattttacc  16380
tagcatgaaa ttttatcaac agtacagcac tcactaacca agttccaaac taagatgcgc  16440
cattaacatc agccaatagg cattttcagc aaggcgcgta aggggatccg tacgtaagta  16500
cgtactcaaa atgccaacaa ataaaaaaaa agttgcttta ataatgccaa aacaaattaa  16560
taaaacactt acaacaccgg atttttttta attaaaatgt gccatttagg ataaatagtt  16620
aatattttta ataattattt aaaaagccgt atctactaaa atgattttta tttggttgaa  16680
aatattaata tgtttaaatc aacacaatct atcaaaatta aactaaaaaa aaaataagtg  16740
tacgtggtta acattagtac agtaatataa gaggaaaatg agaaattaag aaattgaaag  16800
cgagtctaat ttttaaatta tgaacctgca tatataaaag gaaagaaaga atccaggaag  16860
aaaagaaatg aaaccatgca tggtcccctc gtcatcacga gtttctgcca tttgcaatag  16920
aaacactgaa acacctttct ctttgtcact taattgagat gccgaagcca cctcacacca  16980
tgaacttcat gaggtgtagc acccaaggct tccatagcca tgcatactga agaatgtctc  17040
aagctcagca ccctacttct gtgacgtgtc cctcattcac cttcctctct tccctataaa  17100
taaccacgcc tcaggttctc cgcttcacaa ctcaaacatt ctctccattg gtccttaaac  17160
actcatcagt catcaccgcg gccgcggaat tcatggcttc tatgatatcc tcttccgctg  17220
tgacaacagt cagccgtgcc tctagggggc aatccgccgc agtggctcca ttcggcggcc  17280
tcaaatccat gactggattc ccagtgaaga aggtcaacac tgacattact tccattacaa  17340
gcaatggtgg aagagtaaag tgcatgcagg tgtggcctcc aattggaaag aagaagtttg  17400
agactctttc ctatttgcca ccattgacga gagattctag agtgactgac gttgtcatcg  17460
tatccgccgc ccgcaccgcg gtcggcaagt ttggcggctc gctggccaag atcccggcac  17520
cggaactggg tgccgtggtc atcaaggccg cgctggagcg cgccggcgtc aagccggagc  17580
aggtgagcga agtcatcatg ggccaggtgc tgaccgccgg ttcgggccag aaccccgcac  17640
gccaggccgc gatcaaggcc ggcctgccgg cgatggtgcc ggccatgacc atcaacaagg  17700
tgtgcggctc gggcctgaag gccgtgatgc tggccgccaa cgcgatcatg gcgggcgacg  17760
ccgagatcgt ggtggccggc ggccaggaaa acatgagcgc cgccccgcac gtgctgccgg  17820
gctcgcgcga tggtttccgc atgggcgatg ccaagctggt cgacaccatg atcgtcgacg  17880
gcctgtggga cgtgtacaac cagtaccaca tgggcatcac cgccgagaac gtggccaagg  17940
aatacggcat cacacgcgag gcgcaggatg agttcgccgt cggctcgcag aacaaggccg  18000
aagccgcgca gaaggccggc aagtttgacg aagagatcgt cccggtgctg atcccgcagc  18060
gcaagggcga cccggtggcc ttcaagaccg acgagttcgt gcgccagggc gccacgctgg  18120
acagcatgtc cggcctcaag cccgccttcg acaaggccgg cacggtgacc gcggccaacg  18180
cctcgggcct gaacgacggc gccgccgcgg tggtggtgat gtcggcggcc aaggccaagg  18240
aactgggcct gaccccgctg gccacgatca agagctatgc caacgccggt gtcgatccca  18300
aggtgatggg catgggcccg gtgccggcct ccaagcgcgc cctgtcgcgc gccgagtgga  18360
ccccgcaaga cctggacctg atggagatca acgaggcctt tgccgcgcag gcgctggcgg  18420
tgcaccagca gatgggctgg gacacctcca aggtcaatgt gaacggcggc gccatcgcca  18480
tcggccaccc gatcggcgcg tcgggctgcc gtatcctggt gacgctgctg cacgagatga  18540
agcgccgtga cgcgaagaag ggcctggcct cgctgtgcat cggcggcggc atgggcgtgg  18600
cgctggcagt cgagcgcaaa taactcgagg cggccgcagc ccttttttgta tgtgctaccc  18660
```

```
cacttttgtc tttttggcaa tagtgctagc aaccaataaa taataataat aataatgaat  18720
aagaaaacaa aggctttagc ttgccttttg ttcactgtaa aataataatg taagtactct  18780
ctataatgag tcacgaaact tttgcgggaa taaaaggaga aattccaatg agttttctgt  18840
caaatcttct tttgtctctc tctctctctc tttttttttt ttctttcttc tgagcttctt  18900
gcaaaacaaa aggcaaacaa taacgattgg tccaatgata gttagcttga tcgatgatat  18960
ctttaggaag tgttggcagg acaggacatg atgtagaaga ctaaaattga aagtattgca  19020
gacccaatag ttgaagatta actttaagaa tgaagacgtc ttatcaggtt cttcatgact  19080
taagctttaa gaggagtcca ccatggtaga tctgactagt gatccgtacg taagtacgta  19140
ctcaaaatgc caacaaataa aaaaaaagtt gctttaataa tgccaaaaca aattaataaa  19200
acacttacaa caccggattt tttttaatta aaatgtgcca tttaggataa atagttaata  19260
tttttaataa ttatttaaaa agccgtatct actaaaatga tttttatttg gttgaaaata  19320
ttaatatgtt taaatcaaca caatctatca aaattaaact aaaaaaaaaa taagtgtacg  19380
tggttaacat tagtacagta atataagagg aaaatgagaa attaagaaat tgaaagcgag  19440
tctaattttt aaattatgaa cctgcatata taaaaggaaa gaaagaatcc aggaagaaaa  19500
gaaatgaaac catgcatggt cccctcgtca tcacgagttt ctgccatttg caatagaaac  19560
actgaaacac ctttctcttt gtcacttaat tgagatgccg aagccacctc acaccatgaa  19620
cttcatgagg tgtagcaccc aaggcttcca tagccatgca tactgaagaa tgtctcaagc  19680
tcagcaccct acttctgtga cgtgtccctc attcaccttc ctctcttccc tataaataac  19740
cacgcctcag gttctccgct tcacaactca aacattctct ccattggtcc ttaaacactc  19800
atcagtcatc accatggact ccaaagaatc attaactcct ggtagagaag aaaaccccag  19860
cagtgtgctt gctcaggaga ggggagatgt gatggacttc tataaaaccc taagaggagg  19920
agctactgtg aaggtttctg cgtcttcacc ctcactggct gtcgcttctc aatcagactc  19980
caagcagcga agacttttgg ttgattttcc aaaaggctca gtaagcaatg cgcagcagcc  20040
agatctgtcc aaagcagttt cactctcaat gggactgtat atgggagaga cagaaacaaa  20100
agtgatggga aatgacctgg gattcccaca gcagggccaa atcagccttt cctcggggga  20160
aacagactta aagcttttgg aagaaagcat tgcaaacctc aataggtcga ccagtgttcc  20220
agagaacccc aagagttcag catccactgc tgtgtctgct gcccccacag ctagttctgc  20280
ggcccccccg accgatgtca gcctggggga cgagctccac ttagacggcg aggacgtggc  20340
gatggcgcat gccgacgcgc tagacgattt cgatctggac atgttggggg acggggattc  20400
cccgggtccg ggatttaccc cccacgactc cgccccctac ggcgctctgg atatggccga  20460
cttcgagttt gagcagatgt ttaccgatgc ccttggaatt gacgagtacg gtgggactag  20520
ctccagctcc tcaacagcaa caacaggacc acctcccaaa ctctgcctgg tgtgctctga  20580
tgaagcttca ggatgtcatt atggagtctt aacttgtgga agctgtaaag ttttcttcaa  20640
aagagcagtg gaaggacagc acaattacct atgtgctgga aggaatgatt gcatcatcga  20700
taaaattcga agaaaaaact gcccagcatg ccgctatcga aaatgtcttc aggctggaat  20760
gaacctggaa gctcgaaaaa caaagaaaaa aataaaagga attgctcgac aaaggcccga  20820
gtgcgtggtg ccggagaacc agtgtgcaat gaaacggaaa gagaaaaagg cgcagaggga  20880
aaaagacaaa ttgcccgtca gtacgacgac agtagacgat cacatgcctc ccatcatgca  20940
atgtgaccct ccgcccccag aggccgctag aattctggaa tgtttgcagc acgaggtggt  21000
gccacgattc ctgaatgaga agctaatgga acagaacaga ttgaagaacg tgccccccct  21060
```

```
cactgccaat cagaagtcgt tgatcgcaag gctcgtgtgg taccaggaag gctatgaaca  21120
accttccgag gaagacctga agagggttac acagtcggac gaggacgacg aagactcgga  21180
tatgccgttc cgtcagatta ccgagatgac gattctcaca gtgcagctca tcgtagaatt  21240
cgctaagggc ctcccgggct tcgccaagat ctcgcagtcg gaccagatca cgttattaaa  21300
ggcgtgctca agtgaggtga tgatgctccg agtggctcgg cggtatgacg cggccaccga  21360
cagcgtactg ttcgcgaaca accaggcgta cactcgcgac aactaccgca aggcaggcat  21420
ggcgtacgtc atcgaggacc tgctgcactt ctgtcggtgc atgtactcca tgatgatgga  21480
taacgtgcat tatgcgctgc ttacagccat tgtcatcttc tcagaccggc ccgggcttga  21540
gcaacccctg ttggtggagg agatccagag atattacctg aacacgctac gggtgtacat  21600
cctgaaccag aacagcgcgt cgccccgctg cgccgtcatc ttcggcaaga tcctgggcat  21660
actgacggag atccgcacgc tgggcatgca gaactccaac atgtgcatct ccctcaagct  21720
gaagaacagg aagctgccgc cgttcctcga ggagatctgg gacgtggcgg acgtggcgac  21780
gacggcgacg ccggtggcgg cggaggcgcc ggcgctctag cccccgcgcc gcccgcccgg  21840
ccgcgcgcac gtctagcgcg cctcaggaga gaacgctcat agactggcta gttttagtga  21900
agtgcacgga cactgacgtc ggacgtgatc aacctattta taaggactgc gaattttacc  21960
acttaagagg gcacacccgt acccgatttc gtacgggaat tcctgcagcc cgggggatcc  22020
ttaattaact cgaggaattc atcgattccg cgggtaccga gctcgatccg tcgacctgca  22080
gatcgttcaa acatttggca ataaagtttc ttaagattga atcctgttgc cggtcttgcg  22140
atgattatca tataatttct gttgaattac gttaagcatg taataattaa catgtaatgc  22200
atgacgttat ttatgagatg ggtttttatg attagagtcc cgcaattata catttaatac  22260
gcgatagaaa acaaaatata gcgcgcaaac taggataaat tatcgcgcgc ggtgtcatct  22320
atgttactag atctggcgcg cccctaggtc tagagtcgac tgtttaaacg             22370
```

```
<210> SEQ ID NO 7
<211> LENGTH: 23111
<212> TYPE: DNA
<213> ORGANISM: Artificial Sequuence
<220> FEATURE:
<223> OTHER INFORMATION: Synthetic Vector

<400> SEQUENCE: 7
```

```
ggggatccgt acgtaagtac gtactcaaaa tgccaacaaa taaaaaaaaa gttgctttaa     60
taatgccaaa acaaattaat aaaacactta caacaccgga ttttttttaa ttaaaatgtg    120
ccatttagga taaatagtta atatttttaa taattattta aaaagccgta tctactaaaa    180
tgatttttat ttggttgaaa atattaatat gtttaaatca acacaatcta tcaaaattaa    240
actaaaaaaa aaataagtgt acgtggttaa cattagtaca gtaatataag aggaaaatga    300
gaaattaaga aattgaaagc gagtctaatt tttaaattat gaacctgcat atataaaagg    360
aaagaaagaa tccaggaaga aaagaaatga aaccatgcat ggtcccctcg tcatcacgag    420
tttctgccat ttgcaataga aacactgaaa cacctttctc tttgtcactt aattgagatg    480
ccgaagccac ctcacaccat gaacttcatg aggtgtagca cccaaggctt ccatagccat    540
gcatactgaa gaatgtctca agctcagcac cctacttctg tgacgtgtcc ctcattcacc    600
ttcctctctt ccctataaat aaccacgcct caggttctcc gcttcacaac tcaaacattc    660
tctccattgg tccttaaaca ctcatcagtc atcaccgcgg ccgcggaatt catggcttct    720
```

-continued

```
atgatatcct cttccgctgt gacaacagtc agccgtgcct ctaggggggca atccgccgca    780
gtggctccat tcggcggcct caaatccatg actggattcc cagtgaagaa ggtcaacact    840
gacattactt ccattacaag caatggtgga agagtaaagt gcatgcaggt gtggcctcca    900
attggaaaga agaagtttga gactctttcc tatttgccac cattgacgag agattctaga    960
gtgactgacg ttgtcatcgt atccgccgcc cgcaccgcgg tcggcaagtt tggcggctcg   1020
ctggccaaga tcccggcacc ggaactgggt gccgtggtca tcaaggccgc gctggagcgc   1080
gccggcgtca agccggagca ggtgagcgaa gtcatcatgg gccaggtgct gaccgccggt   1140
tcgggccaga accccgcacg ccaggccgcg atcaaggccg gcctgccggc gatggtgccg   1200
gccatgacca tcaacaaggt gtgcggctcg ggcctgaagg ccgtgatgct ggccgccaac   1260
gcgatcatgg cgggcgacgc cgagatcgtg gtggccggcg gccaggaaaa catgagcgcc   1320
gccccgcacg tgctgccggg ctcgcgcgat ggtttccgca tgggcgatgc caagctggtc   1380
gacaccatga tcgtcgacgg cctgtgggac gtgtacaacc agtaccacat gggcatcacc   1440
gccgagaacg tggccaagga atacggcatc acacgcgagg cgcaggatga gttcgccgtc   1500
ggctcgcaga acaaggccga agccgcgcag aaggccggca agtttgacga agagatcgtc   1560
ccggtgctga tcccgcagcg caagggcgac ccggtggcct tcaagaccga cgagttcgtg   1620
cgccagggcg ccacgctgga cagcatgtcc ggcctcaagc ccgccttcga caaggccggc   1680
acggtgaccg cggccaacgc ctcgggcctg aacgacggcg ccgccgcggt ggtggtgatg   1740
tcggcggcca aggccaagga actgggcctg accccgctgg ccacgatcaa gagctatgcc   1800
aacgccggtg tcgatcccaa ggtgatgggc atgggcccgg tgccggcctc caagcgcgcc   1860
ctgtcgcgcg ccgagtggac cccgcaagac ctggacctga tggagatcaa cgaggccttt   1920
gccgcgcagg cgctggcggt gcaccagcag atgggctggg acacctccaa ggtcaatgtg   1980
aacggcggcg ccatcgccat cggccacccg atcggcgcgt cgggctgccg tatcctggtg   2040
acgctgctgc acgagatgaa gcgccgtgac gcgaagaagg gcctggcctc gctgtgcatc   2100
ggcggcggca tgggcgtggc gctggcagtc gagcgcaaat aactcgaggc ggccgcagcc   2160
ctttttgtat gtgctacccc acttttgtct ttttggcaat agtgctagca accaataaat   2220
aataataata ataatgaata agaaaacaaa ggctttagct tgccttttgt tcactgtaaa   2280
ataataatgt aagtactctc tataatgagt cacgaaactt ttgcgggaat aaaaggagaa   2340
attccaatga gttttctgtc aaatcttctt ttgtctctct ctctctctct tttttttttt   2400
tctttcttct gagcttcttg caaaacaaaa ggcaaacaat aacgattggt ccaatgatag   2460
ttagcttgat cgatgatatc tttaggaagt gttggcagga caggacatga tgtagaagac   2520
taaaattgaa agtattgcag acccaatagt tgaagattaa ctttaagaat gaagacgtct   2580
tatcaggttc ttcatgactt aagcttaact tttgaggcag agcttgtaaa ttgtaacagg   2640
tgaggtagaa agacggaaag tacttttaat aataaaaggt ttgaaaaatt aagaaaagaa   2700
gaagaaaata ttttgtgagt gcacgcgatg gatctaatcc ttccatgaaa aagaatatca   2760
agaataacaa aaattgacaa aatcagcgaa tacttcaccc aaaagtctac acaataataa   2820
atgctaaatc acatataatt tgtgatgcat aacgcattac gctatcgtaa tcctttacaa   2880
caagcaagaa cgtcatccca gaatctcaac tcaaatcaaa accgttcatt cataaataaa   2940
aaatattctt acattctttt gcaaatagaa cctttgccaa attgaaataa caaactctag   3000
gtatttgtca aattaactta ccaacttctc gttatataat tttagattta taatcatgtc   3060
tataaattat ttctatacac tctctctcaa atttgacctt tacattctgt gatttatttg   3120
```

-continued

```
aacagaataa atcactgtaa aactaaacaa ctctttaaaa aaggtaaatt aggaaaagtc   3180
gaaatcaata aattataaat caatccctag aaaactgcaa gataatattc ttaccaaaat   3240
catttaaata aatttgtaag tttttctttt ataccaattt tctgagaccc agagacattc   3300
ttaaattcat aacaacggtt ttaagtatca gagtataaca tctttgtata aatagatttt   3360
tgaacgttca ataactaaca cgtcagtttt tgtttccacg ttgtacgttt aataacaata   3420
aatgcgtgag ttagattact aatcagaagt tagaagtgta caagactaac tttatacaga   3480
aatatattgt ttcagactgc actttatggt gcgtagcacc tcaaaactct tacctttcgc   3540
atacattttc acacttcatc caaacctttc gaaaagtcac ttcccttata ttaaaggact   3600
atgatataaa aaagactata tgtgttacta atttattggt ttgtatattt gtaataaatc   3660
gttccatcaa gaggagctat cacatattga gaacagtaaa aaaaaaaaaa agttggtaaa   3720
aaaacatttt cttatattat atcataaaat cagttaccat agtattttag agttttcaga   3780
ataatgcttc acccaacttg caactcattg tgcctcaaaa caggacgtaa ccatgttact   3840
cactctcctg cacaacccct tgttaaactg atagcgtgat cagcatgcaa gagaaagatg   3900
attcttgaag catacgataa cagattgaat gtgacaaaaa gtttgtgtct cagcttcagg   3960
gtcggcacct aatacaaaag gaaaatttgt caggtttcct tccgtagttt cattcactat   4020
tattgaatcc tttggctacc attcttgaga aacacaaaca cttcttatat ctgttctaca   4080
caattctctg agtgcgtgcc acagtttggt atcttcatga ttgctcattg ttcatgccca   4140
taaggaacat gtaacttcct catttattta ttattgcttt tgttttcttc tcactagtta   4200
actttcgttt ccctatataa accctccttt gttcccttcc cttcccatct tccatttatt   4260
gattccaaac acaaacctcg agaaaatggc ttctatgata tcctcttccg ctgtgacaac   4320
agtcagccgt gcctctaggg ggcaatccgc cgcagtggct ccattcggcg gcctcaaatc   4380
catgactgga ttcccagtga agaaggtcaa cactgacatt acttccatta caagcaatgg   4440
tggaagagta aagtgcatgc aggtgtggcc tccaattgga aagaagaagt ttgagactct   4500
ttcctatttg ccaccattga cgagagattc tagagtgctc taccaattgc atgagttcca   4560
gcgctcgatc ctgcacccgc tgaccgcgtg ggcccaggcg accgccaaga ccttcaccaa   4620
ccccctcagc ccgctctcgc tggttcccgg cgcaccccgc ctggctgccg gctatgaact   4680
gctgtaccgg ctcggcaagg aatacgaaaa gccggcattc gacatcaagt cggtgcgctc   4740
caacgggcgc gacatcccca tcgtcgagca gaccgtgctt gaaaagccgt tctgcaagct   4800
ggtgcgcttc aagcgctatg ccgacgaccc ggagaccatc aagctgctca aggatgagcc   4860
ggtggtgctg gtggccgcgc cgctgtcggg ccaccatgcc acgctgctgc gcgacacggt   4920
gcgcacgctg ctccaggacc acaaggtcta cgtcaccgac tggatcgacg cacgcatggt   4980
gccggtcgag gaaggcgcgt tccacctgtc ggactacatc tactacatcc aggagttcat   5040
ccgccatatc ggcgccgaga acctgcatgt gatctcggta tgccagccca ccgtgccggt   5100
gctggccgcg atctcgctga tggcctcggc cggcgagaag acgccgcgca ccatgaccat   5160
gatgggcggc ccgatcgacg cccgcaagag ccccacggcg gtcaactcgc tggcgaccaa   5220
caagtcgttc gagtggttcg agaacaacgt catctacacc gtgccggcca actaccccgg   5280
ccacggccgc cgcgtctacc caggcttttt gcagcatgcc ggtttcgtgg cgatgaaccc   5340
ggaccggcac ctttcctcgc actatgactt ctacctgagc ctggtcgagg gcgatgcgga   5400
tgacgccgaa gcccacgtgc gcttctacga cgaatacaac gcggtgctcg acatggccgc   5460
```

cgagtactac ctcgacacca tccgcgaggt gttccaggag ttccgcctgg ccaacggcac 5520
ctgggccatc gacggcaatc cggtccggcc gcaggacatc aagagcaccg cgctgatgac 5580
cgtcgagggc gaactggacg acatctcggg cgcgggccag accgcagcgg cgcacgacct 5640
gtgcgccggc atcccgaaaa tccgcaagca gcacctgaac gcggcacact gcggccacta 5700
cggcatcttc tcgggccggc gctggcgcga agagatatac ccgcagctgc gcgactttat 5760
ccgcaagtac caccaggcct cggccaccag gtaagagctc gaattgatcc tctagagctt 5820
tcgttcgtat catcggtttc gacaacgttc gtcaagttca atgcatcagt ttcattgcgc 5880
acacaccaga atcctactga gttcgagtat tatggcattg ggaaaactgt ttttcttgta 5940
ccatttgttg tgcttgtaat ttactgtgtt ttttattcgg ttttcgctat cgaactgtga 6000
aatggaaatg gatggagaag agttaatgaa tgatatggtc cttttgttca ttctcaaatt 6060
aatattattt gtttttttctc ttatttgttg tgtgttgaat ttgaaattat aagagatatg 6120
caaacatttt gttttgagta aaaatgtgtc aaatcgtggc ctctaatgac cgaagttaat 6180
atgaggagta aaacacttgt agttgtacca ttatgcttat tcactaggca acaaatatat 6240
tttcagacct agaaaagctg caaatgttac tgaatacaag tatgtcctct tgtgttttag 6300
acatttatga actttccttt atgtaatttt ccagaatcct tgtcagattc taatcattgc 6360
tttataatta tagttatact catggatttg tagttgagta tgaaaatatt ttttaatgca 6420
ttttatgact tgccaattga ttgacaacat gcatcagtcg acctgaggta attataaccc 6480
gggccctata tatggatcca acttttgagg cagagcttgt aaattgtaac aggtgaggta 6540
gaaagacgga aagtactttt aataataaaa ggtttgaaaa attaagaaaa gaagaagaaa 6600
atattttgtg agtgcacgcg atggatctaa tccttccatg aaaaagaata tcaagaataa 6660
caaaaattga caaaatcagc gaatacttca cccaaaagtc tacacaataa taaatgctaa 6720
atcacatata atttgtgatg cataacgcat tacgctatcg taatccttta caacaagcaa 6780
gaacgtcatc ccagaatctc aactcaaatc aaaaccgttc attcataaat aaaaaatatt 6840
cttacattct tttgcaaata gaacctttgc caaattgaaa taacaaactc taggtatttg 6900
tcaaattaac ttaccaactt ctcgttatat aattttagat ttataatcat gtctataaat 6960
tatttctata cactctctct caaatttgac ctttacattc tgtgatttat ttgaacagaa 7020
taaatcactg taaaactaaa caactcttta aaaaaggtaa attaggaaaa gtcgaaatca 7080
ataaattata aatcaatccc tagaaaactg caagataata ttcttaccaa aatcatttaa 7140
ataaatttgt aagttttttc tttataccaa ttttctgaga cccagagaca ttcttaaatt 7200
cataacaacg gttttaagta tcagagtata acatctttgt ataaatagat ttttgaacgt 7260
tcaataacta acacgtcagt ttttgtttcc acgttgtacg tttaataaca ataaatgcgt 7320
gagttagatt actaatcaga agttagaagt gtacaagact aactttatac agaaatatat 7380
tgtttcagac tgcactttat ggtgcgtagc acctcaaaac tcttaccttt cgcatacatt 7440
ttcacacttc atccaaacct ttcgaaaagt cacttccctt atattaaagg actatgatat 7500
aaaaaagact atatgtgtta ctaatttatt ggtttgtata tttgtaataa atcgttccat 7560
caagaggagc tatcacatat tgagaacagt aaaaaaaaaa aaaagttggt aaaaaaacat 7620
tttcttatat tatatcataa aatcagttac catagtattt tagagttttc agaataatgc 7680
ttcacccaac ttgcaactca ttgtgcctca aaacaggacg taaccatgtt actcactctc 7740
ctgcacaacc ccttgttaaa ctgatagcgt gatcagcatg caagagaaag atgattcttg 7800
aagcatacga taacagattg aatgtgacaa aaagtttgtg tctcagcttc agggtcggca 7860

```
cctaatacaa aaggaaaatt tgtcaggttt ccttccgtag tttcattcac tattattgaa   7920
tcctttggct accattcttg agaaacacaa acacttctta tatctgttct acacaattct   7980
ctgagtgcgt gccacagttt ggtatcttca tgattgctca ttgttcatgc ccataaggaa   8040
catgtaactt cctcatttat ttattattgc ttttgttttc ttctcactag ttaactttcg   8100
tttccctata taaaccctcc tttgttccct tcccttccca tcttccattt attgattcca   8160
aacacaaacc tcgagaaaat ggcttctatg atatcctctt ccgctgtgac aacagtcagc   8220
cgtgcctcta gggggcaatc cgccgcagtg gctccattcg gcggcctcaa atccatgact   8280
ggattcccag tgaagaaggt caacactgac attacttcca ttacaagcaa tggtggaaga   8340
gtaaagtgca tgcaggtgtg gcctccaatt ggaaagaaga agtttgagac tctttcctat   8400
ttgccaccat tgacgagaga ttctagagtg ctcaaaggaa aagtcgcagt cgtcaccggt   8460
tccaccagcg ggatcggcct gggtatcgcc accgcgctgg ccgcgcaggg cgccgatatc   8520
gtcctgaacg gcttcggcga cgccgccgag atcgaaaagg tgcgcgccgg cctggccgcc   8580
cagcatggcg tcaaggtgct gtacgacggc gccgacctgt ccaagggcga ggccgtgcgc   8640
ggcctggtgg acaacgcggt gcgccagatg ggccgcatcg acatcctggt caacaacgcc   8700
ggcatccagc acaccgcgct gatcgaggac tttcccaccg aaaaatggga cgccatcctg   8760
gcgctgaacc tgtcggccgt gttccacggc accgccgccg cgctgccgca catgaagaag   8820
cagggcttcg gccgcatcat caacatcgcc tcggcgcacg gcctggtggc ctcggccaac   8880
aagtcggcct acgtcgccgc caagcacggc gtggtgggct tcaccaaggt gaccgcgctg   8940
gaaaccgccg gccagggcat caccgccaac gccatctgcc caggctgggt gcgcactccg   9000
ctggtcgaaa agcagatatc ggcgctggcc gaaaagaacg gcgtggacca ggaaaccgcc   9060
gcgcgcgaac tgctcagcga aaagcagccg tcgctgcaat tcgtcacgcc cgaacaactg   9120
ggcggcacgg ccgtcttcct ggcctccgat gccgccgcgc aaatcaccgg cacgaccgtc   9180
tccgtcgatg gcggctggac ggcgcgctga gagctcgctt tcgttcgtat catcggtttc   9240
gacaacgttc gtcaagttca atgcatcagt ttcattgcgc acacaccaga atcctactga   9300
gttcgagtat tatggcattg ggaaaactgt ttttcttgta ccatttgttg tgcttgtaat   9360
ttactgtgtt ttttattcgg ttttcgctat cgaactgtga aatggaaatg gatggagaag   9420
agttaatgaa tgatatggtc cttttgttca ttctcaaatt aatattattt gtttttctc    9480
ttatttgttg tgtgttgaat ttgaaattat aagagatatg caaacatttt gttttgagta   9540
aaaatgtgtc aaatcgtggc ctctaatgac cgaagttaat atgaggagta aaacacttgt   9600
agttgtacca ttatgcttat tcactaggca acaaatatat tttcagacct agaaaagctg   9660
caaatgttac tgaatacaag tatgtcctct tgtgttttag acatttatga actttccttt   9720
atgtaatttt ccagaatcct tgtcagattc taatcattgc tttataatta tagttatact   9780
catggatttg tagttgagta tgaaaatatt ttttaatgca ttttatgact tgccaattga   9840
ttgacaacat gcatcagcta gtagaaggta attatccaag atgtagcatc aagaatccaa   9900
tgtttacggg aaaaactatg gaagtattat gtgagctcag caagaagcag atcaatatgc   9960
ggcacatatg caacctatgt tcaaaaatga agaatgtaca gatacaagat cctatactgc  10020
cagaatacga agaagaatac gtagaaattg aaaaagaaga accaggcgaa gaaaagaatc  10080
ttgaagacgt aagcactgac gacaacaatg aaaagaagaa gataaggtcg gtgattgtga  10140
aagagacata gaggacacat gtaaggtgga aaatgtaagg gcggaaagta accttatcac  10200
```

-continued

```
aaaggaatct tatcccccac tacttatcct tttatatttt tccgtgtcat ttttgccctt  10260
gagttttcct atataaggaa ccaagttcgg catttgtgaa aacaagaaaa aattggtgta  10320
agctattttc tttgaagtac tgaggataca acttcagaga aatttgtaag aaagtggatc  10380
gaaaccatgg cctcctccga gaacgtcatc accgagttca tgcgcttcaa ggtgcgcatg  10440
gagggcaccg tgaacggcca cgagttcgag atcgagggcg agggcgaggg ccgcccctac  10500
gagggccaca acaccgtgaa gctgaaggtg accaagggcg gcccccctgcc cttcgcctgg  10560
gacatcctgt ccccccagtt ccagtacggc tccaaggtgt acgtgaagca ccccgccgac  10620
atccccgact acaagaagct gtccttcccc gagggcttca agtgggagcg cgtgatgaac  10680
ttcgaggacg gcggcgtggc gaccgtgacc caggactcct ccctgcagga cggctgcttc  10740
atctacaagg tgaagttcat cggcgtgaac ttcccctccg acggccccgt gatgcagaag  10800
aagaccatgg gctgggaggc ctccaccgag cgcctgtacc cccgcgacgg cgtgctgaag  10860
ggcgagaccc acaaggccct gaagctgaag gacggcggcc actacctggt ggagttcaag  10920
tccatctaca tggccaagaa gcccgtgcag ctgcccggct actactacgt ggacgccaag  10980
ctggacatca cctcccacaa cgaggactac accatcgtgg agcagtacga gcgcaccgag  11040
ggccgccacc acctgttcct ggtaccaatg agctctgtcc aacagtctca gggttaatgt  11100
ctatgtatct taaataatgt tgtcggcgat cgttcaaaca tttggcaata aagtttctta  11160
agattgaatc ctgttgccgg tcttgcgatg attatcatat aatttctgtt gaattacgtt  11220
aagcatgtaa taattaacat gtaatgcatg acgttattta tgagatgggt ttttatgatt  11280
agagtcccgc aattatacat ttaatacgcg atagaaaaca aaatatagcg cgcaaactag  11340
gataaattat cgcgcgcggt gtcatctatg ttactagatc gggaattaaa ctatcagtgt  11400
ttgacaggat atattggcgg gtaaacctaa gagaaaagag cgtttattag aataacggat  11460
atttaaaagg gcgtgaaaag gtttatccgt tcgtccattt gtatgtgcat gccaaccaca  11520
gggttcccct cgggatcaaa gtactttgat ccaacccctc cgctgctata gtgcagtcgg  11580
cttctgacgt tcagtgcagc cgtcttctga aaacgacatg tcgcacaagt cctaagttac  11640
gcgacaggct gccgccctgc ccttttcctg gcgttttctt gtcgcgtgtt ttagtcgcat  11700
aaagtagaat acttgcgact agaaccggag acattacgcc atgaacaaga gcgccgccgc  11760
tggcctgctg ggctatgccc gcgtcagcac cgacgaccag gacttgacca accaacgggc  11820
cgaactgcac gcggccggct gcaccaagct gttttccgag aagatcaccg gcaccaggcg  11880
cgaccgcccg gagctggcca ggatgcttga ccacctacgc cctggcgacg ttgtgacagt  11940
gaccaggcta gaccgcctgg cccgcagcac ccgcgaccta ctggacattg ccgagcgcat  12000
ccaggaggcc ggcgcgggcc tgcgtagcct ggcagagccg tgggccgaca ccaccacgcc  12060
ggccggccgc atggtgttga ccgtgttcgc cggcattgcc gagttcgagc gttccctaat  12120
catcgaccgc acccggagcg ggcgcgaggc cgccaaggcc cgaggcgtga agtttggccc  12180
ccgccctacc ctcaccccgg cacagatcgc gcacgcccgc gagctgatcg accaggaagg  12240
ccgcaccgtg aaagaggcgg ctgcactgct tggcgtgcat cgctcgaccc tgtaccgcgc  12300
acttgagcgc agcgaggaag tgacgcccac cgaggccagg cggcgcggtg ccttccgtga  12360
ggacgcattg accgaggccg acgccctggc ggccgccgag aatgaacgcc aagaggaaca  12420
agcatgaaac cgcaccagga cggccaggac gaaccgtttt tcattaccga agagatcgag  12480
gcggagatga tcgcggccgg gtacgtgttc gagccgcccg cgcacgtctc aaccgtgcgg  12540
ctgcatgaaa tcctggccgg tttgtctgat gccaagctgg cggcctggcc ggccagcttg  12600
```

gccgctgaag aaaccgagcg ccgccgtcta aaaaggtgat gtgtatttga gtaaaacagc 12660
ttgcgtcatg cggtcgctgc gtatatgatg cgatgagtaa ataaacaaat acgcaagggg 12720
aacgcatgaa ggttatcgct gtacttaacc agaaaggcgg gtcaggcaag acgaccatcg 12780
caacccatct agcccgcgcc ctgcaactcg ccggggccga tgttctgtta gtcgattccg 12840
atccccaggg cagtgcccgc gattgggcgg ccgtgcggga agatcaaccg ctaaccgttg 12900
tcggcatcga ccgcccgacg attgaccgcg acgtgaaggc catcggccgg cgcgacttcg 12960
tagtgatcga cggagcgccc caggcggcgg acttggctgt gtccgcgatc aaggcagccg 13020
acttcgtgct gattccggtg cagccaagcc cttacgacat atgggccacc gccgacctgg 13080
tggagctggt taagcagcgc attgaggtca cggatggaag gctacaagcg gcctttgtcg 13140
tgtcgcgggc gatcaaaggc acgcgcatcg gcggtgaggt tgccgaggcg ctggccgggt 13200
acgagctgcc cattcttgag tcccgtatca cgcagcgcgt gagctaccca ggcactgccg 13260
ccgccggcac aaccgttctt gaatcagaac ccgagggcga cgctgcccgc gaggtccagg 13320
cgctggccgc tgaaattaaa tcaaaactca tttgagttaa tgaggtaaag agaaaatgag 13380
caaaagcaca aacacgctaa gtgccggccg tccgagcgca cgcagcagca aggctgcaac 13440
gttggccagc ctggcagaca cgccagccat gaagcgggtc aactttcagt tgccggcgga 13500
ggatcacacc aagctgaaga tgtacgcggt acgccaaggc aagaccatta ccgagctgct 13560
atctgaatac atcgcgcagc taccagagta aatgagcaaa tgaataaatg agtagatgaa 13620
ttttagcggc taaaggaggc ggcatggaaa atcaagaaca accaggcacc gacgccgtgg 13680
aatgccccat gtgtggagga acgggcggtt ggccaggcgt aagcggctgg gttgtctgcc 13740
ggccctgcaa tggcactgga acccccaagc ccgaggaatc ggcgtgacgg tcgcaaacca 13800
tccggcccgg tacaaatcgg cgcggcgctg ggtgatgacc tggtggagaa gttgaaggcc 13860
gcgcaggccg cccagcggca acgcatcgag gcagaagcac gccccggtga atcgtggcaa 13920
gcggccgctg atcgaatccg caaagaatcc cggcaaccgc cggcagccgg tgcgccgtcg 13980
attaggaagc cgcccaaggg cgacgagcaa ccagattttt tcgttccgat gctctatgac 14040
gtgggcaccc gcgatagtcg cagcatcatg gacgtggccg ttttccgtct gtcgaagcgt 14100
gaccgacgag ctggcgaggt gatccgctac gagcttccag acgggcacgt agaggtttcc 14160
gcagggccgg ccggcatggc cagtgtgtgg gattacgacc tggtactgat ggcggtttcc 14220
catctaaccg aatccatgaa ccgataccgg gaagggaagg gagacaagcc cggccgcgtg 14280
ttccgtccac acgttgcgga cgtactcaag ttctgccggc gagccgatgg cggaaagcag 14340
aaagacgacc tggtagaaac ctgcattcgg ttaaacacca cgcacgttgc catgcagcgt 14400
acgaagaagg ccaagaacgg ccgcctggtg acggtatccg agggtgaagc cttgattagc 14460
cgctacaaga tcgtaaagag cgaaaccggg cggccggagt acatcgagat cgagctagct 14520
gattggatgt accgcgagat cacagaaggc aagaacccgg acgtgctgac ggttcacccc 14580
gattactttt tgatcgatcc cggcatcggc cgttttctct accgcctggc acgccgcgcc 14640
gcaggcaagg cagaagccag atggttgttc aagacgatct acgaacgcag tggcagcgcc 14700
ggagagttca agaagttctg tttcaccgtg cgcaagctga tcgggtcaaa tgacctgccg 14760
gagtacgatt tgaaggagga ggcggggcag gctggcccga tcctagtcat gcgctaccgc 14820
aacctgatcg agggcgaagc atccgccggt tcctaatgta cggagcagat gctagggcaa 14880
attgccctag caggggaaaa aggtcgaaaa ggtctctttc ctgtggatag cacgtacatt 14940
gggaacccaa agccgtacat tgggaaccgg aacccgtaca ttgggaaccc aaagccgtac 15000
attgggaacc ggtcacacat gtaagtgact gatataaaag agaaaaaagg cgatttttcc 15060
gcctaaaact ctttaaaact tattaaaact cttaaaaccc gcctggcctg tgcataactg 15120
tctggccagc gcacagccga agagctgcaa aaagcgccta cccttcggtc gctgcgctcc 15180
ctacgccccg ccgcttcgcg tcggcctatc gcggccgctg gccgctcaaa aatggctggc 15240
ctacggccag gcaatctacc agggcgcgga caagccgcgc cgtcgccact cgaccgccgg 15300
cgcccacatc aaggcaccct gcctcgcgcg tttcggtgat gacggtgaaa acctctgaca 15360
catgcagctc ccggagacgg tcacagcttg tctgtaagcg gatgccggga gcagacaagc 15420
ccgtcagggc gcgtcagcgg gtgttggcgg gtgtcggggc gcagccatga cccagtcacg 15480
tagcgatagc ggagtgtata ctggcttaac tatgcggcat cagagcagat tgtactgaga 15540
gtgcaccata tgcggtgtga aataccgcac agatgcgtaa ggagaaaata ccgcatcagg 15600
cgctcttccg cttcctcgct cactgactcg ctgcgctcgg tcgttcggct gcggcgagcg 15660
gtatcagctc actcaaaggc ggtaatacgg ttatccacag aatcagggga taacgcagga 15720
aagaacatgt gagcaaaagg ccagcaaaag gccaggaacc gtaaaaaggc cgcgttgctg 15780
gcgtttttcc ataggctccg cccccctgac gagcatcaca aaaatcgacg ctcaagtcag 15840
aggtggcgaa acccgacagg actataaaga taccaggcgt ttccccctgg aagctccctc 15900
gtgcgctctc ctgttccgac cctgccgctt accggatacc tgtccgcctt tctcccttcg 15960
ggaagcgtgg cgctttctca tagctcacgc tgtaggtatc tcagttcggt gtaggtcgtt 16020
cgctccaagc tgggctgtgt gcacgaaccc cccgttcagc ccgaccgctg cgccttatcc 16080
ggtaactatc gtcttgagtc caacccggta agacacgact tatcgccact ggcagcagcc 16140
actggtaaca ggattagcag agcgaggtat gtaggcggtg ctacagagtt cttgaagtgg 16200
tggcctaact acggctacac tagaaggaca gtatttggta tctgcgctct gctgaagcca 16260
gttaccttcg gaaaaagagt tggtagctct tgatccggca aacaaaccac cgctggtagc 16320
ggtggttttt ttgtttgcaa gcagcagatt acgcgcagaa aaaaaggatc tcaagaagat 16380
cctttgatct tttctacggg gtctgacgct cagtggaacg aaaactcacg ttaagggatt 16440
ttggtcatgc attctaggta ctaaaacaat tcatccagta aaatataata ttttattttc 16500
tcccaatcag gcttgatccc cagtaagtca aaaaatagct cgacatactg ttcttccccg 16560
atatcctccc tgatcgaccg gacgcagaag gcaatgtcat accacttgtc cgccctgccg 16620
cttctcccaa gatcaataaa gccacttact ttgccatctt tcacaaagat gttgctgtct 16680
cccaggtcgc cgtgggaaaa gacaagttcc tcttcgggct tttccgtctt taaaaaatca 16740
tacagctcgc gcggatcttt aaatggagtg tcttcttccc agttttcgca atccacatcg 16800
gccagatcgt tattcagtaa gtaatccaat tcggctaagc ggctgtctaa gctattcgta 16860
tagggacaat ccgatatgtc gatggagtga aagagcctga tgcactccgc atacagctcg 16920
ataatctttt cagggctttg ttcatcttca tactcttccg agcaaaggac gccatcggcc 16980
tcactcatga gcagattgct ccagccatca tgccgttcaa agtgcaggac ctttggaaca 17040
ggcagctttc cttccagcca tagcatcatg tccttttccc gttccacatc ataggtggtc 17100
cctttatacc ggctgtccgt catttttaaa tataggtttt cattttctcc caccagctta 17160
tataccttag caggagacat tccttccgta tcttttacgc agcggtattt ttcgatcagt 17220
tttttcaatt ccggtgatat tctcatttta gccatttatt atttccttcc tcttttctac 17280
agtatttaaa gataccccaa gaagctaatt ataacaagac gaactccaat tcactgttcc 17340

-continued

```
ttgcattcta aaaccttaaa taccagaaaa cagctttttc aaagttgttt tcaaagttgg  17400
cgtataacat agtatcgacg gagccgattt tgaaaccgcg gtgatcacag gcagcaacgc  17460
tctgtcatcg ttacaatcaa catgctaccc tccgcgagat catccgtgtt tcaaacccgg  17520
cagcttagtt gccgttcttc cgaatagcat cggtaacatg agcaaagtct gccgccttac  17580
aacggctctc ccgctgacgc cgtcccggac tgatgggctg cctgtatcga gtggtgattt  17640
tgtgccgagc tgccggtcgg ggagctgttg gctggctggt ggcaggatat attgtggtgt  17700
aaacaaattg acgcttagac aacttaataa cacattgcgg acgtttttaa tgtactgaat  17760
taacgccgaa ttaattccta ggccaccatg ttgggcccgg ggcgcgccgt acgtagtgtt  17820
tatctttgtt gcttttctga acaatttatt tactatgtaa atatattatc aatgtttaat  17880
ctattttaat ttgcacatga attttcattt tatttttact ttacaaaaca aataaatata  17940
tatgcaaaaa aatttacaaa cgatgcacgg gttacaaact aatttcatta aatgctaatg  18000
cagattttgt gaagtaaaac tccaattatg atgaaaaata ccaccaacac cacctgcgaa  18060
actgtatccc aactgtcctt aataaaaatg ttaaaaagta tattattctc atttgtctgt  18120
cataatttat gtaccccact ttaatttttc tgatgtacta aaccgagggc aaactgaaac  18180
ctgttcctca tgcaaagccc ctactcacca tgtatcatgt acgtgtcatc acccaacaac  18240
tccacttttg ctatataaca acacccccgt cacactctcc ctctctaaca cacaccccac  18300
taacaattcc ttcacttgca gcactgttgc atcatcatct tcattgcaaa accctaaact  18360
tcaccttcaa ccgcggccgc atggcttcta tgatatcctc ttccgctgtg acaacagtca  18420
gccgtgcctc taggggggcaa tccgccgcag tggctccatt cggcggcctc aaatccatga  18480
ctggattccc agtgaagaag gtcaacactg acattacttc cattacaagc aatggtggaa  18540
gagtaaagtg catgcaggtg tggcctccaa ttggaaagaa gaagtttgag actctttcct  18600
atttgccacc attgacgaga gattctagag tgagtaacaa gaacaacgat gagctgcagt  18660
ggcaatcctg gttcagcaag gcgcccacca ccgaggcgaa cccgatggcc accatgttgc  18720
aggatatcgg cgttgcgctc aaaccggaag cgatggagca gctgaaaaac gattatctgc  18780
gtgacttcac cgcgttgtgg caggattttt tggctggcaa ggcgccagcc gtcagcgacc  18840
gccgcttcag ctcggcagcc tggcagggca atccgatgtc ggccttcaat gccgcatctt  18900
acctgctcaa cgccaaattc ctcagtgcca tggtggaggc ggtggacacc gcaccccagc  18960
aaaagcagaa aatacgcttt gccgtgcagc aggtgattga tgccatgtcg cccgcgaact  19020
tcctcgccac caacccggaa gcgcagcaaa aactgattga aaccaagggc gagagcctga  19080
cgcgtggcct ggtcaatatg ctgggcgata tcaacaaggg ccatatctcg ctgtcggacg  19140
aatcggcctt tgaagtgggc cgcaacctgg ccattacccc gggcaccgtg atttacgaaa  19200
atccgctgtt ccagctgatc cagtacacgc cgaccacgcc gacggtcagc cagcgcccgc  19260
tgttgatggt gccgccgtgc atcaacaagt tctacatcct cgacctgcaa ccggaaaatt  19320
cgctggtgcg ctacgcggtg gagcagggca acaccgtgtt cctgatctcg tggagcaatc  19380
cggacaagtc gctggccggc accacctggg acgactacgt ggagcagggc gtgatcgaag  19440
cgatccgcat cgtccaggac gtcagcggcc aggacaagct gaacatgttc ggcttctgcg  19500
tgggcggcac catcgttgcc accgcactgg cggtactggc ggcgcgtggc cagcacccgg  19560
cggccagcct gaccctgctg accaccttcc tcgacttcag cgacaccggc gtgctcgacg  19620
tcttcgtcga tgaaacccag gtcgcgctgc gtgaacagca attgcgcgat ggcggcctga  19680
```

-continued tgccgggccg tgacctggcc tcgaccttct cgagcctgcg tccgaacgac ctggtatgga 19740
actatgtgca gtcgaactac ctcaaaggca atgagccggc ggcgtttgac ctgctgttct 19800
ggaattcgga cagcaccaat ttgccgggcc cgatgttctg ctggtacctg cgcaacacct 19860
acctggaaaa cagcctgaaa gtgccgggca agctgacggt ggccggcgaa aagatcgacc 19920
tcggcctgat cgacgccccg gccttcatct acggttcgcg cgaagaccac atcgtgccgt 19980
ggatgtcggc gtacggttcg ctcgacatcc tcaaccaggg caagccgggc gccaaccgct 20040
tcgtgctggg cgcgtccggc catatcgccg gcgtgatcaa ctcggtggcc aagaacaagc 20100
gcagctactg gatcaacgac ggtggcgccg ccgatgccca ggcctggttc gatggcgcgc 20160
aggaagtgcc gggcagctgg tggccgcaat gggccgggtt cctgacccag catggcggca 20220
agaaggtcaa gcccaaggcc aagcccggca acgcccgcta caccgcgatc gaggcggcgc 20280
ccggccgtta cgtcaaagcc aagggctgag cggccgctga gtaattctga tattagaggg 20340
agcattaatg tgttgttgtg atgtggttta tatggggaaa ttaaataaat gatgtatgta 20400
cctcttgcct atgtaggttt gtgtgttttg ttttgttgtc tagctttggt tattaagtag 20460
tagggacgtt cgttcgtgtc tcaaaaaaag gggtactacc actctgtagt gtatatggat 20520
gctggaaatc aatgtgtttt gtatttgttc acctccattg ttgaattcaa tgtcaaatgt 20580
gttttgcgtt ggttatgtgt aaaattacta tctttctcgt ccgatgatca aagttttaag 20640
caacaaaacc aagggtgaaa tttaaactgt gctttgttga agattctttt atcatattga 20700
aaatcaaatt actagcagca gattttacct agcatgaaat tttatcaaca gtacagcact 20760
cactaaccaa gttccaaact aagatgcgcc attaacatca gccaataggc attttcagca 20820
aggcgcgccc gcgccgatgt atgtgacaac cctcgggatt gttgatttat ttcaaaacta 20880
agagtttttg tcttattgtt ctcgtctatt ttggatatca atcttagttt tatatctttt 20940
ctagttctct acgtgttaaa tgttcaacac actagcaatt tggcctgcca gcgtatggat 21000
tatggaacta tcaagtctgt gacgcgccgt acgtagtgtt tatctttgtt gcttttctga 21060
acaatttatt tactatgtaa atatattatc aatgtttaat ctattttaat ttgcacatga 21120
attttcattt tatttttact ttacaaaaca aataaatata tatgcaaaaa aatttacaaa 21180
cgatgcacgg gttacaaact aatttcatta aatgctaatg cagattttgt gaagtaaaac 21240
tccaattatg atgaaaaata ccaccaacac cacctgcgaa actgtatccc aactgtcctt 21300
aataaaaatg ttaaaaagta tattattctc atttgtctgt cataatttat gtaccccact 21360
ttaatttttc tgatgtacta aaccgagggc aaactgaaac ctgttcctca tgcaaagccc 21420
ctactcacca tgtatcatgt acgtgtcatc acccaacaac tccacttttg ctatataaca 21480
acacccccgt cacactctcc ctctctaaca cacaccccac taacaattcc ttcacttgca 21540
gcactgttgc atcatcatct tcattgcaaa accctaaact tcaccttcaa ccgcggccgc 21600
atggcttcta tgatatcctc ttccgctgtg acaacagtca gccgtgcctc taggggggcaa 21660
tccgccgcag tggctccatt cggcggcctc aaatccatga ctggattccc agtgaagaag 21720
gtcaacactg acattacttc cattacaagc aatggtggaa gagtaaagtg catgcaggtg 21780
tggcctccaa ttggaaagaa gaagtttgag actctttcct atttgccacc attgacgaga 21840
gattctagag tgactcagcg cattgcgtat gtgaccggcg gcatgggtgg tatcggaacc 21900
gccatttgcc agcggctggc caaggatggc tttcgtgtgg tggccggttg cggccccaac 21960
tcgccgcgcc gcgaaaagtg gctggagcag cagaaggccc tgggcttcga tttcattgcc 22020
tcggaaggca atgtggctga ctgggactcg accaagaccg cattcgacaa ggtcaagtcc 22080
gaggtcggcg aggttgatgt gctgatcaac aacgccggta tcacccgcga cgtggtgttc 22140
cgcaagatga cccgcgccga ctgggatgcg gtgatcgaca ccaacctgac ctcgctgttc 22200
aacgtcacca agcaggtgat cgacggcatg gccgaccgtg gctggggccg catcgtcaac 22260
atctcgtcgg tgaacgggca gaagggccag ttcggccaga ccaactactc caccgccaag 22320
gccggcctgc atggcttcac catggcactg gcgcaggaag tggcgaccaa gggcgtgacc 22380
gtcaacacgg tctctccggg ctatatcgcc accgacatgg tcaaggcgat ccgccaggac 22440
gtgctcgaca agatcgtcgc gacgatcccg gtcaagcgcc tgggcctgcc ggaagagatc 22500
gcctcgatct gcgcctggtt gtcgtcggag gagtccggtt tctcgaccgg cgccgacttc 22560
tcgctcaacg gcggcctgca tatgggctga gcggccgctg agtaattctg atattagagg 22620
gagcattaat gtgttgttgt gatgtggttt atatggggaa attaaataaa tgatgtatgt 22680
acctcttgcc tatgtaggtt tgtgtgtttt gttttgttgt ctagctttgg ttattaagta 22740
gtagggacgt tcgttcgtgt ctcaaaaaaa ggggtactac cactctgtag tgtatatgga 22800
tgctggaaat caatgtgttt tgtatttgtt cacctccatt gttgaattca atgtcaaatg 22860
tgttttgcgt tggttatgtg taaaattact atctttctcg tccgatgatc aaagttttaa 22920
gcaacaaaac caagggtgaa atttaaactg tgctttgttg aagattcttt tatcatattg 22980
aaaatcaaat tactagcagc agattttacc tagcatgaaa ttttatcaac agtacagcac 23040
tcactaacca agttccaaac taagatgcgc cattaacatc agccaatagg cattttcagc 23100
aaggcgcgta a 23111

<210> SEQ ID NO 8
<211> LENGTH: 23068
<212> TYPE: DNA
<213> ORGANISM: Artificial Sequence
<220> FEATURE:
<223> OTHER INFORMATION: Synthetic Vector

<400> SEQUENCE: 8
ggggatccgt acgtaagtac gtactcaaaa tgccaacaaa taaaaaaaaa gttgctttaa 60
taatgccaaa acaaattaat aaaacactta caacaccgga ttttttttaa ttaaaatgtg 120
ccatttagga taaatagtta atatttttaa taattattta aaaagccgta tctactaaaa 180
tgatttttat ttggttgaaa atattaatat gtttaaatca acacaatcta tcaaaattaa 240
actaaaaaaa aaataagtgt acgtggttaa cattagtaca gtaatataag aggaaaatga 300
gaaattaaga aattgaaagc gagtctaatt tttaaattat gaacctgcat atataaaagg 360
aaagaaagaa tccaggaaga aaagaaatga aaccatgcat ggtcccctcg tcatcacgag 420
tttctgccat ttgcaataga aacactgaaa cacctttctc tttgtcactt aattgagatg 480
ccgaagccac ctcacaccat gaacttcatg aggtgtagca cccaaggctt ccatagccat 540
gcatactgaa gaatgtctca agctcagcac cctacttctg tgacgtgtcc ctcattcacc 600
ttcctctctt ccctataaat aaccacgcct caggttctcc gcttcacaac tcaaacattc 660
tctccattgg tccttaaaca ctcatcagtc atcaccgcgg ccgcggaatt catggcttct 720
atgatatcct cttccgctgt gacaacagtc agccgtgcct ctagggggca atccgccgca 780
gtggctccat tcggcggcct caaatccatg actggattcc cagtgaagaa ggtcaacact 840
gacattactt ccattacaag caatggtgga agagtaaagt gcatgcaggt gtggcctcca 900
attggaaaga agaagtttga gactctttcc tatttgccac cattgacgag agattctaga 960

-continued

```
gtgactgacg ttgtcatcgt atccgccgcc cgcaccgcgg tcggcaagtt tggcggctcg   1020
ctggccaaga tcccggcacc ggaactgggt gccgtggtca tcaaggccgc gctggagcgc   1080
gccggcgtca agccggagca ggtgagcgaa gtcatcatgg gccaggtgct gaccgccggt   1140
tcgggccaga accccgcacg ccaggccgcg atcaaggccg gcctgccggc gatggtgccg   1200
gccatgacca tcaacaaggt gtgcggctcg ggcctgaagg ccgtgatgct ggccgccaac   1260
gcgatcatgg cgggcgacgc cgagatcgtg gtggccggcg gccaggaaaa catgagcgcc   1320
gccccgcacg tgctgccggg ctcgcgcgat ggtttccgca tgggcgatgc caagctggtc   1380
gacaccatga tcgtcgacgg cctgtgggac gtgtacaacc agtaccacat gggcatcacc   1440
gccgagaacg tggccaagga atacggcatc acacgcgagg cgcaggatga gttcgccgtc   1500
ggctcgcaga acaaggccga agccgcgcag aaggccggca agtttgacga agagatcgtc   1560
ccggtgctga tcccgcagcg caagggcgac ccggtggcct tcaagaccga cgagttcgtg   1620
cgccagggcg ccacgctgga cagcatgtcc ggcctcaagc ccgccttcga caaggccggc   1680
acggtgaccg cggccaacgc ctcgggcctg aacgacggcg ccgccgcggt ggtggtgatg   1740
tcggcggcca aggccaagga actgggcctg accccgctgg ccacgatcaa gagctatgcc   1800
aacgccggtg tcgatcccaa ggtgatgggc atgggcccgg tgccggcctc caagcgcgcc   1860
ctgtcgcgcg ccgagtggac cccgcaagac ctggacctga tggagatcaa cgaggccttt   1920
gccgcgcagg cgctggcggt gcaccagcag atgggctggg acacctccaa ggtcaatgtg   1980
aacggcggcg ccatcgccat cggccacccg atcggcgcgt cgggctgccg tatcctggtg   2040
acgctgctgc acgagatgaa gcgccgtgac gcgaagaagg gcctggcctc gctgtgcatc   2100
ggcggcggca tgggcgtggc gctggcagtc gagcgcaaat aactcgaggc ggccgcagcc   2160
ctttttgtat gtgctacccc acttttgtct ttttggcaat agtgctagca accaataaat   2220
aataataata ataatgaata agaaaacaaa ggctttagct tgccttttgt tcactgtaaa   2280
ataataatgt aagtactctc tataatgagt cacgaaactt ttgcgggaat aaaaggagaa   2340
attccaatga gttttctgtc aaatcttctt ttgtctctct ctctctctct tttttttttt   2400
tctttcttct gagcttcttg caaaacaaaa ggcaaacaat aacgattggt ccaatgatag   2460
ttagcttgat cgatgatatc tttaggaagt gttggcagga caggacatga tgtagaagac   2520
taaaattgaa agtattgcag acccaatagt tgaagattaa ctttaagaat gaagacgtct   2580
tatcaggttc ttcatgactt aagcttctgc agggagtact gtcctccgag cggagtactg   2640
tcctccgagc ggagtactgt cctccgagcg gagtactgtc ctccgagcgg agtactgtcc   2700
tccgagcgga gactctagtg caagaccctt cctctatata aggaagttca tttcatttgg   2760
agaggacacg ctgaaatcac cagtctctct ctaagctagc ttggatcctc gagaaaatgg   2820
cttctatgat atcctcttcc gctgtgacaa cagtcagccg tgcctctagg gggcaatccg   2880
ccgcagtggc tccattcggc ggcctcaaat ccatgactgg attcccagtg aagaaggtca   2940
acactgacat tacttccatt acaagcaatg gtggaagagt aaagtgcatg caggtgtggc   3000
ctccaattgg aaagaagaag tttgagactc tttcctattt gccaccattg acgagagatt   3060
ctagagtgct ctaccaattg catgagttcc agcgctcgat cctgcacccg ctgaccgcgt   3120
gggcccaggc gaccgccaag accttcacca accccctcag cccgctctcg ctggttcccg   3180
gcgcaccccg cctggctgcc ggctatgaac tgctgtaccg gctcggcaag gaatacgaaa   3240
agccggcatt cgacatcaag tcggtgcgct ccaacgggcg cgacatcccc atcgtcgagc   3300
agaccgtgct tgaaaagccg ttctgcaagc tggtgcgctt caagcgctat gccgacgacc   3360
```

cggagaccat caagctgctc aaggatgagc cggtggtgct ggtggccgcg ccgctgtcgg 3420
gccaccatgc cacgctgctg cgcgacacgg tgcgcacgct gctccaggac cacaaggtct 3480
acgtcaccga ctggatcgac gcacgcatgg tgccggtcga ggaaggcgcg ttccacctgt 3540
cggactacat ctactacatc caggagttca tccgccatat cggcgccgag aacctgcatg 3600
tgatctcggt atgccagccc accgtgccgg tgctggccgc gatctcgctg atggcctcgg 3660
ccggcgagaa gacgccgcgc accatgacca tgatgggcgg cccgatcgac gcccgcaaga 3720
gccccacggc ggtcaactcg ctggcgacca acaagtcgtt cgagtggttc gagaacaacg 3780
tcatctacac cgtgccggcc aactaccccg gccacggccg ccgcgtctac ccaggctttt 3840
tgcagcatgc cggtttcgtg gcgatgaacc cggaccggca cctttcctcg cactatgact 3900
tctacctgag cctggtcgag ggcgatgcgg atgacgccga agcccacgtg cgcttctacg 3960
acgaatacaa cgcggtgctc gacatggccg ccgagtacta cctcgacacc atccgcgagg 4020
tgttccagga gttccgcctg gccaacggca cctgggccat cgacggcaat ccggtccggc 4080
cgcaggacat caagagcacc gcgctgatga ccgtcgaggg cgaactggac gacatctcgg 4140
gcgcgggcca gaccgcagcg gcgcacgacc tgtgcgccgg catcccgaaa atccgcaagc 4200
agcacctgaa cgcggcacac tgcggccact acggcatctt ctcgggccgg cgctggcgcg 4260
aagagatata cccgcagctg cgcgacttta tccgcaagta ccaccaggcc tcggccacca 4320
ggtaagagct cgaattgatc ctctagagct ttcgttcgta tcatcggttt cgacaacgtt 4380
cgtcaagttc aatgcatcag tttcattgcg cacacaccag aatcctactg agttcgagta 4440
ttatggcatt gggaaaactg tttttcttgt accatttgtt gtgcttgtaa tttactgtgt 4500
tttttattcg gttttcgcta tcgaactgtg aaatggaaat ggatggagaa gagttaatga 4560
atgatatggt ccttttgttc attctcaaat taatattatt tgttttttct cttatttgtt 4620
gtgtgttgaa tttgaaatta taagagatat gcaaacattt tgttttgagt aaaaatgtgt 4680
caaatcgtgg cctctaatga ccgaagttaa tatgaggagt aaaacacttg tagttgtacc 4740
attatgctta ttcactaggc aacaaatata ttttcagacc tagaaaagct gcaaatgtta 4800
ctgaatacaa gtatgtcctc ttgtgtttta gacatttatg aactttcctt tatgtaattt 4860
tccagaatcc ttgtcagatt ctaatcattg ctttataatt atagttatac tcatggattt 4920
gtagttgagt atgaaaatat tttttaatgc attttatgac ttgccaattg attgacaaca 4980
tgcatcagtc gagggagtac tgtcctccga gcggagtact gtcctccgag cggagtactg 5040
tcctccgagc ggagtactgt cctccgagcg gagtactgtc ctccgagcgg agactctagt 5100
gcaagaccct tcctctatat aaggaagttc atttcatttg gagaggacac gctgaaatca 5160
ccagtctctc tctaagctag cttggatcct cgagaaaatg gcttctatga tatcctcttc 5220
cgctgtgaca acagtcagcc gtgcctctag ggggcaatcc gccgcagtgg ctccattcgg 5280
cggcctcaaa tccatgactg gattcccagt gaagaaggtc aacactgaca ttacttccat 5340
tacaagcaat ggtggaagag taaagtgcat gcaggtgtgg cctccaattg gaaagaagaa 5400
gtttgagact ctttcctatt tgccaccatt gacgagagat tctagagtgc tcaaaggaaa 5460
agtcgcagtc gtcaccggtt ccaccagcgg gatcggcctg ggtatcgcca ccgcgctggc 5520
cgcgcagggc gccgatatcg tcctgaacgg cttcggcgac gccgccgaga tcgaaaaggt 5580
gcgcgccggc ctggccgccc agcatggcgt caaggtgctg tacgacggcg ccgacctgtc 5640
caagggcgag gccgtgcgcg gcctggtgga caacgcggtg cgccagatgg gccgcatcga 5700
catcctggtc aacaacgccg gcatccagca caccgcgctg atcgaggact ttcccaccga 5760
aaaatgggac gccatcctgg cgctgaacct gtcggccgtg ttccacggca ccgccgccgc 5820
gctgccgcac atgaagaagc agggcttcgg ccgcatcatc aacatcgcct cggcgcacgg 5880
cctggtggcc tcggccaaca agtcggccta cgtcgccgcc aagcacggcg tggtgggctt 5940
caccaaggtg accgcgctgg aaaccgccgg ccagggcatc accgccaacg ccatctgccc 6000
aggctgggtg cgcactccgc tggtcgaaaa gcagatatcg gcgctggccg aaaagaacgg 6060
cgtggaccag gaaaccgccg cgcgcgaact gctcagcgaa aagcagccgt cgctgcaatt 6120
cgtcacgccc gaacaactgg gcggcacggc cgtcttcctg gcctccgatg ccgccgcgca 6180
aatcaccggc acgaccgtct ccgtcgatgg cggctggacg gcgcgctgag agctcgaatt 6240
gatcctctag agctttcgtt cgtatcatcg gtttcgacaa cgttcgtcaa gttcaatgca 6300
tcagtttcat tgcgcacaca ccagaatcct actgagttcg agtattatgg cattgggaaa 6360
actgtttttc ttgtaccatt tgttgtgctt gtaatttact gtgtttttta ttcggttttc 6420
gctatcgaac tgtgaaatgg aaatggatgg agaagagtta atgaatgata tggtcctttt 6480
gttcattctc aaattaatat tatttgtttt ttctcttatt tgttgtgtgt tgaatttgaa 6540
attataagag atatgcaaac attttgtttt gagtaaaaat gtgtcaaatc gtggcctcta 6600
atgaccgaag ttaatatgag gagtaaaaca cttgtagttg taccattatg cttattcact 6660
aggcaacaaa tatattttca gacctagaaa agctgcaaat gttactgaat acaagtatgt 6720
cctcttgtgt tttagacatt tatgaacttt cctttatgta attttccaga atccttgtca 6780
gattctaatc attgctttat aattatagtt atactcatgg atttgtagtt gagtatgaaa 6840
atatttttta atgcatttta tgacttgcca attgattgac aacatgcatc aactagtaga 6900
aggtaattat ccaagatgta gcatcaagaa tccaatgttt acgggaaaaa ctatggaagt 6960
attatgtgag ctcagcaaga agcagatcaa tatgcggcac atatgcaacc tatgttcaaa 7020
aatgaagaat gtacagatac aagatcctat actgccagaa tacgaagaag aatacgtaga 7080
aattgaaaaa gaagaaccag gcgaagaaaa gaatcttgaa gacgtaagca ctgacgacaa 7140
caatgaaaag aagaagataa ggtcggtgat tgtgaaagag acatagagga cacatgtaag 7200
gtggaaaatg taagggcgga aagtaacctt atcacaaagg aatcttatcc cccactactt 7260
atccttttat atttttccgt gtcatttttg cccttgagtt ttcctatata aggaaccaag 7320
ttcggcattt gtgaaaacaa gaaaaaattg gtgtaagcta ttttctttga agtactgagg 7380
atacaacttc agagaaattt gtaagaaagt ggatcgaaac catggcctcc tccgagaacg 7440
tcatcaccga gttcatgcgc ttcaaggtgc gcatggaggg caccgtgaac ggccacgagt 7500
tcgagatcga gggcgagggc gagggccgcc cctacgaggg ccacaacacc gtgaagctga 7560
aggtgaccaa gggcggcccc ctgcccttcg cctgggacat cctgtccccc cagttccagt 7620
acggctccaa ggtgtacgtg aagcaccccg ccgacatccc cgactacaag aagctgtcct 7680
tccccgaggg cttcaagtgg gagcgcgtga tgaacttcga ggacggcggc gtggcgaccg 7740
tgacccagga ctcctccctg caggacggct gcttcatcta caaggtgaag ttcatcggcg 7800
tgaacttccc ctccgacggc cccgtgatgc agaagaagac catgggctgg gaggcctcca 7860
ccgagcgcct gtaccccgc gacggcgtgc tgaagggcga gacccacaag gccctgaagc 7920
tgaaggacgg cggccactac ctggtggagt tcaagtccat ctacatggcc aagaagcccg 7980
tgcagctgcc cggctactac tacgtggacg ccaagctgga catcacctcc cacaacgagg 8040
actacaccat cgtggagcag tacgagcgca ccgagggccg ccaccacctg ttcctggtac 8100

-continued

```
caatgagctc tgtccaacag tctcagggtt aatgtctatg tatcttaaat aatgttgtcg   8160

gcgatcgttc aaacatttgg caataaagtt tcttaagatt gaatcctgtt gccggtcttg   8220

cgatgattat catataattt ctgttgaatt acgttaagca tgtaataatt aacatgtaat   8280

gcatgacgtt atttatgaga tgggttttta tgattagagt cccgcaatta tacatttaat   8340

acgcgataga aaacaaaata tagcgcgcaa actaggataa attatcgcgc gcggtgtcat   8400

ctatgttact agatcgggaa ttaaactatc agtgtttgac aggatatatt ggcgggtaaa   8460

cctaagagaa aagagcgttt attagaataa cggatattta aaagggcgtg aaaaggttta   8520

tccgttcgtc catttgtatg tgcatgccaa ccacagggtt cccctcggga tcaaagtact   8580

ttgatccaac ccctccgctg ctatagtgca gtcggcttct gacgttcagt gcagccgtct   8640

tctgaaaacg acatgtcgca caagtcctaa gttacgcgac aggctgccgc cctgcccttt   8700

tcctggcgtt ttcttgtcgc gtgttttagt cgcataaagt agaatacttg cgactagaac   8760

cggagacatt acgccatgaa caagagcgcc gccgctggcc tgctgggcta tgcccgcgtc   8820

agcaccgacg accaggactt gaccaaccaa cgggccgaac tgcacgcggc cggctgcacc   8880

aagctgtttt ccgagaagat caccggcacc aggcgcgacc gcccggagct ggccaggatg   8940

cttgaccacc tacgccctgg cgacgttgtg acagtgacca ggctagaccg cctggcccgc   9000

agcacccgcg acctactgga cattgccgag cgcatccagg aggccggcgc gggcctgcgt   9060

agcctggcag agccgtgggc cgacaccacc acgccggccg gccgcatggt gttgaccgtg   9120

ttcgccggca ttgccgagtt cgagcgttcc ctaatcatcg accgcacccg gagcgggcgc   9180

gaggccgcca aggcccgagg cgtgaagttt ggcccccgcc ctaccctcac cccggcacag   9240

atcgcgcacg cccgcgagct gatcgaccag gaaggccgca ccgtgaaaga ggcggctgca   9300

ctgcttggcg tgcatcgctc gaccctgtac cgcgcacttg agcgcagcga ggaagtgacg   9360

cccaccgagg ccaggcggcg cggtgccttc cgtgaggacg cattgaccga ggccgacgcc   9420

ctggcggccg ccgagaatga acgccaagag gaacaagcat gaaaccgcac caggacggcc   9480

aggacgaacc gtttttcatt accgaagaga tcgaggcgga gatgatcgcg gccgggtacg   9540

tgttcgagcc gcccgcgcac gtctcaaccg tgcggctgca tgaaatcctg gccggtttgt   9600

ctgatgccaa gctggcggcc tggccggcca gcttggccgc tgaagaaacc gagcgccgcc   9660

gtctaaaaag gtgatgtgta tttgagtaaa acagcttgcg tcatgcggtc gctgcgtata   9720

tgatgcgatg agtaaataaa caaatacgca aggggaacgc atgaaggtta tcgctgtact   9780

taaccagaaa ggcgggtcag gcaagacgac catcgcaacc catctagccc gcgccctgca   9840

actcgccggg gccgatgttc tgttagtcga ttccgatccc cagggcagtg cccgcgattg   9900

ggcggccgtg cgggaagatc aaccgctaac cgttgtcggc atcgaccgcc cgacgattga   9960

ccgcgacgtg aaggccatcg gccggcgcga cttcgtagtg atcgacggag cgccccaggc  10020

ggcggacttg gctgtgtccg cgatcaaggc agccgacttc gtgctgattc cggtgcagcc  10080

aagcccttac gacatatggg ccaccgccga cctggtggag ctggttaagc agcgcattga  10140

ggtcacggat ggaaggctac aagcggcctt tgtcgtgtcg cgggcgatca aaggcacgcg  10200

catcggcggt gaggttgccg aggcgctggc cgggtacgag ctgcccattc ttgagtcccg  10260

tatcacgcag cgcgtgagct acccaggcac tgccgccgcc ggcacaaccg ttcttgaatc  10320

agaacccgag ggcgacgctg cccgcgaggt ccaggcgctg gccgctgaaa ttaaatcaaa  10380

actcatttga gttaatgagg taaagagaaa atgagcaaaa gcacaaacac gctaagtgcc  10440
```

-continued

```
ggccgtccga gcgcacgcag cagcaaggct gcaacgttgg ccagcctggc agacacgcca  10500
gccatgaagc gggtcaactt tcagttgccg gcggaggatc acaccaagct gaagatgtac  10560
gcggtacgcc aaggcaagac cattaccgag ctgctatctg aatacatcgc gcagctacca  10620
gagtaaatga gcaaatgaat aaatgagtag atgaatttta gcggctaaag gaggcggcat  10680
ggaaaatcaa gaacaaccag gcaccgacgc cgtggaatgc cccatgtgtg gaggaacggg  10740
cggttggcca ggcgtaagcg gctgggttgt ctgccggccc tgcaatggca ctggaacccc  10800
caagcccgag gaatcggcgt gacggtcgca aaccatccgg cccggtacaa atcggcgcgg  10860
cgctgggtga tgacctggtg gagaagttga aggccgcgca ggccgcccag cggcaacgca  10920
tcgaggcaga agcacgcccc ggtgaatcgt ggcaagcggc cgctgatcga atccgcaaag  10980
aatcccggca accgccggca gccggtgcgc cgtcgattag gaagccgccc aagggcgacg  11040
agcaaccaga tttttcgtt ccgatgctct atgacgtggg cacccgcgat agtcgcagca  11100
tcatggacgt ggccgttttc cgtctgtcga agcgtgaccg acgagctggc gaggtgatcc  11160
gctacgagct tccagacggg cacgtagagg tttccgcagg gccggccggc atggccagtg  11220
tgtgggatta cgacctggta ctgatggcgg tttcccatct aaccgaatcc atgaaccgat  11280
accgggaagg gaagggagac aagcccggcc gcgtgttccg tccacacgtt gcggacgtac  11340
tcaagttctg ccggcgagcc gatggcggaa agcagaaaga cgacctggta gaaacctgca  11400
ttcggttaaa caccacgcac gttgccatgc agcgtacgaa gaaggccaag aacggccgcc  11460
tggtgacggt atccgagggt gaagccttga ttagccgcta caagatcgta aagagcgaaa  11520
ccgggcggcc ggagtacatc gagatcgagc tagctgattg gatgtaccgc gagatcacag  11580
aaggcaagaa cccggacgtg ctgacggttc accccgatta ctttttgatc gatcccggca  11640
tcggccgttt tctctaccgc ctggcacgcc gcgccgcagg caaggcagaa gccagatggt  11700
tgttcaagac gatctacgaa cgcagtggca gcgccggaga gttcaagaag ttctgtttca  11760
ccgtgcgcaa gctgatcggg tcaaatgacc tgccggagta cgatttgaag gaggaggcgg  11820
ggcaggctgg cccgatccta gtcatgcgct accgcaacct gatcgagggc gaagcatccg  11880
ccggttccta atgtacggag cagatgctag ggcaaattgc cctagcaggg gaaaaaggtc  11940
gaaaaggtct ctttcctgtg gatagcacgt acattgggaa cccaaagccg tacattggga  12000
accggaaccc gtacattggg aacccaaagc cgtacattgg gaaccggtca cacatgtaag  12060
tgactgatat aaaagagaaa aaaggcgatt tttccgccta aaactcttta aaacttatta  12120
aaactcttaa aacccgcctg gcctgtgcat aactgtctgg ccagcgcaca gccgaagagc  12180
tgcaaaaagc gcctaccctt cggtcgctgc gctccctacg ccccgccgct tcgcgtcggc  12240
ctatcgcggc cgctggccgc tcaaaaatgg ctggcctacg gccaggcaat ctaccagggc  12300
gcggacaagc cgcgccgtcg ccactcgacc gccggcgccc acatcaaggc accctgcctc  12360
gcgcgtttcg gtgatgacgg tgaaaacctc tgacacatgc agctcccgga gacggtcaca  12420
gcttgtctgt aagcggatgc cgggagcaga caagcccgtc agggcgcgtc agcgggtgtt  12480
ggcgggtgtc ggggcgcagc catgacccag tcacgtagcg atagcggagt gtatactggc  12540
ttaactatgc ggcatcagag cagattgtac tgagagtgca ccatatgcgg tgtgaaatac  12600
cgcacagatg cgtaaggaga aaataccgca tcaggcgctc ttccgcttcc tcgctcactg  12660
actcgctgcg ctcggtcgtt cggctgcggc gagcggtatc agctcactca aaggcggtaa  12720
tacggttatc cacagaatca ggggataacg caggaaagaa catgtgagca aaaggccagc  12780
aaaaggccag gaaccgtaaa aaggccgcgt tgctggcgtt tttccatagg ctccgccccc  12840
```

ctgacgagca tcacaaaaat cgacgctcaa gtcagaggtg gcgaaacccg acaggactat 12900
aaagatacca ggcgtttccc cctggaagct ccctcgtgcg ctctcctgtt ccgaccctgc 12960
cgcttaccgg atacctgtcc gcctttctcc cttcgggaag cgtggcgctt tctcatagct 13020
cacgctgtag gtatctcagt tcggtgtagg tcgttcgctc caagctgggc tgtgtgcacg 13080
aaccccccgt tcagcccgac cgctgcgcct tatccggtaa ctatcgtctt gagtccaacc 13140
cggtaagaca cgacttatcg ccactggcag cagccactgg taacaggatt agcagagcga 13200
ggtatgtagg cggtgctaca gagttcttga agtggtggcc taactacggc tacactagaa 13260
ggacagtatt tggtatctgc gctctgctga agccagttac cttcggaaaa agagttggta 13320
gctcttgatc cggcaaacaa accaccgctg gtagcggtgg tttttttgtt tgcaagcagc 13380
agattacgcg cagaaaaaaa ggatctcaag aagatccttt gatcttttct acggggtctg 13440
acgctcagtg gaacgaaaac tcacgttaag ggattttggt catgcattct aggtactaaa 13500
acaattcatc cagtaaaata taatatttta ttttctccca atcaggcttg atccccagta 13560
agtcaaaaaa tagctcgaca tactgttctt ccccgatatc ctccctgatc gaccggacgc 13620
agaaggcaat gtcataccac ttgtccgccc tgccgcttct cccaagatca ataaagccac 13680
ttactttgcc atctttcaca aagatgttgc tgtctcccag gtcgccgtgg gaaaagacaa 13740
gttcctcttc gggcttttcc gtctttaaaa aatcatacag ctcgcgcgga tctttaaatg 13800
gagtgtcttc ttcccagttt tcgcaatcca catcggccag atcgttattc agtaagtaat 13860
ccaattcggc taagcggctg tctaagctat tcgtataggg acaatccgat atgtcgatgg 13920
agtgaaagag cctgatgcac tccgcataca gctcgataat cttttcaggg ctttgttcat 13980
cttcatactc ttccgagcaa aggacgccat cggcctcact catgagcaga ttgctccagc 14040
catcatgccg ttcaaagtgc aggacctttg gaacaggcag ctttccttcc agccatagca 14100
tcatgtcctt ttcccgttcc acatcatagg tggtcccttt ataccggctg tccgtcattt 14160
ttaaatatag gttttcattt tctcccacca gcttatatac cttagcagga gacattcctt 14220
ccgtatcttt tacgcagcgg tatttttcga tcagtttttt caattccggt gatattctca 14280
ttttagccat ttattatttc cttcctcttt tctacagtat ttaaagatac cccaagaagc 14340
taattataac aagacgaact ccaattcact gttccttgca ttctaaaacc ttaaatacca 14400
gaaaacagct tttcaaagt tgttttcaaa gttggcgtat aacatagtat cgacggagcc 14460
gattttgaaa ccgcggtgat cacaggcagc aacgctctgt catcgttaca atcaacatgc 14520
taccctccgc gagatcatcc gtgtttcaaa cccggcagct tagttgccgt tcttccgaat 14580
agcatcggta acatgagcaa agtctgccgc cttacaacgg ctctcccgct gacgccgtcc 14640
cggactgatg ggctgcctgt atcgagtggt gattttgtgc cgagctgccg gtcggggagc 14700
tgttggctgg ctggtggcag gatatattgt ggtgtaaaca aattgacgct tagacaactt 14760
aataacacat tgcggacgtt tttaatgtac tgaattaacg ccgaattaat tcctagtcca 14820
atactcaact tcaaggaatc tcacccatgc gcgccggcgg ggaaccggag ttcccttcag 14880
tgaacgttat tagttcgccg ctcggtgtgt cgtagatact agcccctggg gccttttgaa 14940
atttgaataa gatttatgta atcagtcttt taggtttgac cggttctgcc gcttttttta 15000
aaattggatt tgtaataata aaacgcaatt gtttgttatt gtggcgctct atcatagatg 15060
tcgctataaa cctattcagc acaatatatt gttttcattt taatattgta catataagta 15120
gtagggtaca atcagtaaat tgaacggaga atattattca taaaaatacg atagtaacgg 15180
gtgatatatt cattcattag aatgaaccga aaccggcggt aaggatctga gctacacatg 15240
ctcaggtttt ttacaacgtg cacaacagaa ttgaaagcaa atatcatgcg atcataggcg 15300
tctcgcatat ctcattaaag cagctggaag atttgattct agattagaga ttcgtggggg 15360
actcgagata ggcggcggtt gggtgtgcga catgtcctgc cacatcccag atctcctcga 15420
ggaaaggcgg cagctttctg ttcttgagct tgagggagat gcacatgttg gagttttgca 15480
tgccgagcgt gcgtagctca gagaggattg agaggatctt gccgtatatg acggacgaac 15540
gcgccgaccc gctcagctgg ttcaggatat agatgcggag cgtattcagg tagtaccgct 15600
ggatttcttc caccagttgc ggctgctcca accctggccg gtcagaaaag atgacgacag 15660
ccgtgagcag cgcgtaatgg atgttgtcca acgccataga gtacatgcac cggcagaagt 15720
gcagtagatc ctcgatgact tcggccatgc cagccttgcg gtagttgtcg cgagtgtacg 15780
cttggttgtt cgggaacaga atactgtctg aggccgcatc gtactgctgc gcgactcgga 15840
gcatcattac ctcacttgag caagccttaa gcagcgtaat ttgatcaggc tgcgagatct 15900
tggcgaaccc tggcaatccc ttcgcgaact ccacgataag ttggaccgtg aggatagtca 15960
tctctacgat ctggcggaag ggagtgtcag actcttcgtt ttcatcgtcc gcttgctgcc 16020
acgtctgcgt aatcctcttc aaatcttcat cagaaggctg ctcgtacccg tcctggtacc 16080
agatgagcct ggcgataagg aactgctggt tggctgtcaa ctgggggatg tttttctgcc 16140
ggtttgtctc caacagcttg tcggagagaa accttggaac cacttcgtga atccttgctg 16200
cttcaggagg tggaggttca cactgcataa tgggcggcat gtggtcgtcc accgtcgtcg 16260
tgctgacagg cagtttgtcc ttctccttct gtgctttctt ctctttccgc ttcatggcgc 16320
actgagtctc gggtactacg cactcaggcc tgatccccgg gaattccggc gatacagtca 16380
actgtctttg acctttgtta ctactctctt ccgatgatga tgtcgcactt attctatgct 16440
gtctcaatgt tagaggcata tcagtctcca ctgaagccaa tctatctgtg acggcatctt 16500
tattcacatt atcttgtaca aataatcctg ttaacaatgc ttttatatcc tgtaaagaat 16560
ccattttcaa aatcatgtca aggtcttctc gaggaaaaat cagtagaaat agctgttcca 16620
gtctttctag ccttgattcc acttctgtca gatgtgccct agtcagcgga gaccttttgg 16680
ttttgggaga gtagcgacac tcccagttgt tcttcagaca cttggcgcac ttcggttttt 16740
ctttggagca cttgagcttt ttaagtcggc aaatatcgca tgcttgttcg atagaagaca 16800
gtagcttcag tcgacggatc cctggcgatc ccggacccgg ggaatccccg tcccccaaca 16860
tgtccagatc gaaatcgtct agcgcgtcgg catgcgccat cgccacgtcc tcgccgtcta 16920
agtggagctc gtcccccagg ctgacatcgg tcgggggggc cgtcgagatc cccgggaatt 16980
catctacctt tctcttcttt tttgggcatg cttgttcgat agaagacagt agcttcatct 17040
ttcaggaggc ttgcttcaag ctggctagac tcgagagatg agagatttcg attccgattt 17100
tgatttcgat tccgattttg atttcgattg atctcttcct tctgatttgt gttccttata 17160
taaggaaatt cttgtgggat tagacgtcat ggcttacgtc atttccttcg tcctgttgct 17220
cactgattga gctgtgagtg gagggaccac tggaagatgc ttcactaatt ttcttagtgg 17280
agggaccggc ttcacatgct tcacacaagt ggctgtcggg catcatcttt tttagctttt 17340
gacaaagcaa tgttttagtg gtggctccca ctcttatctt caacattatt atcttatctt 17400
caaaggacga taagatgttg atgtctgtgg acgaagttgg gattagacgt catggcttac 17460
gtcatttcct tcgtcctgtt gctcactgat tgagctgtga gtggagggac cactggaaga 17520
tgcttcacta attttcttag tggagggacc ggcttcacat gcttcacaca agtggctgtc 17580
gggcatcatc ttttttagct tttgacaaag caatgtttta gtggtggctc ccactcttat 17640
cttcaacatt attatcttat cttcaaagga cgataagatg ttgatgtctg tggacgaagt 17700
tgacgaattc ctgcaggcgg ccgccatatg catcctaggc caccatgttg ggcccggggc 17760
gcgccgtacg tagtgtttat ctttgttgct tttctgaaca atttatttac tatgtaaata 17820
tattatcaat gtttaatcta ttttaatttg cacatgaatt ttcattttat ttttacttta 17880
caaaacaaat aaatatatat gcaaaaaaat ttacaaacga tgcacgggtt acaaactaat 17940
ttcattaaat gctaatgcag attttgtgaa gtaaaactcc aattatgatg aaaaatacca 18000
ccaacaccac ctgcgaaact gtatcccaac tgtccttaat aaaaatgtta aaaagtatat 18060
tattctcatt tgtctgtcat aatttatgta ccccacttta atttttctga tgtactaaac 18120
cgagggcaaa ctgaaacctg ttcctcatgc aaagccccta ctcaccatgt atcatgtacg 18180
tgtcatcacc caacaactcc acttttgcta tataacaaca cccccgtcac actctccctc 18240
tctaacacac accccactaa caattccttc acttgcagca ctgttgcatc atcatcttca 18300
ttgcaaaacc ctaaacttca ccttcaaccg cggccgcatg gcttctatga tatcctcttc 18360
cgctgtgaca acagtcagcc gtgcctctag ggggcaatcc gccgcagtgg ctccattcgg 18420
cggcctcaaa tccatgactg gattcccagt gaagaaggtc aacactgaca ttacttccat 18480
tacaagcaat ggtggaagag taaagtgcat gcaggtgtgg cctccaattg gaaagaagaa 18540
gtttgagact ctttcctatt tgccaccatt gacgagagat tctagagtga gtaacaagaa 18600
caacgatgag ctgcagtggc aatcctggtt cagcaaggcg cccaccaccg aggcgaaccc 18660
gatggccacc atgttgcagg atatcggcgt tgcgctcaaa ccggaagcga tggagcagct 18720
gaaaaacgat tatctgcgtg acttcaccgc gttgtggcag gattttttgg ctggcaaggc 18780
gccagccgtc agcgaccgcc gcttcagctc ggcagcctgg cagggcaatc cgatgtcggc 18840
cttcaatgcc gcatcttacc tgctcaacgc caaattcctc agtgccatgg tggaggcggt 18900
ggacaccgca ccccagcaaa agcagaaaat acgctttgcc gtgcagcagg tgattgatgc 18960
catgtcgccc gcgaacttcc tcgccaccaa cccggaagcg cagcaaaaac tgattgaaac 19020
caagggcgag agcctgacgc gtggcctggt caatatgctg ggcgatatca acaagggcca 19080
tatctcgctg tcggacgaat cggcctttga agtgggccgc aacctggcca ttaccccggg 19140
caccgtgatt tacgaaaatc cgctgttcca gctgatccag tacacgccga ccacgccgac 19200
ggtcagccag cgcccgctgt tgatggtgcc gccgtgcatc aacaagttct acatcctcga 19260
cctgcaaccg gaaaattcgc tggtgcgcta cgcggtggag cagggcaaca ccgtgttcct 19320
gatctcgtgg agcaatccgg acaagtcgct ggccggcacc acctgggacg actacgtgga 19380
gcagggcgtg atcgaagcga tccgcatcgt ccaggacgtc agcggccagg acaagctgaa 19440
catgttcggc ttctgcgtgg gcggcaccat cgttgccacc gcactggcgg tactggcggc 19500
gcgtggccag cacccggcgg ccagcctgac cctgctgacc accttcctcg acttcagcga 19560
caccggcgtg ctcgacgtct tcgtcgatga aacccaggtc gcgctgcgtg aacagcaatt 19620
gcgcgatggc ggcctgatgc cgggccgtga cctggcctcg accttctcga gcctgcgtcc 19680
gaacgacctg gtatggaact atgtgcagtc gaactacctc aaaggcaatg agccggcggc 19740
gtttgacctg ctgttctgga attcggacag caccaatttg ccgggcccga tgttctgctg 19800
gtacctgcgc aacacctacc tggaaaacag cctgaaagtg ccgggcaagc tgacggtggc 19860
cggcgaaaag atcgacctcg gcctgatcga cgccccggcc ttcatctacg gttcgcgcga 19920
agaccacatc gtgccgtgga tgtcggcgta cggttcgctc gacatcctca accagggcaa 19980
gccgggcgcc aaccgcttcg tgctgggcgc gtccggccat atcgccggcg tgatcaactc 20040
ggtggccaag aacaagcgca gctactggat caacgacggt ggcgccgccg atgcccaggc 20100
ctggttcgat ggcgcgcagg aagtgccggg cagctggtgg ccgcaatggg ccgggttcct 20160
gacccagcat ggcggcaaga aggtcaagcc caaggccaag cccggcaacg cccgctacac 20220
cgcgatcgag gcggcgcccg gccgttacgt caaagccaag ggctgagcgg ccgctgagta 20280
attctgatat tagagggagc attaatgtgt tgttgtgatg tggtttatat ggggaaatta 20340
aataaatgat gtatgtacct cttgcctatg taggtttgtg tgttttgttt tgttgtctag 20400
ctttggttat taagtagtag ggacgttcgt tcgtgtctca aaaaaagggg tactaccact 20460
ctgtagtgta tatggatgct ggaaatcaat gtgttttgta tttgttcacc tccattgttg 20520
aattcaatgt caaatgtgtt ttgcgttggt tatgtgtaaa attactatct ttctcgtccg 20580
atgatcaaag ttttaagcaa caaaaccaag ggtgaaattt aaactgtgct ttgttgaaga 20640
ttcttttatc atattgaaaa tcaaattact agcagcagat tttacctagc atgaaatttt 20700
atcaacagta cagcactcac taaccaagtt ccaaactaag atgcgccatt aacatcagcc 20760
aataggcatt ttcagcaagg cgcgcccgcg ccgatgtatg tgacaaccct cgggattgtt 20820
gatttatttc aaaactaaga gtttttgtct tattgttctc gtctattttg gatatcaatc 20880
ttagttttat atcttttcta gttctctacg tgttaaatgt tcaacacact agcaatttgg 20940
cctgccagcg tatggattat ggaactatca agtctgtgac gcgccgtacg tagtgtttat 21000
ctttgttgct tttctgaaca atttatttac tatgtaaata tattatcaat gtttaatcta 21060
ttttaatttg cacatgaatt ttcattttat ttttacttta caaaacaaat aaatatatat 21120
gcaaaaaaat ttacaaacga tgcacgggtt acaaactaat ttcattaaat gctaatgcag 21180
attttgtgaa gtaaaactcc aattatgatg aaaaatacca ccaacaccac ctgcgaaact 21240
gtatcccaac tgtccttaat aaaaatgtta aaaagtatat tattctcatt tgtctgtcat 21300
aatttatgta ccccacttta atttttctga tgtactaaac cgagggcaaa ctgaaacctg 21360
ttcctcatgc aaagccccta ctcaccatgt atcatgtacg tgtcatcacc caacaactcc 21420
acttttgcta tataacaaca cccccgtcac actctccctc tctaacacac accccactaa 21480
caattccttc acttgcagca ctgttgcatc atcatcttca ttgcaaaacc ctaaacttca 21540
ccttcaaccg cggccgcatg gcttctatga tatcctcttc cgctgtgaca acagtcagcc 21600
gtgcctctag ggggcaatcc gccgcagtgg ctccattcgg cggcctcaaa tccatgactg 21660
gattcccagt gaagaaggtc aacactgaca ttacttccat tacaagcaat ggtggaagag 21720
taaagtgcat gcaggtgtgg cctccaattg gaaagaagaa gtttgagact ctttcctatt 21780
tgccaccatt gacgagagat tctagagtga ctcagcgcat tgcgtatgtg accggcggca 21840
tgggtggtat cggaaccgcc atttgccagc ggctggccaa ggatggcttt cgtgtggtgg 21900
ccggttgcgg ccccaactcg ccgcgccgcg aaaagtggct ggagcagcag aaggccctgg 21960
gcttcgattt cattgcctcg gaaggcaatg tggctgactg ggactcgacc aagaccgcat 22020
tcgacaaggt caagtccgag gtcggcgagg ttgatgtgct gatcaacaac gccggtatca 22080
cccgcgacgt ggtgttccgc aagatgaccc gcgccgactg ggatgcggtg atcgacacca 22140
acctgacctc gctgttcaac gtcaccaagc aggtgatcga cggcatggcc gaccgtggct 22200
ggggccgcat cgtcaacatc tcgtcggtga acgggcagaa gggccagttc ggccagacca 22260
actactccac cgccaaggcc ggcctgcatg gcttcaccat ggcactggcg caggaagtgg 22320
cgaccaaggg cgtgaccgtc aacacggtct ctccgggcta tatcgccacc gacatggtca 22380
aggcgatccg ccaggacgtg ctcgacaaga tcgtcgcgac gatcccggtc aagcgcctgg 22440
gcctgccgga agagatcgcc tcgatctgcg cctggttgtc gtcggaggag tccggtttct 22500
cgaccggcgc cgacttctcg ctcaacggcg gcctgcatat gggctgagcg gccgctgagt 22560
aattctgata ttagagggag cattaatgtg ttgttgtgat gtggtttata tggggaaatt 22620
aaataaatga tgtatgtacc tcttgcctat gtaggtttgt gtgttttgtt ttgttgtcta 22680
gctttggtta ttaagtagta gggacgttcg ttcgtgtctc aaaaaaaggg gtactaccac 22740
tctgtagtgt atatggatgc tggaaatcaa tgtgttttgt atttgttcac ctccattgtt 22800
gaattcaatg tcaaatgtgt tttgcgttgg ttatgtgtaa aattactatc tttctcgtcc 22860
gatgatcaaa gttttaagca acaaaaccaa gggtgaaatt taaactgtgc tttgttgaag 22920
attcttttat catattgaaa atcaaattac tagcagcaga ttttacctag catgaaattt 22980
tatcaacagt acagcactca ctaaccaagt tccaaactaa gatgcgccat taacatcagc 23040
caataggcat tttcagcaag gcgcgtaa 23068

<210> SEQ ID NO 9
<211> LENGTH: 18329
<212> TYPE: DNA
<213> ORGANISM: Artificial Sequence
<220> FEATURE:
<223> OTHER INFORMATION: Synthetic Vector

<400> SEQUENCE: 9
ggggatccgt acgtaagtac gtactcaaaa tgccaacaaa taaaaaaaaa gttgctttaa 60
taatgccaaa acaaattaat aaaacactta caacaccgga ttttttttaa ttaaaatgtg 120
ccatttagga taaatagtta atatttttaa taattattta aaaagccgta tctactaaaa 180
tgatttttat ttggttgaaa atattaatat gtttaaatca acacaatcta tcaaaattaa 240
actaaaaaaa aaataagtgt acgtggttaa cattagtaca gtaatataag aggaaaatga 300
gaaattaaga aattgaaagc gagtctaatt tttaaattat gaacctgcat atataaaagg 360
aaagaaagaa tccaggaaga aaagaaatga aaccatgcat ggtcccctcg tcatcacgag 420
tttctgccat ttgcaataga aacactgaaa cacctttctc tttgtcactt aattgagatg 480
ccgaagccac ctcacaccat gaacttcatg aggtgtagca cccaaggctt ccatagccat 540
gcatactgaa gaatgtctca agctcagcac cctacttctg tgacgtgtcc ctcattcacc 600
ttcctctctt ccctataaat aaccacgcct caggttctcc gcttcacaac tcaaacattc 660
tctccattgg tccttaaaca ctcatcagtc atcaccgcgg ccgcggaatt catggcttct 720
atgatatcct cttccgctgt gacaacagtc agccgtgcct ctagggggca atccgccgca 780
gtggctccat tcggcggcct caaatccatg actggattcc cagtgaagaa ggtcaacact 840
gacattactt ccattacaag caatggtgga agagtaaagt gcatgcaggt gtggcctcca 900
attggaaaga agaagtttga gactctttcc tatttgccac cattgacgag agattctaga 960
gtgactgacg ttgtcatcgt atccgccgcc cgcaccgcgg tcggcaagtt tggcggctcg 1020
ctggccaaga tcccggcacc ggaactgggt gccgtggtca tcaaggccgc gctggagcgc 1080
gccggcgtca agccggagca ggtgagcgaa gtcatcatgg gccaggtgct gaccgccggt 1140
tcgggccaga accccgcacg ccaggccgcg atcaaggccg gcctgccggc gatggtgccg 1200
gccatgacca tcaacaaggt gtgcggctcg ggcctgaagg ccgtgatgct ggccgccaac 1260

-continued

```
gcgatcatgg cgggcgacgc cgagatcgtg gtggccggcg gccaggaaaa catgagcgcc   1320
gccccgcacg tgctgccggg ctcgcgcgat ggtttccgca tgggcgatgc caagctggtc   1380
gacaccatga tcgtcgacgg cctgtgggac gtgtacaacc agtaccacat gggcatcacc   1440
gccgagaacg tggccaagga atacggcatc acacgcgagg cgcaggatga gttcgccgtc   1500
ggctcgcaga acaaggccga agccgcgcag aaggccggca agtttgacga agagatcgtc   1560
ccggtgctga tcccgcagcg caagggcgac ccggtggcct tcaagaccga cgagttcgtg   1620
cgccagggcg ccacgctgga cagcatgtcc ggcctcaagc ccgccttcga caaggccggc   1680
acggtgaccg cggccaacgc ctcgggcctg aacgacggcg ccgccgcggt ggtggtgatg   1740
tcggcggcca aggccaagga actgggcctg accccgctgg ccacgatcaa gagctatgcc   1800
aacgccggtg tcgatcccaa ggtgatgggc atgggcccgg tgccggcctc caagcgcgcc   1860
ctgtcgcgcg ccgagtggac cccgcaagac ctggacctga tggagatcaa cgaggccttt   1920
gccgcgcagg cgctggcggt gcaccagcag atgggctggg acacctccaa ggtcaatgtg   1980
aacggcggcg ccatcgccat cggccacccg atcggcgcgt cgggctgccg tatcctggtg   2040
acgctgctgc acgagatgaa gcgccgtgac gcgaagaagg gcctggcctc gctgtgcatc   2100
ggcggcggca tgggcgtggc gctggcagtc gagcgcaaat aactcgaggc ggccgcagcc   2160
ctttttgtat gtgctacccc acttttgtct tttggcaat agtgctagca accaataaat   2220
aataataata ataatgaata agaaaacaaa ggctttagct tgccttttgt tcactgtaaa   2280
ataataatgt aagtactctc tataatgagt cacgaaactt ttgcgggaat aaaaggagaa   2340
attccaatga gttttctgtc aaatcttctt ttgtctctct ctctctctct ttttttttt   2400
tctttcttct gagcttcttg caaaacaaaa ggcaaacaat aacgattggt ccaatgatag   2460
ttagcttgat cgatgatatc tttaggaagt gttggcagga caggacatga tgtagaagac   2520
taaaattgaa agtattgcag acccaatagt tgaagattaa ctttaagaat gaagacgtct   2580
tatcaggttc ttcatgactt aagctttaag aggagtccac catggtagat ctgactagta   2640
acggccgcca gtgtgctgga attctgcaga tgtggagcac gacactctcg tctactccaa   2700
gaatatcaaa gatacagtct cagaagacca aagggctatt gagacttttc aacaaagggt   2760
aatatcggga aacctcctcg gattccattg cccagctatc tgtcacttca tcaaaaggac   2820
agtagaaaag gaaggtggca cctacaaatg ccatcattgc gataaaggaa aggctatcgt   2880
tcaagatgcc tctgccgaca gtggtcccaa agatggaccc ccacccacga ggagcatcgt   2940
ggaaaaagaa gacgttccaa ccacgtcttc aaagcaagtg gattgatgtg ataacatggt   3000
ggagcacgac actctcgtct actccaagaa tatcaaagat acagtctcag aagaccaaag   3060
ggctattgag acttttcaac aaagggtaat atcgggaaac ctcctcggat tccattgccc   3120
agctatctgt cacttcatca aaaggacagt agaaaaggaa ggtggcacct acaaatgcca   3180
tcattgcgat aaaggaaagg ctatcgttca agatgcctct gccgacagtg gtcccaaaga   3240
tggaccccca cccacgagga gcatcgtgga aaaagaagac gttccaacca cgtcttcaaa   3300
gcaagtggat tgatgtgata tctccactga cgtaagggat gacgcacaat cccactatcc   3360
ttcgcaagac cttcctctat ataaggaagt tcatttcatt tggagaggac acgctgaaat   3420
caccagtctc tctctacaaa tctatctctc tcgagttaat taaaatggct tctatgatat   3480
cctcttccgc tgtgacaaca gtcagccgtg cctctagggg gcaatccgcc gcagtggctc   3540
cattcggcgg cctcaaatcc atgactggat tcccagtgaa gaaggtcaac actgacatta   3600
cttccattac aagcaatggt ggaagagtaa agtgcatgca ggtgtggcct ccaattggaa   3660
```

-continued agaagaagtt tgagactctt tcctatttgc caccattgac gagagattct agagtggaga 3720
agacgatcgg tctcgagatt attgaagttg tcgagcaggc agcgatcgcc tcggcccgcc 3780
tgatgggcaa aggcgaaaag aatgaagccg atcgcgtcgc agtagaagcg atgcgggtgc 3840
ggatgaacca agtggaaatg ctgggccgca tcgtcatcgg tgaaggcgag cgcgacgaag 3900
caccgatgct ctatatcggt gaagaagtgg gcatctaccg cgatgcagac aagcgggctg 3960
gcgtaccggc tggcaagctg gtggaaatcg acatcgccgt tgacccctgc gaaggcacca 4020
acctctgcgc ctacggtcag cccggctcga tggcagtttt ggccatctcc gagaaaggcg 4080
gcctgtttgc agctcccgac ttctacatga agaaactggc tgcacccccca gctgccaaag 4140 gcaaagtaga catcaataag tccgcgaccg aaaacctgaa aattctctcg gaatgtctcg 4200
atcgcgccat cgatgaattg gtggtcgtgg tcatggatcg tccccgccac aaagagctaa 4260
tccaagagat ccgccaagcg ggtgcccgcg tccgtctgat cagcgatggt gacgtttcgg 4320
ccgcgatctc ctgcggtttt gctggcacca acacccacgc cctgatgggc atcggtgcag 4380
ctcccgaggg tgtgatttcg gcagcagcaa tgcgttgcct cggcggtcac ttccaaggcc 4440
agctgatcta cgacccagaa gtggtcaaaa ccggcctgat cggtgaaagc cgtgagagca 4500
acatcgctcg cctgcaagaa atgggcatca ccgatcccga tcgcgtctac gacgccaacg 4560
aactggcttc gggtcaagaa gtgctgtttg cggcttgcgg tatcaccccg ggcttgctga 4620
tggaaggcgt gcgcttcttc aaaggcggcg ctcgcaccca gagcttggtg atctccagcc 4680
agtcacggac ggctcgcttc gttgacaccg ttcacatgtt cgacgatgtc aaaacggtta 4740
gcctccgtta attcctgatc ccaaatggcg gccggagcgg tagggcgcgc catcgttcaa 4800
acatttggca ataaagtttc ttaagattga atcctgttgc cggtcttgcg atgattatca 4860
tataatttct gttgaattac gttaagcatg taataattaa catgtaatgc atgacgttat 4920
ttatgagatg ggtttttatg attagagtcc cgcaattata catttaatac gcgatagaaa 4980
acaaaatata gcgcgcaaac taggataaat tatcgcgcgc ggtgtcatct atgttactag 5040
atccgatgat aagctgtcaa acatgaattt aaatactagt agaaggtaat tatccaagat 5100
gtagcatcaa gaatccaatg tttacgggaa aaactatgga agtattatgt gagctcagca 5160
agaagcagat caatatgcgg cacatatgca acctatgttc aaaaatgaag aatgtacaga 5220
tacaagatcc tatactgcca gaatacgaag aagaatacgt agaaattgaa aaagaagaac 5280
caggcgaaga aaagaatctt gaagacgtaa gcactgacga caacaatgaa aagaagaaga 5340
taaggtcggt gattgtgaaa gagacataga ggacacatgt aaggtggaaa atgtaagggc 5400
ggaaagtaac cttatcacaa aggaatctta tcccccacta cttatccttt tatatttttc 5460
cgtgtcattt ttgcccttga gttttcctat ataaggaacc aagttcggca tttgtgaaaa 5520
caagaaaaaa ttggtgtaag ctattttctt tgaagtactg aggatacaac ttcagagaaa 5580
tttgtaagaa agtggatcga aaccatggcc tcctccgaga acgtcatcac cgagttcatg 5640
cgcttcaagg tgcgcatgga gggcaccgtg aacggccacg agttcgagat cgagggcgag 5700
ggcgagggcc gcccctacga gggccacaac accgtgaagc tgaaggtgac caagggcggc 5760
cccctgccct tcgcctggga catcctgtcc ccccagttcc agtacggctc caaggtgtac 5820
gtgaagcacc ccgccgacat ccccgactac aagaagctgt ccttccccga gggcttcaag 5880
tgggagcgcg tgatgaactt cgaggacggc ggcgtggcga ccgtgaccca ggactcctcc 5940
ctgcaggacg gctgcttcat ctacaaggtg aagttcatcg gcgtgaactt cccctccgac 6000

-continued ggccccgtga tgcagaagaa gaccatgggc tgggaggcct ccaccgagcg cctgtacccc 6060
cgcgacggcg tgctgaaggg cgagacccac aaggccctga agctgaagga cggcggccac 6120
tacctggtgg agttcaagtc catctacatg gccaagaagc ccgtgcagct gcccggctac 6180
tactacgtgg acgccaagct ggacatcacc tcccacaacg aggactacac catcgtggag 6240
cagtacgagc gcaccgaggg ccgccaccac ctgttcctgg taccaatgag ctctgtccaa 6300
cagtctcagg gttaatgtct atgtatctta aataatgttg tcggcgatcg ttcaaacatt 6360
tggcaataaa gtttcttaag attgaatcct gttgccggtc ttgcgatgat tatcatataa 6420
tttctgttga attacgttaa gcatgtaata attaacatgt aatgcatgac gttatttatg 6480
agatgggttt ttatgattag agtcccgcaa ttatacattt aatacgcgat agaaaacaaa 6540
atatagcgcg caaactagga taaattatcg cgcgcggtgt catctatgtt actagatcgg 6600
gaattaaact atcagtgttt gacaggatat attggcgggt aaacctaaga gaaaagagcg 6660
tttattagaa taacggatat ttaaaagggc gtgaaaaggt ttatccgttc gtccatttgt 6720
atgtgcatgc caaccacagg gttcccctcg ggatcaaagt actttgatcc aacccctccg 6780
ctgctatagt gcagtcggct tctgacgttc agtgcagccg tcttctgaaa acgacatgtc 6840
gcacaagtcc taagttacgc gacaggctgc cgccctgccc ttttcctggc gttttcttgt 6900
cgcgtgtttt agtcgcataa agtagaatac ttgcgactag aaccggagac attacgccat 6960
gaacaagagc gccgccgctg gcctgctggg ctatgcccgc gtcagcaccg acgaccagga 7020
cttgaccaac caacgggccg aactgcacgc ggccggctgc accaagctgt tttccgagaa 7080
gatcaccggc accaggcgcg accgcccgga gctggccagg atgcttgacc acctacgccc 7140
tggcgacgtt gtgacagtga ccaggctaga ccgcctggcc cgcagcaccc gcgacctact 7200
ggacattgcc gagcgcatcc aggaggccgg cgcgggcctg cgtagcctgg cagagccgtg 7260
ggccgacacc accacgccgg ccggccgcat ggtgttgacc gtgttcgccg gcattgccga 7320
gttcgagcgt tccctaatca tcgaccgcac ccggagcggg cgcgaggccg ccaaggcccg 7380
aggcgtgaag tttggccccc gccctaccct caccccggca cagatcgcgc acgcccgcga 7440
gctgatcgac caggaaggcc gcaccgtgaa agaggcggct gcactgcttg gcgtgcatcg 7500
ctcgaccctg taccgcgcac ttgagcgcag cgaggaagtg acgcccaccg aggccaggcg 7560
gcgcggtgcc ttccgtgagg acgcattgac cgaggccgac gccctggcgg ccgccgagaa 7620
tgaacgccaa gaggaacaag catgaaaccg caccaggacg gccaggacga accgtttttc 7680
attaccgaag agatcgaggc ggagatgatc gcggccgggt acgtgttcga gccgcccgcg 7740
cacgtctcaa ccgtgcggct gcatgaaatc ctggccggtt tgtctgatgc caagctggcg 7800
gcctggccgg ccagcttggc cgctgaagaa accgagcgcc gccgtctaaa aaggtgatgt 7860
gtatttgagt aaaacagctt gcgtcatgcg gtcgctgcgt atatgatgcg atgagtaaat 7920
aaacaaatac gcaaggggaa cgcatgaagg ttatcgctgt acttaaccag aaaggcgggt 7980
caggcaagac gaccatcgca acccatctag cccgcgccct gcaactcgcc ggggccgatg 8040
ttctgttagt cgattccgat ccccagggca gtgcccgcga ttgggcggcc gtgcgggaag 8100
atcaaccgct aaccgttgtc ggcatcgacc gcccgacgat tgaccgcgac gtgaaggcca 8160
tcggccggcg cgacttcgta gtgatcgacg gagcgcccca ggcggcggac ttggctgtgt 8220
ccgcgatcaa ggcagccgac ttcgtgctga ttccggtgca gccaagccct tacgacatat 8280
gggccaccgc cgacctggtg gagctggtta agcagcgcat tgaggtcacg gatggaaggc 8340
tacaagcggc ctttgtcgtg tcgcgggcga tcaaaggcac gcgcatcggc ggtgaggttg 8400

```
ccgaggcgct ggccgggtac gagctgccca ttcttgagtc ccgtatcacg cagcgcgtga   8460
gctacccagg cactgccgcc gccggcacaa ccgttcttga atcagaaccc gagggcgacg   8520
ctgcccgcga ggtccaggcg ctggccgctg aaattaaatc aaaactcatt tgagttaatg   8580
aggtaaagag aaaatgagca aaagcacaaa cacgctaagt gccggccgtc cgagcgcacg   8640
cagcagcaag gctgcaacgt tggccagcct ggcagacacg ccagccatga agcgggtcaa   8700
ctttcagttg ccggcggagg atcacaccaa gctgaagatg tacgcggtac gccaaggcaa   8760
gaccattacc gagctgctat ctgaatacat cgcgcagcta ccagagtaaa tgagcaaatg   8820
aataaatgag tagatgaatt ttagcggcta aaggaggcgg catggaaaat caagaacaac   8880
caggcaccga cgccgtggaa tgccccatgt gtggaggaac gggcggttgg ccaggcgtaa   8940
gcggctgggt tgtctgccgg ccctgcaatg gcactggaac ccccaagccc gaggaatcgg   9000
cgtgacggtc gcaaaccatc cggcccggta caaatcggcg cggcgctggg tgatgacctg   9060
gtggagaagt tgaaggccgc gcaggccgcc cagcggcaac gcatcgaggc agaagcacgc   9120
cccggtgaat cgtggcaagc ggccgctgat cgaatccgca aagaatcccg gcaaccgccg   9180
gcagccggtg cgccgtcgat taggaagccg cccaagggcg acgagcaacc agattttttc   9240
gttccgatgc tctatgacgt gggcacccgc gatagtcgca gcatcatgga cgtggccgtt   9300
ttccgtctgt cgaagcgtga ccgacgagct ggcgaggtga tccgctacga gcttccagac   9360
gggcacgtag aggtttccgc agggccggcc ggcatggcca gtgtgtggga ttacgacctg   9420
gtactgatgg cggtttccca tctaaccgaa tccatgaacc gataccggga agggaaggga   9480
gacaagcccg gccgcgtgtt ccgtccacac gttgcggacg tactcaagtt ctgccggcga   9540
gccgatggcg gaaagcagaa agacgacctg gtagaaacct gcattcggtt aaacaccacg   9600
cacgttgcca tgcagcgtac gaagaaggcc aagaacggcc gcctggtgac ggtatccgag   9660
ggtgaagcct tgattagccg ctacaagatc gtaaagagcg aaaccgggcg gccggagtac   9720
atcgagatcg agctagctga ttggatgtac cgcgagatca cagaaggcaa gaacccggac   9780
gtgctgacgg ttcaccccga ttactttttg atcgatcccg gcatcggccg ttttctctac   9840
cgcctggcac gccgcgccgc aggcaaggca gaagccagat ggttgttcaa gacgatctac   9900
gaacgcagtg gcagcgccgg agagttcaag aagttctgtt tcaccgtgcg caagctgatc   9960
gggtcaaatg acctgccgga gtacgatttg aaggaggagg cggggcaggc tggcccgatc  10020
ctagtcatgc gctaccgcaa cctgatcgag ggcgaagcat ccgccggttc ctaatgtacg  10080
gagcagatgc tagggcaaat tgccctagca ggggaaaaag gtcgaaaagg tctctttcct  10140
gtggatagca cgtacattgg gaacccaaag ccgtacattg ggaaccggaa cccgtacatt  10200
gggaacccaa agccgtacat tgggaaccgg tcacacatgt aagtgactga tataaaagag  10260
aaaaaaggcg atttttccgc ctaaaactct ttaaaactta ttaaaactct taaaacccgc  10320
ctggcctgtg cataactgtc tggccagcgc acagccgaag agctgcaaaa agcgcctacc  10380
cttcggtcgc tgcgctccct acgccccgcc gcttcgcgtc ggcctatcgc ggccgctggc  10440
cgctcaaaaa tggctggcct acggccaggc aatctaccag ggcgcggaca agccgcgccg  10500
tcgccactcg accgccggcg cccacatcaa ggcaccctgc ctcgcgcgtt tcggtgatga  10560
cggtgaaaac ctctgacaca tgcagctccc ggagacggtc acagcttgtc tgtaagcgga  10620
tgccgggagc agacaagccc gtcagggcgc gtcagcgggt gttggcgggt gtcggggcgc  10680
agccatgacc cagtcacgta gcgatagcgg agtgtatact ggcttaacta tgcggcatca  10740
```

-continued

```
gagcagattg tactgagagt gcaccatatg cggtgtgaaa taccgcacag atgcgtaagg  10800
agaaaatacc gcatcaggcg ctcttccgct tcctcgctca ctgactcgct gcgctcggtc  10860
gttcggctgc ggcgagcggt atcagctcac tcaaaggcgg taatacggtt atccacagaa  10920
tcaggggata acgcaggaaa gaacatgtga gcaaaaggcc agcaaaaggc caggaaccgt  10980
aaaaaggccg cgttgctggc gtttttccat aggctccgcc cccctgacga gcatcacaaa  11040
aatcgacgct caagtcagag gtggcgaaac ccgacaggac tataaagata ccaggcgttt  11100
ccccctggaa gctccctcgt gcgctctcct gttccgaccc tgccgcttac cggatacctg  11160
tccgcctttc tcccttcggg aagcgtggcg ctttctcata gctcacgctg taggtatctc  11220
agttcggtgt aggtcgttcg ctccaagctg ggctgtgtgc acgaaccccc cgttcagccc  11280
gaccgctgcg ccttatccgg taactatcgt cttgagtcca acccggtaag acacgactta  11340
tcgccactgg cagcagccac tggtaacagg attagcagag cgaggtatgt aggcggtgct  11400
acagagttct tgaagtggtg gcctaactac ggctacacta gaaggacagt atttggtatc  11460
tgcgctctgc tgaagccagt taccttcgga aaaagagttg gtagctcttg atccggcaaa  11520
caaaccaccg ctggtagcgg tggttttttt gtttgcaagc agcagattac gcgcagaaaa  11580
aaaggatctc aagaagatcc tttgatcttt tctacggggt ctgacgctca gtggaacgaa  11640
aactcacgtt aagggatttt ggtcatgcat tctaggtact aaaacaattc atccagtaaa  11700
atataatatt ttattttctc ccaatcaggc ttgatcccca gtaagtcaaa aaatagctcg  11760
acatactgtt cttccccgat atcctccctg atcgaccgga cgcagaaggc aatgtcatac  11820
cacttgtccg ccctgccgct tctcccaaga tcaataaagc cacttacttt gccatctttc  11880
acaaagatgt tgctgtctcc caggtcgccg tgggaaaaga caagttcctc ttcgggcttt  11940
tccgtcttta aaaaatcata cagctcgcgc ggatctttaa atggagtgtc ttcttcccag  12000
ttttcgcaat ccacatcggc cagatcgtta ttcagtaagt aatccaattc ggctaagcgg  12060
ctgtctaagc tattcgtata gggacaatcc gatatgtcga tggagtgaaa gagcctgatg  12120
cactccgcat acagctcgat aatcttttca gggctttgtt catcttcata ctcttccgag  12180
caaaggacgc catcggcctc actcatgagc agattgctcc agccatcatg ccgttcaaag  12240
tgcaggacct ttggaacagg cagctttcct tccagccata gcatcatgtc cttttcccgt  12300
tccacatcat aggtggtccc tttataccgg ctgtccgtca tttttaaata taggttttca  12360
ttttctccca ccagcttata taccttagca ggagacattc cttccgtatc ttttacgcag  12420
cggtattttt cgatcagttt tttcaattcc ggtgatattc tcattttagc catttattat  12480
ttccttcctc ttttctacag tatttaaaga taccccaaga agctaattat aacaagacga  12540
actccaattc actgttcctt gcattctaaa accttaaata ccagaaaaca gctttttcaa  12600
agttgttttc aaagttggcg tataacatag tatcgacgga gccgattttg aaaccgcggt  12660
gatcacaggc agcaacgctc tgtcatcgtt acaatcaaca tgctaccctc cgcgagatca  12720
tccgtgtttc aaacccggca gcttagttgc cgttcttccg aatagcatcg gtaacatgag  12780
caaagtctgc cgccttacaa cggctctccc gctgacgccg tcccggactg atgggctgcc  12840
tgtatcgagt ggtgattttg tgccgagctg ccggtcgggg agctgttggc tggctggtgg  12900
caggatatat tgtggtgtaa acaaattgac gcttagacaa cttaataaca cattgcggac  12960
gtttttaatg tactgaatta acgccgaatt aattcctagg ccaccatgtt gggcccgggg  13020
cgcgccgtac gtagtgttta tctttgttgc ttttctgaac aatttattta ctatgtaaat  13080
atattatcaa tgtttaatct attttaattt gcacatgaat tttcatttta tttttacttt  13140
```

acaaaacaaa taaatatata tgcaaaaaaa tttacaaacg atgcacgggt tacaaactaa 13200
tttcattaaa tgctaatgca gattttgtga agtaaaactc caattatgat gaaaaatacc 13260
accaacacca cctgcgaaac tgtatcccaa ctgtccttaa taaaaatgtt aaaaagtata 13320
ttattctcat ttgtctgtca taatttatgt accccacttt aatttttctg atgtactaaa 13380
ccgagggcaa actgaaacct gttcctcatg caaagcccct actcaccatg tatcatgtac 13440
gtgtcatcac ccaacaactc cacttttgct atataacaac acccccgtca cactctccct 13500
ctctaacaca caccccacta acaattcctt cacttgcagc actgttgcat catcatcttc 13560
attgcaaaac cctaaacttc accttcaacc gcggccgcat ggcttctatg atatcctctt 13620
ccgctgtgac aacagtcagc cgtgcctcta gggggcaatc cgccgcagtg gctccattcg 13680
gcggcctcaa atccatgact ggattcccag tgaagaaggt caacactgac attacttcca 13740
ttacaagcaa tggtggaaga gtaaagtgca tgcaggtgtg gcctccaatt ggaaagaaga 13800
agtttgagac tctttcctat ttgccaccat tgacgagaga ttctagagtg agtaacaaga 13860
acaacgatga gctgcagtgg caatcctggt tcagcaaggc gcccaccacc gaggcgaacc 13920
cgatggccac catgttgcag gatatcggcg ttgcgctcaa accggaagcg atggagcagc 13980
tgaaaaacga ttatctgcgt gacttcaccg cgttgtggca ggattttttg gctggcaagg 14040
cgccagccgt cagcgaccgc cgcttcagct cggcagcctg gcagggcaat ccgatgtcgg 14100
ccttcaatgc cgcatcttac ctgctcaacg ccaaattcct cagtgccatg gtggaggcgg 14160
tggacaccgc accccagcaa aagcagaaaa tacgctttgc cgtgcagcag gtgattgatg 14220
ccatgtcgcc cgcgaacttc ctcgccacca acccggaagc gcagcaaaaa ctgattgaaa 14280
ccaagggcga gagcctgacg cgtggcctgg tcaatatgct gggcgatatc aacaagggcc 14340
atatctcgct gtcggacgaa tcggcctttg aagtgggccg caacctggcc attaccccgg 14400
gcaccgtgat ttacgaaaat ccgctgttcc agctgatcca gtacacgccg accacgccga 14460
cggtcagcca gcgcccgctg ttgatggtgc cgccgtgcat caacaagttc tacatcctcg 14520
acctgcaacc ggaaaattcg ctggtgcgct acgcggtgga gcagggcaac accgtgttcc 14580
tgatctcgtg gagcaatccg gacaagtcgc tggccggcac cacctgggac gactacgtgg 14640
agcagggcgt gatcgaagcg atccgcatcg tccaggacgt cagcggccag gacaagctga 14700
acatgttcgg cttctgcgtg ggcggcacca tcgttgccac cgcactggcg gtactggcgg 14760
cgcgtggcca gcacccggcg gccagcctga ccctgctgac caccttcctc gacttcagcg 14820
acaccggcgt gctcgacgtc ttcgtcgatg aaacccaggt cgcgctgcgt gaacagcaat 14880
tgcgcgatgg cggcctgatg ccgggccgtg acctggcctc gaccttctcg agcctgcgtc 14940
cgaacgacct ggtatggaac tatgtgcagt cgaactacct caaaggcaat gagccggcgg 15000
cgtttgacct gctgttctgg aattcggaca gcaccaattt gccgggcccg atgttctgct 15060
ggtacctgcg caacacctac ctggaaaaca gcctgaaagt gccgggcaag ctgacggtgg 15120
ccggcgaaaa gatcgacctc ggcctgatcg acgccccggc cttcatctac ggttcgcgcg 15180
aagaccacat cgtgccgtgg atgtcggcgt acggttcgct cgacatcctc aaccagggca 15240
agccgggcgc caaccgcttc gtgctgggcg cgtccggcca tatcgccggc gtgatcaact 15300
cggtggccaa gaacaagcgc agctactgga tcaacgacgg tggcgccgcc gatgcccagg 15360
cctggttcga tggcgcgcag gaagtgccgg gcagctggtg gccgcaatgg gccgggttcc 15420
tgacccagca tggcggcaag aaggtcaagc ccaaggccaa gcccggcaac gcccgctaca 15480
ccgcgatcga ggcggcgccc ggccgttacg tcaaagccaa gggctgagcg gccgctgagt 15540
aattctgata ttagagggag cattaatgtg ttgttgtgat gtggtttata tggggaaatt 15600
aaataaatga tgtatgtacc tcttgcctat gtaggtttgt gtgttttgtt ttgttgtcta 15660
gctttggtta ttaagtagta gggacgttcg ttcgtgtctc aaaaaaaggg gtactaccac 15720
tctgtagtgt atatggatgc tggaaatcaa tgtgttttgt atttgttcac ctccattgtt 15780
gaattcaatg tcaaatgtgt tttgcgttgg ttatgtgtaa aattactatc tttctcgtcc 15840
gatgatcaaa gttttaagca acaaaaccaa gggtgaaatt taaactgtgc tttgttgaag 15900
attcttttat catattgaaa atcaaattac tagcagcaga ttttacctag catgaaattt 15960
tatcaacagt acagcactca ctaaccaagt tccaaactaa gatgcgccat taacatcagc 16020
caataggcat tttcagcaag gcgcgcccgc gccgatgtat gtgacaaccc tcgggattgt 16080
tgatttattt caaaactaag agtttttgtc ttattgttct cgtctatttt ggatatcaat 16140
cttagtttta tatcttttct agttctctac gtgttaaatg ttcaacacac tagcaatttg 16200
gcctgccagc gtatggatta tggaactatc aagtctgtga cgcgccgtac gtagtgttta 16260
tctttgttgc ttttctgaac aatttattta ctatgtaaat atattatcaa tgtttaatct 16320
attttaattt gcacatgaat tttcatttta tttttacttt acaaaacaaa taaatatata 16380
tgcaaaaaaa tttacaaacg atgcacgggt tacaaactaa tttcattaaa tgctaatgca 16440
gattttgtga agtaaaactc caattatgat gaaaaatacc accaacacca cctgcgaaac 16500
tgtatcccaa ctgtccttaa taaaaatgtt aaaaagtata ttattctcat ttgtctgtca 16560
taatttatgt accccacttt aatttttctg atgtactaaa ccgagggcaa actgaaacct 16620
gttcctcatg caaagcccct actcaccatg tatcatgtac gtgtcatcac ccaacaactc 16680
cacttttgct atataacaac acccccgtca cactctccct ctctaacaca caccccacta 16740
acaattcctt cacttgcagc actgttgcat catcatcttc attgcaaaac cctaaacttc 16800
accttcaacc gcggccgcat ggcttctatg atatcctctt ccgctgtgac aacagtcagc 16860
cgtgcctcta gggggcaatc cgccgcagtg gctccattcg gcggcctcaa atccatgact 16920
ggattcccag tgaagaaggt caacactgac attacttcca ttacaagcaa tggtggaaga 16980
gtaaagtgca tgcaggtgtg gcctccaatt ggaaagaaga agtttgagac tctttcctat 17040
ttgccaccat tgacgagaga ttctagagtg actcagcgca ttgcgtatgt gaccggcggc 17100
atgggtggta tcggaaccgc catttgccag cggctggcca aggatggctt tcgtgtggtg 17160
gccggttgcg gccccaactc gccgcgccgc gaaaagtggc tggagcagca gaaggccctg 17220
ggcttcgatt tcattgcctc ggaaggcaat gtggctgact gggactcgac caagaccgca 17280
ttcgacaagg tcaagtccga ggtcggcgag gttgatgtgc tgatcaacaa cgccggtatc 17340
acccgcgacg tggtgttccg caagatgacc cgcgccgact gggatgcggt gatcgacacc 17400
aacctgacct cgctgttcaa cgtcaccaag caggtgatcg acggcatggc cgaccgtggc 17460
tggggccgca tcgtcaacat ctcgtcggtg aacgggcaga agggccagtt cggccagacc 17520
aactactcca ccgccaaggc cggcctgcat ggcttcacca tggcactggc gcaggaagtg 17580
gcgaccaagg gcgtgaccgt caacacggtc tctccgggct atatcgccac cgacatggtc 17640
aaggcgatcc gccaggacgt gctcgacaag atcgtcgcga cgatcccggt caagcgcctg 17700
ggcctgccgg aagagatcgc ctcgatctgc gcctggttgt cgtcggagga gtccggtttc 17760
tcgaccggcg ccgacttctc gctcaacggc ggcctgcata tgggctgagc ggccgctgag 17820
taattctgat attagaggga gcattaatgt gttgttgtga tgtggtttat atggggaaat 17880

```
taaataaatg atgtatgtac ctcttgccta tgtaggtttg tgtgttttgt tttgttgtct  17940

agctttggtt attaagtagt agggacgttc gttcgtgtct caaaaaaagg ggtactacca  18000

ctctgtagtg tatatggatg ctggaaatca atgtgttttg tatttgttca cctccattgt  18060

tgaattcaat gtcaaatgtg ttttgcgttg gttatgtgta aaattactat ctttctcgtc  18120

cgatgatcaa agttttaagc aacaaaacca agggtgaaat ttaaactgtg ctttgttgaa  18180

gattctttta tcatattgaa aatcaaatta ctagcagcag attttaccta gcatgaaatt  18240

ttatcaacag tacagcactc actaaccaag ttccaaacta agatgcgcca ttaacatcag  18300

ccaataggca ttttcagcaa ggcgcgtaa                                    18329


<210> SEQ ID NO 10
<211> LENGTH: 345
<212> TYPE: PRT
<213> ORGANISM: Unknown
<220> FEATURE:
<223> OTHER INFORMATION: FBPase from pMBXS407

<400> SEQUENCE: 10

Val Glu Lys Thr Ile Gly Leu Glu Ile Ile Glu Val Val Glu Gln Ala
1               5                   10                  15

Ala Ile Ala Ser Ala Arg Leu Met Gly Lys Gly Glu Lys Asn Glu Ala
            20                  25                  30

Asp Arg Val Ala Val Glu Ala Met Arg Val Arg Met Asn Gln Val Glu
        35                  40                  45

Met Leu Gly Arg Ile Val Ile Gly Glu Gly Glu Arg Asp Glu Ala Pro
    50                  55                  60

Met Leu Tyr Ile Gly Glu Glu Val Gly Ile Tyr Arg Asp Ala Asp Lys
65                  70                  75                  80

Arg Ala Gly Val Pro Ala Gly Lys Leu Val Glu Ile Asp Ile Ala Val
                85                  90                  95

Asp Pro Cys Glu Gly Thr Asn Leu Cys Ala Tyr Gly Gln Pro Gly Ser
            100                 105                 110

Met Ala Val Leu Ala Ile Ser Glu Lys Gly Gly Leu Phe Ala Ala Pro
        115                 120                 125

Asp Phe Tyr Met Lys Lys Leu Ala Ala Pro Pro Ala Ala Lys Gly Lys
    130                 135                 140

Val Asp Ile Asn Lys Ser Ala Thr Glu Asn Leu Lys Ile Leu Ser Glu
145                 150                 155                 160

Cys Leu Asp Arg Ala Ile Asp Glu Leu Val Val Val Val Met Asp Arg
                165                 170                 175

Pro Arg His Lys Glu Leu Ile Gln Glu Ile Arg Gln Ala Gly Ala Arg
            180                 185                 190

Val Arg Leu Ile Ser Asp Gly Asp Val Ser Ala Ala Ile Ser Cys Gly
        195                 200                 205

Phe Ala Gly Thr Asn Thr His Ala Leu Met Gly Ile Gly Ala Ala Pro
    210                 215                 220

Glu Gly Val Ile Ser Ala Ala Ala Met Arg Cys Leu Gly Gly His Phe
225                 230                 235                 240

Gln Gly Gln Leu Ile Tyr Asp Pro Glu Val Val Lys Thr Gly Leu Ile
                245                 250                 255

Gly Glu Ser Arg Glu Ser Asn Ile Ala Arg Leu Gln Glu Met Gly Ile
            260                 265                 270

Thr Asp Pro Asp Arg Val Tyr Asp Ala Asn Glu Leu Ala Ser Gly Gln
        275                 280                 285
```

```
Glu Val Leu Phe Ala Ala Cys Gly Ile Thr Pro Gly Leu Leu Met Glu
    290                 295                 300

Gly Val Arg Phe Phe Lys Gly Gly Ala Arg Thr Gln Ser Leu Val Ile
305                 310                 315                 320

Ser Ser Gln Ser Arg Thr Ala Arg Phe Val Asp Thr Val His Met Phe
                325                 330                 335

Asp Asp Val Lys Thr Val Ser Leu Arg
            340                 345


<210> SEQ ID NO 11
<211> LENGTH: 356
<212> TYPE: PRT
<213> ORGANISM: Unknown
<220> FEATURE:
<223> OTHER INFORMATION: FBPase from pMBXS408

<400> SEQUENCE: 11

Val Glu Lys Thr Ile Gly Leu Glu Ile Ile Glu Val Val Glu Gln Ala
1               5                   10                  15

Ala Ile Ala Ser Ala Arg Leu Met Gly Lys Gly Glu Lys Asn Glu Ala
            20                  25                  30

Asp Arg Val Ala Val Glu Ala Met Arg Val Arg Met Asn Gln Val Glu
        35                  40                  45

Met Leu Gly Arg Ile Val Ile Gly Glu Gly Glu Arg Asp Glu Ala Pro
    50                  55                  60

Met Leu Tyr Ile Gly Glu Glu Val Gly Ile Tyr Arg Asp Ala Asp Lys
65                  70                  75                  80

Arg Ala Gly Val Pro Ala Gly Lys Leu Val Glu Ile Asp Ile Ala Val
                85                  90                  95

Asp Pro Cys Glu Gly Thr Asn Leu Cys Ala Tyr Gly Gln Pro Gly Ser
            100                 105                 110

Met Ala Val Leu Ala Ile Ser Glu Lys Gly Gly Leu Phe Ala Ala Pro
        115                 120                 125

Asp Phe Tyr Met Lys Lys Leu Ala Ala Pro Pro Ala Ala Lys Gly Lys
    130                 135                 140

Glu Thr Ser Ile Lys Ser Ala Thr Glu Asn Leu Lys Ile Leu Ser Glu
145                 150                 155                 160

Cys Leu Asp Arg Ala Ile Asp Glu Leu Val Val Val Val Met Asp Arg
                165                 170                 175

Pro Arg His Lys Glu Leu Ile Gln Glu Ile Arg Gln Ala Gly Ala Arg
            180                 185                 190

Val Arg Leu Ile Ser Asp Gly Asp Val Ser Ala Ala Ile Ser Cys Gly
        195                 200                 205

Phe Ala Gly Thr Asn Thr His Ala Leu Met Gly Ile Gly Ala Ala Pro
    210                 215                 220

Glu Gly Val Ile Ser Ala Ala Ala Met Arg Cys Leu Gly Gly His Phe
225                 230                 235                 240

Gln Gly Gln Leu Ile Tyr Asp Pro Glu Val Val Lys Thr Gly Leu Ile
                245                 250                 255

Gly Glu Ser Arg Glu Ser Asn Ile Ala Arg Leu Gln Glu Met Gly Ile
            260                 265                 270

Thr Asp Pro Asp Arg Val Tyr Asp Ala Asn Glu Leu Ala Ser Gly Gln
        275                 280                 285

Glu Val Leu Phe Ala Ala Cys Gly Ile Thr Pro Gly Leu Leu Met Glu
    290                 295                 300
```

-continued

| | | | | | | | | | | | | | | | |
|---|---|---|---|---|---|---|---|---|---|---|---|---|---|---|---|
| Gly | Val | Arg | Phe | Phe | Lys | Gly | Gly | Ala | Arg | Thr | Gln | Ser | Leu | Val | Ile |
| 305 | | | | | 310 | | | | | 315 | | | | | 320 |
| Ser | Ser | Gln | Ser | Arg | Thr | Ala | Arg | Phe | Val | Asp | Thr | Val | His | Met | Phe |
| | | | | 325 | | | | | 330 | | | | | 335 | |
| Asp | Asp | Val | Lys | Thr | Val | Ser | Leu | Pro | Leu | Ile | Pro | Asp | Pro | Lys | Trp |
| | | | 340 | | | | | 345 | | | | | 350 | | |
| Arg | Pro | Glu | Arg | | | | | | | | | | | | |
| | | 355 | | | | | | | | | | | | | |